United States Patent
McBride et al.

(10) Patent No.: US 12,234,245 B2
(45) Date of Patent: Feb. 25, 2025

(54) SULFONIMIDAMIDE COMPOUNDS AS INHIBITORS OF INTERLEUKIN-1 ACTIVITY

(71) Applicant: Genentech, Inc., South San Francisco, CA (US)

(72) Inventors: Christopher McBride, South San Francisco, CA (US); Lynnie Lin Trzoss, South San Francisco, CA (US); Amogh Boloor, South San Francisco, CA (US); Nadezda V. Sokolova, South San Francisco, CA (US); Richard M. Pastor, South San Francisco, CA (US); Steven Thomas Staben, South San Francisco, CA (US); Craig Stivala, South San Francisco, CA (US); Matthew Volgraf, South San Francisco, CA (US); Sarah M. Bronner, South San Francisco, CA (US)

(73) Assignee: Genentech, Inc., South San Francisco, CA (US)

( * ) Notice: Subject to any disclaimer, the term of this patent is extended or adjusted under 35 U.S.C. 154(b) by 980 days.

(21) Appl. No.: 17/150,349

(22) Filed: Jan. 15, 2021

(65) Prior Publication Data

US 2021/0253596 A1    Aug. 19, 2021

Related U.S. Application Data

(63) Continuation of application No. PCT/US2019/042711, filed on Jul. 19, 2019.

(60) Provisional application No. 62/701,313, filed on Jul. 20, 2018.

(51) Int. Cl.
| | |
|---|---|
| C07D 498/04 | (2006.01) |
| A61P 31/04 | (2006.01) |
| A61P 31/12 | (2006.01) |
| A61P 31/14 | (2006.01) |
| A61P 31/16 | (2006.01) |
| A61P 31/18 | (2006.01) |
| C07D 231/18 | (2006.01) |
| C07D 471/04 | (2006.01) |
| C07D 487/04 | (2006.01) |
| C07D 513/04 | (2006.01) |

(52) U.S. Cl.
CPC ............ C07D 498/04 (2013.01); A61P 31/04 (2018.01); A61P 31/12 (2018.01); A61P 31/14 (2018.01); A61P 31/16 (2018.01); A61P 31/18 (2018.01); C07D 231/18 (2013.01); C07D 471/04 (2013.01); C07D 487/04 (2013.01); C07D 513/04 (2013.01)

(58) Field of Classification Search
CPC ............................. C07D 498/04; A61P 31/12
See application file for complete search history.

(56) References Cited

U.S. PATENT DOCUMENTS

| | | |
|---|---|---|
| 6,147,115 A | 11/2000 | Crowell et al. |
| 10,538,487 B2 | 1/2020 | O'Neill et al. |
| 11,040,985 B2 | 6/2021 | Stafford et al. |
| 11,203,579 B2 | 12/2021 | Franchi et al. |
| 11,236,045 B2 | 2/2022 | Sharma et al. |
| 11,623,922 B2 | 4/2023 | Miller et al. |
| 11,702,428 B2 | 7/2023 | Stafford et al. |
| 2014/0221340 A1 | 8/2014 | Yamamoto et al. |
| 2016/0052876 A1 | 2/2016 | Abbate et al. |
| 2019/0119203 A1 | 4/2019 | Glick et al. |
| 2019/0119224 A1 | 4/2019 | Glick et al. |
| 2019/0119241 A1 | 4/2019 | Glick et al. |
| 2019/0337965 A1 | 11/2019 | Stafford et al. |
| 2020/0024281 A1 | 1/2020 | Jakob et al. |
| 2020/0306243 A1 | 10/2020 | Howard et al. |
| 2021/0253596 A1 | 8/2021 | McBride et al. |
| 2021/0261568 A1 | 8/2021 | Stafford et al. |
| 2021/0395268 A1 | 12/2021 | Stafford et al. |
| 2022/0306649 A1 | 9/2022 | Stafford et al. |
| 2023/0159555 A1 | 5/2023 | Gibbons et al. |

FOREIGN PATENT DOCUMENTS

| | | |
|---|---|---|
| CL | 2021-000126 A1 | 7/2021 |
| CO | 2020-0000527 A2 | 5/2020 |
| EP | 4094804 A1 | 11/2022 |
| RU | 2180658 C2 | 3/2020 |
| TW | 202016078 A | 5/2020 |
| WO | 98/032733 A1 | 7/1998 |
| WO | 01/019390 A1 | 3/2001 |
| WO | 2003/045400 A1 | 6/2003 |
| WO | 2011/102149 A1 | 8/2011 |
| WO | 2016/131098 A1 | 8/2016 |
| WO | 2017/129897 A1 | 8/2017 |

(Continued)

OTHER PUBLICATIONS

Asano, T., et al., "Identification, synthesis, and biological evaluation of 6-[(6R)-2-(4-fluorophenyl)-6-(hydroxymethyl)-4,5,6,7-tetrahydropyrazolo[1,5-a]pyrimidin-3-yl]-2-(2-methylphenyl)pyridazin-3(2H)-one (AS1940477), a potent p38 MAP kinase inhibitor" J Med Chem 55(17):7772-7785 (Sep. 13, 2012).

(Continued)

*Primary Examiner* — Kamal A Saeed
(74) *Attorney, Agent, or Firm* — Eric Silverman

(57) ABSTRACT

The present disclosure relates to novel sulfonimidamide compounds and related compounds and their use in treating a disorder responsive to modulation of cytokines such as IL-1β and IL-18, modulation of NLRP3 or inhibition of the activation of NLRP3 or related components of the inflammatory process.

19 Claims, No Drawings

(56) References Cited

FOREIGN PATENT DOCUMENTS

| | | | |
|---|---|---|---|
| WO | 2017/140778 | A1 | 8/2017 |
| WO | 2017/184604 | A1 | 10/2017 |
| WO | 2017/184623 | A1 | 10/2017 |
| WO | 2017/184624 | A1 | 10/2017 |
| WO | 2018/136890 | A1 | 7/2018 |
| WO | 2018/215818 | A1 | 11/2018 |
| WO | 2018/225018 | A1 | 12/2018 |
| WO | 2019/008025 | A1 | 1/2019 |
| WO | 2019/008029 | A1 | 1/2019 |
| WO | 2019/023147 | A1 | 1/2019 |
| WO | 2019/034686 | A1 | 2/2019 |
| WO | 2019/034688 | A1 | 2/2019 |
| WO | 2019/034690 | A1 | 2/2019 |
| WO | 2019/034692 | A1 | 2/2019 |
| WO | 2019/034693 | A1 | 2/2019 |
| WO | 2019/034696 | A1 | 2/2019 |
| WO | 2019/034697 | A1 | 2/2019 |
| WO | 2019/043610 | A1 | 3/2019 |
| WO | 2019/068772 | A1 | 4/2019 |
| WO | 2019/092170 | A1 | 5/2019 |
| WO | 2019/092171 | A1 | 5/2019 |
| WO | 2019/092172 | A1 | 5/2019 |
| WO | 2019/121691 | A1 | 6/2019 |
| WO | 2019/166619 | A1 | 9/2019 |
| WO | 2019/166621 | A1 | 9/2019 |
| WO | 2019/166623 | A1 | 9/2019 |
| WO | 2019/206871 | A1 | 10/2019 |
| WO | 2020/010118 | A1 | 1/2020 |
| WO | 2020/010143 | A1 | 1/2020 |
| WO | 2020/016452 | | 1/2020 |
| WO | 2020/018970 | A1 | 1/2020 |
| WO | 2020/018975 | A1 | 1/2020 |
| WO | 2020/035464 | A1 | 2/2020 |
| WO | 2020/035465 | A1 | 2/2020 |
| WO | 2020/035466 | A1 | 2/2020 |
| WO | 2020/079207 | A1 | 4/2020 |
| WO | 2020/086732 | A1 | 4/2020 |
| WO | 2020/102096 | A1 | 5/2020 |
| WO | 2020/102100 | A1 | 5/2020 |
| WO | 2020/102576 | A1 | 5/2020 |
| WO | 2020/104657 | A1 | 5/2020 |
| WO | 2020/154321 | A1 | 7/2020 |
| WO | 2020/154499 | A1 | 7/2020 |
| WO | 2020/200880 | A1 | 10/2020 |
| WO | 2020/254697 | A1 | 12/2020 |
| WO | 2021/002887 | A1 | 1/2021 |
| WO | 2021/121367 | A1 | 6/2021 |
| WO | 2021/147974 | A1 | 7/2021 |
| WO | 2021/149776 | A1 | 7/2021 |
| WO | 2021/150574 | A1 | 7/2021 |
| WO | 2021/152201 | A1 | 8/2021 |
| WO | 2021/214284 | A1 | 10/2021 |
| WO | 2021/219784 | A1 | 11/2021 |
| WO | 2021/234608 | A1 | 11/2021 |
| WO | 2021/239885 | A1 | 12/2021 |
| WO | 2021/255279 | A1 | 12/2021 |
| WO | 2022/063896 | A1 | 3/2022 |
| WO | 2022/064490 | A1 | 3/2022 |
| WO | 2022/184842 | A1 | 9/2022 |
| WO | 2022/229315 | A1 | 11/2022 |
| WO | 2022/237781 | A1 | 11/2022 |
| WO | 2023/275230 | A1 | 1/2023 |

OTHER PUBLICATIONS

Cable News Network, "FDA mulls drug to slow late-stage Alzheimer's" CNN News:1-2 (Sep. 24, 2003).
Damasio, A., "Alzheimer's Disease and Related Dementias" Cecil Textbook of Medicine 20(2):1992-1996 (Jan. 1, 1996).
Golub, T.R., et al., "Molecular Classification of Cancer: Class Discovery and Class Prediction of Gene Expression" Science 286(5439):531-537 (Oct. 15, 1999).
"International Preliminary Report on Patentability—PCT/US2021/014133" (Report Issuance Date: Jul. 26, 2022; Chapter I),:pp. 1-12 (Aug. 4, 2022).
"International Search Report—PCT/US2021/014133" (w/Written Opinion),:pp. 1-17 (May 3, 2021).
Johnson, C., et al., "Preparation and reactions of sulfonimidoyl chlorides" J Org Chem 44(13):2055-2061 (Jun. 22, 1979).
Lala, P.K., et al., "Role of nitric oxide in tumor progression: Lessons from experimental tumors" Cancer Metast Rev 17(1):91-106 (Mar. 1, 1998).
Layzer, R., "Section Five: Degenerative Diseases of the Nervous System" Cecil Textbook of Medicine 20(2):2050-2057 (Jan. 1, 1996).
"U.S. Appl. No. 17/814,115, filed Jul. 21, 2022".
Baldwin, A.G., et al., "Inhibiting the Inflammasome: A Chemical Perspective" J Med Chem 59(5):1691-1710 (Mar. 10, 2016).
Hill, J., et al., "Sulfonylureas as Concomitant Insulin Secretagogues and NLRP3 Inflammasome Inhibitors" ChemMedChem 12(17):1449-1457 (Sep. 7, 2017).
Howbert, J.J., et al., "Novel agents effective against solid tumors: The Diarylsulfonylureas. Synthesis, Activities, and Analysis of Quantitative Structure-Activity Relationships" J Med Chem 33(9):2393-2407 (Sep. 1, 1990).
International Preliminary Report on Patentability—PCT/US2018/014728 (Report Issuance Date: Jul. 23, 2019, Chapter I),:1-6 (Jul. 23, 2019).
International Preliminary Report on Patentability for PCT/US2019/042711 :pp. 1-7 issued on Jan. 26, 2021.
International Search Report—PCT/US2018/014728 :pp. 1-5 (Mar. 20, 2018).
International Search Report for PCT/US2019/042711 :pp. 1-14 mailed on Sep. 26, 2019.
Shah, F., et al., "Analysis of Pfizer Compounds in EPA's ToxCast Chemicals-Assay Space" Chem Res Toxicol 27(1):86-98 (Jan. 21, 2014).
Toth, J.E., et al., "Sulfonimidamide Analogs of Oncolytic Sulfonylureas" J Med Chem 40(6):1018-1025 (Mar. 14, 1997).
USPTO, U.S. Appl. No. 17/150,380, filed Jan. 15, 2021.
USPTO, "U.S. Appl. No. 17/157,749, filed Jan. 25, 2021".
Mangan et al., "Targeting the NLRP3 inflammasome in inflammatory diseases" Nature Reviews, Drug Discovery 17:588-606 (Aug. 2018).
McBride et al., "Overcoming Preclinical Safety Obstacles to Discover (S)-N-((1,2,3,5,6,7-Hexahydro-s-indacen-4-yl)carbamoyl)-6-(methylamino)-6,7-dihydro-5H-pyrazolo[5,1-b][1,3]oxazine-3-sulfonamide (GDC-2394): A Potent and Selective NLRP3 Inhibitor" J. Med. Chem. 65(21):14721-14739 (Oct. 24, 2022).
International Preliminary Report on Patentability—PCT/US2022/073756 issued Jan. 18, 2024.
International Search Report with Written Opinion—PCT/US2022/073756 mailed Oct. 17, 2022, pp. 1-12.
Zhang, Y., et al., "Research Progress on the Relationship between Type-2 Diabetes, Hypoglycemic drugs and Cancer" J Shandong Medicine—PDR China (Chinese w/Eng. Translation), 59(33):109-111 (Dec. 31, 2019).

SULFONIMIDAMIDE COMPOUNDS AS INHIBITORS OF INTERLEUKIN-1 ACTIVITY

CROSS REFERENCE TO RELATED APPLICATIONS

This application is a continuation of International Application No. PCT/US2019/042711, filed Jul. 19, 2019, which claims the benefit of U.S. Provisional Application No. 62/701,313 filed Jul. 20, 2018, which are incorporated herein by reference in their entireties.

FIELD OF DISCLOSURE

The present disclosure relates to novel sulfonimidamide compounds and related compounds and their use in treating a disorder responsive to modulation of cytokines such as IL-1β and IL-18, modulation of NLRP3, or inhibition of the activation of NLRP3 or related components of the inflammatory process.

BACKGROUND

The NOD-like receptor (NLR) family, pyrin domain-containing protein 3 (NLRP3) inflammasome is a component of the inflammatory process, and its aberrant activation is pathogenic in inherited disorders such as cryopyrin-associated periodic syndromes (CAPS) and complex diseases such as multiple sclerosis, type 2 diabetes, Alzheimer's disease and atherosclerosis.

NLRP3 is an intracellular receptor protein that senses certain inflammatory signals. Upon activation, NLRP3 binds to apoptosis-associated speck-like protein containing a caspase activation and recruitment domain (ASC). The NLRP3-ASC complex then polymerizes to form a large aggregate known as an ASC speck. Polymerized NLRP3-ASC in turn interacts with the cysteine protease caspase-1 to form a complex termed the inflammasome. This results in the activation of caspase-1, which cleaves the proinflammatory cytokines IL-1β and IL-18 to their active forms and mediates a type of inflammatory cell death known as pyroptosis. The ASC speck can also recruit and activate caspase-8, which can process pro-IL-1β and pro-IL-18 and trigger apoptotic cell death.

Caspase-1 cleaves pro-IL-1β and pro-IL-18 to their active forms, which are secreted from the cell. Active caspase-1 also cleaves gasdermin-D to trigger pyroptosis. Through its control of the pyroptotic cell death pathway, caspase-1 also mediates the release of alarmin molecules such as IL-33 and high mobility group box 1 protein (HMGB1). Caspase-1 also cleaves intracellular IL-1R2 resulting in its degradation and allowing the release of IL-1α. In human cells caspase-1 may also control the processing and secretion of IL-37. A number of other caspase-1 substrates such as components of the cytoskeleton and glycolysis pathway may contribute to caspase-1-dependent inflammation.

NLRP3-dependent ASC specks are released into the extracellular environment where they can activate caspase-1, induce processing of caspase-1 substrates and propagate inflammation.

Active cytokines derived from NLRP3 inflammasome activation are important drivers of inflammation and interact with other cytokine pathways to shape the immune response to infection and injury. For example, IL-1β signalling induces the secretion of the proinflammatory cytokines IL-6 and TNF. IL-1β and IL-18 synergize with IL-23 to induce IL-17 production by memory CD4 Th17 cells and by γδ T cells in the absence of T cell receptor engagement. IL-18 and IL-12 also synergize to induce IFN-γ production from memory T cells and NK cell driving a Th1 response.

Other intracellular pattern recognition receptors (PRRs) are also capable of forming inflammasomes. These include other NLR family members such as NLRP1 and NLRC4, as well as non-NLR PRRs such as the double-stranded DNA (dsDNA) sensors absent in melanoma 2 (AIM2) and interferon, gamma inducible protein 16 (IFI16). NLRP3-dependent IL-1β processing can also be activated by an indirect, non-canonical pathway downstream of caspase-11.

The inherited CAPS disease Muckle-Wells syndrome (MWS), familial cold autoinflammatory syndrome and neonatal-onset multisystem inflammatory disease are caused by gain-of-function mutations in NLRP3, thus defining NLRP3 as a critical component of the inflammatory process. NLRP3 has also been implicated in the pathogenesis of a number of complex diseases, notably including metabolic disorders such as type 2 diabetes, atherosclerosis, obesity and gout.

A role for NLRP3 in diseases of the central nervous system is emerging, and lung diseases have also been shown to be influenced by NLRP3. Furthermore, NLRP3 has a role in the development of liver disease, kidney disease and aging. Many of these associations were defined using mice with constitutive NLRP3 activation, but there have also been insights into the specific activation of NLRP3 in these diseases. In type 2 diabetes, the deposition of islet amyloid polypeptide in the pancreas activates NLRP3 and IL-1β signaling, resulting in cell death and inflammation.

There is a need to provide compounds and pharmaceutical compositions with improved pharmacological and/or physiological and/or physicochemical properties and/or those that provide a useful alternative to known compounds and pharmaceutical compositions.

SUMMARY

The present disclosure provides compounds and pharmaceutical compositions that are useful for inhibiting an inflammasome, such as the NLRP3 inflammasome. The compounds and pharmaceutical compositions are also useful in modulating interleukins. The disclosed compounds have desirable molecular weights, physico-chemical properties, and lipophilicity, which are features that help with achieving therapeutic efficacy and decreasing unintended liabilities.

The present disclosure provides a compound having the structure of Formula (I),

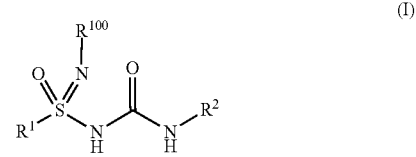

(I)

and pharmaceutically acceptable salts, solvates, isomers, prodrugs, and tautomers thereof, wherein the substituents are as described herein (e.g., such as described with respect to Formulae (I-1), (I-2), (I-3), (I-4), (I-5), and (I-6)).

The present disclosure provides a compound having the structure of Formula (I),

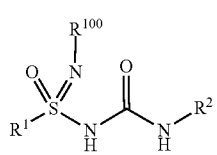

(I)

or a pharmaceutically acceptable salt, solvate, isomer, or tautomer thereof, wherein:

$R^1$ is (i) or (ii):

(i): $R^1$ is a monocyclic pyrazole of formula

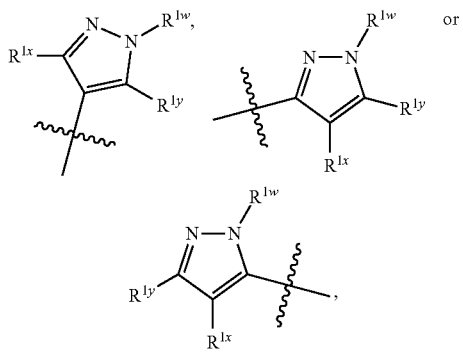

wherein $R^{1w}$ is selected from the group consisting of H, D, —CN, —C(O)$R^{5b}$, —S(O)$_2R^{5b}$, —S(O)$R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, $C_3$-$C_{10}$cycloalkyl, $C_6$aryl, 3-7-membered heterocyclyl, and 5-6-membered heteroaryl; and each $R^{1x}$ and $R^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6-membered heteroaryl; or (ii): $R^1$ is a fused pyrazole of formula

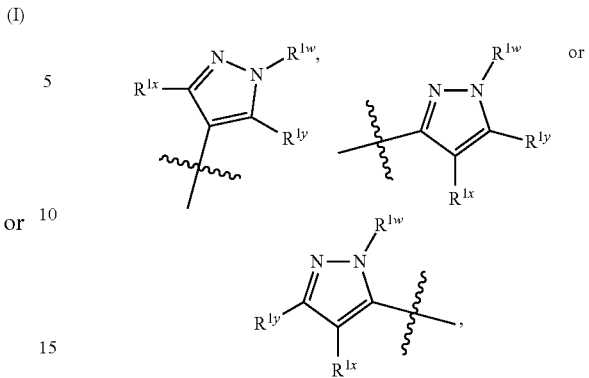

wherein (ii-a): $R^{1w}$ and $R^{1y}$, together with the atoms to which they are attached can form a 3-7-membered heterocyclyl or 5-6-membered heteroaryl; wherein the 3-7-membered heterocyclyl and 5-6-membered heteroaryl are independently unsubstituted or substituted with one or more substituents, or optionally two of the substituents when present, together with the atoms to which they are attached can form a ring; and $R^{1x}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6-membered heteroaryl;

or (ii-b): $R^{1x}$ and $R^{1y}$, together with the atoms to which they are attached can form a $C_3$-$C_{10}$cycloalkyl, 3-7-membered heterocyclyl, or a 5-6-membered aryl or heteroaryl; wherein the $C_3$-$C_{10}$cycloalkyl, 3-7-membered heterocyclyl, and 5-6-membered aryl or heteroaryl are independently unsubstituted or substituted with one or more substituents, or optionally two of the substituents when present, together with the atoms to which they are attached can form a ring; and $R^{1w}$ is selected from the group consisting of H, D, —CN, —C(O)R$^{5b}$, —S(O)$_2$R$^{5b}$, —S(O)R$^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, $C_3$-$C_{10}$cycloalkyl, $C_6$aryl, 3-7-membered heterocyclyl, and 5-6-membered heteroaryl;

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6-membered heteroaryl;

R$^2$ is selected from the group consisting of C$_1$-C$_6$alkyl, C$_3$-C$_{10}$cycloalkyl, 3-7-membered heterocyclyl, 5-membered heteroaryl, 6-membered heteroaryl, C$_6$aryl, and —NR$^{2g}$R$^{2h}$; wherein the C$_1$-C$_6$alkyl, C$_3$-C$_{10}$cycloalkyl, 3-7-membered heterocyclyl, 5-membered heteroaryl, 6-membered heteroaryl, and C$_6$aryl are independently unsubstituted or substituted with one or more substituents, or optionally two of the substituents when present, together with the atoms to which they are attached can form a ring;

each R$^{2g}$ and R$^{2h}$ is independently H, D, C$_1$-C$_6$alkyl, C$_3$-C$_{10}$cycloalkyl, C$_6$aryl, 3-7-membered heterocyclyl, or 5-6-membered heteroaryl, wherein the C$_1$-C$_6$alkyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

R$^{3a}$, R$^{4a}$, R$^{5a}$, R$^{6a}$, R$^{7a}$, R$^{8a}$, R$^{9a}$, R$^{10a}$, R$^{21a}$, and R$^{22a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6-membered heteroaryl; and R$^{4b}$, R$^{5b}$, R$^{6b}$, R$^{7b}$, R$^{8b}$, R$^{9b}$, R$^{10b}$, R$^{21b}$, and R$^{22b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$ alkyl)$_2$, C$_3$-C$_{10}$cycloalkyl, C$_6$aryl, 3-7-membered heterocyclyl, and 5-6-membered heteroaryl.

The present disclosure provides a compound having the structure of Formula (I-1),

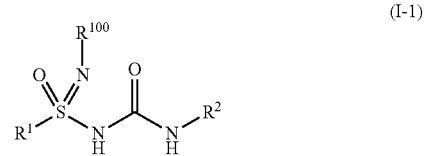

(I-1)

and pharmaceutically acceptable salts, solvates, isomers, prodrugs, and tautomers thereof, wherein:

R$^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_1$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

R$^1$ is selected from the group consisting of

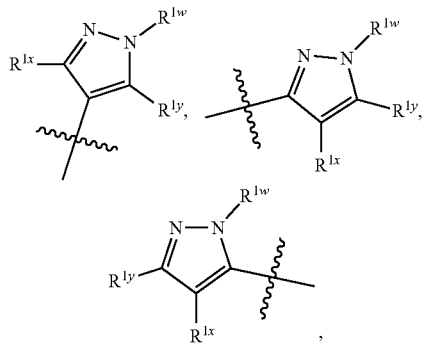

wherein R$^{1w}$ is selected from the group consisting of H, D, —CN, —C(O)R$^{5b}$, —S(O)$_2$R$^{5b}$, —S(O)R$^{5b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, C$_3$-C$_{10}$cycloalkyl, C$_6$aryl, 3-7-membered heterocyclyl, and 5-6 membered heteroaryl;

each R$^{1x}$ and R$^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —C(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl; or wherein R$^{1w}$ and R$^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, C$_1$-C$_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$; or wherein R$^{1x}$ and R$^{1y}$, together with the atoms to which they are attached can form a C$_3$-C$_{10}$cycloalkyl, 3-7-membered heterocyclyl, or a 5-6 membered aryl or heteroaryl; wherein the C$_3$-C$_{10}$cycloalkyl, 3-7-membered heterocyclyl, and 5-6 membered aryl or heteroaryl are independently unsubstituted or substituted with one or more substituents selected from the group consisting of D, —CN, halogen, C$_1$-C$_6$alkyl, —OR$^{9a}$, —C(O)R$^{9bs}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$;

R$^2$ is selected from the group consisting of C$_1$-C$_6$alkyl, C$_3$-C$_{10}$cycloalkyl, 3-7-membered heterocyclyl, 5-membered heteroaryl, 6-membered heteroaryl, C$_6$aryl, and —NR$^{2g}$R$^{2h}$; wherein the C$_1$-C$_6$alkyl, C$_3$-C$_{10}$cycloalkyl, 3-7-membered heterocyclyl, 5-membered heteroaryl, 6-membered heteroaryl, and C$_6$aryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

each R$^{2g}$ and R$^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6 membered heteroaryl;

R$^{3a}$, R$^{4a}$, R$^{5a}$, R$^{6a}$, R$^{7a}$, R$^{8a}$, R$^{9a}$, R$^{10a}$, R$^{21a}$, R$^{22a}$, R$^{23a}$, and R$^{24a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl;

R$^{3b}$, R$^{4b}$, R$^{5b}$, R$^{6b}$, R$^{7b}$, R$^{8b}$, R$^{9b}$, R$^{10b}$, R$^{21b}$, R$^{22b}$, R$^{23b}$, and R$^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

The present disclosure provides a compound having the structure of Formula (I-2),

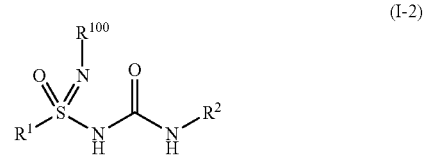

(I-2)

and pharmaceutically acceptable salts, solvates, isomers, prodrugs, and tautomers thereof, wherein:

R$^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

$R^1$ is selected from the group consisting of

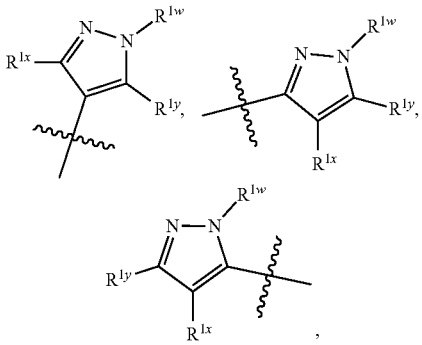

$R^2$ is selected from the group consisting of $C_1$-$C_6$alkyl, $C_3$-$C_{10}$cycloalkyl, 3-7-membered heterocyclyl, 5-membered heteroaryl, $—NR^{2g}R^{2h}$,

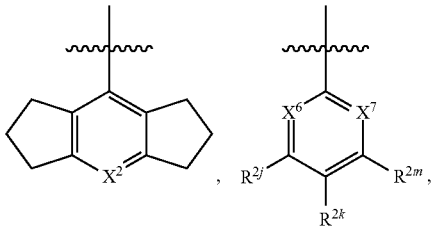

and

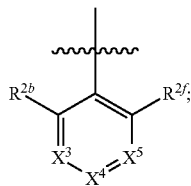

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, $—OR^{23a}$, $—C(O)R^{23b}$, $—P(O)R^{23b}R^{24b}$, $—S(O)_2R^{23b}$, $—S(O)R^{23b}$, $—NR^{23a}R^{24a}$, $—NR^{23a}C(O)R^{24a}$, $—NR^{23a}C(O)OR^{24a}$, $—NR^{23a}C(O)NR^{24a}$, $—NR^{23a}S(O)_2R^{24a}$, $—(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$X^2$ is N or $CR^{2a}$;
$X^3$ is N or $CR^{2c}$;
$X^4$ is N or $CR^{2d}$;
$X^5$ is N or $CR^{2e}$;
$X^6$ and $X^7$ are independently N or $CR^{2n}$, wherein at least one of $X^6$ and $X^7$ is N;

wherein $R^{1w}$ is selected from the group consisting of H, D, —CN, $—C(O)R^{5b}$, $—S(O)_2R^{5b}$, $—S(O)R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, $—OR^{5a}$, $—C(O)R^{5b}$, $—P(O)R^{5b}R^{6b}$, $—S(O)_2R^{5b}$, $—S(O)R^{5b}$, $—NR^{5a}R^{6a}$, $—NR^{5a}C(O)R^{6a}$, $—NR^{5a}C(O)OR^{6a}$, $—NR^{5a}C(O)NR^{6a}$, $—NR^{5a}S(O)_2R^{6a}$, $C_3$-$C_{10}$cycloalkyl, $C_6$aryl, 3-7-membered heterocyclyl, and 5-6 membered heteroaryl;

each $R^{1x}$ and $R^{1y}$ is independently, H, D, halogen, —CN, $—NO_2$, $—SR^{7a}$, $—OR^{7a}$, $—C(O)R^{7b}$, $—P(O)R^{7b}R^{8b}$, $—S(O)_2R^{7b}$, $—S(O)R^{7b}$, $—NR^{7a}R^{8a}$, $—NR^{7a}C(O)R^{8a}$, $—NR^{7a}C(O)OR^{8a}$, $—NR^{7a}C(O)NR^{8a}$, $—NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, $—OR^{7a}$, $—C(O)R^{7b}$, $—P(O)R^{7b}R^{8b}$, $—S(O)_2R^{7b}$, $—S(O)R^{7b}$, $—NR^{7a}R^{8a}$, $—NR^{7a}C(O)R^{8a}$, $—NR^{7a}C(O)OR^{8a}$, $—NR^{7a}C(O)NR^{8a}$, $—NR^{7a}S(O)_2R^{8a}$, $C_3$-$C_{10}$cycloalkyl, $C_6$aryl, 3-7-membered heterocyclyl, and 5-6 membered heteroaryl; or wherein $R^{1w}$ and $R^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, $C_1$-$C_6$alkyl, $—OR^{9a}$, $—C(O)R^{9b}$, $—P(O)R^{9b}R^{10b}$, $—S(O)_2R^{9b}$, $—S(O)R^{9b}$, $—NR^{9a}R^{10a}$, $—NR^{9a}C(O)R^{10a}$, $—NR^{9a}C(O)OR^{10a}$, $—NR^{9a}C(O)NR^{10a}$, and $—NR^{9a}S(O)_2R^{10a}$; or wherein $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, $—OR^{9a}$, $—C(O)R^{9b}$, $—P(O)R^{9b}R^{10b}$, $—S(O)_2R^{9b}$, $—S(O)R^{9b}$, $—NR^{9a}R^{10a}$, $—NR^{9a}C(O)R^{10a}$, $—NR^{9a}C(O)OR^{10a}$, $—NR^{9a}C(O)NR^{10a}$, and $—NR^{9a}S(O)_2R^{10a}$;

$R^{2a}$ is H, D, halogen, —CN, $—OR^{15a}$, $C_1$-$C_6$alkyl, $C_3$-$C_{10}$cycloalkyl, $—C(O)NR^{15a}R^{16a}$, $—C(O)OR^{15a}$; $—NR^{15a}R^{16a}$, $—NR^{15a}C(O)R^{16a}$, $—NR^{15a}C(O)OR^{16a}$, $—NR^{15a}C(O)NR^{16a}$, or $—NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, $—OR^{15a}$, $—C(O)R^{15b}$, $—NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, $—NO_2$, $—SR^{17a}$, $—OR^{17a}$, $—C(O)R^{17b}$, $—P(O)R^{17b}R^{18b}$, $—S(O)_2R^{17b}$, $—S(O)R^{17b}$, $—NR^{17a}R^{18a}$, $—NR^{17a}C(O)R^{18a}$, $—NR^{17a}C(O)R^{18a}$, $—NR^{17a}C(O)OR^{18a}$, $—NR^{17a}C(O)NR^{18a}$, $—NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O) R$^{17b}$, —NR$^{17a}$R$^{18a}$, —NR$^{17a}$C(O)R$^{18a}$, —NR$^{17a}$C(O) OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2b}$, R$^{2c}$, R$^{2d}$, R$^{2e}$, and R$^{2f}$ together with the atoms to which they are attached can form C$_3$-C$_{10}$cycloalkyl, C$_6$aryl, 3-7-membered heterocyclyl, 5-6-membered heteroaryl, wherein the C$_3$-C$_{10}$cycloalkyl, C$_6$aryl, 3-7-membered heterocyclyl, and 5-6-membered heteroaryl are independently unsubstituted or substituted with one or more substituents selected from the group consisting of halogen, D, —CN, C$_1$-C$_6$alkyl, —OR$^{19a}$, and NR$^{19a}$R$^{20a}$;

each R$^{2j}$, R$^{2k}$, R$^{2m}$, and R$^{2n}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6 membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2j}$, R$^{2k}$, R$^{2m}$, and R$^{2n}$ together with the atoms to which they are attached can form C$_3$-C$_{10}$cycloalkyl, C$_6$aryl, 3-7-membered heterocyclyl, 5-6-membered heteroaryl, wherein the C$_3$-C$_{10}$cycloalkyl, C$_6$aryl, 3-7-membered heterocyclyl, and 5-6-membered heteroaryl are independently unsubstituted or substituted with one or more substituents selected from the group consisting of halogen, D, —CN, C$_1$-C$_6$alkyl, —OR$^{19a}$, and NR$^{19a}$R$^{20a}$;

each R$^{2g}$ and R$^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

R$^{3a}$, R$^{4a}$, R$^{5a}$, R$^{6a}$, R$^{7a}$, R$^{8a}$, R$^{9a}$, R$^{10a}$, R$^{15a}$, R$^{16a}$, R$^{17a}$, R$^{18a}$, R$^{19a}$, R$^{20a}$, R$^{21a}$, R$^{22a}$, R$^{23a}$, and R$^{24a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl;

R$^{3b}$, R$^{4b}$, R$^{5b}$, R$^{6b}$, R$^{7b}$, R$^{8b}$, R$^{9b}$, R$^{10b}$, R$^{15b}$, R$^{17b}$, R$^{18b}$, R$^{21b}$, R$^{22b}$, R$^{23b}$, and R$^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

The present disclosure provides a compound having the structure of Formula (I-3),

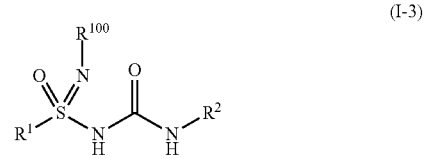

(I-3)

and pharmaceutically acceptable salts, solvates, isomers, prodrugs, and tautomers thereof, wherein:

R$^{100}$ is selected from the group consisting of H, D, —Cl, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

R$^1$ is selected from the group consisting of

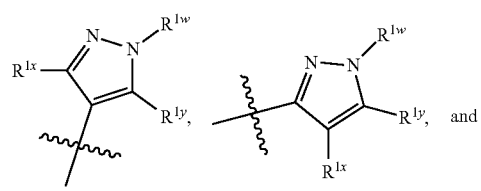

-continued

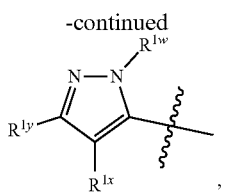

$R^2$ is

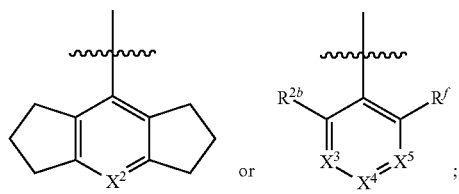

$X^2$ is N or $CR^{2a}$;
$X^3$ is N or $CR^{2c}$;
$X^4$ is N or $CR^{2d}$;
$X^5$ is N or $CR^{2e}$;
wherein $R^{1w}$ is selected from the group consisting of H, D, —CN, —C(O)$R^{5b}$, —S(O)$_2R^{5b}$, —S(O)$R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —O$R^{5a}$, —C(O)$R^{5b}$, —P(O)$R^{5b}R^{6b}$, —S(O)$_2R^{5b}$, —S(O)$R^{5b}$, —N$R^{5a}R^{6a}$, —N$R^{5a}$C(O)$R^{6a}$, —N$R^{5a}$C(O)O$R^{6a}$, —N$R^{5a}$C(O)N$R^{6a}$, —N$R^{5a}$S(O)$_2R^{6a}$, $C_3$-$C_{10}$cycloalkyl, $C_6$aryl, 3-7-membered heterocyclyl, and 5-6 membered heteroaryl;
each $R^{1x}$ and $R^{1y}$ is independently, H, D, halogen, —CN, —NO$_2$, —S$R^{7a}$, —O$R^{7a}$, —C(O)$R^{7b}$, —P(O)$R^{7b}R^{8b}$, —S(O)$_2R^{7b}$, —S(O)$R^{7b}$, —N$R^{7a}R^{8a}$, —N$R^{7a}$C(O)$R^{8a}$, —N$R^{7a}$C(O)O$R^{8a}$, —N$R^{7a}$C(O)N$R^{8a}$, —N$R^{7a}$S(O)$_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl and 5-6 membered heteroaryl are independently unsubstituted or substituted with one or more substituents selected from the group consisting of D, —CN, halogen, $C_1$-$C_6$alkyl, —O$R^{7a}$, —C(O)$R^{7b}$, —P(O)$R^{7b}R^{8b}$, —S(O)$_2R^{7b}$, —S(O)$R^{7b}$, —N$R^{7a}R^{8a}$, —N$R^{7a}$C(O)$R^{8a}$, —N$R^{7a}$C(O)O$R^{8a}$, —N$R^{7a}$C(O)N$R^{8a}$, —N$R^{7a}$S(O)$_2R^{8a}$, $C_3$-$C_{10}$cycloalkyl, $C_6$aryl, 3-7-membered heterocyclyl, and 5-6 membered heteroaryl; or
wherein $R^{1w}$ and $R^{1y}$, together with the atoms to which they are attached can form a 3-7-membered heterocyclyl; wherein the 3-7-membered heterocyclyl are independently unsubstituted or substituted with one or more substituents selected from the group consisting of D, —CN, halogen, $C_1$-$C_6$alkyl, —O$R^{9a}$, —C(O)$R^{9b}$, —P(O)$R^{9b}R^{10b}$, —S(O)$_2R^{9b}$, —S(O)$R^{9b}$, —N$R^{9a}R^{10a}$, —N$R^{9a}$C(O)$R^{10a}$, —N$R^{9a}$C(O)O$R^{10a}$, —N$R^{9a}$C(O)N$R^{10a}$, and —N$R^{9a}$S(O)$_2R^{10a}$; or
wherein $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, —O$R^{9a}$, —C(O)$R^{9b}$, —P(O)$R^{9b}R^{10b}$, —S(O)$_2R^{9b}$, —S(O)$R^{9b}$, —N$R^{9a}R^{10a}$, —N$R^{9a}$C(O)$R^{10a}$, —N$R^{9a}$C(O)O$R^{10a}$, —N$R^{9a}$C(O)N$R^{10a}$, and —N$R^{9a}$S(O)$_2R^{10a}$;
$R^{2a}$ is H, D, halogen, —CN, —O$R^{15a}$, $C_1$-$C_6$alkyl, $C_3$-$C_{10}$cycloalkyl, —C(O)N$R^{15a}R^{16a}$, —C(O)O$R^{15a}$, —N$R^{15a}R^{16a}$, —N$R^{15a}$C(O)$R^{16a}$, —N$R^{15a}$C(O)O$R^{16a}$, —N$R^{15a}$C(O)N$R^{16a}$, or —N$R^{15a}$S(O)$_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —O$R^{15a}$, —C(O)$R^{15b}$, —N$R^{15a}R^{16a}$, $C_3$-$C_{10}$cycloalkyl, $C_6$aryl, 3-7-membered heterocyclyl, and 5-6 membered heteroaryl;
each $R^{2b}$, $R^{2c}$, $R^{2d}$, $R^{2e}$, and $R^{2f}$ is independently H, D, halogen, —CN, —NO$_2$, —S$R^{17a}$, —O$R^{17a}$, —C(O)$R^{17b}$, —P(O)$R^{17b}R^{18b}$, —S(O)$_2R^{17b}$, —S(O)$R^{17b}$, —N$R^{17a}R^{18a}$, —N$R^{17a}$C(O)$R^{18a}$, —N$R^{17a}$C(O)O$R^{18a}$, —N$R^{17a}$C(O)O$R^{18a}$, —N$R^{17a}$C(O)N$R^{18a}$, —N$R^{17a}$S(O)$_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —O$R^{17a}$, —C(O)$R^{17b}$, —P(O)$R^{17b}R^{18b}$, —S(O)$_2R^{17b}$, —S(O)$R^{17b}$, —N$R^{17a}R^{18a}$, —N$R^{17a}$C(O)$R^{18a}$, —N$R^{17a}$C(O)O$R^{18a}$, —N$R^{17a}$C(O)N$R^{18a}$, —N$R^{17a}$S(O)$_2R^{18a}$, $C_3$-$C_{10}$cycloalkyl, $C_6$aryl, 3-7-membered heterocyclyl, and 5-6 membered heteroaryl; or
two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —O$R^{19a}$, and N$R^{19a}R^{20a}$;
$R^{3a}$, $R^{4a}$, $R^{5a}$, $R^{6a}$, $R^{7a}$, $R^{8a}$, $R^{9a}$, $R^{10a}$, $R^{15a}$, $R^{16a}$, $R^{17a}$, $R^{18a}$, $R^{19a}$ and $R^{20a}$ are independently, at each occurrence, H, D, $C_1$-$C_6$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;
$R^{3b}$, $R^{4b}$, $R^{5b}$, $R^{6b}$, $R^{7b}$, $R^{8b}$, $R^{9b}$, $R^{10b}$, $R^{15b}$, $R^{17b}$, and $R^{18b}$ are independently, at each occurrence, H, D, —OH, —O($C_1$-$C_6$alkyl), —$NH_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-4),

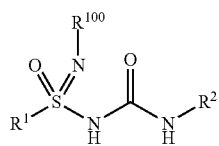

(I-4)

and pharmaceutically acceptable salts, solvates, isomers, prodrugs, and tautomers thereof, wherein:

$R^{100}$ is selected from the group consisting of H, Cl, D, —CN, —$NO_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

$R^1$ is selected from the group consisting of

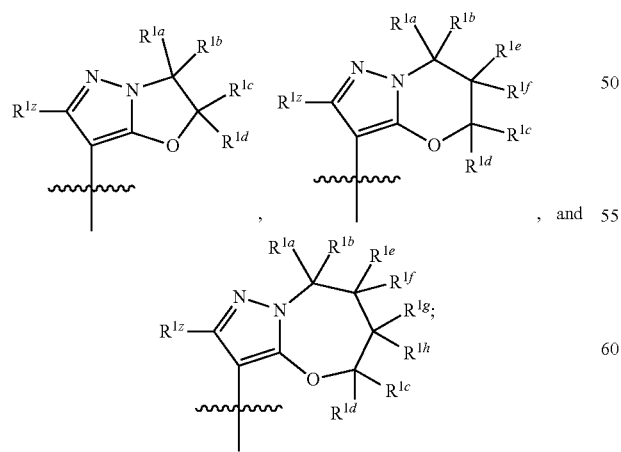

, and $R^{1z}$ is H, D, halogen, —CN, —$NO_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —$NO_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^2$ is selected from the group consisting of $C_1$-$C_6$alkyl, $C_3$-$C_{10}$cycloalkyl, 3-7-membered heterocyclyl, 5-membered heteroaryl, 6-membered heteroaryl, $C_6$aryl, and —NR$^{2g}$R$^{2h}$; wherein the $C_1$-$C_6$alkyl, $C_3$-$C_{10}$cycloalkyl, 3-7-membered heterocyclyl, 5-membered heteroaryl, 6-membered heteroaryl, and $C_6$aryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$$C_3$-$C_{10}$cycloalkyl, $C_3$-$C_{10}$cycloalkyl, $C_6$aryl, 3-7-membered heterocyclyl, and 5-6-membered heteroaryl;

each $R^{2g}$ and $R^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —$OR^{21a}$, —$C(O)R^{21b}$, —$P(O)R^{21b}R^{22b}$, —$S(O)_2R^{21b}$, —$S(O)R^{21b}$, —$NR^{21a}R^{22a}$, —$NR^{21a}C(O)R^{22a}$, —$NR^{21a}C(O)OR^{22a}$, —$NR^{21a}C(O)NR^{22a}$, —$NR^{21a}S(O)_2R^{22a}$, —$(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$R^{3a}$, $R^{4a}$, $R^{7a}$, $R^{8a}$, $R^{11a}$, $R^{12a}$, $R^{13a}$, $R^{14a}$, $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{21b}$, $R^{22b}$, $R^{23b}$, and $R^{24b}$ are independently, at each occurrence, H, D, —OH, —O($C_1$-$C_6$alkyl), —$NH_2$, —$NH(C_1$-$C_6$alkyl), —$N(C_1$-$C_6$alkyl)$_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-5),

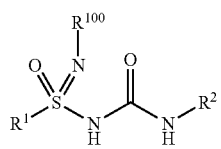

(I-5)

and pharmaceutically acceptable salts, solvates, isomers, prodrugs, and tautomers thereof, wherein:

$R^{100}$ is selected from the group consisting of H, Cl, D, —CN, —$NO_2$, —$OR^{3a}$, —$C(O)R^{3b}$, —$S(O)_2R^{3b}$, —$S(O)R^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{3a}$, —$C(O)R^{3b}$, —$P(O)R^{3b}R^{4b}$, —$S(O)_2R^{3b}$, —$S(O)R^{3b}$, —$NR^{3a}R^{4a}$, —$NR^{3a}C(O)R^{4a}$, —$NR^{3a}C(O)OR^{4a}$, —$NR^{3a}C(O)NR^{4a}$, —$NR^{3a}S(O)_2R^{4a}$, $C_3$-$C_{10}$cycloalkyl, $C_6$aryl, 3-7-membered heterocyclyl, and 5-6 membered heteroaryl;

$R^1$ is selected from the group consisting of

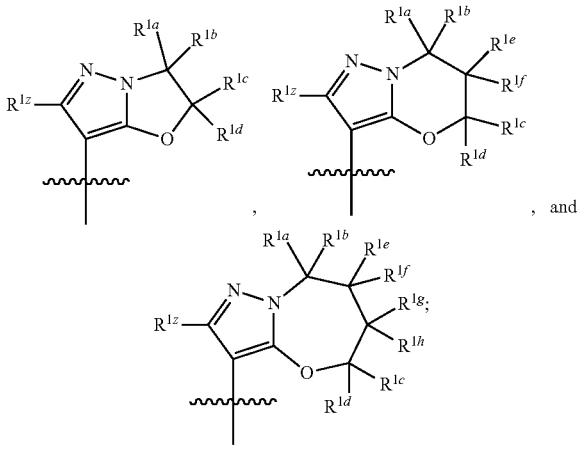

, and $R^2$ is selected from the group consisting of $C_1$-$C_6$alkyl, $C_3$-$C_{10}$cycloalkyl, 3-7-membered heterocyclyl, 5-membered heteroaryl, —$NR^{2g}R^{2h}$,

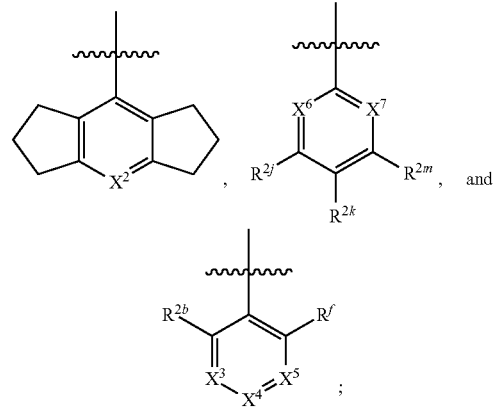

, and

;

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —$OR^{23a}$, —$C(O)R^{23b}$, —$P(O)R^{23b}R^{24b}$, —$S(O)_2R^{23b}$, —$S(O)R^{23b}$, —$NR^{23a}R^{24a}$, —$NR^{23a}C(O)R^{24a}$, —$NR^{23a}C(O)OR^{24a}$, —$NR^{23a}C(O)NR^{24a}$, —$NR^{23a}S(O)_2R^{24a}$, —$(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$X^2$ is N or $CR^{2a}$;
$X^3$ is N or $CR^{2c}$;
$X^4$ is N or $CR^{2d}$;
$X^5$ is N or $CR^{2e}$;
$X^6$ and $X^7$ are independently N or $CR^{2n}$, wherein at least one of $X^6$ and $X^7$ is N;

$R^{1z}$ is H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, $-NR^{7a}R^{8a}$, $-NR^{7a}C(O)R^{8a}$, $-NR^{7a}C(O)OR^{8a}$, $-NR^{7a}C(O)NR^{8a}$, $-NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, $-CN$, halogen, $C_1$-$C_6$alkyl, $-OR^{7a}$, $-C(O)R^{7b}$, $-P(O)R^{7b}R^{8b}$, $-S(O)_2R^{7b}$, $-S(O)R^{7b}$, $-NR^{7a}R^{8a}$, $-NR^{7a}C(O)R^{8a}$, $-NR^{7a}C(O)OR^{8a}$, $-NR^{7a}C(O)NR^{8a}$, $-NR^{7a}S(O)_2R^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1b}$ is independently selected from H, D, halogen, $-CN$, $-NO_2$, $-SR^{11a}$, $-OR^{11a}$, $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, $-CN$, halogen, $C_1$-$C_6$alkyl, $-OR^{11a}$, $-C(O)R^{11b}$, $-P(O)R^{11b}R^{12b}$, $-S(O)_2R^{11b}$, $-S(O)R^{11b}$, $-NR^{11a}R^{12a}$, $-NR^{11a}C(O)R^{12a}$, $-NR^{11a}C(O)OR^{12a}$, $-NR^{11a}C(O)NR^{12a}$, $-NR^{11a}S(O)_2R^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1b}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, $-CN$, halogen, $C_1$-$C_6$alkyl, $-OR^{13a}$, $-C(O)R^{13b}$, $-P(O)R^{13b}R^{14b}$, $-S(O)_2R^{13b}$, $-S(O)R^{13b}$, $-NR^{13a}R^{14a}$, $-NR^{13a}C(O)R^{14a}$, $-NR^{13a}C(O)OR^{14a}$, $-NR^{13a}C(O)NR^{14a}$, and $-NR^{13a}S(O)_2R^{14a}$; or two geminal groups $R^{1a}$ and $R^{1b}$; $R^{1c}$ and $R^{1d}$; $R^{1e}$ and $R^{1f}$; or $R^{1g}$ and $R^{1b}$, when present, can form an oxo group;

$R^{2a}$ is H, D, halogen, $-CN$, $-OR^{15a}$, $C_1$-$C_6$alkyl, $C_3$-$C_{10}$cycloalkyl, $-C(O)NR^{15a}R^{16a}$, $-C(O)OR^{15a}$; $-NR^{15a}R^{16a}$, $-NR^{15a}C(O)R^{16a}$, $-NR^{15a}C(O)OR^{16a}$, $-NR^{15a}C(O)NR^{16a}$, or $-NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, $-CN$, $-OR^{15a}$, $-C(O)R^{15b}$, $-NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, $-CN$, $-NO_2$, $-SR^{17a}$, $-OR^{17a}$, $-C(O)R^{17b}$, $-P(O)R^{17b}R^{18b}$, $-S(O)_2R^{17b}$, $-S(O)R^{17b}$, $-NR^{17a}R^{18a}$, $-NR^{17a}C(O)R^{18a}$, $-NR^{17a}C(O)OR^{18a}$, $-NR^{17a}C(O)NR^{18a}$, $-NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, $-CN$, halogen, $-OR^{17a}$, $-C(O)R^{17b}$, $-P(O)R^{17b}R^{18b}$, $-S(O)_2R^{17b}$, $-S(O)R^{17b}$, $-NR^{17a}R^{18a}$, $-NR^{17a}C(O)R^{18a}$, $-NR^{17a}C(O)OR^{18a}$, $-NR^{17a}C(O)NR^{18a}$, $-NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, $-CN$, $C_1$-$C_6$alkyl, $-OR^{19a}$, and $NR^{19a}R^{20a}$;

each $R^{2j}$, $R^{2k}$, $R^{2m}$, and $R^{2n}$ is independently H, D, halogen, $-CN$, $-NO_2$, $-SR^{17a}$, $-OR^{17a}$, $-C(O)R^{17b}$, $-P(O)R^{17b}R^{18b}$, $-S(O)_2R^{17b}$, $-S(O)R^{17b}$, $-NR^{17a}R^{18a}$, $-NR^{17a}C(O)R^{18a}$, $-NR^{17a}C(O)OR^{18a}$, $-NR^{17a}C(O)OR^{18a}$, $-NR^{17a}C(O)NR^{18a}$, $-NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, $-CN$, halogen, $-OR^{17a}$, $-C(O)R^{17b}$, $-P(O)R^{17b}R^{18b}$, $-S(O)_2R^{17b}$, $-S(O)R^{17b}$, $-NR^{17a}R^{18a}$, $-NR^{17a}C(O)R^{18a}$, $-NR^{17a}C(O)OR^{18a}$, $-NR^{17a}C(O)NR^{18a}$, $-NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2j}$, $R^{2k}$, $R^{2m}$, and $R^{2n}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, $-CN$, $C_1$-$C_6$alkyl, $-OR^{19a}$, and $NR^{19a}R^{20a}$;

each $R^{2g}$ and $R^{2h}$ is independently H, $C_1$-$C_6$alkyl, $C_3$-$C_{10}$cycloalkyl, 3-7-membered heterocyclyl, $C_6$aryl, or 5-membered heteroaryl, wherein the 3-7-membered heterocyclyl and 5-membered heteroaryl are attached to the nitrogen at a carbon on the 3-7-membered heterocyclyl or 5-membered heteroaryl, and wherein the $C_1$-$C_6$alkyl, $C_3$-$C_{10}$cycloalkyl. 3-7-membered heterocyclyl, $C_6$aryl, or 5-membered heteroaryl are independently unsubstituted or substituted with one or more substituents selected from the group consisting of D, $-CN$, halogen, $C_1$-$C_6$alkyl, $-OR^{21a}$, $-C(O)R^{21b}$, $-P(O)R^{21b}R^{22b}$, $-S(O)_2R^{21b}$, $-S(O)R^{21b}$, $-NR^{21a}R^{22a}$, $-NR^{21a}C(O)R^{22a}$, $-NR^{21a}C(O)OR^{22a}$, $-NR^{21a}C(O)NR^{22a}$, $-NR^{21a}S(O)_2R^{22a}$, $C_3$-$C_{10}$cycloalkyl, $C_6$aryl, 3-7-membered heterocyclyl, and 5-membered heteroaryl;

$R^{3a}$, $R^{4a}$, $R^{7a}$, $R^{8a}$, $R^{11a}$, $R^{12a}$, $R^{13a}$, $R^{14a}$, $R^{15a}$, $R^{16a}$, $R^{17a}$, $R^{18a}$, $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{15b}$, $R^{17b}$, $R^{18b}$, $R^{21b}$, $R^{22b}$, $R^{23b}$, and $R^{24b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-6),

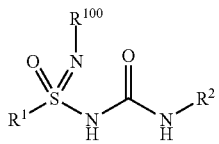

(I-6)

and pharmaceutically acceptable salts, solvates, isomers, prodrugs, and tautomers thereof, wherein:

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

$R^1$ is selected from the group consisting of

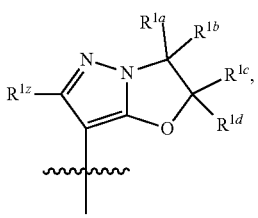

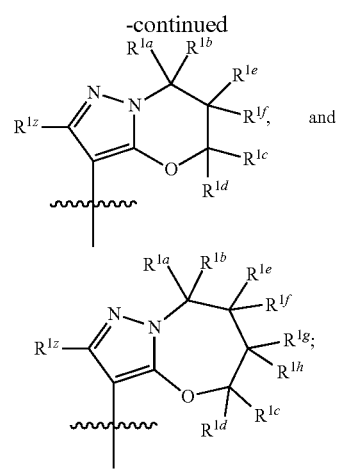

and $R^2$ is

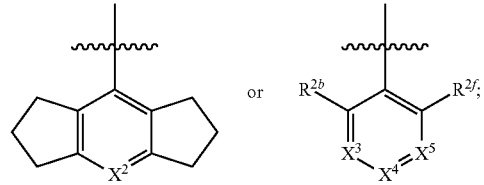

$X^2$ is N or CR$^{2a}$;
$X^3$ is N or CR$^{2c}$;
$X^4$ is N or CR$^{2d}$;
$X^5$ is N or CR$^{2e}$;

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{11a}$, —C(O)R$^{11b}$, —P(O)R$^{11b}$R$^{12b}$, —S(O)$_2$R$^{11b}$, —S(O)$R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —$OR^{13a}$, —$C(O)R^{13b}$, —$P(O)R^{13b}R^{14b}$, —$S(O)_2R^{13b}$, —$S(O)R^{13b}$, —$NR^{13a}R^{14a}$, —$NR^{13a}C(O)R^{14a}$, —$NR^{13a}C(O)OR^{14a}$, —$NR^{13a}C(O)NR^{14a}$, and —$NR^{13a}S(O)_2R^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^{2a}$ is H, D, halogen, —CN, —$OR^{15a}$, $C_1$-$C_6$alkyl, $C_3$-$C_{10}$cycloalkyl, —$C(O)NR^{15a}R^{16a}$, —$C(O)OR^{15a}$; —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

$R^{3a}$, $R^{4a}$, $R^{7a}$, $R^{8a}$, $R^{11a}$, $R^{12a}$, $R^{13a}$, $R^{14a}$, $R^{15a}$, $R^{16a}$, $R^{17a}$, and $R^{18a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{15b}$, $R^{17b}$, and $R^{18b}$ are independently, at each occurrence, H, D, —OH, —O($C_1$-$C_6$alkyl), —$NH_2$, —$NH(C_1$-$C_6$alkyl), —$N(C_1$-$C_6$alkyl)$_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl.

The present disclosure provides pharmaceutical compositions comprising one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof, and a pharmaceutically acceptable carrier.

The present disclosure provides methods of treating disorders including the step of administering an effective amount of one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof, to thereby treat the disorder in a subject in need thereof.

The present disclosure provides a methods of treating disorders including the step of administering an effective amount of one or more pharmaceutical compositions of the present disclosure to thereby treat the disorder in a subject in need thereof.

The present disclosure provides one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof, or one or more pharmaceutical compositions of the present disclosure for use in the treatment of a disorder in a subject in need thereof.

The present disclosure provides for the use of one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof, for the treatment of a disorder in a subject in need thereof.

The present disclosure provides for the use of one or more pharmaceutical compositions of the present disclosure for the treatment of a disorder in a subject in need thereof.

The present disclosure provides for the use of one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof, in the manufacture of a medicament for the treatment of a disorder.

The present disclosure provides for the use of one or more pharmaceutical compositions of the present disclosure in the manufacture of a medicament for the treatment of a disorder.

In some embodiments, the disorder is responsive to inflammasome inhibition.

In some embodiments, the disorder is responsive to inhibition of activation of the NLRP3 inflammasome.

In some embodiments, the disorder is a disorder of the immune system, the liver, the lung, the skin, the cardiovascular system, the renal system, the gastrointestinal tract, the respiratory system, the endocrine system, the central nervous system, or is a cancer or other malignancy, or is caused by or associated with a pathogen.

The present disclosure provides methods of modulating the activity of a biological target comprising the step of exposing the biological target to one or more compounds of the present disclosure, e.g., compounds of Formula (I), any variations thereof detailed herein, one or more of Compound Nos. 1-210 in Table 1, and pharmaceutically acceptable salts, solvates (e.g., hydrates), isomers, prodrugs, and tautomers thereof.

The present disclosure provides methods of modulating the activity of a biological target comprising the step of exposing the biological target to one or more pharmaceutical compositions of the present disclosure.

The biological target may be selected from a group consisting of the NLRP3 inflammasome, IL-6, IL-1β, IL-17, IL-18, IL-1α, IL-37, IL-22, IL-33 and Th17 cells.

DETAILED DESCRIPTION

Definitions

As used throughout this disclosure, the following terms, unless otherwise indicated, shall be understood to have the following meanings. If a term is missing, the conventional term as known to one skilled in the art controls.

It should also be noted that any carbon as well as any heteroatom with unsatisfied valences in the text, schemes, examples and Tables herein is assumed to have the sufficient number of hydrogen atom(s) to satisfy the valences.

As described herein, compounds of the present disclosure may optionally be substituted with one or more substituents, such as those illustrated generally herein, or as exemplified by particular classes, subclasses, and species of the present disclosure. In general, the term "substituted" refers to the replacement of a hydrogen atom in a given structure with a specified substituent. Combinations of substituents envisioned by the present disclosure are typically those that result in the formation of stable or chemically feasible compounds.

As used herein, the terms "including," "containing," and "comprising" are used in their open, non-limiting sense.

The articles "a" and "an" as used in this disclosure may refer to one or more than one (i.e., to at least one) of the grammatical object of the article. By way of example, "an element" may mean one element or more than one element.

The term "and/or" as used in this disclosure may mean either "and" or "or" unless indicated otherwise.

To provide a more concise description, some of the quantitative expressions given herein are not qualified with the term "about." It is understood that, whether the term "about" is used explicitly or not, every quantity given herein is meant to refer to the actual given value, and it is also meant to refer to the approximation to such given value that would reasonably be inferred based on the ordinary skill in the art, including equivalents and approximations due to the experimental and/or measurement conditions for such given value. Whenever a yield is given as a percentage, such yield refers to a mass of the entity for which the yield is given with respect to the maximum amount of the same entity that could be obtained under the particular stoichiometric conditions. Concentrations that are given as percentages refer to mass ratios, unless indicated differently.

A "patient" or "subject" may encompass both mammals and non-mammals. Examples of mammals may include, but are not limited to, any member of the class Mammalia: humans; non-human primates such as chimpanzees, monkeys, baboons, or rhesus monkeys, as well as other apes and monkey species; farm animals such as cattle, horses, sheep, goats, and swine; companion animals such as rabbits, dogs, and cats; laboratory animals including rodents, such as rats, mice and guinea pigs; and the like. Examples of non-mammals include, but are not limited to, birds, fish, and the like. "Patient" or "subject" may include both human and animals. In some embodiments, the patient or subject is a human.

The term "inhibitor" may refer to a molecule such as a compound, a drug, enzyme, or a hormone that blocks or otherwise interferes with a particular biologic activity.

The terms "effective amount" or "therapeutically effective amount" when used in connection with one or more compounds or pharmaceutical compositions may refer to a sufficient amount of the one or more compounds or pharmaceutical compositions to provide the desired biological result. That result can be reduction and/or alleviation of the signs, symptoms, or causes of a disorder, or any other desired alteration of a biological system. For example, an "effective amount" for therapeutic use may be the amount of the pharmaceutical composition comprising one or more compounds, or pharmaceutically acceptable salts, prodrugs, solvates, hydrates, isomers, prodrugs, and tautomers thereof, as disclosed herein required to provide a clinically significant decrease in a disorder. An appropriate "effective amount" in any individual case may be determined by one of ordinary skill in the art using routine experimentation. Thus, the expression "effective amount" may generally refer to the quantity for which the active substance has therapeutic effects. In the present case the active substance may be an inhibitor of the inflammasome.

As used herein, the terms "treat" or "treatment" are meant to indicate a postponement of development of disorders; preventing the development of disorders; and/or reducing severity of such symptoms that will or are expected to develop. Thus, these terms may include ameliorating existing disorder symptoms; preventing additional symptoms; ameliorating or preventing the underlying causes of symptoms; inhibiting the disorder, e.g., arresting the development of the disorder; relieving the disorder; causing regression of the disorder; relieving a symptom caused by the disorder; or stopping or alleviating the symptoms of the disorder.

The terms "pharmaceutically acceptable" or "pharmacologically acceptable" may refer to a material which is not biologically, or otherwise, undesirable—the material may be administered to an individual without causing any substantially undesirable biological effects or interacting in a deleterious manner with any of the components of the composition in which it is contained.

The term "carrier," as used in this disclosure, may encompass carriers, excipients, and diluents and may mean a material, composition or vehicle, such as a liquid or solid filler, diluent, excipient, solvent or encapsulating material, involved in carrying or transporting a pharmaceutical agent, such as one or more compounds, or pharmaceutically acceptable salts, prodrugs, solvates, hydrates, isomers, prodrugs, and tautomers thereof, of the disclosure, from one organ, or portion of the body, to another organ, or portion of the body of a subject. Carriers should be selected on the basis of compatibility and the release profile properties of the desired dosage form. Exemplary carrier materials may include, e.g., binders, suspending agents, disintegration agents, filling agents, surfactants, solubilizers, stabilizers, lubricants, wetting agents, diluents, spray-dried dispersions, and the like. See, e.g., Hoover, John E., Remington's Pharmaceutical Sciences, Mack Publishing Co., Easton, Pa. 1975.

The term "$IC_{50}$", as used herein, may refer to concentrations at which a measurable activity, phenotype or response, for example growth or proliferation of cells such as tumor cells, is inhibited by 50%. $IC_{50}$ values can be estimated from an appropriate dose-response curve, for example by eye or by using appropriate curve fitting or statistical software. More accurately, $IC_{50}$ values may be determined using non-linear regression analysis.

The terms "administered," "administration," or "administering" as used in this disclosure may refer to either directly administering one or more compounds, and pharmaceutically acceptable salts, solvates (e.g., hydrates), isomers, prodrugs, and tautomers thereof, or pharmaceutical compositions of the disclosure to a subject.

As used herein, "alkyl" may mean a straight chain or branched saturated chain having from 1 to 10 carbon atoms. Representative saturated alkyl groups include, but are not limited to, methyl, ethyl, n-propyl, isopropyl, 2-methyl-1-propyl, 2-methyl-2-propyl, 2-methyl-1-butyl, 3-methyl-1-butyl, 2-methyl-3-butyl, 2,2-dimethyl-1-propyl, 2-methyl-1-pentyl, 3-methyl-1-pentyl, 4-methyl-1-pentyl, 2-methyl-2-pentyl, 3-methyl-2-pentyl, 4-methyl-2-pentyl, 2,2-dimethyl-1-butyl, 3,3-dimethyl-1-butyl, 2-ethyl-1-butyl, butyl, isobutyl, t-butyl, n-pentyl, isopentyl, neopentyl, n-hexyl and the like, and longer alkyl groups, such as heptyl, and octyl and the like. An alkyl group can be unsubstituted or substituted. Alkyl groups containing three or more carbon atoms may be straight or branched. As used herein, "lower alkyl" means an alkyl having from 1 to 6 carbon atoms.

As used herein, an "alkenyl" may include an unbranched or branched hydrocarbon chain containing 2-12 carbon atoms. The "alkenyl" group contains at least one double bond. The double bond of an alkenyl group can be unconjugated or conjugated to another unsaturated group. Examples of alkenyl groups may include, but are not limited to, ethylenyl, vinyl, allyl, butenyl, pentenyl, hexenyl, butadienyl, pentadienyl, hexadienyl, 2-ethylhexenyl, 2-propyl-2-butenyl, 4-(2-methyl-3-butene)-pentenyl and the like. An alkenyl group can be unsubstituted or substituted. Alkenyl, as defined herein, may also be branched or straight.

As used herein, "alkynyl" may include an unbranched or branched unsaturated hydrocarbon chain containing 2-12 carbon atoms. The "alkynyl" group contains at least one triple bond. The triple bond of an alkynyl group can be unconjugated or conjugated to another unsaturated group. Examples of alkynyl groups include, but are not limited to, ethynyl, propynyl, butynyl, pentynyl, hexynyl, methylpropynyl, 4-methyl-1-butynyl, 4-propyl-2-pentynyl, 4-butyl-2-hexynyl and the like. An alkynyl group can be unsubstituted or substituted.

The term "halo" or "halogen" refers to fluorine, chlorine, bromine, or iodine.

The term "haloalkyl" refers to an alkyl radical, as defined above, that is substituted by one or more halo radicals, as defined above, e.g., trifluoromethyl, difluoromethyl, fluoromethyl, trichloromethyl, 2,2,2-trifluoroethyl, 1,2-difluoroethyl, 3-bromo-2-fluoropropyl, 1,2-dibromoethyl, and the like.

The term "annular atoms" used in conjunction with terms relating to ring systems described herein (e.g., cycloalkyl, cycloalkenyl, aryl, heterocyclyl, and heteroaryl) refers to the total number of ring atoms present in the system. "Annular atoms" therefore does not include the atoms present in a substituent attached to the ring. Thus, the number of "annular atoms" includes all atoms present in a fused ring. For example, an 2-indolyl ring,

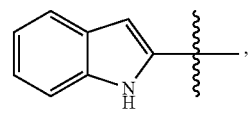 [SMILES: *c1cc2ccccc2[nH]1]

is considered a 5-membered heteroaryl, but is also a heteroaryl containing 9 annular atoms. In another example, pyridine is considered a 6-membered heteroaryl, and is a heteroaryl containing 6 annular atoms.

"Cycloalkyl" refers to a single saturated all carbon ring having 3 to 20 annular carbon atoms (i.e., $C_3$-$C_{20}$ cycloalkyl), for example from 3 to 15 annular atoms, for example, from 3 to 12 annular atoms. In certain embodiments, the cycloalkyl group is either monocyclic ("monocyclic cycloalkyl") or contains a fused, bridged or spiro ring system such as a bicyclic system ("bicyclic cycloalkyl") and can be saturated. "Cycloalkyl" includes ring systems where the cycloalkyl ring, as defined above, is fused with one or more cycloalkyl, cycloalkenyl, heterocyclyl, aryl or heteroaryl groups, wherein the point of attachment is on a cycloalkyl ring, and, in such instances, the number of carbon atoms recited continues to designate the number of carbons in the cycloalkyl ring containing the point of attachment. Examples of cycloalkyl groups include cyclohexyl, cycloheptyl, 2-adamantyl

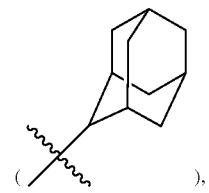

2-(2,3-dihydro-1H-indene)

and 9-fluorenyl

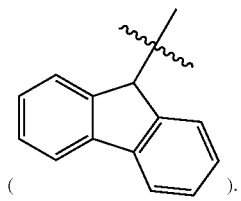 [SMILES: *C1c2ccccc2-c2ccccc21]

( ).

As noted above, cycloalkyl rings can be further characterized by the number of annular atoms. For example, a cyclohexyl ring is a $C_6$cycloalkyl ring with 6 annular atoms, while 2-(2,3-dihydro-1H-indene) is a $C_5$cycloalkyl ring with 9 annular atoms. Also, for example, 9-fluorenyl is a $C_5$cycloalkyl ring with 13 annular atoms and 2-adamantyl is a $C_6$cycloalkyl with 10 annular atoms.

In certain embodiments, a $C_3$-$C_{10}$cycloalkyl has 3-14 annular atoms. In certain embodiments, a $C_3$-$C_{10}$cycloalkyl has 3-10 annular atoms. In certain embodiments, a $C_3$-$C_{10}$cycloalkyl has 3-12 annular atoms. In certain embodiments, a $C_3$-$C_7$cycloalkyl has 3-7 annular atoms. In certain embodiments, a $C_3$-$C_9$cycloalkyl has 3-14 annular atoms. In certain embodiments, a $C_3$-$C_9$cycloalkyl has 3-10 annular atoms. In certain embodiments, a $C_3$-$C_9$cycloalkyl has 3-9 annular atoms. In certain embodiments, a $C_3$-$C_8$cycloalkyl has 3-8 annular atoms. In certain embodiments, a $C_3$-$C_8$cycloalkyl has 3-14 annular atoms. In certain embodiments, a $C_3$-$C_7$cycloalkyl has 3-14 annular atoms. In certain embodiments, a $C_3$-$C_7$cycloalkyl has 3-10 annular atoms. In certain embodiments, a $C_3$-$C_7$cycloalkyl has 3-7 annular atoms.

As used herein, the term "cycloalkenyl" may refer to a partially saturated, monocyclic, fused or spiro polycyclic, all carbon ring having from 3 to 18 carbon atoms per ring and contains at least one double bond. "Cycloalkenyl" includes ring systems where the cycloalkenyl ring, as defined above, is fused with one or more cycloalkyl, cycloalkenyl, heterocyclyl, aryl or heteroaryl groups, wherein the point of attachment is on a cycloalkenyl ring, and, in such instances, the number of carbon atoms recited continues to designate the number of carbons in the cycloalkenyl ring containing the point of attachment. Cycloalkenyl rings can be further characterized by the number of annular atoms. Examples of cycloalkenyl include 1-cyclohex-1-enyl and cyclopent-1-enyl.

In certain embodiments, the cycloalkenyl has 3-14 annular atoms. In certain embodiments, the cycloalkenyl has 3-10 annular atoms. In certain embodiments, the cycloalkenyl has 3-9 annular atoms. In certain embodiments, the cycloalkenyl has 3-7 annular atoms. In certain embodiments, a $C_3$-$C_{10}$cycloalkenyl has 3-14 annular atoms. In certain embodiments, a $C_3$-$C_{10}$cycloalkenyl has 3-10 annular atoms. In certain embodiments, a $C_3$-$C_9$cycloalkenyl has 3-9 annular atoms. In certain embodiments, a $C_3$-$C_8$cycloalkenyl has 3-8 annular atoms. In certain embodiments, a $C_3$-$C_8$cycloalkenyl has 3-14 annular atoms. In certain embodiments, a $C_3$-$C_7$cycloalkenyl has 3-14 annular atoms. In certain embodiments, a $C_3$-$C_7$cycloalkenyl has 3-10 annular atoms. In certain embodiments, a $C_3$-$C_7$cycloalkenyl has 3-7 annular atoms.

The term "aryl" as used herein refers to a single all carbon aromatic ring or a multiple condensed all carbon ring system wherein at least one of the rings is aromatic. For example, in certain embodiments, an aryl group has 5 to 20 annular carbon atoms, 5 to 14 annular carbon atoms, or 5 to 12 annular carbon atoms. Aryl also includes multiple condensed ring systems (e.g., ring systems comprising 2, 3 or 4 rings) having about 9 to 20 carbon atoms in which at least one ring is aromatic and wherein the other rings may be aromatic or not aromatic (i.e., cycloalkyl). "Aryl" includes ring systems where the aryl ring, as defined above, is fused with one or more cycloalkyl, cycloalkenyl, heterocyclyl, aryl or heteroaryl groups, and wherein the point of attachment is on an aryl ring, and, in such instances, the number of carbon atoms recited continues to designate the number of carbon atoms in the aryl ring containing the point of attachment. Examples of aryl groups include phenyl and 5-(2,3-dihydro-1H-indene):

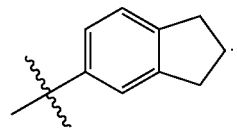 [SMILES: *c1ccc2c(c1)CCC2]

As noted above, aryl rings can be further characterized by the number of annular atoms. For example, phenyl is a $C_6$ aryl with 6 annular atoms, while 5-(2,3-dihydro-1H-indene) is a $C_6$ aryl with 9 annular atoms.

In certain embodiments the aryl ring is a $C_6$-aryl with 6-14 annular atoms. In certain embodiments the aryl ring is a $C_6$ aryl with 6-10 annular atoms. In certain embodiments the aryl ring is a $C_6$ aryl with 6-12 annular atoms. In certain embodiments the aryl ring is a $C_6$ aryl with 6 annular atoms.

"Heterocyclyl" as used herein refers to a single saturated or partially unsaturated non-aromatic ring or a non-aromatic multiple ring system that has at least one heteroatom in the ring (at least one annular heteroatom selected from oxygen, nitrogen, and sulfur). Unless otherwise specified, a heterocyclyl group has from 5 to about 20 annular atoms, for example from 5 to 15 annular atoms, for example from 5 to 10 annular atoms. Thus, the term includes single saturated or partially unsaturated rings (e.g., 3, 4, 5, 6 or 7-membered rings) having from about 1 to 6 annular carbon atoms and from about 1 to 3 annular heteroatoms selected from the group consisting of oxygen, nitrogen and sulfur in the ring. The term also includes single saturated or partially unsaturated rings (e.g., 5, 6, 7, 8, 9, or 10-membered rings) having from about 4 to 9 annular carbon atoms and from about 1 to 3 annular heteroatoms selected from the group consisting of oxygen, nitrogen and sulfur in the ring. "Heterocyclyl" includes ring systems where the heterocyclyl ring, as defined above, is fused with one or more cycloalkyl, cycloalkenyl, heterocyclyl, aryl or heteroaryl groups, wherein the point of attachment is on a heterocyclic ring, and, in such instances, the number of ring members recited continues to designate the number of annular atoms in the heterocyclic ring containing the point of attachment. Heterocyclic rings can be further characterized by the number of annular atoms. Examples of heterocyclic groups include piperidinyl (6-membered heterocycle with 6 annular atoms), azepanyl (7-membered heterocycle with 7 annular atoms), and 3-chromanyl (6-membered heterocycle with 10 annular atoms)

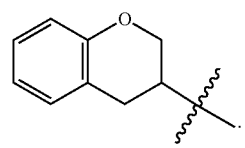 [SMILES: *C1COc2ccccc2C1]

In certain embodiments, a 3-7 membered heteocyclyl has 3-7 annular atoms. In certain embodiments, a 3-6 membered heteocyclyl has 3-6 annular atoms. In certain embodiments, a 3-5 membered heteocyclyl has 3-5 annular atoms. In certain embodiments, a 3-5 membered heteocyclyl has 3-9 annular atoms. In certain embodiments, a 3-7 membered heteocyclyl has 3-14 annular atoms. In certain embodiments, a 3-7 membered heteocyclyl has 3-12 annular atoms. In certain embodiments, a 3-7 membered heteocyclyl has 3-10 annular atoms.

The term "heteroaryl" as used herein refers to a single aromatic ring that has at least one atom other than carbon in the ring, wherein the atom is selected from the group consisting of oxygen, nitrogen and sulfur; the term also includes multiple condensed ring systems that have at least one such aromatic ring. Thus, the term includes single heteroaryl rings of from about 1 to 6 annular carbon atoms and about 1-4 annular heteroatoms selected from the group consisting of oxygen, nitrogen and sulfur in the rings. The sulfur and nitrogen atoms may also be present in an oxidized form provided the ring is aromatic. "Heteroaryl" includes ring systems where the heteroaryl ring, as defined above, is fused with one or more cycloalkyl, cycloalkenyl, heterocyclyl, aryl or heteroaryl groups, wherein the point of attachment is on a heteroaryl ring, and, in such instances, the number of ring members continues to designate the number of ring members in the heteroaryl ring containing the point of attachment. Heteroaryl rings can be further characterized by the number of annular atoms. For example, pyridine is a 6-membered heteroaryl having 6 annular atoms.

In certain embodiments the heteroaryl ring is a 5-6 membered heteroaryl with 5-15 annular atoms. In certain embodiments the heteroaryl ring is a 5-6 membered heteroaryl with 5-10 annular atoms. In certain embodiments the heteroaryl ring is a 5-6 membered heteroaryl with 5-6 annular atoms. In certain embodiments the heteroaryl ring is a 5-6 membered heteroaryl with 5-12 annular atoms. In certain embodiments the heteroaryl ring is a 5-membered heteroaryl with 5-15 annular atoms. In certain embodiments, the 5-membered heteroaryl has 5 annular atoms. In certain embodiments, the 5-membered heteroaryl has 5-8 annular atoms. In certain embodiments, the 5-membered heteroaryl has 5-9 annular atoms. In certain embodiments, the 5-membered heteroaryl has 5-10 annular atoms. In certain embodiments, the 5-membered heteroaryl has 5-12 annular atoms. In certain embodiments the heteroaryl ring is a 6-membered heteroaryl with 6-15 annular atoms. In certain embodiments the heteroaryl ring is a 6-membered heteroaryl with 6-10 annular atoms. In certain embodiments the heteroaryl ring is a 6 membered heteroaryl with 6-14 annular atoms. In certain embodiments, the 6-membered heteroaryl has 6-13 annular atoms. In certain embodiments, the 6-membered heteroaryl has 6 annular atoms. In certain embodiments, the 6-membered heteroaryl has 6-9 annular atoms. In certain embodiments, the 6-membered heteroaryl has 6-10 annular atoms. In certain embodiments, the 6-membered heteroaryl has 6-12 annular atoms.

Numerical ranges, as used herein, may include sequential integers. For example, a range expressed as "from 0 to 5" would include 0, 1, 2, 3, 4 and 5.

As used herein, the term "unsubstituted" may mean that the specified group bears no substituents beyond the moiety recited (e.g., where valency satisfied by hydrogen).

The term "oxo" as used herein refers to an "=O" group. It can also be abbreviated herein as C(O) or as C=O.

The present disclosure is directed to compounds as described herein and pharmaceutically acceptable salts, solvates (e.g., hydrates), isomers, prodrugs, and tautomers thereof, and pharmaceutical compositions comprising one or more compounds as described herein, and pharmaceutically acceptable salts, solvates (e.g., hydrates), isomers, prodrugs, and tautomers thereof.

The disclosure is directed to compounds as described herein and pharmaceutically acceptable salts, enantiomers, hydrates, solvates, prodrugs, isomers, prodrugs, or tautomers thereof. The use of the terms "salt," "hydrate," "solvate," "prodrug," "ester," and the like, is intended to equally apply to the salt, hydrate, solvate, prodrug, or ester of enantiomers, isomers, prodrugs, rotamers, tautomers, positional isomers, or racemates of the disclosed compounds.

It should be understood that all isomeric forms are included within the present disclosure, including mixtures thereof. The term "isomer" may refer to compounds that have the same composition and molecular weight but differ in physical and/or chemical properties. The structural difference may be in constitution (geometric or positional isomers) or in the ability to rotate the plane of polarized light (stereoisomers). With regard to stereoisomers, the compounds of the disclosure may have one or more asymmetric carbon atom and may occur as racemates, racemic mixtures and as individual enantiomers or diastereomers. Individual isomers of the compounds of the disclosure may, for example, be substantially free of other isomers, or may be admixed, for example, as racemates or with all other, or other selected, isomers. If the compound contains a double bond, the substituent may be in the E or Z configuration or cis or trans configuration or mixtures of any of the foregoing. Disclosed assay results may reflect the data collected for the racemic form, the enantiomerically pure form, or any other form in terms of stereochemistry or constitution (e.g., geometric or positional isomers).

The compounds of the disclosure may contain asymmetric or chiral centers, and, therefore, exist in different stereoisomeric forms. The term "stereoisomers" may refer to the set of compounds which have the same number and type of atoms and share the same bond connectivity between those atoms, but differ in three dimensional structure. The term "stereoisomer" may refer to any member of this set of compounds. For instance, a stereoisomer may be an enantiomer or a diastereomer. It is intended that all stereoisomeric forms of the compounds of the disclosure as well as mixtures thereof, including racemic mixtures, form part of the present disclosure.

The term "enantiomers" may refer to a pair of stereoisomers which are non-superimposable mirror images of one another. The term "enantiomer" may refer to a single member of this pair of stereoisomers. The term "racemic" may refer to a 1:1 mixture of a pair of enantiomers. Each compound herein disclosed may include all the enantiomers (which may exist even in the absence of asymmetric carbons) that conform to the general structure of the compound, unless the stereochemistry is specifically indicated. The compounds may be in a racemic or enantiomerically pure form, or any other form in terms of stereochemistry. The chiral centers of the present disclosure may have the S or R configuration as defined by the IUPAC 1974 Recommendations. In some examples presented, the synthetic route may produce a single enantiomer or a mixture of enantiomers. In some embodiments of the disclosure, the compounds of the disclosure are enantiomers. In some embodiments, the compounds of the disclosure are the (S)-enantiomer. In some embodiments, the compounds of the disclosure are the (R)-enantiomer. In some embodiments, the compounds of the disclosure may be (+) or (−) enantiomers.

The term "diastereomers" may refer to the set of stereoisomers which cannot be made superimposable by rotation around single bonds. For example, cis- and trans-double bonds, endo- and exo-substitution on bicyclic ring systems, and compounds containing multiple stereogenic centers with different relative configurations may be considered to be diastereomers. The term "diastereomer" may refer to any member of this set of compounds. In some examples presented, the synthetic route may produce a single diastereomer or a mixture of diastereomers. The disclosure may include diastereomers of the compounds described herein.

In some embodiments, pharmaceutical compositions of the disclosure may be enriched to provide predominantly one enantiomer of a compound described herein. An enantiomerically enriched mixture may comprise, for example, at least 60 mol percent of one enantiomer, or more preferably at least 75, at least 80, at least 85, at least 90, at least 95, at least 96, at least 97, at least 98, at least 99, at least 99.5 or even 100 mol percent. In some embodiments, the compositions described herein enriched in one enantiomer may be substantially free of the other enantiomer, wherein substantially free may mean that the substance in question makes up less than 10%, or less than 5%, or less than 4%, or less than 3%, or less than 2%, or less than 1% as compared to the amount of the other enantiomer, e.g., in the pharmaceutical composition or compound mixture. For example, if a pharmaceutical composition or compound mixture contains 98 grams of a first enantiomer and 2 grams of a second enantiomer, it would be said to contain 98 mol percent of the first enantiomer and only 2 mol percent of the second enantiomer.

In some embodiments, the pharmaceutical compositions of the disclosure may be enriched to provide predominantly one diastereomer of a compound disclosed herein. A diastereomerically enriched mixture may comprise, for example, at least 60 mol percent of one diastereomer, or more preferably at least 75, at least 80, at least 85, at least 90, at least 95, at least 96, at least 97, at least 98, at least 99, at least 99.5, or even 100 mol percent. In some embodiments, the compositions described herein enriched in one diastereomer may be substantially free of other diastereomers, wherein substantially free may mean that the substance in question makes up less than 10%, or less than 5%, or less than 4%, or less than 3%, or less than 2%, or less than 1% as compared to the amount of other diastereomers, e.g., in the pharmaceutical composition or compound mixture.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Enantiomers can also be separated by use of a chiral HPLC column. Also, some of the compounds of the disclosure may be atropisomers or rotameric forms and are considered as part of this disclosure.

Compounds of the disclosure may exist in their tautomeric form (for example, as an amide or imino ether). All such tautomeric forms are contemplated herein as part of the present disclosure. Also, for example, all keto-enol and imine-enamine forms of the compounds are included in the present disclosure. Also, it should be noted that the sulfonimidamidyl ureas described here have tautomeric forms. The structures have been graphically represented as one form throughout this document, but it is noted that the tautomers can exist in an equilibrium.

For example,

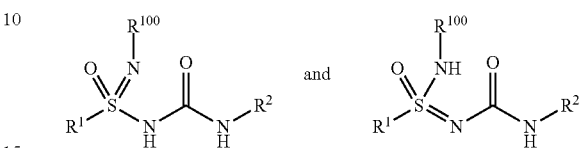

are tautomers. All tautomeric forms for each compound are embraced although only one tautomeric form may be represented for each compound, which may be a major tautomeric form or a minor tautomeric form.

The disclosure may include pharmaceutically acceptable salts of the compounds disclosed herein. A "pharmaceutically acceptable salt" may be acceptable for use in humans or domestic animals and may refer to those salts that retain the biological effectiveness and properties of the free forms, which are not biologically or otherwise undesirable. Representative "pharmaceutically acceptable salts" may include, e.g., water-soluble and water-insoluble salts, such as the acetate, amsonate (4,4-diaminostilbene-2,2-disulfonate), benzenesulfonate, benzonate, bicarbonate, bisulfate, bitartrate, borate, bromide, butyrate, calcium, calcium edetate, camsylate, carbonate, chloride, citrate, clavulariate, dihydrochloride, edetate, edisylate, estolate, esylate, fiunarate, gluceptate, gluconate, glutamate, glycollylarsanilate, hexafluorophosphate, hexylresorcinate, hydrabamine, hydrobromide, hydrochloride, hydroxynaphthoate, iodide, sethionate, lactate, lactobionate, laurate, magnesium, malate, maleate, mandelate, mesylate, methylbromide, methylnitrate, methylsulfate, mucate, napsylate, nitrate, N-methylglucamine ammonium salt, 3-hydroxy-2-naphthoate, oleate, oxalate, palmitate, pamoate, 1,1-methene-bis-2-hydroxy-3-naphthoate, einbonate, pantothenate, phosphate/diphosphate, picrate, polygalacturonate, propionate, p-toluenesulfonate, salicylate, stearate, subacetate, succinate, sulfate, sulfosalicylate, suramate, tannate, tartrate, teoclate, tosylate, triethiodide, and valerate salts.

Pharmaceutically acceptable salts may also include both acid and base addition salts. "Pharmaceutically acceptable acid addition salt" may refer to those salts which retain the biological effectiveness and properties of the free bases, which are not biologically or otherwise undesirable, and which may be formed with inorganic acids such as, but are not limited to, hydrochloric acid, hydrobromic acid, sulfuric acid, nitric acid, phosphoric acid and the like, and organic acids such as, but not limited to, acetic acid, 2,2-dichloroacetic acid, adipic acid, alginic acid, ascorbic acid, aspartic acid, benzenesulfonic acid, benzoic acid, 4-acetamidobenzoic acid, camphoric acid, camphor-10-sulfonic acid, capric acid, caproic acid, caprylic acid, carbonic acid, cinnamic acid, citric acid, cyclamic acid, dodecylsulfuric acid, ethane-1,2-disulfonic acid, ethanesulfonic acid, 2-hydroxyethanesulfonic acid, formic acid, fumaric acid, galactaric acid, gentisic acid, glucoheptonic acid, gluconic acid, glucuronic acid, glutamic acid, glutaric acid, 2-oxo-glutaric acid, glycerophosphoric acid, glycolic acid, hippuric acid, isobutyric acid, lactic acid, lactobionic acid, lauric acid, maleic acid, malic acid, malonic acid, mandelic acid, methanesulfonic acid, mucic acid, naphthalene-1,5-disulfonic acid, naphthalene-2-sulfonic acid, 1-hydroxy-2-naphthoic acid, nicotinic acid, oleic acid, orotic acid, oxalic acid, palmitic acid, pamoic acid, propionic acid, pyroglutamic acid, pyruvic acid, salicylic acid, 4-aminosalicylic acid, sebacic acid, stearic acid, succinic acid, tartaric acid, thiocyanic acid, p-toluenesulfonic acid, trifluoroacetic acid, undecylenic acid, and the like.

"Pharmaceutically acceptable base addition salt" may refer to those salts that retain the biological effectiveness and properties of the free acids, which are not biologically or otherwise undesirable. These salts may be prepared from addition of an inorganic base or an organic base to the free acid. Salts derived from inorganic bases may include, but are not limited to, the sodium, potassium, lithium, ammonium, calcium, magnesium, iron, zinc, copper, manganese, aluminum salts and the like. For example, inorganic salts may include, but are not limited to, ammonium, sodium, potassium, calcium, and magnesium salts. Salts derived from organic bases may include, but are not limited to, salts of primary, secondary, and tertiary amines, substituted amines including naturally occurring substituted amines, cyclic amines and basic ion exchange resins, such as ammonia, isopropylamine, trimethylamine, diethylamine, triethylamine, tripropylamine, diethanolamine, ethanolamine, deanol, 2-dimethylaminoethanol, 2-diethylaminoethanol, dicyclohexylamine, lysine, arginine, histidine, caffeine, procaine, hydrabamine, choline, betaine, benethamine, benzathine, ethylenediamine, glucosamine, methylglucamine, theobromine, triethanolamine, tromethamine, purines, piperazine, piperidine, N-ethylpiperidine, polyamine resins and the like.

The disclosure may include zwitterions of the compounds disclosed herein. A "zwitterion" may refer to a molecule that has both positively-charged and negatively-charged groups but has no overall charge, i.e., the + and − charges are balanced within the molecule. For examples, the compounds of the disclosure may include protonated amino groups and deprotonated sulfate groups.

Compounds of the disclosure may exist as solvates. The term "solvate" may refer to a complex of variable stoichiometry formed by a solute and solvent. Such solvents for the purpose of the disclosure may not interfere with the biological activity of the solute. Examples of suitable solvents include, but are not limited to, water, MeOH, EtOH, and AcOH. Solvates wherein water is the solvent molecule are typically referred to as hydrates. Hydrates may include compositions containing stoichiometric amounts of water, as well as compositions containing variable amounts of water.

The compounds described herein further include all pharmaceutically acceptable isotopically labeled compounds. An "isotopically" or "radio-labeled" compound may be a compound where one or more atoms are replaced or substituted by an atom having an atomic mass or mass number different from the atomic mass or mass number typically found in nature (i.e., naturally occurring). For example, in some embodiments, in the compounds described herein hydrogen atoms are replaced or substituted by one or more deuterium or tritium. Certain isotopically labeled compounds of this disclosure, for example, those incorporating a radioactive isotope, may be useful in drug and/or substrate tissue distribution studies. The radioactive isotopes tritium, i.e., $^3H$, and carbon 14, i.e., $^{14}C$, may be particularly useful for this purpose in view of their ease of incorporation and ready means of detection. Substitution with heavier isotopes such as deuterium, i.e., $^2H$, may afford certain therapeutic advantages resulting from greater metabolic stability, for example, increased in vivo half-life or reduced dosage requirements, and hence may be preferred in some circumstances. In some embodiments, the compound comprises at least one deuterium atom. For example, one or more hydrogen atoms in a compound of the present disclosure can be replaced or substituted by deuterium. In some embodiments, the compound comprises two or more deuterium atoms. In some embodiments, the compound comprises 1, 2, 3, 4, 5, 6, 7, 8, 9, 10, 11 or 12 deuterium atoms. Suitable isotopes that may be incorporated in compounds described herein include but are not limited to $^2H$ (also written as D for deuterium), $^3H$ (also written as T for tritium), $^{11}C$, $^{13}C$, $^{14}C$, $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$, and $^{131}I$. Substitution with positron emitting isotopes, such as $^{11}C$, $^{18}F$, $^{15}O$, and $^{13}N$, can be useful in Positron Emission Topography (PET) studies.

Isotopically labelled compounds of the compounds disclosed herein can generally be prepared by following procedures analogous to those disclosed in the Schemes and/or in the Examples herein, by substituting an appropriate isotopically labelled reagent for a non-isotopically labelled reagent.

Compounds

The present disclosure provides a compound having the structure of Formula (I),

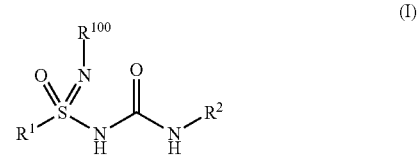

and pharmaceutically acceptable salts, solvates, isomers, prodrugs, and tautomers thereof, wherein the substituents are as described herein (e.g., such as described with respect to Formulae (I-1), (I-2), (I-3), (I-4), (I-5), and (I-6)).

In one aspect, provided is a compound having the structure of Formula (I),

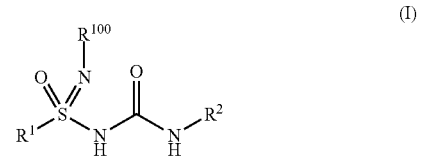

or a pharmaceutically acceptable salt, solvate, isomer, or tautomer thereof, wherein:

$R^1$ is (i) or (ii):

(i): $R^1$ is a monocyclic pyrazole of formula

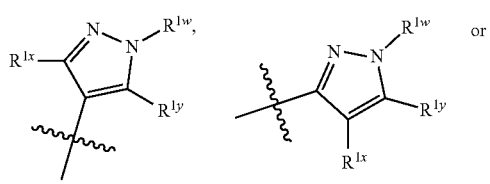

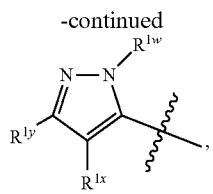

wherein R$^{1w}$ is selected from the group consisting of H, D, —CN, —C(O)R$^{5b}$, —S(O)$_2$R$^{5b}$, —S(O)R$^{5b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, C$_3$-C$_{10}$cycloalkyl, C$_6$aryl, 3-7-membered heterocyclyl, and 5-6-membered heteroaryl; and each R$^{1x}$ and R$^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl. —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6-membered heteroaryl; or (ii): R$^1$ is a fused pyrazole of formula

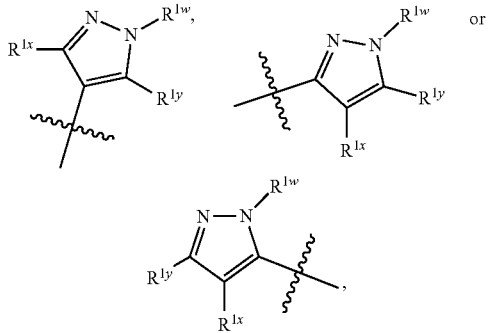

wherein (ii-a): R$^{1w}$ and R$^{1y}$, together with the atoms to which they are attached can form a 3-7-membered heterocyclyl or 5-6-membered heteroaryl; wherein the 3-7-membered heterocyclyl and 5-6-membered heteroaryl are independently unsubstituted or substituted with one or more substituents, or optionally two of the substituents when present, together with the atoms to which they are attached can form a ring; and R$^{1x}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6-membered heteroaryl;

or (ii-b): R$^{1x}$ and R$^{1y}$, together with the atoms to which they are attached can form a C$_3$-C$_{10}$cycloalkyl, 3-7-membered heterocyclyl, or a 5-6-membered aryl or heteroaryl; wherein the C$_3$-C$_{10}$cycloalkyl, 3-7-membered heterocyclyl, and 5-6-membered aryl or heteroaryl are independently unsubstituted or substituted with one or more substituents, or optionally two of the substituents when present, together with the atoms to which they are attached can form a ring; and R$^{1w}$ is selected from the group consisting of H, D, —CN, —C(O)R$^{5b}$, —S(O)$_2$R$^{5b}$, —S(O)R$^{5b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, C$_3$-C$_{10}$cycloalkyl, C$_6$aryl, 3-7-membered heterocyclyl, and 5-6-membered heteroaryl;

R$^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6-membered heteroaryl;

R$^2$ is selected from the group consisting of C$_1$-C$_6$alkyl, C$_3$-C$_{10}$cycloalkyl, 3-7-membered heterocyclyl, 5-membered heteroaryl, 6-membered heteroaryl, C$_6$aryl, and —NR$^{2g}$R$^{2h}$; wherein the C$_1$-C$_6$alkyl, C$_3$-C$_{10}$cycloalkyl, 3-7-membered heterocyclyl, 5-membered heteroaryl, 6-membered heteroaryl, and C$_6$aryl are independently unsubstituted or substituted with one or more substituents, or optionally two of the substituents when present, together with the atoms to which they are attached can form a ring;

each $R^{2g}$ and $R^{2h}$ is independently H, D, $C_1$-$C_6$alkyl, $C_3$-$C_{10}$cycloalkyl, $C_6$aryl, 3-7-membered heterocyclyl, or 5-6-membered heteroaryl, wherein the $C_1$-$C_6$alkyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —$OR^{21a}$, —$C(O)R^{21b}$, —$P(O)R^{21b}R^{22b}$, —$S(O)_2R^{21b}$, —$S(O)R^{21b}$, —$NR^{21a}R^{22a}$, —$NR^{21a}C(O)R^{22a}$, —$NR^{21a}C(O)OR^{22a}$, —$NR^{21a}C(O)NR^{22a}$, —$NR^{21a}S(O)_2R^{22a}$, —$(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$R^{3a}$, $R^{4a}$, $R^{5a}$, $R^{6a}$, $R^{7a}$, $R^{8a}$, $R^{9a}$, $R^{10a}$, $R^{21a}$, and $R^{22a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_1$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6-membered heteroaryl; and $R^{3b}$, $R^{4b}$, $R^{5b}$, $R^{6b}$, $R^{7b}$, $R^{8b}$, $R^{9b}$, $R^{10b}$, $R^{21b}$, and $R^{22b}$ are independently, at each occurrence, H, D, —OH, —O($C_1$-$C_6$alkyl), —$NH_2$, —$NH(C_1$-$C_6$alkyl), —$N(C_1$-$C_6$alkyl)$_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6-membered heteroaryl.

In some embodiments, the compound is other than a compound in Table 1X and pharmaceutically acceptable salts, solvates, isomers, and tautomers thereof. In some embodiments, the compound herein, such as a compound of Formula (I), is other than a compound selected from one or more of Compound Nos. 1x-30x in Table 1X, and pharmaceutically acceptable salts, solvates, isomers, prodrugs, and tautomers thereof. In some embodiments, the compounds of the disclosure, and methods of using the compounds detailed herein, encompass any of the compounds of Formula (I), including those listed Table 1X and pharmaceutically acceptable salts, solvates, isomers, prodrugs, and tautomers thereof.

TABLE 1X

| No. | Name |
| --- | --- |
| 1x | N-[[[4-fluoro-2,6-bis(1-methylethyl)phenyl]amino]carbonyl]-1,3-dimethyl-1H-pyrazole-4-sulfonimidamide |
| 2x | [S(S)]-1-isopropyl-N-((5-(2-methoxypyridin-4-yl)-2,3-dihydro-1H-inden-4-yl)carbamoyl)-1H-pyrazole-3-sulfonimidamide |
| 3x | [S(R)]-1-isopropyl-N-((5-(2-methoxypyridin-4-yl)-2,3-dihydro-1H-inden-4-yl)carbamoyl)-1H-pyrazole-3-sulfonimidamide |
| 4x | 4-chloro-N-[[7-fluoro-2,3-dihydro-5-(4-pyridinyl)-1H-inden-4-yl]amino]carbonyl]-1-(1-methylethyl)-1H-pyrazole-3-sulfonimidamide |
| 5x | N-[[[7-fluoro-2,3-dihydro-5-(4-pyridinyl)-1H-inden-4-yl]amino]carbonyl]-1-[(2R)-2-hydroxypropyl]-1H-pyrazole-3-sulfonimidamide |
| 6x | N-[[[7-fluoro-2,3-dihydro-5-(4-pyridinyl)-1H-inden-4-yl]amino]carbonyl]-1-(1-methylethyl)-1H-pyrazole-3-sulfonimidamide |
| 7x | 5-(azetidin-1-ylmethyl)-N-((4-fluoro-2,6-diisopropylphenyl)carbamoyl)-1-methyl-1H-pyrazole-3-sulfonimidamide |
| 8x | 5-[1-(1-azetidinyl)ethyl]-N-[[[(1,2,3,5,6,7-hexahydro-s-indacen-4-yl)amino]carbonyl]-1-methyl-1H-pyrazole-3-sulfonimidamide |
| 9x | 5-(1-chloroethyl)-N-[[[(1,2,3,5,6,7-hexahydro-s-indacen-4-yl)amino]carbonyl]-1-methyl-1H-pyrazole-3-sulfonimidamide |
| 10x | N-[[[(1,2,3,5,6,7-hexahydro-s-indacen-4-yl)amino]carbonyl]-5-(1-hydroxyethyl)-1-methyl-1H-pyrazole-3-sulfonimidamide |
| 11x | N-((4-fluoro-2-isopropyl-6-(2-methoxypyridin-4-yl)phenyl)carbamoyl)-1-((R)-2-hydroxypropyl)-1H-pyrazole-3-sulfonimidamide |
| 12x | N-((2-(2-cyanopyridin-4-yl)-4-fluoro-6-isopropylphenyl)carbamoyl)-1-((R)-2-hydroxypropyl)-1H-pyrazole-3-sulfonimidamide |
| 13x | N-[[[2,3-dihydro-5-(2-methoxy-4-pyridinyl)-1H-inden-4-yl]amino]carbonyl]-1-[(2R)-2-hydroxypropyl]-1H-pyrazole-3-sulfonimidamide |
| 14x | N-((4-fluoro-2-isopropyl-6-(2-methoxypyridin-4-yl)phenyl)carbamoyl)-1-isopropyl-1H-pyrazole-3-sulfonimidamide |
| 15x | N-((2-(2-cyanopyridin-4-yl)-4-fluoro-6-isopropylphenyl)carbamoyl)-1-isopropyl-1H-pyrazole-3-sulfonimidamide |
| 16x | N-[[[2,3-dihydro-5-(2-methoxy-4-pyridinyl)-1H-inden-4-yl]amino]carbonyl]-1-(1-methylethyl)-1H-pyrazole-3-sulfonimidamide |
| 17x | 4-chloro-N-((4-fluoro-2-isopropyl-6-(2-methoxypyridin-4-yl)phenyl)carbamoyl)-1-isopropyl-1H-pyrazole-3-sulfonimidamide |
| 18x | 4-chloro-N-((2-(2-cyanopyridin-4-yl)-4-fluoro-6-isopropylphenyl)carbamoyl)-1-isopropyl-1H-pyrazole-3-sulfonimidamide |
| 19x | 4-chloro-1-isopropyl-N-((5-(2-methoxypyridin-4-yl)-2,3-dihydro-1H-inden-4-yl)carbamoyl)-1H-pyrazole-3-sulfonimidamide |
| 20x | 1-[2-(dimethylamino)ethyl]-N-[[[(1,2,3,5,6,7-hexahydro-s-indacen-4-yl)amino]carbonyl]-1H-pyrazole-3-sulfonimidamide |

TABLE 1X-continued

| No. | Name |
|---|---|
| 21x | 2-(3-(N-((1,2,3,5,6,7-hexahydro-s-indacen-4-yl)carbamoyl)sulfamidimidoyl)-1H-pyrazol-1-yl)ethyl methanesulfonate |
| 22x | N-[[(1,2,3,5,6,7-hexahydro-s-indacen-4-yl)amino]carbonyl]-1-(2-hydroxyethyl)-1H-pyrazole-3-sulfonimidamide |
| 23x | N-[[(1,2,3,5,6,7-hexahydro-s-indacen-4-yl)amino]carbonyl]-1-[(2R)-2-hydroxypropyl]-1H-pyrazole-3-sulfonimidamide |
| 24x | 4-chloro-N-[[(1,2,3,5,6,7-hexahydro-s-indacen-4-yl)amino]carbonyl]-1-(1-methylethyl)-1H-pyrazole-3-sulfonimidamide |
| 25x | [S(S)]-N-[[(1,2,3,5,6,7-hexahydro-s-indacen-4-yl)amino]carbonyl]-5-(1-hydroxy-1-methylethyl)-1-phenyl-1H-pyrazole-3-sulfonimidamide |
| 26x | [S(R)]-N-[[(1,2,3,5,6,7-hexahydro-s-indacen-4-yl)amino]carbonyl]-5-(1-hydroxy-1-methylethyl)-1-phenyl-1H-pyrazole-3-sulfonimidamide |
| 27x | N-[[(1,2,3,5,6,7-hexahydro-s-indacen-4-yl)amino]carbonyl]-5-(1-hydroxy-1-methylethyl)-1-phenyl-1H-pyrazole-3-sulfonimidamide |
| 28x | [S(S)]-N-[[(1,2,3,5,6,7-hexahydro-s-indacen-4-yl)amino]carbonyl]-1-(1-methylethyl)-1H-pyrazole-3-sulfonimidamide |
| 29x | [S(R)]-N-[[(1,2,3,5,6,7-hexahydro-s-indacen-4-yl)amino]carbonyl]-1-(1-methylethyl)-1H-pyrazole-3-sulfonimidamide |
| 30x | N-[[(1,2,3,5,6,7-hexahydro-s-indacen-4-yl)amino]carbonyl]-1-(1-methylethyl)-1H-pyrazole-3-sulfonimidamide |

In one aspect, provided is a compound of Formula (I), or a salt (e.g., a pharmaceutically acceptable salt), solvate (e.g., hydrate), prodrug, metabolite or derivative thereof, wherein $R^2$ is as defined herein, and $R^1$ is a monocyclic pyrazole which is optionally substituted as detailed herein. In one variation, the compound is other than a compound selected from one or more of Compound Nos. 1x-30x in Table 1X and pharmaceutically acceptable salts, solvates, isomers, prodrugs, and tautomers thereof. In some embodiments, $R^2$ is a 4-pyrazolyl which is optionally substituted as detailed herein, provided that $R^1$ is other than 1,3-dimethylpyrazol-4-yl. In some embodiments, $R^2$ is 4-pyrazolyl which is optionally substituted as detailed herein, provided that the compound is other than Compound 1x in Table 1 and pharmaceutically acceptable salts, solvates, isomers, prodrugs, and tautomers thereof. In some embodiments, $R^2$ is a 3-pyrazolyl which is optionally substituted as detailed herein, provided that the compound is other than a compound selected from one or more of Compound Nos. 2x-30x in Table 1X and pharmaceutically acceptable salts, solvates, isomers, prodrugs, and tautomers thereof.

In some embodiments, $R^{100}$ is H, —CN, —C(O)$R^{3b}$, or $C_1$-$C_6$alkyl; wherein the $C_1$-$C_6$alkyl is unsubstituted or substituted with $C_6$aryl. In one variation, $R^{100}$ is H.

In some embodiments, $R^2$ is selected from the group consisting of $C_1$-$C_6$alkyl, $C_3$-$C_{10}$cycloalkyl, 3-7-membered heterocyclyl, 5-membered heteroaryl, 6-membered heteroaryl, $C_6$aryl, and —NR$^{2g}$R$^{2h}$; wherein the $C_1$-$C_6$alkyl, $C_3$-$C_{10}$cycloalkyl, 3-7-membered heterocyclyl, 5-membered heteroaryl, 6-membered heteroaryl, and $C_6$aryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

$R^{23a}$ and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6-membered heteroaryl; and $R^{23b}$, and $R^{24b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_6$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6-membered heteroaryl.

In some embodiments, $R^2$ is selected from the group consisting of $C_1$-$C_6$alkyl, $C_3$-$C_{10}$cycloalkyl, 3-7-membered heterocyclyl, 5-membered heteroaryl, —NR$^{2g}$R$^{2h}$,

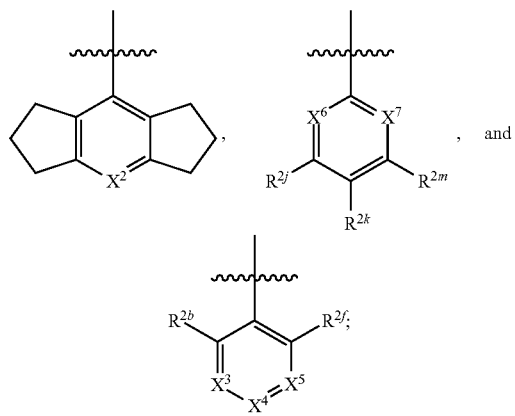

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_1$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-$C_{10}$cycloalkyl, $C_3$-$C_{10}$cycloalkyl, $C_6$aryl, 3-7-membered heterocyclyl, and 5-6-membered heteroaryl;

$X^2$ is N or CR$^{2a}$;

$X^3$ is N or CR$^{2c}$;

$X^4$ is N or CR$^{2d}$;

$X^5$ is N or CR$^{2e}$;

$X^6$ and $X^7$ are independently N or CR$^{2n}$, wherein at least one of $X^6$ and $X^7$ is N;

$R^{2a}$ is H, D, halogen, —CN, —OR$^{15a}$, $C_1$-$C_6$alkyl, $C_3$-$C_{10}$cycloalkyl, —C(O)NR$^{15a}$R$^{16a}$, —C(O)OR$^{15a}$; —P(O)R$^{15b}$R$^{16b}$, —NR$^{15a}$R$^{16a}$, —NR$^{15a}$C(O)R$^{16a}$, —NR$^{15a}$C(O)OR$^{16a}$, —NR$^{15a}$C(O)NR$^{16a}$, or —NR$^{15a}$S(O)$_2$R$^{16a}$, wherein the $C_1$-$C_6$alkyl and $C_3$-$C_{10}$cycloalkyl are independently unsubstituted or substituted with one or more substituents selected from the group consisting of D, halogen, —CN, —OR$^{15a}$, —C(O)R$^{15b}$, —P(O)R$^{15b}$R$^{16b}$, —NR$^{15a}$R$^{16a}$, $C_3$-$C_{10}$cycloalkyl, $C_6$aryl, 3-7-membered heterocyclyl, and 5-6-membered heteroaryl;

each $R^{2b}$, $R^{2c}$, $R^{2d}$, $R^{2e}$, and $R^{2f}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_3$-$C_{10}$cycloalkyl, $C_6$aryl, 3-7-membered heterocyclyl, and 5-6-membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —OR$^{19a}$, and NR$^{19a}$R$^{20a}$;

each $R^{2j}$, $R^{2k}$, $R^{2m}$, and $R^{2n}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_3$-$C_{10}$cycloalkyl, $C_6$aryl, 3-7-membered heterocyclyl, and 5-6-membered heteroaryl; or two adjacent $R^{2j}$, $R^{2k}$, $R^{2m}$, and $R^{2n}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —OR$^{19a}$, and NR$^{19a}$R$^{20a}$;

$R^{15a}$. $R^{16a}$, $R^{17a}$, $R^{18a}$, $R^{19a}$, and $R^{20a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6-membered heteroaryl; and $R^{15b}$. $R^{16b}$, $R^{17b}$, and $R^{18b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6-membered heteroaryl.

In some of these embodiments, $R^{2a}$ is H, D, halogen, —CN, —OR$^{15a}$, $C_1$-$C_6$alkyl, $C_3$-$C_{10}$cycloalkyl, —C(O)NR$^{15a}$R$^{16a}$, —C(O)OR$^{15a}$; —NR$^{15a}$R$^{16a}$, —NR$^{15a}$C(O)R$^{16a}$, —NR$^{15a}$C(O)OR$^{16a}$, —NR$^{15a}$C(O)NR$^{16a}$, or —NR$^{15a}$S(O)$_2$R$^{16a}$, wherein the $C_1$-$C_6$alkyl and $C_3$-$C_{10}$cycloalkyl are independently unsubstituted or substituted with one or more substituents selected from the group consisting of D, halogen, —CN, —OR$^{15a}$, —C(O)R$^{15b}$, —NR$^{15a}$R$^{16a}$, $C_3$-$C_{10}$cycloalkyl, $C_6$aryl, 3-7-membered heterocyclyl, and 5-6-membered heteroaryl.

In some of these embodiments, $R^{2a}$ is H, halogen, —CN, —OR$^{15a}$, —C(O)OR$^{15a}$, or $C_1$-$C_6$alkyl; wherein the $C_1$-$C_6$alkyl is unsubstituted or substituted with one or more substituents selected from the group consisting of D, halogen, —CN, —OR$^{15a}$, —C(O)R$^{15b}$, —P(O)R$^{15b}$R$^{16b}$, —NR$^{15a}$R$^{16a}$, $C_3$-$C_{10}$cycloalkyl, $C_6$aryl, 3-7-membered heterocyclyl, and 5-6-membered heteroaryl.

In some of these embodiments, $R^{2a}$ is H, halogen, —CN, —OR$^{15a}$, —C(O)OR$^{15a}$, or $C_1$-$C_6$alkyl; wherein the $C_1$-$C_6$alkyl is unsubstituted or substituted with one or more substituents selected from the group consisting of D, halogen, —CN, —OR$^{15a}$, —C(O)R$^{15b}$, —NR$^{15a}$R$^{16a}$, $C_3$-$C_{10}$cycloalkyl, $C_6$aryl, 3-7-membered heterocyclyl, and 5-6-membered heteroaryl. In one variation, $R^{2a}$ is H or F. In another variation, $R^{2a}$ is H. In another variation, $R^{2a}$ is F.

In some embodiments, $R^2$ is

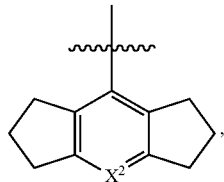

selected from the group consisting of

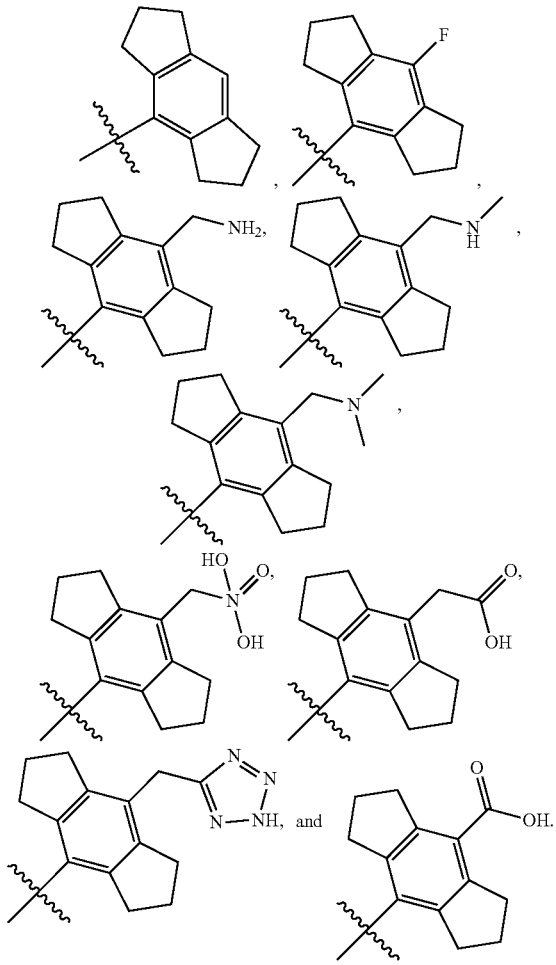

In some embodiments, $R^2$ is

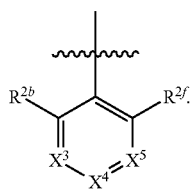

In some of these embodiments, $X^3$ is $CR^{2c}$; $X^4$ is $CR^{2d}$; and $X^5$ is $CR^{2e}$. In one variation, each $R^{2b}$, $R^{2c}$, $R^{2d}$, $R^{2e}$, and $R^{2f}$ is independently selected from the group consisting of H, D, halogen, $C_1$-$C_6$alkyl, $C_3$-$C_{10}$cycloalkyl, and —CN. In some of these embodiments, $R^2$ is selected from the group consisting of

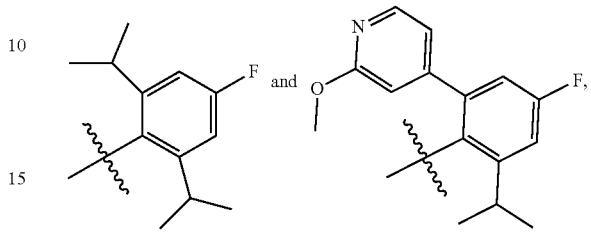

In some of these embodiments, $X^3$ is $CR^{2c}$; $X^4$ is $CR^{2d}$; and $X^5$ is $CR^{2e}$, wherein:

$R^{2b}$ and $R^{2c}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —OR$^{19a}$, and NR$^{19a}$R$^{20a}$; and each $R^{2d}$, $R^{2e}$, and $R^{2f}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_3$-$C_{10}$cycloalkyl, $C_6$aryl, 3-7-membered heterocyclyl, and 5-6-membered heteroaryl.

In some of these embodiments, $R^2$ is selected from the group consisting of

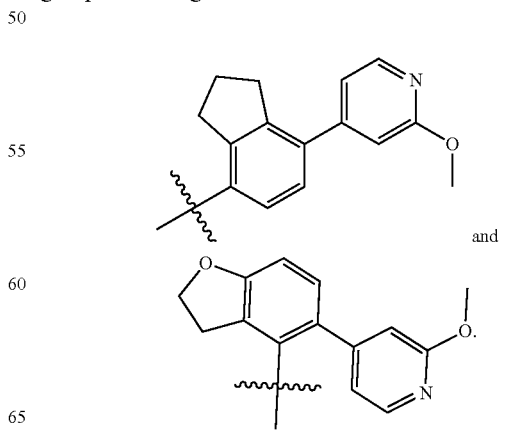

In some of these embodiments, $X^3$ is $CR^{2c}$; $X^4$ is $CR^{2d}$; and $X^5$ is $CR^{2e}$, wherein: $R^{2b}$ and $R^{2c}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

$R^{2e}$ and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$; and $R^{2d}$ is H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl. $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6-membered heteroaryl.

In some of these embodiments, $R^2$ is selected from the group consisting of

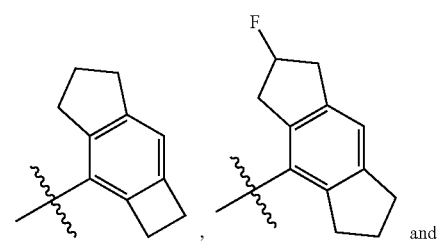, and

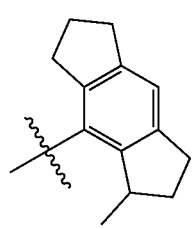

In some of these embodiments, $R^2$ is selected from the group consisting of

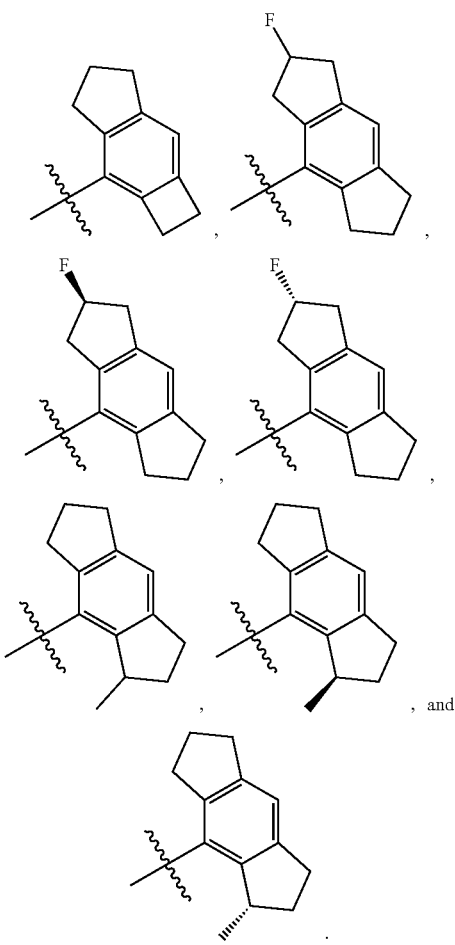

In some embodiments, $R^2$ is

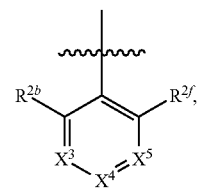

$X^3$ is $CR^{2c}$; $X^4$ is $CR^{2d}$; $X^5$ is $CR^{2e}$; and $R^2$ is selected from the group consisting of

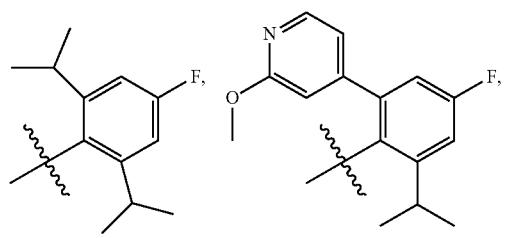

49
-continued

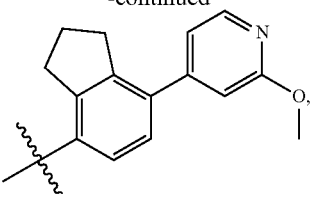

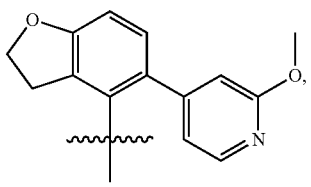

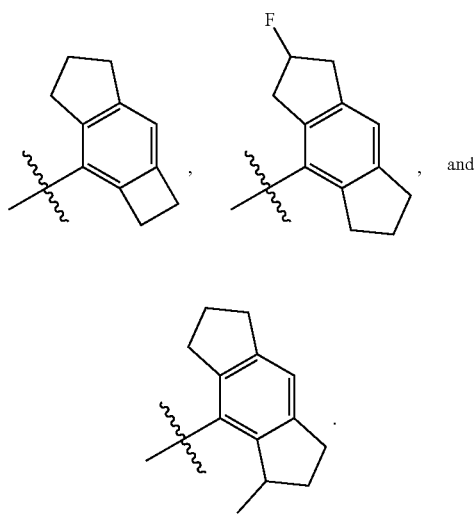

In some embodiments, wherein R² is

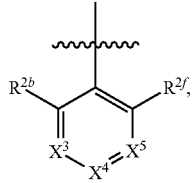

X³ is N and X⁴ is $CR^{2d}$. In some of these embodiments, X⁵ is $CR^{2e}$. In some of these embodiments, X⁵ is N. In some of these embodiments, R² is selected from the group consisting of

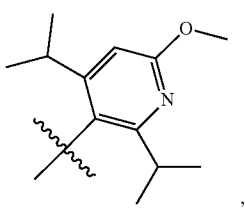

50
-continued

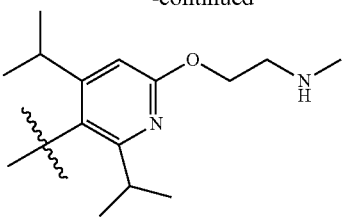

, and

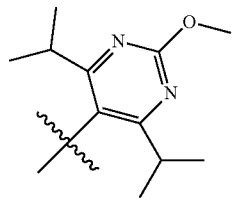

.

In one aspect, provided is a compound of Formula (I), or a salt (e.g., a pharmaceutically acceptable salt), solvate (e.g., hydrate), prodrug, metabolite or derivative thereof, wherein R² is as defined herein, and R¹ is a monocyclic pyrazole of formula

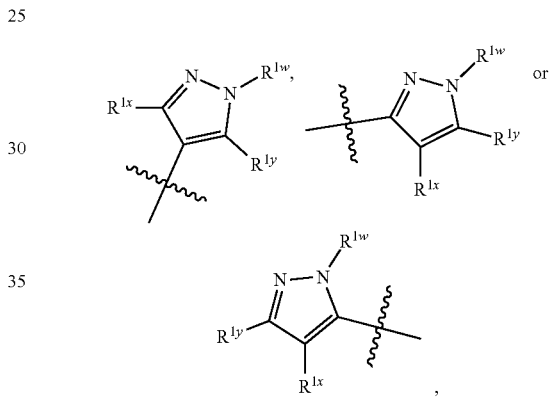

wherein $R^{1w}$, $R^{1x}$ and $R^{1y}$ are discrete substituents. In some of these embodiments, $R^{1w}$ is selected from the group consisting of H, D, —CN, —C(O)$R^{5b}$, —S(O)$_2R^{5b}$, —S(O)$R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, $C_3$-$C_{10}$cycloalkyl, $C_6$aryl, 3-7-membered heterocyclyl, and 5-6-membered heteroaryl; and each $R^{1x}$ and $R^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6-membered heteroaryl.

In one aspect, provided is a compound of Formula (I), or a salt (e.g., a pharmaceutically acceptable salt), solvate (e.g., hydrate), prodrug, metabolite or derivative thereof, wherein $R^2$ is as defined herein, and $R^1$ is a fused pyrazole of formula

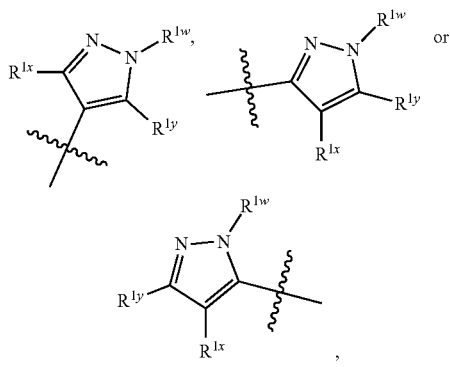

wherein either $R^{1w}$ and $R^{1y}$ together with the atoms to which they are attached can form a fused ring or $R^{1x}$ and $R^{1y}$ together with the atoms to which they are attached can form a fused ring.

In some of these embodiments, $R^{1w}$ and $R^{1y}$, together with the atoms to which they are attached can form a 3-7-membered heterocyclyl or 5-6-membered heteroaryl; wherein the 3-7-membered heterocyclyl and 5-6-membered heteroaryl are independently unsubstituted or substituted with one or more substituents, or optionally two of the substituents when present, together with the atoms to which they are attached can form a ring; and $R^{1x}$ is H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6-membered heteroaryl. In some embodiments, $R^{1w}$ and $R^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$.

In some of these embodiments, $R^{1x}$ and $R^{1y}$, together with the atoms to which they are attached can form a $C_3$-$C_{10}$cycloalkyl, 3-7-membered heterocyclyl, or a 5-6-membered aryl or heteroaryl; wherein the $C_3$-$C_{10}$cycloalkyl, 3-7-membered heterocyclyl, and 5-6-membered aryl or heteroaryl are independently unsubstituted or substituted with one or more substituents, or optionally two of the substituents when present, together with the atoms to which they are attached can form a ring; and $R^{1w}$ is selected from the group consisting of H, D, —CN, —$C(O)R^{5b}$, —$S(O)_2R^{5b}$, —$S(O)R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —$OR^{5a}$, —$C(O)R^{5b}$, —$P(O)R^{5b}R^{6b}$, —$S(O)_2R^{5b}$, —$S(O)R^{5b}$, —$NR^{5a}R^{6a}$, —$NR^{5a}C(O)R^{6a}$, —$NR^{5a}C(O)OR^{6a}$, —$NR^{5a}C(O)NR^{6a}$, —$NR^{5a}S(O)_2R^{6a}$, $C_3$-$C_{10}$cycloalkyl, $C_6$aryl, 3-7-membered heterocyclyl, and 5-6-membered heteroaryl. In some embodiments, $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$.

In some embodiments, provided is a compound of Formula (I), or a salt (e.g., a pharmaceutically acceptable salt), solvate (e.g., hydrate), prodrug, metabolite or derivative thereof, wherein $R^2$ is as defined herein, and $R^1$ is selected from the group consisting of

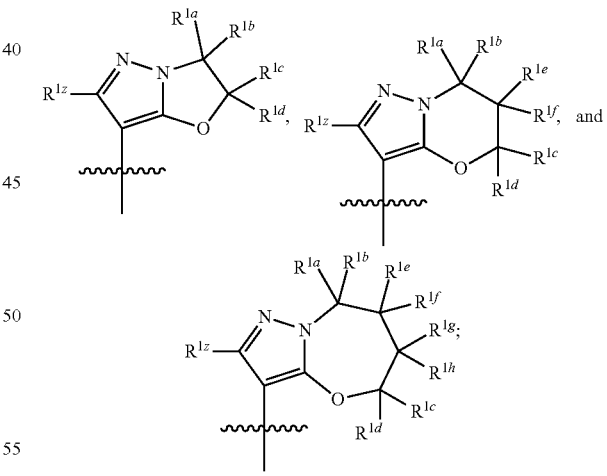

wherein $R^{1z}$ is H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6-membered heteroaryl;

each R$^{1a}$, R$^{1b}$, R$^{1c}$, R$^{1d}$, R$^{1e}$, R$^{1f}$, R$^{1g}$, and R$^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OR$^{11b}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_3$-$C_{10}$cycloalkyl, $C_6$aryl, 3-7-membered heterocyclyl, and 5-6-membered heteroaryl; or two of the following groups, R$^{1a}$, R$^{1b}$, R$^{1c}$, R$^{1d}$, R$^{1e}$, R$^{1f}$, R$^{1g}$, and R$^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups R$^{1a}$ and R$^{1b}$; R$^{1c}$ and R$^{1d}$; R$^{1e}$ and R$^{1f}$; or R$^{1g}$ and R$^{1h}$, when present, can form an oxo group;

R$^{7a}$, R$^{8a}$, R$^{11a}$, R$^{12a}$, R$^{13a}$, and R$^{14a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_6$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6-membered heteroaryl;

R$^{7b}$, R$^{8b}$, R$^{11b}$, R$^{12b}$, R$^{13b}$, and R$^{14b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$ alkyl)$_2$, $C_3$-$C_{10}$cycloalkyl, $C_6$aryl, 3-7-membered heterocyclyl, and 5-6-membered heteroaryl.

The present disclosure provides a compound having the structure of Formula (I-1),

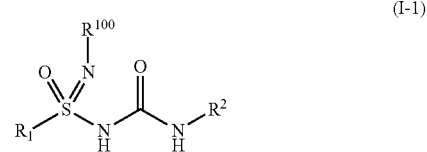

(I-1)

and pharmaceutically acceptable salts, solvates, isomers, prodrugs, and tautomers thereof, wherein:

R$^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

R$^1$ is selected from the group consisting of

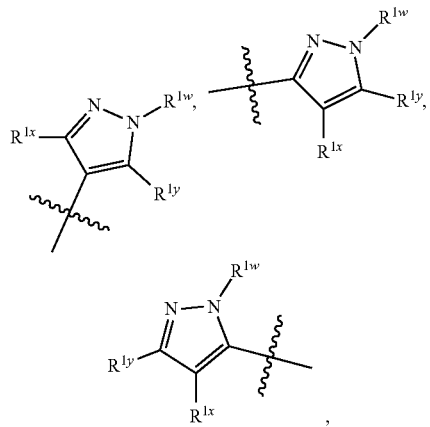

wherein R$^{1w}$ is selected from the group consisting of H, D, —CN, —C(O)R$^{5b}$, —S(O)$_2$R$^{5b}$, —S(O)R$^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, $C_3$-$C_{10}$cycloalkyl, $C_6$aryl, 3-7-membered heterocyclyl, and 5-6 membered heteroaryl;

each $R^{1x}$ and $R^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl; or wherein $R^{1w}$ and $R^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, $C_1$-$C_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$; or wherein $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$;

$R^2$ is selected from the group consisting of $C_1$-$C_6$alkyl, $C_3$-$C_{10}$cycloalkyl, 3-7-membered heterocyclyl, 5-membered heteroaryl, 6-membered heteroaryl, $C_6$aryl, and —NR$^{2g}$R$^{2h}$; wherein the $C_1$-$C_6$alkyl, $C_3$-$C_{10}$cycloalkyl, 3-7-membered heterocyclyl, 5-membered heteroaryl, 6-membered heteroaryl, and $C_6$aryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

each $R^{2g}$ and $R^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

$R^{3a}$, $R^{4a}$, $R^{5a}$, $R^{6a}$, $R^{7a}$, $R^{8a}$, $R^{9a}$, $R^{10a}$, $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{5b}$, $R^{6b}$, $R^{7b}$, $R^{8b}$, $R^{9b}$, $R^{10b}$, $R^{21b}$, $R^{22b}$, $R^{23b}$, and $R^{24b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-2),

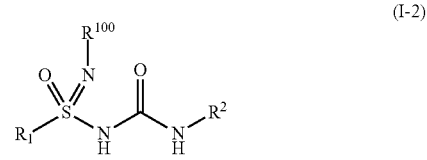

(I-2)

and pharmaceutically acceptable salts, solvates, isomers, prodrugs, and tautomers thereof, wherein:

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

$R^1$ is selected from the group consisting of

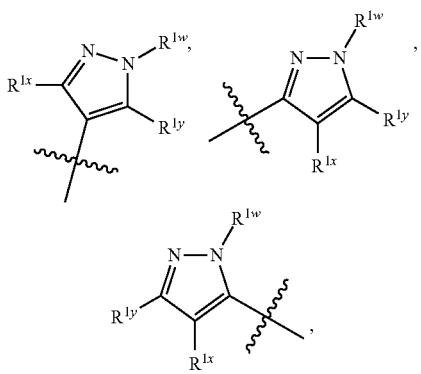

$R^2$ is selected from the group consisting of $C_1$-$C_6$alkyl, $C_3$-$C_{10}$cycloalkyl, 3-7-membered heterocyclyl, 5-membered heteroaryl, —$NR^{2g}R^{2h}$,

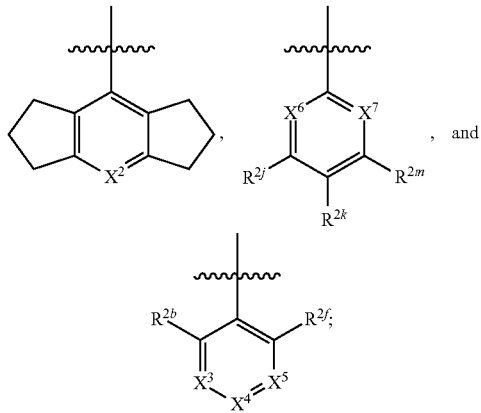

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —$OR^{23a}$, —$C(O)R^{23b}$, —$P(O)R^{23b}R^{24b}$, —$S(O)_2R^{23b}$, —$S(O)R^{23b}$, —$NR^{23a}R^{24a}$, —$NR^{23a}C(O)R^{24a}$, —$NR^{23a}C(O)OR^{24a}$, —$NR^{23a}C(O)NR^{24a}$, —$NR^{23a}S(O)_2R^{24a}$, —$(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$X^2$ is N or $CR^{2a}$;
$X^3$ is N or $CR^{2c}$;
$X^4$ is N or $CR^{2d}$;
$X^5$ is N or $CR^{2e}$;
$X^6$ and $X^7$ are independently N or $CR^{2n}$, wherein at least one of $X^6$ and $X^7$ is N;
wherein $R^{1w}$ is selected from the group consisting of H, D, —CN, —$C(O)R^{5b}$, —$S(O)_2R^{5b}$, —$S(O)R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{5a}$, —$C(O)R^{5b}$, —$P(O)R^{5b}R^{6b}$, —$S(O)_2R^{5b}$, —$S(O)R^{5b}$, —$NR^{5a}R^{6a}$, —$NR^{5a}C(O)R^{6a}$, —$NR^{5a}C(O)OR^{6a}$, —$NR^{5a}C(O)NR^{6a}$, —$NR^{5a}S(O)_2R^{6a}$, $C_3$-$C_{10}$cycloalkyl, $C_6$aryl, 3-7-membered heterocyclyl, and 5-6 membered heteroaryl;

each $R^{1x}$ and $R^{1y}$ is independently, H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6 membered heteroaryl; or wherein $R^{1w}$ and $R^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$; or wherein $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$;

$R^{2a}$ is H, D, halogen, —CN, —$OR^{15a}$, $C_1$-$C_6$alkyl, $C_3$-$C_{10}$cycloalkyl, —$C(O)NR^{15a}R^{16a}$, —$C(O)OR^{15a}$, —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2b}$, R$^{2c}$, R$^{2d}$, R$^{2e}$, and R$^{2f}$ together with the atoms to which they are attached can form C$_3$-C$_{10}$cycloalkyl, C$_6$aryl, 3-7-membered heterocyclyl, 5-6-membered heteroaryl, wherein the C$_3$-C$_{10}$cycloalkyl, C$_6$aryl, 3-7-membered heterocyclyl, and 5-6-membered heteroaryl are independently unsubstituted or substituted with one or more substituents selected from the group consisting of halogen, D, —CN, C$_1$-C$_6$alkyl, —OR$^{19a}$, and NR$^{19a}$R$^{20a}$, each R$^{2j}$, R$^{2k}$, R$^{2m}$, and R$^{2n}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6 membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2j}$, R$^{2k}$, R$^{2m}$, and R$^{2n}$ together with the atoms to which they are attached can form C$_1$-C$_{10}$cycloalkyl, C$_6$aryl, 3-7-membered heterocyclyl, 5-6-membered heteroaryl, wherein the C$_3$-C$_{10}$cycloalkyl, C$_6$aryl, 3-7-membered heterocyclyl, and 5-6-membered heteroaryl are independently unsubstituted or substituted with one or more substituents selected from the group consisting of halogen, D, —CN, C$_1$-C$_6$alkyl, —OR$^{19a}$, and NR$^{19a}$R$^{20a}$;

each R$^{2g}$ and R$^{2h}$ is independently H, D, C$_1$-C$_6$alkyl, C$_3$-C$_{10}$cycloalkyl, C$_6$aryl, 3-7 membered heterocyclyl, or 5-6 membered heteroaryl; wherein the C$_1$-C$_6$alkyl, C$_3$-C$_{10}$cycloalkyl, C$_6$aryl, 3-7 membered heterocyclyl, and 5-6-membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

R$^{3a}$, R$^{4a}$, R$^{5a}$, R$^{6a}$, R$^{7a}$, R$^{8a}$, R$^{9a}$, R$^{15a}$, R$^{16a}$, R$^{17a}$, R$^{18a}$, R$^{19a}$, R$^{20a}$, R$^{21a}$, R$^{22a}$, R$^{23a}$, and R$^{24a}$ are independently, at each occurrence, H, D, C$_1$-C$_6$alkyl, C$_1$-C$_6$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl;

R$^{3b}$, R$^{4b}$, R$^{5b}$, R$^{6b}$, R$^{7b}$, R$^{8b}$, R$^{9b}$, R$^{10b}$, R$^{15b}$, R$^{17b}$, R$^{18b}$, R$^{21b}$, R$^{22b}$, R$^{23b}$, and R$^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_1$-C$_6$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_1$-C$_6$alkenyl, C$_1$-C$_6$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

The present disclosure provides a compound having the structure of Formula (I-3),

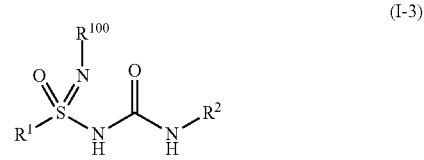

(I-3)

and pharmaceutically acceptable salts, solvates, isomers, prodrugs, and tautomers thereof, wherein:

R$^{100}$ is selected from the group consisting of H, D, —Cl, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

R$^1$ is selected from the group consisting of

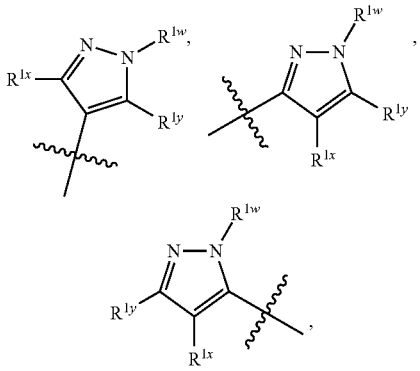

$R^2$ is

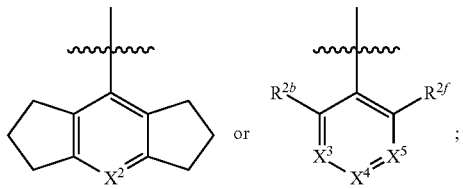

$X^2$ is N or $CR^{2a}$;
$X^3$ is N or $CR^{2c}$;
$X^4$ is N or $CR^{2d}$;
$X^5$ is N or $CR^{2e}$;
wherein $R^{1w}$ is selected from the group consisting of H, D, —CN, $C(O)R^{5b}$, —$S(O)_2R^{5b}$, —$S(O)R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{5a}$, —$C(O)R^{5b}$, —$P(O)R^{5b}R^{6b}$, —$S(O)_2R^{5b}$, —$S(O)R^{5b}$, —$NR^{5a}R^{6a}$, —$NR^{5a}C(O)R^{6a}$, —$NR^{5a}C(O)OR^{6a}$, —$NR^{5a}C(O)NR^{6a}$, —$NR^{5a}S(O)_2R^{6a}$, $C_3$-$C_{10}$cycloalkyl, $C_6$aryl, 3-7-membered heterocyclyl, and 5-6 membered heteroaryl;

each $R^{1x}$ and $R^{1y}$ is independently, H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6 membered heteroaryl; or wherein $R^{1w}$ and $R^{1y}$, together with the atoms to which they are attached can form a 3-7-membered heterocyclyl; wherein the 3-7-membered heterocyclyl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$; or wherein $R^{1x}$ and $R^{1y}$, together with the atoms to which they are attached can form a $C_3$-$C_{10}$cycloalkyl, 3-7-membered heterocyclyl, or a 5-6 membered aryl or heteroaryl; wherein the $C_3$-$C_{10}$cycloalkyl, 3-7-membered heterocyclyl, and 5-6 membered aryl or heteroaryl are independently unsubstituted or substituted with one or more substituents selected from the group consisting of D, —CN, halogen, $C_1$-$C_6$alkyl, —$OR^{9a}$, —$C(O)R^{9b}$, —$P(O)R^{9b}R^{10b}$, —$S(O)_2R^{9b}$, —$S(O)R^{9b}$, —$NR^{9a}R^{10a}$, —$NR^{9a}C(O)R^{10a}$, —$NR^{9a}C(O)OR^{10a}$, —$NR^{9a}C(O)NR^{10a}$, and —$NR^{9a}S(O)_2R^{10a}$;

$R^{2a}$ is H, D, halogen, —CN, —$OR^{15a}$, $C_1$-$C_6$alkyl, $C_3$-$C_{10}$cycloalkyl, —$C(O)NR^{15a}R^{16a}$, —$C(O)OR^{15a}$; —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

$R^{3a}$, $R^{4a}$, $R^{5a}$, $R^{6a}$, $R^{7a}$, $R^{8a}$, $R^{9a}$, $R^{10a}$, $R^{15a}$, $R^{16a}$, $R^{17a}$, $R^{18a}$, $R^{19a}$ and $R^{20a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl$)_2$, $C_3$-$C_{10}$cycloalkyl, $C_6$aryl, 3-7-membered heterocyclyl, and 5-6 membered heteroaryl;

$R^{3b}$, $R^{4b}$, $R^{5b}$, $R^{6b}$, $R^{7b}$, $R^{8b}$, $R^{9b}$, $R^{10b}$, $R^{15b}$, $R^{17b}$, and $R^{18b}$ are independently, at each occurrence, H, D, —OH, —O($C_1$-$C_6$alkyl), —$NH_2$, —$NH(C_1$-$C_6$alkyl), —$N(C_1$-$C_6$alkyl$)_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-

$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-4),

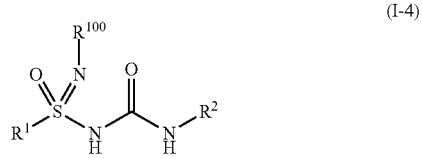

and pharmaceutically acceptable salts, solvates, isomers, prodrugs, and tautomers thereof, wherein:

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

$R^1$ is selected from the group consisting of

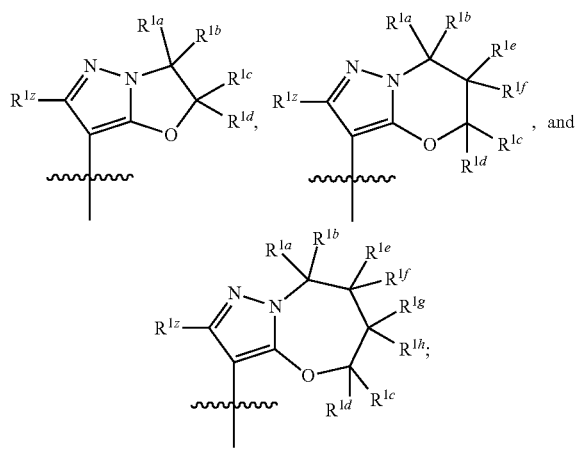

$R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups $R^{1a}$ and $R^{1b}$; $R^{1c}$ and $R^{1d}$; $R^{1e}$ and $R^{1f}$; or $R^{1g}$ and $R^{1b}$, when present, can form an oxo group;

$R^2$ is selected from the group consisting of $C_1$-$C_6$alkyl, $C_3$-$C_{10}$cycloalkyl, 3-7-membered heterocyclyl, 5-membered heteroaryl, 6-membered heteroaryl, $C_6$aryl, and —NR$^{2g}$R$^{2h}$; wherein the $C_1$-$C_6$alkyl, $C_3$-$C_{10}$cycloalkyl, 3-7-membered heterocyclyl, 5-membered heteroaryl, 6-membered heteroaryl, and $C_6$aryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

each $R^{2g}$ and $R^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

$R^{3a}$, $R^{4a}$, $R^{7a}$, $R^{8a}$, $R^{11a}$, $R^{12a}$, $R^{13a}$, $R^{14a}$, $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{21b}$, $R^{22b}$, $R^{23b}$, and $R^{24b}$ are independently, at each occurrence, H, D, —OH, —O($C_1$-$C_6$alkyl), —$NH_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-5), (I-5)

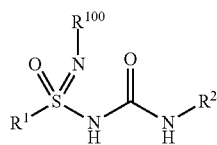

and pharmaceutically acceptable salts, solvates, isomers, prodrugs, and tautomers thereof, wherein:

$R^{100}$ is selected from the group consisting of H, Cl, D, —CN, —$NO_2$, —OR$^{3a}$, —C(O)R$^{3b}$, —S(O)$_2$R$^{3b}$, —S(O)R$^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, $C_3$-$C_{10}$cycloalkyl, $C_6$aryl, 3-7-membered heterocyclyl, and 5-6 membered heteroaryl;

$R^1$ is selected from the group consisting of

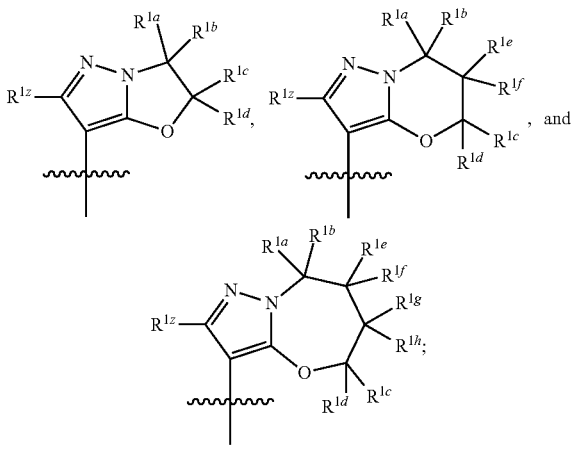

$R^2$ is selected from the group consisting of $C_1$-$C_6$alkyl, $C_3$-$C_{10}$cycloalkyl, 3-7-membered heterocyclyl, 5-membered heteroaryl, —NR$^{2g}$R$^{2h}$,

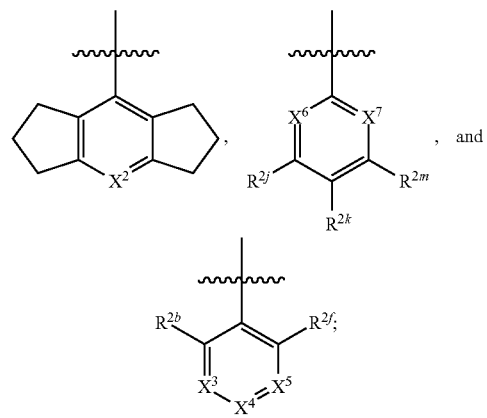

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-$C_{10}$cycloalkyl, $C_3$-$C_{10}$cycloalkyl, $C_6$aryl, 3-7-membered heterocyclyl, and 5-6-membered heteroaryl;

$X^2$ is N or CR$^{2a}$;
$X^3$ is N or CR$^{2c}$;
$X^4$ is N or CR$^{2d}$;
$X^5$ is N or CR$^{2e}$;
$X^6$ and $X^7$ are independently N or CR$^{2n}$, wherein at least one of $X^6$ and $X^7$ is N;

$R^{1z}$ is H, D, halogen, —CN, —$NO_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —$NO_2$, —$SR^{11a}$, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —$OR^{13a}$, —$C(O)R^{13b}$, —$P(O)R^{13b}R^{14b}$, —$S(O)_2R^{13b}$, —$S(O)R^{13b}$, —$NR^{13a}R^{14a}$, —$NR^{13a}C(O)R^{14a}$, —$NR^{13a}C(O)OR^{14a}$, —$NR^{13a}C(O)NR^{14a}$, and —$NR^{13a}S(O)_2R^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^{2a}$ is H, D, halogen, —CN, —$OR^{15a}$, $C_1$-$C_6$alkyl, $C_3$-$C_{10}$cycloalkyl, —$C(O)NR^{15a}R^{16a}$, —$C(O)OR^{15a}$, —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$, each $R^{2j}$, $R^{2k}$, $R^{2m}$, and $R^{2n}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2j}$, $R^{2k}$, $R^{2m}$, and $R^{2n}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

each $R^{2g}$ and $R^{2h}$ is independently H, $C_1$-$C_6$alkyl, $C_3$-$C_{10}$cycloalkyl, 3-7-membered heterocyclyl, $C_6$aryl, or 5-membered heteroaryl, wherein the 3-7-membered heterocyclyl and 5-membered heteroaryl are attached to the nitrogen at a carbon on the 3-7-membered heterocyclyl or 5-membered heteroaryl, and wherein the $C_1$-$C_6$alkyl, $C_3$-$C_{10}$cycloalkyl. 3-7-membered heterocyclyl, $C_6$aryl, or 5-membered heteroaryl are independently unsubstituted or substituted with one or more substituents selected from the group consisting of D, —CN, halogen, $C_1$-$C_6$alkyl, —$OR^{21a}$, —$C(O)R^{21b}$, —$P(O)R^{21b}R^{22b}$, —$S(O)_2R^{21b}$, —$S(O)R^{21b}$, —$NR^{21a}R^{22a}$, —$NR^{21a}C(O)R^{22a}$, —$NR^{21a}C(O)OR^{22a}$, —$NR^{21a}C(O)NR^{22a}$, —$NR^{21a}S(O)_2R^{22a}$, $C_3$-$C_{10}$cycloalkyl, $C_6$aryl, 3-7-membered heterocyclyl, and 5-membered heteroaryl;

$R^{3a}$, $R^{4a}$, $R^{7a}$, $R^{8a}$, $R^{11a}$, $R^{12a}$, $R^{13a}$, $R^{14a}$, $R^{15a}$, $R^{16a}$, $R^{17a}$, $R^{18a}$, $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$ alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{15b}$, $R^{17b}$, $R^{18b}$, $R^{21b}$, $R^{22b}$, $R^{23b}$, and $R^{24b}$ are independently, at each occurrence, H, D, —OH, —O($C_1$-$C_6$alkyl), —$NH_2$, —NH($C_1$-$C_6$alkyl), —N($C_1$-$C_6$alkyl)$_2$, —NHS(O)$_2$$CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$ alkyl)$_2$, $C_3$-$C_{10}$cycloalkyl, $C_6$aryl, 3-7-membered heterocyclyl, and 5-6 membered heteroaryl.

The present disclosure provides a compound having the structure of Formula (I-6),

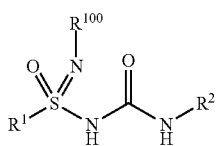

(I-6)

and pharmaceutically acceptable salts, solvates, isomers, prodrugs, and tautomers thereof, wherein:

$R^{100}$ is selected from the group consisting of H, Cl, D, —CN, —$NO_2$, —$OR^{3a}$, —C(O)$R^{3b}$, —S(O)$_2$$R^{3b}$, —S(O)$R^{3b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{3a}$, —C(O)$R^{3b}$, —P(O)$R^{3b}R^{4b}$, —S(O)$_2$$R^{3b}$, —S(O)$R^{3b}$, —$NR^{3a}R^{4a}$, —$NR^{3a}$C(O)$R^{4a}$, —$NR^{3a}$C(O)O$R^{4a}$, —$NR^{3a}$C(O)$NR^{4a}$, —$NR^{3a}$S(O)$_2$$R^{4a}$, $C_3$-$C_{10}$cycloalkyl, $C_6$aryl, 3-7-membered heterocyclyl, and 5-6 membered heteroaryl;

$R^1$ is selected from the group consisting of

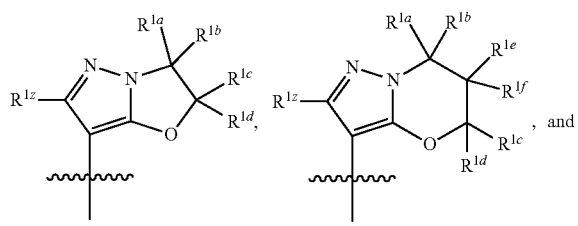
, and

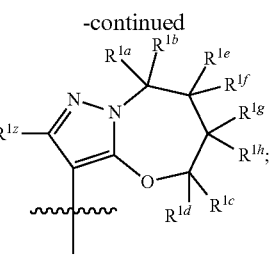

$R^2$ is

$X^2$ is N or $CR^{2a}$;
$X^3$ is N or $CR^{2c}$;
$X^4$ is N or $CR^{2d}$;
$X^5$ is N or $CR^{2e}$;

$R^{1z}$ is H, D, halogen, —CN, —$NO_2$, —$SR^{7a}$, —$OR^{7a}$, —C(O)$R^{7b}$, —P(O)$R^{7b}R^{8b}$, —S(O)$_2$$R^{7b}$, —S(O)$R^{7b}$, —$NR^{7a}R^{8a}$, —$NR^{7a}$C(O)$R^{8a}$, —$NR^{7a}$C(O)O$R^{8a}$, —$NR^{7a}$C(O)$NR^{8a}$, —$NR^{7a}$S(O)$_2$$R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{7a}$, —C(O)$R^{7b}$, —P(O)$R^{7b}R^{8b}$, —S(O)$_2$$R^{7b}$, —S(O)$R^{7b}$, —$NR^{7a}R^{8a}$, —$NR^{7a}$C(O)$R^{8a}$, —$NR^{7a}$C(O)O$R^{8a}$, —$NR^{7a}$C(O)$NR^{8a}$, —$NR^{7a}$S(O)$_2$$R^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —$NO_2$, —$SR^{11a}$, —$OR^{11a}$, —C(O)$R^{11b}$, —P(O)$R^{11b}R^{12b}$, —S(O)$_2$$R^{11b}$, —S(O)$R^{11b}$, —$NR^{11a}R^{12a}$, —$NR^{11a}$C(O)$R^{12a}$, —$NR^{11a}$C(O)O$R^{12a}$, —$NR^{11a}$C(O)$NR^{12a}$, —$NR^{11a}$S(O)$_2$$R^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{11a}$, —C(O)$R^{11b}$, —P(O)$R^{11b}R^{12b}$, —S(O)$_2$$R^{11b}$, —S(O)$R^{11b}$, —$NR^{11a}R^{12a}$, —$NR^{11a}$C(O)$R^{12a}$, —$NR^{11a}$C(O)O$R^{12a}$, —$NR^{11a}$C(O)$NR^{12a}$, —$NR^{11a}$S(O)$_2$$R^{12a}$, $C_3$-$C_{10}$cycloalkyl, $C_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —$OR^{13a}$, —$C(O)R^{13b}$, —$P(O)R^{13b}R^{14b}$, —$S(O)_2R^{13b}$, —$S(O)R^{13b}$, —$NR^{13a}R^{14a}$, —$NR^{13a}C(O)R^{14a}$, —$NR^{13a}C(O)OR^{14a}$, —$NR^{13a}C(O)NR^{14a}$, and —$NR^{13a}S(O)_2R^{14a}$; or two geminal groups $R^{1a}$ and $R^{1b}$; $R^{1c}$ and $R^{1d}$; $R^{1e}$ and $R^{1f}$; or $R^{1g}$ and $R^{1h}$, when present, can form an oxo group;

$R^{2a}$ is H, D, halogen, —CN, —$OR^{15a}$, $C_1$-$C_6$alkyl, $C_3$-$C_{10}$cycloalkyl, —$C(O)NR^{15a}R^{16a}$, —$C(O)OR^{15a}$; —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$.

$R^{3a}$, $R^{4a}$, $R^{7a}$, $R^{8a}$, $R^{11a}$, $R^{12a}$, $R^{13a}$, $R^{14a}$, $R^{15a}$, $R^{16a}$, $R^{17a}$, and $R^{18a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{15b}$, $R^{17b}$, and $R^{18b}$ are independently, at each occurrence, H, D, —OH, —$O(C_1$-$C_6$alkyl), —$NH_2$, —$NH(C_1$-$C_6$alkyl), —$N(C_1$-$C_6$alkyl)$_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl)$_2$, $C_3$-$C_{10}$cycloalkyl, $C_6$aryl, 3-7-membered heterocyclyl, and 5-6 membered heteroaryl.

In certain embodiments, $R^1$ is selected from the group consisting of

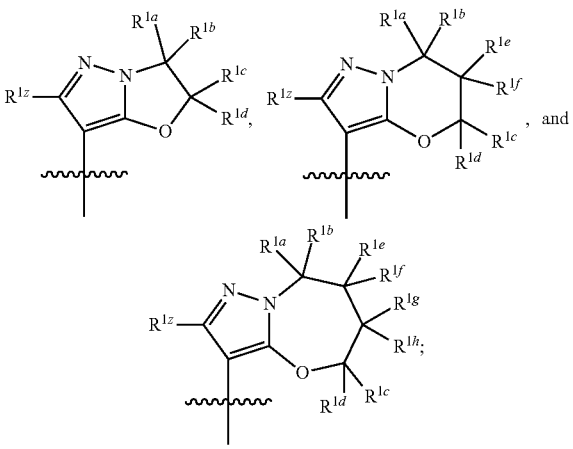

$R^{1z}$ is H, D, halogen, —CN, —$NO_2$, —$SR^{7a}$, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{7a}$, —$C(O)R^{7b}$, —$P(O)R^{7b}R^{8b}$, —$S(O)_2R^{7b}$, —$S(O)R^{7b}$, —$NR^{7a}R^{8a}$, —$NR^{7a}C(O)R^{8a}$, —$NR^{7a}C(O)OR^{8a}$, —$NR^{7a}C(O)NR^{8a}$, —$NR^{7a}S(O)_2R^{8a}$, $C_3$-$C_{10}$cycloalkyl, $C_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from H, D, halogen, —CN, —$NO_2$, —$SR^{11a}$, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —$OR^{11a}$, —$C(O)R^{11b}$, —$P(O)R^{11b}R^{12b}$, —$S(O)_2R^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, R$^{1a}$, R$^{1b}$, R$^{1c}$, R$^{1d}$, R$^{1e}$, R$^{1f}$, R$^{1g}$, and R$^{1b}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, C$_1$-C$_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups R$^{1a}$ and R$^{1b}$; R$^{1c}$ and R$^{1d}$; R$^{1e}$ and R$^{1f}$; or R$^{1g}$ and R$^{1b}$, when present, can form an oxo group;

R$^{7a}$, R$^{8a}$, R$^{11a}$, R$^{12a}$, R$^{13a}$, and R$^{14a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl;

R$^{7b}$, R$^{8b}$, R$^{11b}$, R$^{12b}$, R$^{13b}$, and R$^{14b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

In certain embodiments, R$^{100}$ is H. In certain embodiments, R$^{100}$ is C$_1$-C$_6$alkyl, wherein the C$_1$-C$_6$alkyl is unsubstituted or substituted with one or more substituents selected from the group consisting of C$_3$-C$_{10}$cycloalkyl, C$_6$aryl, 3-7-membered heterocyclyl, and 5-6 membered heteroaryl. In certain embodiments, R$^{100}$ is C$_1$-C$_6$alkyl, wherein the C$_1$-C$_6$alkyl is unsubstituted or substituted with C$_6$aryl.

As described above, R$^2$ is selected from the group consisting of C$_1$-C$_6$alkyl, C$_3$-C$_{10}$cycloalkyl, 3-7-membered heterocyclyl, 5-membered heteroaryl, 6-membered heteroaryl, C$_6$aryl, and —NR$^{2g}$R$^{2h}$; wherein the C$_1$-C$_6$alkyl, C$_3$-C$_{10}$cycloalkyl, 3-7-membered heterocyclyl, 5-membered heteroaryl, 6-membered heteroaryl, and C$_6$aryl are independently unsubstituted or substituted with one or more substituents selected from the group consisting of D, —CN, halogen, C$_1$-C$_6$alkyl, C$_1$-C$_6$haloalkyl, C$_1$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl.

In certain embodiments, R$^2$ is 6-membered heteroaryl. In certain embodiments, the 6-membered heteroaryl has 6-10 annular atoms. In certain embodiments, the 6-membered heteroaryl has 6-9 annular atoms. In certain embodiments, the 6-membered heteroaryl has 6 annular atoms.

In certain embodiments, R$^2$ is a 6-membered heteroaryl containing 1 or 2 nitrogens. In certain embodiments, R$^2$ is a 6-membered heteroaryl containing 1 nitrogen. In certain embodiments, R$^2$ is a 6-membered heteroaryl containing 2 nitrogens.

In certain embodiments, the 6-membered heteroaryl is

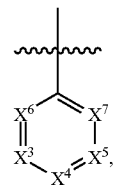

wherein X$^3$ is N or CR$^{2c}$; X$^4$ is N or CR$^{2d}$; X$^5$ is N or CR$^{2e}$; and X$^6$ and X$^7$ are independently N or CR$^{2n}$.

In certain embodiments, R$^2$ is an unsubstituted or substituted 6-membered heteroaryl, where the 6-membered heteroaryl is selected from the group consisting of

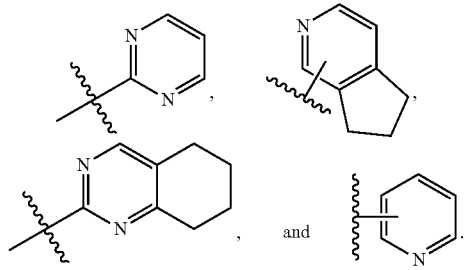

In certain embodiments, R$^2$ is 6-membered heteroaryl is substituted with one or more substituents selected from the group consisting of halogen, C$_1$-C$_6$alkyl, C$_1$-C$_6$haloalkyl, C$_6$aryl, —OR$^{23a}$, C$_3$-C$_{10}$cycloalkyl, C$_2$-C$_6$alkenyl, —CN, and —NR$^{23a}$R$^{24a}$.

In certain embodiments, R$^2$ is C$_6$aryl. In certain embodiments the aryl ring is a C$_6$-aryl with 6-14 annular atoms. In certain embodiments the aryl ring is a C$_6$ aryl with 6-10 annular atoms. In certain embodiments the aryl ring is a C$_6$ aryl with 6-12 annular atoms. In certain embodiments the aryl ring is a C$_6$ aryl with 6 annular atoms.

In certain embodiments, R$^2$ is selected from the group consisting of C$_1$-C$_6$alkyl, C$_3$-C$_{10}$cycloalkyl, 3-7-membered heterocyclyl, 5-membered heteroaryl, —NR$^{2g}$R$^{2h}$,

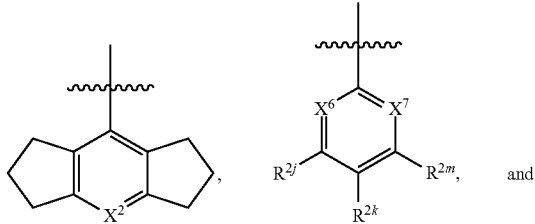

and 9-fluorenyl

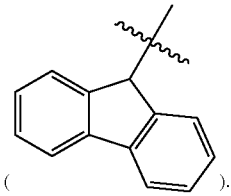

As noted above, cycloalkyl rings can be further characterized by the number of annular atoms. For example, a cyclohexyl ring is a $C_6$cycloalkyl ring with 6 annular atoms, while 2-(2,3-dihydro-1H-indene) is a $C_5$cycloalkyl ring with 9 annular atoms. Also, for example, 9-fluorenyl is a $C_5$cycloalkyl ring with 13 annular atoms and 2-adamantyl is a $C_6$cycloalkyl ring with 10 annular atoms.

In certain embodiments, $R^2$ is an unsubstituted or substituted $C_3$-$C_{10}$cycloalkyl, where the $C_3$-$C_{10}$cycloalkyl is selected from the group consisting of

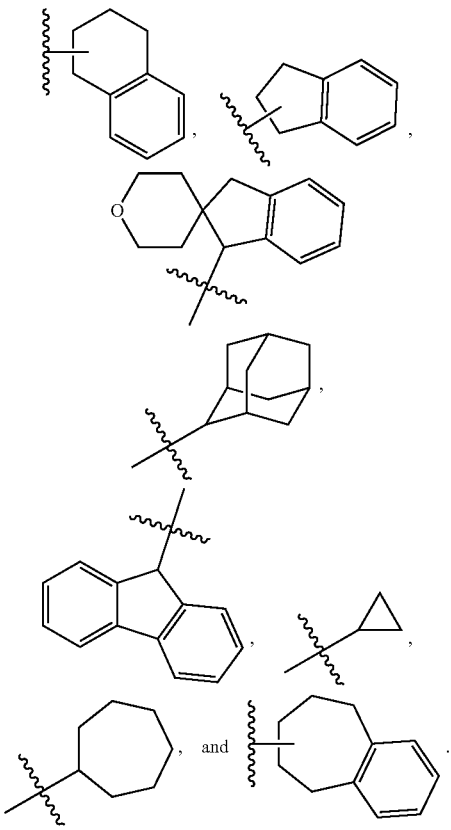

In certain embodiments, $R^2$ is $C_3$-$C_{10}$cycloalkyl substituted with one or more substituents selected from the group consisting of $C_1$-$C_6$alkyl and $C_6$aryl.

In certain embodiments, $R^2$ is a 3-7 membered heteocyclyl. In certain embodiments, the 3-7 membered heteocyclyl has 3-7 annular atoms. In certain embodiments, the 3-7 membered heteocyclyl has 3-14 annular atoms. In certain embodiments, the 3-7 membered heteocyclyl has 3-12 annular atoms. In certain embodiments, the 3-7 membered heteocyclyl has 3-10 annular atoms. In certain embodiments, $R^2$ is a 3-6 membered heteocyclyl. In certain embodiments, the 3-6 membered heteocyclyl has 3-6 annular atoms. In In certain embodiments, $R^2$ is

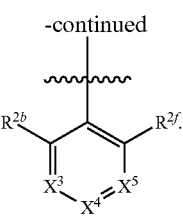

In certain embodiments, $R^2$ is

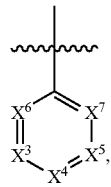

wherein $X^3$ is N or $CR^{2c}$; $X^4$ is N or $CR^{2d}$; $X^5$ is N or $CR^{2e}$; and $X^6$ and $X^7$ are independently N or $CR^{2n}$.

In certain embodiments, $R^2$ is $C_1$-$C_6$alkyl. In certain embodiments, $R^2$ is $C_1$alkyl, $C_2$alkyl, $C_3$alkyl, $C_4$alkyl, $C_5$alkyl, or $C_6$alkyl. In certain embodiments, $R^2$ is $C_1$-$C_6$alkyl substituted with one or more $C_6$aryl.

In certain embodiments, $R^2$ is a $C_3$-$C_{10}$cycloalkyl. In certain embodiments, the $C_3$-$C_{10}$cycloalkyl has 3-14 annular atoms. In certain embodiments, the $C_3$-$C_{10}$cycloalkyl has 3-12 annular atoms. In certain embodiments, the $C_3$-$C_{10}$cycloalkyl has 3-10 annular atoms. In certain embodiments, $R_2$ is a $C_3$-$C_9$cycloalkyl with 3-9 annular atoms. In certain embodiments, $R^2$ is a $C_3$-$C_9$cycloalkyl with 3-14 annular atoms. In certain embodiments, $R_2$ is a $C_3$-$C_9$cycloalkyl with 3-10 annular atoms. In certain embodiments, $R_2$ is a $C_3$-$C_8$cycloalkyl with 3-8 annular atoms. In certain embodiments, $R_2$ is a $C_3$-$C_8$cycloalkyl with 3-14 annular atoms. In certain embodiments, $R_2$ is a $C_3$-$C_7$cycloalkyl with 3-14 annular atoms. In certain embodiments, $R_2$ is a $C_3$-$C_7$cycloalkyl with 3-10 annular atoms. In certain embodiments, $R_2$ is a $C_3$-$C_7$cycloalkyl with 3-7 annular atoms.

In certain embodiments, $R^2$ is $C_5$cycloalkyl, $C_6$cycloalkyl, or $C_7$cycloalkyl.

Examples of cycloalkyl groups include cyclohexyl, cycloheptyl, 2-adamantyl

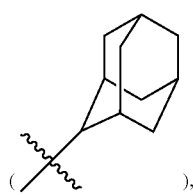 [SMILES: *C1C2CC3CC(C2)CC1C3]

2-(2,3-dihydro-1H-indene)

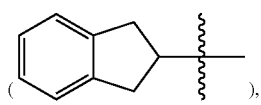 [SMILES: *C1Cc2ccccc2C1]

certain embodiments, R² is a 3-5 membered heteocyclyl. In certain embodiments, the 3-5 membered heteocyclyl has 3-5 annular atoms. In certain embodiments, the 3-5 membered heteocyclyl has 3-9 annular atoms.

In certain embodiments, R² is an unsubstituted or substituted 3-7 membered heterocyclyl, where the 3-7 membered heterocyclyl is selected from the group consisting of

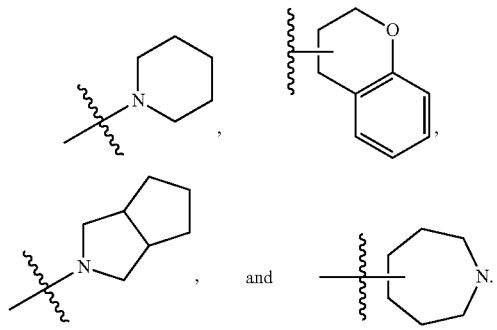

In certain embodiments, R² is 3-7 membered heterocyclyl substituted with one or more $C_1$-$C_6$alkyl.

In certain embodiments, R² is a 5-membered heteroaryl. In certain embodiments, the 5-membered heteroaryl has 5 annular atoms. In certain embodiments, the 5-membered heteroaryl has 5-8 annular atoms. In certain embodiments, the 5-membered heteroaryl has 5-9 annular atoms. In certain embodiments, the 5-membered heteroaryl has 5-10 annular atoms. In certain embodiments, the 5-membered heteroaryl has 5-12 annular atoms.

In certain embodiments, R² is a 5-membered heteroaryl containing 1 or 2 nitrogens. In certain embodiments, R² is a 5-membered heteroaryl containing 1 nitrogen. In certain embodiments, R² is a 5-membered heteroaryl containing 2 nitrogens.

In certain embodiments, R² is an unsubstituted or substituted 5-membered heteroaryl, where the 5-membered heteroaryl is selected from the group consisting of

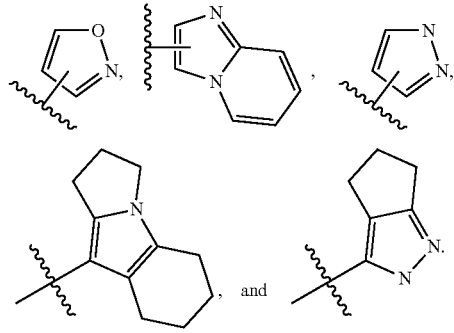

In certain embodiments, R² is 5-membered heteroaryl substituted with one or more substituents selected from the group consisting of $C_1$-$C_6$alkyl, $C_6$aryl, oxo, and —(CH₂)₁₋₄$C_3$-$C_{10}$cycloalkyl.

In certain embodiments, R² is 5-membered heteroaryl is selected from the group consisting of

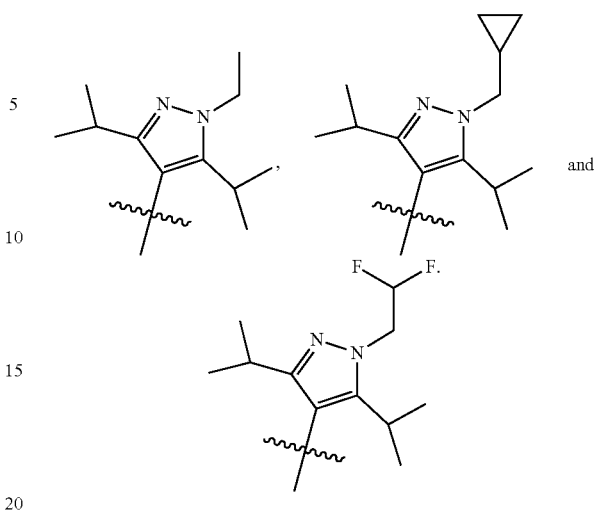

In certain embodiments, R² is

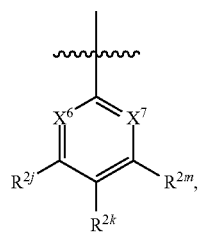

$X^6$ and $X^7$ are independently N or $CR^{2n}$, wherein at least one of $X^6$ and $X^7$ is N. In certain embodiments, one of $X^6$ and $X^7$ is N. In certain embodiments, $X^6$ and $X^7$ are N.

In certain embodiments, R² is —NR$^{2g}$R$^{2h}$. As described above, each R$^{2g}$ and R$^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{21a}$, —C(O)R$^{21b}$, —P(O)R$^{21b}$R$^{22b}$, —S(O)₂R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)₂R$^{22a}$, —(CH₂)₁₋₄$C_3$-$C_{10}$cycloalkyl, $C_3$-$C_{10}$cycloalkyl, $C_6$aryl, 3-7-membered heterocyclyl, and 5-6-membered heteroaryl. In certain embodiments, R$^{2g}$ is H and R$^{2b}$ is D, $C_1$-$C_6$alkyl, $C_3$-$C_{10}$cycloalkyl, $C_6$aryl, 3-7 membered heterocyclyl, or 5-6 membered heteroaryl.

In certain embodiments, R² is

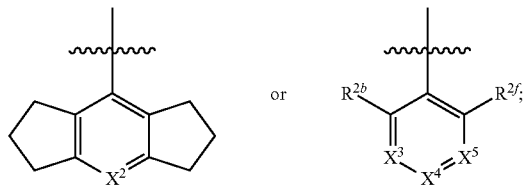

wherein $X^2$ is N or $CR^{2a}$; $X^3$ is N or $CR^{2c}$; $X^4$ is N or $CR^{2d}$; and $X^5$ is N or $CR^{2e}$.

In certain embodiments, $R^2$ is

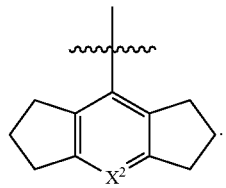

In certain embodiments, $X^2$ is $CR^{2a}$. In certain embodiments, $X^2$ is N.

In certain embodiments, $R^{2a}$ is H, halogen, $C_1$-$C_6$alkyl, or —$COR^{3b}$. In certain instances, $R^{2a}$ is H, fluoro, chloro, methyl, or —COOH.

In certain embodiments, $R^2$ is

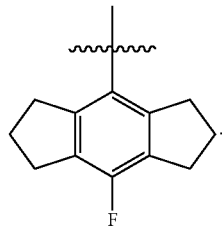 [SMILES: *c1c2c(c(F)c3c1CCC3)CCC2]

In certain embodiments, $R^2$ is

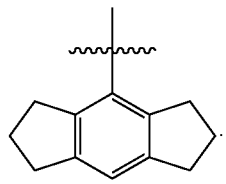 [SMILES: *c1c2c(cc3c1CCC3)CCC2]

In certain embodiments, $R^2$ is

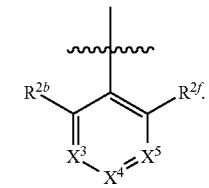

In certain embodiments, $X^3$ is $CR^{2c}$; $X^4$ is $CR^{2d}$; and $X^5$ is $CR^{2d}$.

In certain embodiments, each $R^{2b}$, $R^{2c}$, $R^{2d}$, $R^{2e}$, and $R^{2f}$ is independently selected from the group consisting of H, D, halogen, $C_1$-$C_6$alkyl, $C_3$-$C_{10}$cycloalkyl, and —CN. In certain instances, each $R^{2b}$, $R^{2c}$, $R^{2d}$, $R^{2e}$, and $R^{2f}$ is independently selected from the group consisting of H, halogen, and $C_1$-$C_6$alkyls. In certain instances, two of $R^{2b}$, $R^{2c}$, $R^{2d}$, $R^{2e}$, and $R^{2f}$ is independently selected from the group consisting of halogen and $C_1$-$C_6$alkyl. In certain instances, three of $R^{2b}$, $R^{2c}$, $R^{2d}$, $R^{2e}$, and $R^{2f}$ is independently selected from the group consisting of halogen and $C_1$-$C_6$alkyl.

In certain embodiments, $R^2$ is

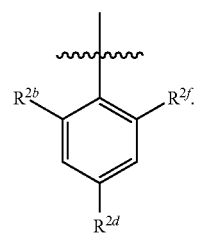

In certain instances, $R^{2b}$ and $R^{2f}$ are $C_1$-$C_6$alkyl. In certain instances, $R^{2d}$ is halogen.

In certain embodiments, $R^2$ is

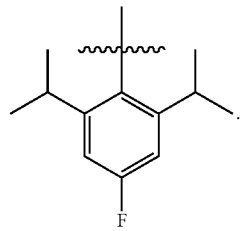 [SMILES: *c1c(C(C)C)cc(F)cc1C(C)C]

In certain embodiments, $X^3$ is N; $X^4$ is $CR^{2d}$; and $X^5$ is $CR^{2d}$. In certain embodiments, $X^3$ is $CR^{2c}$; $X^4$ is N; and $X^5$ is $CR^{2d}$. In certain embodiments, $X^3$ is $CR^{2c}$; $X^4$ is $CR^{2d}$; and $X^5$ is N.

As described above, $R^1$ is selected from the group consisting of

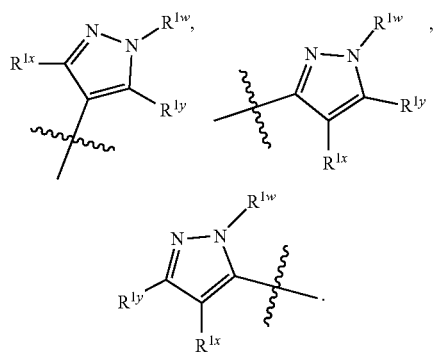

In certain embodiments, $R^1$ is

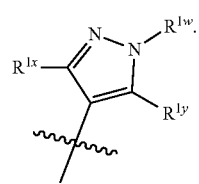

In certain embodiments, $R^1$ is

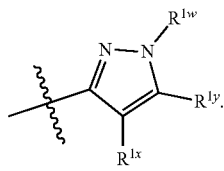

In certain embodiments, $R^1$ is

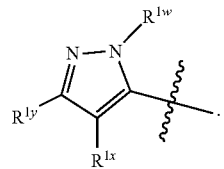

In certain embodiments, $R^{1w}$ and $R^{1y}$ do not come together with the atoms to which they are attached to form a 3-7-membered heterocyclyl.

In certain embodiments, $R^{1x}$ and $R^{1y}$ do not come together with the atoms to which they are attached to form a $C_3$-$C_{10}$cycloalkyl or a 3-7-membered heterocyclyl.

In certain embodiments, $R^{1y}$, and the atoms to which it is attached, does not come together with either $R^{1x}$ or $R^{1w}$, or their attached atoms, to form a $C_1$-$C_{10}$cycloalkyl or a 3-7-membered heterocyclyl.

In certain embodiments, at least one of $R^{1w}$, $R^{1x}$, and R1y is other than H. In certain embodiments one of $R^{1w}$, $R^{1x}$, and $R^{1y}$ is other than H. In certain embodiments, $R^{1w}$, $R^{1x}$, and $R^{1y}$ are other than H. In certain embodiments, $R^{1w}$, $R^{1x}$, and $R^{1y}$ are H.

In certain embodiments, $R^{1w}$ is selected from the group consisting of H, D, —CN, —C(O)$R^{5b}$, —S(O)$_2R^{5b}$, —S(O)$R^{5b}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, $C_3$-$C_{10}$cycloalkyl, $C_6$aryl, 3-7-membered heterocyclyl, and 5-6 membered heteroaryl.

In certain embodiments, each $R^{1x}$ and $R^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl.

In certain embodiments, $R^{1w}$ is H or $C_1$-$C_6$alkyl. In certain embodiments, $R^{1x}$ is H or $C_1$-$C_6$alkyl. In certain embodiments, $R^{1y}$ is H or $C_1$-$C_6$alkyl.

In certain embodiments, $R^{1w}$ and $R^{1y}$, together with the atoms to which they are attached can form a 3-7-membered heterocyclyl; wherein the 3-7-membered heterocyclyl are independently unsubstituted or substituted with one or more substituents selected from the group consisting of D, —CN, halogen, $C_1$-$C_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$.

In certain embodiments, when $R^{1w}$ and $R^{1y}$ come together with the atoms to which they are attached to form a 3-7-membered heterocyclyl, $R^{1w}$ and $R^{1y}$ are adjacent.

In certain embodiments, $R^{1x}$ and $R^{1y}$, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$.

In certain embodiments, when $R^{1x}$ and $R^{1y}$ come together with the atoms to which they are attached to form a $C_3$-$C_{10}$cycloalkyl or a 3-7-membered heterocyclyl, $R^{1x}$ and $R^{1y}$ are adjacent.

In certain embodiments, when $R^{1x}$ and $R^{1y}$ come together with the atoms to which they are attached to form a 5-6 membered aryl or heteroaryl, $R^{1x}$ and $R^{1y}$ are adjacent.

In certain embodiments, $R^{1z}$ is H.

As described above, in certain embodiments, $R^1$ is selected from the group consisting of

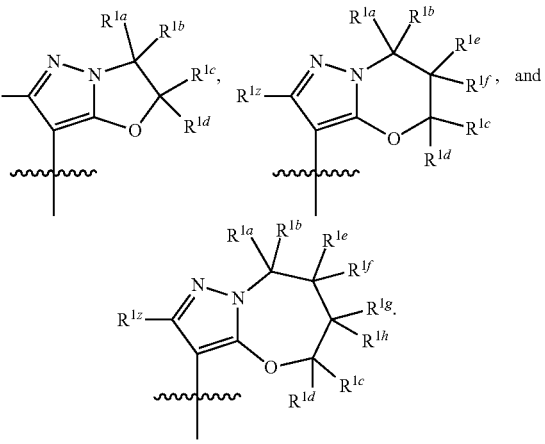

In certain embodiments, $R^1$ is

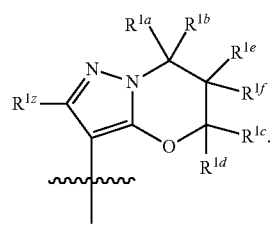

In certain embodiments, $R^1$ is
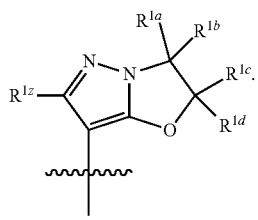
In certain embodiments, $R^1$ is
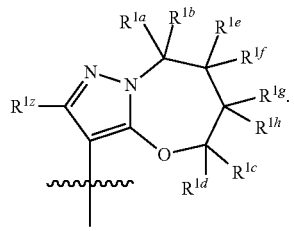
In certain embodiments, $R^1$ is
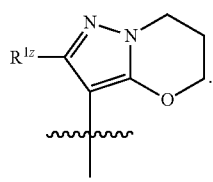
In certain embodiments, $R^1$ is
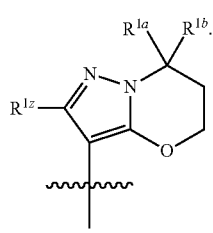
In certain embodiments, $R^1$ is
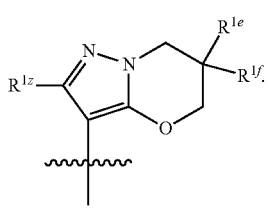
In certain embodiments, $R^1$ is
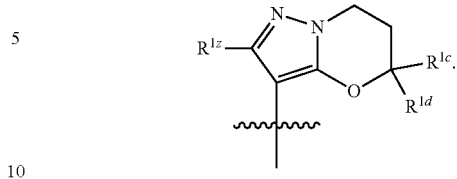
In certain embodiments, $R^1$ is selected from the group consisting of
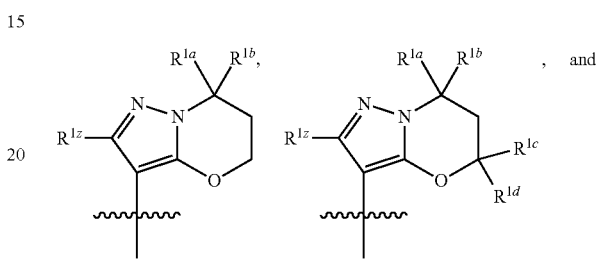
In certain embodiments, $R^1$ is selected from the group consisting of
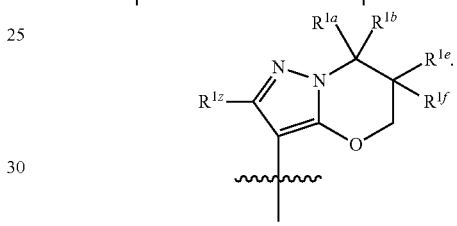
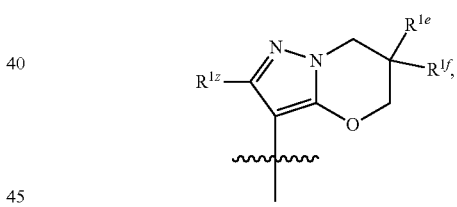
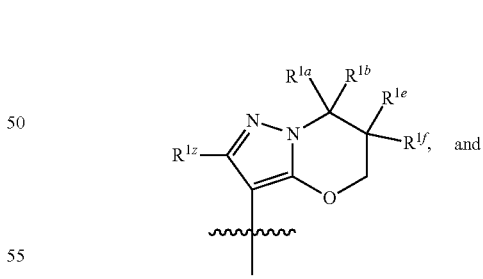
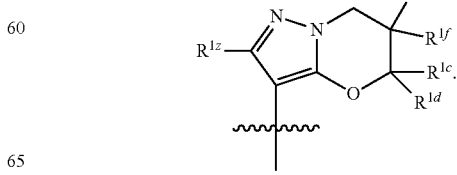

In certain embodiments, R¹ is selected from the group consisting of

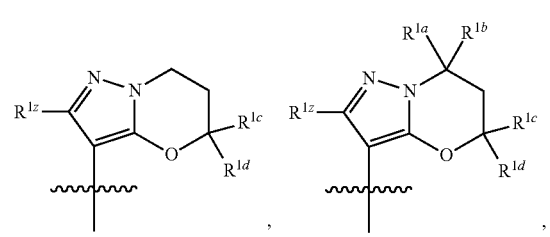

, and


.

In certain embodiments, R¹ is


In certain embodiments, R¹ is

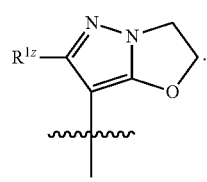

In certain embodiments, R¹ is

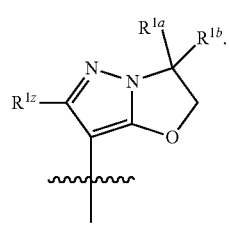

.

In certain embodiments, R¹ is

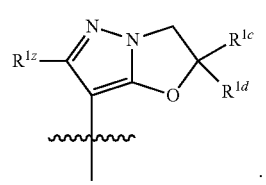

In certain embodiments, R¹ is

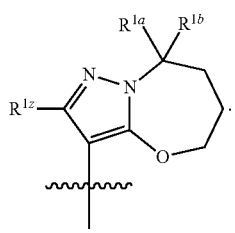

.

In certain embodiments, R¹ is

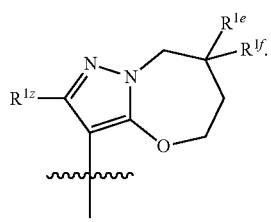

.

In certain embodiments, R¹ is

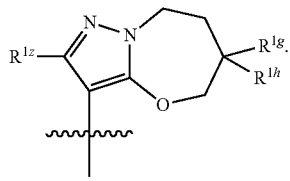

.

In certain embodiments, R¹ is

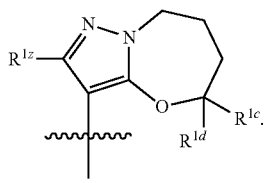

.

In certain embodiments, R¹ is selected from the group consisting of

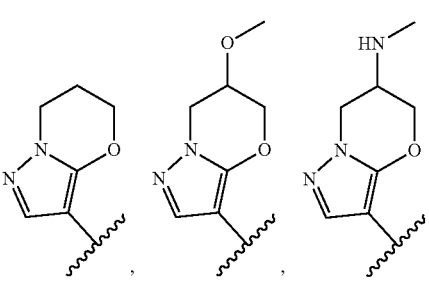

,

-continued
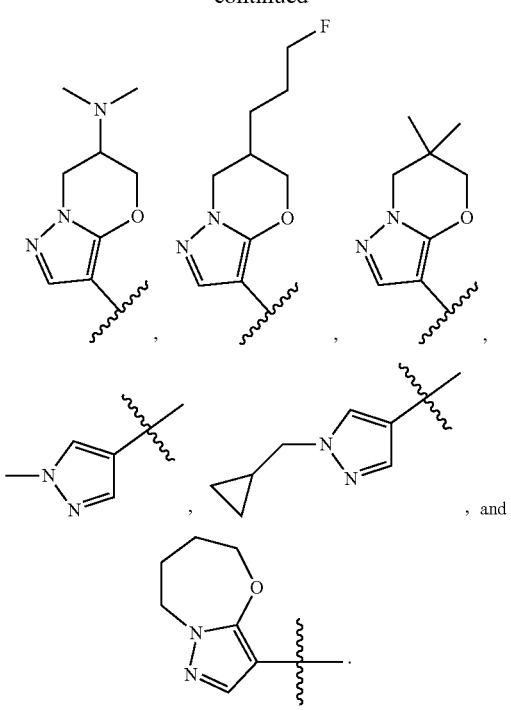
In certain embodiments, $R^1$ is selected from the group consisting of
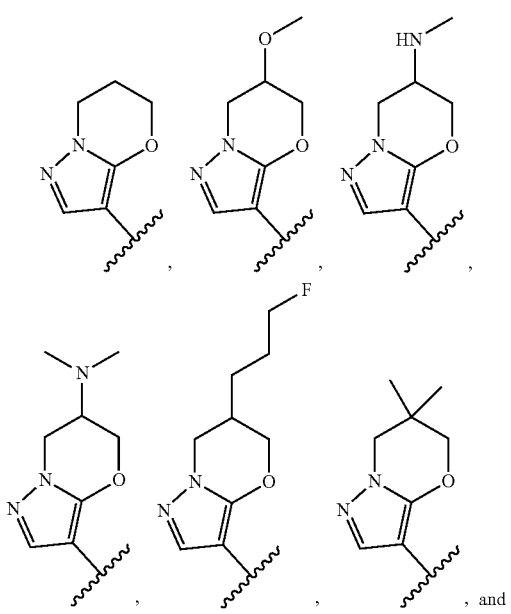
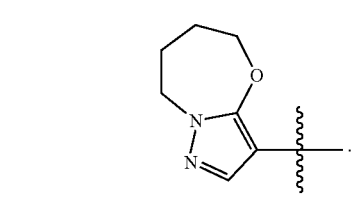
In certain embodiments, $R^1$ is selected from the group consisting of
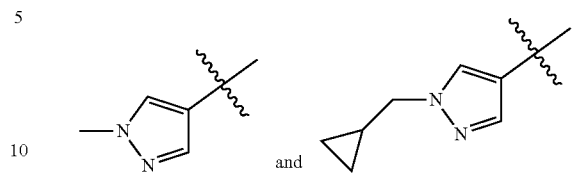
In certain embodiments, $R^1$ is selected from the group consisting of
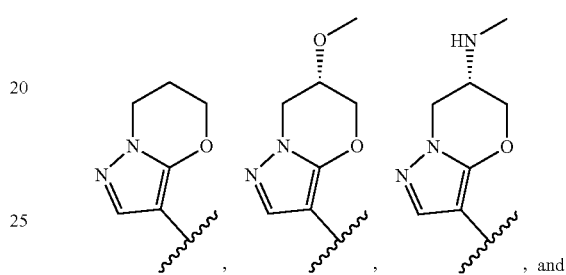
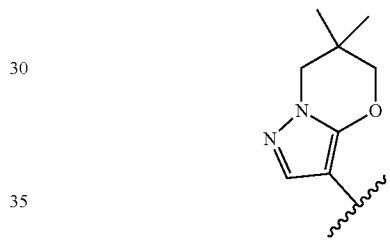
In certain embodiments, $R^1$ is selected from the group consisting of
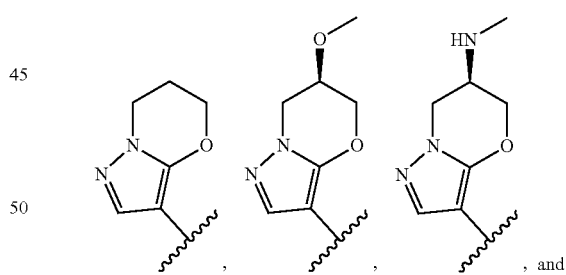
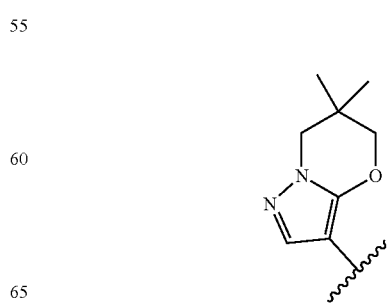

In certain embodiments, $R^1$ is selected from the group consisting of
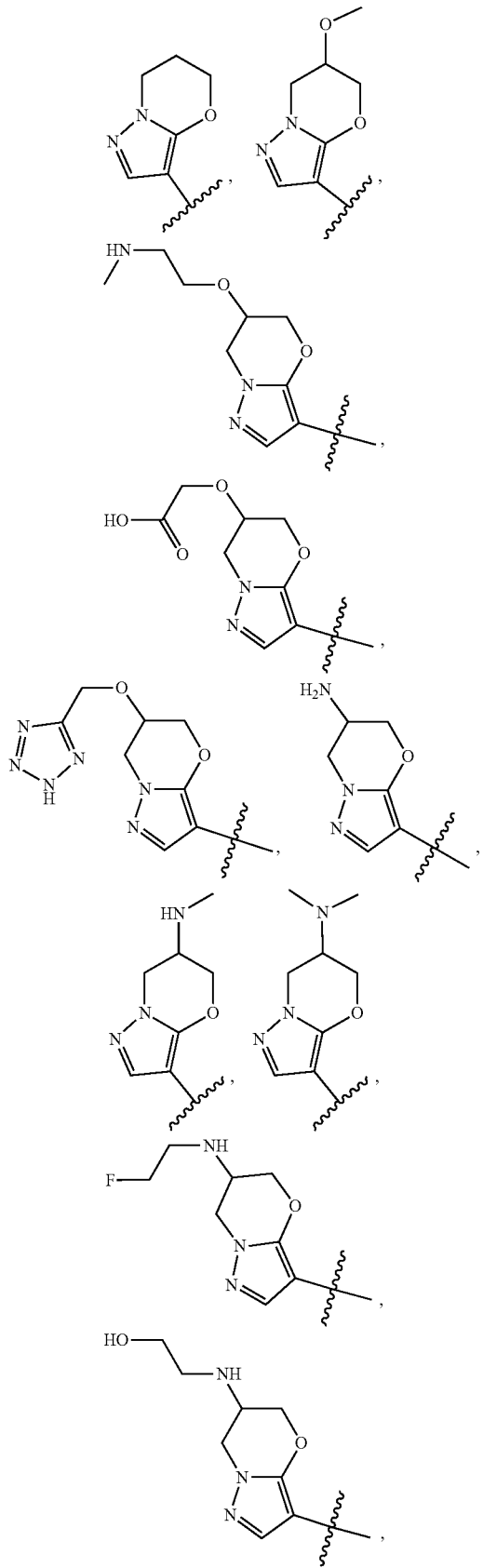
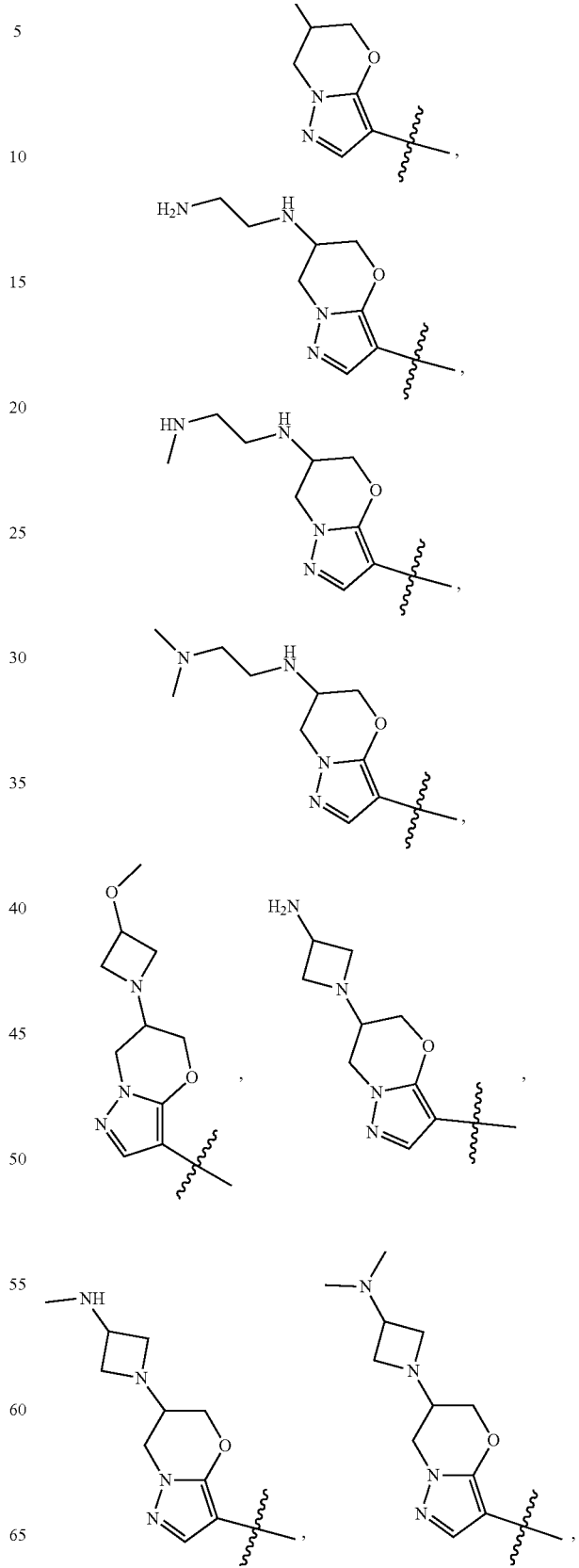

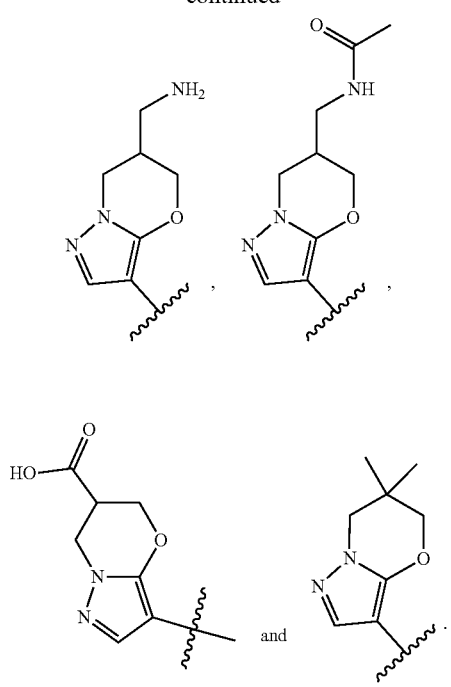
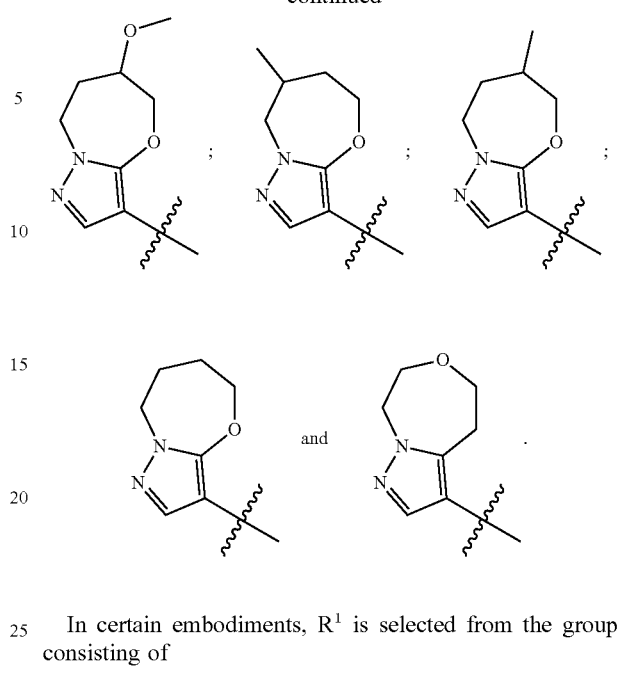
In certain embodiments, $R^1$ is selected from the group consisting of
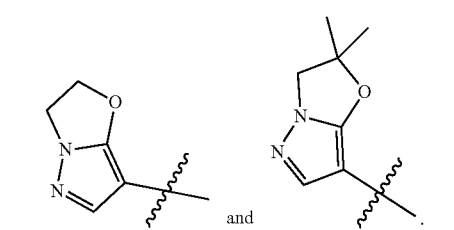 [SMILES: *c1cnn2c1OCC2 ; *c1cnn2c1OC(C)(C)C2]
In certain embodiments, $R^1$ is selected from the group consisting of
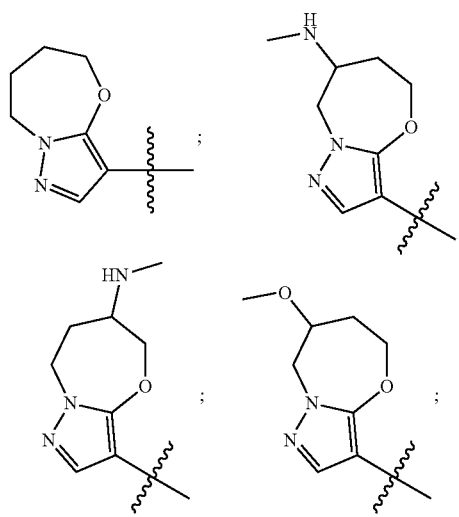
In certain embodiments, $R^1$ is selected from the group consisting of
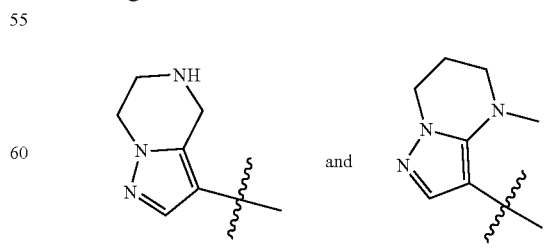
In certain embodiments, $R^1$ is selected from the group consisting of

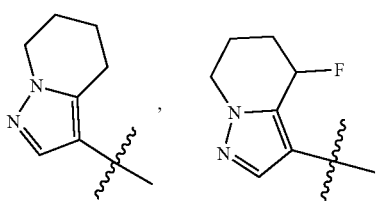 and
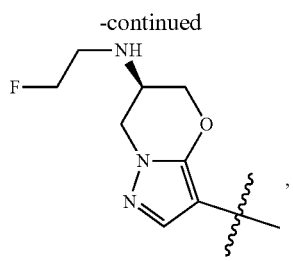
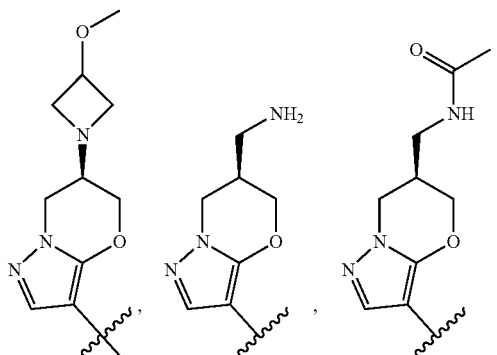
In certain embodiments, R¹ is
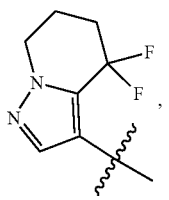
In certain embodiments, R¹ is selected from the group consisting of
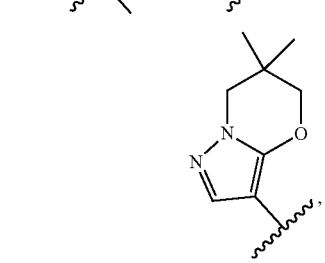
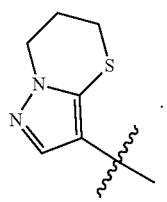 [SMILES: *c1cnn2c1SCCC2]
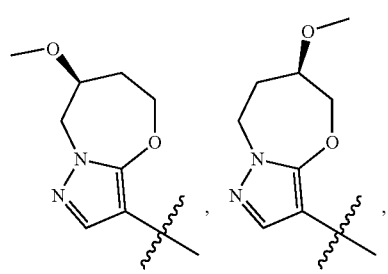
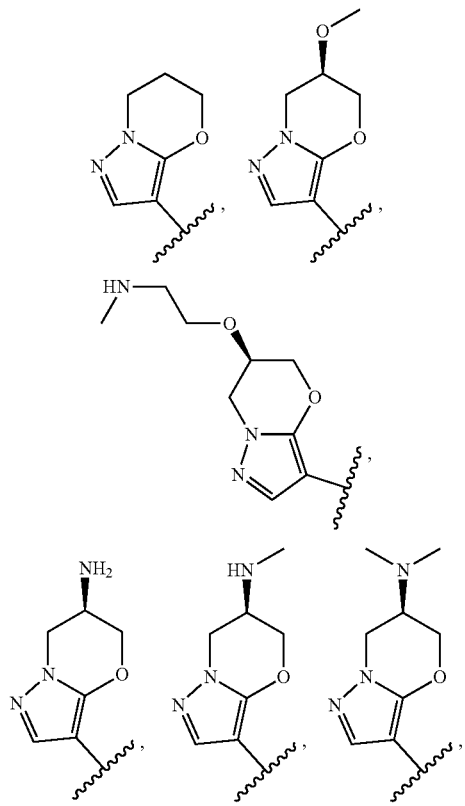
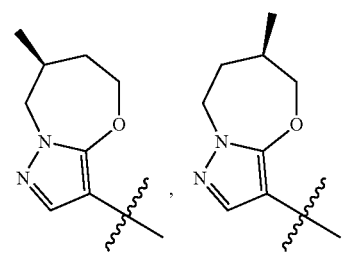
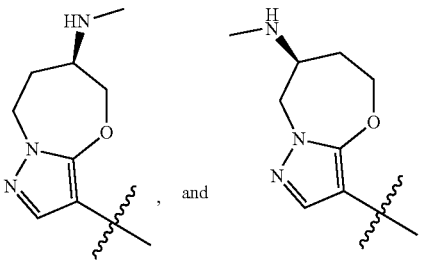
In certain embodiments, R¹ is selected from the group consisting of

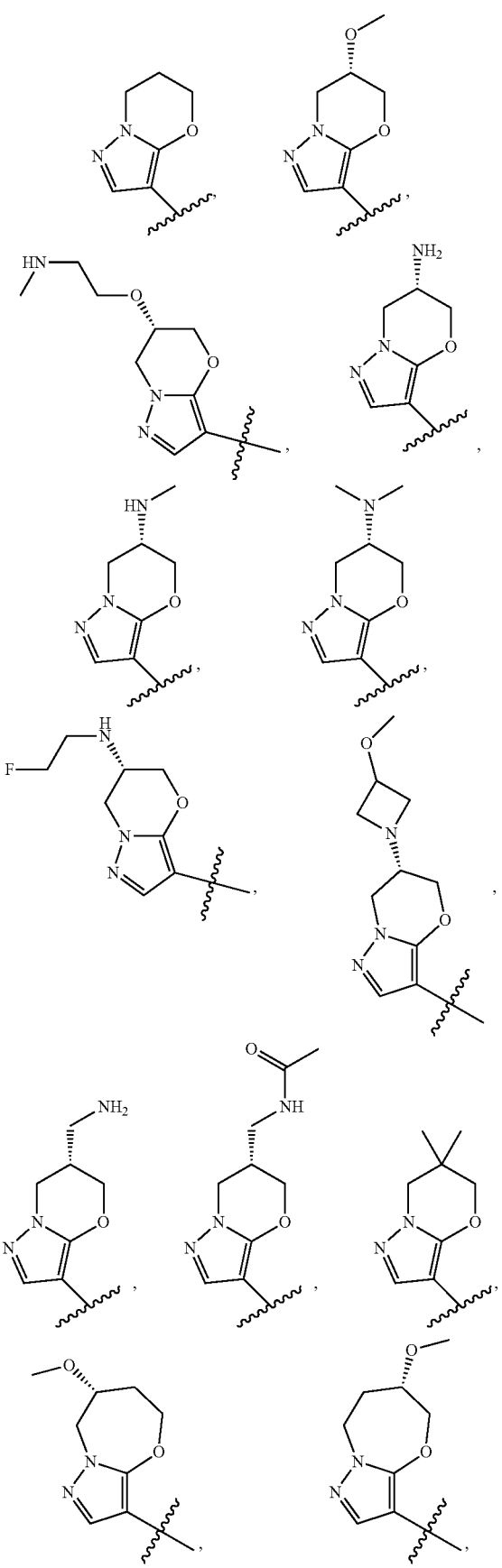

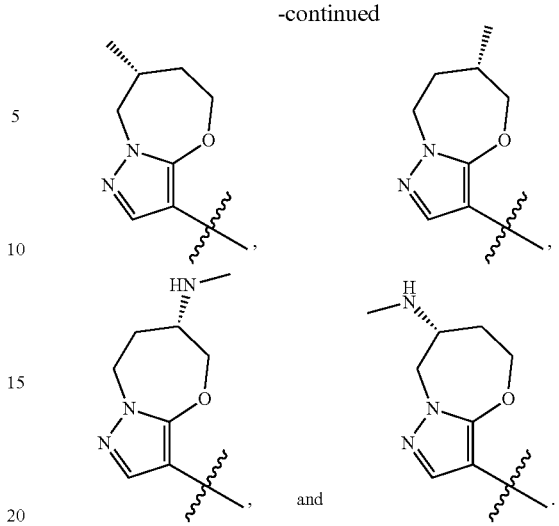

In certain embodiments, $R^{1a}$ and $R^{1b}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H. In certain embodiments, $R^{1a}$ and $R^{1b}$ are H.

In certain embodiments, $R^{1c}$ and $R^{1d}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H. In certain embodiments, $R^{1c}$ and $R^{1d}$ are H.

In certain embodiments, $R^{1e}$ and $R^{1f}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl. In certain embodiments, at least one of $R^{1e}$ and $R^{1f}$ is other than H. In certain embodiments one of $R^{1e}$ and $R^{1f}$ is other than H. In certain embodiments, both $R^{1e}$ and $R^{1f}$ are other than H. In certain embodiments, $R^{1e}$ and $R^{1f}$ are H.

In certain embodiments, $R^{1g}$ and $R^{1b}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl. In certain embodiments, at least one of $R^{1g}$ and $R^{1b}$ is other than H. In certain embodiments one of $R^{1g}$ and $R^{1b}$ is other than H. In certain embodiments, both $R^{1g}$ and $R^{1b}$ are other than H. In certain embodiments, $R^{1g}$ and $R^{1b}$ are H.

Compounds of the present disclosure can contain a basic amino group. Incorporation of a basic amino group to a compound of the present disclosure, which can also bear an acidic moiety, would be expected to exist as a zwitterion, having a net zero charge. Zwitterionic compounds can have different physicochemical properties than weak organic acids. Notably, there may be increased volumes of distribution in vivo as well as lowered plasma protein binding.

In certain embodiments, at least one of $R^{1a}$, $R^{1b}$, $R^{1c}$, $R^{1d}$, $R^{1e}$, $R^{1f}$, $R^{1g}$, and $R^{1b}$ is —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, the 3-7-membered heterocyclyl contains a nitrogen.

In certain embodiments, at least one of $R^{1a}$, $R^{1b}$, $R^{1c}$, $R^{1d}$, $R^{1e}$, $R^{1f}$, $R^{1g}$, and $R^{1b}$ is —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, the 3-7-membered heterocyclyl contains a nitrogen.

In certain embodiments, $R^{1a}$ and $R^{1b}$ are independently H, —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, $R^{1a}$ is H and $R^{1b}$ is —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, the 3-7-membered heterocyclyl contains a nitrogen. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H.

In certain embodiments, $R^{1a}$ and $R^{1b}$ are independently H, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, $R^{1a}$ is H and $R^{1b}$ is —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, the 3-7-membered heterocyclyl contains a nitrogen. In certain embodiments, at least one of $R^{1a}$ and $R^{1b}$ is other than H. In certain embodiments one of $R^{1a}$ and $R^{1b}$ is other than H. In certain embodiments, both $R^{1a}$ and $R^{1b}$ are other than H. In certain embodiments, $R^{1a}$ and $R^{1b}$ are H.

In certain embodiments, $R^{1c}$ and $R^{1d}$ are independently H, —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, $R^{1c}$ is H and $R^{1d}$ is —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, —NR$^{11a}$S(O)$_2R^{12a}$, $C_1$-$C_6$alkyl, or 3-7-membered heterocyclyl; wherein the $C_1$-$C_6$alkyl is substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$; and wherein the 3-7-membered heterocyclyl is unsubstituted or substituted with one or more substituents selected from the group consisting of —C(O)$R^{11b}$, —P(O)$R^{11b}R^{12b}$, —S(O)$_2R^{11b}$, —S(O)$R^{11b}$, —NR$^{11a}R^{12a}$, —NR$^{11a}$C(O)$R^{12a}$, —NR$^{11a}$C(O)O$R^{12a}$, —NR$^{11a}$C(O)NR$^{12a}$, and —NR$^{11a}$S(O)$_2R^{12a}$. In certain embodiments, the 3-7-membered heterocyclyl contains a nitrogen. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H.

In certain embodiments, $R^{1c}$ and $R^{1d}$ are independently H, —NR$^{11a}R^{12a}$, —NR$^{11a}$C(O)$R^{12a}$, —NR$^{11a}$C(O)O$R^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$ In certain embodiments, $R^{1c}$ is H and $R^{1d}$ is —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, the 3-7-membered heterocyclyl contains a nitrogen. In certain embodiments, at least one of $R^{1c}$ and $R^{1d}$ is other than H. In certain embodiments one of $R^{1c}$ and $R^{1d}$ is other than H. In certain embodiments, both $R^{1c}$ and $R^{1d}$ are other than H.

In certain embodiments, $R^{1e}$ and $R^{1f}$ are independently H, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, $R^{1e}$ is H and $R^{1f}$ is —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, the 3-7-membered heterocyclyl contains a nitrogen. In certain embodiments, at least one of $R^{1e}$ and $R^{1f}$ is other than H. In certain embodiments one of $R^{1e}$ and $R^{1f}$ is other than H. In certain embodiments, both $R^{1e}$ and $R^{1f}$ are other than H.

In certain embodiments, $R^{1g}$ and $R^{1h}$ are independently H, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, $R^{1g}$ is H and $R^{1h}$ is —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, the 3-7-membered heterocyclyl contains a nitrogen. In certain embodiments, at least one of $R^{1g}$ and $R^{1h}$ is other than H. In certain embodiments one of $R^{1g}$ and $R^{1h}$ is other than H. In certain embodiments, both $R^{1g}$ and $R^{1h}$ are other than H.

In certain embodiments, $R^{1g}$ and $R^{1h}$ are independently H, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, $R^{1g}$ is H and $R^{1h}$ is —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$. In certain embodiments, the 3-7-membered heterocyclyl contains a nitrogen. In certain embodiments, at least one of $R^{1g}$ and $R^{1h}$ is other than H. In certain embodiments one of $R^{1g}$ and $R^{1h}$ is other than H. In certain embodiments, both $R^{1g}$ and $R^{1h}$ are other than H.

The present disclosure provides a compound, and pharmaceutically acceptable salts, solvates (e.g., hydrates), isomers, prodrugs, and tautomers thereof, in which the formula is Formula (I) (e.g, Formula (I-1), (I-2), (I-3), (I-4), (I-5), and (I-6)):

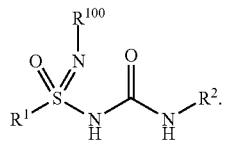

(I)

The present disclosure provides a compound, and pharmaceutically acceptable salts, solvates (e.g., hydrates), isomers, prodrugs, and tautomers thereof, in which the formula is Formula (Ia):

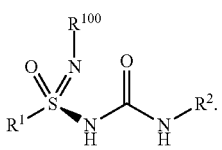

(Ia)

The present disclosure provides a compound, and pharmaceutically acceptable salts, solvates (e.g., hydrates), isomers, prodrugs, and tautomers thereof, in which the formula is Formula (Ib):

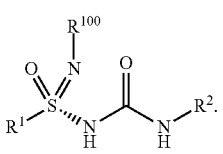

(Ib)

In some embodiments, the present disclosure provides a compound of formulae (I), (Ia), or (Ib), having one, two, or three of the following features:

a) $R^{100}$ is H;
b) $R^1$ is

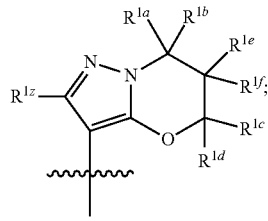

c) $R^2$ is

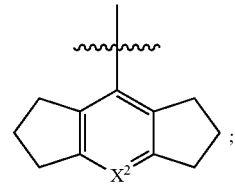

and
d) $X^2$ is CH or CF.

In some embodiments, the present disclosure provides a compound of formulae (I), (Ia), or (Ib), having one, two, or three of the following features:

a) $R^{100}$ is H;
b) $R^1$ is

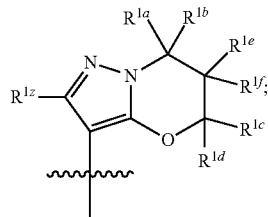

c) $R^2$ is

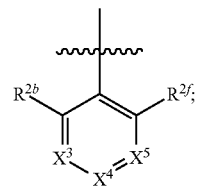

and
d) $X^3$ is $CR^{2c}$; $X^4$ is $CR^{2d}$; and $X^5$ is $CR^{2d}$.

Representative compounds are listed in Table 1. It is understood that individual enantiomers and diastereomers are included in the table below by Compound No. and Compound Name, and their corresponding structures can be readily determined therefrom. In some instances, the enantiomers or diastereomers are identified by their respective properties, for example, retention times on a chiral HPLC or its biological activities, and the absolute stereo configurations of the chiral centers are arbitrarily assigned.

TABLE 1

| Ex. No. | Compound Structure | Name |
|---|---|---|
| 1 | 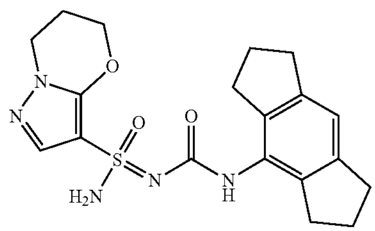 [SMILES: NS(=O)(=NC(=O)Nc1c2c(cc3c1CCC3)CCC2)c1cnn2c1OCCC2] | N'-((1,2,3,5,6,7-hexahydro-s-indacen-4-yl)carbamoyl)-6,7-dihydro-5H-pyrazolo[5,1-b][1,3]oxazine-3-sulfonimidamide |
| 2, 19, 20 | | N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide |
| 3 | 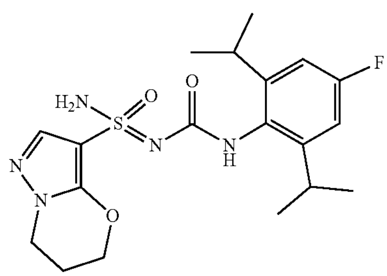 [SMILES: CC(C)c1cc(F)cc(C(C)C)c1NC(=O)N=S(N)(=O)c1cnn2c1OCCC2] | N'-((4-fluoro-2,6-diisopropylphenyl)carbamoyl)-6,7-dihydro-5H-pyrazolo[5,1-b][1,3]oxazine-3-sulfonimidamide |
| 4, 21, 22 | | N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide |
| 5 | 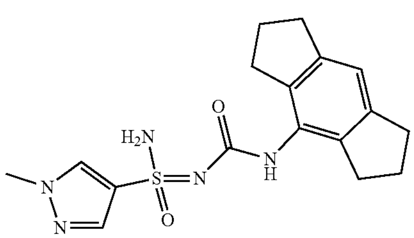 [SMILES: Cn1cc(S(N)(=O)=NC(=O)Nc2c3c(cc4c2CCC4)CCC3)cn1] | N'-((1,2,3,5,6,7-hexahydro-s-indacen-4-yl)carbamoyl)-1-methyl-1H-pyrazole-4-sulfonimidamide |
| 6, 80, 81 | | N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |

TABLE 1-continued

| Ex. No. | Compound Structure | Name |
|---|---|---|
| 7 8 | | N'-((4-fluoro-2,6-diisopropylphenyl)carbamoyl)-6,7-dihydro-5H-pyrazolo[5,1-b][1,3]oxazine-3-sulfonimidamide |
| 9 | 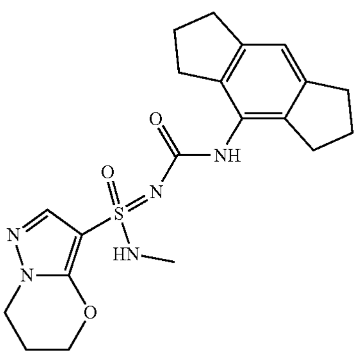 [SMILES: CNS(=O)(=NC(=O)Nc1c2c(cc3c1CCC3)CCC2)c1cnn2c1OCCC2] | N'-((1,2,3,5,6,7-hexahydro-s-indacen-4-yl)carbamoyl)-N-methyl-6,7-dihydro-5H-pyrazolo[5,1-b][1,3]oxazine-3-sulfonimidamide |
| 10 | 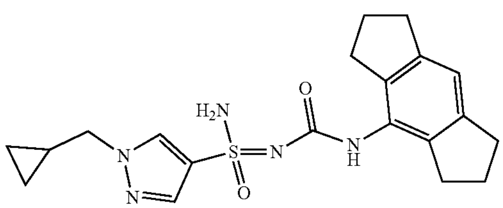 [SMILES: NS(=O)(=NC(=O)Nc1c2c(cc3c1CCC3)CCC2)c1cnn(CC2CC2)c1] | 1-(cyclopropylmethyl)-N'-((1,2,3,5,6,7-hexahydro-s-indacen-4-yl)carbamoyl)-1H-pyrazole-4-sulfonimidamide |
| 11 | 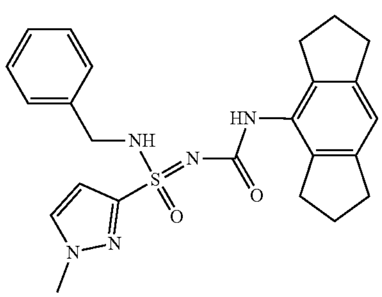 | N-benzyl-N'-((1,2,3,5,6,7-hexahydro-s-indacen-4-yl)carbamoyl)-1-methyl-1H-pyrazole-3-sulfonimidamide |
| 12 | 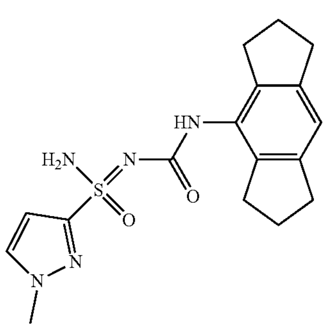 [SMILES: Cn1ccc(S(N)(=O)=NC(=O)Nc2c3c(cc4c2CCC4)CCC3)n1] | N'-((1,2,3,5,6,7-hexahydro-s-indacen-4-yl)carbamoyl)-1-methyl-1H-pyrazole-3-sulfonimidamide |

TABLE 1-continued

| Ex. No. | Compound Structure | Name |
|---|---|---|
| 13 14 | | N'-((1,2,3,5,6,7-hexahydro-s-indacen-4-yl)carbamoyl)-6,7-dihydro-5H-pyrazolo[5,1-b][1,3]oxazine-3-sulfonimidamide |
| 15 23 24 | | N'-((4-fluoro-2,6-diisopropylphenyl)carbamoyl)-6-methoxy-6,7-dihydro-5H-pyrazolo[5,1-b][1,3]oxazine-3-sulfonimidamide |
| 16 27 28 | | N'-((4-fluoro-2,6-diisopropylphenyl)carbamoyl)-6-(methylamino)-6,7-dihydro-5H-pyrazolo[5,1-b][1,3]oxazine-3-sulfonimidamide |
| 17 25 26 | | N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide |
| 18 31 32 | | N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide |
| 29 | | N'-((8-fluoro-1,2,3,5,6,7-hexahydro-s-indacen-4-yl)carbamoyl)-2,3-dihydropyrazolo[5,1-b]oxazole-7-sulfonimidamide |

TABLE 1-continued

| Ex. No. | Compound Structure | Name |
|---|---|---|
| 30 | 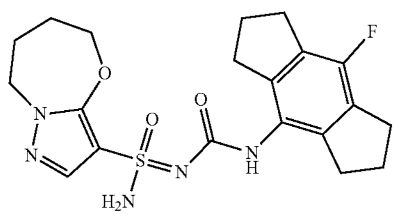 [SMILES: NS(=O)(=NC(=O)Nc1c2c(c(F)c3c1CCC3)CCC2)c1cnn2c1OCCCC2] | N'-((8-fluoro-1,2,3,5,6,7-hexahydro-s-indacen-4-yl)carbamoyl)-5,6,7,8-tetrahydropyrazolo[5,1-b][1,3]oxazepine-3-sulfonimidamide |
| 33 34 | | 6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6R)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonimidamide |
| | | 6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6R)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 37 | 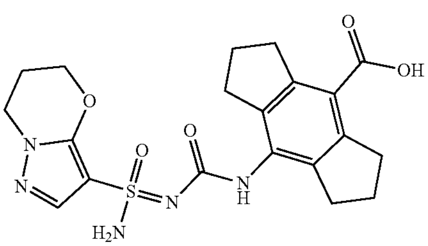 [SMILES: NS(=O)(=NC(=O)Nc1c2c(c(C(=O)O)c3c1CCC3)CCC2)c1cnn2c1OCCC2] | 8-(3-(amino(6,7-dihydro-5H-pyrazolo[5,1-b][1,3]oxazin-3-yl)(oxo)-26-sulfaneylidene)ureido)-1,2,3,5,6,7-hexahydro-s-indacene-4-carboxylic acid |
| 38 39 | | N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide<br>(6S)-N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide<br>(6R)-N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide |

TABLE 1-continued

| Ex. No. | Compound Structure | Name |
|---|---|---|
| 40 41 82 83 | | N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (6S)-N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (6R)-N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide |
| 42 43 | | N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (6S)-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (6R)-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide |
| 44 45 | | 6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (6R)-6-(dimethylamino)-N-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide |
| 46 47 | | N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide (6S)-N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide (6R)-N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide |

TABLE 1-continued

| Ex. No. | Compound Structure | Name |
|---|---|---|
| 48 49 | | N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide<br>(6S)-N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide<br>(6R)-N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide |
| 50 51 | | N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide<br>(6S)-N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide<br>(6R)-N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide |
| 52 53 | | N'-((2,4-diisopropyl-6-methoxypyridin-3-yl)carbamoyl)-6-methoxy-6,7-dihydro-5H-pyrazolo[5,1-b][1,3]oxazine-3-sulfonimidamide<br>(6S)-N'-((2,4-diisopropyl-6-methoxypyridin-3-yl)carbamoyl)-6-methoxy-6,7-dihydro-5H-pyrazolo[5,1-b][1,3]oxazine-3-sulfonimidamide<br>(6R)-N'-((2,4-diisopropyl-6-methoxypyridin-3-yl)carbamoyl)-6-methoxy-6,7-dihydro-5H-pyrazolo[5,1-b][1,3]oxazine-3-sulfonimidamide |
| 54 55 | | N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide<br>(6S)-N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide<br>(6R)-N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide |
| 56 57 | | N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide<br>(6S)-N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide<br>(6R)-N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide |

TABLE 1-continued

| Ex. No. | Compound Structure | Name |
|---|---|---|
| 58 59 | | 6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6S)-6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide<br>(6R)-6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 60 | | N'-((1,2,3,5,6,7-hexahydro-s-indacen-4-yl)carbamoyl)-4,5,6,7-tetrahydropyrazolo[1,5-a]pyridine-3-sulfonimidamide |
| 61 62 | | N'-((1,2,3,5,6,7-hexahydro-s-indacen-4-yl)carbamoyl)-7,8-dihydro-4H,6H-pyrazolo[5,1-c][1,4]oxazepine-3-sulfonimidamide |
| 63 | | N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide<br>(6S)-N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide<br>(6R)-N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide |
| 64 65 66 67 | | N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide<br>(7S)-N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide<br>(7R)-N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide |

TABLE 1-continued

| Ex. No. | Compound Structure | Name |
|---|---|---|
| 68 69 | | N-cyano-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 70 71 | | N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide |
| 72 73 | | N'-((1,2,3,5,6,7-hexahydro-s-indacen-4-yl)carbamoyl)-4,5,6,7-tetrahydropyrazolo[1,5-a]pyrimidine-3-sulfonimidamide |
| 74 75 78 79 | | N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide (6R)-N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide (6S)-N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide |
| 76 77 | | N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide |
| 84 85 | | N'-((2,4-diisopropyl-6-((methylamino)methyl)pyridin-3-yl)carbamoyl)-6,7-dihydro-5H-pyrazolo[5,1-b][1,3]oxazine-3-sulfonimidamide |

TABLE 1-continued

| Ex. No. | Compound Structure | Name |
|---|---|---|
| 86 87 92 93 | 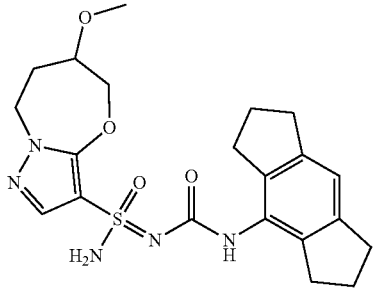 [SMILES: COC1CCn2ncc(S(N)(=O)=NC(=O)Nc3c4c(cc5c3CCC5)CCC4)c2OC1] | N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide<br>(6R)-N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide<br>(6S)-N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide |
| 88 89 90 91 | 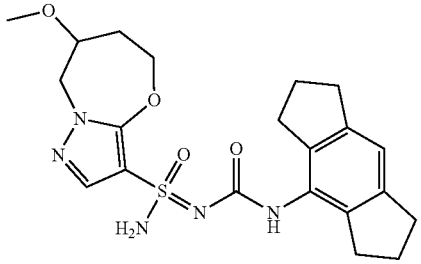 [SMILES: COC1CCOc2c(S(N)(=O)=NC(=O)Nc3c4c(cc5c3CCC5)CCC4)cnn2C1] | N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide<br>(7S)-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide<br>(7R)-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide |
| 94 | 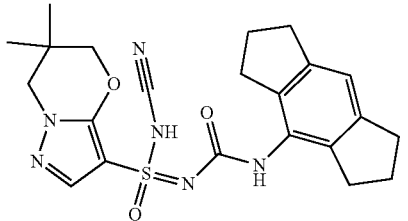 [SMILES: CC1(C)COc2c(S(=O)(=NC(=O)Nc3c4c(cc5c3CCC5)CCC4)NC#N)cnn2C1] | N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 95 | 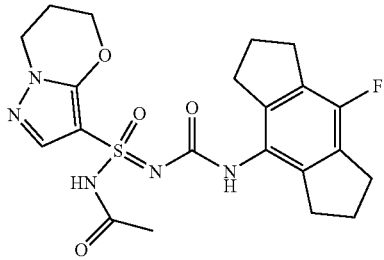 [SMILES: CC(=O)NS(=O)(=NC(=O)Nc1c2c(c(F)c3c1CCC3)CCC2)c1cnn2c1OCCC2] | N-(N-((8-fluoro-1,2,3,5,6,7-hexahydro-s-indacen-4-yl)carbamoyl)-6,7-dihydro-5H-pyrazolo[5,1-b][1,3]oxazine-3-sulfonimidoyl)acetamide |
| 96 97 | 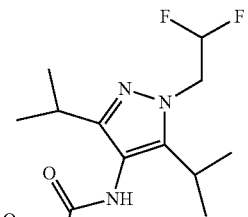 | N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide |

| Ex. No. | Compound Structure | Name |
|---|---|---|
| 98 99 | 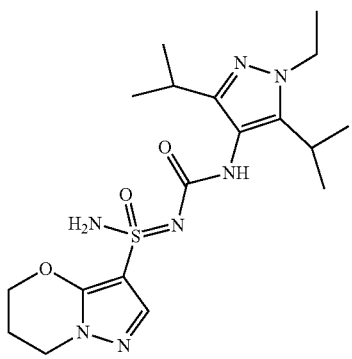 [SMILES: CCn1nc(C(C)C)c(NC(=O)N=S(N)(=O)c2cnn3c2OCCC3)c1C(C)C] | N'-((1-ethyl-3,5-diisopropyl-1H-pyrazol-4-yl)carbamoyl)-6,7-dihydro-5H-pyrazolo[5,1-b][1,3]oxazine-3-sulfonimidamide |
| 100 101 | 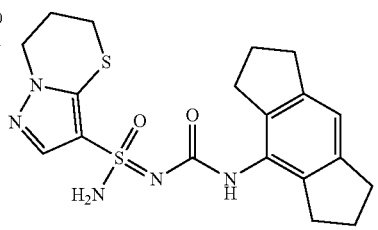 | N'-((1,2,3,5,6,7-hexahydro-s-indacen-4-yl)carbamoyl)-6,7-dihydro-5H-pyrazolo[5,1-b][1,3]thiazine-3-sulfonimidamide |
| 102 103 | 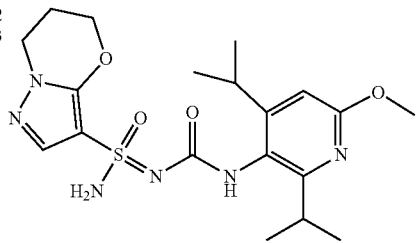 | N'-((2,4-diisopropyl-6-methoxypyridin-3-yl)carbamoyl)-6,7-dihydro-5H-pyrazolo[5,1-b][1,3]oxazine-3-sulfonimidamide |
| 104 111 | 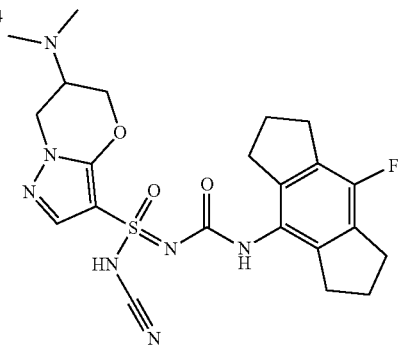 | N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (6S)-N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (6R)-N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide |
| 105 106 109 110 | 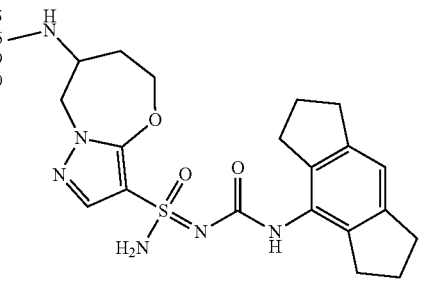 | N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (7S)-N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (7R)-N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide |

TABLE 1-continued

| Ex. No. | Compound Structure | Name |
|---|---|---|
| 107 108 | | N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide |
| 112 121 122 123 | | N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (7R)-N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (7S)-N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide |
| 113 114 | | N'-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonimidamide |
| 115 116 | | N-(N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide N-((6S)-N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide N-((6R)-N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide |
| 117 118 | | N'-((1,2,3,5,6,7-hexahydro-s-indacen-4-yl)carbamoyl)-4,5,7,8-tetrahydropyrazolo[1,5-d][1,4]oxazepine-3-sulfonimidamide |

TABLE 1-continued

| Ex. No. | Compound Structure | Name |
|---|---|---|
| 119 120 | 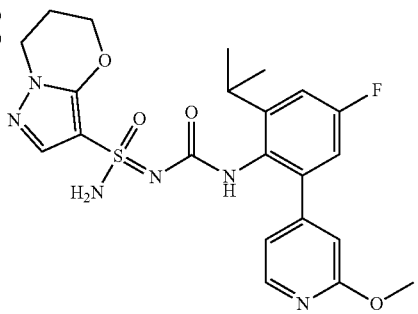 | N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide |
| 124 125 | 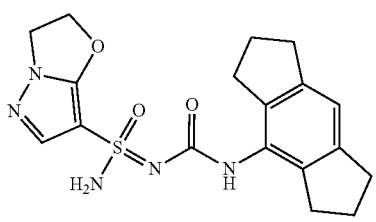 [SMILES: NS(=O)(=NC(=O)Nc1c2c(cc3c1CCC3)CCC2)c1cnn2c1OCC2] | N'-((1,2,3,5,6,7-hexahydro-s-indacen-4-yl)carbamoyl)-2,3-dihydropyrazolo[5,1-b]oxazole-7-sulfonimidamide |
| 126 127 128 129 | 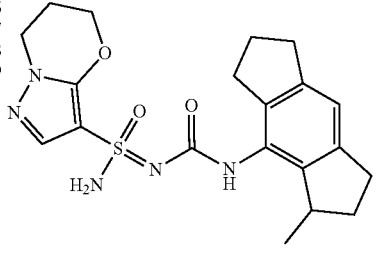 | N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide<br>N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 130 131 132 | | N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide<br>(6R)-N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide<br>(6S)-N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide |
| 133 134 | 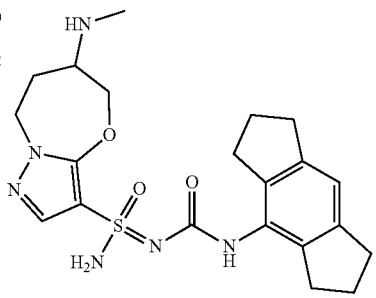 | 4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide |

TABLE 1-continued

| Ex. No. | Compound Structure | Name |
|---|---|---|
| 135 136 137 138 | | 6,6-dimethyl-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide 6,6-dimethyl-N-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide 6,6-dimethyl-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |
| 139 140 | | N'-((1,2,3,5,6,7-hexahydro-s-indacen-4-yl)carbamoyl)-2,2-dimethyl-2,3-dihydropyrazolo[5,1-b]oxazole-7-sulfonimidamide |
| 141 142 | | N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide |
| 143 144 145 146 | | N'-((3-methyl-1,2,3,5,6,7-hexahydro-s-indacen-4-yl)carbamoyl)-2,3-dihydropyrazolo[5,1-b]oxazole-7-sulfonimidamide N'-(((S)-3-methyl-1,2,3,5,6,7-hexahydro-s-indacen-4-yl)carbamoyl)-2,3-dihydropyrazolo[5,1-b]oxazole-7-sulfonimidamide N'-(((R)-3-methyl-1,2,3,5,6,7-hexahydro-s-indacen-4-yl)carbamoyl)-2,3-dihydropyrazolo[5,1-b]oxazole-7-sulfonimidamide |
| 147 148 149 150 | | 6-methoxy-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (6S)-6-methoxy-N'-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (6S)-6-methoxy-N-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (6R)-6-methoxy-N-(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (6R)-6-methoxy-N'-(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Name |
|---|---|---|
| 151 152 | | 6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (6R)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide |
| 153 154 155 156 | | N'-((2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide N'-(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide N'-(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide |
| 157 158 | | N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide |
| 159 | | N'-((4,6-diisopropyl-2-methoxypyrimidin-5-yl)carbamoyl)-6,7-dihydro-5H-pyrazolo[5,1-b][1,3]oxazine-3-sulfonimidamide |
| 160 | | 2-((3-(N'-((1,2,3,5,6,7-hexahydro-s-indacen-4-yl)carbamoyl)sulfamidimidoyl)-6,7-dihydro-5H-pyrazolo[5,1-b][1,3]oxazin-6-yl)oxy)acetic acid |

TABLE 1-continued

| Ex. No. | Compound Structure | Name |
|---|---|---|
| 161 | 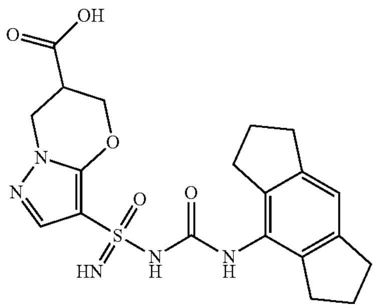 [SMILES: N=S(=O)(NC(=O)Nc1c2c(cc3c1CCC3)CCC2)c1cnn2c1OCC(C(=O)O)C2] | 3-(N'-((1,2,3,5,6,7-hexahydro-s-indacen-4-yl)carbamoyl)sulfamidimidoyl)-6,7-dihydro-5H-pyrazolo[5,1-b][1,3]oxazine-6-carboxylic acid |
| 162 | 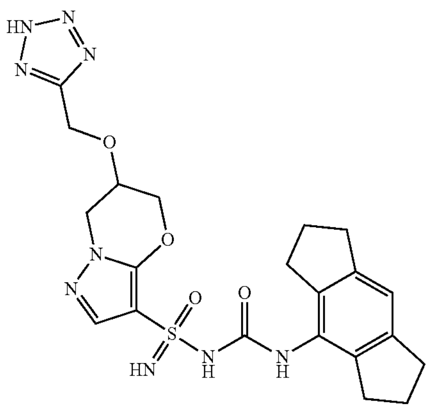 [SMILES: N=S(=O)(NC(=O)Nc1c2c(cc3c1CCC3)CCC2)c1cnn2c1OCC(OCc1nn[nH]n1)C2] | 6-((2H-tetrazol-5-yl)methoxy)-N'-((1,2,3,5,6,7-hexahydro-s-indacen-4-yl)carbamoyl)-6,7-dihydro-5H-pyrazolo[5,1-b][1,3]oxazine-3-sulfonimidamide |
| 163 | 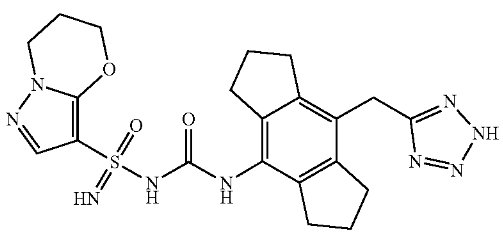 [SMILES: N=S(=O)(NC(=O)Nc1c2c(c(Cc3nn[nH]n3)c3c1CCC3)CCC2)c1cnn2c1OCCC2] | N'-((8-((2H-tetrazol-5-yl)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 164 | 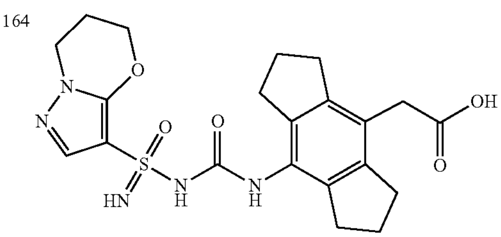 | 2-(8-(3-(6,7-dihydro-5H-pyrazolo[5,1-b][1,3]oxazine-3-sulfonimidoyl)ureido)-1,2,3,5,6,7-hexahydro-s-indacen-4-yl)acetic acid |
| 165 | 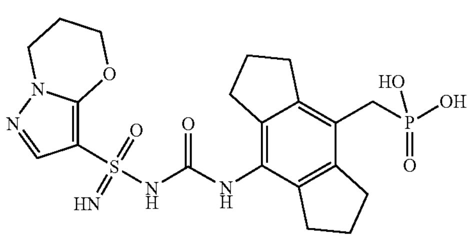 [SMILES: N=S(=O)(NC(=O)Nc1c2c(c(CP(=O)(O)O)c3c1CCC3)CCC2)c1cnn2c1OCCC2] | ((8-(3-(6,7-dihydro-5H-pyrazolo[5,1-b][1,3]oxazine-3-sulfonimidoyl)ureido)-1,2,3,5,6,7-hexahydro-s-indacen-4-yl)methyl)phosphonic acid |

TABLE 1-continued

| Ex. No. | Compound Structure | Name |
|---|---|---|
| 166 | 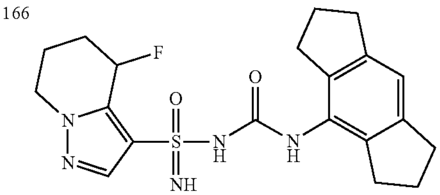 | 4-fluoro-N-((1,2,3,5,6,7-hexahydro-s-indacen-4-yl)carbamoyl)-4,5,6,7-tetrahydropyrazolo[1,5-a]pyridine-3-sulfonimidamide |
| 167 | 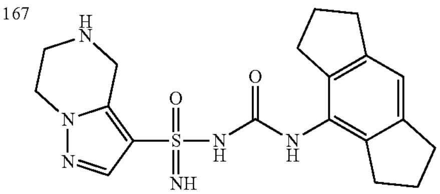 | N-((1,2,3,5,6,7-hexahydro-s-indacen-4-yl)carbamoyl)-4,5,6,7-tetrahydropyrazolo[1,5-a]pyrazine-3-sulfonimidamide |
| 168 | 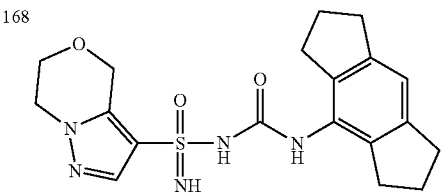 | N-((1,2,3,5,6,7-hexahydro-s-indacen-4-yl)carbamoyl)-6,7-dihydro-4H-pyrazolo[5,1-c][1,4]oxazine-3-sulfonimidamide |
| 169 | 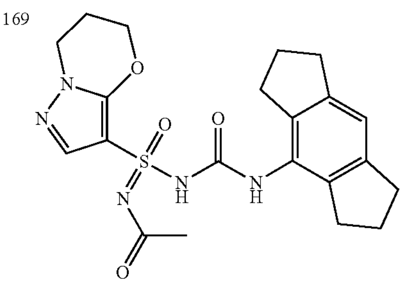 | N-(N-((1,2,3,5,6,7-hexahydro-s-indacen-4-yl)carbamoyl)-6,7-dihydro-5H-pyrazolo[5,1-b][1,3]oxazine-3-sulfonimidoyl)acetamide |
| 170 | 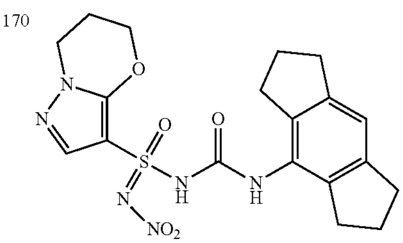 | N-((1,2,3,5,6,7-hexahydro-s-indacen-4-yl)carbamoyl)-N'-nitro-6,7-dihydro-5H-pyrazolo[5,1-b][1,3]oxazine-3-sulfonimidamide |
| 171 | 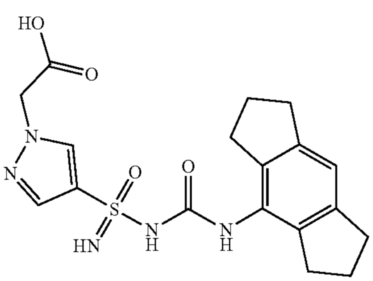 [SMILES: N=S(=O)(NC(=O)Nc1c2c(cc3c1CCC3)CCC2)c1cnn(CC(=O)O)c1] | 2-(4-(N-((1,2,3,5,6,7-hexahydro-s-indacen-4-yl)carbamoyl)sulfamidimidoyl)-1H-pyrazol-1-yl)acetic acid |

TABLE 1-continued

| Ex. No. | Compound Structure | Name |
|---|---|---|
| 172 | 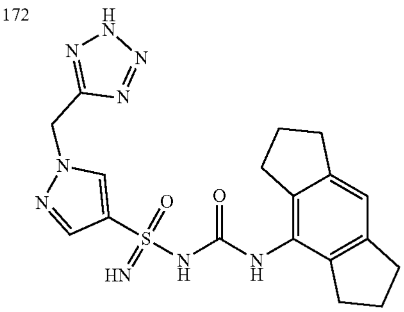 | 1-((2H-tetrazol-5-yl)methyl)-N-((1,2,3,5,6,7-hexahydro-s-indacen-4-yl)carbamoyl)-1H-pyrazole-4-sulfonimidamide |
| 173 | 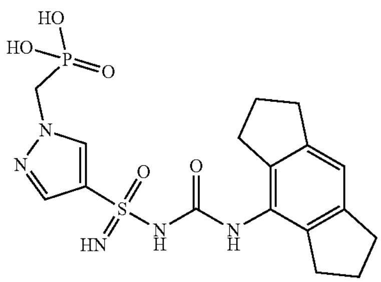 [SMILES: N=S(=O)(NC(=O)Nc1c2c(cc3c1CCC3)CCC2)c1cnn(CP(=O)(O)O)c1] | ((4-(N-((1,2,3,5,6,7-hexahydro-s-indacen-4-yl)carbamoyl)sulfamidimidoyl)-1H-pyrazol-1-yl)methyl)phosphonic acid |
| 174 | 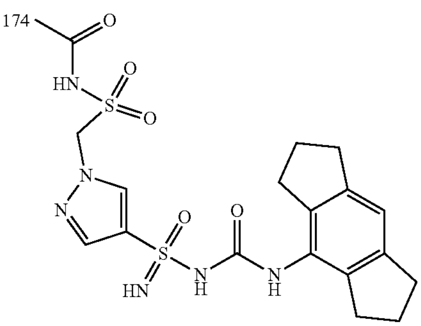 | N-(((4-(N-((1,2,3,5,6,7-hexahydro-s-indacen-4-yl)carbamoyl)sulfamidimidoyl)-1H-pyrazol-1-yl)methyl)sulfonyl)acetamide |
| 175 | 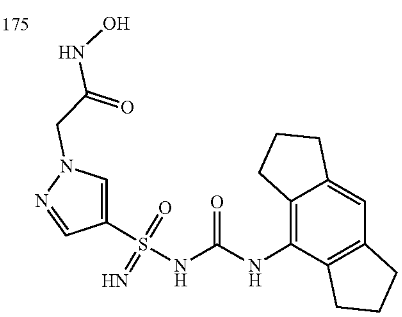 | 2-(4-(N-((1,2,3,5,6,7-hexahydro-s-indacen-4-yl)carbamoyl)sulfamidimidoyl)-1H-pyrazol-1-yl)-N-hydroxyacetamide |
| 176 | 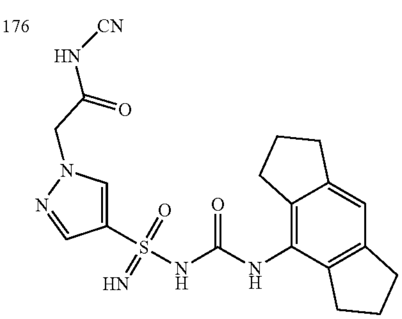 | N-cyano-2-(4-(N-((1,2,3,5,6,7-hexahydro-s-indacen-4-yl)carbamoyl)sulfamidimidoyl)-1H-pyrazol-1-yl)acetamide |

TABLE 1-continued

| Ex. No. | Compound Structure | Name |
|---|---|---|
| 177 | 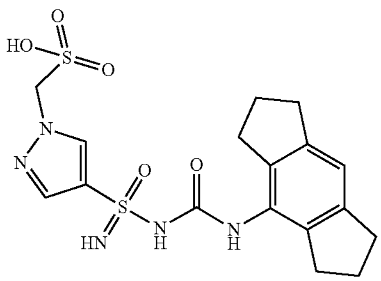 [SMILES: N=S(=O)(NC(=O)Nc1c2c(cc3c1CCC3)CCC2)c1cnn(CS(=O)(=O)O)c1] | (4-(N-((1,2,3,5,6,7-hexahydro-s-indacen-4-yl)carbamoyl)sulfamidimidoyl)-1H-pyrazol-1-yl)methanesulfonic acid |
| 178 | 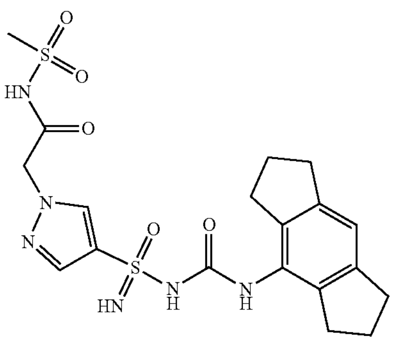 [SMILES: CS(=O)(=O)NC(=O)Cn1cc(S(=N)(=O)NC(=O)Nc2c3c(cc4c2CCC4)CCC3)cn1] | 2-(4-(N-((1,2,3,5,6,7-hexahydro-s-indacen-4-yl)carbamoyl)sulfamidimidoyl)-1H-pyrazol-1-yl)-N-(methylsulfonyl)acetamide |
| 179 | 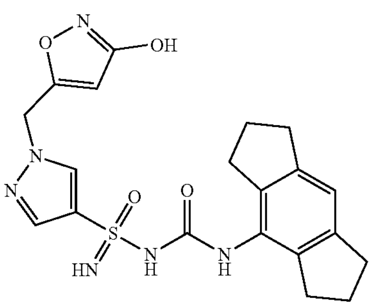 [SMILES: N=S(=O)(NC(=O)Nc1c2c(cc3c1CCC3)CCC2)c1cnn(Cc2cc(O)no2)c1] | N-((1,2,3,5,6,7-hexahydro-s-indacen-4-yl)carbamoyl)-1-((3-hydroxyisoxazol-5-yl)methyl)-1H-pyrazole-4-sulfonimidamide |
| 180 | 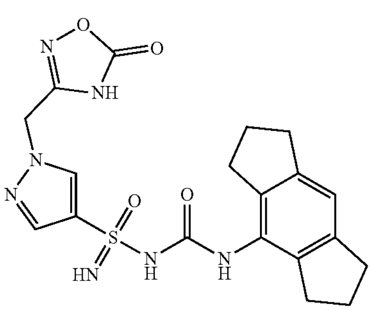 [SMILES: N=S(=O)(NC(=O)Nc1c2c(cc3c1CCC3)CCC2)c1cnn(Cc2noc(=O)[nH]2)c1] | N-((1,2,3,5,6,7-hexahydro-s-indacen-4-yl)carbamoyl)-1-((5-oxo-4,5-dihydro-1,2,4-oxadiazol-3-yl)methyl)-1H-pyrazole-4-sulfonimidamide |
| 181 | 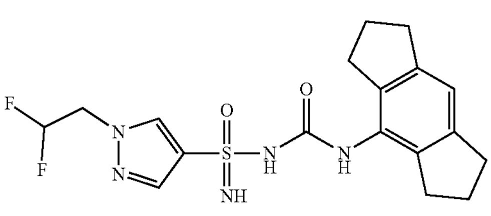 [SMILES: N=S(=O)(NC(=O)Nc1c2c(cc3c1CCC3)CCC2)c1cnn(CC(F)F)c1] | 1-(2,2-difluoroethyl)-N-((1,2,3,5,6,7-hexahydro-s-indacen-4-yl)carbamoyl)-1H-pyrazole-4-sulfonimidamide |

TABLE 1-continued

| Ex. No. | Compound Structure | Name |
|---|---|---|
| 182 | 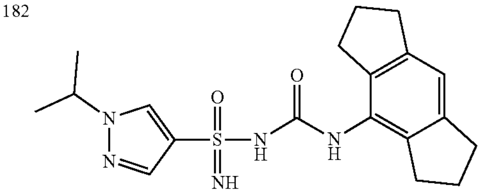 | N-((1,2,3,5,6,7-hexahydro-s-indacen-4-yl)carbamoyl)-1-isopropyl-1H-pyrazole-4-sulfonimidamide |
| 183 | 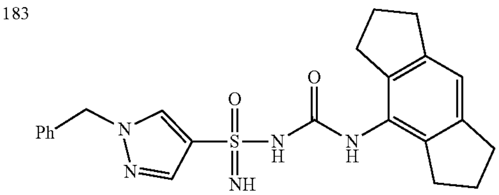 | 1-benzyl-N-((1,2,3,5,6,7-hexahydro-s-indacen-4-yl)carbamoyl)-1H-pyrazole-4-sulfonimidamide |
| 184 | 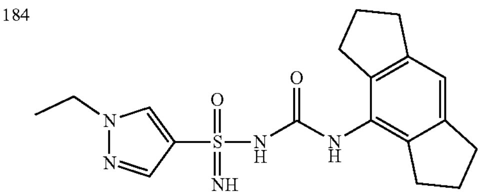 | 1-ethyl-N-((1,2,3,5,6,7-hexahydro-s-indacen-4-yl)carbamoyl)-1H-pyrazole-4-sulfonimidamide |
| 185 | 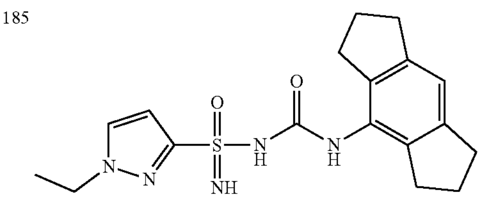 | 1-ethyl-N-((1,2,3,5,6,7-hexahydro-s-indacen-4-yl)carbamoyl)-1H-pyrazole-3-sulfonimidamide |
| 186 | 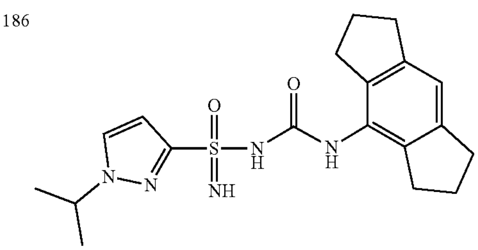 | N-((1,2,3,5,6,7-hexahydro-s-indacen-4-yl)carbamoyl)-1-isopropyl-1H-pyrazole-3-sulfonimidamid2-(4-(N-((1,2,3,5,6,7-hexahydro-s-indacen-4-yl)carbamoyl)sulfamidimidoyl)-1H-pyrazol-1-yl)acetamidee |
| 187 | 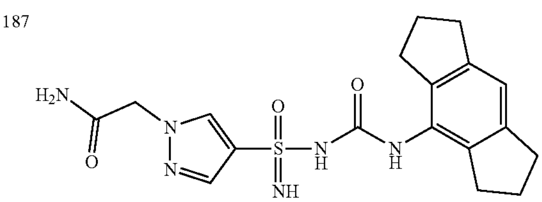 | 2-(4-(N-((1,2,3,5,6,7-hexahydro-s-indacen-4-yl)carbamoyl)sulfamidimidoyl)-1H-pyrazol-1-yl)acetamide |
| 188 | 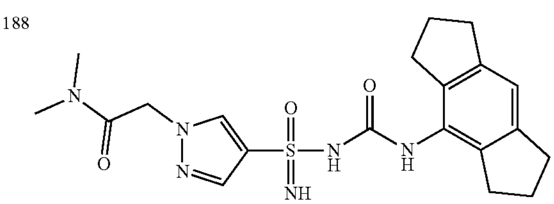 | 2-(4-(N-((1,2,3,5,6,7-hexahydro-s-indacen-4-yl)carbamoyl)sulfamidimidoyl)-1H-pyrazol-1-yl)-N,N-dimethylacetamide |

TABLE 1-continued

| Ex. No. | Compound Structure | Name |
|---|---|---|
| 189 | 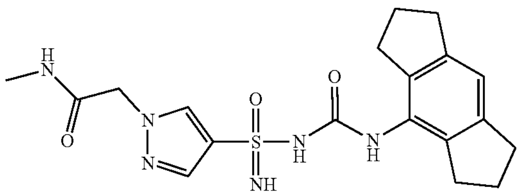 [SMILES: CNC(=O)Cn1cc(S(=N)(=O)NC(=O)Nc2c3c(cc4c2CCC4)CCC3)cn1] | 2-(4-(N-((1,2,3,5,6,7-hexahydro-s-indacen-4-yl)carbamoyl)sulfamidimidoyl)-1H-pyrazol-1-yl)-N-methylacetamide |
| 190 | 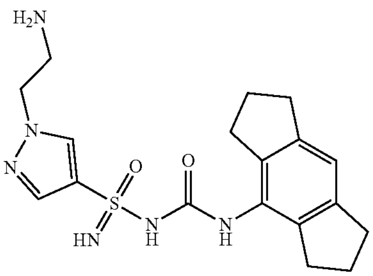 [SMILES: N=S(=O)(NC(=O)Nc1c2c(cc3c1CCC3)CCC2)c1cnn(CCN)c1] | 1-(2-aminoethyl)-N-((1,2,3,5,6,7-hexahydro-s-indacen-4-yl)carbamoyl)-1H-pyrazole-4-sulfonimidamide |
| 191 | 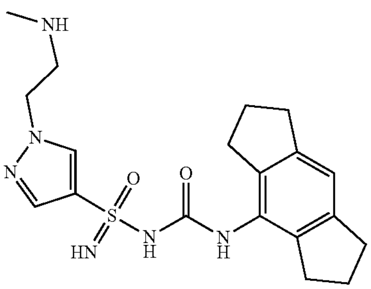 [SMILES: CNCCn1cc(S(=N)(=O)NC(=O)Nc2c3c(cc4c2CCC4)CCC3)cn1] | N-((1,2,3,5,6,7-hexahydro-s-indacen-4-yl)carbamoyl)-1-(2-(methylamino)ethyl)-1H-pyrazole-4-sulfonimidamide |
| 192 | 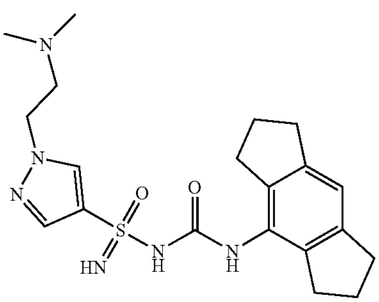 [SMILES: CN(C)CCn1cc(S(=N)(=O)NC(=O)Nc2c3c(cc4c2CCC4)CCC3)cn1] | 1-(2-(dimethylamino)ethyl)-N-((1,2,3,5,6,7-hexahydro-s-indacen-4-yl)carbamoyl)-1H-pyrazole-4-sulfonimidamide |
| 193 | 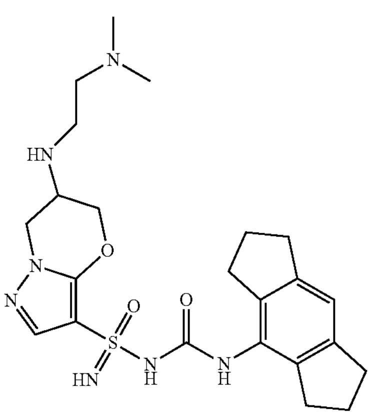 [SMILES: CN(C)CCNC1COc2c(S(=N)(=O)NC(=O)Nc3c4c(cc5c3CCC5)CCC4)cnn2C1] | 6-((2-(dimethylamino)ethyl)amino)-N-((1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Name |
|---|---|---|
| 194 | 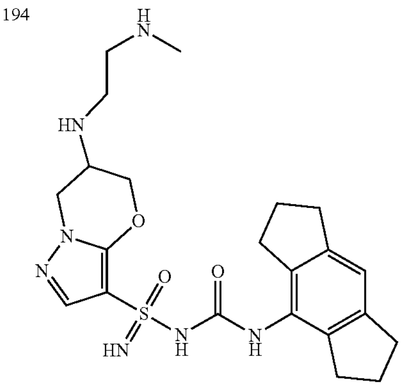 | N-((1,2,3,5,6,7-hexahydro-s-indacen-4-yl)carbamoyl)-6-((2-(methylamino)ethyl)amino)-6,7-dihydro-5H-pyrazolo[5,1-b][1,3]oxazine-3-sulfonimidamide |
| 195 | 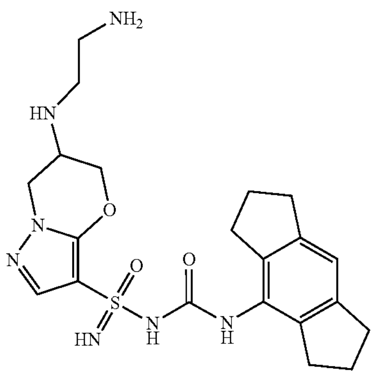 [SMILES: N=S(=O)(NC(=O)Nc1c2c(cc3c1CCC3)CCC2)c1cnn2c1OCC(NCCN)C2] | 6-((2-aminoethyl)amino)-N-((1,2,3,5,6,7-hexahydro-s-indacen-4-yl)carbamoyl)-6,7-dihydro-5H-pyrazolo[5,1-b][1,3]oxazine-3-sulfonimidamide |
| 196 | 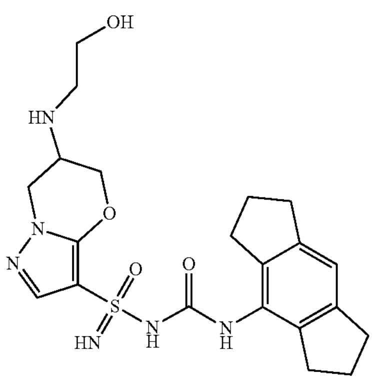 [SMILES: N=S(=O)(NC(=O)Nc1c2c(cc3c1CCC3)CCC2)c1cnn2c1OCC(NCCO)C2] | N-((1,2,3,5,6,7-hexahydro-s-indacen-4-yl)carbamoyl)-6-((2-hydroxyethyl)amino)-6,7-dihydro-5H-pyrazolo[5,1-b][1,3]oxazine-3-sulfonimidamide |
| 197 | 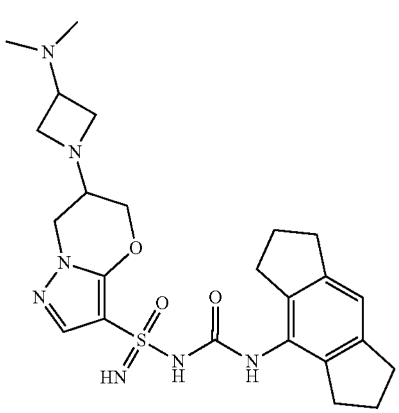 [SMILES: CN(C)C1CN(C2COc3c(S(=N)(=O)NC(=O)Nc4c5c(cc6c4CCC6)CCC5)cnn3C2)C1] | 6-(3-(dimethylamino)azetidin-1-yl)-N-((1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Name |
|---|---|---|
| 198 | 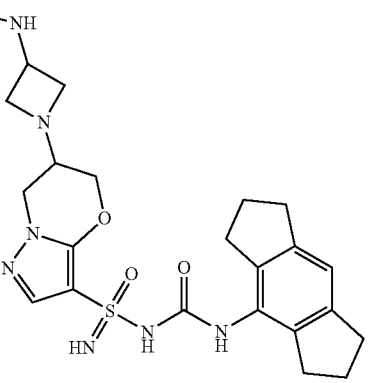 | N-((1,2,3,5,6,7-hexahydro-s-indacen-4-yl)carbamoyl)-6-(3-(methylamino)azetidin-1-yl)-6,7-dihydro-5H-pyrazolo[5,1-b][1,3]oxazine-3-sulfonimidamide |
| 199 | 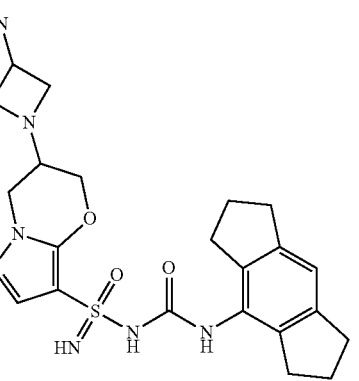 | 6-(3-aminoazetidin-1-yl)-N-((1,2,3,5,6,7-hexahydro-s-indacen-4-yl)carbamoyl)-6,7-dihydro-5H-pyrazolo[5,1-b][1,3]oxazine-3-sulfonimidamide |
| 200 | 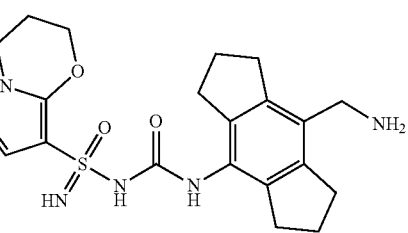 | N-((8-(aminomethyl)-1,2,3,5,6,7-hexahydro-s-indacen-4-yl)carbamoyl)-6,7-dihydro-5H-pyrazolo[5,1-b][1,3]oxazine-3-sulfonimidamide |
| 201 | 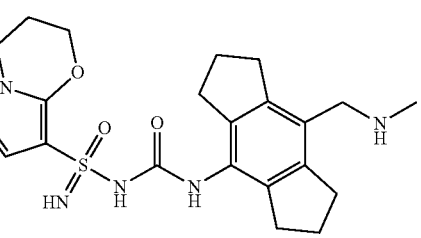 | N-((8-((methylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide |
| 202 | 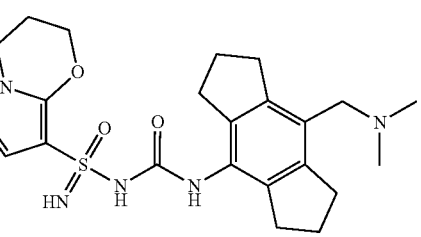 | N-((8-((dimethylamino)methyl)-1,2,3,5,6,7-hexahydro-s-indacen-4-yl)carbamoyl)-6,7-dihydro-5H-pyrazolo[5,1-b][1,3]oxazine-3-sulfonimidamide |

TABLE 1-continued

| Ex. No. | Compound Structure | Name |
|---|---|---|
| 203 | 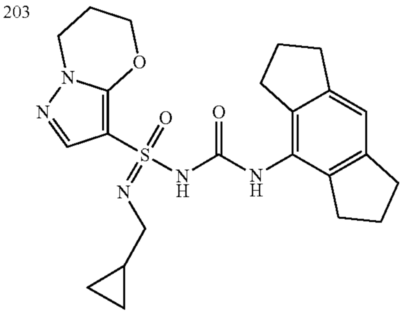 | N'-(cyclopropylmethyl)-N-((1,2,3,5,6,7-hexahydro-s-indacen-4-yl)carbamoyl)-6,7-dihydro-5H-pyrazolo[5,1-b][1,3]oxazine-3-sulfonimidamide |
| 204 | 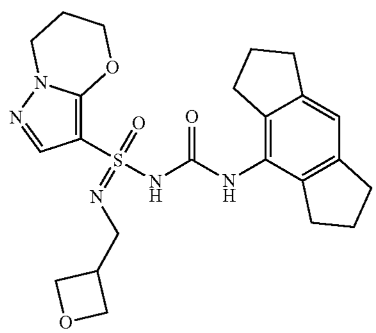 [SMILES: O=C(Nc1c2c(cc3c1CCC3)CCC2)NS(=O)(=NCC1COC1)c1cnn2c1OCCC2] | N-((1,2,3,5,6,7-hexahydro-s-indacen-4-yl)carbamoyl)-N'-(oxetan-3-ylmethyl)-6,7-dihydro-5H-pyrazolo[5,1-b][1,3]oxazine-3-sulfonimidamide |
| 205 | 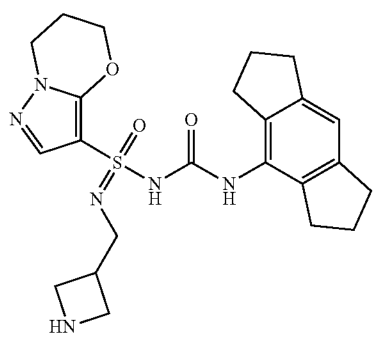 [SMILES: O=C(Nc1c2c(cc3c1CCC3)CCC2)NS(=O)(=NCC1CNC1)c1cnn2c1OCCC2] | N'-(azetidin-3-ylmethyl)-N-((1,2,3,5,6,7-hexahydro-s-indacen-4-yl)carbamoyl)-6,7-dihydro-5H-pyrazolo[5,1-b][1,3]oxazine-3-sulfonimidamide |
| 206 | 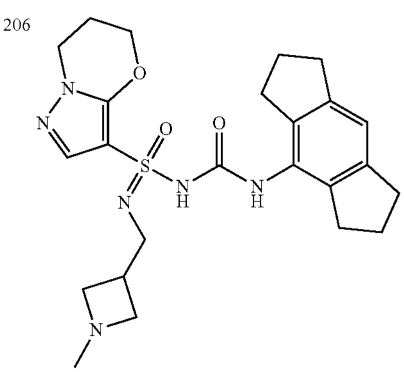 | N-((1,2,3,5,6,7-hexahydro-s-indacen-4-yl)carbamoyl)-N'-((1-methylazetidin-3-yl)methyl)-6,7-dihydro-5H-pyrazolo[5,1-b][1,3]oxazine-3-sulfonimidamide |

TABLE 1-continued

| Ex. No. | Compound Structure | Name |
|---|---|---|
| 207 | 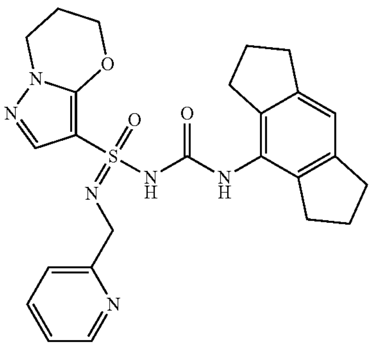 [SMILES: O=C(Nc1c2c(cc3c1CCC3)CCC2)NS(=O)(=NCc1ccccn1)c1cnn2c1OCCC2] | N-((1,2,3,5,6,7-hexahydro-s-indacen-4-yl)carbamoyl)-N'-(pyridin-2-ylmethyl)-6,7-dihydro-5H-pyrazolo[5,1-b][1,3]oxazine-3-sulfonimidamide |
| 208 | 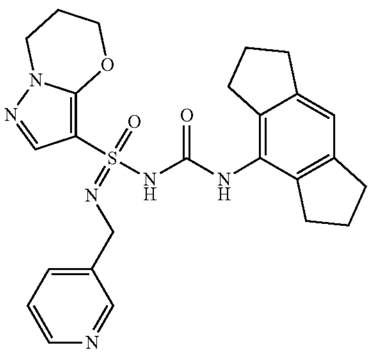 [SMILES: O=C(Nc1c2c(cc3c1CCC3)CCC2)NS(=O)(=NCc1cccnc1)c1cnn2c1OCCC2] | N-((1,2,3,5,6,7-hexahydro-s-indacen-4-yl)carbamoyl)-N'-(pyridin-3-ylmethyl)-6,7-dihydro-5H-pyrazolo[5,1-b][1,3]oxazine-3-sulfonimidamide |
| 209 | 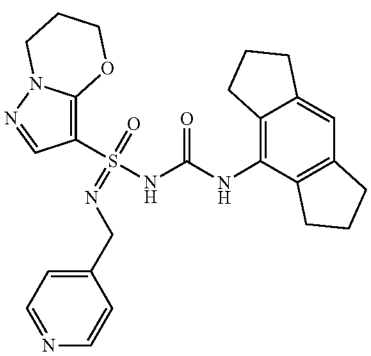 [SMILES: O=C(Nc1c2c(cc3c1CCC3)CCC2)NS(=O)(=NCc1ccncc1)c1cnn2c1OCCC2] | N-((1,2,3,5,6,7-hexahydro-s-indacen-4-yl)carbamoyl)-N'-(pyridin-4-ylmethyl)-6,7-dihydro-5H-pyrazolo[5,1-b][1,3]oxazine-3-sulfonimidamide |
| 210 | 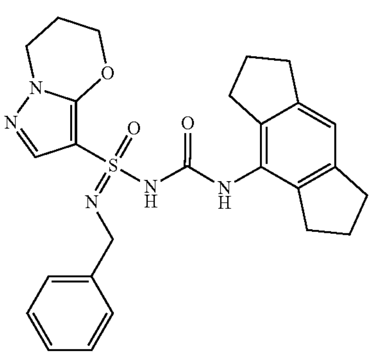 [SMILES: O=C(Nc1c2c(cc3c1CCC3)CCC2)NS(=O)(=NCc1ccccc1)c1cnn2c1OCCC2] | N'-benzyl-N-((1,2,3,5,6,7-hexahydro-s-indacen-4-yl)carbamoyl)-6,7-dihydro-5H-pyrazolo[5,1-b][1,3]oxazine-3-sulfonimidamide |

In some embodiments, provided is a compound selected from Compound Nos. 1-210 in Table 1, or a salt (e.g., a pharmaceutically acceptable salt), solvate (e.g., hydrate), isomer, or tautomer thereof. In some embodiments, provided is a compound selected from Compound Nos. 1-158 in Table 1, or a salt (e.g., a pharmaceutically acceptable salt), solvate (e.g., hydrate), isomer, or tautomer thereof. In some embodiments, provided is a compound selected from Compound Nos. 159-158 in Table 1, or a salt (e.g., a pharmaceutically acceptable salt), solvate (e.g., hydrate), isomer, or tautomer thereof. In some embodiments, the compound is selected from Compound Nos. 1-158 in Table 1, or a salt (e.g., a pharmaceutically acceptable salt), solvate (e.g., hydrate), isomer, or tautomer thereof. In some embodiments, the compound is selected from Compound Nos. 1-39 in Table 1, or a salt (e.g., a pharmaceutically acceptable salt), solvate (e.g., hydrate), isomer, or tautomer thereof. In some embodiments, the compound is selected from Compound Nos. 37, 60, 68-69, 72-73, 102-103 and 159-170 in Table 1, or a salt (e.g., a pharmaceutically acceptable salt), solvate (e.g., hydrate), isomer, or tautomer thereof. In some embodiments, the compound is selected from Compound Nos. 171-189 in Table 1, or a salt (e.g., a pharmaceutically acceptable salt), solvate (e.g., hydrate), isomer, or tautomer thereof. In some embodiments, the compound is selected from Compound Nos. 190-202 in Table 1, or a salt (e.g., a pharmaceutically acceptable salt), solvate (e.g., hydrate), isomer, or tautomer thereof. In some embodiments, the compound is selected from Compound Nos. 203-210 in Table 1, or a salt (e.g., a pharmaceutically acceptable salt), solvate (e.g., hydrate), isomer, or tautomer thereof.

In certain embodiments, the present disclosure provides a compound, and pharmaceutically acceptable salts, solvates (e.g., hydrates), isomers, and tautomers thereof, that is selected from the group consisting of

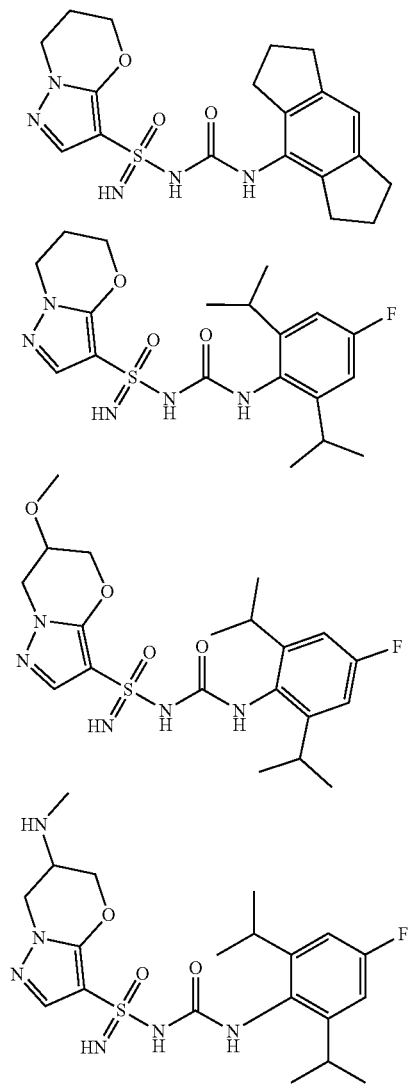

-continued

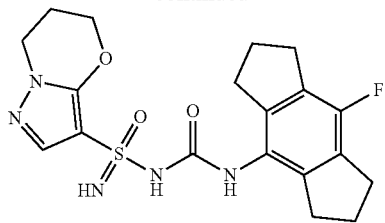

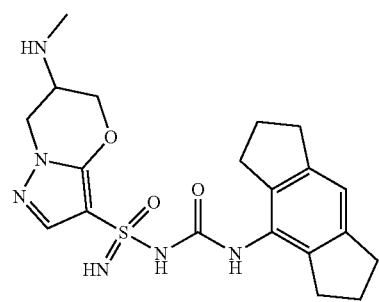

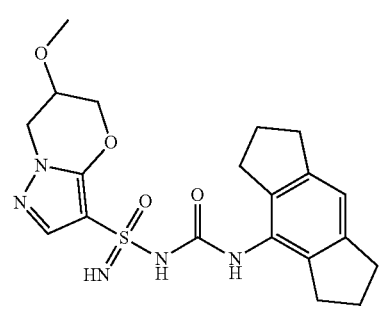

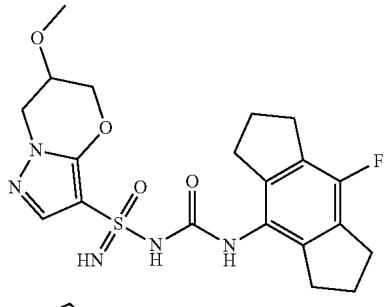

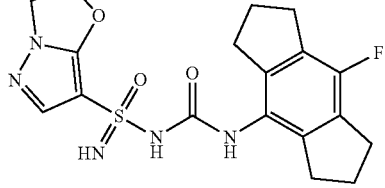

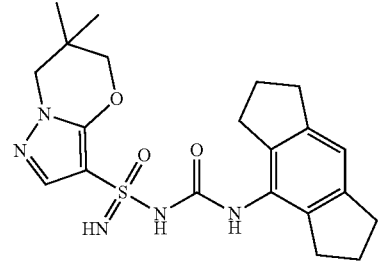

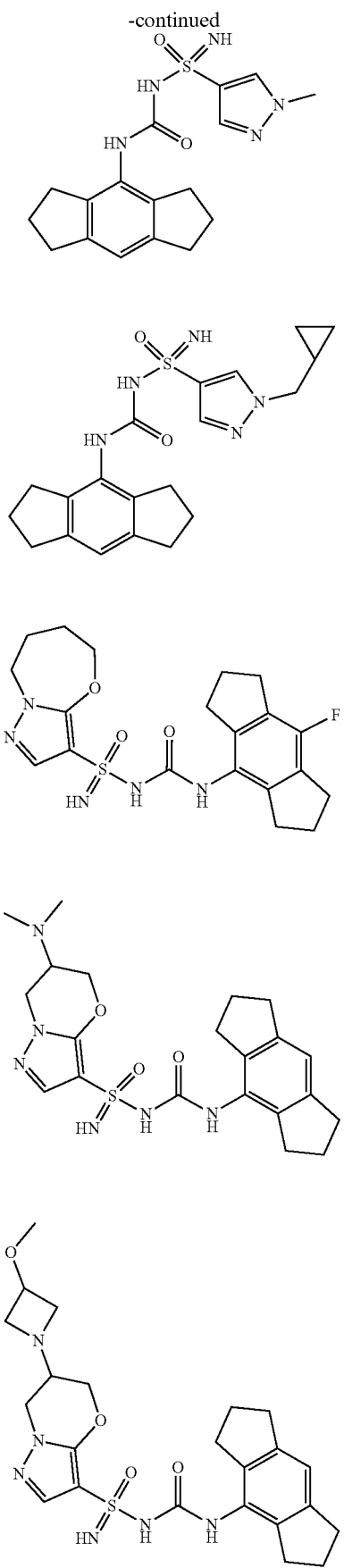
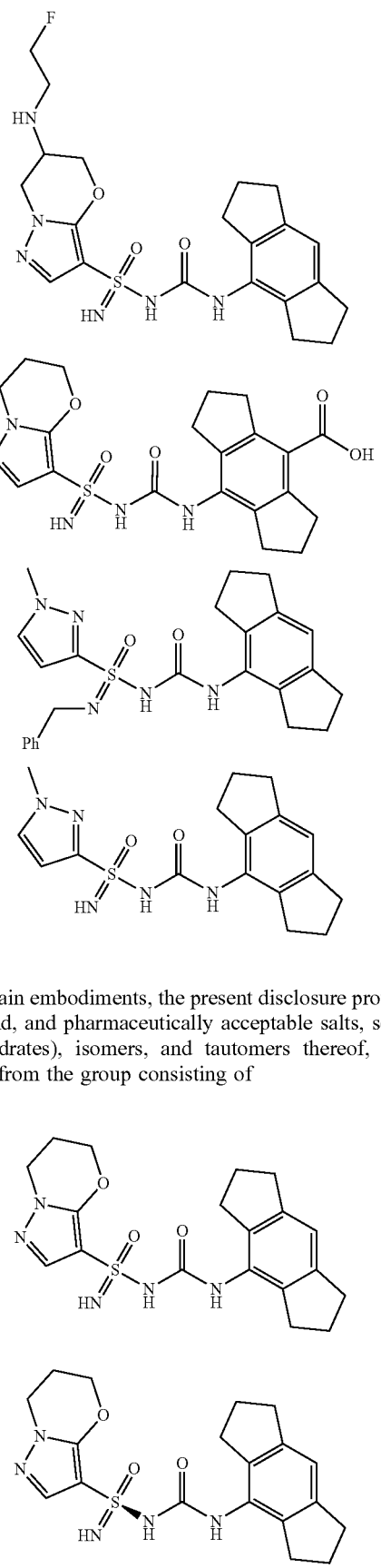
In certain embodiments, the present disclosure provides a compound, and pharmaceutically acceptable salts, solvates (e.g., hydrates), isomers, and tautomers thereof, that is selected from the group consisting of

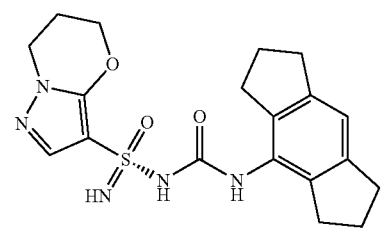
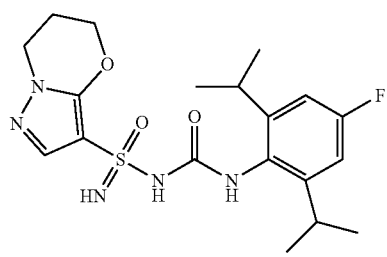
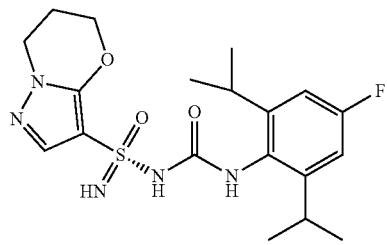
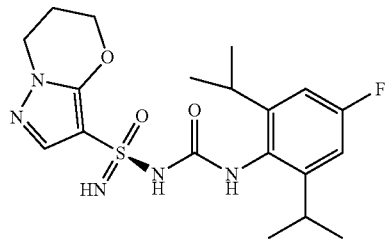
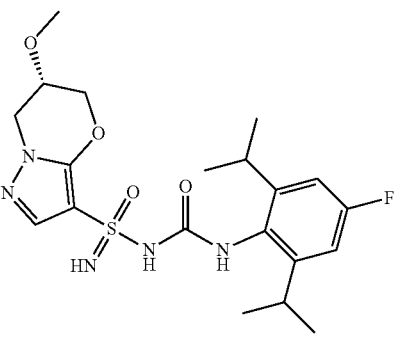
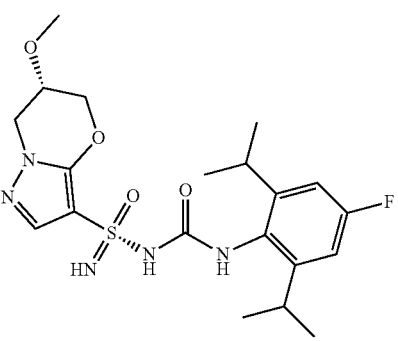
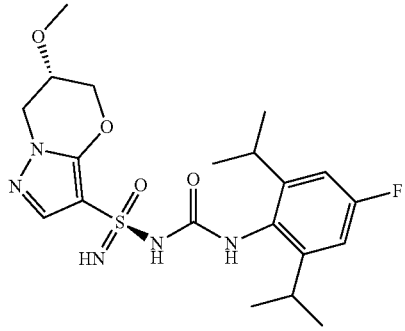
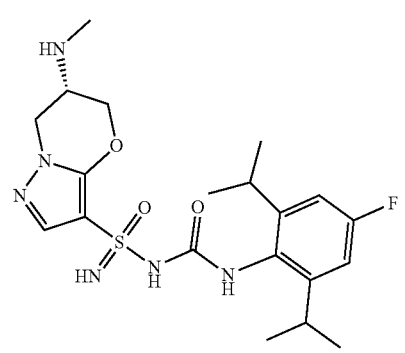
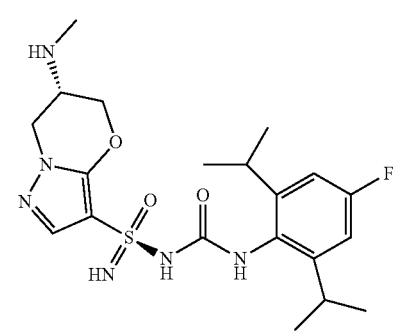
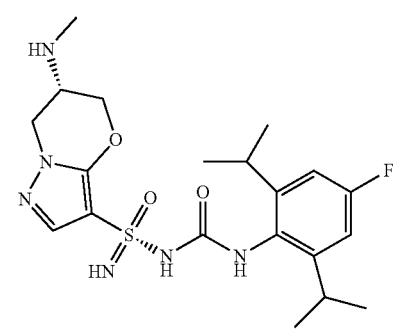
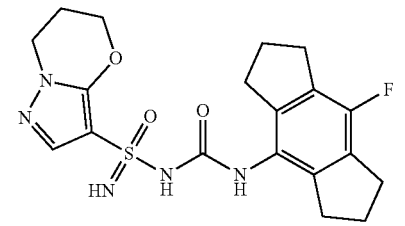

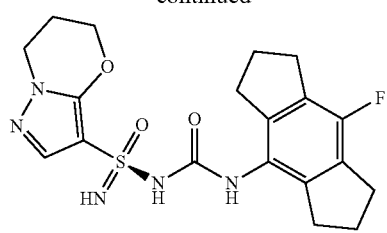
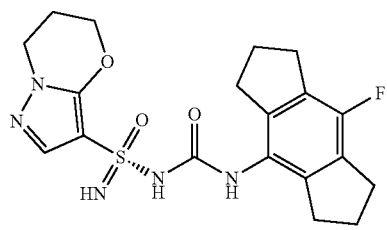
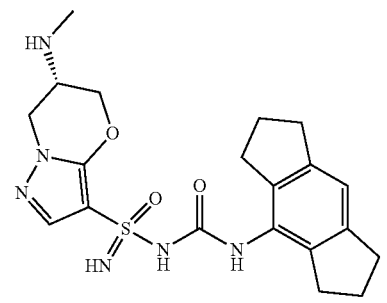
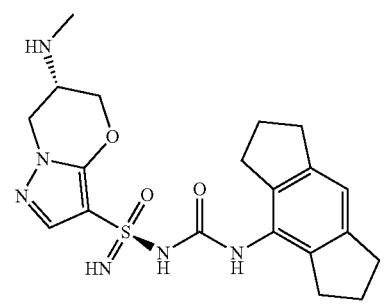
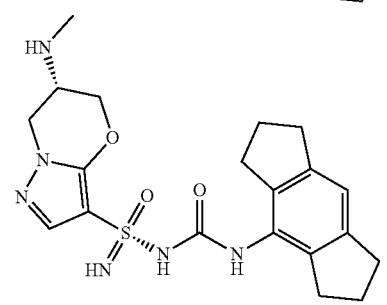
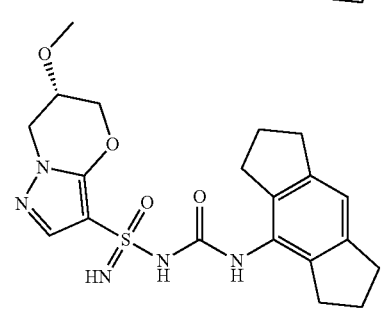
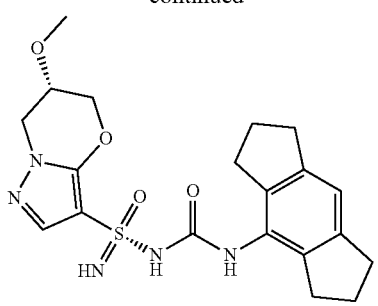
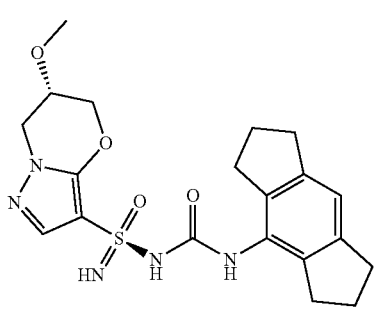
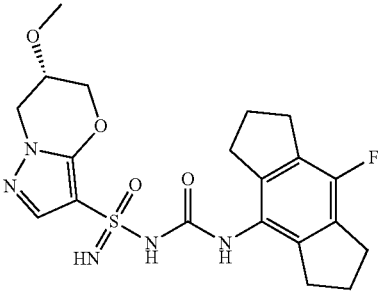
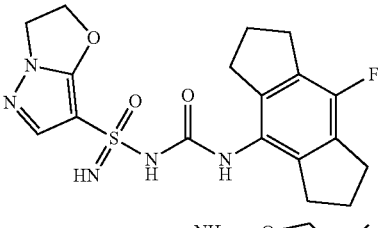
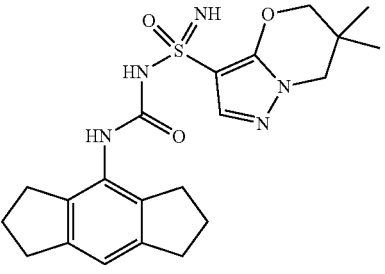
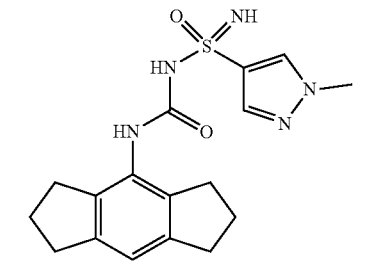

159
-continued
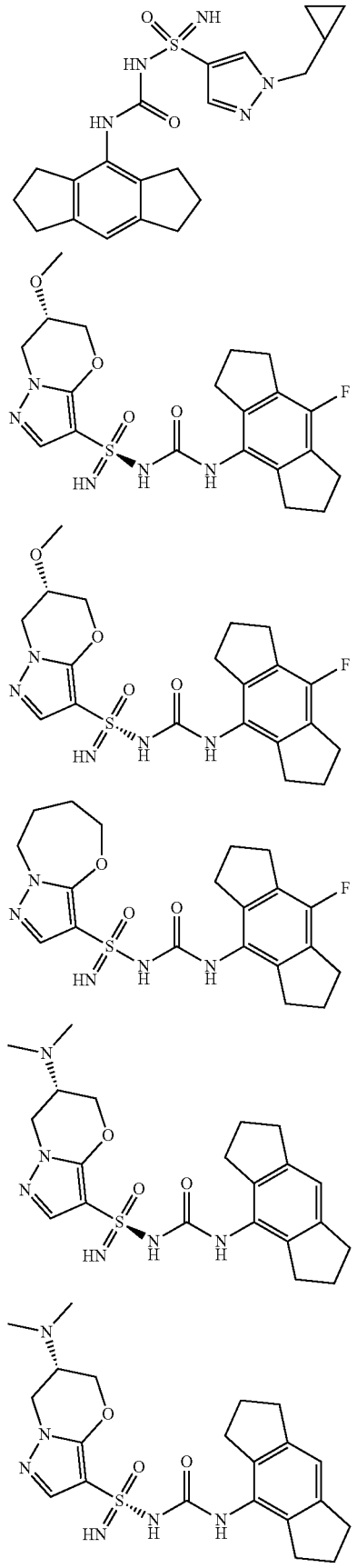
160
-continued
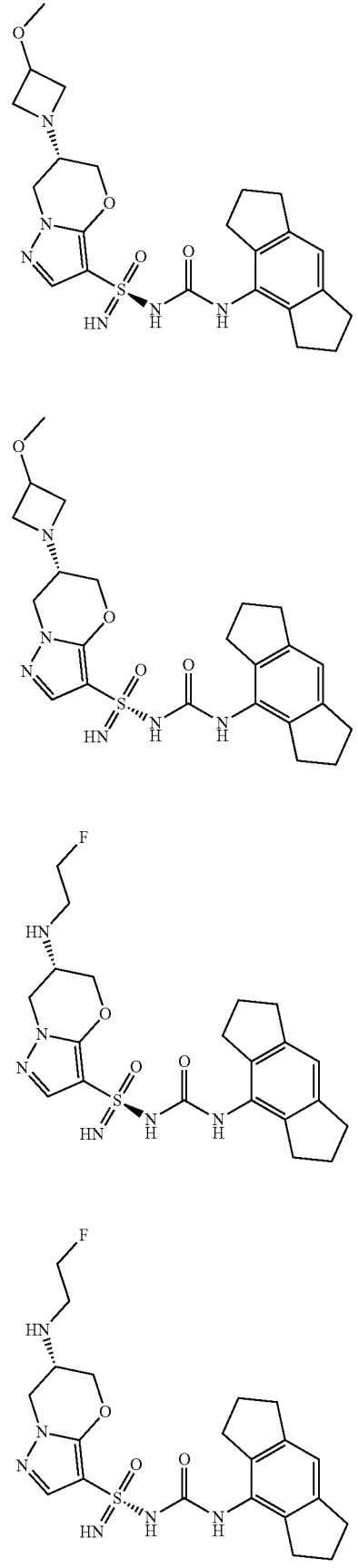

161
-continued
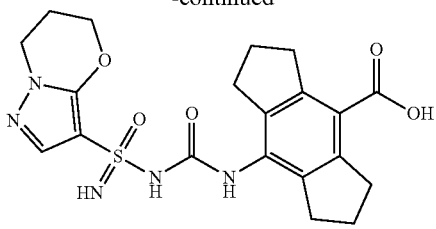
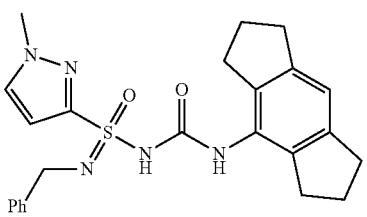
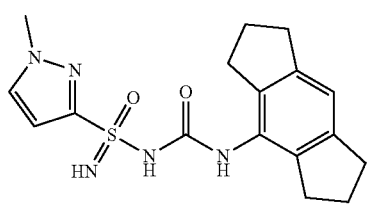 [SMILES: Cn1ccc(S(=N)(=O)NC(=O)Nc2c3c(cc4c2CCC4)CCC3)n1]
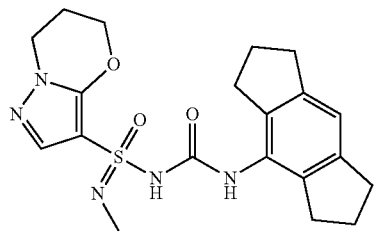
The present disclosure provides a compound, and pharmaceutically acceptable salts, solvates (e.g., hydrates), isomers, and tautomers thereof, that is selected from the group consisting of
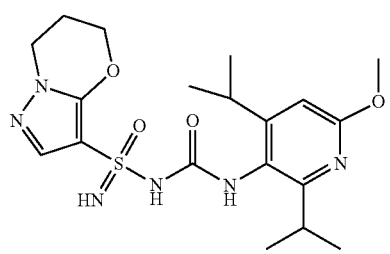
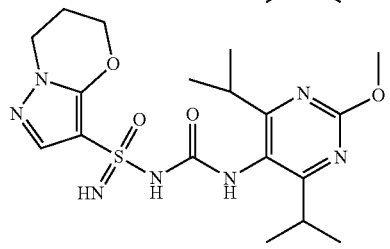
162
-continued
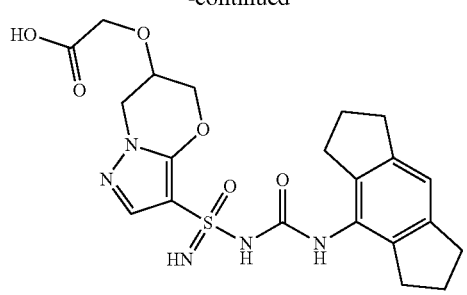
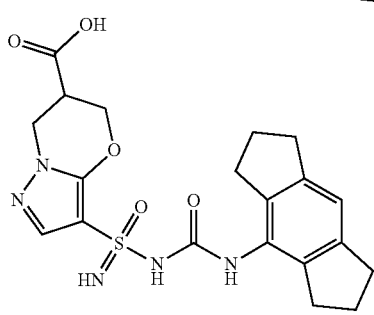
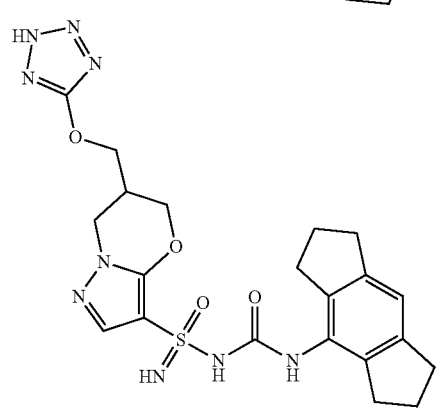
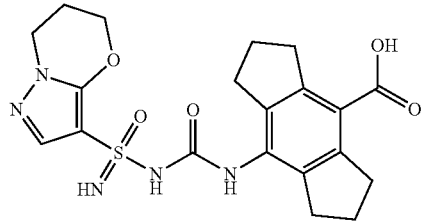
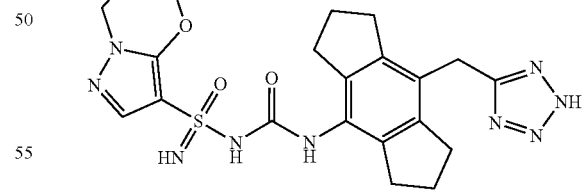
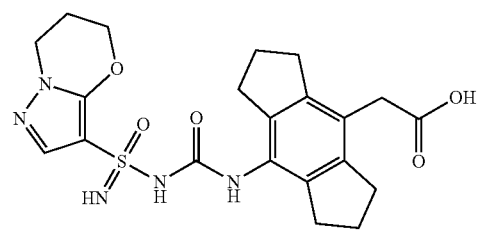

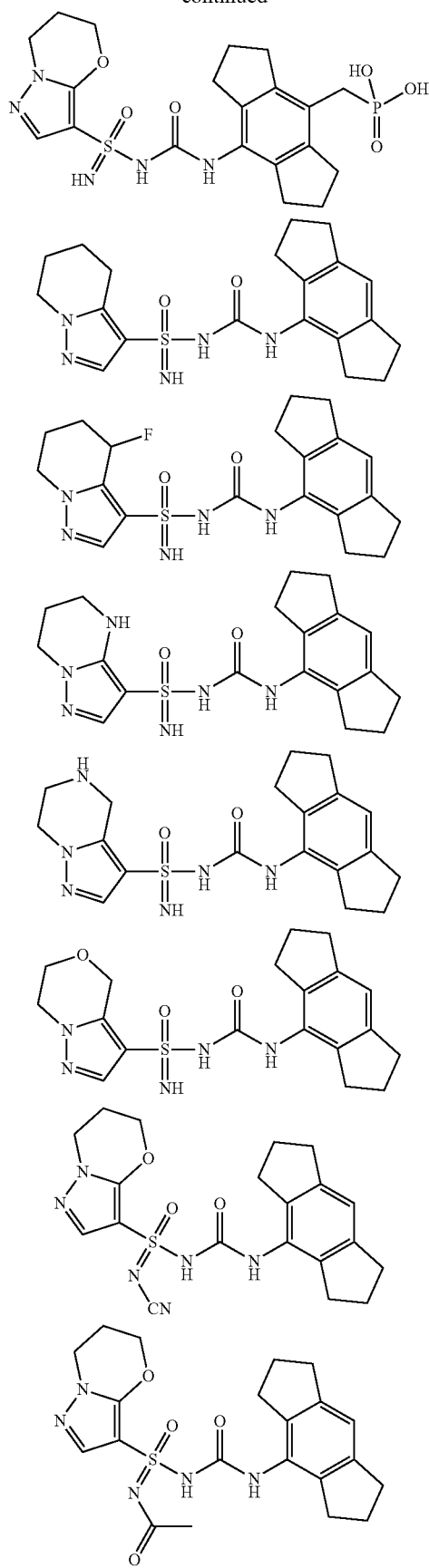
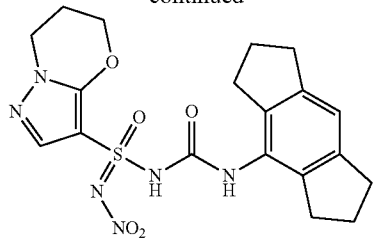
The present disclosure provides a compound, and pharmaceutically acceptable salts, solvates (e.g., hydrates), isomers, and tautomers thereof, that is selected from the group consisting of
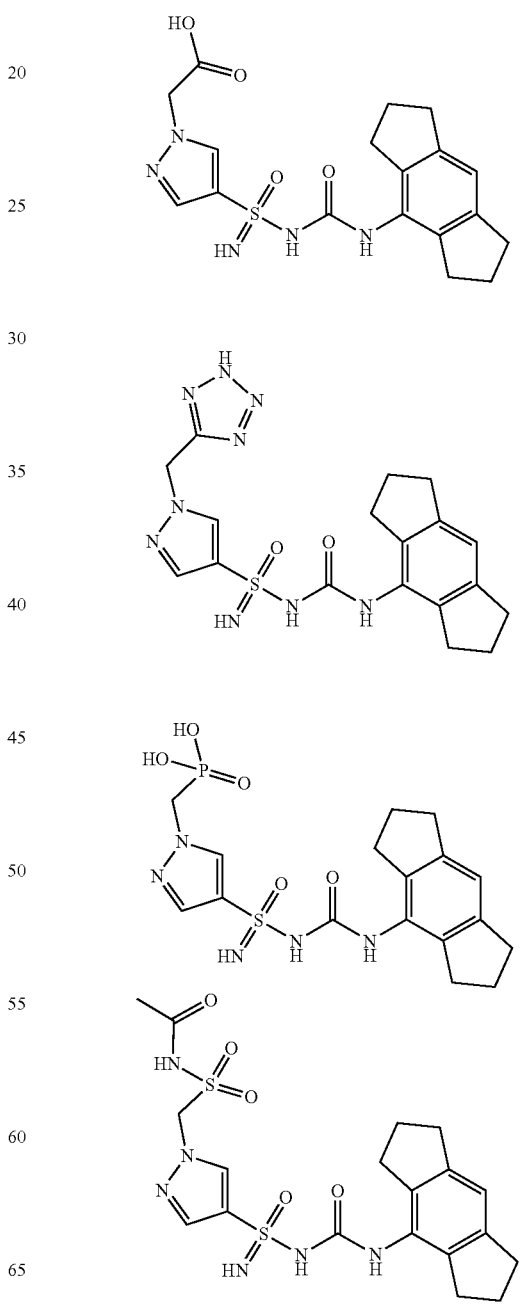

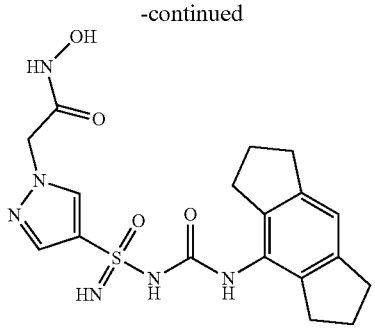
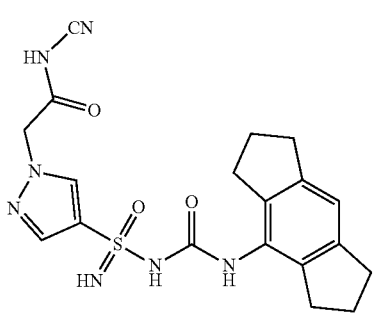
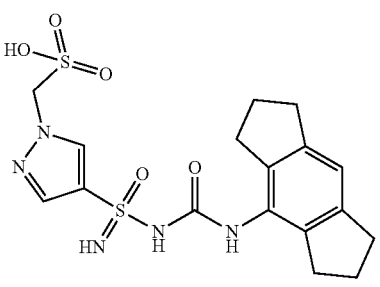
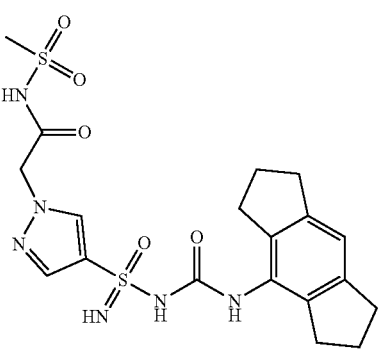
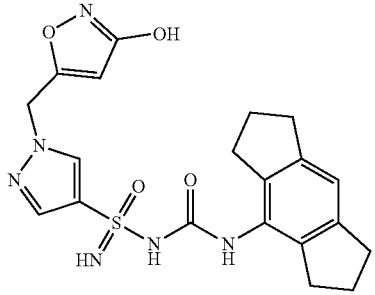
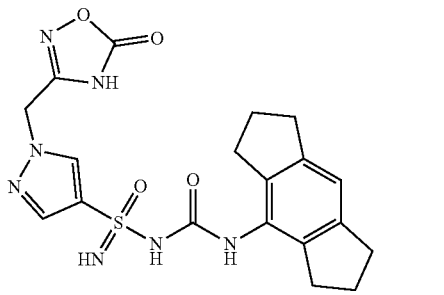
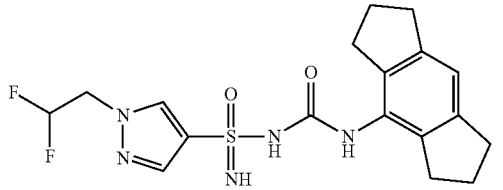
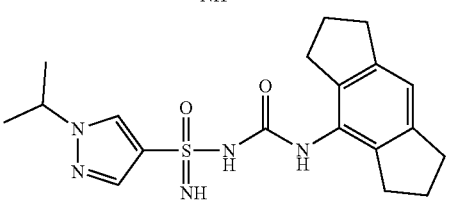
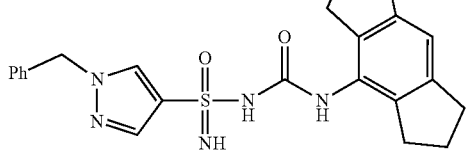
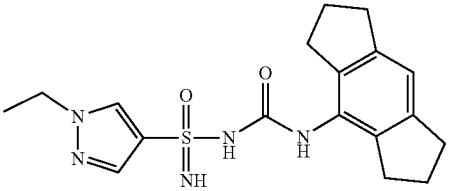
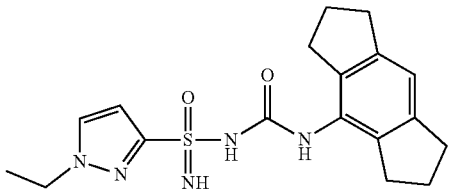
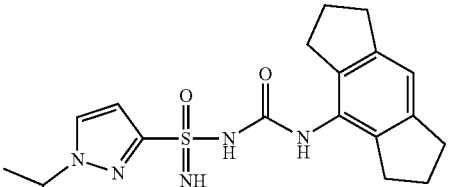
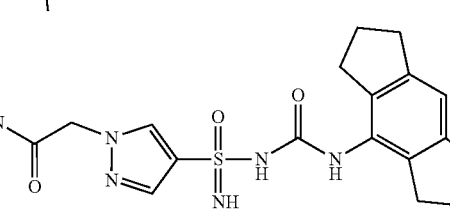

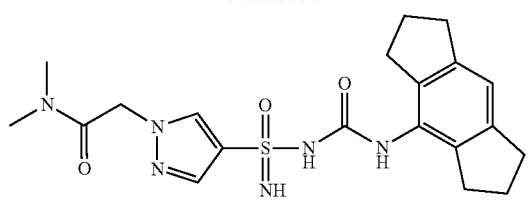
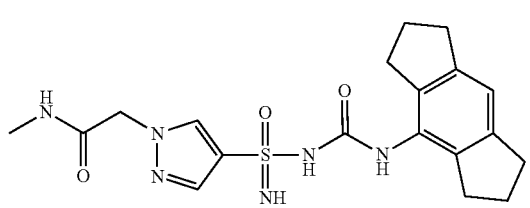
The present disclosure provides a compound, and pharmaceutically acceptable salts, solvates (e.g., hydrates), isomers, and tautomers thereof, that is selected from the group consisting of
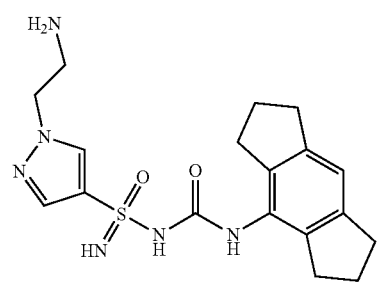
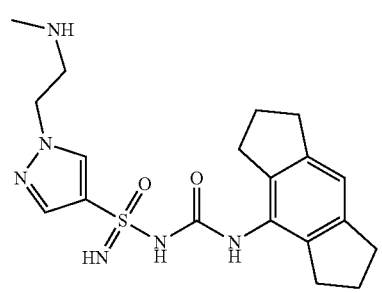
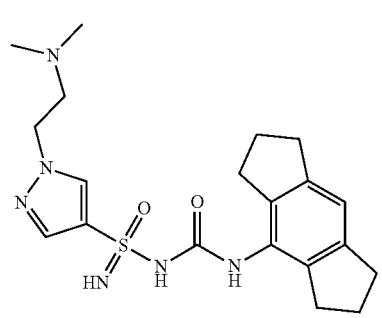
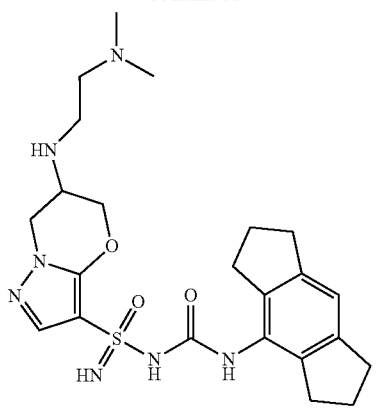
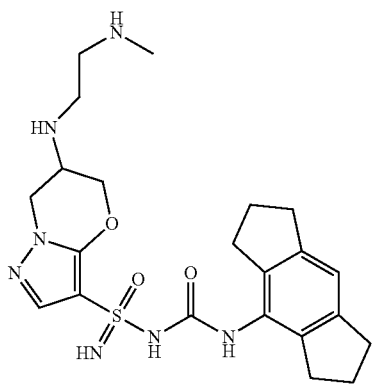
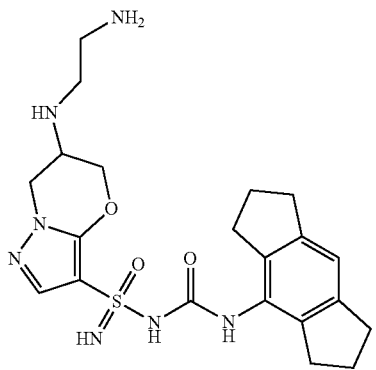
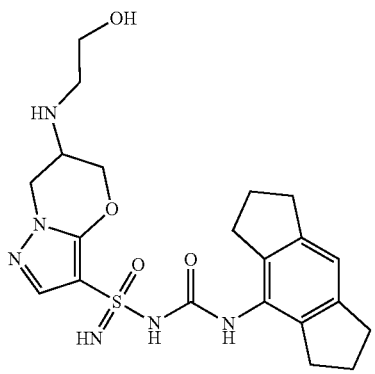

169
-continued
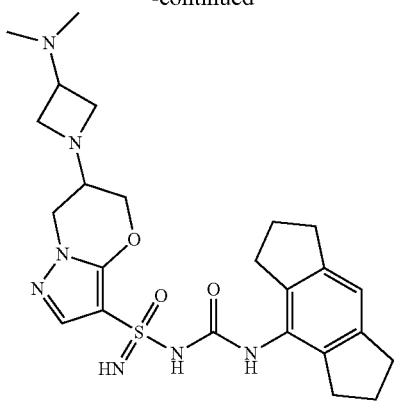
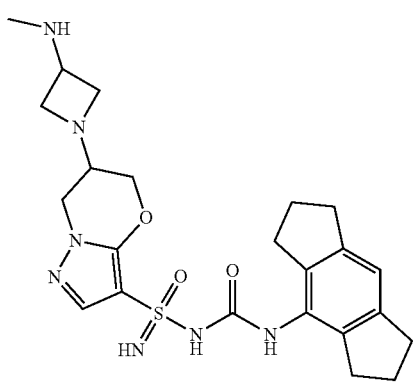
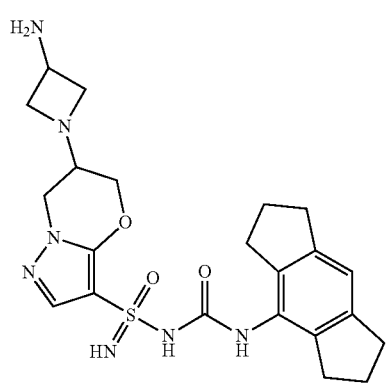
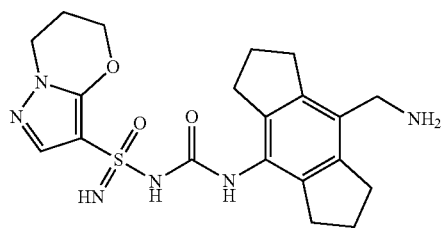
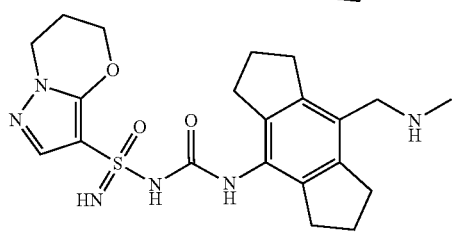
170
-continued
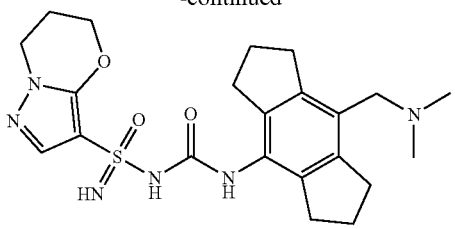
The present disclosure provides a compound, and pharmaceutically acceptable salts, solvates (e.g., hydrates), isomers, and tautomers thereof, that is selected from the group consisting of
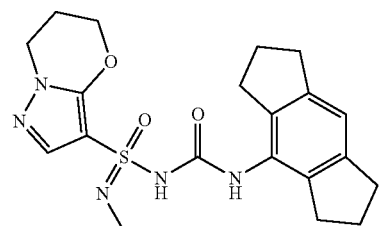
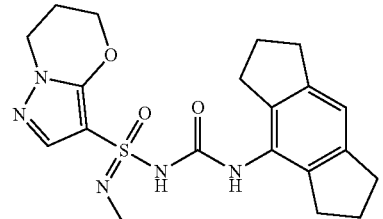
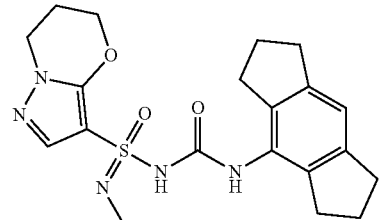
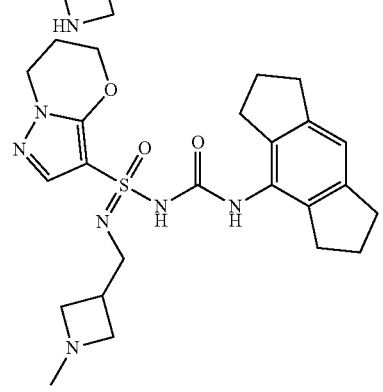

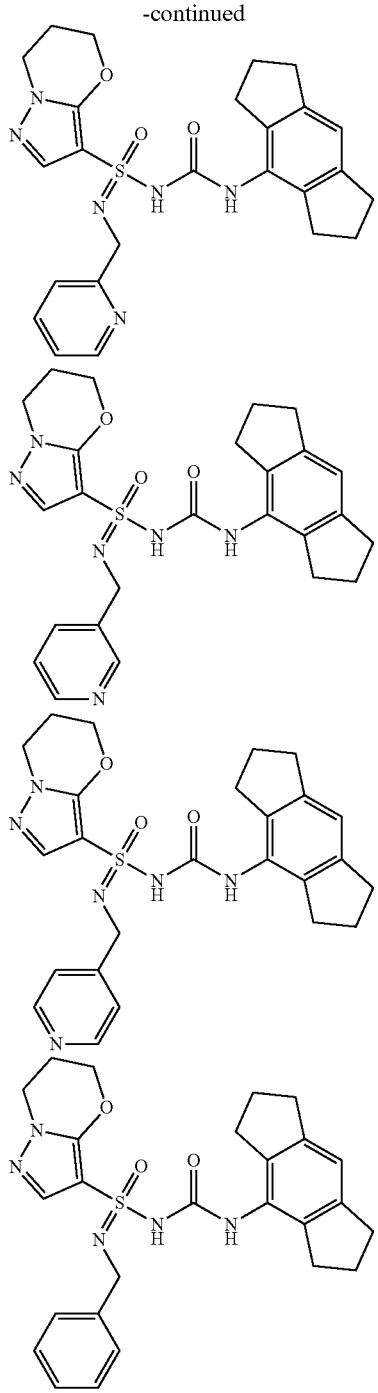

Methods of Synthesizing the Compounds

The compounds of the present disclosure may be made by a variety of methods, including standard chemistry. Suitable synthetic routes are depicted in the schemes given herein.

The compounds disclosed herein may be prepared by methods known in the art of organic synthesis as set forth in part by the following synthetic schemes. In the schemes described herein, it is well understood that protecting groups for sensitive or reactive groups are employed where necessary in accordance with general principles or chemistry. Protecting groups are manipulated according to standard methods of organic synthesis (T. W. Greene and P. G. M. Wuts, "Protective Groups in Organic Synthesis," Third edition, Wiley, New York 1999). These groups are removed at a convenient stage of the compound synthesis using methods that are readily apparent to those skilled in the art. The selection processes, as well as the reaction conditions and order of their execution, shall be consistent with the preparation of compounds of disclosed herein.

Those skilled in the art will recognize if a stereocenter exists in the compounds disclosed herein. In some embodiments, compounds of the disclosure can exist as enantiomeric or diastereomeric stereoisomers. Accordingly, the present disclosure includes both possible stereoisomers (unless specified in the synthesis) and includes not only racemic compounds but the individual enantiomers and/or diastereomers as well. When a compound is desired as a single enantiomer or diastereomer, it may be obtained by stereospecific synthesis or by resolution of the final product or any convenient intermediate. For example, enantiomerically pure compounds of the disclosure can be prepared using enantiomerically pure chiral building blocks. Alternatively, racemic mixtures of the final compounds or a racemic mixture of an advanced intermediate can be subjected to chiral purification as described herein to deliver the desired enantiomerically pure intermediates or final compounds. In the instances where an advanced intermediate is purified into its individual enantiomers, each individual enantiomer can be carried on separately to deliver the final enantiomerically pure compounds of the disclosure. Resolution of the final product, an intermediate, or a starting material may be affected by any suitable method known in the art. See, for example, "Stereochemistry of Organic Compounds," by E. L. Eliel, S. H. Wilen, and L. N. Mander (Wiley-Interscience, 1994).

The compounds described herein may be made from commercially available starting materials or synthesized using known organic, inorganic, and/or enzymatic processes.

Preparation of Compounds

By way of example, compounds of the present disclosure can be synthesized by following the steps outlined in General Schemes 1 and 2 which comprise examples of sequence of assembling compounds of the disclosure. Starting materials are either commercially available or made by known procedures in the reported literature or as illustrated. Preferred methods include, but are not limited to, those methods described herein.

General Scheme 1

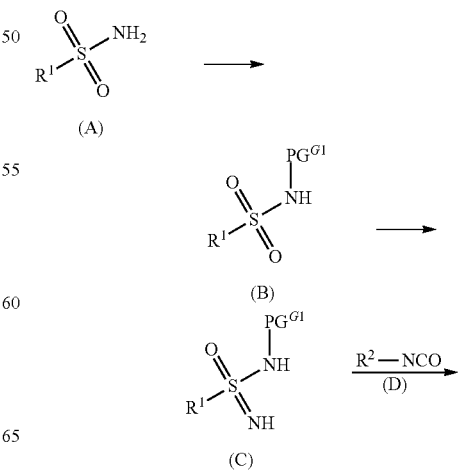

173

-continued

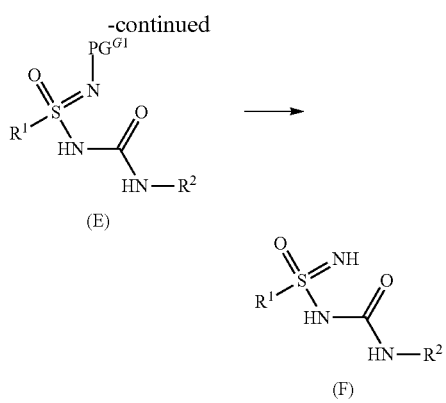

Formula I (Compound F) can be prepared according to the general procedures outlined in General Scheme 1. In General Scheme 1, $PG^{G1}$ is a protecting group. A sulfonamide (A) is protected to yield a protected sulfonamide (B). The protected sulfonamide (B) is converted to a protected sulfonimidamide (C) via activation (i.e. deoxychlorination or catalysis) and treatment with reaction with an ammonia source (or an amine to yield $R^{100}$—not shown). The protected sulfonimidamide (C) is reacted with an isocyanate (D) to yield compound (E). Then, the Compound (E) is deprotected to yield Compound (F).

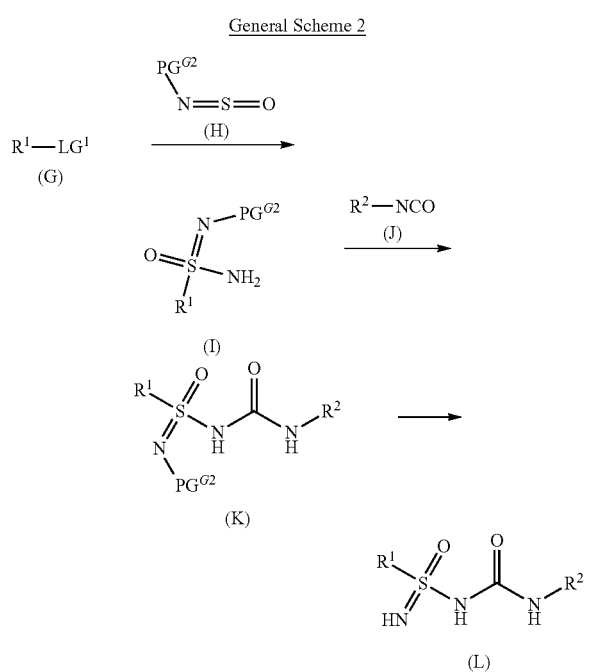

Formula I (Compound L) can also be prepared according to the general procedures outlined in General Scheme 2. In General Scheme 2, $PG^{G2}$ is a protecting group and $LG^1$ is a a leaving group (usually a halogen which can be activated as reactive species, i.e. via lithium-halogen exchange). Reaction of Compound (G) and Compound (H) followed by activation and treatment with an ammonia source (pictured) or primary amine (for substituted N—$R^{100}$, not pictured) produces a protected sulfonimidamide (I). Then, the Compound (K) is deprotected to yield Compound (L).

174

General Scheme 3 shows a representative synthesis of an $R^1$ moiety.

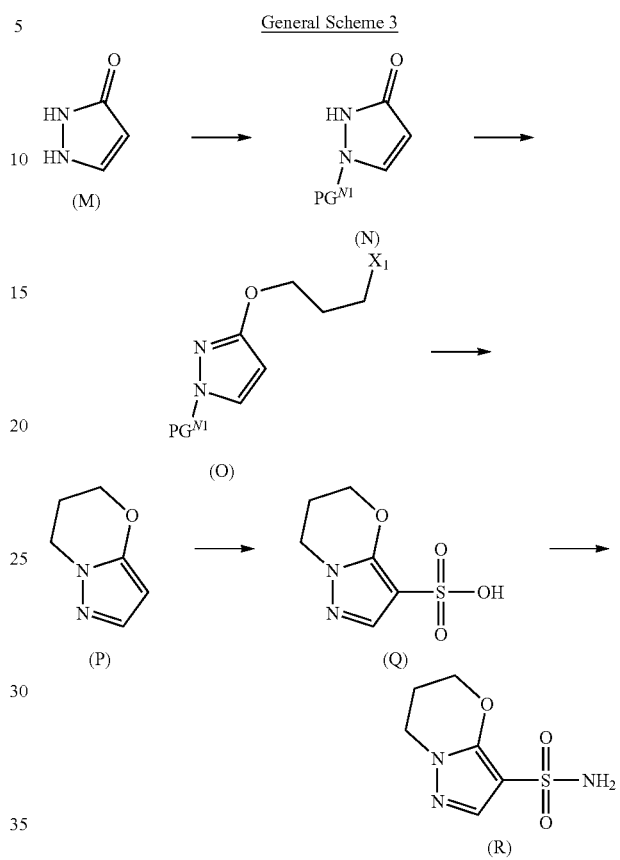

General Scheme 3 shows the preparation of a Compound (R), or a salt or solvate thereof. In General Scheme 3, $X^1$ is a halogen (e.g., chloro, bromo, iodo, or fluoro), sulfonate (e.g., nosylate, tosylate, or mesylate), nitrate, phosphate, or other suitable leaving group and $PG^{N1}$ is an amino protecting group.

Compound (M) is protected to yield compound (N). Compound (N) is then alkylated to form compound (O), for example with a Mitsonobu reaction. Compound (O) undergoes a deprotection and cyclization to form compound (P). Then, compound (P) is reacted with a sulfonating reagent to form compound (Q). Then, compound (Q) is activated (i.e. via chlorination) and then reacted with an ammonia source to form compound (R). Alternatively, compound (P) could be brominated to give starting materials such as compound (G) in General Scheme 2.

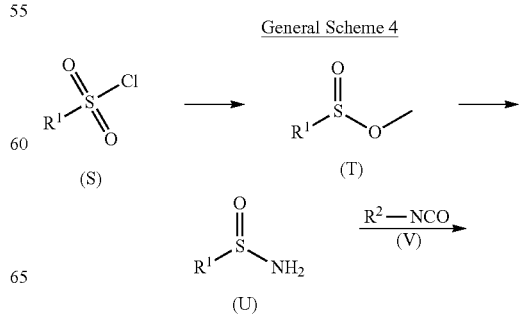

-continued (W) → [1. "Cl⁺"; 2. R¹⁰⁰—NH₂] → (X)

Formula I (Compound X) can be prepared according to the general procedures outlined in General Scheme 4. A sulfonyl chloride (S) is converted to sulfnic acid methyl ester (T) via reduction, followed by sulfinyl chloride formation and subsequent esterification. The sulfnic acid methyl ester (T) is converted to sulfinamide (U) via reaction with an amine source (such as LiHMDS), followed by hydrolysis. The sulfinamide (U) is reacted with an isocyanate (V) to yield compound (W). Then, the Compound (W) is converted to sulfonimidamide (X) via oxidative chlorination followed by reaction with amine or ammonia source.

Pharmaceutical Compositions

The disclosed compounds, and pharmaceutically acceptable salts, solvates (e.g., hydrates), isomers, prodrugs, and tautomers thereof, may be used on their own but will generally be administered in the form of a pharmaceutical composition in which one or more disclosed compounds, and pharmaceutically acceptable salts, solvates (e.g., hydrates), isomers, prodrugs, and tautomers thereof (active ingredient), is in association with a pharmaceutically acceptable adjuvant or carrier. Conventional procedures for the selection and preparation of suitable pharmaceutical compositions are described in, for example, "Pharmaceuticals— The Science of Dosage Form Designs," M. E. Aulton, Churchill Livingstone, 1988, which is hereby incorporated by reference in its entirety. In certain embodiments, the compound, or pharmaceutically acceptable salts, isomers, prodrugs, and tautomers thereof, is in the form of a hydrate.

Depending on the mode of administration, the pharmaceutical composition will comprise from about 0.05 to about 99 wt % (percent by weight), more particularly from about 0.05 to about 80 wt %, still more particularly from about 0.10 to about 70 wt %, and even more particularly from about 0.10 to about 50 wt %, of one or more disclosed compounds, and pharmaceutically acceptable salts, solvates (e.g., hydrates), isomers, prodrugs, and tautomers thereof, all percentages by weight being based on total composition.

The present disclosure also provides a pharmaceutical composition comprising one or more disclosed compounds, and pharmaceutically acceptable salts, solvates (e.g., hydrates), isomers, prodrugs, and tautomers thereof, as hereinbefore defined, in association with a pharmaceutically acceptable carrier.

The present disclosure further provides a process for the preparation of a pharmaceutical composition of the present disclosure which comprises mixing one or more disclosed compounds, and pharmaceutically acceptable salts, solvates (e.g., hydrates), isomers, prodrugs, and tautomers thereof, as hereinbefore defined with a pharmaceutically acceptable adjuvant or carrier. Pharmaceutical compositions of the disclosure can also be prepared according to conventional mixing, granulating or coating methods.

Pharmaceutical compositions of the present disclosure may comprise a therapeutically effective amount of one or more disclosed compounds, and pharmaceutically acceptable salts, solvates (e.g., hydrates), isomers, prodrugs, and tautomers thereof, formulated together with one or more pharmaceutically acceptable carriers. Some examples of materials that can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil, and soybean oil; glycols such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol; and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the pharmaceutical composition, according to the judgment of the formulator.

Depending on the intended mode of administration, the disclosed pharmaceutical compositions can be in solid, semi-solid or liquid dosage form, such as, for example, injectables, tablets, suppositories, pills, time-release capsules, elixirs, tinctures, emulsions, syrups, powders, liquids, suspensions, or the like, sometimes in unit dosages and consistent with conventional pharmaceutical practices. These modes may include systemic or local administration such as oral, nasal, parenteral (as by intravenous (both bolus and infusion), intramuscular, or subcutaneous injection), transdermal, vaginal, buccal, rectal or topical (as by powders, ointments, or drops) administration modes. These modes may also include intracisternally, intraperitoneally, as an oral or nasal spray, or as a liquid aerosol or dry powder pharmaceutical composition for inhalation. In some embodiments, the pharmaceutical composition of disclosure comprising one or more disclosed compounds, and pharmaceutically acceptable salts, solvates (e.g., hydrates), isomers, prodrugs, and tautomers thereof, is for oral administration. In some embodiments, the pharmaceutical composition of disclosure comprising one or more disclosed compounds, and pharmaceutically acceptable salts, solvates (e.g., hydrates), isomers, prodrugs, and tautomers thereof, is for intravenous administration.

Solid dosage forms for oral administration may include capsules, tablets, pills, powders, and granules. In such solid dosage forms, one or more disclosed compounds, and pharmaceutically acceptable salts, solvates (e.g., hydrates), isomers, prodrugs, and tautomers thereof, may be mixed with at least one inert, pharmaceutically acceptable excipient or carrier such as a diluent, fillers or extenders, binders, humectants, disintegrating agents, solution retarding agents, absorption accelerators, wetting agents, absorbents, lubricants, an emulsifier or dispersing agent, and/or an agent that enhances absorption of the one or more disclosed compounds, and pharmaceutically acceptable salts, solvates (e.g., hydrates), isomers, prodrugs, and tautomers thereof. In the case of capsules, tablets and pills, the dosage form may also comprise buffering agents.

Solid pharmaceutical compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the one or more disclosed compounds, and pharmaceutically acceptable salts, solvates (e.g., hydrates), isomers, prodrugs, and tautomers thereof, only, or preferentially, in a certain part of the intestinal tract, optionally, in a delayed manner. Examples of embedding compositions that can be used include polymeric substances and waxes.

The one or more disclosed compounds, and pharmaceutically acceptable salts, solvates (e.g., hydrates), isomers, prodrugs, and tautomers thereof, can also be in microencapsulated form with one or more excipients as noted herein. The solid dosage forms of tablets, dragees, capsules, pills, and granules can be prepared with coatings and shells such as enteric coatings, release controlling coatings and other coatings well known in the pharmaceutical formulating art. In such solid dosage forms, one or more disclosed compounds, and pharmaceutically acceptable salts, solvates (e.g., hydrates), isomers, prodrugs, and tautomers thereof, may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the one or more disclosed compounds, and pharmaceutically acceptable salts, solvates (e.g., hydrates), isomers, prodrugs, and tautomers thereof, only, or preferentially, in a certain part of the intestinal tract, optionally, in a delayed manner. Examples of embedding compositions that can be used may include polymeric substances and waxes.

Liquid dosage forms for oral administration may include pharmaceutically acceptable emulsions, microemulsions, solutions, suspensions, syrups and elixirs. In addition to the one or more disclosed compounds, and pharmaceutically acceptable salts, solvates (e.g., hydrates), isomers, prodrugs, and tautomers thereof, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral pharmaceutical compositions can also include adjuvants such as wetting agents, emulsifying and suspending agents, sweetening, flavoring, and perfuming agents.

Injectable pharmaceutical compositions, for example, sterile injectable aqueous or oleaginous suspensions comprising one or more disclosed compounds, and pharmaceutically acceptable salts, solvates (e.g., hydrates), isomers, prodrugs, and tautomers thereof, may be formulated according to the known art using suitable dispersing or wetting agents and suspending agents. The sterile injectable pharmaceutical composition may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, 1% lidocaine, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the composition of injectables.

The injectable pharmaceutical compositions can be sterilized, for example, by filtration through a bacterial-retaining filter, or by incorporating sterilizing agents in the form of sterile solid pharmaceutical compositions that can be dissolved or dispersed in sterile water or other sterile injectable medium prior to use.

In order to prolong the effect of one or more disclosed compounds, and pharmaceutically acceptable salts, solvates (e.g., hydrates), isomers, prodrugs, and tautomers thereof, it may desirable to slow the absorption of the one or more disclosed compounds, and pharmaceutically acceptable salts, solvates (e.g., hydrates), isomers, prodrugs, and tautomers thereof, from subcutaneous or intramuscular injection. This may be accomplished by the use of a liquid suspension of crystalline or amorphous material with poor water solubility. The rate of absorption of the one or more disclosed compounds, and pharmaceutically acceptable salts, solvates (e.g., hydrates), isomers, prodrugs, and tautomers thereof, then depends upon its rate of dissolution that, in turn, may depend upon crystal size and crystalline form. Alternatively, delayed absorption of a parenterally administered one or more disclosed compounds, and pharmaceutically acceptable salts, solvates (e.g., hydrates), isomers, prodrugs, and tautomers thereof, may be accomplished by dissolving or suspending the one or more disclosed compounds, and pharmaceutically acceptable salts, solvates (e.g., hydrates), isomers, prodrugs, and tautomers thereof, in an oil vehicle. Injectable depot forms are made by forming microencapsule matrices of the one or more disclosed compounds, and pharmaceutically acceptable salts, solvates (e.g., hydrates), isomers, prodrugs, and tautomers thereof, in biodegradable polymers such as polylactide-polyglycolide. Depending upon the ratio of the one or more disclosed compounds, and pharmaceutically acceptable salts, solvates (e.g., hydrates), isomers, prodrugs, and tautomers thereof, to polymer and the nature of the particular polymer employed, the rate of release for the one or more disclosed compounds, and pharmaceutically acceptable salts, solvates (e.g., hydrates), isomers, prodrugs, and tautomers thereof, can be controlled. Examples of other biodegradable polymers include poly(orthoesters) and poly (anhydrides). Depot injectable pharmaceutical compositions may also be prepared by entrapping the one or more disclosed compounds, and pharmaceutically acceptable salts, solvates (e.g., hydrates), isomers, prodrugs, and tautomers thereof, in liposomes or microemulsions that are compatible with body tissues.

Pharmaceutical compositions for rectal or vaginal administration may be suppositories that can be prepared by mixing the one or more disclosed compounds, and pharmaceutically acceptable salts, solvates (e.g., hydrates), isomers, prodrugs, and tautomers thereof, with suitable non-irritating excipients or carriers such as cocoa butter, polyethylene glycol or a suppository wax which are solid at ambient temperature but liquid at body temperature and therefore melt in the rectum or vaginal cavity and release the one or more disclosed compounds, and pharmaceutically acceptable salts, solvates (e.g., hydrates), isomers, prodrugs, and tautomers thereof.

The one or more disclosed compounds, and pharmaceutically acceptable salts, solvates (e.g., hydrates), isomers, prodrugs, and tautomers thereof, can be also formulated as a suppository that can be prepared from fatty emulsions or suspensions; using polyalkylene glycols such as propylene glycol, as the carrier.

Dosage forms for topical or transdermal administration of one or more disclosed compounds, and pharmaceutically acceptable salts, solvates (e.g., hydrates), isomers, prodrugs, and tautomers thereof, include ointments, pastes, creams, lotions, gels, powders, solutions, sprays, inhalants or patches. The one or more disclosed compounds, and pharmaceutically acceptable salts, solvates (e.g., hydrates), isomers, prodrugs, and tautomers thereof, is admixed under sterile conditions with a pharmaceutically acceptable carrier and any needed preservatives or buffers as may be required. Ophthalmic pharmaceutical compositions, ear drops, and the like are also contemplated as being within the scope of this disclosure.

The ointments, pastes, creams and gels may contain, in addition to one or more disclosed compounds, and pharmaceutically acceptable salts, solvates (e.g., hydrates), isomers, prodrugs, and tautomers thereof, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

One or more disclosed compounds, and pharmaceutically acceptable salts, solvates (e.g., hydrates), isomers, prodrugs, and tautomers thereof, may also be formulated for use as topical powders and sprays that can contain, in addition to one or more disclosed compounds, and pharmaceutically acceptable salts, solvates (e.g., hydrates), isomers, prodrugs, and tautomers thereof, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of one or more disclosed compounds, and pharmaceutically acceptable salts, solvates (e.g., hydrates), isomers, prodrugs, and tautomers thereof, across the skin. The rate can be controlled by either providing a rate controlling membrane or by dispersing the one or more disclosed compounds, and pharmaceutically acceptable salts, solvates (e.g., hydrates), isomers, prodrugs, and tautomers thereof, in a polymer matrix or gel.

Pharmaceutical compositions of the disclosure may also be formulated for delivery as a liquid aerosol or inhalable dry powder. Liquid aerosol pharmaceutical compositions may be nebulized predominantly into particle sizes that can be delivered to the terminal and respiratory bronchioles. Liquid aerosol and inhalable dry powder pharmaceutical compositions may be delivered throughout the endobronchial tree to the terminal bronchioles and eventually to the parenchymal tissue.

Aerosolized pharmaceutical compositions of the disclosure may be delivered using an aerosol forming device, such as a jet, vibrating porous plate or ultrasonic nebulizer, selected to allow the formation of an aerosol particles having with a mass medium average diameter predominantly between 1 to 5 μm. Further, the pharmaceutical composition may have balanced osmolarity ionic strength and chloride concentration, and the smallest aerosolizable volume able to deliver effective dose of the one or more disclosed compounds, and pharmaceutically acceptable salts, solvates (e.g., hydrates), isomers, prodrugs, and tautomers thereof. Additionally, the aerosolized pharmaceutical composition may not impair negatively the functionality of the airways and does not cause undesirable side effects.

Aerosolization devices suitable for administration of aerosol pharmaceutical compositions of the disclosure include, for example, jet, vibrating porous plate, ultrasonic nebulizers and energized dry powder inhalers, that are able to nebulize the pharmaceutical composition of the disclosure into aerosol particle size predominantly in the size range from 1-5 μm. Predominantly in this application means that at least 70% but optionally more than 90% of all generated aerosol particles are 1 to 5 μm range. A jet nebulizer works by air pressure to break a liquid solution into aerosol droplets. Vibrating porous plate nebulizers work by using a sonic vacuum produced by a rapidly vibrating porous plate to extrude a solvent droplet through a porous plate. An ultrasonic nebulizer works by a piezoelectric crystal that shears a liquid into small aerosol droplets. A variety of suitable devices are available, including, for example, AeroNeb and AeroDose vibrating porous plate nebulizers (AeroGen, Inc., Sunnyvale, Calif.), Sidestream7 nebulizers (Medic-Aid Ltd., West Sussex, England), Pari LC7 and Pari LC Star7 jet nebulizers (Pari Respiratory Equipment, Inc., Richmond, Va.), and Aerosonic (DeVilbiss Medizinische Produkte (Deutschland) GmbH, Heiden, Germany) and μLtraAire7 (Omron Healthcare, Inc., Vernon Hills, Ill.) ultrasonic nebulizers.

Methods of Use

The disclosed compounds, and pharmaceutically acceptable salts, solvates (e.g., hydrates), isomers, prodrugs, and tautomers thereof, and compositions may be useful as pharmaceuticals, as discussed herein.

The present disclosure provides methods for treating a disorder including the step of administering an effective amount of one or more compounds of the present disclosure, and pharmaceutically acceptable salts, solvates (e.g., hydrates), isomers, prodrugs, and tautomers thereof, to thereby treat the disorder in a subject in need thereof.

The present disclosure provides methods for treating a disorder including the step of administering an effective amount of one or more pharmaceutical compositions of the present disclosure to thereby treat the disorder in a subject in need thereof.

The present disclosure provides one or more compounds of the present disclosure, and pharmaceutically acceptable salts, solvates (e.g., hydrates), isomers, prodrugs, and tautomers thereof, or one or more pharmaceutical compositions of the present disclosure for use in the treatment of a disorder in a subject in need thereof.

The present disclosure provides for use of one or more compounds of the present disclosure, and pharmaceutically acceptable salts, solvates (e.g., hydrates), isomers, prodrugs, and tautomers thereof, for the treatment of a disorder in a subject in need thereof. The present disclosure also provides for use of one or more compounds of the present disclosure, and pharmaceutically acceptable salts, solvates (e.g., hydrates), isomers, prodrugs, and tautomers thereof, for the treatment of a disorder in a subject in need thereof, wherein the disorder is responsive to inflammasome inhibition.

The present disclosure provides for use of one or more compositions of the present disclosure for the treatment of a disorder in a subject in need thereof. The present disclosure also provides for use of one or more compositions of the present disclosure for the treatment of a disorder in a subject in need thereof, wherein the disorder is responsive to inflammasome inhibition.

The present disclosure provides for use of one or more compounds of the present disclosure, and pharmaceutically acceptable salts, solvates (e.g., hydrates), isomers, prodrugs, and tautomers thereof, in the manufacture of a medicament for the treatment of a disorder. The present disclosure also provides for use of one or more compounds of the present disclosure, and pharmaceutically acceptable salts, solvates (e.g., hydrates), isomers, prodrugs, and tautomers thereof, in the manufacture of a medicament for the treatment of a disorder that is responsive to inflammasome inhibition.

The present disclosure provides for use of one or more compositions of the present disclosure in the manufacture of a medicament for the treatment of a disorder. The present disclosure also provides for use of one or more compositions of the present disclosure in the manufacture of a medicament for the treatment of a disorder that is responsive to inflammasome inhibition.

The present disclosure provides for use of one or more compounds of the present disclosure, and pharmaceutically acceptable salts, solvates (e.g., hydrates), isomers, prodrugs, and tautomers thereof, as a medicament for the treatment of a disorder.

The present disclosure provides for use of one or more compositions of the present disclosure as a medicament for the treatment of a disorder.

In some embodiments, the disorder is one which is responsive to inhibition of activation of an inflammasome. In some embodiments, the disorder is one which is responsive to inhibition of activation of the NLRP3 inflammasome.

According to some embodiments, one or more compounds, and pharmaceutically acceptable salts, solvates (e.g., hydrates), isomers, prodrugs, and tautomers thereof, or pharmaceutical compositions of the present disclosure is useful as a specific inhibitor of NLRP3.

In some embodiments, the disorder is responsive to modulation of one or more of IL-6, IL-1β, IL-17, IL-18, IL-1α, IL-37, IL-22, IL-33, and Th17 cells. In some embodiments, the disorder is responsive to modulation of one or more of IL-1β and IL-18.

In some embodiments, the modulation is inhibition of one or more of IL-6, IL-1β, IL-17, IL-18, IL-1α, IL-37, IL-22, and IL-33. In some embodiments, the modulation is inhibition of one or more of IL-1β and IL-18.

In some embodiments, the modulation of Th17 cells is by inhibition of production and/or secretion of IL-17.

In some embodiments, the disorder is a disorder of the immune system, the cardiovascular system, the endocrine system, the gastrointestinal tract, the renal system, the respiratory system, the central nervous system, is a cancer or other malignancy and/or is caused by or associated with a pathogen.

It will be appreciated that general embodiments defined according to broad categories of disorders are not mutually exclusive. In this regard any particular disorder may be categorized according to more than one of the general embodiments disclosed herein. A non-limiting example is Type I diabetes which is an autoimmune disease and a disease of the endocrine system.

In some embodiments, the disorder is of the immune system. In some embodiments, the disorder is an inflammatory disorder or an autoimmune disorder.

In some embodiments, the disorder is of the liver.
In some embodiments, the disorder is of the lung.
In some embodiments, the disorder is of the skin.
In some embodiments, the disorder is of the cardiovascular system.

In some embodiments, the disorder is a cancer, tumor or other malignancy. As used herein, cancers, tumors, and malignancies, refer to disorders, or to cells or tissues associated with the disorders, characterized by aberrant or abnormal cell proliferation, differentiation and/or migration often accompanied by an aberrant or abnormal molecular phenotype that includes one or more genetic mutations or other genetic changes associated with oncogenesis, expression of tumor markers, loss of tumor suppressor expression or activity and/or aberrant or abnormal cell surface marker expression. In some embodiments, cancers, tumors, and malignancies may include sarcomas, lymphomas, leukemias, solid tumors, blastomas, gliomas, carcinomas, melanomas and metastatic cancers, although without limitation thereto. A more comprehensive listing of cancers, tumors, and malignancies may be found at the National Cancer Institutes website http://www.cancer.gov/cancertopics/types/alphalist, which is hereby incorporated by reference in its entirety.

In some embodiments, the disorder is of the renal system.
In some embodiments, the disorder is of the gastrointestinal tract.
In some embodiments, the disorder is of the respiratory system.
In some embodiments, the disorder is of the endocrine system.
In some embodiments, the disorder is of the central nervous system (CNS).

In some embodiments, the disorder is caused by, or is associated with, a pathogen. The pathogen may be a virus, a bacterium, a protist, a worm or a fungus or any other organism capable of infecting a mammal, although without limitation thereto.

Non-limiting examples of viruses include influenza virus, cytomegalovirus, Epstein Barr Virus, human immunodeficiency virus (HIV), alphavirus such as Chikungunya and Ross River virus, flaviviruses such as Dengue virus, Zika virus and papillomavirus, although without limitation thereto.

Non-limiting examples of pathogenic bacteria include *Staphylococcus aureus, Helicobacter pylori, Bacillus anthracis, Bordatella pertussis, Corynebacterium diptheriae, Clostridium tetani, Clostridium botulinum, Streptococcus pneumoniae, Streptococcus pyogenes, Listeria monocytogenes, Hemophilus influenzae, Pasteureiia multicida, Shigella dysenteriae, Mycobacterium tuberculosis, Mycobacterium leprae, Mycoplasma pneumoniae, Mycoplasma hominis, Neisseria meningitidis, Neisseria gonorrhoeae, Rickehsia rickehsii, Legionella pneumophila, Klebsiella pneumoniae, Pseudomonas aeruginosa, Propionibacterium acnes, Treponema pallidum, Chlamydia trachomatis, Vibrio cholerae, Salmonella typhimurium, Salmonella typhi, Borrelia burgdorferi* and *Yersinia pestis*, although without limitation thereto.

Non-limiting examples of protists include *Plasmodium, Babesia, Giardia, Entamoeba, Leishmania* and Trypanosomes, although without limitation thereto.

Non-limiting examples of worms include helminths inclusive of schistisimes, roundworms, tapeworms and flukes, although without limitation thereto.

Non-limiting examples of fungi include *Candida* and *Aspergillus* species, although without limitation thereto.

In some embodiments, the disorder is selected from a group consisting of: constitutive inflammation including a cryopyrin-associated periodic syndrome (CAPS): Muckle-Wells syndrome (MWS), familial cold autoinflammatory syndrome (FCAS) and neonatal-onset multisystem inflammatory disease (NOMID); an autoinflammatory disease: familial Mediterranean fever (FMF), TNF receptor associated periodic syndrome (TRAPS), mevalonate kinase deficiency (MKD), hyperimmunoglobulinemia D and periodic fever syndrome (H IDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, and developmental delay (SIFD); Sweet's syndrome; chronic nonbacterial osteomyelitis (CNO); chronic recurrent multifocal osteomyelitis (CRMO) and synovitis; acne; pustulosis; hyperostosis; osteitis syndrome (SAPHO); an autoimmune disease including multiple sclerosis (MS), type-1 diabetes, psoriasis, rheumatoid arthritis, Behcet's disease, Sjogren's syndrome, and Schnitzler syndrome; a respiratory disease including idiopathic pulmonary fibrosis (IPF), chronic obstructive pulmonary disorder (COPD), steroid-resistant asthma, asbestosis, silicosis and cystic fibrosis; a central nervous system disease including Parkinson's disease, Alzheimer's disease, motor neuron disease, Huntington's disease, cerebral malaria and brain injury from pneumococcal meningitis; a metabolic disease including Type 2 diabetes, atherosclerosis, obesity, gout, and pseudo-gout; an ocular disease including those of the ocular epithelium, age-related macular degeneration (AMD), corneal infection, uveitis and dry eye; a kidney disease including chronic kidney disease, oxalate nephropathy, and diabetic nephropathy; a liver disease including non-alcoholic steatohepatitis and alcoholic liver disease; an inflammatory reaction in the skin including contact hypersensitivity, and sunburn; an inflammatory reaction in the joints including osteoarthritis, systemic juvenile idiopathic arthritis, adult-onset Still's disease, and relapsing polychondritis; a viral infection including alpha vims (Chikungunya, Ross River) and flavivirus (Dengue and Zika Virus), flu, and HIV; hidradenitis suppurativa (HS) and other cyst-causing skin diseases; cancer including lung cancer metastasis, pancreatic cancer, gastric cancer, myelodisplastic syndrome, and leukemia; polymyositis; stroke; myocardial infarction; Graft versus Host Disease; hypertension; colitis; helminth infection; bacterial infection; abdominal aortic aneurism; wound healing; depression, psychological stress; pericarditis including Dressler's syndrome; ischaemia reperfusion injury; and any disorder where an individual has been determined to carry a germline or somatic non-silent mutation in NLRP3.

In some embodiments, the disorder is a cryopyrin-associated periodic syndrome (CAPS).

In some embodiments, the disorder is atherosclerosis.

In one non-limiting example of those described, the disorder being treated is NASH. NLRP3 inflammasome activation is central to inflammatory recruitment in NASH, and inhibition of NLRP3 may both prevent and reverse liver fibrosis. One or more compounds, or pharmaceutically acceptable salts, prodrugs, solvates, hydrates, isomers, prodrugs, and tautomers thereof, or pharmaceutical compositions of the present disclosure, by interrupting the function of NLRP3 inflammasomes in liver tissue, can cause histological reductions in liver inflammation, decreased recruitment of macrophages and neutrophils, and suppression of NF-κB activation. Inhibition of the NLRP3 can reduce hepatic expression of pro-IL-1β and normalized hepatic and circulating IL-1β, IL-6 and MCP-1 levels thereby assisting in treatment of the disorder.

In a further non-limiting example of those described, the disorder being treated is severe steroid resistant (SSR) asthma. Respiratory infections induce an NLRP3 inflammasome/caspase-1/IL-Iβ signaling axis in the lungs that promotes SSR asthma. The NLRP3 inflammasome recruits, and activates, pro-caspase-1 to induce IL-1β responses. NLRP3 inflammasome-induced IL-β responses are therefore important in the control of infections, however, excessive activation results in aberrant inflammation and has been associated with the pathogenesis of SSR asthma and COPD. The administration of one or more compounds, or pharmaceutically acceptable salts, prodrugs, solvates, hydrates, isomers, prodrugs, and tautomers thereof, or pharmaceutical compositions of the present disclosure that target specific disease processes, are more therapeutically attractive than non-specifically inhibiting inflammatory responses with steroids or IL-1β. Targeting the NLRP3 inflammasome/caspase-1/IL-1β signaling axis with one or more compounds, or pharmaceutically acceptable salts, prodrugs, solvates, hydrates, isomers, prodrugs, and tautomers thereof, or pharmaceutical compositions of the present disclosure may therefore be useful in the treatment of SSR asthma and other steroid-resistant inflammatory conditions.

In one further non-limiting example of those described, the disorder being treated is Parkinson's disease. Parkinson's is the most common neurodegenerative movement disorder and is characterized by a selective loss of dopaminergic neurons, accompanied by the accumulation of misfolded a-synuclein (Syn) into Lewy bodies that are pathological hallmarks of the disease. Chronic microglial neuroinflammation is evident early in the disease, and has been proposed to drive pathology.

A central role for microglial NLRP3 is postulated in Parkinson's progression. The NLRP3 inflammasome is activated by fibrillar Syn via a Syk kinase dependent mechanism, and also occurs in the absence of Syn pathology at the early stages of dopaminergic degeneration, and drives neuronal loss. One or more compounds, or pharmaceutically acceptable salts, prodrugs, solvates, hydrates, isomers, prodrugs, and tautomers thereof, or pharmaceutical compositions of the present disclosure may block NLRP3 inflammasome activation by fibrillar Syn or mitochondrial dysfunction and thereby confer effective neuroprotection of the nigrostriatal dopaminergic system and assist with treatment of Parkinson's.

In some embodiments, the method treats a disorder, including, but not limited to, a bacterial infection, a viral infection, a fungal infection, inflammatory bowel disease, celiac disease, colitis, intestinal hyperplasia, cancer, metabolic syndrome, obesity, rheumatoid arthritis, liver disease, liver fibrosis, hepatic steatosis, fatty liver disease, gout, lupus, lupus nephritis, Crohn's disease, IBD (inflammatory bowel disease), myelodysplastic syndrome (MDS), myeloproliferative neoplasm (MPN), non-alcoholic fatty liver disease (NAFLD), and non-alcoholic steatohepatitis (NASH).

In some embodiments, the disorder is selected from a group consisting of: NASH (nonalcoholic steatohepatitis); myelodysplastic syndrome (MDS); myeloproliferative neoplasm (MPN); CAPS (Cryopyrin Associated Periodic Syndromes); IPF (Idiopathic pulmonary fibrosis); MI (R/I) (myocardial infarction and reperfusion injury); Gout; I/O (immuno-oncology); Asthma; IBD (inflammatory bowel disease); Renal fibrosis; adult onset Still's disease; systemic juvenile idiopathic arthritis; tumor necrosis factor receptor-associated periodic syndrome (TRAPS); colchicine-resistant familial Mediterranean fever (FMF); hyper IgD syndrome (HIDS)/Mevalonate Kinase Deficiency (MKD); traumatic brain injury; Parkinson's Disease; moderate to severe inflammatory acne; acute non-anterior non-infectious uveitis (NIU); AD (Alzheimer's disease); COPD (Chronic Obstructive Pulmonary Disease); Sepsis; MS (multiple sclerosis); Behcet's disease; Crohn's disease; RA (rheumatoid arthritis); erosive osteoarthritis; T1D (Type 1 diabetes); T2D (Type 2 diabetes); Obesity; osteoporosis; cystic fibrosis; alcoholic liver disease; aging; HCC (hepatocellular carcinoma); depression; endometriosis; pyoderma gangrenosum ("PG"), a rare ulcerative skin disease; Lupus, Lupus Nephritis; Epilepsy; ischemic stroke; deafness; sickle cell disease; SLE (Systemic Lupus Erythematosus); and Spinal cord injury.

In some embodiments, the disorder is selected from the group consisting of lupus, lupus nephritis, cryopyrin-associated periodic syndromes (CAPS), myelodysplastic syndromes (MDS), gout, myeloproliferative neoplasms (MPN), atherosclerosis, Crohn's disease, and inflammatory bowel disease (IBD).

In some embodiments, the disorder is gout.

In some embodiments, the disorder is lupus

In some embodiments, the disorder is lupus nephritis.

In some embodiments, the disorder is Crohn's disease.

In some embodiments, the disorder is IBD (inflammatory bowel disease).

In some embodiments, the disorder is MDS (myelodysplastic syndromes).

In some embodiments, the disorder is MPN (myeloproliferative neoplasms).

For the therapeutic uses mentioned herein, the dosage administered will, of course, vary with the one or more compounds, and pharmaceutically acceptable salts, solvates (e.g., hydrates), isomers, prodrugs, and tautomers thereof, or pharmaceutical compositions employed, the mode of administration, the treatment desired and the disorder indicated. For example, the daily dosage of the one or more compounds, and pharmaceutically acceptable salts, solvates (e.g., hydrates), isomers, prodrugs, and tautomers thereof, of the present disclosure, if inhaled, may be in the range from about 0.05 micrograms per kilogram body weight (μg/kg) to about 100 micrograms per kilogram body weight (μg/kg). Alternatively, if the one or more compounds, and pharmaceutically acceptable salts, solvates (e.g., hydrates), isomers, prodrugs, and tautomers thereof, is administered orally, then the daily dosage of the one or more compounds of the present disclosure may be in the range from about 0.01 micrograms per kilogram body weight (μg/kg) to about 100 milligrams per kilogram body weight (mg/kg).

It will be understood, however, that the total daily usage of the one or more compounds, and pharmaceutically acceptable salts, solvates (e.g., hydrates), isomers, prodrugs, and tautomers thereof, and pharmaceutical compositions of the present disclosure will be decided by the attending physician within the scope of sound medical judgment. The specific therapeutically effective dose level for any particular patient will depend upon a variety of factors including the disorder being treated and the severity of the disorder; the activity of the specific compound employed; the specific pharmaceutical composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts. A physician or veterinarian of ordinary skill in the art can readily determine and prescribe the therapeutically effective amount of the one or more compounds, and pharmaceutically acceptable salts, solvates (e.g., hydrates), isomers, prodrugs, and tautomers thereof, or pharmaceutical compositions disclosed herein required to treat, counter, or arrest the progress of the disorder.

Combination Therapy

In some embodiments, one or more compounds, and pharmaceutically acceptable salts, solvates (e.g., hydrates), isomers, prodrugs, and tautomers thereof, or pharmaceutical compositions described herein may be used alone or together or conjointly administered, or used in combination, with a known therapeutic agent or pharmaceutical composition. Conjoint administration or used in combination may refer to any form of administration of two or more different compounds or pharmaceutical compositions such that the second compound or pharmaceutical composition is administered while the previously administered compound or pharmaceutical composition is still effective in the body. For example, the different compounds or pharmaceutical compositions can be administered either in the same formulation or in a separate formulation, either simultaneously, sequentially, or by separate dosing of the individual components of the treatment. In some embodiments, the different compounds or pharmaceutical compositions can be administered within one hour, 12 hours, 24 hours, 36 hours, 48 hours, 72 hours, or a week of one another. Thus, an individual who receives such treatment can benefit from a combined effect of different compounds or pharmaceutical compositions.

In some embodiments, one or more of the compounds, and pharmaceutically acceptable salts, solvates (e.g., hydrates), isomers, prodrugs, and tautomers thereof, or pharmaceutical compositions of the disclosure are used in combination with one or more other compounds, and pharmaceutically acceptable salts, solvates (e.g., hydrates), isomers, prodrugs, and tautomers thereof, or pharmaceutical compositions of the disclosure in the methods or uses of the disclosure. In certain such embodiments, the combination of one or more other compounds, and pharmaceutically acceptable salts, solvates (e.g., hydrates), isomers, prodrugs, and tautomers thereof, or pharmaceutical compositions of the disclosure is used in a method for treating one or more of the disorders listed herein.

In some embodiments, combinations of one or more compounds, and pharmaceutically acceptable salts, solvates (e.g., hydrates), isomers, prodrugs, and tautomers thereof, or pharmaceutical compositions provided herein, or combinations of other known agents or pharmaceutical compositions and one or more compounds, and pharmaceutically acceptable salts, solvates (e.g., hydrates), isomers, prodrugs, and tautomers thereof, or pharmaceutical compositions provided herein, are formulated into pharmaceutical compositions and medicaments that are useful in the methods and uses of the disclosure. The disclosure also provides for use of such combinations in treating one or more of the disorders listed herein.

In some embodiments of the disclosure, one or more compounds, and pharmaceutically acceptable salts, solvates (e.g., hydrates), isomers, prodrugs, and tautomers thereof, or pharmaceutical compositions of the disclosure are administered at a sub-therapeutic dose, wherein a subtherapeutic dose is a dose that would be insufficient to treat one of the disorders listed herein if administered alone.

EXEMPLARY EMBODIMENTS

Some embodiments of this disclosure are Embodiments I, as follows:

Embodiment I-1. A compound having the structure of Formula (I),

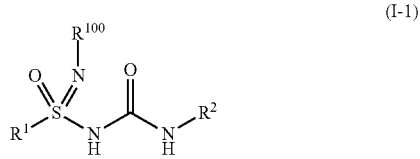

(I-1)

or a pharmaceutically acceptable salt, solvate, isomer, or tautomer thereof, wherein:

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

$R^1$ is selected from the group consisting of

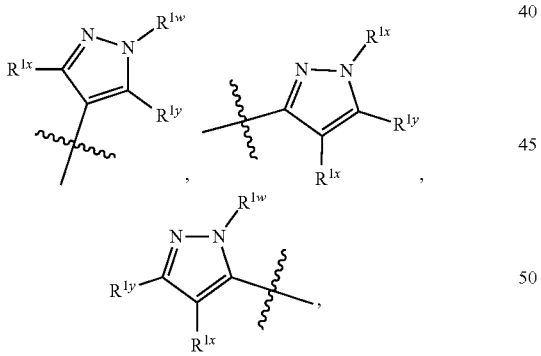

wherein $R^{1w}$ is selected from the group consisting of H, D, —CN, —C(O)R$^{5b}$, —S(O)$_2$R$^{5b}$, —S(O)R$^{5b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{5a}$, —C(O)R$^{5b}$, —P(O)R$^{5b}$R$^{6b}$, —S(O)$_2$R$^{5b}$, —S(O)R$^{5b}$, —NR$^{5a}$R$^{6a}$, —NR$^{5a}$C(O)R$^{6a}$, —NR$^{5a}$C(O)OR$^{6a}$, —NR$^{5a}$C(O)NR$^{6a}$, —NR$^{5a}$S(O)$_2$R$^{6a}$, C$_3$-C$_{10}$cycloalkyl, C$_6$aryl, 3-7-membered heterocyclyl, and 5-6 membered heteroaryl;

each $R^{1x}$ and $R^{1y}$ is independently, H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl; or wherein $R^{1w}$ and $R^{1y}$, together with the atoms to which they are attached can form a 3-7-membered heterocyclyl or 5-6 membered heteroaryl; wherein the 3-7-membered heterocyclyl and 5-6 membered heteroaryl are independently unsubstituted or substituted with one or more substituents selected from the group consisting of D, —CN, halogen, C$_1$-C$_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$; or wherein $R^{1x}$ and $R^{1y}$, together with the atoms to which they are attached can form a C$_3$-C$_{10}$cycloalkyl, 3-7-membered heterocyclyl, or a 5-6 membered aryl or heteroaryl; wherein the C$_3$-C$_{10}$cycloalkyl, 3-7-membered heterocyclyl, and 5-6 membered aryl or heteroaryl are independently unsubstituted or substituted with one or more substituents selected from the group consisting of D, —CN, halogen, C$_1$-C$_6$alkyl, —OR$^{9a}$, —C(O)R$^{9b}$, —P(O)R$^{9b}$R$^{10b}$, —S(O)$_2$R$^{9b}$, —S(O)R$^{9b}$, —NR$^{9a}$R$^{10a}$, —NR$^{9a}$C(O)R$^{10a}$, —NR$^{9a}$C(O)OR$^{10a}$, —NR$^{9a}$C(O)NR$^{10a}$, and —NR$^{9a}$S(O)$_2$R$^{10a}$;

$R^2$ is selected from the group consisting of C$_1$-C$_6$alkyl, C$_3$-C$_{10}$cycloalkyl, 3-7-membered heterocyclyl, 5-membered heteroaryl, 6-membered heteroaryl, C$_6$aryl, and —NR$^{2g}$R$^{2h}$; wherein the C$_1$-C$_6$alkyl, C$_3$-C$_{10}$cycloalkyl, 3-7-membered heterocyclyl, 5-membered heteroaryl, 6-membered heteroaryl, and C$_6$aryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

each $R^{2g}$ and $R^{2h}$ is independently H, D, C$_1$-C$_6$alkyl, C$_3$-C$_{10}$cycloalkyl, C$_6$aryl, 3-7 membered heterocyclyl, or 5-6 membered heteroaryl, wherein the C$_1$-C$_6$alkyl, C$_3$-C$_{10}$cycloalkyl, C$_6$aryl, 3-7 membered heterocyclyl, and 5-6 membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

R$^{3a}$, R$^{4a}$, R$^{5a}$, R$^{6a}$, R$^{7a}$, R$^{8a}$, R$^{9a}$, R$^{10a}$, R$^{21a}$, R$^{22a}$, R$^{23a}$, and R$^{24a}$ are independently, at each occurrence, H, D, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl;

R$^{3b}$, R$^{4b}$, R$^{5b}$, R$^{6b}$, R$^{7b}$, R$^{8b}$, R$^{9b}$, R$^{10b}$, R$^{21b}$, R$^{22b}$, R$^{23b}$, and R$^{24b}$ are independently, at each occurrence, H, D, —OH, —O(C$_1$-C$_6$alkyl), —NH$_2$, —NH(C$_1$-C$_6$alkyl), —N(C$_1$-C$_6$alkyl)$_2$, —NHS(O)$_2$CH$_3$, C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

Embodiment I-2. The compound of Embodiment I-1, or a pharmaceutically acceptable salt, solvate, isomer, or tautomer thereof, wherein R$^2$ is selected from the group consisting of C$_1$-C$_6$alkyl, C$_3$-C$_{10}$cycloalkyl, 3-7-membered heterocyclyl, 5-membered heteroaryl, —NR$^{2g}$R$^{2h}$,

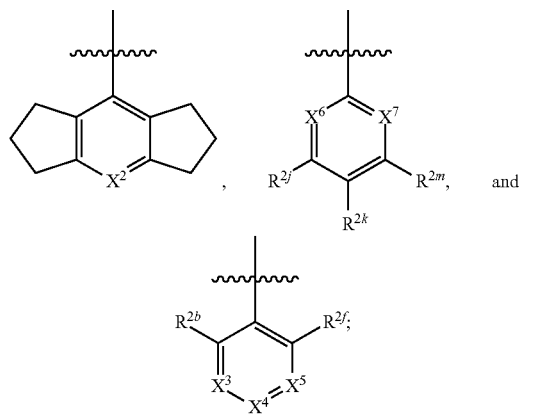

wherein the C$_1$-C$_6$alkyl, C$_3$-C$_{10}$cycloalkyl, 3-7-membered heterocyclyl, and 5-membered heteroaryl are independently unsubstituted or substituted with one or more substituents selected from the group consisting of D, —CN, halogen, C$_1$-C$_6$alkyl, C$_1$-C$_6$haloalkyl, C$_2$-C$_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$C$_3$-C$_{10}$cycloalkyl, C$_3$-C$_{10}$cycloalkyl, C$_6$aryl, 3-7-membered heterocyclyl, and 5-6-membered heteroaryl;

X$^2$ is N or CR$^{2a}$;
X$^3$ is N or CR$^{2c}$;
X$^4$ is N or CR$^{2d}$;
X$^5$ is N or CR$^{2e}$;
X$^6$ and X$^7$ are independently N or CR$^{2n}$, wherein at least one of X$^6$ and X$^7$ is N;

R$^{2a}$ is H, D, halogen, —CN, —OR$^{15a}$, C$_1$-C$_6$alkyl, C$_3$-C$_{10}$cycloalkyl, —C(O)NR$^{15a}$R$^{16a}$, —C(O)OR$^{15a}$, —NR$^{15a}$R$^{16a}$, —NR$^{15a}$C(O)R$^{16a}$, —NR$^{15a}$C(O)OR$^{16a}$, —NR$^{15a}$C(O)NR$^{16a}$, or —NR$^{15a}$S(O)$_2$R$^{16a}$, wherein the C$_1$-C$_6$alkyl and C$_3$-C$_{10}$cycloalkyl are independently unsubstituted or substituted with one or more substituents selected from the group consisting of D, halogen, —CN, —OR$^{15a}$, —C(O)R$^{15b}$, —NR$^{15a}$R$^{16a}$, C$_3$-C$_{10}$cycloalkyl, C$_6$aryl, 3-7-membered heterocyclyl, and 5-6 membered heteroaryl;

each R$^{2b}$, R$^{2c}$, R$^{2d}$, R$^{2e}$, and R$^{2f}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6 membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2b}$, R$^{2c}$, R$^{2d}$, R$^{2e}$, and R$^{2f}$ together with the atoms to which they are attached can form C$_3$-C$_{10}$cycloalkyl, C$_6$aryl, 3-7-membered heterocyclyl, 5-6-membered heteroaryl, wherein the C$_3$-C$_{10}$cycloalkyl, C$_6$aryl, 3-7-membered heterocyclyl, and 5-6-membered heteroaryl are independently unsubstituted or substituted with one or more substituents selected from the group consisting of halogen, D, —CN, C$_1$-C$_6$alkyl, —OR$^{19a}$, and NR$^{19a}$R$^{20a}$;

each R$^{2j}$, R$^{2k}$, R$^{2m}$, and R$^{2n}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6 membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, C$_3$-C$_{10}$cycloalkyl, C$_6$aryl, 3-7-membered heterocyclyl, and 5-6 membered heteroaryl; or two adjacent R$^{2j}$, R$^{2k}$, R$^{2m}$, and R$^{2n}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —OR$^{19a}$, and NR$^{19a}$R$^{20a}$;

each R$^{2g}$ and R$^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_1$-$C_6$alkenyl, oxo, —OR$^{21a}$, —C(O)R$^{21b}$, —P(O)R$^{21b}$R$^{22b}$, —S(O)$_2$R$^{21b}$, —S(O)R$^{21b}$, —NR$^{21a}$R$^{22a}$, —NR$^{21a}$C(O)R$^{22a}$, —NR$^{21a}$C(O)OR$^{22a}$, —NR$^{21a}$C(O)NR$^{22a}$, —NR$^{21a}$S(O)$_2$R$^{22a}$, —(CH$_2$)$_{1-4}$C$_3$-C$_{10}$cycloalkyl, $C_3$-$C_{10}$cycloalkyl, $C_6$aryl, 3-7-membered heterocyclyl, and 5-6-membered heteroaryl;

R$^{15a}$, R$^{16a}$, R$^{17a}$, R$^{18a}$, R$^{19a}$, R$^{20a}$, and R$^{21a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH(C$_1$-$C_6$alkyl), —N(C$_1$-$C_6$alkyl)$_2$, $C_3$-$C_{10}$cycloalkyl, $C_6$aryl, 3-7-membered heterocyclyl, and 5-6 membered heteroaryl;

R$^{15b}$, R$^{17b}$, R$^{18b}$, and R$^{21b}$ are independently, at each occurrence, H, D, —OH, —O(C$_1$-$C_6$alkyl), —NH$_2$, —NH(C$_1$-$C_6$alkyl), —N(C$_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH(C$_1$-$C_6$alkyl), —N(C$_1$-$C_6$alkyl)$_2$, $C_3$-$C_{10}$cycloalkyl, $C_6$aryl, 3-7-membered heterocyclyl, and 5-6 membered heteroaryl.

Embodiment I-3. The compound of any one of Embodiment I-1 to I-2, or a pharmaceutically acceptable salt, solvate, isomer, or tautomer thereof, wherein: R$^2$ is

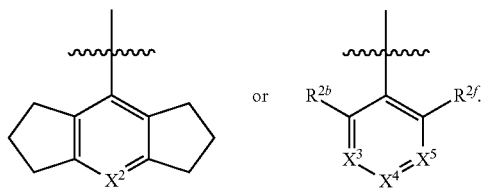

Embodiment I-4. The compound of Embodiment I-1, or a pharmaceutically acceptable salt, solvate, isomer, or tautomer thereof, wherein R$^1$ is selected from the group consisting of

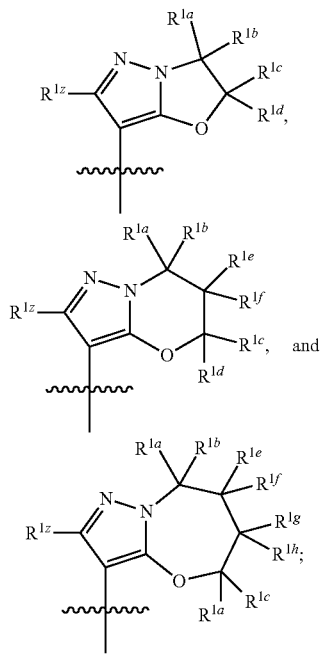

R$^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, $C_3$-$C_{10}$cycloalkyl, $C_6$aryl, 3-7-membered heterocyclyl, and 5-6 membered heteroaryl;

each R$^{1a}$, R$^{1b}$, R$^{1c}$, R$^{1d}$, R$^{1e}$, R$^{1f}$, R$^{1g}$, and R$^{1h}$ is independently selected from H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6-membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, $C_1$-$C_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, $C_3$-$C_{10}$cycloalkyl, $C_6$aryl, 3-7-membered heterocyclyl, and 5-6 membered heteroaryl; or two of the following groups, R$^{1a}$, R$^{1b}$, R$^{1c}$, R$^{1d}$, R$^{1e}$, R$^{1f}$, R$^{1g}$, and R$^{1h}$, when present, together with the atoms to which they are attached can form a $C_3$-$C_{10}$cycloalkyl or a 3-7-membered heterocyclyl; wherein the $C_3$-$C_{10}$cycloalkyl and 3-7-membered heterocyclyl are independently unsubstituted or substituted with one or more substituents selected from the group consisting of D, —CN, halogen, $C_1$-$C_6$alkyl, —OR$^{13a}$, —C(O)R$^{13b}$, —P(O)R$^{13b}$R$^{14b}$, —S(O)$_2$R$^{13b}$, —S(O)R$^{13b}$, —NR$^{13a}$R$^{14a}$, —NR$^{13a}$C(O)R$^{14a}$, —NR$^{13a}$C(O)OR$^{14a}$, —NR$^{13a}$C(O)NR$^{14a}$, and —NR$^{13a}$S(O)$_2$R$^{14a}$; or two geminal groups R$^{1a}$ and R$^{1b}$; R$^{1c}$ and R$^{1d}$; R$^{1e}$ and R$^{1f}$; or R$^{1g}$ and R$^{1h}$, when present, can form an oxo group;

R$^{7a}$, R$^{8a}$, R$^{11a}$, R$^{12a}$, R$^{13a}$, and R$^{14a}$ are independently, at each occurrence, H, D, $C_1$-$C_8$alkyl, $C_2$-$C_8$alkenyl, $C_1$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;

R$^{7b}$, R$^{8b}$, R$^{11b}$, R$^{12b}$, R$^{13b}$, and R$^{14b}$ are independently, at each occurrence, H, D, —OH, —O($C_1$-$C_6$alkyl), —NH$_2$, —NH($C_1$-$C_6$alkyl), —N($C_1$-$C_6$alkyl)$_2$, —NHS(O)$_2$CH$_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —NH$_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl.

Embodiment I-5. The compound of Embodiment I-4, or a pharmaceutically acceptable salt, solvate, isomer, or tautomer thereof, wherein R$^2$ is selected from the group consisting of $C_1$-$C_6$alkyl, $C_3$-$C_{10}$cycloalkyl, 3-7-membered heterocyclyl, 5-membered heteroaryl, —NR$^{2g}$R$^{2h}$,

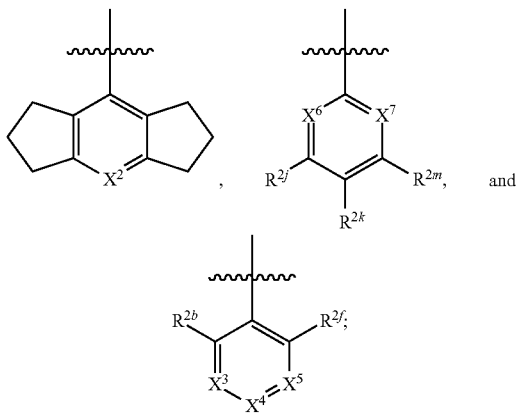

wherein the $C_1$-$C_6$alkyl, $C_3$-$C_{10}$cycloalkyl, 3-7-membered heterocyclyl, and 5-membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —OR$^{23a}$, —C(O)R$^{23b}$, —P(O)R$^{23b}$R$^{24b}$, —S(O)$_2$R$^{23b}$, —S(O)R$^{23b}$, —NR$^{23a}$R$^{24a}$, —NR$^{23a}$C(O)R$^{24a}$, —NR$^{23a}$C(O)OR$^{24a}$, —NR$^{23a}$C(O)NR$^{24a}$, —NR$^{23a}$S(O)$_2$R$^{24a}$, —(CH$_2$)$_{1-4}$$C_3$-$C_{10}$cycloalkyl, $C_3$-$C_{10}$cycloalkyl, $C_6$aryl, 3-7-membered heterocyclyl, and 5-6-membered heteroaryl;

$X^2$ is N or CR$^{2a}$;

$X^3$ is N or CR$^{2c}$;

$X^4$ is N or CR$^{2d}$;

$X^5$ is N or CR$^{2e}$;

$X^6$ and $X^7$ are independently N or CR$^{2n}$, wherein at least one of $X^6$ and $X^7$ is N;

R$^{2a}$ is H, D, halogen, —CN, —OR$^{15a}$, $C_1$-$C_6$alkyl, $C_3$-$C_{10}$cycloalkyl, —C(O)NR$^{15a}$R$^{16a}$, —C(O)OR$^{15a}$; —NR$^{15a}$R$^{16a}$, —NR$^{15a}$C(O)R$^{16a}$, —NR$^{15a}$C(O)OR$^{16a}$, —NR$^{15a}$C(O)NR$^{16a}$, or —NR$^{15a}$S(O)$_2$R$^{16a}$, wherein the $C_1$-$C_6$alkyl and $C_3$-$C_{10}$cycloalkyl are independently unsubstituted or substituted with one or more substituents selected from the group consisting of D, halogen, —CN, —OR$^{15a}$, —C(O)R$^{15b}$, —NR$^{15a}$R$^{16a}$, $C_3$-$C_{10}$cycloalkyl, $C_6$aryl, 3-7-membered heterocyclyl, and 5-6 membered heteroaryl;

each R$^{2b}$, R$^{2c}$, R$^{2d}$, R$^{2e}$, and R$^{2f}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_3$-$C_{10}$cycloalkyl, $C_6$aryl, 3-7-membered heterocyclyl, and 5-6 membered heteroaryl; or two adjacent R$^{2b}$, R$^{2c}$, R$^{2d}$, R$^{2e}$, and R$^{2f}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —OR$^{19a}$, and NR$^{19a}$R$^{20a}$;

each R$^{2j}$, R$^{2k}$, R$^{2m}$, and R$^{2n}$ is independently H, D, halogen, —CN, —NO$_2$, —SR$^{17a}$, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —OR$^{17a}$, —C(O)R$^{17b}$, —P(O)R$^{17b}$R$^{18b}$, —S(O)$_2$R$^{17b}$, —S(O)R$^{17b}$, —NR$^{17a}$R$^{18a}$, —NR$^{17a}$C(O)R$^{18a}$, —NR$^{17a}$C(O)OR$^{18a}$, —NR$^{17a}$C(O)NR$^{18a}$, —NR$^{17a}$S(O)$_2$R$^{18a}$, $C_3$-$C_{10}$cycloalkyl, $C_6$aryl, 3-7-membered heterocyclyl, and 5-6 membered heteroaryl; or two adjacent $R^{2j}$, $R^{2k}$, $R^{2m}$, and $R^{2n}$ together with the atoms to which they are attached can form $C_3$-$C_{10}$cycloalkyl, $C_6$aryl, 3-7-membered heterocyclyl, 5-6-membered heteroaryl, wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

each $R^{2g}$ and $R^{2h}$ is independently H, D, $C_1$-$C_6$alkyl, $C_3$-$C_{10}$cycloalkyl, $C_6$aryl, 3-7 membered heterocyclyl, or 5-6 membered heteroaryl, wherein the $C_1$-$C_6$alkyl, $C_3$-$C_{10}$cycloalkyl, $C_6$aryl, 3-7 membered heterocyclyl, and 5-6 membered heteroaryl are independently unsubstituted or substituted with one or more substituents selected from the group consisting of D, —CN, halogen, $C_1$-$C_6$alkyl, $C_1$-$C_6$haloalkyl, $C_2$-$C_6$alkenyl, oxo, —$OR^{21a}$, —$C(O)R^{21b}$, —$P(O)R^{21b}R^{22b}$, —$S(O)_2R^{21b}$, —$S(O)R^{21b}$, —$NR^{21a}R^{22a}$, —$NR^{21a}C(O)R^{22a}$, —$NR^{21a}C(O)OR^{22a}$, —$NR^{21a}C(O)NR^{22a}$, —$NR^{21a}S(O)_2R^{22a}$, —$(CH_2)_{1-4}C_3$-$C_{10}$cycloalkyl, $C_3$-$C_{10}$cycloalkyl, $C_6$aryl, 3-7-membered heterocyclyl, and 5-6-membered heteroaryl;

$R^{15a}$, $R^{16a}$, $R^{17a}$, $R^{18a}$, $R^{19a}$, $R^{20a}$, and $R^{21a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_6$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl$)_2$, $C_3$-$C_{10}$cycloalkyl, $C_6$aryl, 3-7-membered heterocyclyl, and 5-6 membered heteroaryl;

$R^{15b}$, $R^{17b}$, $R^{18b}$, and $R^{21b}$ are independently, at each occurrence, H, D, —OH, —$O(C_1$-$C_6$alkyl), —$NH_2$, —$NH(C_1$-$C_6$alkyl), —$N(C_1$-$C_6$alkyl$)_2$, —$NHS(O)_2CH_3$, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_6$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —$NH(C_1$-$C_6$alkyl), —$N(C_1$-$C_6$alkyl$)_2$, $C_3$-$C_{10}$cycloalkyl, $C_6$aryl, 3-7-membered heterocyclyl, and 5-6 membered heteroaryl.

Embodiment I-6. The compound of Embodiment I-4 or I-5, or a pharmaceutically acceptable salt, solvate, isomer, or tautomer thereof, wherein $R^2$ is

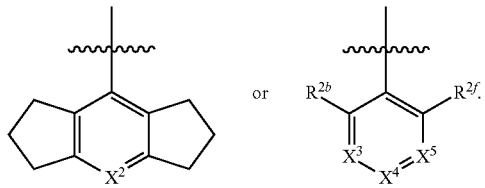

Embodiment I-7. The compound of any one of Embodiment I-1 to I-6, or a pharmaceutically acceptable salt, solvate, isomer, or tautomer thereof, wherein $R^{100}$ is H.

Embodiment I-8. The compound of any one of Embodiment I-1 to I-7, or a pharmaceutically acceptable salt, solvate, isomer, or tautomer thereof, wherein $R^2$ is

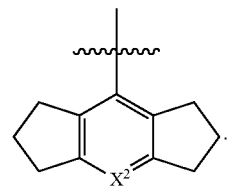

Embodiment I-9. The compound of any one of Embodiment I-1 to I-8, or a pharmaceutically acceptable salt, solvate, isomer, or tautomer thereof, wherein $X^2$ is $CR^{2a}$.

Embodiment I-10. The compound of any one of Embodiment I-1 to I-8, or a pharmaceutically acceptable salt, solvate, isomer, or tautomer thereof, wherein $X^2$ is N.

Embodiment I-11. The compound of any one of Embodiment I-1 to I-9, or a pharmaceutically acceptable salt, solvate, isomer, or tautomer thereof, wherein $R^{2a}$ is H, halogen, $C_1$-$C_6$alkyl, or —$C(O)R^{3b}$.

Embodiment I-12. The compound of any one of Embodiment I-1 to I-9, or a pharmaceutically acceptable salt, solvate, isomer, or tautomer thereof, wherein $R^{2a}$ is H, fluoro, chloro, methyl, or —COOH.

Embodiment I-13. The compound of any one of Embodiment I-1 to I-9 and I-11 to I-12, or a pharmaceutically acceptable salt, solvate, isomer, or tautomer thereof, wherein $R^2$ is

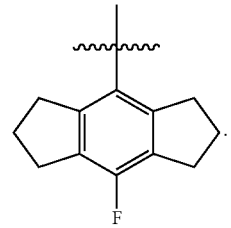

Embodiment I-14. The compound of any one of Embodiment I-1 to I-9 and I-11 to I-12, or a pharmaceutically acceptable salt, solvate, isomer, or tautomer thereof, wherein $R^2$ is

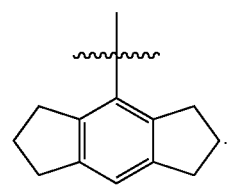 [SMILES: *c1c2c(cc3c1CCC3)CCC2]

Embodiment I-15. The compound of any one of Embodiment I-1 to I-7, or a pharmaceutically acceptable salt, solvate, isomer, or tautomer thereof, wherein $R^2$ is

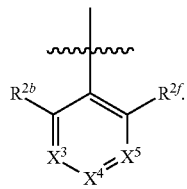

Embodiment I-16. The compound of Embodiment I-15, or a pharmaceutically acceptable salt, solvate, isomer, or tautomer thereof, wherein $X^3$ is $CR^{2c}$; $X^4$ is $CR^{2d}$; and $X^5$ is $CR^{2d}$.

Embodiment I-17. The compound of any one of Embodiment I-15 to I-16, or a pharmaceutically acceptable salt, solvate, isomer, or tautomer thereof, wherein each $R^{2b}$, $R^{2c}$, $R^{2d}$, $R^{2e}$, and $R^{2f}$ is independently selected from the group consisting of H, D, halogen, $C_1$-$C_6$alkyl, $C_3$-$C_{10}$cycloalkyl, and —CN.

Embodiment I-18. The compound of any one of Embodiment I-15 to I-17, or a pharmaceutically acceptable salt, solvate, isomer, or tautomer thereof, wherein $R^2$ is

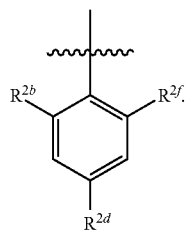

Embodiment I-19. The compound of any one of Embodiment I-15 to I-18, or a pharmaceutically acceptable salt, solvate, isomer, or tautomer thereof, wherein $R^2$ is

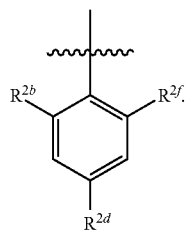

Embodiment I-20. The compound of Embodiment I-15, or a pharmaceutically acceptable salt, solvate, isomer, or tautomer thereof, wherein $X^3$ is N; $X^4$ is $CR^{2d}$; and $X^5$ is $CR^{2d}$.

Embodiment I-21. The compound of Embodiment I-15, or a pharmaceutically acceptable salt, solvate, isomer, or tautomer thereof, wherein $X^3$ is $CR^{2c}$; $X^4$ is N; and $X^5$ is $CR^{2d}$.

Embodiment I-22. The compound of Embodiment I-15, or a pharmaceutically acceptable salt, solvate, isomer, or tautomer thereof, wherein $X^3$ is $CR^{2c}$; $X^4$ is $CR^{2d}$; and $X^5$ is N.

Embodiment I-23. The compound of any one of Embodiment I-1 to I-22, or a pharmaceutically acceptable salt, solvate, isomer, or tautomer thereof, wherein $R^1$ is

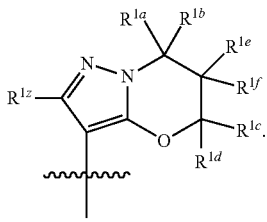

Embodiment I-24. The compound of any one of Embodiment I-1 to I-22, or a pharmaceutically acceptable salt, solvate, isomer, or tautomer thereof, wherein $R^1$ is

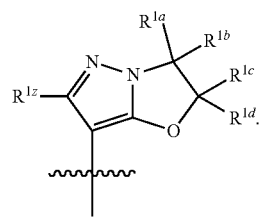

Embodiment I-25. The compound of any one of Embodiment I-1 to I-22, or a pharmaceutically acceptable salt, solvate, isomer, or tautomer thereof, wherein $R^1$ is

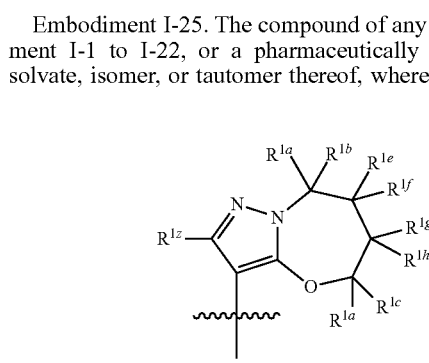

Embodiment I-26. The compound of any one of Embodiment I-1 to I-23, or a pharmaceutically acceptable salt, solvate, isomer, or tautomer thereof, wherein $R^1$ is

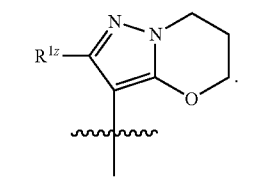

Embodiment I-27. The compound of any one of Embodiment I-1 to I-23, or a pharmaceutically acceptable salt, solvate, isomer, or tautomer thereof, wherein $R^1$ is

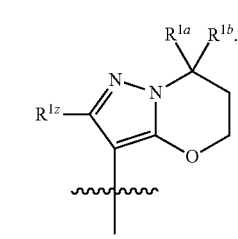

Embodiment I-28. The compound of any one of Embodiment I-1 to I-23, or a pharmaceutically acceptable salt, solvate, isomer, or tautomer thereof, wherein $R^1$ is

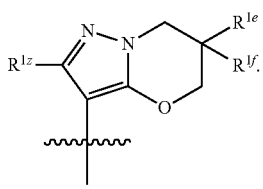

Embodiment I-29. The compound of any one of Embodiment I-1 to I-23, or a pharmaceutically acceptable salt, solvate, isomer, or tautomer thereof, wherein $R^1$ is

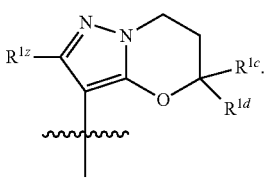

Embodiment I-30. The compound of any one of Embodiment I-1 to I-23, or a pharmaceutically acceptable salt, solvate, isomer, or tautomer thereof, wherein $R^1$ is selected from the group consisting of

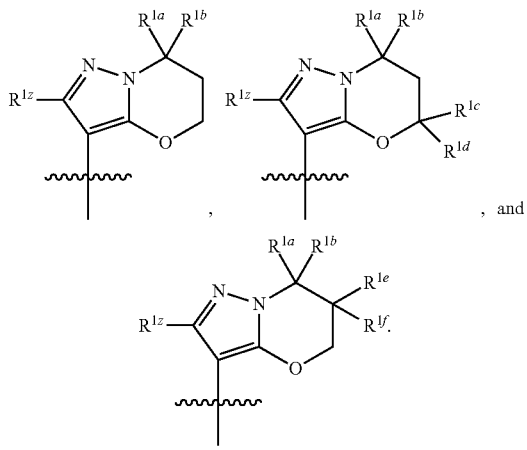

Embodiment I-31. The compound of any one of Embodiment I-1 to I-23, or a pharmaceutically acceptable salt, solvate, isomer, or tautomer thereof, wherein $R^1$ is selected from the group consisting of

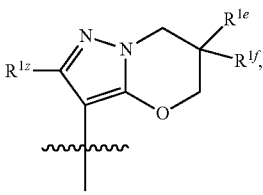

-continued

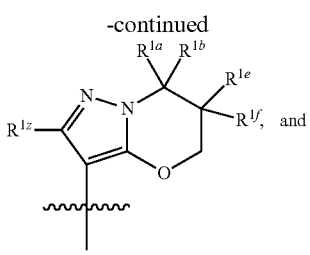

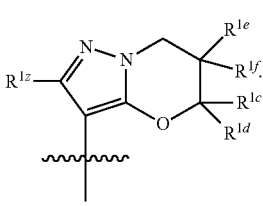

Embodiment I-32. The compound of any one of Embodiment I-1 to I-23, or a pharmaceutically acceptable salt, solvate, isomer, or tautomer thereof, wherein $R^1$ is selected from the group consisting of

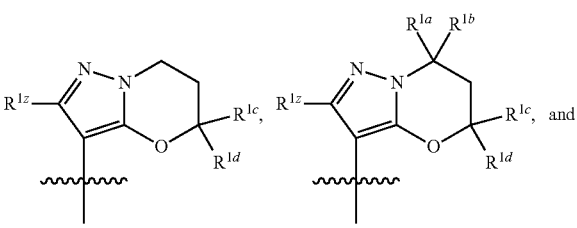

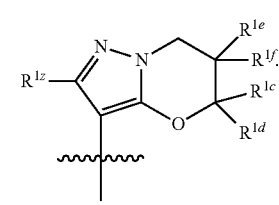

Embodiment I-33. The compound of any one of Embodiment I-1 to I-32, or a pharmaceutically acceptable salt, solvate, isomer, or tautomer thereof, wherein $R^{1z}$ is H.

Embodiment I-34. The compound of any one of Embodiment I-1 to I-23, or a pharmaceutically acceptable salt, solvate, isomer, or tautomer thereof, wherein $R^1$ is selected from the group consisting of

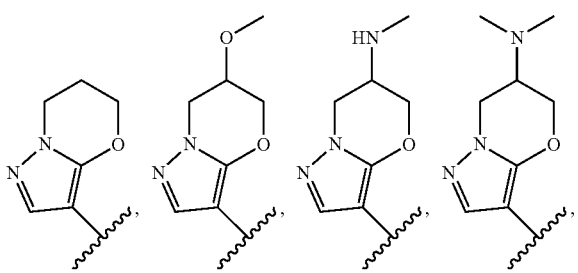

201

-continued

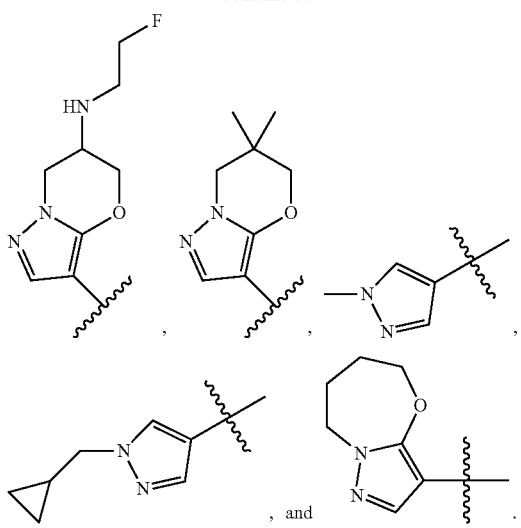

Embodiment I-35. The compound of any one of Embodiment I-1 to I-23, or a pharmaceutically acceptable salt, solvate, isomer, or tautomer thereof, wherein $R^1$ is selected from the group consisting of

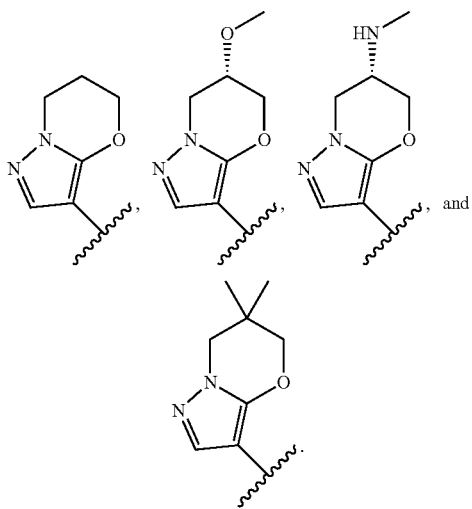

Embodiment I-36. The compound of any one of Embodiment I-1 to I-23, or a pharmaceutically acceptable salt, solvate, isomer, or tautomer thereof, wherein $R^1$ is selected from the group consisting of

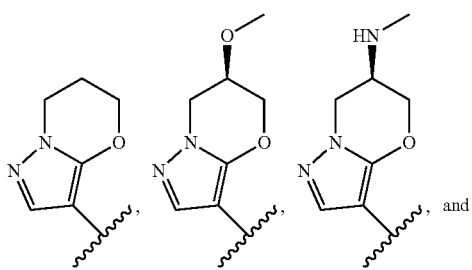

202

-continued

Embodiment I-37. The compound of any one of Embodiment I-1 to I-25, I-27 and I-30 to I-33, or a pharmaceutically acceptable salt, solvate, isomer, or tautomer thereof, wherein $R^{1a}$ and $R^{1b}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-38. The compound of any one of Embodiment I-1 to I-25 and I-29 to I-33, or a pharmaceutically acceptable salt, solvate, isomer, or tautomer thereof, wherein $R^{1c}$ and $R^{1d}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-39. The compound of any one of Embodiment I-1 to I-23, I-25, I-28, and 1-30 to I-33, or a pharmaceutically acceptable salt, solvate, isomer, or tautomer thereof, wherein $R^{1e}$ and $R^{1f}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-40. The compound of any one of Embodiment I-1 to I-22, I-25, and I-33, or a pharmaceutically acceptable salt, solvate, isomer, or tautomer thereof, wherein $R^{1g}$ and $R^{1b}$ are independently H, halogen, —$OR^{11a}$, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, $C_3$-$C_{10}$cycloalkyl, $C_6$aryl, 3-7-membered heterocyclyl, or 5-6-membered heteroaryl.

Embodiment I-41. The compound of any one of Embodiment I-1 to I-25, I-27 and I-30 to I-33, or a pharmaceutically acceptable salt, solvate, isomer, or tautomer thereof, wherein $R^{1a}$ and $R^{1b}$ are independently H, —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, —$NR^{11a}S(O)_2R^{12a}$, $C_1$-$C_6$alkyl, or 3-7-membered heterocyclyl; wherein the $C_1$-$C_6$alkyl is substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$; and wherein the 3-7-membered heterocyclyl is unsubstituted or substituted with one or more substituents selected from the group consisting of —$C(O)R^{11b}$, —$P(O)R^{11b}R^{12b}$, —$S(O)_2R^{11b}$, —$S(O)R^{11b}$, —$NR^{11a}R^{12a}$, —$NR^{11a}C(O)R^{12a}$, —$NR^{11a}C(O)OR^{12a}$, —$NR^{11a}C(O)NR^{12a}$, and —$NR^{11a}S(O)_2R^{12a}$.

Embodiment I-42. The compound of any one of Embodiment I-1 to I-25, I-27 and I-30 to I-33, or a pharmaceutically acceptable salt, solvate, isomer, or tautomer thereof, wherein $R^{1a}$ and $R^{1b}$ are independently H, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-43. The compound of any one of Embodiment I-1 to I-25 and I-29 to 1-33, or a pharmaceutically acceptable salt, solvate, isomer, or tautomer thereof, wherein $R^{1c}$ and $R^{1d}$ are independently H, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-44. The compound of any one of Embodiment I-1 to I-25 and I-29 to 1-33, or a pharmaceutically acceptable salt, solvate, isomer, or tautomer thereof, wherein $R^{1c}$ and $R^{1d}$ are independently independently H, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-45. The compound of any one of Embodiment I-1 to I-23, I-25, I-28, and 1-30 to I-33, or a pharmaceutically acceptable salt, solvate, isomer, or tautomer thereof, wherein $R^{1e}$ and $R^{1f}$ are independently H, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-46. The compound of any one of Embodiment I-1 to I-23, I-25, I-28, and 1-30 to I-33, or a pharmaceutically acceptable salt, solvate, isomer, or tautomer thereof, wherein $R^{1e}$ and $R^{1f}$ are independently independently H, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-47. The compound of any one of Embodiment I-1 to I-22, I-25, and I-33, or a pharmaceutically acceptable salt, solvate, isomer, or tautomer thereof, wherein $R^{1g}$ and $R^{1b}$ are independently are independently H, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or 3-7-membered heterocyclyl; wherein the C$_1$-C$_6$alkyl is substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-48. The compound of any one of Embodiment I-1 to I-22, I-25, and I-33, or a pharmaceutically acceptable salt, solvate, isomer, or tautomer thereof, wherein $R^{1g}$ and $R^{1b}$ are independently independently H, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, or a 3-7-membered heterocyclyl; wherein the C$_1$-C$_6$alkyl is substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$; and wherein the 3-7-membered heterocyclyl is unsubstituted or substituted with one or more substituents selected from the group consisting of —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, and —NR$^{11a}$S(O)$_2$R$^{12a}$.

Embodiment I-49. The compound of any one of Embodiment I-41 to I-48, or a pharmaceutically acceptable salt, solvate, isomer, or tautomer thereof, wherein the 3-7-membered heterocyclyl contains a nitrogen.

Embodiment I-50. The compound of any one of Embodiment I-1 to I-49, or a pharmaceutically acceptable salt, solvate, isomer, or tautomer thereof, wherein the compound is of formula:

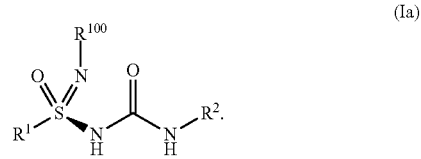

(Ia)

Embodiment I-51. The compound of any one of Embodiment I-1 to I-49, or a pharmaceutically acceptable salt, solvate, isomer, or tautomer thereof, wherein the compound is of formula:

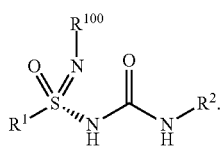
(Ib)
Embodiment I-52. The compound of Embodiment I-1, or a pharmaceutically acceptable salt, solvate, isomer, or tautomer thereof, wherein the compound is selected from the group consisting of
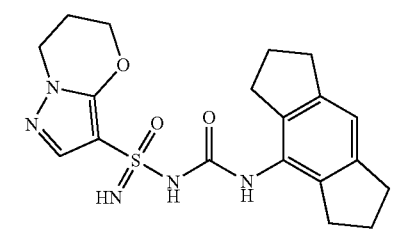
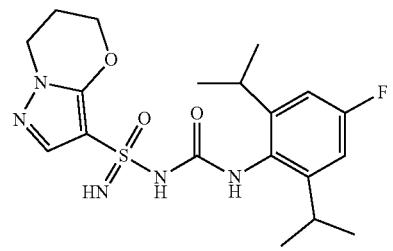
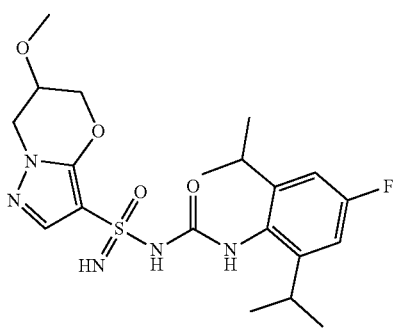
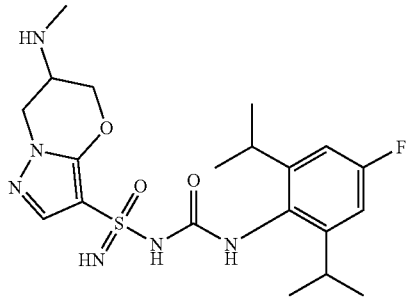
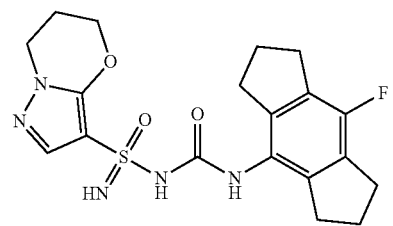
-continued
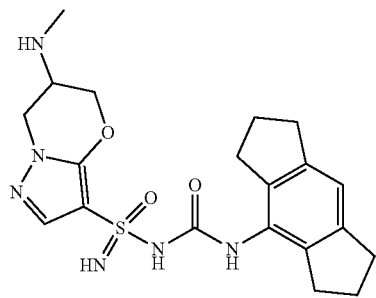
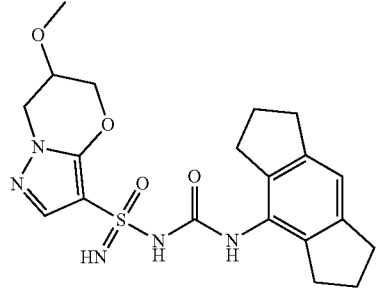
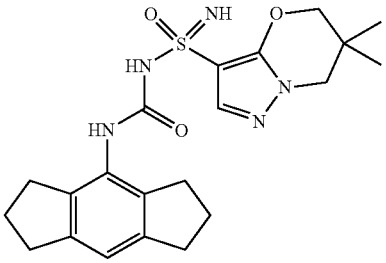
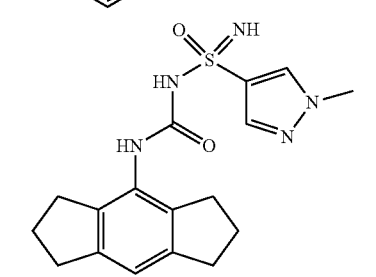

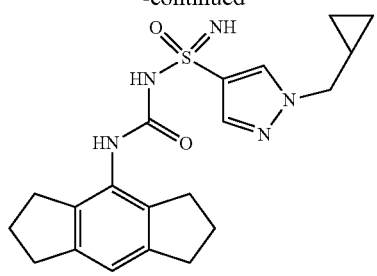
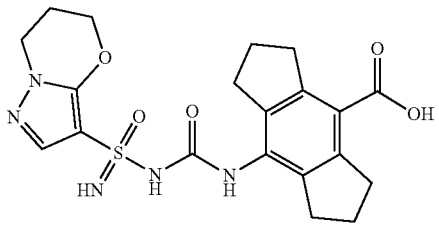
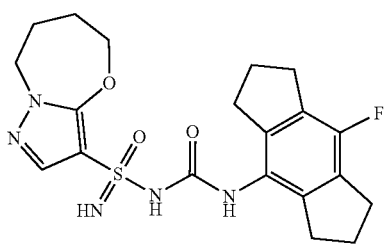
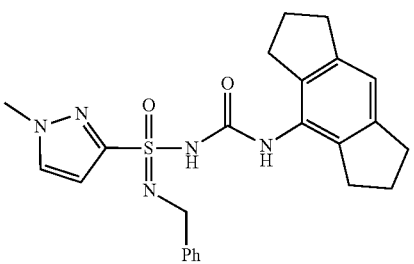
6
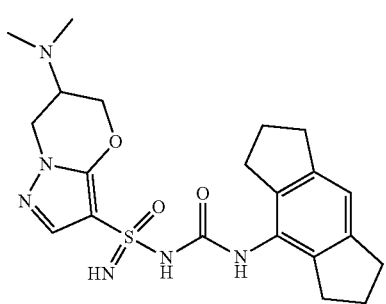
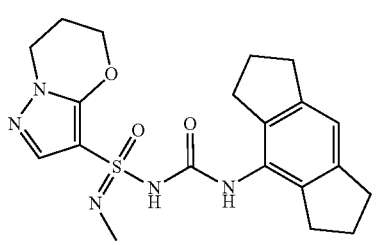 [SMILES: CN=S(=O)(NC(=O)Nc1c2c(cc3c1CCC3)CCC2)c1cnn2c1OCCC2]
Embodiment I-53. The compound of Embodiment I-1, or a pharmaceutically acceptable salt, solvate, isomer, or tautomer thereof, wherein the compound is selected from the group consisting of
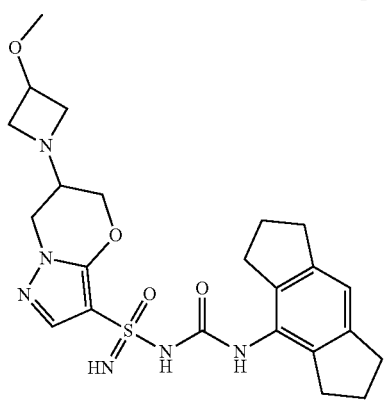
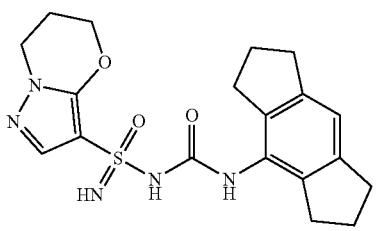
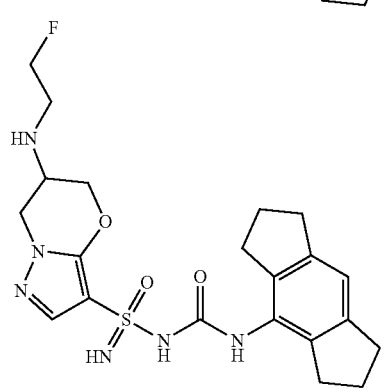
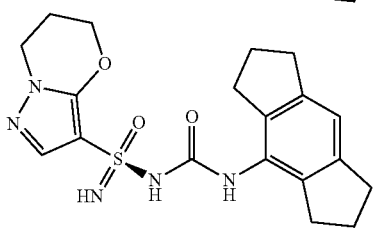
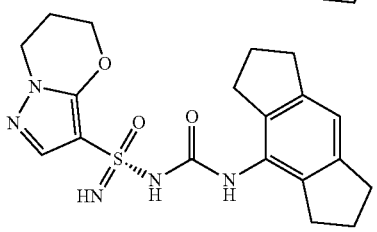

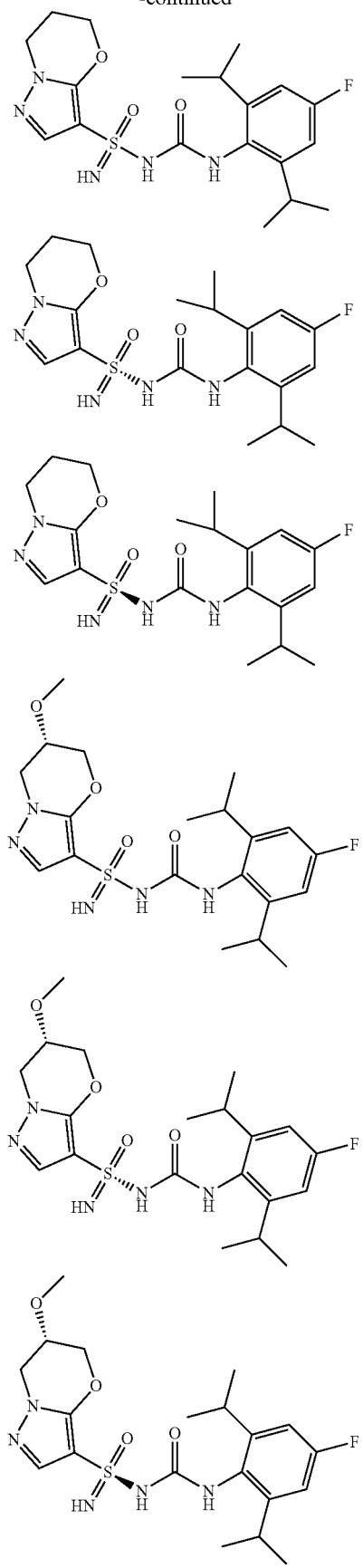
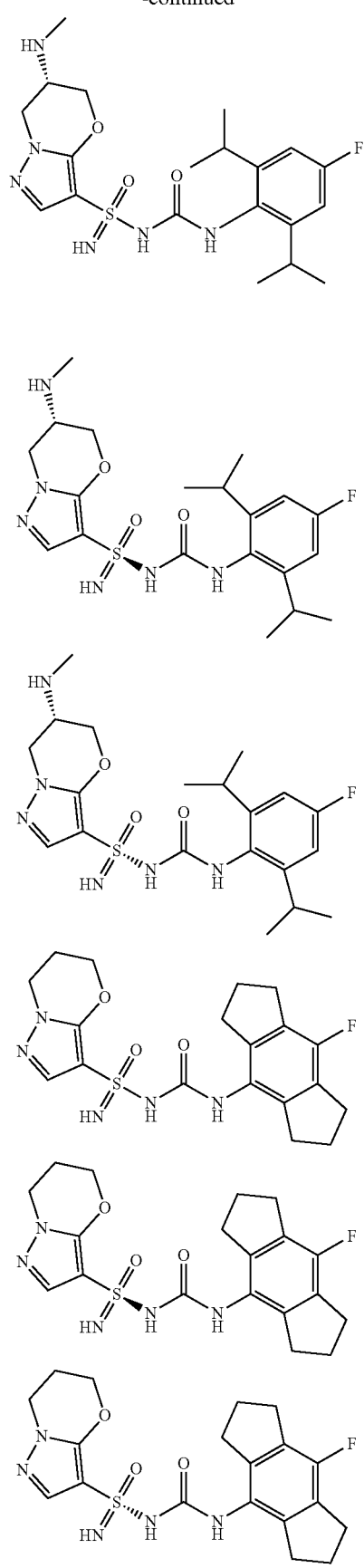

211
-continued
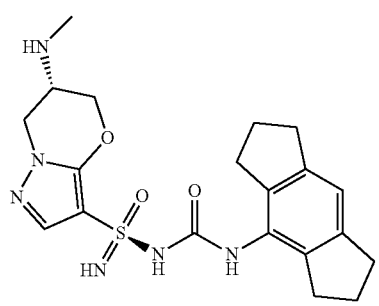
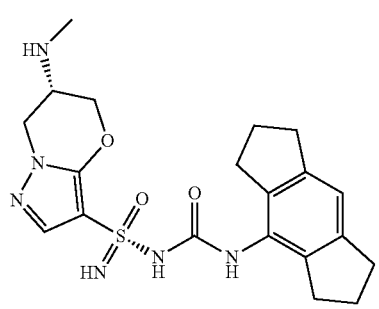
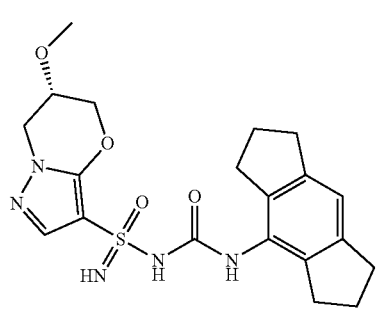
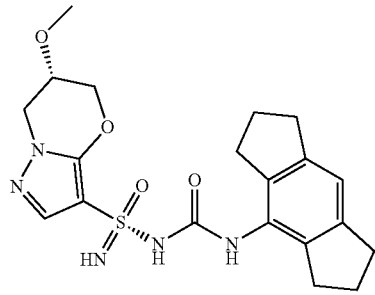
212
-continued
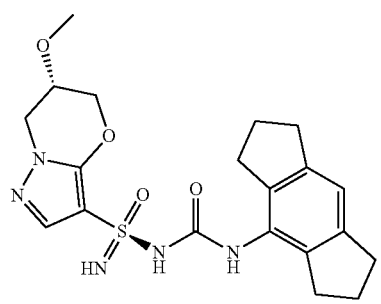
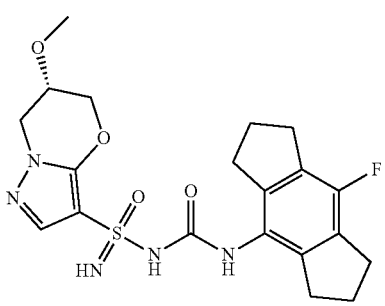
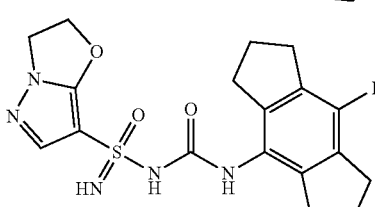
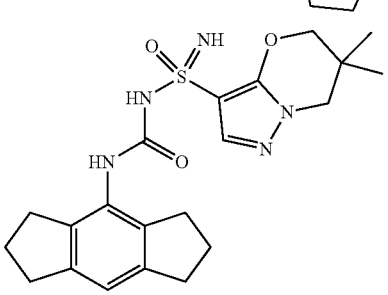
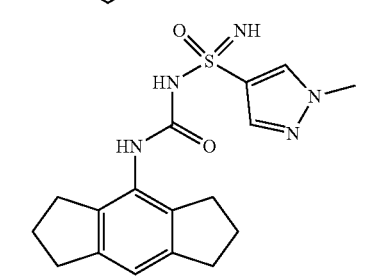
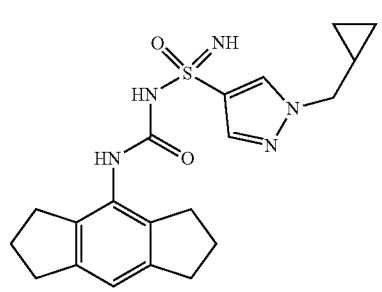

213
-continued
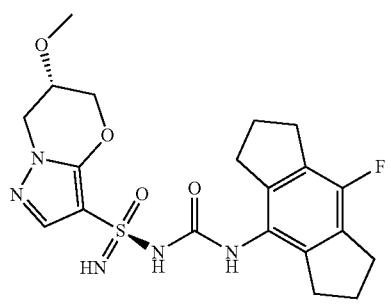
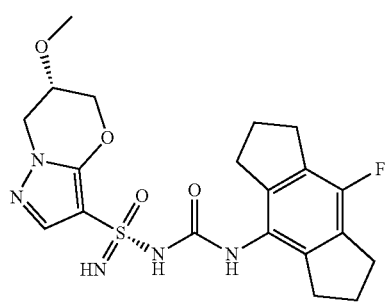
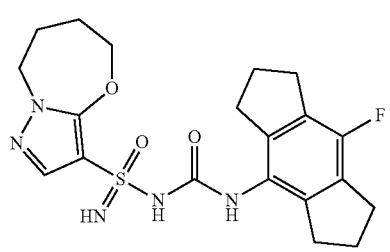
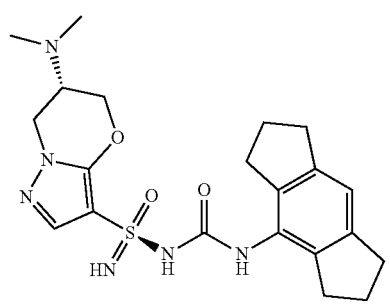
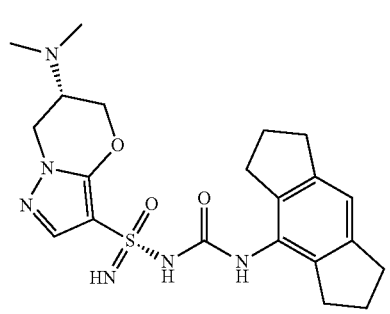
214
-continued
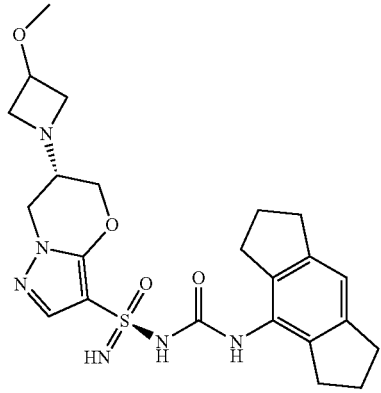
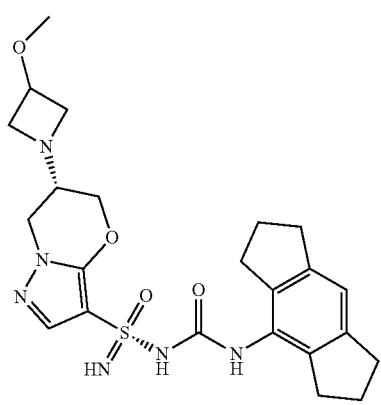
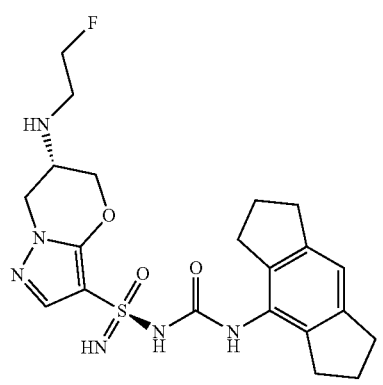
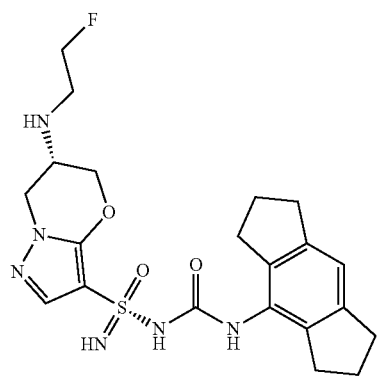

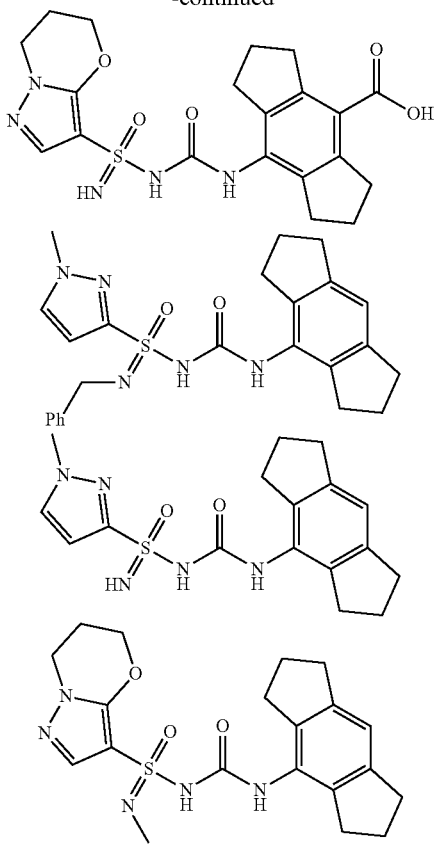

Embodiment I-54. A pharmaceutical composition comprising a compound of any one of Embodiment I-1 to I-53, or a pharmaceutically acceptable salt, solvate, isomer, or tautomer thereof, and a pharmaceutically acceptable carrier.

Embodiment I-55. A method of treatment of a disorder that is responsive to inhibition of inflammasome, comprising administering an effective amount of a compound of any one of Embodiment I-1 to I-53 to thereby treat the disorder in a subject in need thereof.

Embodiment I-56. The method of Embodiment I-55, wherein the disorder is one which is responsive to inhibition of activation of the NLRP3 inflammasome.

Embodiment I-57. The method of Embodiment I-54 or I-55, wherein the disorder is responsive to modulation of one or more of IL-6, IL-1β, IL-17, IL-18, IL-1α, IL-37, IL-22, IL-33 and Th17 cells.

Embodiment I-58. The method of Embodiment I-54 or I-55, wherein the disorder is responsive to modulation of one or more of IL-1β and IL-18.

Embodiment I-59. The method of any one of Embodiment I-55 to I-58, wherein the disorder is disorder of the immune system.

Embodiment I-60. The method of any one of Embodiment I-55 to I-58, wherein the disorder is an inflammatory disorder or an autoimmune disorder.

Embodiment I-61. The method of any one of Embodiment I-55 to I-58, wherein the disorder is disorder of the liver.

Embodiment I-62. The method of any one of Embodiment I-55 to I-58, wherein the disorder is a disorder of the lung.

Embodiment I-63. The method of any one of Embodiment I-55 to I-58, wherein the disorder is a disorder of the skin.

Embodiment I-64. The method of any one of Embodiment I-55 to I-58, wherein the disorder is a disorder of the cardiovascular system.

Embodiment I-65. The method of any one of Embodiment I-55 to I-58, wherein the disorder is a cancer, tumor or other malignancy.

Embodiment I-66. The method of any one of Embodiment I-55 to I-58, wherein the disorder is a disorder of the renal system.

Embodiment I-67. The method of any one of Embodiment I-55 to I-58, wherein the disorder is a disorder of the gastro-intestinal tract.

Embodiment I-68. The method of any one of Embodiment I-55 to I-58, wherein the disorder is a disorder of the respiratory system.

Embodiment I-69. The method of any one of Embodiment I-55 to I-58, wherein the disorder is a disorder of the endocrine system.

Embodiment I-70. The method of any one of Embodiment I-55 to I-58, wherein the disorder is a disorder of the central nervous system (CNS).

Embodiment I-71. The method of any one of Embodiment I-55 to I-58, wherein the disorder is selected from the group consisting of constitutive inflammation, the cryopyrin-associated periodic syndromes (CAPS), Muckle-Wells syndrome (MWS), familial cold autoinflammatory syndrome (FCAS), neonatal-onset multisystem inflammatory disease (NOMID), autoinflammatory diseases, familial Mediterranean fever (FMF), TNF receptor associated periodic syndrome (TRAPS), mevalonate kinase deficiency (MKD), hyperimmunoglobulinemia D, periodic fever syndrome (HIDS), deficiency of interleukin 1 receptor (DIRA) antagonist, Majeed syndrome, pyogenic arthritis, pyoderma gangrenosum and acne (PAPA), haploinsufficiency of A20 (HA20), pediatric granulomatous arthritis (PGA), PLCG2-associated antibody deficiency and immune dysregulation (PLAID), PLCG2-associated autoinflammation, antibody deficiency and immune dysregulation (APLAID), sideroblastic anemia with B-cell immunodeficiency, periodic fevers, developmental delay (SIFD), Sweet's syndrome, chronic nonbacterial osteomyelitis (CNO), chronic recurrent multifocal osteomyelitis (CRMO) and synovitis, acne, pustulosis, hyperostosis, osteitis syndrome (SAPHO), autoimmune diseases including multiple sclerosis (MS), type-1 diabetes, psoriasis, rheumatoid arthritis, Behcet's disease, Sjogren's syndrome, Schnitzler syndrome, respiratory diseases, idiopathic pulmonary fibrosis (IPF), chronic obstructive pulmonary disorder (COPD), steroid-resistant asthma, asbestosis, silicosis, cystic fibrosis, central nervous system diseases, Parkinson's disease, Alzheimer's disease, motor neuron disease, Huntington's disease, cerebral malaria, brain injury from pneumococcal meningitis, metabolic diseases, Type 2 diabetes, atherosclerosis, obesity, gout, pseudo-gout, ocular disease, disease of the ocular epithelium, age-related macular degeneration (AMD), corneal infection, uveitis, dry eye, kidney disease, chronic kidney disease, oxalate nephropathy, diabetic nephropathy, liver disease, non-alcoholic steatohepatitis, alcoholic liver disease, inflammatory reactions in skin, contact hypersensitivity, sunburn, inflammatory reactions in the joints, osteoarthritis, systemic juvenile idiopathic arthritis, adult-onset Still's disease, relapsing polychondritis, viral infections, alpha virus infection, Chikungunya virus infection, Ross River virus infection, flavivirus infection, Dengue virus infection, Zika virus infection, flu, HIV infection, hidradenitis suppurativa (HS), cyst-causing skin diseases, cancers, lung cancer metastasis, pancreatic cancers, gastric cancers, myelodisplastic syndrome, leukemia, polymyositis, stroke, myocardial infarction, Graft versus Host Disease, hypertension, colitis, helminth infection, bacterial infection, abdominal aortic aneurism, wound healing, depression, psychological stress, pericarditis, Dressler's syndrome, ischaemia reperfusion injury, and any disease where an individual has been determined to carry a germ line or somatic non-silent mutation in NLRP3.

Embodiment I-72. The method of any one of Embodiment I-55 to I-58, wherein the disorder is selected from the group consisting of a bacterial infection, a viral infection, a fungal infection, inflammatory bowel disease, celiac disease, colitis, intestinal hyperplasia, cancer, metabolic syndrome, obesity, rheumatoid arthritis, liver disease, hepatic steatosis, fatty liver disease, liver fibrosis, non-alcoholic fatty liver disease (NAFLD), and non-alcoholic steatohepatitis (NASH).

Embodiment I-73. The method of Embodiment I-68, wherein the disorder is non-alcoholic steatohepatitis (NASH).

Embodiment I-74. The method of any one of Embodiment I-55 to I-58, wherein the disorder is selected from the group consisting of lupus, lupus nephritis, cryopyrin-associated periodic syndromes (CAPS), myelodysplastic syndromes (MDS), gout, myeloproliferative neoplasms (MPN), atherosclerosis, Crohn's disease, and inflammatory bowel disease (IBD).

Embodiment I-75. A compound of any one of Embodiment I-1 to I-53, or a pharmaceutically acceptable salt, solvate, isomer, or tautomer thereof, for use as a medicament.

Embodiment I-76. A compound any one of Embodiment I-1 to I-53, or a pharmaceutically acceptable salt, solvate, isomer, or tautomer thereof, for use in treating a disorder that is responsive to inhibition of inflammasome.

Embodiment I-77. Use of a compound of any one of Embodiment I-1 to I-53, or a pharmaceutically acceptable salt, solvate, isomer, or tautomer thereof, in the manufacture of a medicament for treating a disorder that is responsive to inhibition of inflammasome.

Embodiment I-78. A pharmaceutical composition of Embodiment I-54 for use as a medicament.

Embodiment I-79. A pharmaceutical composition of Embodiment I-54 for use in treating a disorder that is responsive to inhibition of inflammasome.

Embodiment I-80. Use of pharmaceutical composition of Embodiment I-54 in the manufacture of a medicament for treating a disorder that is responsive to inhibition of inflammasome.

EXAMPLES

The following examples are provided to illustrate the present disclosure, and should not be construed as limiting thereof. In these examples, all parts and percentages are by weight, unless otherwise noted. Abbreviations in the examples are noted below.

Abbreviations aq. aqueous
EtOAc ethyl acetate
h hour
HMDS hexamethyldisilazide
HPLC high performance liquid chromatography
LHMDS lithium hexamethyldisilazide
min minutes
mL milliliter
mmol millimole
MeOH methanol
$MeSO_3H$ Methane sulfonic acid
NMR nuclear magnetic resonance
sat. saturated
sat. $NaHCO_3$ saturated aqueous $NaHCO_3$
TEA triethylamine
THF tetrahydrofuran
TLC thin layer chromatography Chiral HPLC Analytical Methods:
Method A—
  Column: Chiralcel OD-3 50×4.6 mm I.D., 3 μm
  Mobile phase: A: $CO_2$ B: methanol (0.05% DEA)
  Gradient: from 5% to 40% of B in 2 min and hold 40% for 1.2 min, then 5% of B for 0.8 min
  Flow rate: 4 mL/min
  Column temp.: 35° C.
  ABPR: 1500 psi
Method B—
  Column: Chiralpak AD-3 150×4.6 mm I.D., 3 μm
  Mobile phase: A: $CO_2$ B: ethanol (0.05% DEA)
  Isocratic: 40% B
  Flow rate: 2.5 mL/min
  Column temp.: 40° C.
  ABPR: 100 bar
Method C—
  Column: Chiralpak AS-3 100×4.6 mm I.D., 3 μm
  Mobile phase: A: CO2 B: ethanol (0.05% DEA)
  Gradient: from 5% to 40% of B in 4 min and hold 40% for 2.5 min, then 5% of B for 1.5 min
  Flowrate: 2.8 mL/min
  Column temp.: 35° C.
  ABPR: 1500 psi
Method D—
  Column: Chiralpak IC-3 150×4.6 mm I.D., 3 μm
  Mobile phase: A: CO2 B: ethanol (0.05% DEA)
  Gradient: from 5% to 40% of B in 5 min and hold 40% for 2.5 min, then 5% of B for 2.5 min
  Flow rate: 2.5 mL/min
  Column temp.: 35° C.
  ABPR: 1500 psi
Method E—
  Column: Chiralpak AD-3 50×4.6 mm I.D., 3 μm
  Mobile phase: A: CO2 B: ethanol (0.05% DEA)
  Gradient: from 5% to 40% of B in 2 min and hold 40% for 1.2 min, then 5% of B for 0.8 min
  Flow rate: 4 mL/min
  Column temp.: 35° C.
  ABPR: 1500 psi
Method F—
  Column: Chiralpak IC-3 150×4.6 mm I.D., 3 μm
  Mobile phase: A: CO2 B: ethanol (0.05% DEA)
  Isocratic: 40% B
  Flow rate: 2.5 mL/min
  Column temp.: 40° C.
  ABPR: 100 bar
Method G—
  Column: Cellulose 2 150×4.6 mm I.D., 5 μm
  Mobile phase: A: CO2 B: Methanol (0.05% DEA)
  Isocratic: 40% B
  Flow rate: 2.5 mL/min
  Column temp.: 35° C.
  ABPR: 1500 psi
Method H—
  Column: Chiralpak AD-3 150×4.6 mm I.D., 3 μm
  Mobile phase: 40% of methanol (0.05% DEA) in CO2
  Flow rate: 2.5 mL/min
  Column temp.: 35° C.
  ABPR: 1500 psi Method I—
  Column: Chiralpak AD-3 150×4.6 mm I.D., 3 μm
  Mobile phase: 40% of ethanol (0.05% DEA) in CO2
  Flow rate: 2.5 mL/min
  Column temp.: 35° C.
  ABPR: 1500 psi
Method J—
  Column: Chiralcel OJ-3 150×4.6 mm I.D., 3 μm
  Mobile phase: A: CO2 B: ethanol (0.05% DEA)
  Gradient: from 5% to 40% of B in 5 min and from 40% to 5% of B in 0.5 min, hold 5% of B for 1.5 min
  Flow rate: 2.5 mL/min
  Column temp.: 35° C.
  ABPR: 1500 psi
Method K—
  Column: Chiralcel OD-3 150×4.6 mm I.D., 3 μm
  Mobile phase: A: CO2 B: methanol (0.05% DEA)
  Gradient: from 5% to 40% of B in 5 min and hold 40% for 2.5 min, then 5% of B for 2.5 min
  Flow rate: 2.5 mL/min
  Column temp.: 35° C.
  ABPR: 1500 psi
Method L—
  Column: Chiralpak IC-3 150×4.6 mm I.D., 3 μm
  Mobile phase: 40% of ethanol (0.05% DEA) in CO2
  Flow rate: 2.5 mL/min
  Column temp.: 35° C.
  ABPR: 1500 psi
Method M—
  Column: ChiralCel OD-3 150×4.6 mm I.D., 3 μm
  Mobile phase: A: CO2 B: Methanol (0.05% DEA)
  Gradient: from 5% to 40% of B in 5.5 min and hold 40% for 3 min, then 5% of B for 1.5 min
  Flow rate: 2.5 mL/min
  Column temp.: 40° C.
  ABPR: 100 bar
Method N—
  Column: Chiralpak AD-3 150×4.6 mm I.D., 3 μm
  Mobile phase: A: CO2 B: ethanol (0.05% DEA)
  Gradient: from 5% to 40% of B in 5 min and hold 40% for 2.5 min, then 5% of B for 2.5 min
  Flow rate: 2.5 mL/min
  Column temp.: 35° C.
  ABPR: 1500 psi
Method O—
  Column: ChiralPak AD-3 150×4.6 mm I.D., 3 μm Mobile phase: A: CO2 B: Methanol (0.05% DEA)

Gradient: from 5% to 40% of B in 5.5 min and hold 40% for 3 min, then 5% of B for 1.5 min
  Flow rate: 2.5 mL/min
  Column temp.: 40° C.
  Backpressure: 100 bar
Method P—
  Column: Cellulose 2 150×4.6 mm I.D., 5 μm
  Mobile phase: A: CO2 B: ethanol (0.05% DEA)
  Isocratic: 40% B
  Flow rate: 2.5 mL/min
  Column temp.: 35° C.
  ABPR: 1500 psi
Method Q—
  Column: Chiralcel OD-3 150×4.6 mm I.D., 3 μm
  Mobile phase: A: CO2 B: methanol (0.05% DEA)
  Gradient: from 5% to 40% of B in 5 min and from 40% to 5% of B in 0.5 min, hold 5% of B for 1.5 min
  Flow rate: 2.5 mL/min
  Column temp.: 35° C.
  ABPR: 1500 psi
Method R—
  Column: Chiralcel OJ-H 150×4.6 mm I.D., 5 μm
  Mobile phase: A: CO2 B: IPA (0.05% DEA)
  Isocratic: 40% B
  Flow rate: 2.5 mL/min
  Column temp.: 40° C.
  ABPR: 100 bar
Method S—
  Column: Chiralpak AD-3 150×4.6 mm I.D., 3 μm
  Mobile phase: A: CO2 B: Ethanol (0.05% DEA)
  Gradient: from 5% to 40% of B in 5.5 min and hold 40% for 3 min, then 5% of B for 1.5 min
  Flow rate: 2.5 mL/min
  Column temp.: 40° C.
  ABPR: 100 bar
Method T—
  Column: Chiracel OX, 50×4.6 mm, I.D. 3 μm
  Mobile phase: A: $CO_2$ B: methanol (0.1% $NH_4OH$)
  Gradient: Isocratic at 30% B
  Flow rate: 4 mL/min
  Column temp.: 40° C.
  ABPR: 120 bar
Method U—
  Column: Chiralpak IA, 50×4.6 mm, I.D. 3 μm
  Mobile phase: A: $CO_2$ B: methanol (0.1% $NH_4OH$)
  Gradient: Isocratic at 35% B
  Flow rate: 4 mL/min
  Column temp.: 40° C.
  ABPR: 120 bar
Method V—
  Column: Chiracel OX, 50×4.6 mm, I.D. 3 μm
  Mobile phase: A: $CO_2$ B: methanol (0.1% $NH_4OH$)
  Gradient: Isocratic at 40% B
  Flow rate: 4 mL/min
  Column temp.: 40° C.
  ABPR: 120 bar
Method W—
  Column: WhelkO-1(s,s), 100×4.6 mm, I.D. 3 μm
  Mobile phase: A: $CO_2$ B: ethanol (0.1% $NH_4OH$)
  Gradient: Isocratic at 30% B
  Flow rate: 4 mL/min
  Column temp.: 40° C.
  ABPR: 125 bar

SYNTHETIC EXAMPLES

Example A

Synthesis of a Brominated Pyrazolo[5,1-b][1,3]oxazine: (S)-3-bromo-6-methoxy-6,7-dihydro-5H-pyrazolo[5,1-b][1,3]oxazine -continued

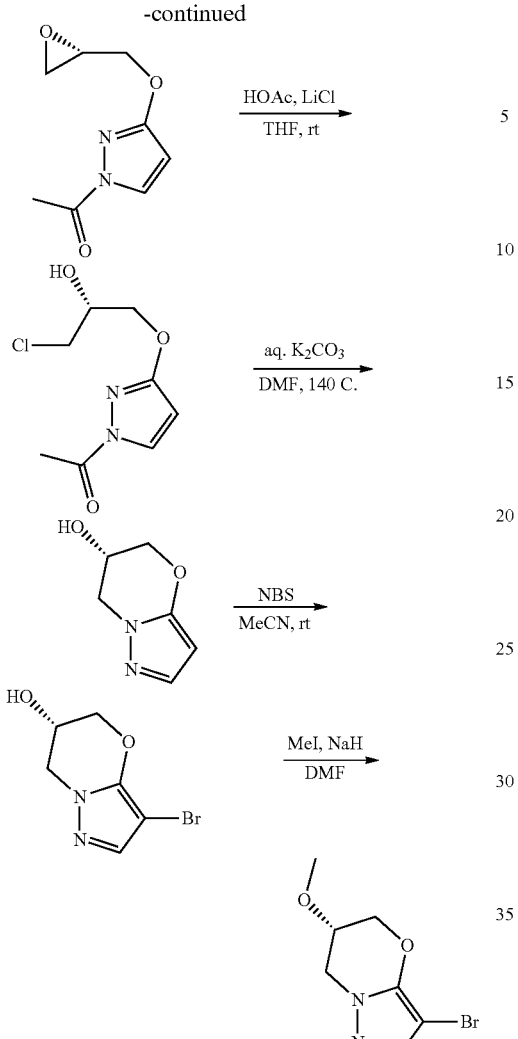

Step 1—Synthesis of 1-acetyl-1,2-dihydro-pyrazol-3-one

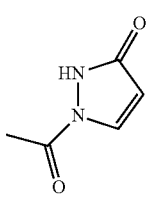

A solution of 1,2-dihydro-pyrazol-3-one (50.0 g, 600 mmol) in pyridine (300 mL) was heated to 95° C. To the solution, a solution of acetic anhydride (61.2 g, 600 mmol) in pyridine (100 mL) was added slowly over 0.5 hour. The reaction was heated for an additional 1 hour at 95° C. The reaction mixture was concentrated in vacuo resulting in a dark red oil which was triturated with MeOH (150 mL) and filtered to give 1-acetyl-1,2-dihydro-pyrazol-3-one (54.0 g, yield: 71%) as a white solid. $^1$H NMR (300 MHz, DMSO-$d_6$): δ=10.92 (s, 1H), 8.08 (s, 1H), 5.96 (s, 1H), 2.45 (overlap, 3H).

Step 2—Synthesis of (S)-1-(3-(oxiran-2-yl-methoxy)-1H-pyrazol-1-yl)ethan-1-one

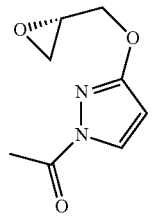

A mixture of 1-acetyl-1,2-dihydro-pyrazol-3-one (34.7 g, 280 mmol) and PPh$_3$ (24.9 g, 420 mmol) in THF (400 mL) was cooled to 0° C. under an atmosphere of N$_2$. To the mixture was added DIAD (84.8 g, 420 mmol) slowly. The reaction was stirred for 1 hour at 0° C., then (R)-oxiran-2-ylmethanol (25.2 g, 340 mmol) was added slowly. The reaction was then stirred at room temperature overnight. The reaction mixture was concentrated in vacuo and the residue was purified by silica gel column (PE/EtOAc=10/1) to give (S)-1-(3-(oxiran-2-ylmethoxy)-1H-pyrazol-1-yl)ethan-1-one (34.8 g, yield: 68%) as a white solid. $^1$H NMR (400 MHz, CDCl$_3$): δ=8.06 (d, J=2.8 Hz, 1H), 6.00 (d, J=3.2 Hz, 1H), 4.55 (dd, J=12.0, 3.2 Hz, 1H), 4.20 (dd, J=12.0, 3.2 Hz, 1H), 3.39 (q, J=3.2 Hz, 1H), 2.92 (t, J=4.4 Hz, 1H), 2.76 (dd, J=4.4, 2.4 Hz, 1H), 2.57 (s, 3H).

Step 3—Synthesis of (R)-1-(3-(3-chloro-2-hydroxy-propoxy)-1H-pyrazol-1-yl)ethan-1-one

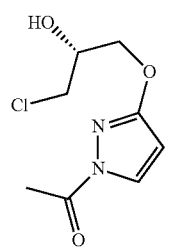

To a solution of (S)-1-(3-(oxiran-2-ylmethoxy)-1H-pyrazol-1-yl)ethan-1-one (34.8 g, 190 mmol) in AcOH (34.2 g, 570 mmol) and THF (200 mL), was added LiCl (13.1 g, 310 mmol) at room temperature. The reaction was then stirred at room temperature overnight. The reaction was partitioned between EtOAc (200 mL) and water (200 mL). The organic layer was washed with saturated aqueous NaHCO$_3$ (100 mL), brine (100 mL), dried over Na$_2$SO$_4$ and concentrated in vacuo to give crude (R)-1-(3-(3-chloro-2-hydroxy-propoxy)-1H-pyrazol-1-yl)ethan-1-one as a colorless oil which was used in the next step directly without any purification. $^1$H NMR (300 MHz, DMSO-$d_6$): δ=8.25 (d, J=2.7 Hz, 1H), 6.23 (d, J=3.0 Hz, 1H), 5.59 (brs, 1H), 4.24-4.19 (m, 2H), 4.07-4.04 (m, 1H), 3.75-3.62 (m, 2H), 2.50 (overlap, 3H). MS: m/z 219.4 (M+H$^+$).

Step 4—Synthesis of (S)-6,7-dihydro-H-pyrazolo[5,1-b][1,3]oxazin-6-ol

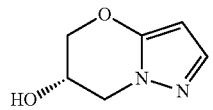

A mixture of (R)-1-(3-(3-chloro-2-hydroxypropoxy)-1H-pyrazol-1-yl)ethan-1-one (crude, 190 mmol) and K$_2$CO$_3$ (78.7 g, 570 mmol) in DMF (400 mL) was stirred at 135° C. overnight. The solvent was removed under reduced pressure. The residue was purified by silica gel column (EtOAc) to give (S)-6,7-dihydro-5H-pyrazolo[5,1-b][1,3]oxazin-6-ol (12.8 g, yield: 48%) as a white solid. $^1$H NMR (400 MHz, DMSO-d$_6$): δ=7.21 (d, J=1.6 Hz, 1H), 5.51 (d, J=3.2 Hz, 1H), 5.44 (d, J=1.6 Hz, 1H), 4.24-4.13 (m, 4H), 3.92 (d, J=12.4 Hz, 1H).

Step 5—Synthesis of (S)-3-bromo-6,7-dihydro-5H-pyrazolo[5,1-b][1,3]oxazin-6-ol

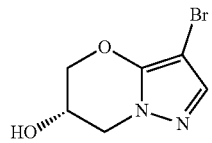 [SMILES: O[C@@H]1COc2c(Br)cnn2C1]

To a solution of (S)-6,7-dihydro-5H-pyrazolo[5,1-b][1,3]oxazin-6-ol (12.8 g, 91.4 mmol) in MeCN (200 mL) was added NBS (17.9 g, 100.6 mmol) at 0° C. under an atmosphere of N$_2$ in two portions. The reaction was warmed to room temperature and was allowed to stir for 1 hour. The reaction was partitioned between EtOAc (200 mL) and water (200 mL). The organic layer was washed with saturated aqueous NaHCO$_3$ (100 mL), brine (100 mL), dried over Na$_2$SO$_4$ and concentrated in vacuo. The crude residue was triturated with EtOAc (50 mL) and filtered to give (S)-3-bromo-6,7-dihydro-5H-pyrazolo[5,1-b][1,3]oxazin-6-ol (11.3 g, yield: 57%) as a white solid. MS: m/z 219.3 (M+H$^+$).

Step 6—Synthesis of (S)-3-bromo-6-methoxy-6,7-dihydro-5H-pyrazolo[5,1-b][1,3]oxazine

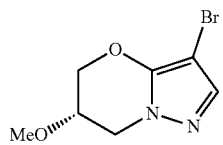 [SMILES: CO[C@@H]1COc2c(Br)cnn2C1]

To a solution of (S)-3-bromo-6,7-dihydro-5H-pyrazolo[5,1-b][1,3]oxazin-6-ol (12.2 g, 55.7 mmol) in DMF (60 mL) was added NaH (60% in mineral oil, 2.7 g, 66.8 mmol) under an atmosphere of N$_2$ at room temperature. After 1 hour, MeI (9.5 g, 66.8 mmol) was added. The reaction was allowed to stir for an additional 2 hours at room temperature. Then, the reaction was poured into water (200 mL) and extracted with EtOAc (100 mL×2). The organic layer was washed with water (100 mL), brine (100 mL), dried over Na$_2$SO$_4$ and concentrated. The crude residue was triturated with MeOH/H$_2$O (2/1, 100 mL) and filtered to give (S)-3-bromo-6-methoxy-6,7-dihydro-5H-pyrazolo[5,1-b][1,3]oxazine (9.5 g, yield: 73%) as a white solid. MS: m/z 233.3 (M+H$^+$).

Example 1

N'-((1,2,3,5,6,7-hexahydro-s-indacen-4-yl)carbamoyl)-6,7-dihydro-5H-pyrazolo[5,1-b][1,3]oxazine-3-sulfonimidamide

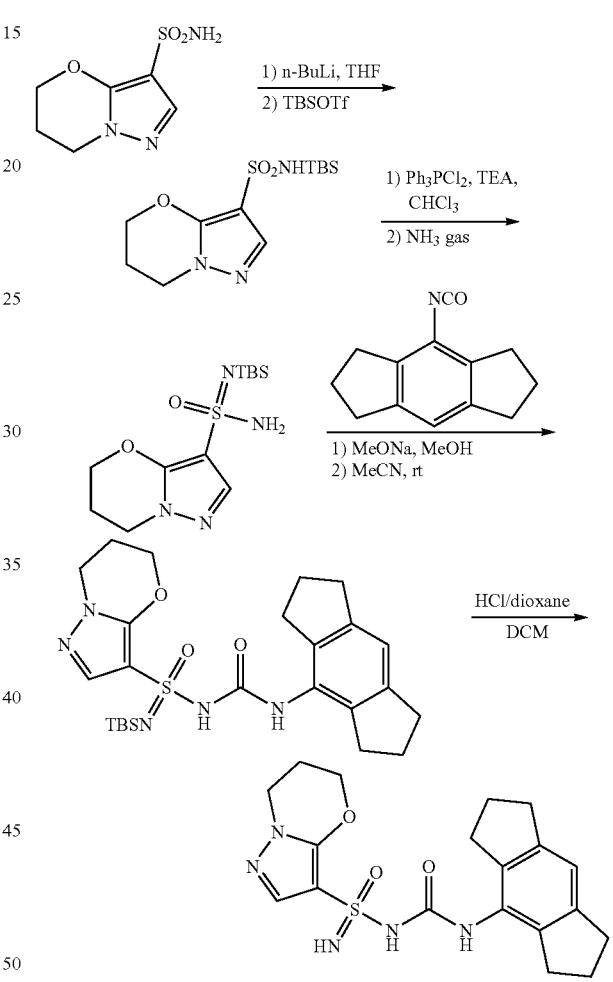

Step 1—Synthesis of N-(tert-butyldimethylsilyl)-6,7-dihydro-5H-pyrazolo[5,1-b][1,3]oxazine-3-sulfonamide

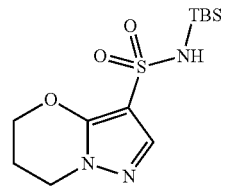

To a solution of 6,7-dihydro-5H-pyrazolo[5,1-b][1,3]oxazine-3-sulfonamide (1.0 g, 4.9 mmol) in dry THF (20 mL) was added n-BuLi (2.5 M in hexane, 2.4 mL, 5.9 mmol) slowly at −78° C. under N$_2$. After stirring with cooling for 2 hours, TBSOTf (1.6 g, 5.9 mmol) was added slowly. The cooling bath was removed and the reaction mixture was stirred at room temperature for 16 hours. The reaction mixture was quenched with sat. aqueous NH$_4$Cl (10 mL) and the resulting solution was directly purified by reverse phase column (MeCN/H$_2$O) to give N-(tert-butyldimethylsilyl)-6,7-dihydro-5H-pyrazolo[5,1-b][1,3]oxazine-3-sulfonamide (610 mg, yield: 38%) as a white solid. $^1$H NMR (400 MHz, DMSO-d$_6$): δ=7.42 (s, 1H), 7.36 (s, 1H), 4.40 (t, J=5.2 Hz, 2H), 4.11 (t, J=6.0 Hz, 2H), 2.20-2.15 (m, 2H), 0.87 (s, 9H), 0.11 (s, 6H). MS: m/z 318.3 (M+H$^+$).

Step 2—Synthesis of N-(tert-butyldimethylsilyl)-6,7-dihydro-5H-pyrazolo[5,1-b][1,3]oxazine-3-sulfonimidamide

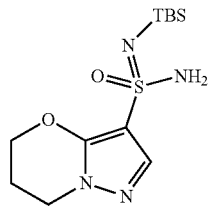

To a stirred suspension of Ph$_3$PCl$_2$ (363 mg, 1.1 mmol) in dry CHCl$_3$ (3.0 mL) under an atmosphere of N$_2$, was added triethylamine (125 mg, 1.5 mmol). The mixture was stirred for 10 minutes at room temperature and a yellow suspension immediately formed. The reaction mixture was cooled to 0° C. and a solution of N-(tert-butyldimethylsilyl)-6,7-dihydro-5H-pyrazolo[5,1-b][1,3]oxazine-3-sulfonamide (316 mg, 1.0 mmol) in dry CHCl$_3$ (3 mL) was added. After being stirred for 20 minutes at 0° C., NH$_3$ gas was bubbled through the mixture for 10 minutes at 0° C.

After, the resulting solution was stirred for 30 minutes at room temperature at which point it was concentrated to dryness. The residue was purified by reverse phase column (MeCN/H$_2$O) to give N-(tert-butyldimethylsilyl)-6,7-dihydro-5H-pyrazolo[5,1-b][1,3]oxazine-3-sulfonimidamide (mixed with Ph$_3$P=O) which was used directly in the next step without further purification. MS: m/z 317.3 (M+H$^+$).

Step 3—Synthesis of N-(tert-butyldimethylsilyl)-N-((1,2,3,5,6,7-hexahydro-s-indacen-4-yl)carbamoyl)-6,7-dihydro-5H-pyrazolo[5,1-b][1,3]oxazine-3-sulfonimidamide

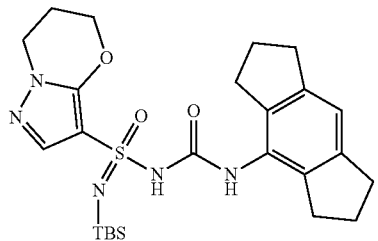

A suspension of N-(tert-butyldimethylsilyl)-6,7-dihydro-5H-pyrazolo[5,1-b][1,3]oxazine-3-sulfonimidamide (~1.0 mmol) in MeOH (10 mL) was stirred at 80° C. resulting in a clear solution. MeONa (54 mg, 1.0 mmol) was added and the mixture was stirred for 5 minutes. The solution was concentrated to dryness and the residue was co-evaporated with MeCN (5 mL). The residual solid was suspended in MeCN (5 mL) and 4-isocyanato-1,2,3,5,6,7-hexahydro-s-indacene (199 mg, 1.0 mmol) was added at room temperature. After 16 hours, the reaction was filtered. The solid was dried to give N-(tert-butyldimethylsilyl)-N-((1,2,3,5,6,7-hexahydro-s-indacen-4-yl)carbamoyl)-6,7-dihydro-5H-pyrazolo[5,1-b][1,3]oxazine-3-sulfonimidamide as a white solid, which was used in the next step without further purification.

Step 4—Synthesis of N'-((1,2,3,5,6,7-hexahydro-s-indacen-4-yl)carbamoyl)-6,7-dihydro-5H-pyrazolo[5,1-b][1,3]oxazine-3-sulfonimidamide (Example 1)

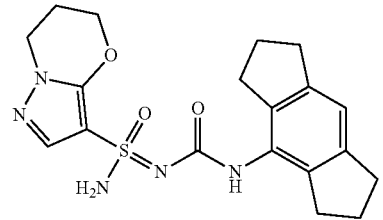 [SMILES: NS(=O)(=NC(=O)Nc1c2c(cc3c1CCC3)CCC2)c1cnn2c1OCCC2]

To a solution of N-(tert-butyldimethylsilyl)-N'-((1,2,3,5,6,7-hexahydro-s-indacen-4-yl)carbamoyl)-6,7-dihydro-5H-pyrazolo[5,1-b][1,3]oxazine-3-sulfonimidamide (40 mg, 0.08 mmol) in DCM (5 mL) was added HCl/dioxane (2 M, 2 mL) at room temperature. After 2 hours, the reaction was first purified by reverse phase column (MeCN/H$_2$O) to give crude product. Then the crude product was purified by prep-HPLC (NH$_3$—H$_2$O) to give N'-((1,2,3,5,6,7-hexahydro-s-indacen-4-yl)carbamoyl)-6,7-dihydro-5H-pyrazolo[5,1-b][1,3]oxazine-3-sulfonimidamide (4.6 mg, yield: 15%, mixture of enantiomers) as a white solid. $^1$H NMR (400 MHz, DMSO-d$_6$): δ=8.18 (brs, 1H), 7.50 (s, 1H), 7.23 (brs, 2H), 6.85 (s, 1H), 4.39 (t, J=6.4 Hz, 2H), 4.12 (t, J=6.0 Hz, 2H), 2.79 (t, J=7.2 Hz, 4H), 2.70 (t, J=7.2 Hz, 4H), 2.20-2.15 (m, 2H), 1.96-1.89 (m, 4H). MS: m/z 402.1 (M+H$^+$).

Example 2

(6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

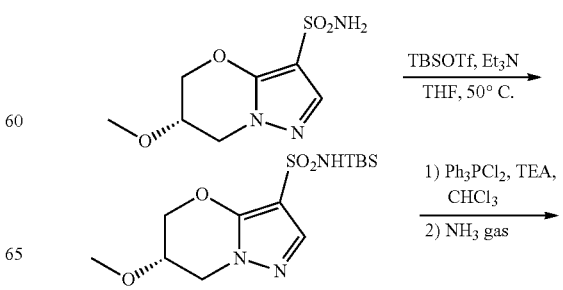

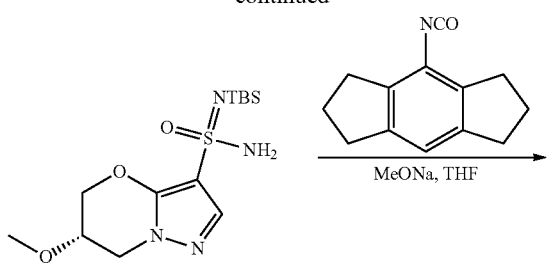

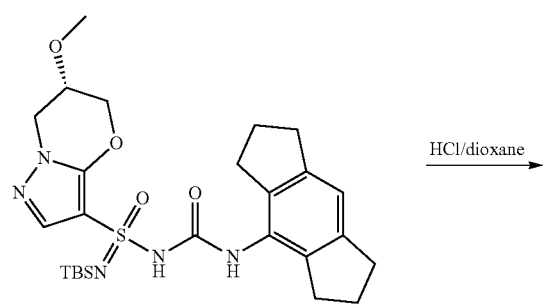

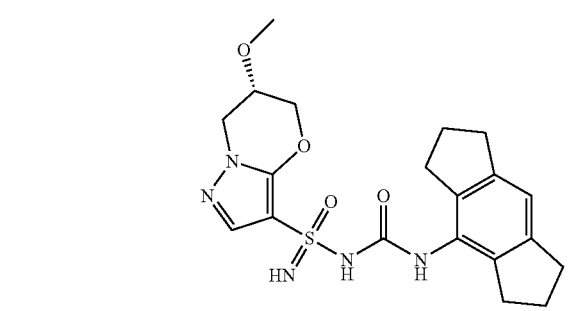

Step 1—Synthesis of (S)—N-(tert-butyldimethylsilyl)-6-methoxy-6,7-dihydro-5H-pyrazolo[5,1-b][1,3]oxazine-3-sulfonamide

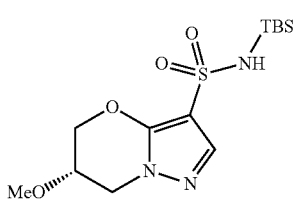

To a suspension of (S)-6-methoxy-6,7-dihydro-5H-pyrazolo[5,1-b][1,3]oxazine-3-sulfonamide (2.0 g, 8.6 mmol) in THF (20 mL) was added Et₃N (2.1 g, 21.5 mmol) and TBSOTf (3.0 g, 11.2 mmol) at room temperature. After being stirred at 50° C. for 16 hrs, the reaction mixture was cooled to room temperature, concentrated and purified by reverse phase column (5% 95% MeCN in H₂O) to give (S)—N-(tert-butyldimethylsilyl)-6-methoxy-6,7-dihydro-5H-pyrazolo[5,1-b][1,3]oxazine-3-sulfonamide (2.6 g, yield: 87%) as a yellow solid. MS: m/z 348.3 (M+H⁺).

Step 2—Synthesis of (6S)—N-(tert-butyldimethylsilyl)-6-methoxy-6,7-dihydro-5H-pyrazolo[5,1-b][1,3]oxazine-3-sulfonimidamide

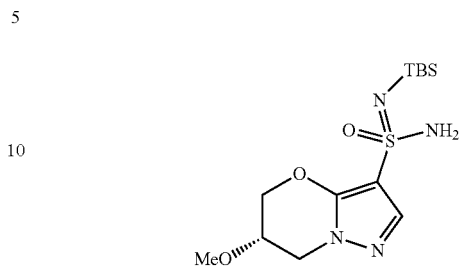

To a suspension of Ph₃PCl₂ (1.8 g, 5.5 mmol) in CHCl₃ (15 mL) was added Et₃N (860 mg, 8.6 mmol) at room temperature. The mixture was stirred at room temperature for 0.5 hour, then (S)—N-(tert-butyldimethylsilyl)-6-methoxy-6,7-dihydro-5H-pyrazolo[5,1-b][1,3]oxazine-3-sulfonamide (1.6 g, 4.6 mmol) in CHCl₃ (5 mL) was added at 0° C. The reaction mixture was stirred at room temperature for another 2 hours, then NH₃ (gas) was bubbled through the mixture for 5 mins. The resulting solution was stirred for 30 minutes at room temperature and concentrated to dryness. The residue was purified by silica gel column (DCM/MeOH=20/1) to give (6S)—N'-(tert-butyldimethylsilyl)-6-methoxy-6,7-dihydro-5H-pyrazolo[5,1-b][1,3]oxazine-3-sulfonimidamide (920 mg, mixed with Ph₃PO) as a yellow solid. MS: m/z 347.3 (M+H⁺).

Step 3—Synthesis of (6S)—N'-(tert-butyldimethylsilyl)-N-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

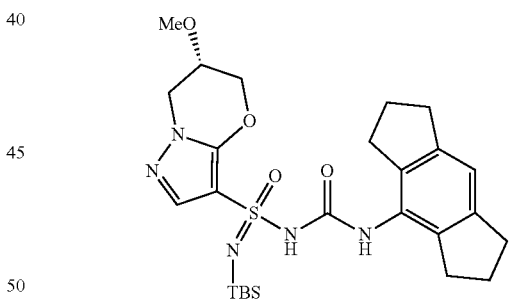

To a suspension of (6S)—N'-(tert-butyldimethylsilyl)-6-methoxy-6,7-dihydro-5H-pyrazolo[5,1-b][1,3]oxazine-3-sulfonimidamide (110 mg, mixed with Ph₃PO) in THF (2 mL) was added MeONa (19 mg, 0.35 mmol) and the mixture was stirred at room temperature for 20 minutes. Then 4-isocyanato-1,2,3,5,6,7-hexahydro-s-indacene (75 mg, 0.4 mmol) was added and the resulting mixture was stirred at room temperature for 16 hrs. Water (0.5 mL) was then added to the above suspension. The precipitate was collected by filtration and purified by reverse phase column (MeCN/H₂O) to give (6S)—N'-(tert-butyldimethylsilyl)-N-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (45 mg, purity: 62%) as a white solid. MS: m/z 546.4 (M+H⁺).

Step 4—Synthesis of (6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 2)

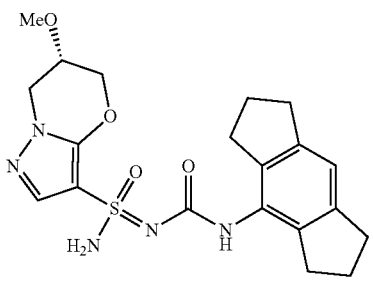 [SMILES: CO[C@@H]1COc2c(S(N)(=O)=NC(=O)Nc3c4c(cc5c3CCC5)CCC4)cnn2C1]

To a suspension of (6S)—N'-(tert-butyldimethylsilyl)-N-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (45 mg, purity: 62%) in MeOH (0.5 mL) was added HCl/dioxane (2 M, 2 mL) at room temperature. After being stirred at room temperature for 16 hours, the reaction mixture was concentrated and purified by reverse phase column (5-95% MeCN in H$_2$O) to give (6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (7 mg, yield: 21%, mixture of stereoisomers) as a white solid. $^1$H NMR (400 MHz, DMSO-d$_6$): δ=8.22 (brs, 1H), 7.56 (d, J=5.2 Hz, 1H), 7.31 (brs, 2H), 6.89 (s, 1H), 4.63 (d, J=7.2 Hz, 1H), 4.37-4.19 (m, 3H), 4.07 (s, 1H), 3.38 (overlap, 3H), 2.86-2.67 (m, 8H), 2.02-1.91 (m, 4H). MS: m/z 432.2 (M+H$^+$).

Example 3

N'-((4-fluoro-2,6-diisopropylphenyl)carbamoyl)-6,7-dihydro-5H-pyrazolo[5,1-b][1,3]oxazine-3-sulfonimidamide

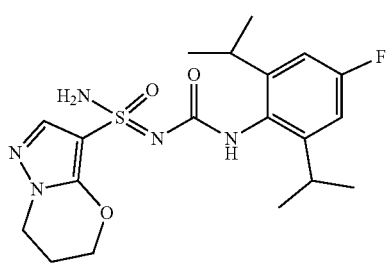

The title compound was prepared using general procedure of N-((1,2,3,5,6,7-hexahydro-s-indacen-4-yl)carbamoyl)-6,7-dihydro-5H-pyrazolo[5,1-b][1,3]oxazine-3-sulfonimidamide to yield a mixture of stereoisomers. Specifically, N'-((4-fluoro-2,6-diisopropylphenyl)carbamoyl)-6,7-dihydro-5H-pyrazolo[5,1-b][1,3]oxazine-3-sulfonimidamide was prepared as a mixture of enantiomers using the general procedure described for the preparation of N'-((1,2,3,5,6,7-hexahydro-s-indacen-4-yl)carbamoyl)-6,7-dihydro-5H-pyrazolo[5,1-b][1,3]oxazine-3-sulfonimidamide (Example 1), by replacing 4-isocyanato-1,2,3,5,6,7-hexahydro-s-indacene with 5-fluoro-2-isocyanato-1,3-diisopropylbenzene in Step 3. $^1$H NMR (400 MHz, DMSO-d$_6$): δ=8.01 (s, 1H), 7.49 (s, 1H), 7.23 (s, 2H), 6.87 (s, 1H), 6.85 (s, 1H), 4.40-4.35 (m, 2H), 4.10 (t, J=6.0 Hz, 2H), 3.14-3.08 (m, 2H), 2.18-2.15 (m, 2H), 1.16-1.07 (m, 12H). MS: m/z 424.2 (M+H$^+$).

Example 4

N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide

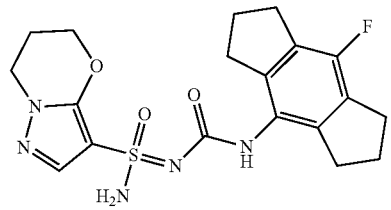 [SMILES: NS(=O)(=NC(=O)Nc1c2c(c(F)c3c1CCC3)CCC2)c1cnn2c1OCCC2]

The title compound was prepared using the general procedure of N-((1,2,3,5,6,7-hexahydro-s-indacen-4-yl)carbamoyl)-6,7-dihydro-5H-pyrazolo[5,1-b][1,3]oxazine-3-sulfonimidamide. N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide was prepared as a mixture of enantiomers using the general procedure described for the preparation of N'-((1,2,3,5,6,7-hexahydro-s-indacen-4-yl)carbamoyl)-6,7-dihydro-5H-pyrazolo[5,1-b][1,3]oxazine-3-sulfonimidamide (Example 1), by replacing 4-isocyanato-1,2,3,5,6,7-hexahydro-s-indacene with 4-fluoro-8-isocyanato-1,2,3,5,6,7-hexahydro-s-indacene in Step 3. $^1$H NMR (400 MHz, DMSO-d$_6$): δ=8.22 (brs, 1H), 7.50 (s, 1H), 7.23 (s, 2H), 4.40-4.35 (m, 2H), 4.10 (t, J=6.0 Hz, 2H), 2.82 (t, J=7.2 Hz, 4H), 2.70 (t, J=7.2 Hz, 4H), 2.20-2.17 (m, 2H), 2.01-1.96 (m, 4H). MS: m/z 420.1 (M+H$^+$).

Example 5

N'-((1,2,3,5,6,7-hexahydro-s-indacen-4-yl)carbamoyl)-1-methyl-1H-pyrazole-4-sulfonimidamide

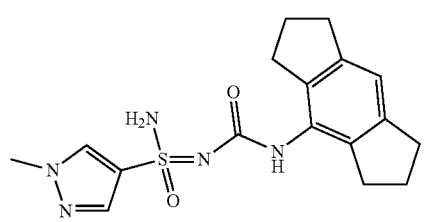 [SMILES: Cn1cc(S(N)(=O)=NC(=O)Nc2c3c(cc4c2CCC4)CCC3)cn1]

N'-((1,2,3,5,6,7-hexahydro-s-indacen-4-yl)carbamoyl)-1-methyl-1H-pyrazole-4-sulfonimidamide was prepared as a mixture of enantiomers using the general procedure described for the preparation of N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 6), by replacing 6,6-dimethyl-6,7-dihydro-5H-pyrazolo[5,1-b][1,3]oxazine-3-sulfonamide with 1-methyl-1H-pyrazole-4-sulfonamide in Step 1 to yield the title compound as a mixture of stereoisomers. MS: m/z 360 (M+H$^+$).

Example 6

N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

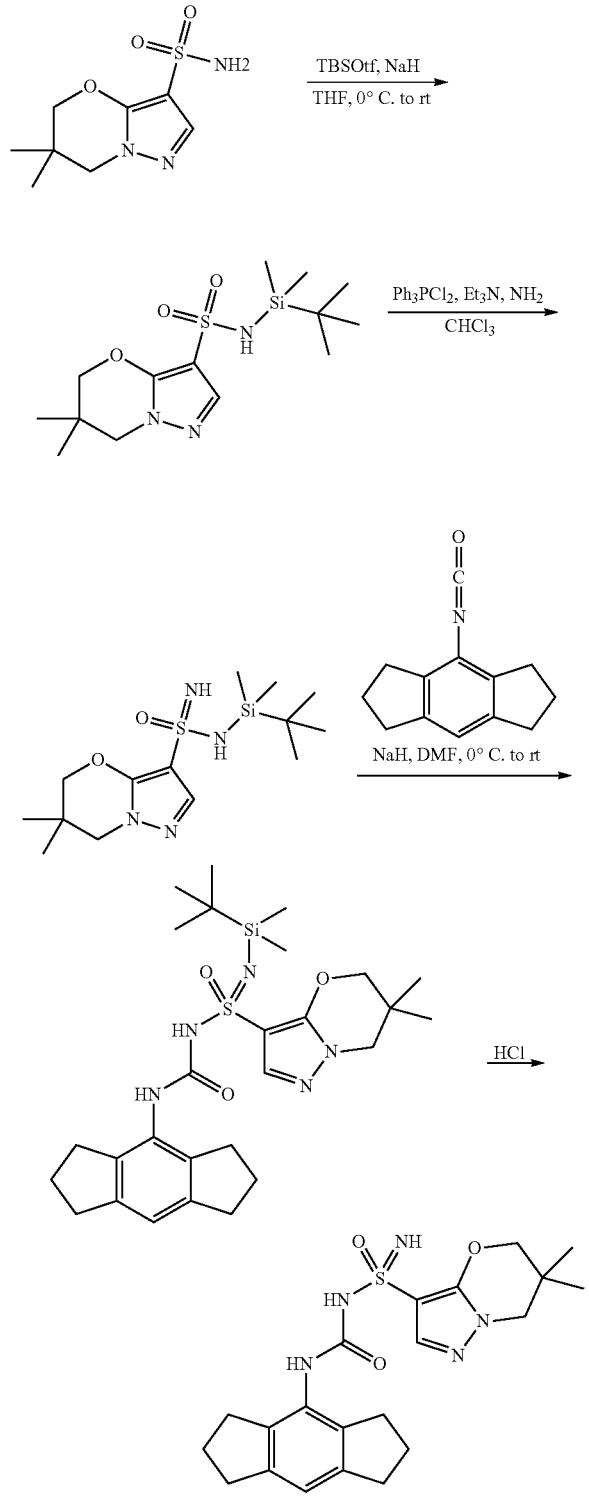

Step 1—Synthesis of N-(tert-butyldimethylsilyl)-6,6-dimethyl-6,7-dihydro-5H-pyrazolo[5,1-b][1,3]oxazine-3-sulfonamide

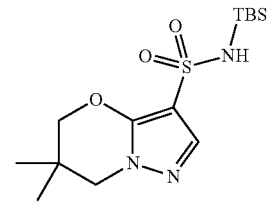

A solution of 6,6-dimethyl-6,7-dihydro-5H-pyrazolo[5,1-b][1,3]oxazine-3-sulfonamide (1.5 g, 6.5 mmol) in THF (28 mL) stirred under nitrogen at 0° C. was treated with sodium hydride (60%, 0.31 g, 7.8 mmol). After 20 minutes, tert-butyldimethylsilyl trifluoromethanesulfonate (2.3 g, 8.4 mmol) was added dropwise over 5 min. The cooling bath was then removed and the reaction mixture was stirred at room temperature for 13 hours. The reaction mixture was quenched by adding saturated $NH_4Cl$ solution (10 mL). The aqueous mixture was extracted with EtOAc (3×20 mL). The combined organic layers were washed with water, brine, dried over $Na_2SO_4$ and concentrated to afford a colorless semisolid residue. The resulting residue was purified by silica gel column (0 to 30% EtOAc in DCM). The clean fractions were combined to afford N-(tert-butyldimethylsilyl)-6,6-dimethyl-6,7-dihydro-5H-pyrazolo[5,1-b][1,3]oxazine-3-sulfonamide (1.15 g, 51%) as a white solid. MS: m/z 346 (M+H$^+$).

Step 2—Synthesis of N'-(tert-butyldimethylsilyl)-6,6-dimethyl-6,7-dihydro-5H-pyrazolo[5,1-b][1,3]oxazine-3-sulfonimidamide

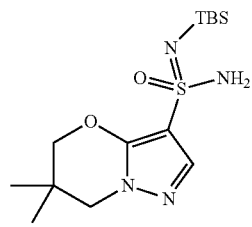

A suspension of triphenylphosphine dichloride (1.16 g, 3.5 mmol), stirred in $CHCl_3$ (12 mL) at 0° C. under nitrogen, was treated with $Et_3N$ (0.52 mL, 3.8 mmol) over 5 minutes. The ice bath was removed and the mixture was stirred for 15 minutes (a white suspension formed). After the mixture was cooled to 0° C., a solution of N-(tert-butyldimethylsilyl)-6,6-dimethyl-6,7-dihydro-5H-pyrazolo[5,1-b][1,3]oxazine-3-sulfonamide (1 g, 2.9 mmol) in $CHCl_3$ (12 mL) was added. After the mixture was stirred for 20 minutes, the ice bath was removed and the mixture was stirred for 20 minutes. The mixture was cooled to 0° C. and was treated with a 0.5M solution of ammonia (20 mL, 11.6 mmol) in 1,4 dioxane. After the mixture stirred for 30 minutes, the ice bath was removed and the mixture was stirred for an additional 1 h. After the mixture was treated with water (50 mL), the mixture was concentrated until only water remained; the resulting aqueous mixture was extracted with EtOAc (3×30 mL). The combined organic layers were washed with brine, dried with $Na_2SO_4$, filtered and concentrated. The resulting solid was purified by silica gel column (0 to 100%, EtOAc in DCM). The fractions containing the desired product were contaminated with triphenylphospine oxide. The fractions were combined and concentrated to afford a white solid. The solid was treated with a solution of 20% EtOAc in hexanes (20 mL), sonicated, and allowed to sit for 20 minutes before a precipitate formed. The suspension was filtered (the solid was determined to be triphenylphosphine oxide) and the filtrate was concentrated to dryness to afford N'-(tert-butyldimethylsilyl)-6,6-dimethyl-6,7-dihydro-5H-pyrazolo[5,1-b][1,3]oxazine-3-sulfonimidamide (850 mg) contaminated with triphenylphosphine oxide. The material was carried forward without any further purification. MS: m/z 345 (M+H⁺).

Step 3—Synthesis of N'-(tert-butyldimethylsilyl)-N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

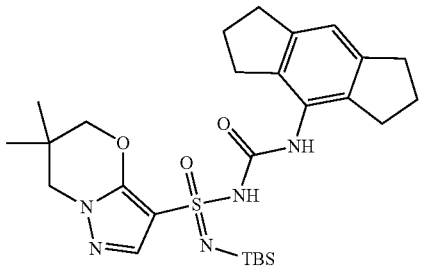

A solution of N'-(tert-butyldimylmetyl)-6,6-dimethyl-6,7-dihydro-5H-pyrazolo[5,1-b][1,3]oxazine-3-sulfonimidamide (400.0 mg, 0.35 mmol, 30% w/w) stirred in DMF (4 mL) at 0° C. under nitrogen was treated with NaH (60%, 18 mg, 0.45 mmol). After 15 minutes, the mixture was treated with 4-isocyanato-1,2,3,5,6,7-hexahydro-s-indacene (76 mg, 0.38 mmol). The ice bath was removed and the mixture was stirred for an additional 2 h. The mixture was treated with saturated $NH_4Cl$ solution and was extracted with EtOAc (3×20 mL). The combined organic layers were washed with brine, dried over sodium sulfate, filtered, and concentrated. The resulting residue was diluted with MeOH, sonicated, and was allowed to sit for 2 hours. After the suspension was filtered, the filter cake was washed with additional MeOH. The filtrate was evaporated to dryness to afford N'-(tert-butyldimethylsilyl)-N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (180 mg) contaminated with triphenylphosphine oxide. The material was carried forward without any further purification. MS: m/z 544 (M+H⁺).

Step 4—Synthesis of N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 6)

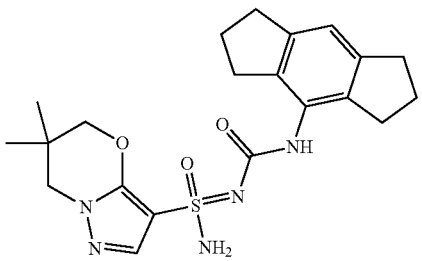 [SMILES: CC1(C)COc2c(S(N)(=O)=NC(=O)Nc3c4c(cc5c3CCC5)CCC4)cnn2C1]

A solution of N'-(tert-butyldimethylsilyl)-N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (180 mg, 0.07 mmol) stirred in 1,4 dioxane (2 mL) was treated with a solution of 4N HCl (2 mL, 6.6 mmol) in 1,4 dioxane. The ice bath was removed and the mixture was stirred for 15 minutes before being concentrated. The resulting solid was diluted with MeOH (30 mL), sonicated and allowed to sit for 30 minutes before being filtered. After the filtrate was concentrated to dryness, the resulting solid was suspended in ethyl ether (20 mL), sonicated and filtered. (the white filter cake was triphenylphosphine oxide; filtrate contained the desired product along with remaining triphenylphosphine oxide and other side products). After the filtrate was concentrated, the ethyl ether trituration was repeated twice more. The filtrate of the last trituration was concentrated. The resulting solid was diluted in MeOH (5 mL) resulting in a slight suspension. The suspension was filtered through a 0.45 A syringe filter; the filtrate was purified by Prep-LCMS (05-95% ACN, 0.1% $NH_4Cl$). The fractions were collected and concentrated to afford N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide as a white solid (6 mg, mixture of stereoisomers). MS: m/z 430 (M+H⁺).

Example 7 and Example 8

(S)—N'-((4-fluoro-2,6-diisopropylphenyl)carbamoyl)-6,7-dihydro-5H-pyrazolo[5,1-b][1,3]oxazine-3-sulfonimidamide and (R)—N'-((4-fluoro-2,6-diisopropylphenyl)carbamoyl)-6,7-dihydro-5H-pyrazolo[5,1-b][1,3]oxazine-3-sulfonimidamide

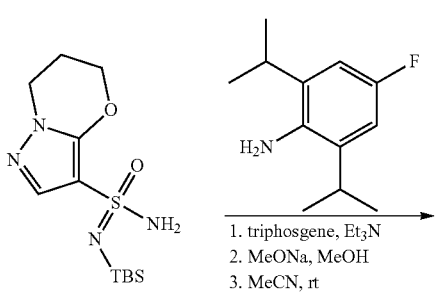

235
-continued

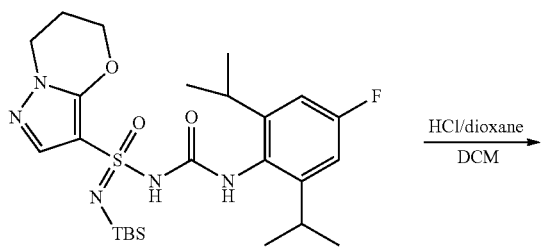

HCl/dioxane
DCM
→

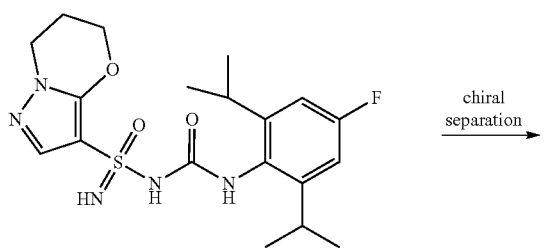

chiral
separation
→

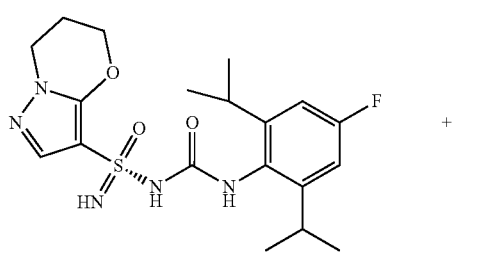

+

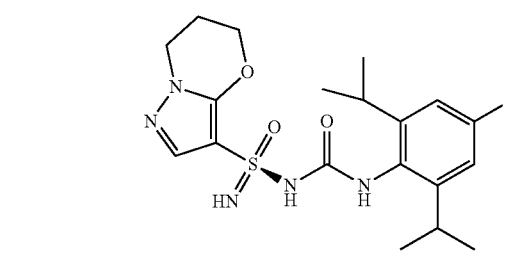

Steps 1 and 2. These two steps were similar to the general procedure of N-((1,2,3,5,6,7-hexahydro-s-indacen-4-yl)carbamoyl)-6,7-dihydro-5H-pyrazolo[5,1-b][1,3]oxazine-3-sulfonimidamide.

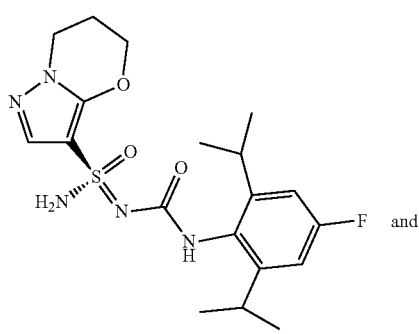

and

236
-continued

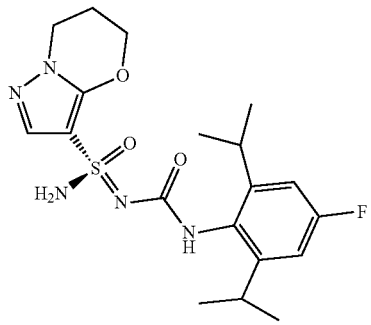

(S)—N'-((4-fluoro-2,6-diisopropylphenyl)carbamoyl)-6,7-dihydro-5H-pyrazolo[5,1-b][1,3]oxazine-3-sulfonimidamide and (R)—N'-((4-fluoro-2,6-diisopropylphenyl)carbamoyl)-6,7-dihydro-5H-pyrazolo[5,1-b][1,3]oxazine-3-sulfonimidamide: N'-((4-fluoro-2,6-diisopropylphenyl)carbamoyl)-6,7-dihydro-5H-pyrazolo[5,1-b][1,3]oxazine-3-sulfonimidamide (80 mg, 0.2 mmol) was separated by chiral prep-HPLC to give two isomers of unknown absolute stereochemistry as white solids.

Peak 1, 21.4 mg, yield: 27% $^1$H NMR (400 MHz, DMSO-$d_6$): δ=7.99 (s, 1H), 7.49 (s, 1H), 7.23 (brs, 2H), 6.86 (s, 1H), 6.84 (s, 1H), 4.40-4.35 (m, 2H), 4.10 (t, J=6.0 Hz, 2H), 3.14-3.08 (m, 2H), 2.18-2.15 (m, 2H), 1.16-1.07 (m, 12H). MS: m/z 424.2 (M+H$^+$).

Peak 2, 18.1 mg, yield: 23% $^1$H NMR (400 MHz, DMSO-$d_6$): δ=7.99 (s, 1H), 7.49 (s, 1H), 7.24 (brs, 2H), 6.87 (s, 1H), 6.84 (s, 1H), 4.40-4.35 (m, 2H), 4.10 (t, J=6.0 Hz, 2H), 3.14-3.08 (m, 2H), 2.18-2.15 (m, 2H), 1.16-1.07 (m, 12H). MS: m/z 424.2 (M+H$^+$).

Example 9

N'-((1,2,3,5,6,7-hexahydro-s-indacen-4-yl)carbamoyl)-N-methyl-6,7-dihydro-5H-pyrazolo[5,1-b][1,3]oxazine-3-sulfonimidamide

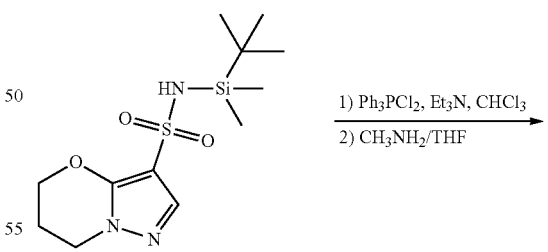

1) Ph$_3$PCl$_2$, Et$_3$N, CHCl$_3$
2) CH$_3$NH$_2$/THF
→

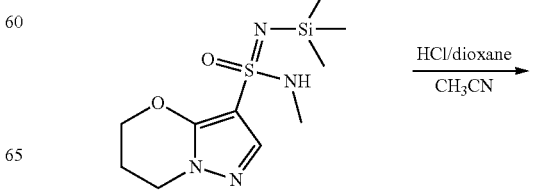

HCl/dioxane
CH$_3$CN
→

-continued

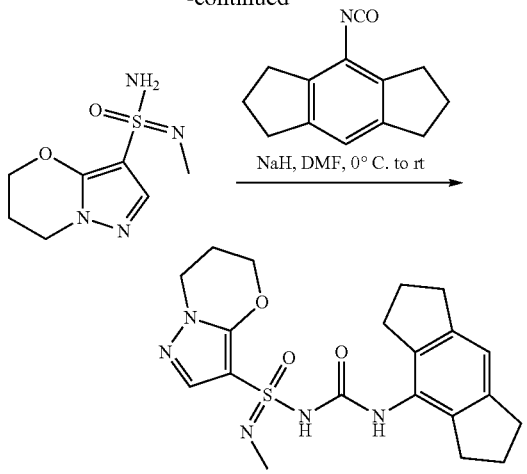

Step 1—Synthesis of N'-(tert-butyldimethylsilyl)-N-methyl-6,7-dihydro-5H-pyrazolo[5,1-b][1,3]oxazine-3-sulfonimidamide

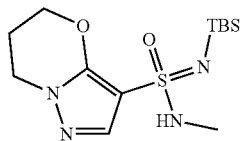

To a stirred suspension of Triphenylphosphine dichloride (1.2 g, 3.5 mmol) in dry $CHCl_3$ (4.5 mL) under a $N_2$ atmosphere, was added triethylamine (0.42 g, 4.2 mmol). The reaction mixture was stirred for 10 min at room temperature (a white suspension formed). The reaction mixture was then cooled to 0° C., and a solution of N-(tert-butyldimethylsilyl)-6,7-dihydro-5H-pyrazolo[5,1-b][1,3]oxazine-3-sulfonamide (0.44 g, 1.4 mmol) in dry $CHCl_3$ (3.5 mL) was added dropwise. The reaction mixture was warmed to 10° C. over 1 h, then cooled back to 0° C., and 2M solution of methanamine (3 mL, 6.9 mmol) in THF was added dropwise. The reaction mixture was stirred at 0° C. for 20 min, then warmed to room temperature over 2 h. Then, the reaction mixture was concentrated to dryness, and the residue was purified by silica gel chromatography (30 to 100% EtOAc in Hexane, then 0 to 10% MeOH in DCM) to afford N'-(tert-butyldimethylsilyl)-N-methyl-6,7-dihydro-5H-pyrazolo[5,1-b][1,3]oxazine-3-sulfonimidamide (0.25 g, ~85% w/w) having triphenylphosphine oxide impurity. The material was used in the next step without additional purification. MS: m/z 331 (M+H$^+$).

Step 2—Synthesis of N'-methyl-6,7-dihydro-5H-pyrazolo[5,1-b][1,3]oxazine-3-sulfonimidamide

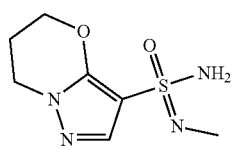

To a solution of N'-(tert-butyldimethylsilyl)-N-methyl-6,7-dihydro-5H-pyrazolo[5,1-b][1,3]oxazine-3-sulfonimidamide (0.25 g, ~0.64 mmol, ~85% w/w) in $CH_3CN$ (3 mL) cooled to 10° C. was added a solution of 4N HCl (0.9 mL, 3.8 mmol) in 1,4-dioxane. The reaction mixture was warmed to room temperature over 2 h. Then, the reaction mixture was concentrated to dryness and the residue was purified by prep-HPLC ($CH_3CN/H_2O$/10 mM aq. $NH_3$) to afford N'-methyl-6,7-dihydro-5H-pyrazolo[5,1-b][1,3]oxazine-3-sulfonimidamide (78 mg, yield: 48%) as a colorless oil. $^1H$ NMR (500 MHz, DMSO-$d_6$): δ=7.44 (s, 1H), 6.32 (br.s, 1H), 4.41-4.35 (m, 2H), 4.11 (t, J=6.1 Hz, 2H), 3.71 (br.s, 1H), 2.41 (s, 3H), 2.22-2.17 (m, 2H). MS: m/z 217 (M+H$^+$).

Step 3—Synthesis of N'-((1,2,3,5,6,7-hexahydro-s-indacen-4-yl)carbamoyl)-N-methyl-6,7-dihydro-5H-pyrazolo[5,1-b][1,3]oxazine-3-sulfonimidamide (Example 9)

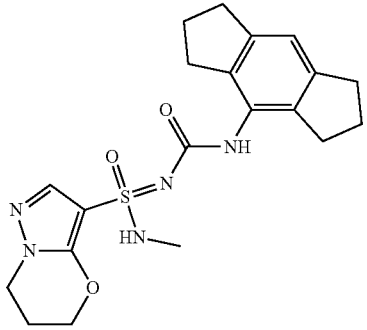 [SMILES: CNS(=O)(=NC(=O)Nc1c2c(cc3c1CCC3)CCC2)c1cnn2c1OCCC2]

To a solution of N'-methyl-6,7-dihydro-5H-pyrazolo[5,1-b][1,3]oxazine-3-sulfonimidamide (44 mg, 0.20 mmol) in DMF (1 mL) cooled to 0° C. was added sodium hydride (60%, 8.1 mg, 0.20 mmol) under a $N_2$ atmosphere, the reaction mixture was stirred for 10 min. Then, 4-isocyanato-1,2,3,5,6,7-hexahydro-s-indacene (41 mg, 0.20 mmol) was added in one portion, the ice-water bath was removed. The reaction mixture was stirred at room temperature for 62 h. The reaction mixture was quenched with MeOH, filtered and purified by prep-HPLC ($CH_3CN/H_2O$/10 mM aq. $NH_3$) to afford N-((1,2,3,5,6,7-hexahydro-s-indacen-4-yl)carbamoyl)-N'-methyl-6,7-dihydro-5H-pyrazolo[5,1-b][1,3]oxazine-3-sulfonimidamide (9.2 mg, yield: 11%, mixture of stereoisomers) as a white solid. $^1H$ NMR (500 MHz, DMSO-$d_6$): δ=8.26 (br.s, 1H), 7.50 (s, 1H), 7.11 (br.s, 1H), 6.87 (s, 1H), 4.45-4.36 (m, 2H), 4.13 (t, J=6.1 Hz, 2H), 2.79 (t, J=7.3 Hz, 4H), 2.71 (t, J=7.3 Hz, 4H), 2.49 (s, 3H), 2.25-2.17 (m, 2H), 1.98-1.92 (m, 4H). MS: m/z 416 (M+H$^+$).

Example 10

1-(cyclopropylmethyl)-N'-((1,2,3,5,6,7-hexahydro-s-indacen-4-yl)carbamoyl)-1H-pyrazole-4-sulfonimidamide

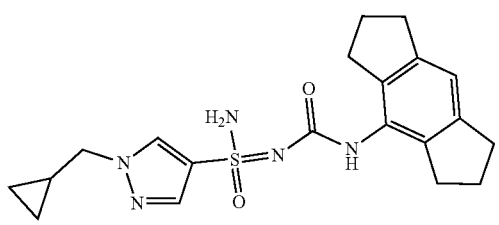 [SMILES: NS(=O)(=NC(=O)Nc1c2c(cc3c1CCC3)CCC2)c1cnn(CC2CC2)c1]

1-(Cyclopropylmethyl)-N'-((1,2,3,5,6,7-hexahydro-s-indacen-4-yl)carbamoyl)-1H-pyrazole-4-sulfonimidamide was prepared as a mixture of enantiomers using the general procedure described for the preparation of N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 6), by replacing 6,6-dimethyl-6,7-dihydro-5H-pyrazolo[5,1-b][1,3]oxazine-3-sulfonamide with 1-(cyclopropylmethyl)-1H-pyrazole-4-sulfonamide in Step 1 to yield the title compound as a mixture of stereoisomers. MS: m/z 400 (M+H$^+$).

Example 11 and Example 12

N'-benzyl-N-((1,2,3,5,6,7-hexahydro-s-indacen-4-yl)carbamoyl)-1-methyl-1H-pyrazole-3-sulfonimidamide and N-((1,2,3,5,6,7-hexahydro-s-indacen-4-yl)carbamoyl)-1-methyl-1H-pyrazole-3-sulfonimidamide

Step 1—Synthesis of methyl 1-methyl-H-pyrazole-3-sulfinate

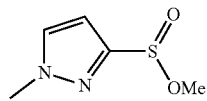

A solution of sodium sulfite (1.4 g, 2 Eq. 11 mmol) and sodium bicarbonate (0.93 g, 2 Eq. 11 mmol) in water (6 mL) was heated to 80° C., and a solution of 1-methyl-H-pyrazole-3-sulfonyl chloride (1.0 g, 1 Eq. 5.5 mmol) in 1,4-dioxane (6 mL) was added slowly. The reaction mixture was stirred at the same temperature for 1 h before concentrated under reduced pressure. Ethanol (100 mL) was added and the mixture was refluxed for 1 h before supernatant was separated while the reaction mixture was hot. Additional ethanol (100 mL) was added to the residue, and the mixture was stirred at room temperature for 30 min before filtered. The filtrates were combined and ethanol was removed under reduced pressure to afford a white solid.

The solid obtained was suspended in chloroform (10 mL) and thionyl chloride (0.86 g, 0.53 mL, 1.3 Eq. 7.2 mmol) was added dropwise at 0° C. under N$_2$. Upon complete addition, the reaction mixture was warmed up to room temperature and stirred for 1 h (solution A). In a separate flask, TEA (1.7 g, 2.3 mL, 3 Eq. 16 mmol), methanol (0.89 g, 1.1 mL, 5 Eq. 28 mmol) in THF (10 mL) was cooled to −78° C., solution A was added slowly under N$_2$. The reaction mixture was then warmed up to 0° C. and stirred for 1 h. TLC (10% MeOH/DCM) indicated the completion of reaction. The mixture was diluted with EtOAc and washed with water, brine, dried over Na$_2$SO$_4$, concentrated under reduced pressure and purified by silica gel chromatography (0 to 100% EtOAc/Hex) to afford methyl 1-methyl-H-pyrazole-3-sulfinate (503 mg, 56%, mixture of stereoisomers) as

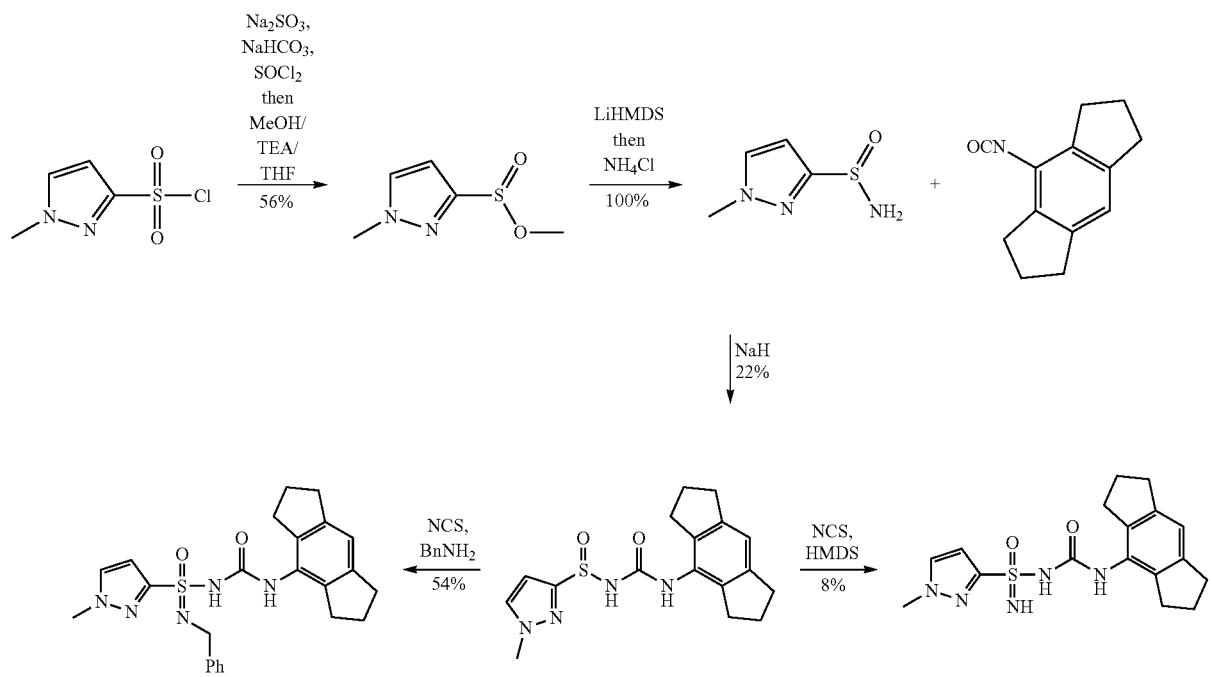

white solids. ¹H NMR (400 MHz, DMSO-d₆) δ 7.93 (s, 1H), 6.68 (s, 1H), 3.93 (s, 3H), 3.52 (s, 3H). LCMS: m/z=161 [M+H]⁺.

Steps 2 and 3—Synthesis of N-((1,2,3,5,6,7-hexahydro-s-indacen-4-yl)carbamoyl)-1-methyl-1H-pyrazole-3-sulfinamide

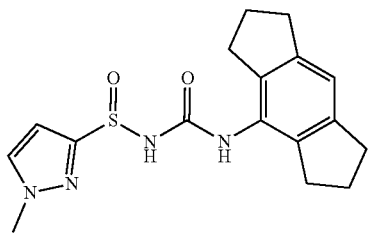 [SMILES: Cn1ccc(S(=O)NC(=O)Nc2c3c(cc4c2CCC4)CCC3)n1]

To a solution of methyl 1-methyl-1H-pyrazole-3-sulfinate (400 mg, 1 Eq. 2.5 mmol) in anhydrous THF (3 mL) was added LHMDS (627 mg, 3.7 mmol, 1.5 Eq. 3.75 mmol, 1 M in THF) under N₂. The reaction was warmed to room temperature and stirred for 2 h before 1 mL of saturated NH₄Cl solution was added, and the mixture was stirred for an additional 1 h. EtOAc (50 mL) was then added and the resulting solution was dried over Na₂SO₄. The mixture was filtered and solvent was removed to afford crude 1-methyl-1H-pyrazole-3-sulfinamide (363 mg, 100%) as white solids. The product was used in next step without additional purification.

1-methyl-1H-pyrazole-3-sulfinamide (363 mg, 1 Eq. 2.5 mmol) obtained as described above was dissolved in anhydrous DMF (3 mL). To this solution was added 4-isocyanato-1,2,3,5,6,7-hexahydro-s-indacene (495 mg, 1 Eq. 2.5 mmol) followed by NaH (0.2 g, 2 Eq. 5.00 mmol, 60% weight) at room temperature. The mixture was stirred for 1 h before quenched with 1 mL MeOH. The mixture was purified by prep-HPLC to afford N-((1,2,3,5,6,7-hexahydro-s-indacen-4-yl)carbamoyl)-1-methyl-1H-pyrazole-3-sulfinamide (190 mg, 22%) as white solids. ¹H NMR (400 MHz, DMSO-d₆) δ 7.76 (s, 1H), 6.85 (s, 1H), 6.62 (s, 1H), 3.88 (s, 3H), 2.80 (t, 4H), 2.73 (t, 4H), 1.95 (t, 4H). LCMS: m/z=367 [M+Na]+.

Synthesis of N'-benzyl-N-((1,2,3,5,6,7-hexahydro-s-indacen-4-yl)carbamoyl)-1-methyl-H-pyrazole-3-sulfonimidamide

Step 4—Synthesis of N-benzyl-N'-((1,2,3,5,6,7-hexahydro-s-indacen-4-yl)carbamoyl)-1-methyl-1H-pyrazole-3-sulfonimidamide

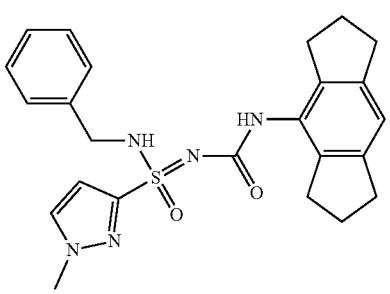 [SMILES: Cn1ccc(S(=O)(=NC(=O)Nc2c3c(cc4c2CCC4)CCC3)NCc2ccccc2)n1]

To a solution of N-((1,2,3,5,6,7-hexahydro-s-indacen-4-yl)carbamoyl)-1-methyl-1H-pyrazole-3-sulfinamide (50.0 mg, 1 Eq. 145 μmol) in anhydrous acetonitrile (1 mL) was added NCS (29.1 mg, 1.5 Eq. 218 μmol) at 0° C. The reaction mixture was warmed up to room temperature and stirred for 1 h before benzyamine (31.1 mg 32 μL, 2 Eq. 290 μmol) was added dropwise under N₂. The reaction mixture was stirred at room temperature for 1 h before water (10 mL) was added. The mixture was extracted with EtOAc (3×10 mL), combined organic extracts were washed with water, brine and dried over Na₂SO₄ and concentrated, purified by silica gel chromatography (EtOAc/Hex 0 to 100% follow by MeOH/DCM 0 to 10%) to afford N'-benzyl-N-((1,2,3,5,6,7-hexahydro-s-indacen-4-yl)carbamoyl)-1-methyl-1H-pyrazole-3-sulfonimidamide (35 mg, 54%, mixture of stereoisomers) as white solids. LCMS: m/z=450 [M+H]⁺.

Step 5—Synthesis of N'-((1,2,3,5,6,7-hexahydro-s-indacen-4-yl)carbamoyl)-1-methyl-1H-pyrazole-3-sulfonimidamide

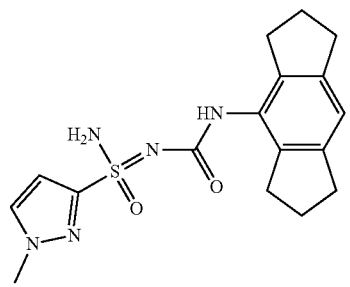 [SMILES: Cn1ccc(S(N)(=O)=NC(=O)Nc2c3c(cc4c2CCC4)CCC3)n1]

To a solution of N-((1,2,3,5,6,7-hexahydro-s-indacen-4-yl)carbamoyl)-1-methyl-1H-pyrazole-3-sulfinamide (50.0 mg, 1 Eq. 145 μmol) in anhydrous acetonitrile (1 mL) was added NCS (29.1 mg, 1.5 Eq. 218 μmol) at 0° C. The reaction mixture was warmed up to room temperature and stirred for 1 h before HMDS (46.9 mg, 61 μL, 2 Eq. 290 mol) was added dropwise under N₂. The reaction was stirred at room temperature for 1 h and the crude mixture was purified by prep-HPLC to afford N-((1,2,3,5,6,7-hexahydro-s-indacen-4-yl)carbamoyl)-1-methyl-1H-pyrazole-3-sulfonimidamide (4 mg, 8%, mixture of stereoisomers) as white solids. LCMS: m/z=360 [M+H]⁺.

Example 13 and Example 14

(R)—N'-((1,2,3,5,6,7-hexahydro-s-indacen-4-yl)carbamoyl)-6,7-dihydro-5H-pyrazolo[5,1-b][1,3]oxazine-3-sulfonimidamide and (S)—N'-((1,2,3,5,6,7-hexahydro-s-indacen-4-yl)carbamoyl)-6,7-dihydro-5H-pyrazolo[5,1-b][1,3]oxazine-3-sulfonimidamide

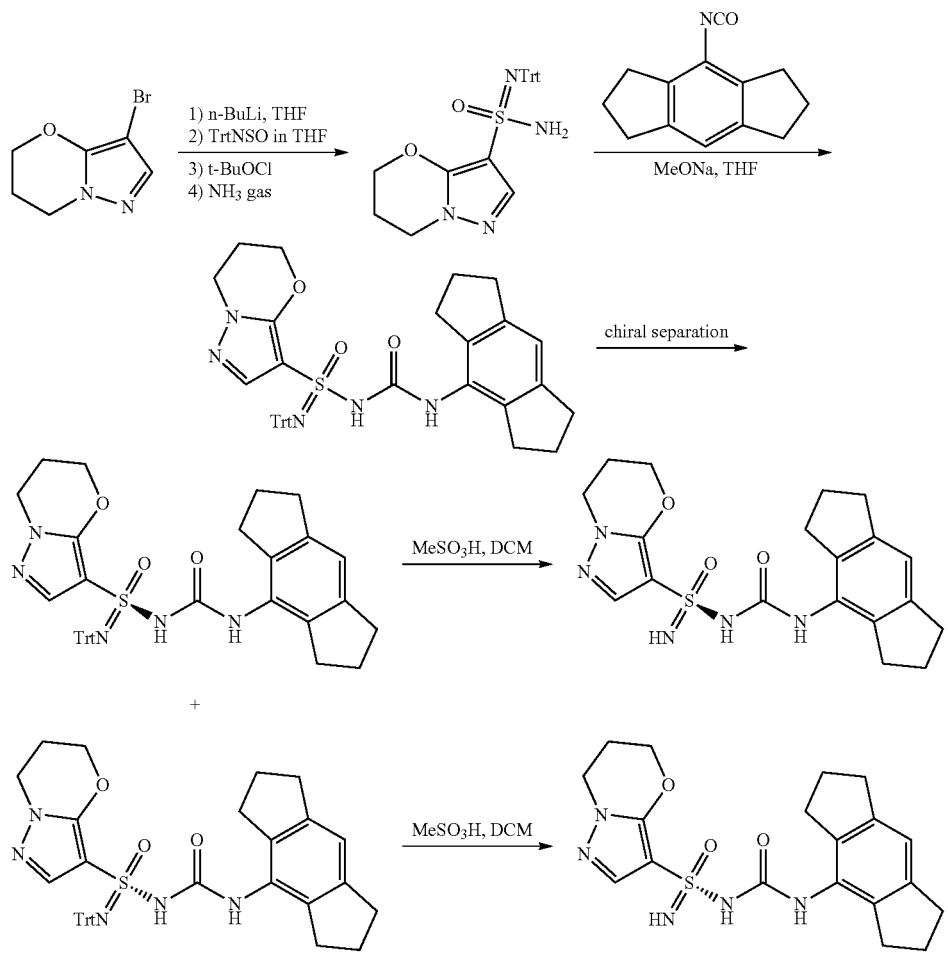

Step 1—Synthesis of N'-trityl-6,7-dihydro-5H-pyrazolo[5,1-b][1,3]oxazine-3-sulfonimidamide

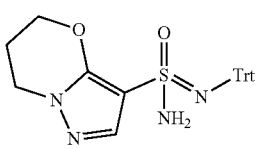

To a solution of 3-bromo-6,7-dihydro-5H-pyrazolo[5,1-b][1,3]oxazine (1.1 g, 5.4 mmol) in THF (20 mL) was added n-BuLi (2.4 mL, 5.9 mmol, 2.5 M in hexane) dropwise at −78° C. and the mixture was stirred for 1 hour. A solution of TrtNSO (1.8 g, 5.9 mmol) in THF (10 mL) was added dropwise and the mixture was stirred at −78° C. for 20 minutes before being placed in an ice bath. After stirring for another 10 minutes, tert-butyl hypochlorite (650 mg, 5.9 mmol) was added and the mixture was stirred for 20 minutes. $NH_3$ gas was then bubbled through the mixture for 5 minutes and the resulting solution was stirred for 16 hours at room temperature. The reaction mixture was concentrated to dryness and the residue was purified by reverse phase column (MeCN/$H_2O$) to give N'-trityl-6,7-dihydro-5H-pyrazolo[5,1-b][1,3]oxazine-3-sulfonimidamide (716 mg, yield: 30%) as a white solid. $^1$H NMR (400 MHz, DMSO-$d_6$): δ=7.43-7.41 (m, 6H), 7.20-7.15 (m, 6H), 7.11-7.07 (m, 3H), 6.99 (s, 1H), 6.20 (brs, 2H), 4.20-4.19 (m, 2H), 3.97-3.89 (m, 2H), 2.10-2.07 (m, 2H).

Step 2—Synthesis of N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide

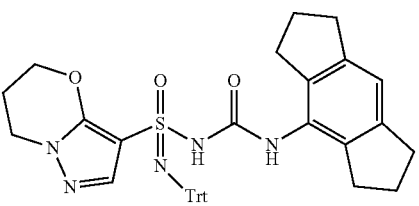

To a solution of N'-trityl-6,7-dihydro-5H-pyrazolo[5,1-b][1,3]oxazine-3-sulfonimidamide (716 mg, 1.6 mmol) in THF (10 mL) was added MeONa (96 mg, 1.8 mmol) and the mixture was stirred for 30 minutes at room temperature. Then, 4-isocyanato-1,2,3,5,6,7-hexahydro-s-indacene (375 mg, 1.7 mmol) was added and the mixture was stirred for 16 hours at room temperature. The reaction mixture was concentrated to dryness and purified by reverse phase column (MeCN/H$_2$O) to give N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide (370 mg, yield: 36%) as a white solid. MS: m/z 644.3 (M+H$^+$).

Step 3—(R)—N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (S)—N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide

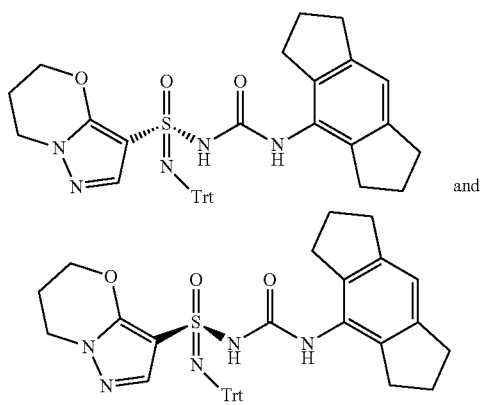

and

N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide (350 mg, 0.5 mmol) was separated by chiral prep-HPLC to give two isomers, (R)—N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (S)—N-((1,2,3,5,6,7-hexahydro-s-indacen-4-yl)carbamoyl)-N'-trityl-6,7-dihydro-5H-pyrazolo[5,1-b][1,3]oxazine-3-sulfonimidamide, of unknown absolute stereochemistry as white solids (peak 1, 80 mg, yield: 23%; peak 2,150 mg, yield: 43%).

Step 4—Synthesis of (R)—N'-((1,2,3,5,6,7-hexahydro-s-indacen-4-yl)carbamoyl)-6,7-dihydro-5H-pyrazolo[5,1-b][1,3]oxazine-3-sulfonimidamide and (S)—N'-((1,2,3,5,6,7-hexahydro-s-indacen-4-yl)carbamoyl)-6,7-dihydro-5H-pyrazolo[5,1-b][1,3]oxazine-3-sulfonimidamide (Example 13 and Example 14)

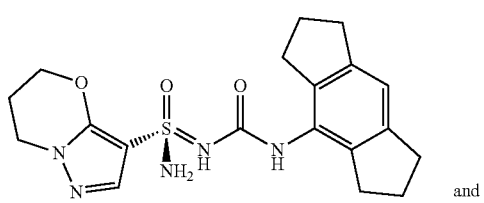

and

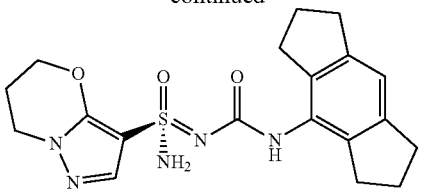

To a solution of the material collected from peak 1 (80 mg, 0.1 mmol) in DCM (5 mL) was added two drops of methane sulfonic acid. After being stirred at room temperature for 0.5 hour, the reaction solution was adjusted to pH=8 by sat. NaHCO$_3$, concentrated to dryness, and purified by reverse phase column (MeCN/H$_2$O) to give crude product. The crude product was further purified by prep-HPLC (NH$_3$—H$_2$O) to give (R)—N'-((1,2,3,5,6,7-hexahydro-s-indacen-4-yl)carbamoyl)-6,7-dihydro-5H-pyrazolo[5,1-b][1,3]oxazine-3-sulfonimidamide (2.2 mg, yield: 5%) as a white solid. Stereochemistry was arbitrarily assigned to each stereoisomer. $^1$H NMR (400 MHz, DMSO-d$_6$): δ=8.01 (s, 1H), 7.43 (s, 1H), 6.82 (s, 1H), 6.71 (brs, 1H), 4.35 (t, J=4.4 Hz, 2H), 4.08 (t, J=6.0 Hz, 2H), 2.77 (t, J=7.2 Hz, 4H), 2.67 (t, J=7.2 Hz, 4H), 2.17-2.15 (m, 2H), 1.96-1.89 (m, 4H). MS: m/z 402.1 (M+H$^+$).

To a solution of the material collected from peak 2 (80 mg, 0.1 mmol) in DCM (4 mL) was added two drops of methane sulfonic acid. After being stirred at room temperature for 0.5 hour, the reaction was adjusted to pH=8 with the addition of sat. NaHCO$_3$. The precipitate was collected by filtration and dried to give (S)—N'-((1,2,3,5,6,7-hexahydro-s-indacen-4-yl)carbamoyl)-6,7-dihydro-5H-pyrazolo[5,1-b][1,3]oxazine-3-sulfonimidamide (10 mg, yield: 23%) as a white solid. Stereochemistry was arbitrarily assigned to each stereoisomer. $^1$H NMR (400 MHz, DMSO-d$_6$): δ=8.17 (s, 1H), 7.50 (s, 1H), 7.21 (s, 2H), 6.85 (s, 1H), 4.41 (t, J=3.2 Hz, 2H), 4.10 (t, J=5.6 Hz, 2H), 2.77 (t, J=7.2 Hz, 4H), 2.67 (t, J=7.2 Hz, 4H), 2.19-2.15 (m, 2H), 1.96-1.89 (m, 4H). MS: m/z 402.1 (M+H$^+$).

Example 15

(6S)—N'-((4-fluoro-2,6-diisopropylphenyl)carbamoyl)-6-methoxy-6,7-dihydro-5H-pyrazolo[5,1-b][1,3]oxazine-3-sulfonimidamide

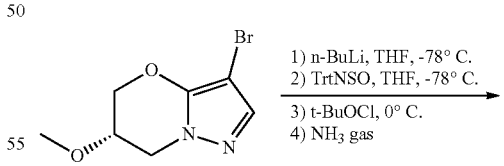

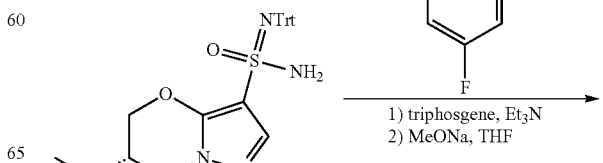

-continued

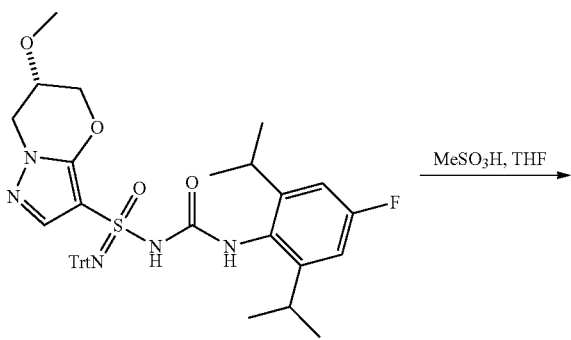

Step 1—Synthesis of (6S)-6-methoxy-N'-trityl-6,7-dihydro-5H-pyrazolo[5,1-b][1,3]oxazine-3-sulfonimidamide

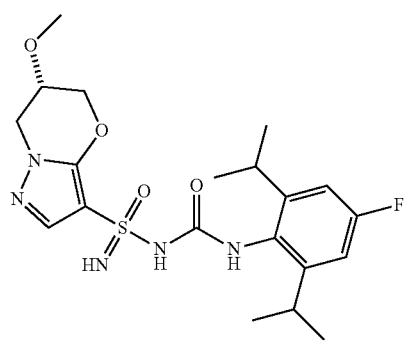

To a solution of (S)-3-bromo-6-methoxy-6,7-dihydro-5H-pyrazolo[5,1-b][1,3]oxazine (1.0 g, 4.3 mmol) in THF (10 mL) was added n-BuLi (1.8 mL, 4.3 mmol, 2.5 M in hexane) dropwise at −78° C. and the mixture was stirred at this temperature for 0.5 hour. A solution of TrtNSO (1.3 g, 4.3 mmol) in THF (5 mL) was added dropwise and the mixture was stirred at −78° C. for 30 minutes before being placed in an ice bath. After stirring for another 10 minutes, tert-butyl hypochlorite (480 mg, 4.5 mmol) was added and the mixture was stirred for 20 minutes. NH₃ gas was bubbled through the mixture for 10 minutes and the resulting solution was stirred for 16 hours at room temperature. The reaction mixture was concentrated to dryness and purified by reverse phase column (MeCN/H₂O) to give (6S)-6-methoxy-N'-trityl-6,7-dihydro-5H-pyrazolo[5,1-b][1,3]oxazine-3-sulfonimidamide (400 mg, yield: 20%) as a yellow solid.

Step 2—Synthesis of (6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide

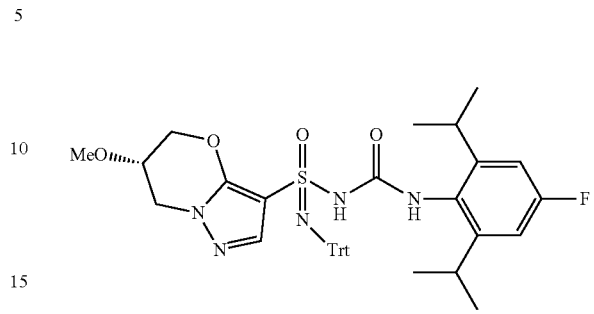

To a solution of (6S)-6-methoxy-N'-trityl-6,7-dihydro-5H-pyrazolo[5,1-b][1,3]oxazine-3-sulfonimidamide (100 mg, 0.2 mmol) in THF (2 mL) was added MeONa (13 mg, 0.2 mmol). The reaction mixture was stirred at room temperature for 20 mins to give a sodium salt suspension.

In another flask, to a solution of 4-fluoro-2,6-diisopropylaniline (49 mg, 0.3 mmol) in THF (3 mL) was added triethylamine (75 mg, 0.8 mmol) and triphosgene (29 mg, 0.1 mmol) in one portion at 0° C. After being stirred at room temperature for 10 minutes under N₂, the reaction mixture was filtered. The filtrate was added to the sodium salt suspension above. The new reaction mixture was stirred at room temperature for 16 hours, then concentrated and purified by reverse phase column (MeCN/H₂O) to give (6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide (49 mg, 33%) as a yellow solid. MS: m/z 696.4 (M+H⁺).

Step 3—Synthesis of (6S)—N'-((4-fluoro-2,6-diisopropylphenyl)carbamoyl)-6-methoxy-6,7-dihydro-5H-pyrazolo[5,1-b][1,3]oxazine-3-sulfonimidamide (Example 15)

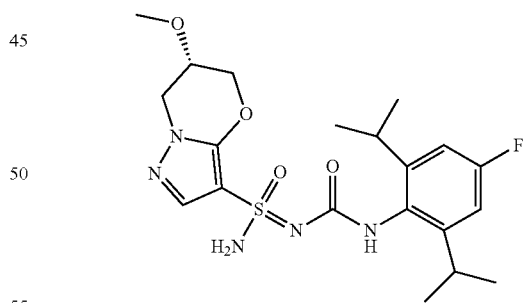

To a solution of (6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide (80 mg, 0.1 mmol) in THF (1.5 mL) was added MeSO₃H (6 drops) at 0° C. After being stirred at this temperature for 0.5 hour, the reaction mixture was concentrated and purified by reverse phase column (MeCN/H₂O) to give (6S)—N-((4-fluoro-2,6-diisopropylphenyl)carbamoyl)-6-methoxy-6,7-dihydro-5H-pyrazolo[5,1-b][1,3]oxazine-3-sulfonimidamide (32 mg, 59%, mixture of diastereomers) as a white solid. ¹H NMR (400 MHz, DMSO-d₆): δ=7.99 (s, 1H), 7.52-7.49 (m, 1H), 7.13 (brs, 2H), 6.88 (s, 1H), 6.85 (s, 1H), 4.64-4.50 (m, 1H), 4.31-4.14 (m, 3H), 4.04 (s, 1H), 3.37 (overlap, 3H), 3.20-3.06 (m, 2H), 1.15-1.02 (m, 12H). MS: m/z 454.1 (M+H$^+$).

Example 16

(6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide

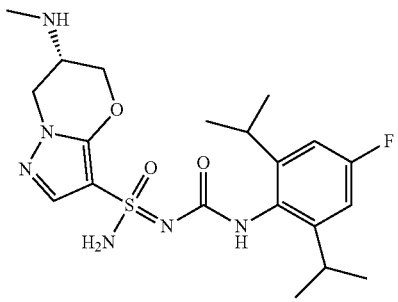 [SMILES: CN[C@@H]1COc2c(S(N)(=O)=NC(=O)Nc3c(C(C)C)cc(F)cc3C(C)C)cnn2C1]

The title compound was prepared using the general procedure of (6S)—N-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide to yield a mixture of stereoisomers. (6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide was prepared as a mixture of diastereomers using the general procedure described for the preparation of (6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 17), by replacing 4-isocyanato-1,2,3,5,6,7-hexahydro-s-indacene with 5-fluoro-2-isocyanato-1,3-diisopropylbenzene in Step 2. $^1$H NMR (400 MHz, DMSO-d$_6$): δ=8.03 (d, J=10.0 Hz, 1H), 7.50 (s, 1H), 7.23 (brs, 2H), 6.86 (s, 1H), 6.84 (s, 1H), 4.40-4.19 (m, 3H), 3.92-3.90 (m, 1H), 3.15-3.10 (m, 3H), 2.33 (s, 3H), 1.07 (s, 12H). MS: m/z 453.2 (M+H$^+$).

Example 17

(6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

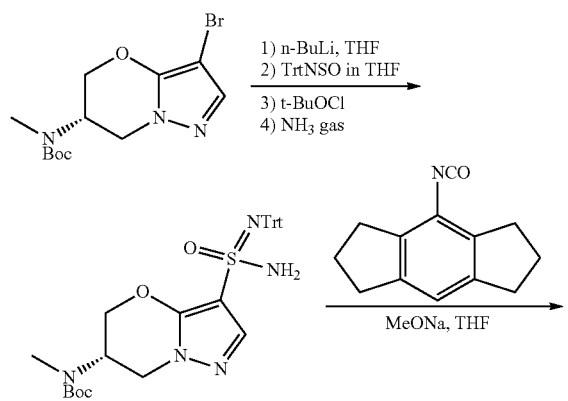

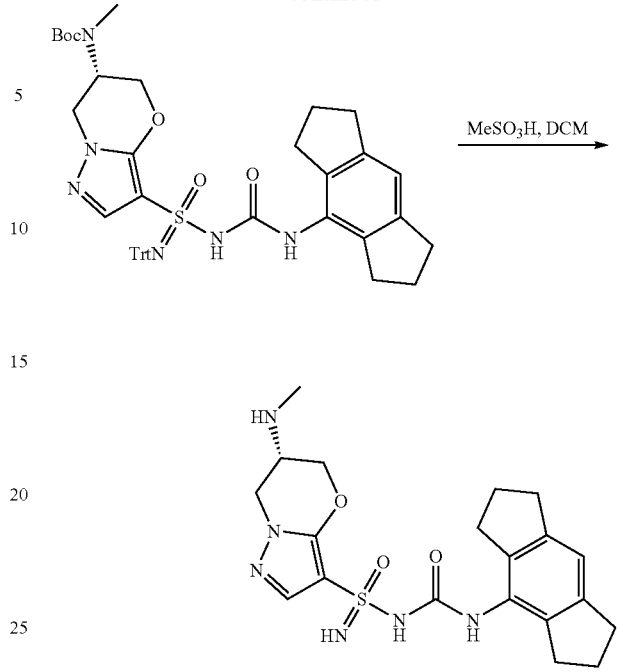

Step 1—Synthesis of tert-butyl methyl((6S)-3-(N'-tritylsulfamidimidoyl)-6,7-dihydro-5H-pyrazolo[5,1-b][1,3]oxazin-6-yl)carbamate

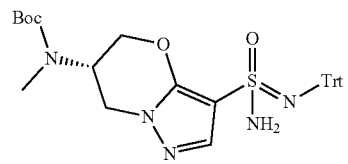

To a solution of (S)-tert-butyl (3-bromo-6,7-dihydro-5H-pyrazolo[5,1-b][1,3]oxazin-6-yl)(methyl)carbamate (570 mg, 1.7 mmol) in THF (15 mL) was added n-BuLi (0.8 mL, 1.9 mmol, 2.5 M in hexanes) dropwise at −78° C. and the mixture stirred at this temperature for 1 hour. A solution of TrNSO (573 mg, 1.9 mmol) in THF (5 mL) was added dropwise and the mixture was stirred at −78° C. for 20 minutes before being placed in an ice bath. After stirring for another 10 minutes, tert-butyl hypochlorite (206 mg, 1.9 mmol) was added and the mixture was stirred for 20 minutes. NH$_3$ gas was bubbled through the mixture for 5 minutes and the resulting solution was stirred for 16 hours at room temperature. The reaction mixture was concentrated to dryness and purified by reverse phase column (MeCN/H$_2$O) to give tert-butyl methyl((6S)-3-(N'-tritylsulfamimidoyl)-6,7-dihydro-5H-pyrazolo[5,1-b][1,3]oxazin-6-yl)carbamate (420 mg, yield: 43%) as a yellow solid. MS: m/z 574.5 (M+H$^+$).

Step 2—Synthesis of tert-butyl ((6S)-3-(N'-((1,2,3,5,6,7-hexahydro-s-indacen-4-yl)carbamoyl)-N'-tritylsulfamidimidoyl)-6,7-dihydro-5H-pyrazolo[5,1-b][1,3]oxazin-6-yl)(methyl)carbamate

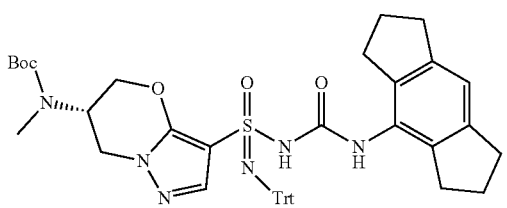

To a solution of tert-butyl methyl((6S)-3-(N'-tritylsulfamimidoyl)-6,7-dihydro-5H-pyrazolo[5,1-b][1,3]oxazin-6-yl)carbamate (200 mg, 0.3 mmol) in THF (10 mL) was added MeONa (21 mg, 0.4 mmol) and the mixture was stirred for 30 minutes at room temperature. Then 4-isocyanato-1,2,3,5,6,7-hexahydro-s-indacene (375 mg, 1.7 mmol) was added. After being stirred for 16 hours at room temperature, the mixture was concentrated to dryness and purified by reverse phase column (MeCN/H$_2$O) to give tert-butyl ((6S)-3-(N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate (110 mg, yield: 42%) as a white solid.

Step 3—Synthesis of (6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide Example 17

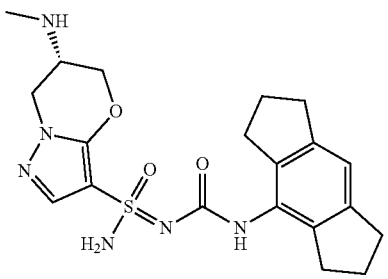 [SMILES: CN[C@@H]1COc2c(S(N)(=O)=NC(=O)Nc3c4c(cc5c3CCC5)CCC4)cnn2C1]

To a solution of (((6S)-3-(N-((1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate (110 mg, 0.1 mmol) in DCM (5 mL) was added two drops of methanesulfonic acid. After being stirred for 0.5 hour at room temperature, the reaction solution was adjusted to pH=8 by sat. NaHCO$_4$. The mixture was concentrated to dryness and purified by reverse phase column (MeCN/H$_2$O) to give the crude product. The crude product was further purified by prep-HPLC (NH$_4$HCO$_3$) to give ((6S)—N-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (3.8 mg, yield: 6%, mixture of diatereoisomers) as a white solid. $^1$H NMR (400 MHz, DMSO-d$_6$): δ=8.18 (brs, 1H), 7.51 (d, J=5.2 Hz, 1H), 7.24 (brs, 2H), 6.86 (s, 1H), 4.30-4.20 (m, 3H), 3.94 (d, J=12.8 Hz, 1H), 3.15-3.14 (m, 1H), 2.79 (t, J=7.2 Hz, 4H), 2.70 (t, J=7.2 Hz, 4H), 2.33 (d, J=2.0 Hz, 3H) 1.96-1.83 (m, 4H). MS: m/z 431.2 (M+H$^+$). Example 18

Example 18

(6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

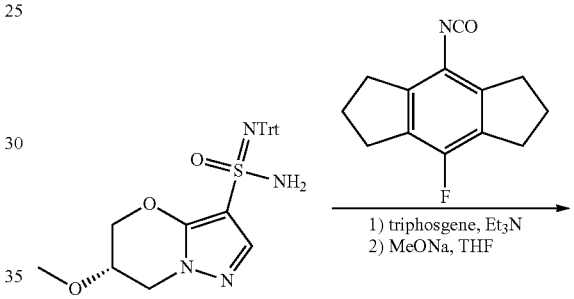

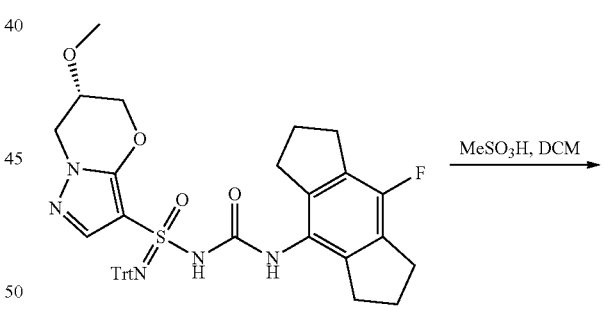

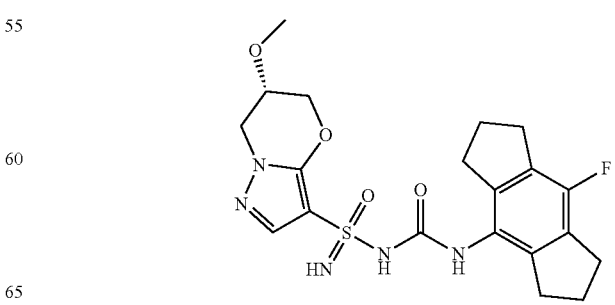

Step 1—Synthesis of (6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

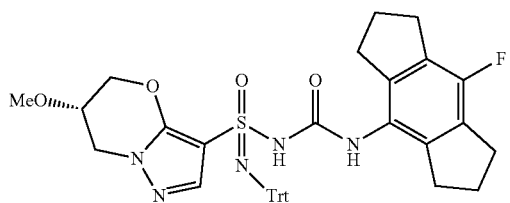

To a solution of (6S)-6-methoxy-N'-trityl-6,7-dihydro-5H-pyrazolo[5,1-b][1,3]oxazine-3-sulfonimidamide (83 mg, 0.2 mmol) in THF (3 mL) was added MeONa (28 mg, 0.5 mmol). The reaction mixture was stirred at 45° C. for 20 minutes to give a sodium salt suspension.

In another flask, to a solution of 8-fluoro-1,2,3,5,6,7-hexahydro-s-indacen-4-amine (191 mg, 1.0 mmol) in THF (5 mL) was added Et₃N (0.2 mL, 1.1 mmol) and triphosgene (100 mg, 0.4 mmol) in one portion with ice-bath. The reaction mixture was stirred at 70° C. for 1 hour under N₂. The reaction mixture was filtered and the filtrate was added to the sodium salt suspension above. The new reaction mixture was stirred at room temperature for 16 hrs and concentrated to give (6S)—N'-(tert-butyldimethylsilyl)-N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (crude) which was used directly for the next step. MS: m/z 692.4 (M+H⁺).

Step 2—Synthesis of (6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 18)

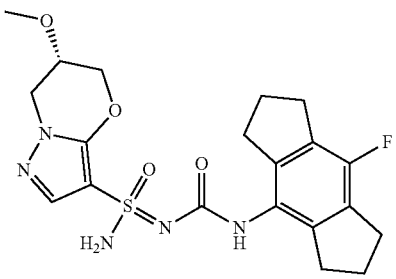 [SMILES: CO[C@@H]1COc2c(S(N)(=O)=NC(=O)Nc3c4c(c(F)c5c3CCC5)CCC4)cnn2C1]

To a solution of (6S)—N'-(tert-butyldimethylsilyl)-N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (crude) in DCM (2 mL) was added MeSO₃H (0.05 mL, 0.88 mmol) at 0° C. After being stirred at this temperature for 5 minutes, the reaction solution was adjusted to pH=8 with sat. NaHCO₃. The resulting mixture was concentrated, diluted with MeCN (3 mL) and filtered. The filtrate was purified by prep-HPLC to give (6S)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (3 mg, yield: 2%, mixture of diastereoisomers) as a white solid. ¹H NMR (400 MHz, DMSO-d₆): δ=8.23 (brs, 1H), 7.53 (s, 1H), 7.23 (brs, 1H), 4.59 (d, J=12.0 Hz, 1H), 4.31-4.17 (m, 3H), 4.03 (s, 1H), 3.36 (overlap, 3H), 2.80 (t, J=6.4 Hz, 4H), 2.72 (t, J=6.0 Hz, 4H), 2.02-1.97 (m, 4H); MS: m/z 450.1 (M+H⁺).

Example 19 and Example 20 (S,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide

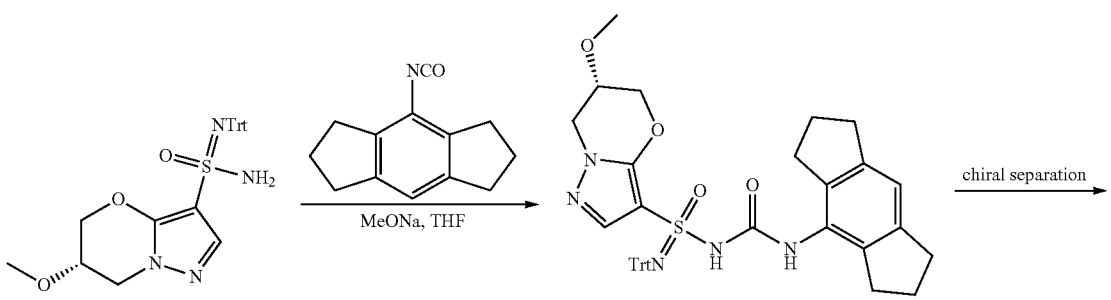

255 256

-continued

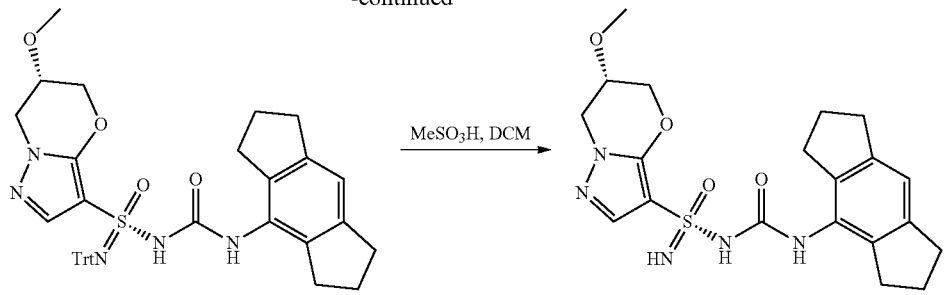

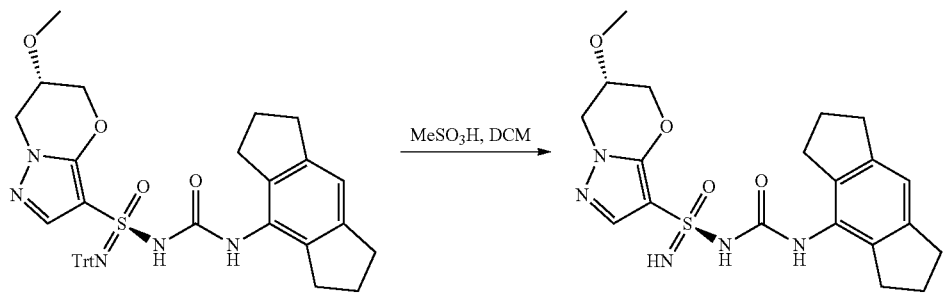

Step 1—Synthesis of (6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide Step 2—(S,6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

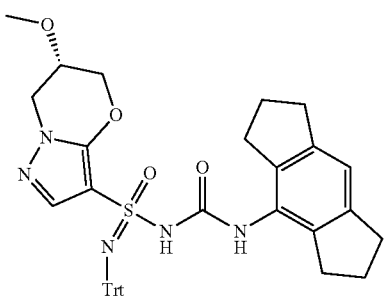

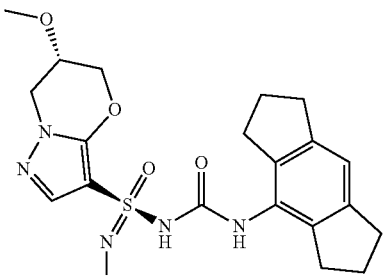

and

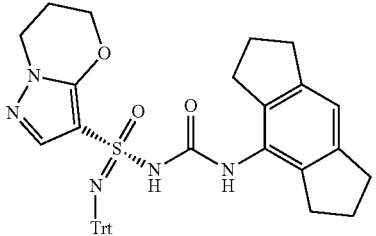

To a solution of (6S)-6-methoxy-N'-trityl-6,7-dihydro-5H-pyrazolo[5,1-b][1,3]oxazine-3-sulfonimidamide (200 mg, 0.4 mmol) in THF (3 mL) at was added MeONa (25 mg, 0.5 mmol) and the mixture was stirred at room temperature for 20 minutes. Then 4-isocyanato-1,2,3,5,6,7-hexahydro-s-indacene (75 mg, 0.4 mmol) was added. The resulting mixture was stirred at room temperature for 16 hours, concentrated and purified by reverse phase column (MeCN/H$_2$O) to give (6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (240 mg, yield: 85%) as a yellow solid. MS: m/z 674.5 (M+H$^+$).

(S,6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (R,6S)—N-((1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide: (6S)—N-((1,2,3,5,6,7-hexahydro-s- indacen-4-yl)carbamoyl)-6-methoxy-N'-trityl-6,7-dihydro-5H-pyrazolo[5,1-b][1,3]oxazine-3-sulfonimidamide (460 mg, 0.7 mmol) was separated by chiral prep-HPLC to give two isomers (peak 1, 200 mg; peak 2, 227 mg), with unknown absolute stereochemistry, as yellow solids. MS: m/z 674.4 (M+H$^+$).

Step 3—Synthesis of (S,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 19 and Example 20)

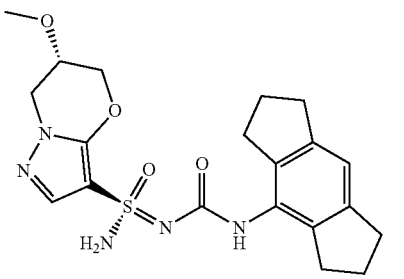

and

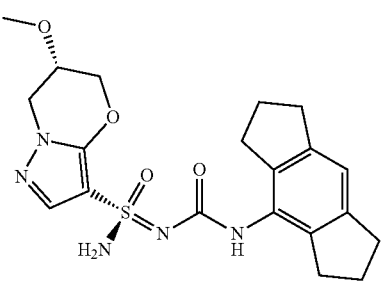

To a solution of the material from peak 1 above (100 mg, 0.2 mmol) in THF (2 mL) was added MeSO$_3$H at 0° C. After being stirred at this temperature for 0.5 hour, the reaction mixture was adjusted to pH=8 by sat. NaHCO$_3$. The precipitate was collected by filtration, washed by water (2 mL), THF (2 mL) and dried to give (S,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (27 mg, yield: 42%) as a white solid. Stereochemistry was arbitrarily assigned to each stereoisomer. $^1$H NMR (400 MHz, DMSO-d$_6$): δ=8.19 (s, 1H), 7.54 (s, 1H), 7.29 (s, 2H), 6.86 (s, 1H), 4.59 (d, J=12 Hz, 1H), 4.35-4.15 (m, 3H), 4.03 (s, 1H), 3.40 (s, 3H), 2.77 (t, J=6.8 Hz, 4H), 2.69 (t, J=6.4 Hz, 4H), 2.01-1.88 (m, 4H). MS: m/z 432.2 (M+H$^+$).

The material from peak 2 was deprotected and isolated in the same manner to yield a white solid. (R,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide. Stereochemistry was arbitrarily assigned to each stereoisomer. $^1$H NMR (400 MHz, DMSO-d$_6$): δ=8.16 (s, 1H), 7.51 (s, 1H), 7.18 (s, 2H), 6.85 (s, 1H), 4.59 (d, J=11.6 Hz, 1H), 4.31-4.15 (m, 3H), 4.03 (s, 1H), 3.36 (s, 3H), 2.77 (t, J=7.2 Hz, 4H), 2.69 (t, J=7.2 Hz, 4H), 1.98-1.88 (m, 4H). MS: m/z 432.2 (M+H$^+$).

Example 21 and Example 22

(S)—N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide and (R)—N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide

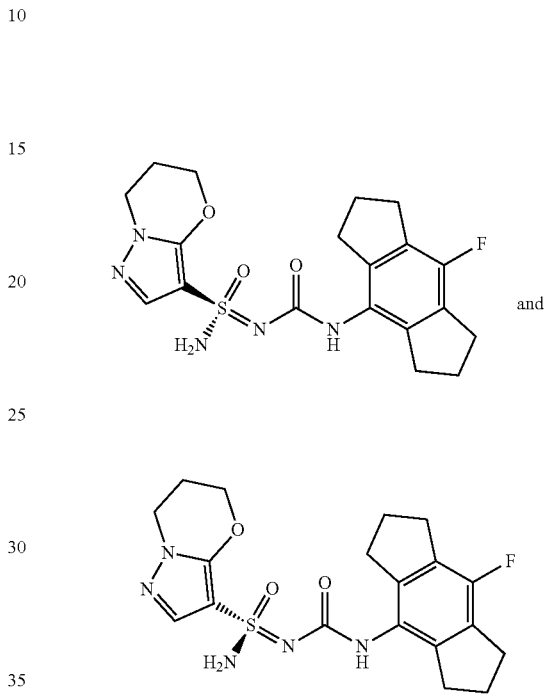

The title compounds were prepared using the general procedure of (S)—N-((1,2,3,5,6,7-hexahydro-s-indacen-4-yl)carbamoyl)-6,7-dihydro-5H-pyrazolo[5,1-b][1,3]oxazine-3-sulfonimidamide to yield a mixture of stereoisomers. (S)—N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide and (R)—N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide were prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]oxazine-3-sulfonimidamide and (R)—N'-((1,2,3,5,6,7-hexahydro-s-indacen-4-yl)carbamoyl)-6,7-dihydro-5H-pyrazolo[5,1-b][1,3]oxazine-3-sulfonimidamide (Example 13 and Example 14) by replacing 4-isocyanato-1,2,3,5,6,7-hexahydro-s-indacene with 4-fluoro-8-isocyanato-1,2,3,5,6,7-hexahydro-s-indacene in Step 2. Two isomers with unknown absolute stereochemistry were isolated after chiral prep-HPLC purification.

Peak 1: $^1$H NMR (400 MHz, DMSO-d$_6$): δ=8.03 (brs, 1H), 7.45 (s, 1H), 6.86 (brs, 2H), 4.36 (t, J=3.6 Hz, 2H), 4.10 (t, J=6.0 Hz, 2H), 2.82 (t, J=7.2 Hz, 4H), 2.72 (t, J=7.2 Hz, 4H), 2.20-2.15 (m, 2H), 2.01-1.96 (m, 4H). MS: m/z 420.1 (M+H$^+$). Compound 22

Peak 2: $^1$H NMR (400 MHz, DMSO-d$_6$): δ=8.20 (brs, 1H), 7.50 (s, 1H), 7.23 (s, 2H), 4.40-4.35 (m, 2H), 4.10 (t, J=6.0 Hz, 2H), 2.82 (t, J=7.2 Hz, 4H), 2.72 (t, J=7.2 Hz, 4H), 2.21-2.17 (m, 2H), 2.01-1.96 (m, 4H). MS: m/z 420.1 (M+H$^+$). Compound 21

Example 23 and Example 24
(S,6S)—N'-((4-fluoro-2,6-diisopropylphenyl)carbamoyl)-6-methoxy-6,7-dihydro-5H-pyrazolo[5,1-b][1,3]oxazine-3-sulfonimidamide and (R,6S)—N'-((4-fluoro-2,6-diisopropylphenyl)carbamoyl)-6-methoxy-6,7-dihydro-5H-pyrazolo[5,1-b][1,3]oxazine-3-sulfonimidamide
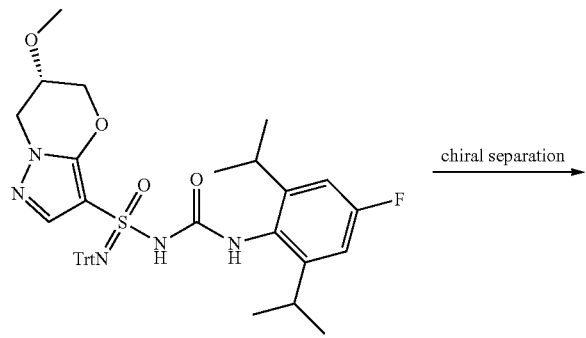
chiral separation
+
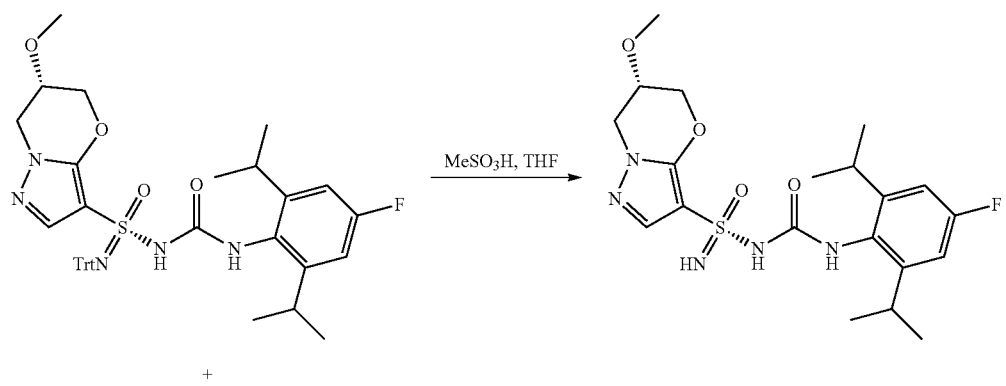
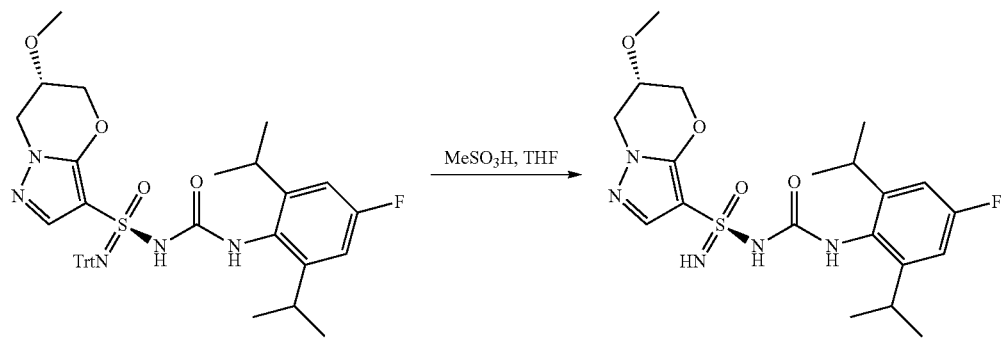

Step 1—(S,6S)—N-((4-fluoro-2,6-diisopropylphenyl) carbamoyl)-6-methoxy-N'-trityl-6,7-dihydro-5H-pyrazolo[5,1-b][1,3]oxazine-3-sulfonimidamide and (R,6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide Step 2—Synthesis of (S,6S)—N'-((4-fluoro-2,6-diisopropylphenyl)carbamoyl)-6-methoxy-6,7-dihydro-5H-pyrazolo[5,1-b][1,3]oxazine-3-sulfonimidamide and (R,6S)—N'-((4-fluoro-2,6-diisopropylphenyl)carbamoyl)-6-methoxy-6,7-dihydro-5H-pyrazolo[5,1-b][1,3]oxazine-3-sulfonimidamide (Example 23 and Example 24)

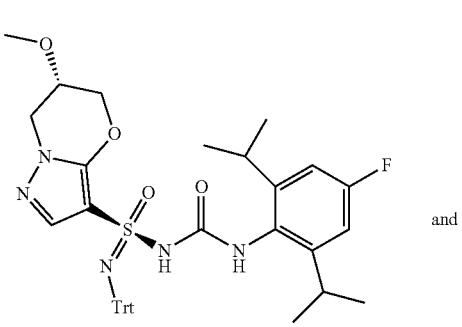

and

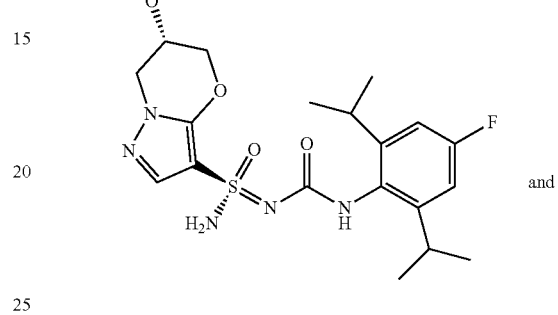

and

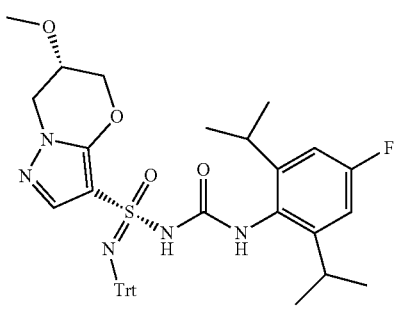

(6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide (280 mg, 0.4 mmol) was separated by chiral prep-HPLC to give two isomers (peak 1, 135 mg; peak 2, 80 mg), of unknown absolute stereochemistry, as yellow solids; (S,6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide and (R,6S)—N-((4-fluoro-2,6-diisopropylphenyl)carbamoyl)-6-methoxy-N'-trityl-6,7-dihydro-5H-pyrazolo[5,1-b][1,3]oxazine-3-sulfonimidamide.

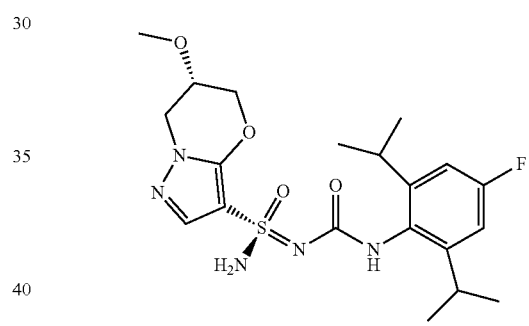

To a solution of the material collected from peak 1 above, (135 mg, 0.2 mmol) in THF (2 mL) was added MeSO$_3$H (6 drops) at 0° C. After being stirred at this temperature for 0.5 hour, the reaction mixture was concentrated and purified by reverse phase column (MeCN/H$_2$O) to give (S,6S)—N'-((4-fluoro-2,6-diisopropylphenyl)carbamoyl)-6-methoxy-6,7-dihydro-5H-pyrazolo[5,1-b][1,3]oxazine-3-sulfonimidamide (40 mg, yield: 46%) as a white solid. Stereochemistry was arbitrarily assigned to each stereoisomer. $^1$H NMR (400 MHz, DMSO-d$_6$): δ=8.01 (s, 1H), 7.52 (m, 1H), 7.33 (s, 2H), 6.86 (s, 1H), 6.84 (s, 1H), 4.60-4.56 (m, 1H), 4.33-4.18 (m, 3H), 4.04 (s, 1H), 3.36 (s, 3H), 3.20-3.06 (m, 2H), 1.17-1.02 (m, 12H). MS: m/z 454.2 (M+H$^+$).

The same was done for peak 2 to yield a white solid. The material from peak 2 was deprotected and isolated in the same manner to deliver (R,6S)—N'-((4-fluoro-2,6-diisopropylphenyl)carbamoyl)-6-methoxy-6,7-dihydro-5H-pyrazolo[5,1-b][1,3]oxazine-3-sulfonimidamide as a white solid. Stereochemistry was arbitrarily assigned to each stereoisomer. $^1$H NMR (400 MHz, DMSO-d$_6$): δ=8.02 (s, 1H), 7.50 (s, 1H), 7.28 (s, 2H), 6.87 (s, 1H), 6.84 (s, 1H), 4.60-4.56 (m, 1H), 4.33-4.18 (m, 3H), 4.04 (s, 1H), 3.36 (s, 3H), 3.20-3.06 (m, 2H), 1.17-1.02 (m, 12H). MS: m/z 454.2 (M+H$^+$).

Example 25 and Example 26

(R,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

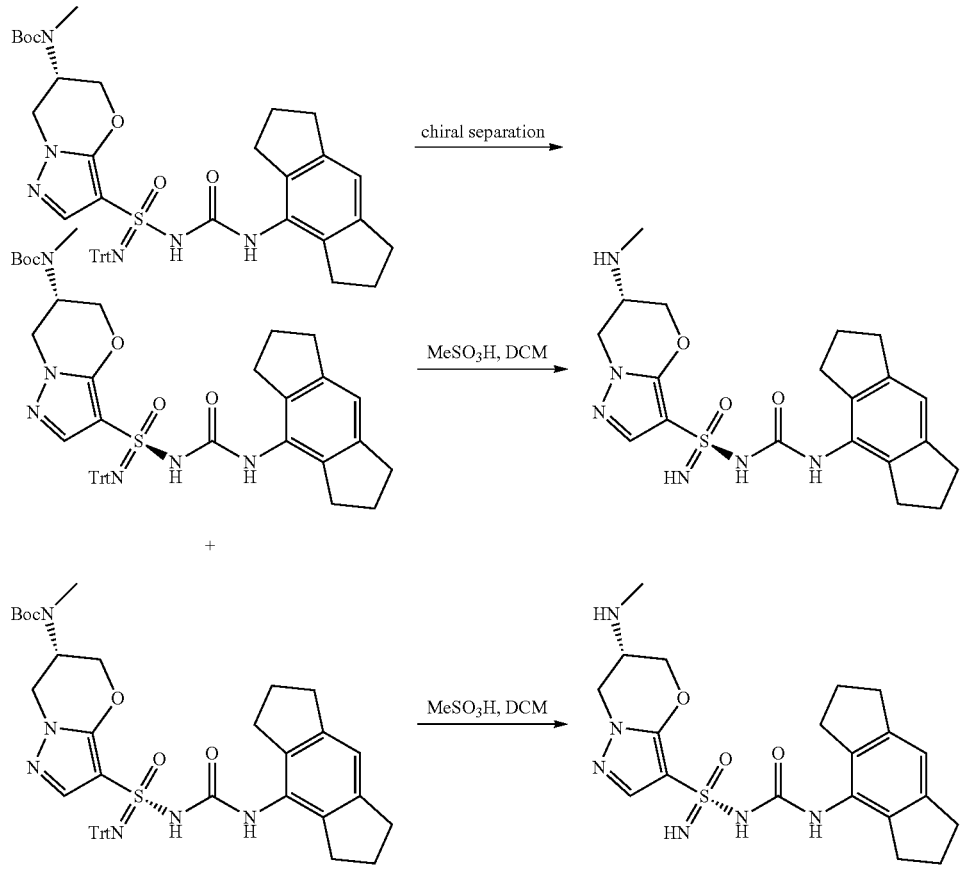

Step 1—tert-butyl ((S)-3-((R)—N-((1,2,3,5,6,7-hexahydro-s-indacen-4-yl)carbamoyl)-N'-tritylsulfamidimidoyl)-6,7-dihydro-5H-pyrazolo[5,1-b][1,3]oxazin-6-yl)(methyl)carbamate and tert-butyl ((S)-3-((S)—N-((1,2,3,5,6,7-hexahydro-s-indacen-4-yl)carbamoyl)-N'-tritylsulfamidimidoyl)-6,7-dihydro-5H-pyrazolo[5,1-b][1,3]oxazin-6-yl)(methyl)carbamate

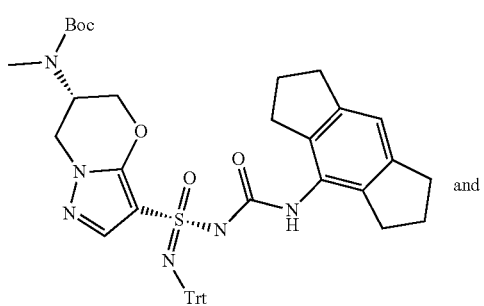

and

-continued

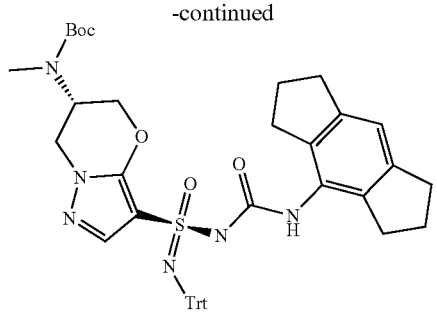

tert-butyl ((S)-3-((R)—N-((1,2,3,5,6,7-hexahydro-s-indacen-4-yl)carbamoyl)-N-tritylsulfamidimidoyl)-6,7-dihydro-5H-pyrazolo[5,1-b][1,3]oxazin-6-yl)(methyl)carbamate and tert-butyl ((S)-3-((S)—N-((1,2,3,5,6,7-hexahydro-s-indacen-4-yl)carbamoyl)-N'-tritylsulfamidimidoyl)-6,7-dihydro-5H-pyrazolo[5,1-b][1,3]oxazin-6-yl)(methyl)carbamate: tert-butyl ((6S)-3-(N-((1,2,3,5,6,7-hexahydro-s-indacen-4-yl)carbamoyl)-N'-tritylsulfamidimidoyl)-6,7-dihydro-5H-pyrazolo[5,1-b][1,3]oxazin-6-yl)(methyl)carbamate (1.0 g, 1.3 mmol) was separated by chiral prep-HPLC to give two isomers of unknown absolute stereochemistry as white solids (peak 1, 410 mg, yield: 41%; peak 2,450 mg, yield: 45%).

Step 2—Synthesis of (R,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 25 and Example 26)

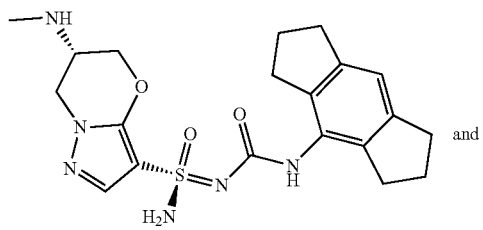

and

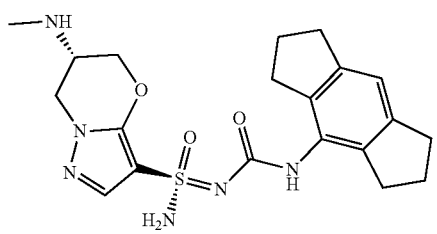

Methanesulfonic acid 3 drops) was added To a solution of the material from peak 1 above (200 mg, 0.3 mmol) in DCM (3 mL) was added three drops of methanesulfonic acid. After being stirred for 0.5 hour at room temperature, the reaction solution was adjusted to pH=8 by sat. NaHCO$_3$. The precipitate was collected by filtration and dried to give (R,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (17.0 mg, yield: 15%) as a white solid. Stereochemistry was arbitrarily assigned to each stereoisomer. $^1$H NMR (400 MHz, DMSO-d$_6$): δ=8.21 (brs, 1H), 7.51 (s, 1H), 7.26 (brs, 2H), 6.86 (s, 1H), 4.36-4.20 (m, 3H), 3.95-3.91 (m, 1H), 3.16-3.15 (m, 1H), 2.77 (t, J=6.8 Hz, 4H), 2.68 (t, J=6.8 Hz, 4H), 2.33 (s, 3H), 2.15 (brs, 1H), 1.96-1.89 (m, 4H). MS: m/z 431.1 (M+H$^+$).

The material from peak 2 above was deprotected and isolated in the same manner to yield a white solid. (S,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide. Stereochemistry was arbitrarily assigned to each stereoisomer. $^1$H NMR (400 MHz, DMSO-d$_6$): δ=8.16 (brs, 1H), 7.51 (s, 1H), 7.23 (brs, 2H), 6.86 (s, 1H), 4.36-4.20 (m, 3H), 3.95-3.91 (m, 1H), 3.16-3.14 (m, 1H), 2.77 (t, J=7.2 Hz, 4H), 2.69 (t, J=6.8 Hz, 4H), 2.33 (s, 3H), 2.07 (brs, 1H), 1.98-1.89 (m, 4H). MS: m/z 431.1 (M+H$^+$).

Example 27 and Example 28

(R,6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide and (S,6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide

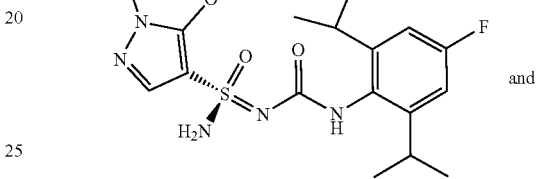

and

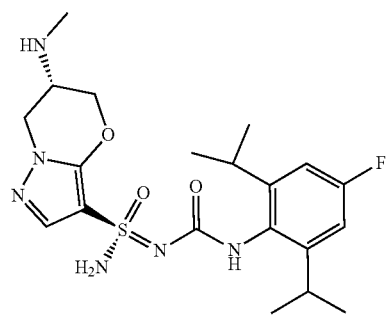

(R,6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide and (S,6S)—N'-((4-fluoro-2,6-diisopropylphenyl)carbamoyl)-6-(methylamino)-6,7-dihydro-5H-pyrazolo[5,1-b][1,3]oxazine-3-sulfonimidamide were prepared using the general procedure described for the preparation of (R,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 25 and Example 26). After chiral prep-HPLC two isomers of unknown absolute stereochemistry were isolated as white solids.

Peak 1: $^1$H NMR (400 MHz, DMSO-d$_6$): δ=7.99 (s, 1H), 7.48 (s, 1H), 7.23 (brs, 2H), 6.86 (s, 1H), 6.84 (s, 1H), 4.33-4.19 (m, 3H), 3.92-3.89 (m, 1H), 3.15-3.10 (m, 3H), 2.13 (s, 3H), 2.06 (brs, 1H), 1.07 (s, 12H). MS: m/z 453.2 (M+H$^+$).

Peak 2: $^1$H NMR (400 MHz, DMSO-d$_6$): δ=8.03 (s, 1H), 7.50 (s, 1H), 7.23 (s, 2H), 6.86 (s, 1H), 6.84 (s, 1H), 4.36-4.19 (m, 3H), 3.93-3.86 (m, 1H), 3.11-3.08 (m, 3H), 2.34 (s, 3H), 2.32 (s, 1H), 0.99 (s, 12H). MS: m/z 453.2 (M+H$^+$).

Example 29

N'-((8-fluoro-1,2,3,5,6,7-hexahydro-s-indacen-4-yl)carbamoyl)-2,3-dihydropyrazolo[5,1-b]oxazole-7-sulfonimidamide

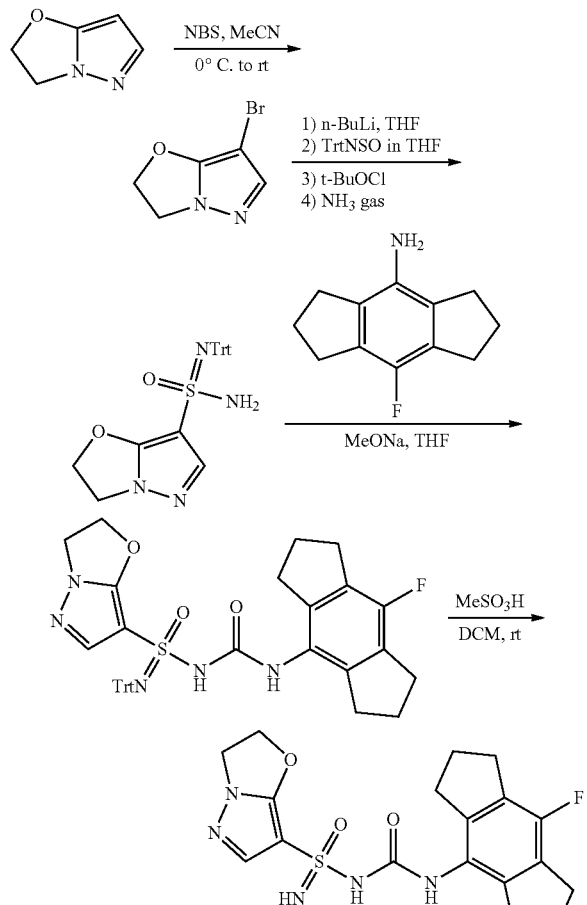

Step 1—Synthesis of 7-bromo-2,3-dihydropyrazolo[5,1-b]oxazole

NBS (3.9 g, 21.8 mmol) was added portion wise to a solution of 2,3-dihydropyrazolo[5,1-b]oxazole (2.0 g, 18.2 mmol) in MeCN (40 mL) at 0° C. and the reaction mixture was stirred for 2 hours at room temperature. The mixture was filtered and the filtrate was purified by reverse phase column (MeCN/H$_2$O) to give 3 7-bromo-2,3-dihydropyrazolo[5,1-b]oxazole (2.4 g, yield: 71%) as a white solid.

$^1$H NMR (400 MHz, CDCl$_3$): δ=7.30 (s, 1H), 5.12 (t, J=8.0 Hz, 2H), 4.35 (t, J=8.0 Hz, 2H).

Steps 2~4—Synthesis of N'-((8-fluoro-1,2,3,5,6,7-hexahydro-s-indacen-4-yl)carbamoyl)-2,3-dihydropyrazolo[5,1-b]oxazole-7-sulfonimidamide (Example 29)

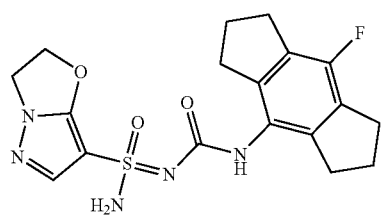 [SMILES: NS(=O)(=NC(=O)Nc1c2c(c(F)c3c1CCC3)CCC2)c1cnn2c1OCC2]

These three steps were similar to the general procedure of (6S)—N-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide to yield the title compound as a white solid.

N'-((8-fluoro-1,2,3,5,6,7-hexahydro-s-indacen-4-yl)carbamoyl)-2,3-dihydropyrazolo[5,1-b]oxazole-7-sulfonimidamide was prepared as a mixture of enantiomers using the general procedure described for the preparation of (6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 17) by replacing (S)-tert-butyl (3-bromo-6,7-dihydro-5H-pyrazolo[5,1-b][1,3]oxazin-6-yl)(methyl)carbamate with 7-bromo-2,3-dihydropyrazolo[5,1-b]oxazole in Step 1. $^1$H NMR (400 MHz, DMSO-d$_6$): δ=8.06 (brs, H), 7.50 (s, 1H), 7.01 (brs, 2H), 5.17 (t, J=8.4 Hz, 2H), 4.31 (t, J=8.4 Hz, 2H), 2.80 (t, J=7.2 Hz, 4H), 2.72 (t, J=7.2 Hz, 4H), 1.96-1.89 (m, 4H). MS: m/z 406.1 (M+H$^+$).

Example 30

N'-((8-fluoro-1,2,3,5,6,7-hexahydro-s-indacen-4-yl)carbamoyl)-5,6,7,8-tetrahydropyrazolo[5,1-b][1,3]oxazepine-3-sulfonimidamide

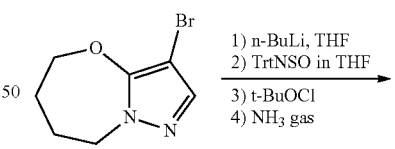

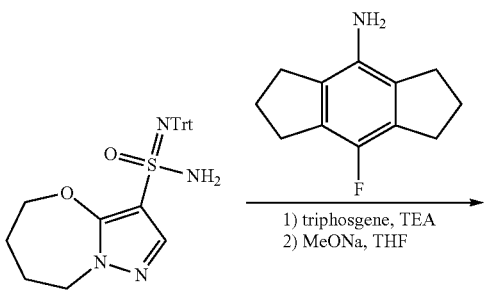

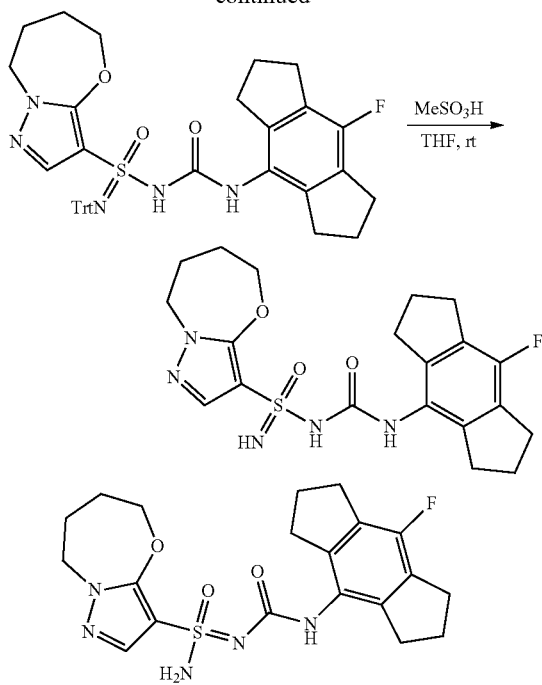

The title compound was prepared using general procedure of (R,6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide to yield a mixture of stereoisomers. N'-((8-fluoro-1,2,3,5,6,7-hexahydro-s-indacen-4-yl)carbamoyl)-5,6,7,8-tetrahydropyrazolo[5,1-b][1,3]oxazepine-3-sulfonimidamide was prepared as a mixture of enantiomers using the general procedure described for the preparation of (6S)—N'-((1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 17) by replacing (S)-tert-butyl (3-bromo-6,7-dihydro-5H-pyrazolo[5,1-b][1,3]oxazin-6-yl)(methyl)carbamate with 3-bromo-5,6,7,8-tetrahydropyrazolo[5,1-b][1,3]oxazepine in Step 1. $^1$H NMR (400 MHz, DMSO-d$_6$): δ=8.08 (brs, 1H), 7.43 (s, 1H), 6.91 (brs, 2H), 4.15 (t, J=5.2 Hz, 2H), 4.10 (t, J=4.8 Hz, 2H), 2.80 (t, J=7.2 Hz, 4H), 2.71 (t, J=7.2 Hz, 4H), 2.03-1.93 (m, 6H), 1.78-1.71 (m, 2H). MS: m/z 434.1 (M+H$^+$).

Example 31 and Example 32

(R,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide

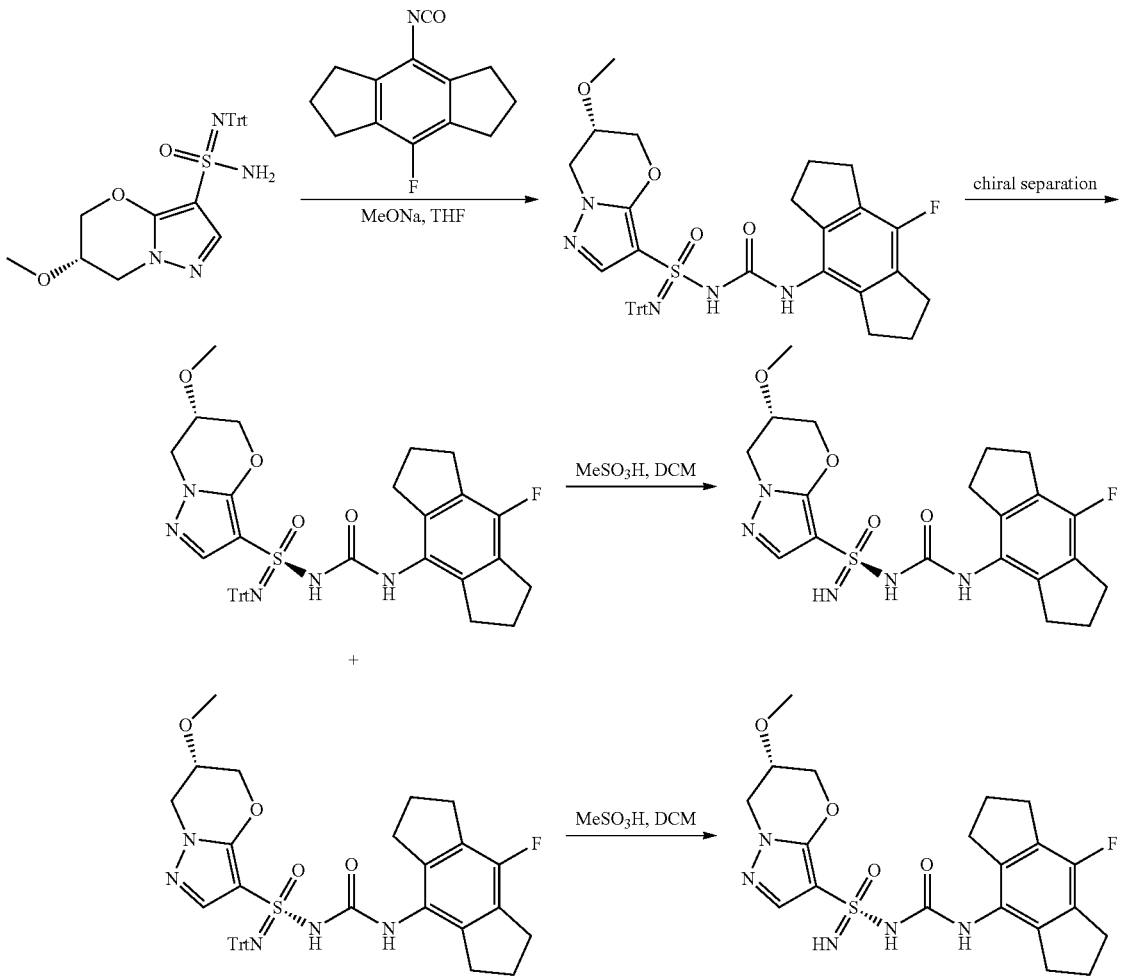

Step 1—Synthesis of (6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

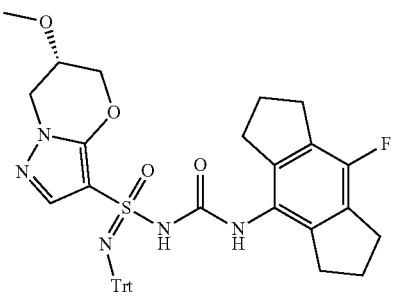

To a solution of (6S)-6-methoxy-N'-trityl-6,7-dihydro-5H-pyrazolo[5,1-b][1,3]oxazine-3-sulfonimidamide (720 mg, 1.5 mmol) in THF (15 mL) was added MeONa (81 mg, 1.5 mmol). The reaction mixture was stirred at 45° C. for 20 mins to give a sodium salt suspension.

Then a solution of 4-fluoro-8-isocyanato-1,2,3,5,6,7-hexahydro-s-indacene (crude, ~1.5 mmol) in THF (15 mL) was added to the sodium salt suspension above. The new reaction mixture was stirred at room temperature for 16 hrs and concentrated to give (6S)—N'-(tert-butyldimethylsilyl)-N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (crude) which was used for the next step directly.

Step 2—(R,6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and (S,6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide

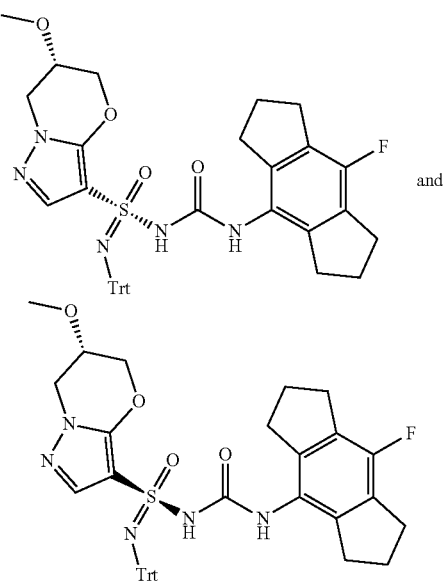

(S,6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide and R,6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide:

(6S)—N-((8-fluoro-1,2,3,5,6,7-hexahydro-s-indacen-4-yl)carbamoyl)-6-methoxy-N'-trityl-6,7-dihydro-5H-pyrazolo[5,1-b][1,3]oxazine-3-sulfonimidamide (210 mg, 0.3 mmol) was separated by chiral prep-HPLC to give two isomers of unknown absolute stereochemistry as yellow solids (peak 1, 60 mg; peak 2, 120 mg).

Step 3—Synthesis of (R,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 31 and Example 32)

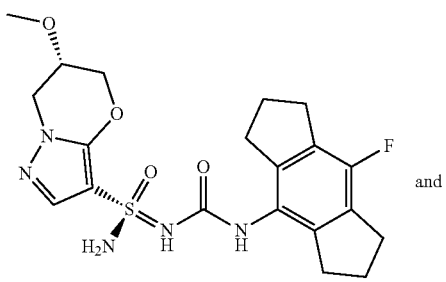

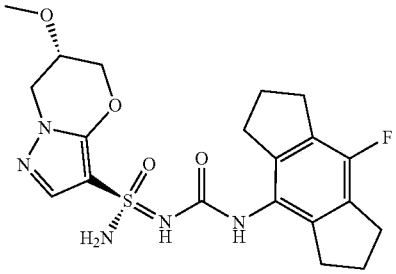

(S,6S)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (R,6S)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide:

To a solution of the material from Peak 1 above (60 mg, 0.09 mmol) in DCM (4 mL) was added MeSO$_3$H (3 drops) at 0° C. After being stirred at this temperature for 0.5 hour, the reaction mixture was adjusted to pH=8 with sat-.NaHCO$_3$. The precipitate was collected by filtration, washed with water (2 mL), DCM (2 mL) and dried to give a white solid (16 mg, yield: 42%). $^1$H NMR (400 MHz, DMSO-d$_6$): δ=8.19 (brs, 1H), 7.52 (s, 1H), 7.26 (s, 2H), 4.59 (d, J=12.0 Hz, 1H), 4.31-4.17 (m, 3H), 4.03 (s, 1H), 3.34 (overlap, 3H), 2.80 (t, J=6.4 Hz, 4H), 2.73 (t, J=6.4 Hz, 4H), 2.01-1.97 (m, 4H). MS: m/z 450.1 (M+H$^+$).

The material from Peak 2 above was deprotected and isolated in the same manner to yield a white solid. $^1$H NMR (400 MHz, DMSO-d$_6$): δ=8.25 (brs, 1H), 7.52 (s, 1H), 7.26 (s, 2H), 4.59 (d, J=12.0 Hz, 1H), 4.31-4.17 (m, 3H), 4.03 (s, 1H), 3.34 (overlap, 3H), 2.80 (t, J=6.4 Hz, 4H), 2.68 (t, J=6.4 Hz, 4H), 2.01-1.97 (m, 4H). MS: m/z 450.1 (M+H$^+$).

Example 33 and Example 34
(R,6S)-6-(dimethylamino)-N'-((1,2,3,5,6,7-hexa-hydro-s-indacen-4-yl)carbamoyl)-6,7-dihydro-5H-pyrazolo[5,1-b][1,3]oxazine-3-sulfonimidamide and (S,6S)-6-(dimethylamino)-N'-((1,2,3,5,6,7-hexa-hydro-s-indacen-4-yl)carbamoyl)-6,7-dihydro-5H-pyrazolo[5,1-b][1,3]oxazine-3-sulfonimidamide
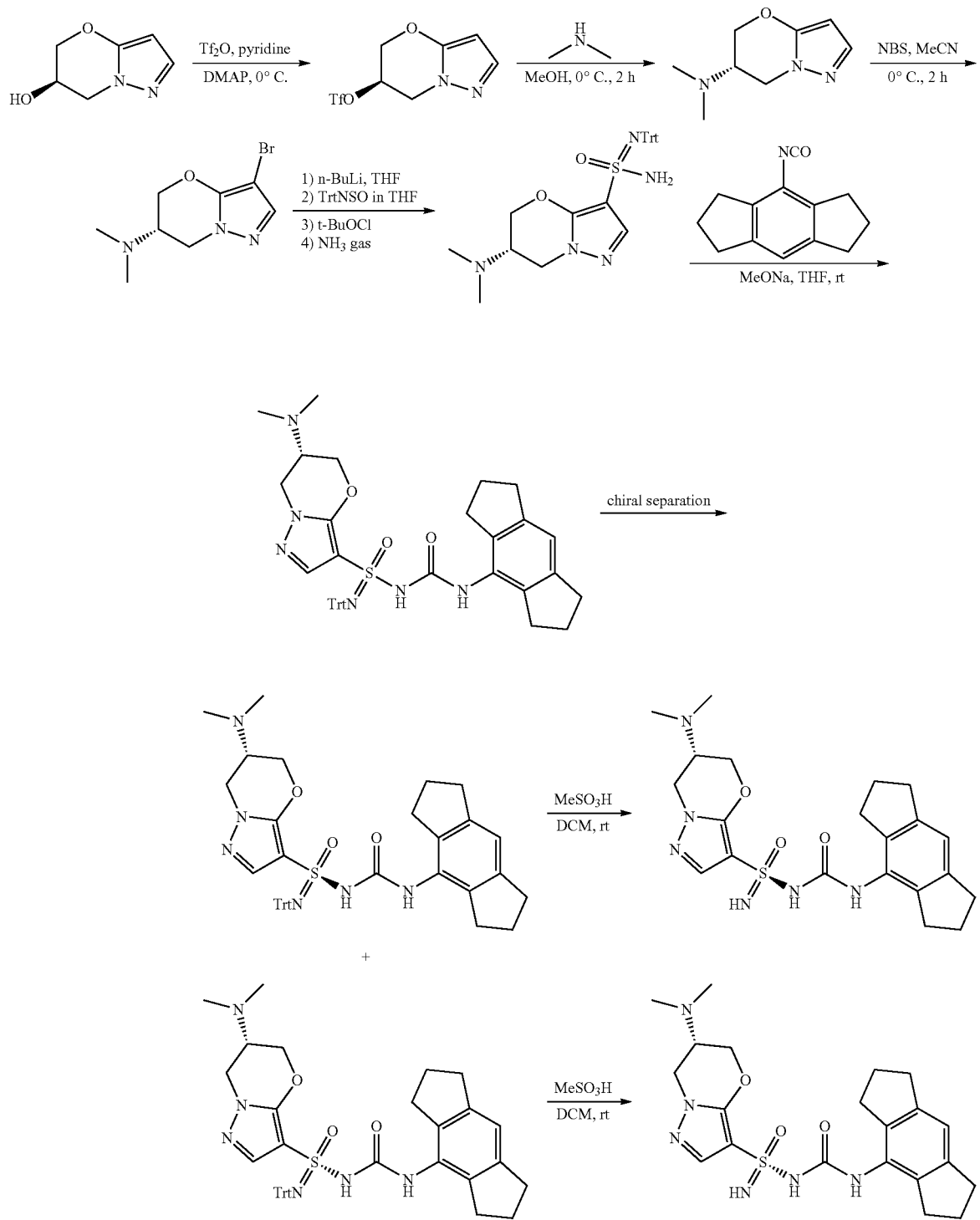

Step 1 and Step 2—Synthesis of (S)—N,N-dimethyl-6,7-dihydro-5H-pyrazolo[5,1-b][1,3]oxazin-6-amine

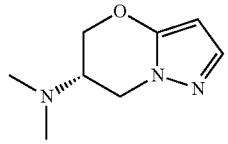

To a solution of (R)-6,7-dihydro-5H-pyrazolo[5,1-b][1,3]oxazin-6-ol (5.0 g, 35.7 mmol) and DMAP (44 mg, 0.4 mmol) in pyridine (40 mL) was added Tf$_2$O (20.2 g, 71.4 mmol) at −10° C. slowly under N$_2$ atmosphere. The mixture was stirred for 2 hours at −10° C. Then a solution of dimethylamine (20 mL, 33% in water) in MeOH (20 mL) was added to the mixture and the resulting reaction mixture was stirred for another 2 hours at room temperature. The reaction mixture was concentrated and purified by reverse phase column (MeCN/H$_2$O) to give (S)—N,N-dimethyl-6,7-dihydro-5H-pyrazolo[5,1-b][1,3]oxazin-6-amine (850 mg, yield: 14%) as a yellow solid.

Step 3—Synthesis of (6S)-6-(dimethylamino)-N'-trityl-6,7-dihydro-5H-pyrazolo[5,1-b][1,3]oxazine-3-sulfonimidamide

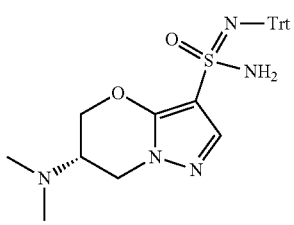

NBS (1.1 g, 6.1 mmol) was added portion wise to a solution of (S)—N,N-dimethyl-6,7-dihydro-5H-pyrazolo[5,1-b][1,3]oxazin-6-amine (850 mg, 5.1 mmol) in MeCN (40 mL) at 0° C. and the reaction mixture was stirred for 2 hours at room temperature. The mixture was filtered and purified by reverse phase column (MeCN/H$_2$O) to give (S)-3-bromo-N,N-dimethyl-6,7-dihydro-5H-pyrazolo[5,1-b][1,3]oxazin-6-amine (770 mg, yield: 59%) as yellow solid.

Step 4—Synthesis of (6S)-6-(dimethylamino)-N'-trityl-6,7-dihydro-5H-pyrazolo[5,1-b][1,3]oxazine-3-sulfonimidamide

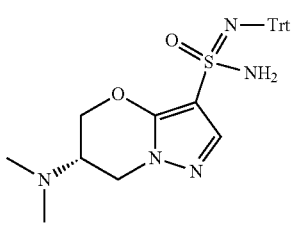

To a solution of (S)-3-bromo-N,N-dimethyl-6,7-dihydro-5H-pyrazolo[5,1-b][1,3]oxazin-6-amine (570 mg, 2.3 mmol) in THF (15 mL) was added n-BuLi (2.5 M in hexane, 1.0 mL, 2.5 mmol) dropwise at −78° C. and the mixture was stirred at the same temperature for 1 hour. A solution of TrtNSO (780 mg, 2.6 mmol) in THF (15 mL) was added dropwise and the mixture was stirred at −78° C. for 20 minutes before being placed in an ice bath at 0° C. After stirring for another 10 minutes, tert-butyl hypochlorite (278 mg, 2.6 mmol) was added and the mixture was stirred for 20 minutes. The mixture was bubbled with NH$_3$ gas for 5 minutes and the resulting mixture stirred for 16 hours at room temperature. The reaction mixture was concentrated to dryness and purified by reverse phase column (MeCN/H$_2$O) to give (6S)-6-(dimethylamino)-N'-trityl-6,7-dihydro-5H-pyrazolo[5,1-b][1,3]oxazine-3-sulfonimidamide (330 mg, yield: 30%) as a yellow solid. MS: m/z 488.5 (M+H$^+$).

Steps 5~7—Synthesis of (R,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 33 and Example 34)

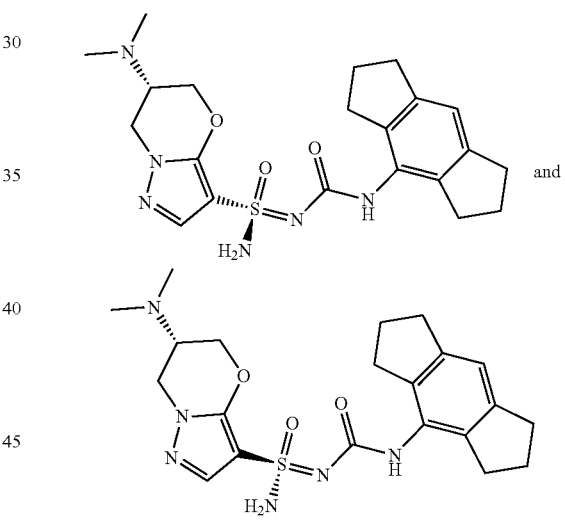

(S,6S)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-(dimethylamino)-N-((1,2,3,5,6,7-hexahydro-s-indacen-4-yl)carbamoyl)-6,7-dihydro-5H-pyrazolo[5,1-b][1,3]oxazine-3-sulfonimidamide: These three steps were similar to general procedure of (S,6S)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide.

(R,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide were prepared using the general procedure described for the preparation of (R,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 31 and Example 32) by replacing (6S)-6-methoxy-N'-trityl-6,7-dihydro-5H-pyrazolo[5,1-b][1,3]oxazine-3-sulfonimidamide with (6S)-6-(dimethylamino)-N'-trityl-6,7-dihydro-5H-pyrazolo[5,1-b][1,3]oxazine-3-sulfonimidamide and 4-fluoro-8-isocyanato-1,2,3,5,6,7-hexahydro-s-indacene with 4-isocyanato-1,2,3,5,6,7-hexahydro-s-indacene in Step 1. After prep-HPLC two isomers of unknown absolute stereochemistry were isolated as white solids.

Peak 1: $^1$H NMR (400 MHz, DMSO-$d_6$): δ=8.19 (brs, 1H), 7.52 (s, 1H), 7.28 (s, 2H), 6.86 (s, 1H), 4.45-4.41 (m, 2H), 4.23-4.13 (m, 2H), 2.91-2.87 (m, 1H), 2.77 (t, J=7.2 Hz, 4H), 2.70-2.67 (m, 4H), 2.26 (s, 6H), 1.98-1.87 (m, 4H). MS: m/z 445.2 (M+H$^+$).

Peak 2: $^1$H NMR (400 MHz, DMSO-$d_6$): δ=8.19 (brs, 1H), 7.52 (s, 1H), 7.25 (s, 2H), 6.86 (s, 1H), 4.45-4.40 (m, 2H), 4.23-4.13 (m, 2H), 2.91-2.87 (m, 1H), 2.77 (t, J=7.2 Hz, 4H), 2.68 (t, J=7.2 Hz, 4H), 2.27 (s, 6H), 1.93-1.89 (m, 4H). MS: m/z 445.1 (M+H$^+$).

Example 35 and Example 36

(R,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide

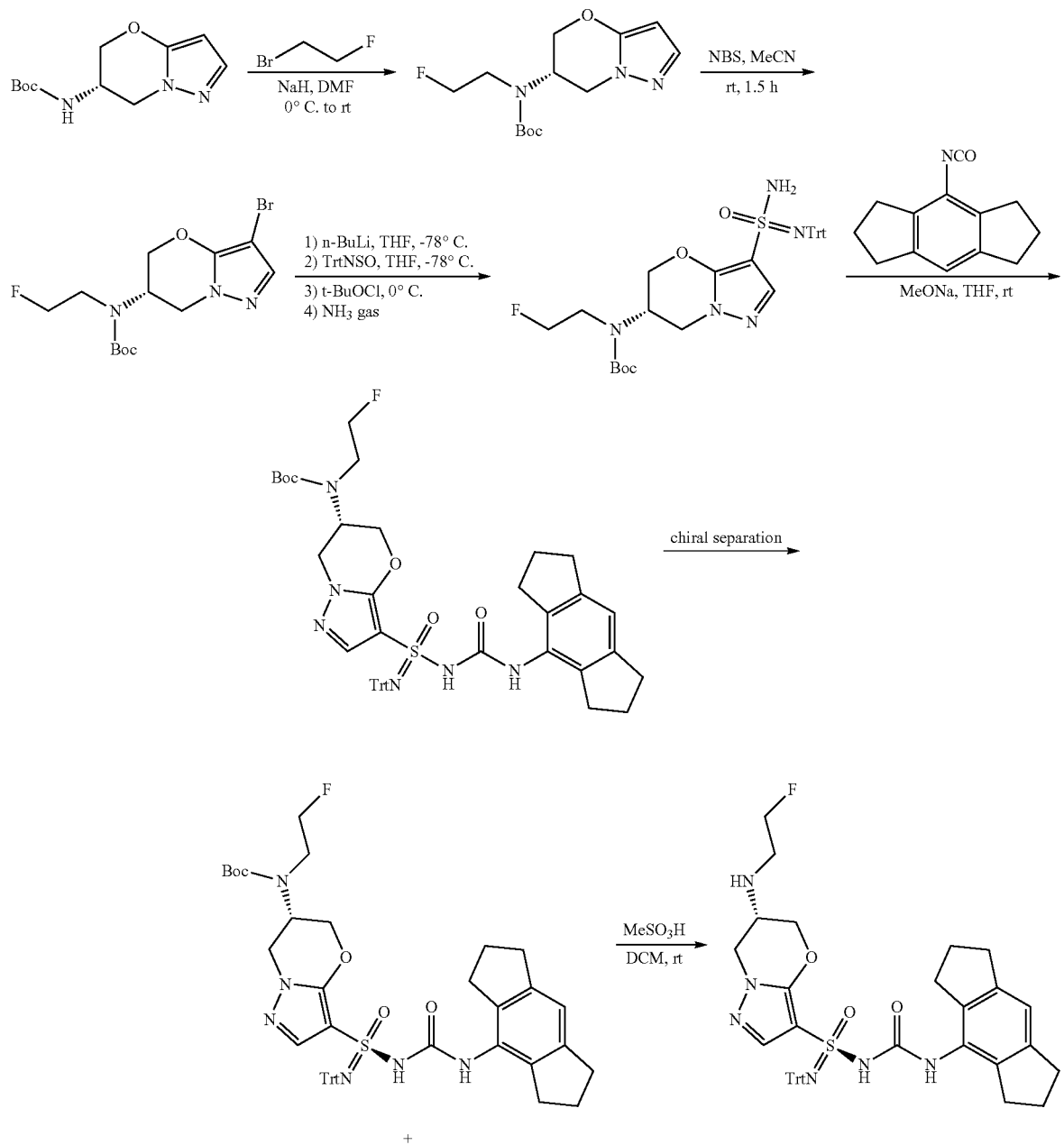

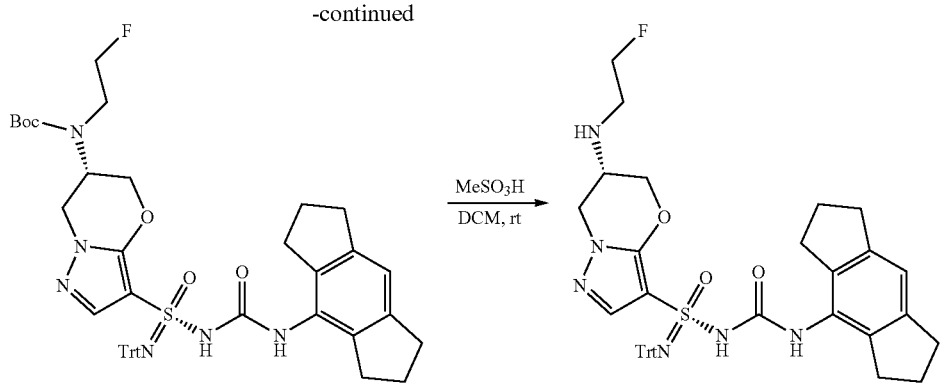

Step 1—Synthesis of tert-butyl (S)-(6,7-dihydro-5H-pyrazolo[5,1-b][1,3]oxazin-6-yl)(2-fluoroethyl)carbamate

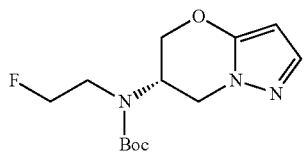 [SMILES: CC(C)(C)OC(=O)N(CCF)[C@@H]1COc2ccnn2C1]

To a solution of (S)-tert-butyl (6,7-dihydro-5H-pyrazolo[5,1-b][1,3]oxazin-6-yl)carbamate (5.0 g, 20.9 mmol) in DMF (30 mL) was added NaH (60% in mineral oil, 1.0 g, 25.1 mmol) portion-wise at 0° C. under an atmosphere of $N_2$. The mixture was stirred at 0° C. for 30 minutes. Then 1-bromo-2-fluoroethane (3.2 g, 25.1 mmol) was added dropwise at 0° C. After being stirred at room temperature for 2 hours, the reaction mixture was poured to water (120 mL) and extracted with EtOAc (100 mL×3). The combined organic layer was washed with brine (100 mL×3), dried over $Na_2SO_4$ and concentrated. The residue was purified by silica flash column (PE/EtOAc) to give (S)-tert-butyl (6,7-dihydro-5H-pyrazolo[5,1-b][1,3]oxazin-6-yl)(2-fluoroethyl)carbamate (4.0 g, yield: 66%) as a white solid.

Steps 2~6—Synthesis of (R,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 35 and Example 36)

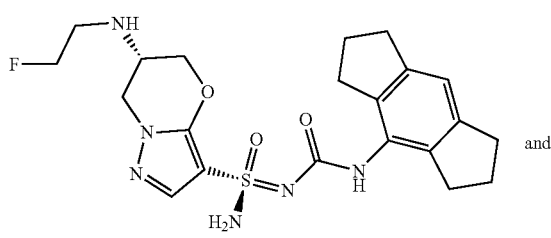

and

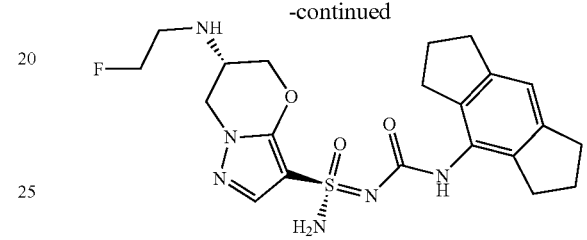

(R,6S)-6-((2-fluoroethyl)amino)-N-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N-((1,2,3,5,6,7-hexahydro-s-indacen-4-yl)carbamoyl)-6,7-dihydro-5H-pyrazolo[5,1-b][1,3]oxazine-3-sulfonimidamide: These five steps were similar to general procedure of (S,6S)—N-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide.

(R,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide were prepared using the general procedure described for the preparation of (R,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 33 and Example 34) by replacing (S)—N,N-dimethyl-6,7-dihydro-5H-pyrazolo[5,1-b][1,3]oxazin-6-amine with tert-butyl (S)-(6,7-dihydro-5H-pyrazolo[5,1-b][1,3]oxazin-6-yl)(2-fluoroethyl)carbamate in Step 2. After prep-HPLC two isomers of unknown absolute stereochemistry were isolated.

Peak 1: $^1$H NMR (400 MHz, DMSO-$d_6$): δ=8.16 (brs, 1H), 7.52 (s, 1H), 7.26 (s, 2H), 6.85 (s, 1H), 4.52 (t, J=4.8 Hz, 1H), 4.40-4.37 (m, 2H), 4.27-4.20 (m, 2H), 3.94 (dd, J=12.0, 5.2 Hz, 1H), 3.34 (overlap, 1H), 2.97-2.93 (m, 1H), 2.90-2.86 (m, 1H), 2.79 (t, J=7.2 Hz, 4H), 2.70 (t, J=7.2 Hz, 4H), 2.29-2.26 (m, 1H), 1.97-1.89 (m, 4H). MS: m/z 463.1 (M+H$^+$).

Peak 2: $^1$H NMR (400 MHz, DMSO-$d_6$): δ=8.16 (brs, 1H), 7.52 (s, 1H), 7.24 (s, 2H), 6.85 (s, 1H), 4.52 (t, J=4.8 Hz, 1H), 4.41-4.367 (m, 2H), 4.27-4.23 (m, 2H), 3.94 (dd, J=12.0, 5.2 Hz, 1H), 3.34 (overlap, 1H), 2.95 (t, J=5.2 Hz, 1H), 2.89 (t, J=5.2 Hz, 1H), 2.77 (t, J=7.2 Hz, 4H), 2.70 (t, J=7.2 Hz, 4H), 2.33-2.31 (m, 1H), 1.97-1.89 (m, 4H). MS: m/z 463.1 (M+H+).

Example 37

8-(3-(6,7-dihydro-5H-pyrazolo[5,1-b][1,3]oxazine-3-sulfonimidoyl)ureido)-1,2,3,5,6,7-hexahydro-s-indacene-4-carboxylic acid

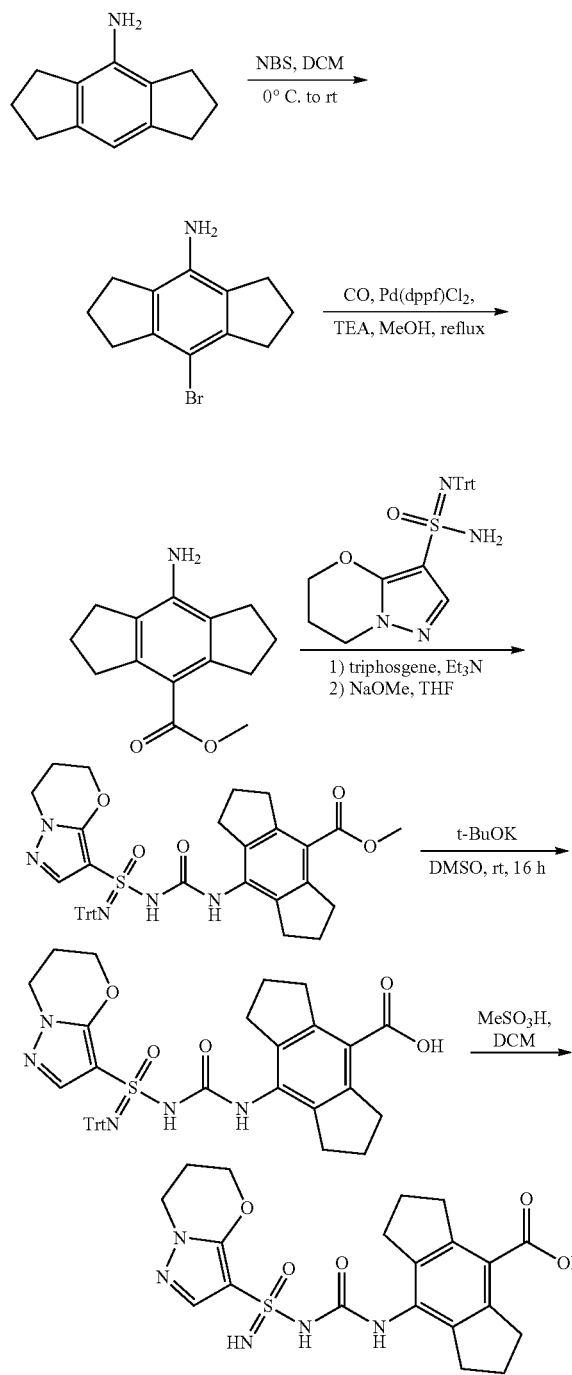

Step 1—Synthesis of 8-bromo-1,2,3,5,6,7-hexahydro-s-indacen-4-amine

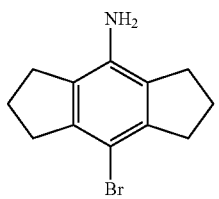 [SMILES: Nc1c2c(c(Br)c3c1CCC3)CCC2]

To a solution of 1,2,3,5,6,7-hexahydro-s-indacen-4-amine (500 mg, 2.9 mmol) in DCM (15 mL) was added NBS (530 mg, 3.0 mmol) portion wise at 0° C. After being stirred at room temperature for 16 hrs, the reaction mixture was diluted with DCM (50 mL), washed with H₂O (40 mL), dried over Na₂SO₄ and concentrated. The residue was purified by silica flash column (0%~20% EtOAc in PE) to give 8-bromo-1,2,3,5,6,7-hexahydro-s-indacen-4-amine (570 mg, yield: 78%) as a red solid. ¹H NMR (400 MHz, CDCl₃): δ=3.44 (brs, 2H), 2.90 (t, J=7.2 Hz, 4H), 2.79 (t, J=7.2 Hz, 4H), 2.17-2.09 (m, 4H).

Step 2—Synthesis of methyl 8-amino-1,2,3,5,6,7-hexahydro-s-indacene-4-carboxylate

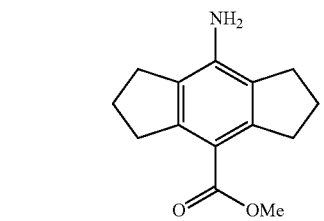 [SMILES: COC(=O)c1c2c(c(N)c3c1CCC3)CCC2]

A mixture of 8-bromo-1,2,3,5,6,7-hexahydro-s-indacen-4-amine (570 mg, 2.3 mmol), TEA (460 mg, 4.5 mmol) and Pd(dppf)Cl₂ (160 mg, 0.2 mmol) in MeOH (25 mL) was stirred for 16 hrs at 75° C. under CO atmosphere (balloon). The reaction mixture was concentrated and purified by silica flash column (0% 20% EtOAc in PE) to give methyl 8-amino-1,2,3,5,6,7-hexahydro-s-indacene-4-carboxylate (410 mg, yield: 78%) as a red solid. ¹H NMR (400 MHz, CDCl₃): δ=3.82 (s, 5H), 3.22 (t, J=7.2 Hz, 4H), 2.67 (t, J=7.2 Hz, 4H), 2.16-2.07 (m, 4H).

Step 3—Synthesis of methyl 8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylate

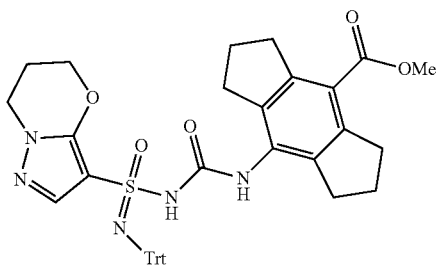

To a solution of N'-trityl-6,7-dihydro-5H-pyrazolo[5,1-b][1,3]oxazine-3-sulfonimidamide (300 mg, 0.7 mmol) in THF (15 mL) was added MeONa (41 mg, 0.8 mmol). The reaction mixture was stirred at room temperature for 20 mins to give a sodium salt suspension.

In another flask, to a solution of methyl 8-amino-1,2,3,5,6,7-hexahydro-s-indacene-4-carboxylate (157 mg, 0.7 mmol) in THF (15 mL) was added triethylamine (137 mg, 1.4 mmol) and triphosgene (62 mg, 0.2 mmol) in one portion at 0° C. After being stirred at room temperature for 10 mins under N₂, the reaction mixture was filtered. The filtrate was added to the sodium salt suspension above. The new reaction mixture was stirred at room temperature for 16 hours, then concentrated and purified by reverse phase column (MeCN/H₂O) to give methyl8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylate (310 mg, yield: 65%) as a white solid.

Step 4—Synthesis of 8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylic acid

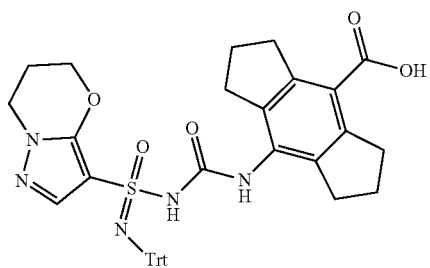

To a solution of methyl 8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylate (200 mg, 0.3 mmol) in DMSO (5 mL) was added t-BuOK (160 mg, 1.4 mmol). After being stirred at room temperature for 16 hours, the reaction mixture was poured into H₂O (20 mL), acidified to pH=6 with 2 M aq.HCl and extracted with EtOAc (15 mL×2). The combined EtOAc was washed with brine (20 mL), dried over Na₂SO₄ and concentrated to give 8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylic acid (190 mg, crude) as a white solid. MS: m/z 688.6 (M+H⁺).

Step 5—Synthesis of 8-(3-(amino(6,7-dihydro-5H-pyrazolo[5,1-b][1,3]oxazin-3-yl)(oxo)-$\lambda^6$-sulfanylidene)ureido)-1,2,3,5,6,7-hexahydro-s-indacene-4-carboxylic acid (Example 37)

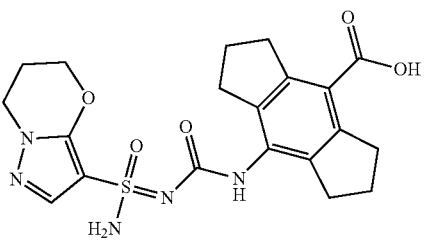 [SMILES: NS(=O)(=NC(=O)Nc1c2c(c(C(=O)O)c3c1CCC3)CCC2)c1cnn2c1OCCC2]

To a solution of 8-(3-(N-trityl-6,7-dihydro-5H-pyrazolo[5,1-b][1,3]oxazine-3-sulfonimidoyl)ureido)-1,2,3,5,6,7-hexahydro-s-indacene-4-carboxylic acid (190 mg, crude) in DCM (5 mL) was added two drops of MeSO₃H at room temperature. After being stirred at this temperature for 5 minutes, the reaction solution was poured into H₂O (15 mL) and basified to pH=8 with Sat.NaHCO₃. The resulting solution was washed by DCM (10 mL×2) and the aqueous phase was acidified to pH=6 with 2 M aq.HCl. The precipitates were collected by filtration and then purified by prep-HPLC (TFA) to give 8-(3-(6,7-dihydro-5H-pyrazolo[5,1-b][1,3]oxazine-3-sulfonimidoyl)ureido)-1,2,3,5,6,7-hexahydro-s-indacene-4-carboxylic acid (26 mg, yield: 20%, mixture of stereoisomers) as a white solid. ¹H NMR (400 MHz, DMSO-d₆): δ=12.46 (brs, 1H), 8.39 (s, 1H), 7.52 (s, 1H), 7.25 (s, 2H), 4.44-4.39 (m, 2H), 4.11 (t, J=6.0 Hz, 2H), 3.05 (t, J=7.2 Hz, 4H), 2.71 (t, J=7.2 Hz, 4H), 2.20-2.15 (m, 2H), 1.96-1.89 (m, 4H). MS: m/z 446.1 (M+H⁺).

Example 38 and Example 39

(R,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide

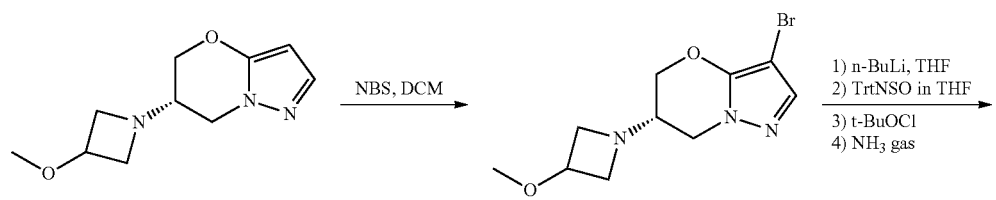

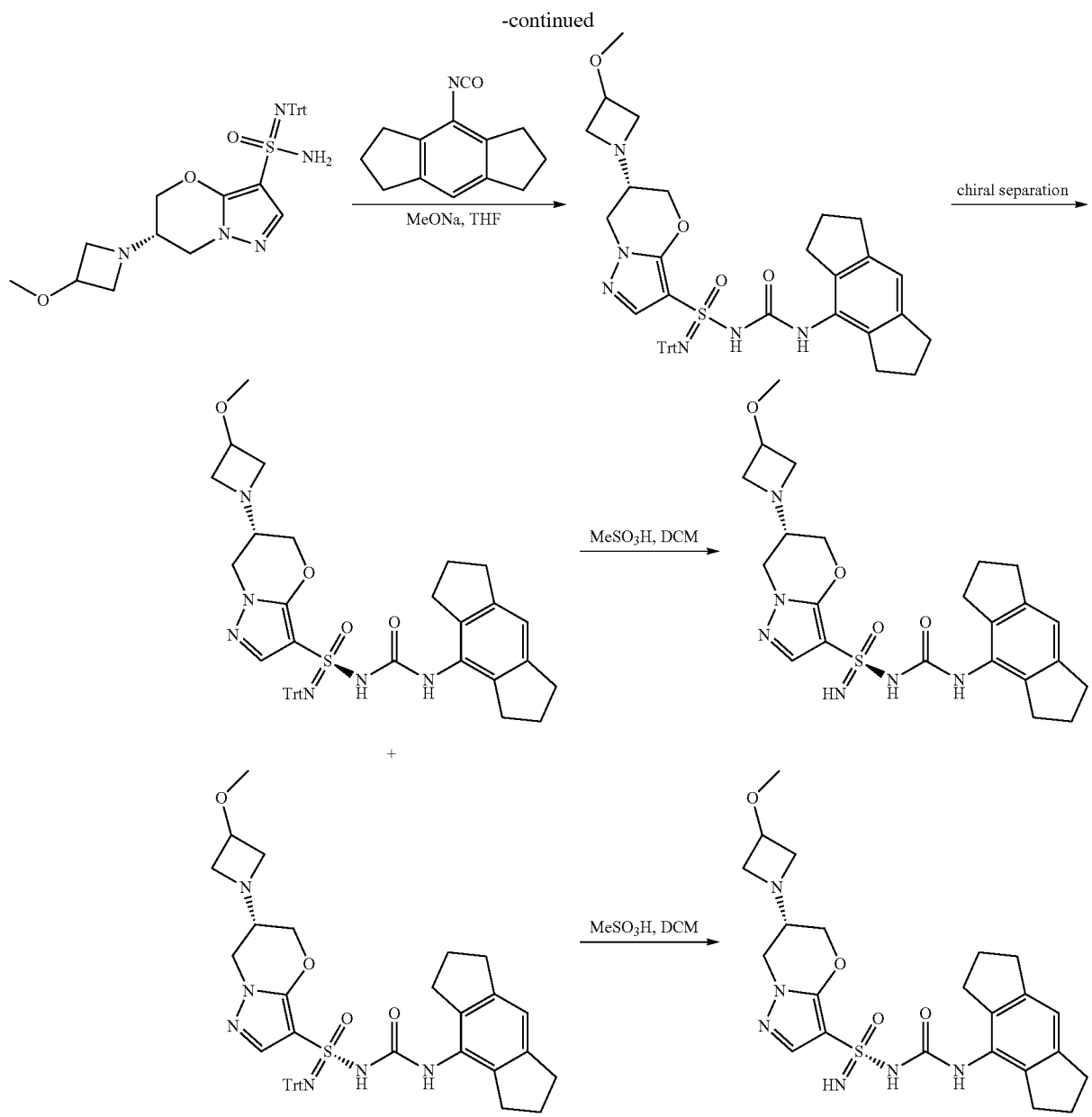

Step 1—Synthesis of (S)-6-(3-methoxyazetidin-1-yl)-6,7-dihydro-5H-pyrazolo[5,1-b][1,3]oxazine

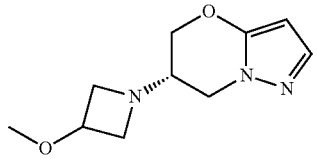

(S)-6-(3-methoxyazetidin-1-yl)-6,7-dihydro-5H-pyrazolo[5,1-b][1,3]oxazine was prepared in the same manner as (S)—N,N-dimethyl-6,7-dihydro-5H-pyrazolo[5,1-b][1,3]oxazin-6-amine, substituting 3-methoxyazetidine for dimethylamine.

Step 2—Synthesis of (S)-3-bromo-6-(3-methoxyazetidin-1-yl)-6,7-dihydro-5H-pyrazolo[5,1-b][1,3]oxazine

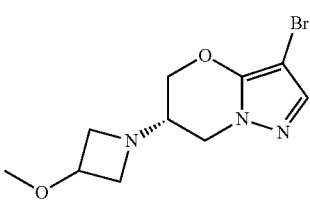 [SMILES: COC1CN([C@@H]2COc3c(Br)cnn3C2)C1]

To a solution of (S)-6-(3-methoxyazetidin-1-yl)-6,7-dihydro-5H-pyrazolo[5,1-b][1,3]oxazine (335 mg, 1.6 mmol) in DCM (5 mL) was added NBS (300 mg, 1.7 mmol) portion wise and the mixture was stirred for 1 hr at room temperature. The reaction mixture was diluted with DCM (15 mL) and washed with sat.NaHCO$_3$ (15 mL). The organic layer was dried by Na$_2$SO$_4$ and concentrated to dryness to obtain (S)-3-bromo-6-(3-methoxyazetidin-1-yl)-6,7-dihydro-5H-pyrazolo[5,1-b][1,3]oxazine (440 mg, yield: 95%) as yellow solid. MS: m/z 290.3 (M+H$^+$).

Step 3—Synthesis of (6S)-6-(3-methoxyazetidin-1-yl)-N'-trityl-6,7-dihydro-5H-pyrazolo[5,1-b][1,3]oxazine-3-sulfonimidamide

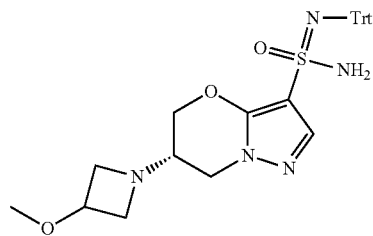

To a solution of (S)-3-bromo-6-(3-methoxyazetidin-1-yl)-6,7-dihydro-5H-pyrazolo[5,1-b][1,3]oxazine (440 mg, 1.5 mmol) in THF (5 mL) was added n-BuLi (0.6 mL, 1.5 mmol, 2.5 M in hexane) dropwise at −78° C. and the mixture was stirred at this temperature for 30 mins. A solution of TrtNSO (466 mg, 1.5 mmol) in THF (2 mL) was added dropwise and the mixture was stirred at −78° C. for 20 minutes before being placed in an ice bath. After stirring for another 10 minutes, tert-butyl hypochlorite (181 mg, 1.7 mmol) was added and the mixture was stirred for 20 mins. NH$_3$ gas was bubbled through the mixture for 5 minutes and the resulting solution was stirred for 16 hours at room temperature. The reaction mixture was quenched by H$_2$O (1 mL) and concentrated to dryness. The residue was purified by reverse phase column (MeCN/H$_2$O) to give (6S)-6-(3-methoxyazetidin-1-yl)-N'-trityl-6,7-dihydro-5H-pyrazolo[5,1-b][1,3]oxazine-3-sulfonimidamide (336 mg, yield: 35%) as a white solid. MS: m/z 530.5 (M+H$^+$).

Step 4—Synthesis of (6S)—N-((1,2,3,5,6,7-hexahydro-s-indacen-4-yl)carbamoyl)-6-(3-methoxyazetidin-1-yl)-N'-trityl-6,7-dihydro-5H-pyrazolo[5,1-b][1,3]oxazine-3-sulfonimidamide

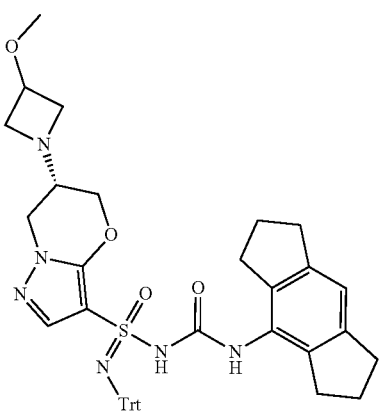

To a solution of (6S)-6-(3-methoxyazetidin-1-yl)-N'-trityl-6,7-dihydro-5H-pyrazolo[5,1-b][1,3]oxazine-3-sulfonimidamide (276 mg, 0.5 mmol) in THF (10 mL) was added MeONa (42 mg, 0.8 mmol) and the mixture was stirred for 30 minutes at room temperature. Then 4-isocyanato-1,2,3,5,6,7-hexahydro-s-indacene (104 mg, 0.5 mmol) was added and the mixture was stirred for 16 hours at room temperature. The reaction mixture was concentrated to dryness and purified by reverse phase column (MeCN/H$_2$O) to give (6S)—N-((1,2,3,5,6,7-hexahydro-s-indacen-4-yl)carbamoyl)-6-(3-methoxyazetidin-1-yl)-N'-trityl-6,7-dihydro-5H-pyrazolo[5,1-b][1,3]oxazine-3-sulfonimidamide (283 mg, yield: 60%) as a white solid. MS: m/z 729.6 (M+H$^+$).

Step 5—(S,6S)—N-((1,2,3,5,6,7-hexahydro-s-indacen-4-yl)carbamoyl)-6-(3-methoxyazetidin-1-yl)-N'-trityl-6,7-dihydro-5H-pyrazolo[5,1-b][1,3]oxazine-3-sulfonimidamide and (R,6S)—N-((1,2,3,5,6,7-hexahydro-s-indacen-4-yl)carbamoyl)-6-(3-methoxyazetidin-1-yl)-N'-trityl-6,7-dihydro-5H-pyrazolo[5,1-b][1,3]oxazine-3-sulfonimidamide

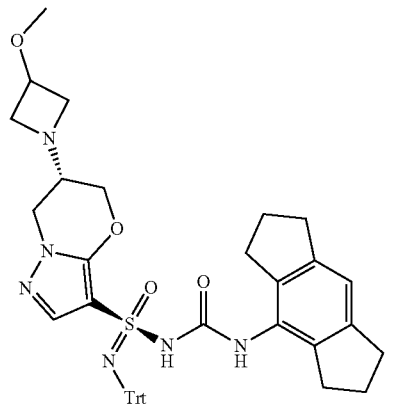

and

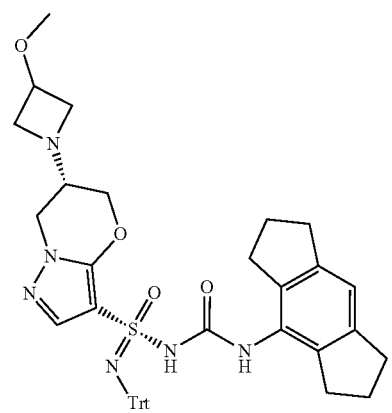

(6S)—N-((1,2,3,5,6,7-hexahydro-s-indacen-4-yl)carbamoyl)-6-(3-methoxyazetidin-1-yl)-N'-trityl-6,7-dihydro-5H-pyrazolo[5,1-b][1,3]oxazine-3-sulfonimidamide (330 mg) was separated by chiral prep-HPLC to give two isomers of unknown absolute stereochemistry as white solids (peak 1, 132 mg, yield: 40%; peak 2,171 mg, yield: 51%).

Step 6—Synthesis of (R,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (Example 38 and Example 39)

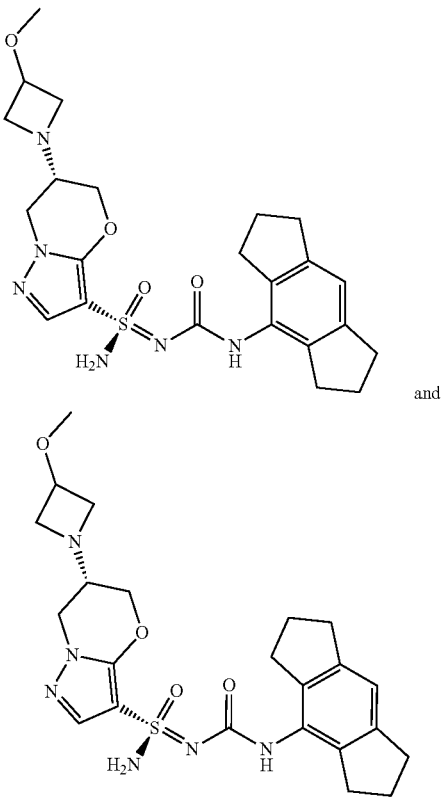

To a solution of the material from Peak 1 above (132 mg, 0.2 mmol) in DCM (3 mL) was added two drops of methanesulfonic acid. After being stirred at room temperature for 10 mins, the reaction solution was adjusted to pH=8 with Sat.NaHCO$_3$. The resulting mixture was concentrated to dryness and purified by reverse phase column (MeCN/H$_2$O) to give (72 mg, yield: 83%) as a white solid (single unknown stereoisomer). $^1$H NMR (400 MHz, DMSO-d$_6$): δ=8.16 (brs, 1H), 7.51 (s, 1H), 7.28 (s, 2H), 6.86 (s, 1H), 4.35-4.22 (m, 2H), 4.14 (dd, J=13.2, 4.4 Hz, 1H), 3.94-3.90 (m, 1H), 3.85 (d, J=13.2 Hz, 1H), 3.53 (t, J=6.4 Hz, 2H), 3.14 (s, 3H), 3.02-2.95 (m, 3H), 2.77 (t, J=7.2 Hz, 4H), 2.69 (t, J=7.2 Hz, 4H), 1.97-1.89 (m, 4H). MS: m/z 487.2 (M+H$^+$).

The material from Peak 2 above was deprotected and isolated in the same manner to yield a white solid (single unknown stereoisomer) (72 mg, yield: 63%). $^1$H NMR (400 MHz, DMSO-d$_6$): δ=8.17 (brs, 1H), 7.48 (s, 1H), 7.24 (s, 2H), 6.86 (s, 1H), 4.30-4.20 (m, 2H), 4.14 (dd, J=12.8, 4.0 Hz, 1H), 3.96-3.90 (m, 1H), 3.85 (d, J=12.8 Hz, 1H), 3.57-3.52 (m, 2H), 3.14 (s, 3H), 3.02-2.95 (m, 3H), 2.77 (t, J=7.2 Hz, 4H), 2.69 (t, J=7.2 Hz, 4H), 1.97-1.90 (m, 4H). MS: m/z 487.2 (M+H$^+$).

Example 40 and Example 41

(R,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

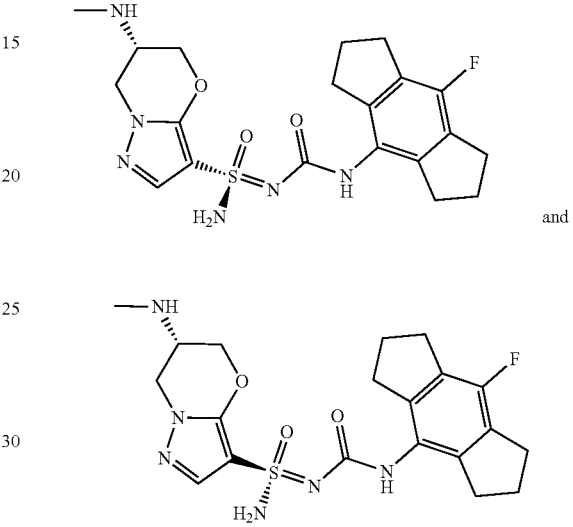

(R,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide were prepared using the general procedure described for the preparation of (R,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 31 and Example 32) by replacing (6S)-6-methoxy-N'-trityl-6,7-dihydro-5H-pyrazolo[5,1-b][1,3]oxazine-3-sulfonimidamide with tert-butyl methyl((6S)-3-(N'-tritylsulfamidimidoyl)-6,7-dihydro-5H-pyrazolo[5,1-b][1,3]oxazin-6-yl)carbamate in Step 1. After prep-HPLC two isomers of unknown absolute stereochemistry were isolated as white solids.

Peak 1: $^1$H NMR (400 MHz, DMSO-d$_6$): δ=8.20 (brs, 1H), 7.50 (s, 1H), 7.24 (s, 2H), 4.35-4.20 (m, 3H), 3.95-3.91 (m, 1H), 3.15-3.14 (m, 1H), 2.81 (t, J=7.2 Hz, 4H), 2.71 (t, J=7.2 Hz, 4H), 2.33 (s, 3H) 2.03-1.96 (m, 4H). MS: m/z 449.1 (M+H$^+$).

Peak 2: $^1$H NMR (400 MHz, DMSO-d$_6$): δ=8.18 (brs, 1H), 7.51 (s, 1H), 7.24 (s, 2H), 4.36-4.20 (m, 3H), 3.93 (dd, J=12.4, 4.0 Hz, 1H), 3.16-3.15 (m, 1H), 2.81 (t, J=7.6 Hz, 4H), 2.71 (t, J=7.2 Hz, 4H), 2.33 (s, 3H) 2.03-1.96 (m, 4H). MS: m/z 449.1 (M+H$^+$).

Example 42 and Example 43

(S,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide and (R,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide

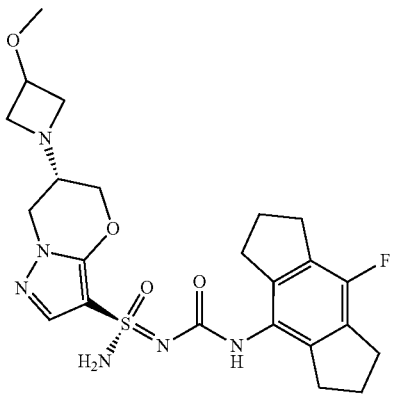

and

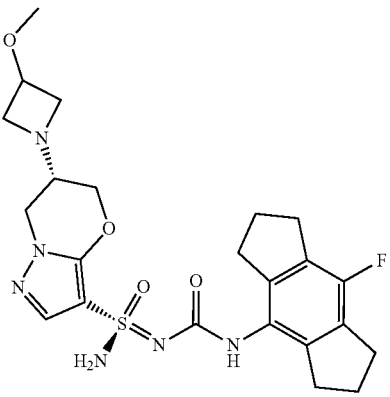

(S,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide and (R,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide were prepared using the general procedure described for the preparation of (R,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-methoxy-6,7-dihydro-5H-pyrazolo[5,1-b][1,3]oxazine-3-sulfonimidamide (Example 31 and Example 32) by replacing (6S)-6-methoxy-N'-trityl-6,7-dihydro-5H-pyrazolo[5,1-b][1,3]oxazine-3-sulfonimidamide with (6S)-6-(3-methoxyazetidin-1-yl)-N'-trityl-6,7-dihydro-5H-pyrazolo[5,1-b][1,3]oxazine-3-sulfonimidamide in Step 1. After prep-HPLC two isomers of unknown absolute stereochemistry were isolated.

Peak 1: $^1$H NMR (400 MHz, DMSO-$d_6$): δ=8.20 (brs, 1H), 7.51 (s, 1H), 7.28 (s, 2H), 4.27-4.17 (m, 2H), 4.15-4.12 (m, 1H), 3.93-3.83 (m, 2H), 3.54-3.51 (m, 2H), 3.14 (s, 3H), 3.02-2.96 (m, 3H), 2.80 (t, J=7.6 Hz, 4H), 2.75-2.50 (m, 4H), 2.03-1.96 (m, 4H). MS: m/z 505.1 (M+H$^+$). Compound 43

Peak 2: $^1$H NMR (400 MHz, DMSO-$d_6$): δ=8.12 (brs, 1H), 7.47 (s, 1H), 7.12 (s, 2H), 4.27-4.19 (m, 3H), 3.94-3.83 (m, 2H), 3.56-3.51 (m, 2H), 3.14 (s, 3H), 3.02-2.96 (m, 3H), 2.80 (t, J=7.2 Hz, 4H), 2.74 (t, J=7.2 Hz, 4H), 2.03-1.96 (m, 4H). MS: m/z 505.2 (M+H$^+$). Compound 42

Example 44 and Example 45

(R,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide

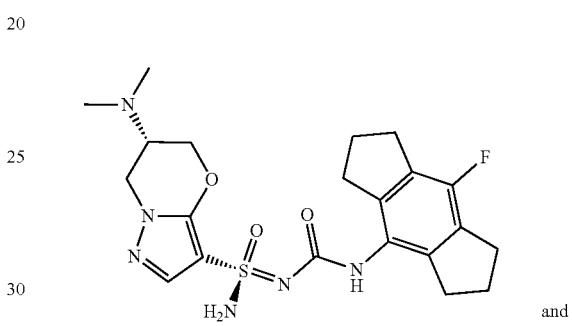

and

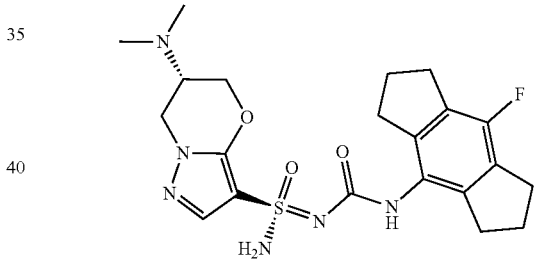

Step 1—Synthesis of (R)-6,7-dihydro-5H-pyrazolo[5,1-b][1,3]oxazin-6-yl trifluoromethanesulfonate

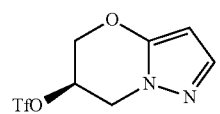

Tf$_2$O (40.4 g, 142.8 mmol) was added dropwise to a solution of (R)-6,7-dihydro-5H-pyrazolo[5,1-b][1,3]oxazin-6-ol (10.0 g, 71.4 mmol) and DMAP (88 mg, 0.7 mmol) in pyridine/DCM (20 mL/80 mL) at −10° C. under an atmosphere of N$_2$. After 2 hours, the mixture was purified by silica column (PE/EtOAc=3/1) to give (R)-6,7-dihydro-5H-pyrazolo[5,1-b][1,3]oxazin-6-yl trifluoromethanesulfonate (12.1 g, yield: 62%) as a yellow oil.

Step 2—Synthesis of (S)—N,N-dimethyl-6,7-di-hydro-5H-pyrazolo[5,1-b][1,3]oxazin-6-amine

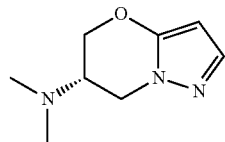

A solution of (R)-6,7-dihydro-5H-pyrazolo[5,1-b][1,3]oxazin-6-yl trifluoromethanesulfonate (12.1 g, 44.5 mmol) and dimethylamine (33% in water, 20 mL) in MeOH (20 mL) was stirred at room temperature for 16 hours. The reaction mixture was concentrated and the crude residue was purified by reverse phase column (0~60% MeCN in H$_2$O) to give (S)—N,N-dimethyl-6,7-dihydro-5H-pyrazolo[5,1-b][1,3]oxazin-6-amine (1.1 g, yield: 15%) as a yellow solid.

Step 3—Synthesis of (S)-3-bromo-N,N-dimethyl-6,7-dihydro-5H-pyrazolo[5,1-b][1,3]oxazin-6-amine

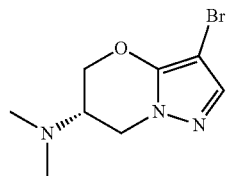

NBS (1.7 g, 11.2 mmol) was added portion-wise to a solution of (S)—N,N-dimethyl-6,7-dihydro-5H-pyrazolo[5,1-b][1,3]oxazin-6-amine (1.7 g, 10.2 mmol) in MeCN (40 mL) at 0° C. at room temperature. After 2 hours, the reaction was filtered and the filtrate was purified by reverse phase column (5% 95% MeCN in H$_2$O) to give (S)-3-bromo-N,N-dimethyl-6,7-dihydro-5H-pyrazolo[5,1-b][1,3]oxazin-6-amine (1.9 g, yield: 76%) as a yellow solid.

Step 4—Synthesis of (6S)-6-(dimethylamino)-N'-trityl-6,7-dihydro-5H-pyrazolo[5,1-b][1,3]oxazine-3-sulfonimidamide

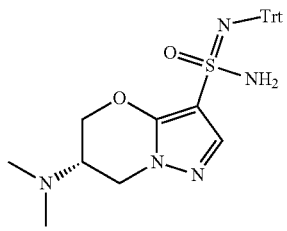

n-BuLi (2.5 M in hexane, 3.0 mL, 7.4 mmol) was added dropwise to a solution of (S)-3-bromo-N,N-dimethyl-6,7-dihydro-5H-pyrazolo[5,1-b][1,3]oxazin-6-amine (1.4 g, 5.7 mmol) in THF (15 mL) at −78° C. After 1 hour, a solution of TrtNSO (2.3 g, 7.4 mmol) in THF (10 mL) was added dropwise. The reaction was allowed to stir for 20 minutes and then was placed in a 0° C. ice bath. After stirring for an additional 10 minutes, tert-butyl hypochlorite (807 mg, 7.4 mmol) was added. The reaction stirred for 20 minutes, then NH$_3$ gas was bubbled through the mixture for 5 minutes. The resulting solution was allowed to warm to room temperature and stirred for an additional 16 hours. The reaction was concentrated to dryness and the crude residue was purified by reverse phase column (5% 95% MeCN in H$_2$O) to give (6S)-6-(dimethylamino)-N'-trityl-6,7-dihydro-5H-pyrazolo[5,1-b][1,3]oxazine-3-sulfonimidamide (1.1 g, yield: 39%) as a yellow solid. MS: m/z 488.6 (M+H$^+$).

Step 5—Synthesis of (6S)-6-(dimethylamino)-N-((8-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

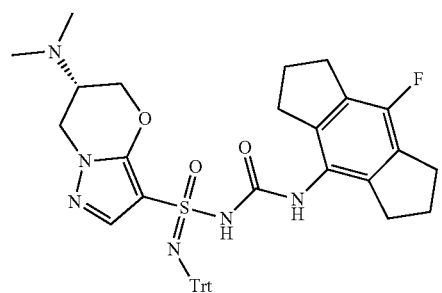

MeONa (73 mg, 1.4 mmol) was added to a solution of (6S)-6-(dimethylamino)-N'-trityl-6,7-dihydro-5H-pyrazolo[5,1-b][1,3]oxazine-3-sulfonimidamide (600 mg, 1.2 mmol) in THF (10 mL) at room temperature. After 5 minutes, the reaction was heated at 45° C. for 20 minutes to give a sodium salt suspension. The reaction was cooled to room temperature and a solution of 4-fluoro-8-isocyanato-1,2,3,5,6,7-hexahydro-s-indacene (crude, ~1.4 mmol) in THF (15 mL) was added. After 16 hours, the reaction was concentrated and the crude residue was purified by reverse phase column (5% 95% MeCN in H$_2$O) to give (6S)-6-(dimethylamino)-N-((8-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide (450 mg, yield: 52%) as a yellow solid. MS: m/z 705.7 (M+H$^+$).

Step 6—(S,6S)-6-(dimethylamino)-N-((8-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide and (R,6S)-6-(dimethylamino)-N-((8-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide

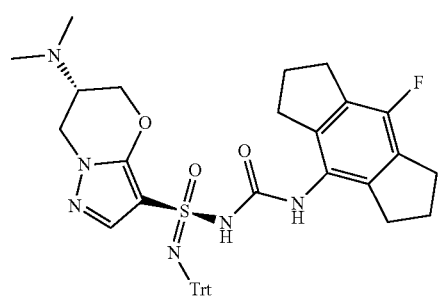

and

-continued

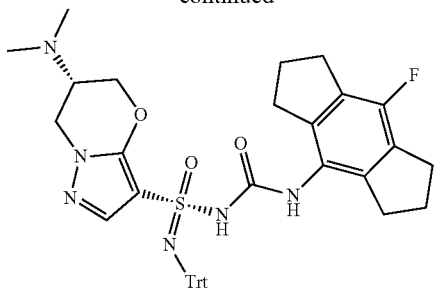

(6S)-6-(dimethylamino)-N-((8-fluoro-1,2,3,5,6,7-hexahydro-s-indacen-4-yl)carbamoyl)-N'-trityl-6,7-dihydro-5H-pyrazolo[5,1-b][1,3]oxazine-3-sulfonimidamide (450 mg, 0.6 mmol) was separated by chiral prep-HPLC to give two isomers of unknown absolute stereochemistry as white solids (peak 1, 160 mg; peak 2, 210 mg).

Step 7—Synthesis of (R,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 44 and example 45)

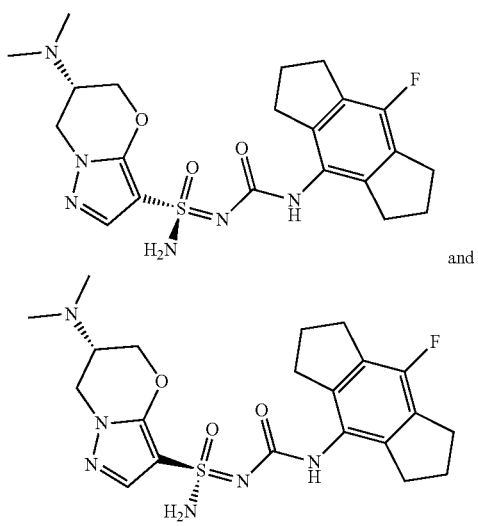

Methanesulfonic acid (3 drops) was added to a solution of the material from Peak 1 (160 mg, 0.2 mmol) in DCM (4 mL) at 0° C. After 30 minutes, the reaction was adjusted to pH=8 with the addition of saturated aqueous NaHCO₃. The resulting precipitate was collected by filtration, washed with water (2 mL), DCM (2 mL) and dried to deliver (R,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (68 mg, yield: 64%) as a white solid. Stereochemistry was arbitrarily assigned to each stereoisomer. $^1$H NMR (400 MHz, DMSO-$d_6$): δ=8.17 (brs, 1H), 7.52 (s, 1H), 7.27 (s, 2H), 4.45-4.41 (m, 2H), 4.24-4.13 (m, 2H), 2.91-2.87 (m, 1H), 2.80 (t, J=7.6 Hz, 4H), 2.70-2.66 (m, 4H), 2.26 (s, 6H), 2.03-1.95 (m, 4H). MS: m/z 463.1 (M+H⁺).

The material from peak 2 was deprotected and isolated in the same manner to deliver (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide. Stereochemistry was arbitrarily assigned to each stereoisomer. $^1$H NMR (400 MHz, DMSO-$d_6$): δ=8.12 (brs, 1H), 7.50 (s, 1H), 7.15 (s, 2H), 4.44-4.42 (m, 2H), 4.25-4.13 (m, 2H), 2.90-2.88 (m, 1H), 2.80 (t, J=7.6 Hz, 4H), 2.73 (t, J=7.6 Hz, 4H), 2.29 (s, 6H), 2.03-1.96 (m, 4H). MS: m/z 463.1 (M+H⁺).

Example 46 and Example 47

(R,6S)—N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide

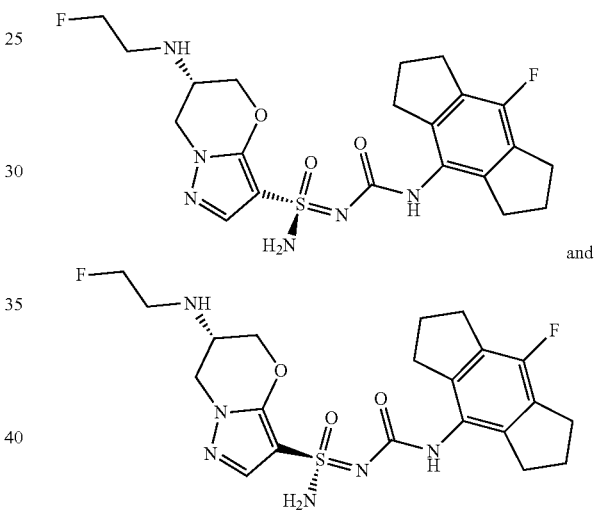

(R,6S)—N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide and (S,6S)—N'-((8-fluoro-1,2,3,5,6,7-hexahydro-s-indacen-4-yl)carbamoyl)-6-((2-fluoroethyl)amino)-6,7-dihydro-5H-pyrazolo[5,1-b][1,3]oxazine-3-sulfonimidamide were prepared using the general procedure described for the preparation of (R,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 44 and example 45) by replacing (S)—N,N-dimethyl-6,7-dihydro-5H-pyrazolo[5,1-b][1,3]oxazin-6-amine with tert-butyl (S)-(6,7-dihydro-5H-pyrazolo[5,1-b][1,3]oxazin-6-yl)(2-fluoroethyl)carbamate in Step 3. After prep-HPLC two isomers of unknown absolute stereochemistry were isolated.

Peak 1: $^1$H NMR (400 MHz, DMSO-$d_6$): δ=8.21 (brs, 1H), 7.57 (s, 1H), 7.23 (s, 2H), 4.70-4.21 (m, 7H), 2.83-2.62 (m, 10H), 2.04-1.97 (m, 5H). MS: m/z 481.1 (M+H⁺).

Peak 2: $^1$H NMR (400 MHz, DMSO-$d_6$): δ=8.22 (brs, 1H), 7.61 (s, 1H), 7.32 (s, 2H), 4.72-4.45 (m, 5H), 4.28-4.22

(m, 1H), 3.95-3.92 (m, 1H), 2.83-2.67 (m, 10H), 2.08-1.97 (m, 5H). MS: m/z 481.1 (M+H⁺).

Example 48 and Example 49

(R,6S)—N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide

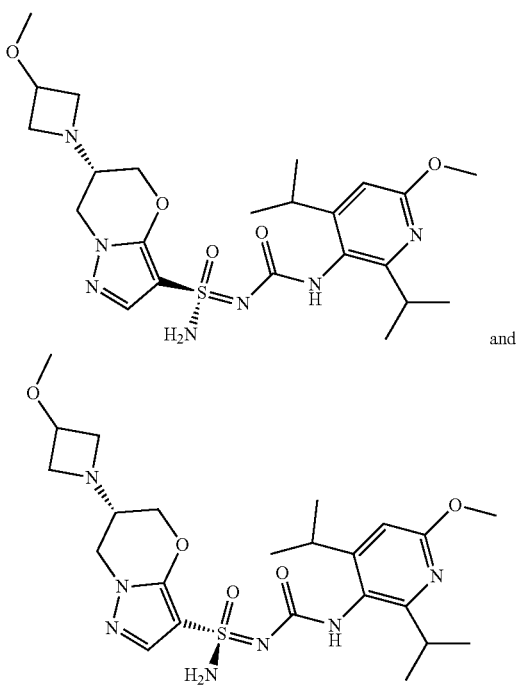

(R,6S)—N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-(3-methoxyazetidin-1-yl)-6,7-dihydro-5H-pyrazolo[5,1-b][1,3]oxazine-3-sulfonimidamide were prepared using the general procedure described for the preparation of (R,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (Example 38 and Example 39) by replacing 4-isocyanato-1,2,3,5,6,7-hexahydro-s-indacene with 3-isocyanato-2,4-diisopropyl-6-methoxypyridine in Step 4. After prep-HPLC two isomers of unknown absolute stereochemistry were isolated.

Peak 1: ¹H NMR (400 MHz, DMSO-d₆): δ=8.02 (s, 1H), 7.51 (s, 1H), 7.33 (s, 2H), 6.45 (s, 1H), 4.26-4.20 (m, 2H), 4.13 (dd, J=12.8, 4.0 Hz, 1H), 3.96-3.91 (m, 1H), 3.88-3.83 (m, 1H), 3.81 (s, 3H), 3.57-3.51 (m, 2H), 3.20-3.18 (m, 1H), 3.15 (s, 3H), 3.03-2.97 (m, 4H), 1.18-1.06 (m, 12H). MS: m/z 522.2 (M+H⁺).

Peak 2: ¹H NMR (400 MHz, DMSO-d₆): δ=8.00 (s, 1H), 7.47 (s, 1H), 7.26 (s, 2H), 6.45 (s, 1H), 4.30-4.28 (m, 1H), 4.20-4.10 (m, 2H), 3.96-3.91 (m, 1H), 3.88-3.85 (m, 1H), 3.81 (s, 3H), 3.58-3.52 (m, 2H), 3.20-3.18 (m, 1H), 3.15 (s, 3H), 3.03-2.97 (m, 4H), 1.18-1.06 (m, 12H). MS: m/z 522.2 (M+H⁺)

Example 50 and Example 51

(R,6S)—N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-(methylamino)-6,7-dihydro-5H-pyrazolo[5,1-b][13]oxazine-3-sulfonimidamide

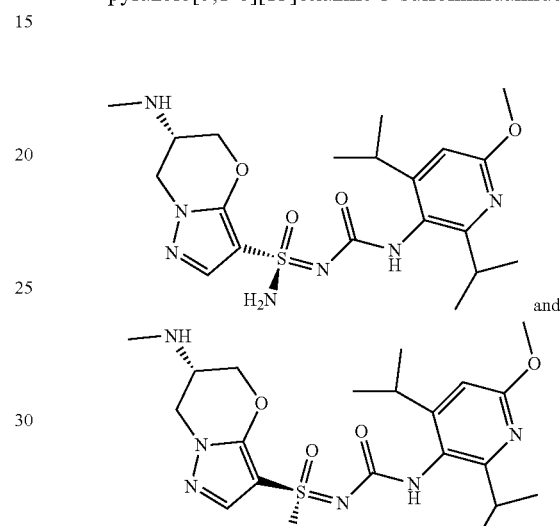

Step 1—Synthesis of tert-butyl ((6S)-3-(N-((2,4-diisopropyl-6-methoxypyridin-3-yl)carbamoyl)-N'-tritylsulfamidimidoyl)-6,7-dihydro-5H-pyrazolo[5,1-b][1,3]oxazin-6-yl)(methyl)carbamate

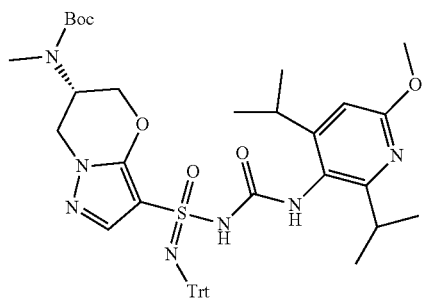

MeONa (81 mg, 1.5 mmol) was added to a solution of tert-butyl methyl((6S)-3-(N-tritylsulfamidimidoyl)-6,7-dihydro-5H-pyrazolo[5,1-b][1,3]oxazin-6-yl)carbamate (573 mg, 1.0 mmol) in THF (10 mL) at room temperature. After 30 minutes, 4-isocyanato-1,2,3,5,6,7-hexahydro-s-indacene (234 mg, 1.0 mmol) was added and the mixture was stirred for an additional 16 hours. The reaction was concentrated and the crude residue was purified by reverse phase column (5~95% MeCN in H₂O) to give tert-butyl ((6S)-3-(N-((2,4-diisopropyl-6-methoxypyridin-3-yl)carbamoyl)-N'-tritylsulfamidimidoyl)-6,7-dihydro-5H-pyrazolo[5,1-b][1,3]oxazin-6-yl)(methyl)carbamate (500 mg, yield: 62%) as a yellow solid.

Step 2—tert-butyl ((S)-3-((S)—N-((2,4-diisopropyl-6-methoxypyridin-3-yl)carbamoyl)-N'-tritylsulfamidimidoyl)-6,7-dihydro-5H-pyrazolo[5,1-b][1,3]oxazin-6-yl)(methyl)carbamate and tert-butyl ((S)-3-((R)—N-((2,4-diisopropyl-6-methoxypyridin-3-yl)carbamoyl)-N'-tritylsulfamidimidoyl)-6,7-dihydro-5H-pyrazolo[5,1-b][1,3]oxazin-6-yl)(methyl)carbamate

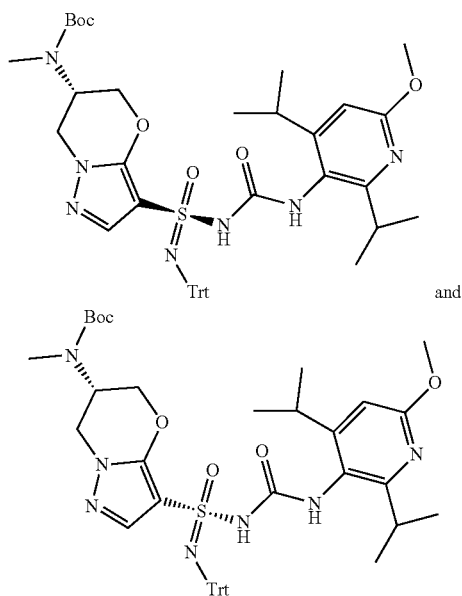

tert-butyl ((6S)-3-(N-((2,4-diisopropyl-6-methoxypyridin-3-yl)carbamoyl)-N-tritylsulfamidimidoyl)-6,7-dihydro-5H-pyrazolo[5,1-b][1,3]oxazin-6-yl)(methyl)carbamate (500 mg, 0.6 mmol) was separated by chiral prep-HPLC to give two isomers of unknown absolute stereochemistry as white solids (peak 1, 201 mg, yield: 40%; peak 2, 200 mg, yield: 44%).

Step 3—Synthesis of (R,6S)—N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide (Example 50 and Example 51)

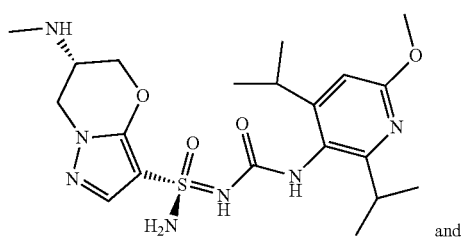

and

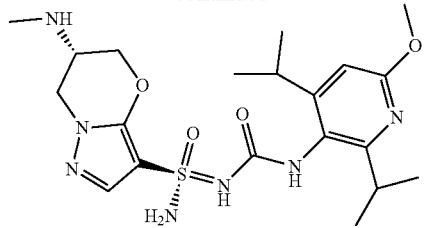

Methanesulfonic acid (5 drops) was added to a solution of the material from peak 1 (200 mg, 0.25 mmol) in DCM (5 mL) at room temperature. After 30 minutes, the reaction was adjusted to pH=8 with the addition of saturated aqueous NaHCO$_3$. The reaction mixture was concentrated and the crude residue was purified by reverse phase column (0~95% MeCN in H$_2$O) to give crude product. The crude material was further purified by prep-HPLC (NH$_4$HCO$_3$) to deliver (R,6S)—N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide (60 mg, yield: 52%) as a white solid. Stereochemistry was arbitrarily assigned to each stereoisomer. $^1$H NMR (400 MHz, DMSO-d$_6$): δ=7.99 (s, 1H), 7.49 (s, 1H), 7.25 (s, 2H), 6.45 (s, 1H), 4.32-4.20 (m, 3H), 3.93 (dd, J=12.4, 4.4 Hz, 1H), 3.80 (s, 3H), 3.21-3.16 (m, 2H), 3.05-2.98 (m, 1H), 2.35 (s, 3H), 1.10-1.06 (m, 12H). MS: m/z 466.1 (M+H$^+$).

Methanesulfonic acid (2 drops) was added to a solution of the material from peak 2 (171 mg, 0.24 mmol) in DCM (4 mL) at room temperature. After 10 minutes, the reaction was adjusted to pH=8 with the addition of saturated aqueous NaHCO$_3$. The precipitate was collected by filtration and dried to deliver (S,6S)—N'-((2,4-diisopropyl-6-methoxypyridin-3-yl)carbamoyl)-6-(methylamino)-6,7-dihydro-5H-pyrazolo[5,1-b][1,3]oxazine-3-sulfonimidamide (86 mg, yield: 67%) as a white solid. Stereochemistry was arbitrarily assigned to each stereoisomer. $^1$H NMR (400 MHz, DMSO-d$_6$): δ=8.02 (s, 1H), 7.51 (s, 1H), 7.27 (s, 2H), 6.45 (s, 1H), 4.37-4.20 (m, 3H), 3.93 (dd, J=12.4, 4.8 Hz, 1H), 3.80 (s, 3H), 3.21-3.16 (m, 2H), 3.05-2.97 (m, 1H), 2.35 (s, 3H), 1.10-1.06 (m, 12H). MS: m/z 466.2 (M+H$^+$).

Example 52 and Example 53

(R,6S)—N-((2,4-diisopropyl-6-methoxypyridin-3-yl)carbamoyl)-6-methoxy-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-methoxy-6,7-dihydro-5H-pyrazolo[5,1-b][1,3]oxazine-3-sulfonimidamide

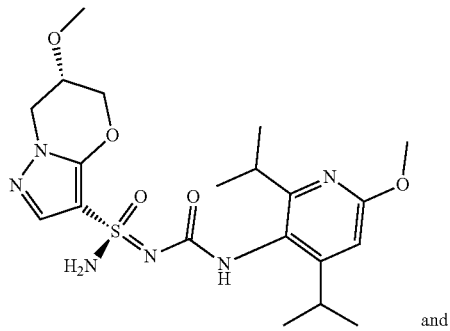

and

-continued

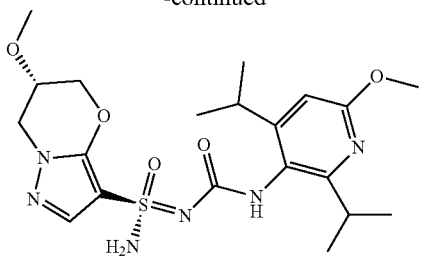

Step 1—Synthesis of (6S)-6-methoxy-N'-trityl-6,7-dihydro-5H-pyrazolo[5,1-b][1,3]oxazine-3-sulfonimidamide

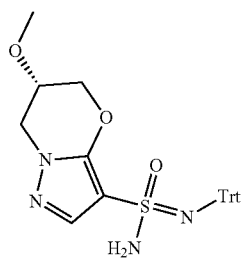

n-BuLi (2.5 M in hexane, 1.5 mL, 3.8 mmol) was added dropwise to a solution of (S)-3-bromo-6-methoxy-6,7-dihydro-5H-pyrazolo[5,1-b][1,3]oxazine (900 mg, 3.8 mmol) in THF (18 mL) at −78° C. After 30 minutes, a solution of TrtNSO (1.2 g, 3.8 mmol) in THF (5 mL) was added dropwise. The reaction was allowed to stir for 30 minutes and then was placed in a 0° C. ice bath. After stirring for an additional 10 minutes, tert-butyl hypochlorite (453 mg, 4.2 mmol) was added. The reaction stirred for 20 minutes, then NH₃ gas was bubbled through the mixture for 5 minutes. The resulting solution was allowed to warm to room temperature and stirred for an additional 16 hours. The reaction mixture was concentrated to dryness and the crude residue was purified by reverse phase column (0~95% MeCN in H₂O) to give (6S)-6-methoxy-N'-trityl-6,7-dihydro-5H-pyrazolo[5,1-b][1,3]oxazine-3-sulfonimidamide (800 mg, yield: 44%) as a yellow solid. MS: m/z 475.5 (M+H⁺).

Step 2—Synthesis of (6S)—N-((2,4-diisopropyl-6-methoxypyridin-3-yl)carbamoyl)-6-methoxy-N'-trityl-6,7-dihydro-5H-pyrazolo[5,1-b][1,3]oxazine-3-sulfonimidamide

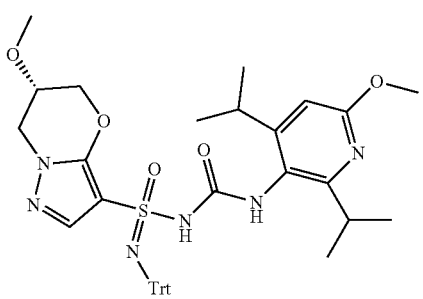

MeONa (43 mg, 0.8 mmol) was added to a solution of (6S)-6-methoxy-N'-trityl-6,7-dihydro-5H-pyrazolo[5,1-b][1,3]oxazine-3-sulfonimidamide (250 mg, 0.5 mmol) in THF (10 mL) at room temperature. After stirring for 20 minutes, a sodium salt suspension had formed.

In a separate flask, triphosgene (98 mg, 0.3 mmol) was added in one portion to a solution of 2,4-diisopropyl-6-methoxypyridin-3-amine (208 mg, 1.0 mmol) and triethylamine (152 mg, 1.5 mmol) in THF (10 mL) at 0° C. under an atmosphere of N₂. After 5 minutes, the reaction was warmed to room temperature and stirred for 10 minutes. The reaction mixture was filtered and the filtrate was added to the sodium salt suspension. After 16 hours, the reaction was concentrated and the crude residue was purified by reverse phase column (5~95% MeCN in H₂O) to give (6S)—N-((2,4-diisopropyl-6-methoxypyridin-3-yl)carbamoyl)-6-methoxy-N'-trityl-6,7-dihydro-5H-pyrazolo[5,1-b][1,3]oxazine-3-sulfonimidamide (244 mg, yield: 65%) as a yellow solid. MS: m/z 709.7 (M+H⁺).

Step 3—(S,6S)—N-((2,4-diisopropyl-6-methoxypyridin-3-yl)carbamoyl)-6-methoxy-N'-trityl-6,7-dihydro-5H-pyrazolo[5,1-b][1,3]oxazine-3-sulfonimidamide and (R,6S)—N-((2,4-diisopropyl-6-methoxypyridin-3-yl)carbamoyl)-6-methoxy-N'-trityl-6,7-dihydro-5H-pyrazolo[5,1-b][1,3]oxazine-3-sulfonimidamide

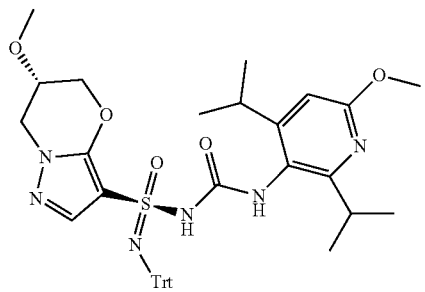

and

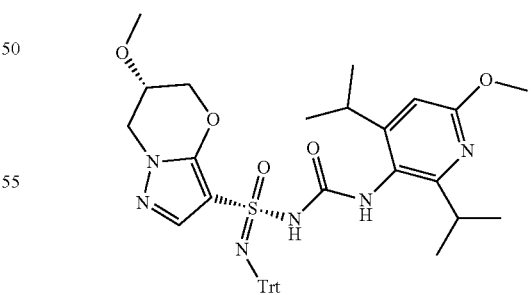

(6S)—N-((2,4-diisopropyl-6-methoxypyridin-3-yl)carbamoyl)-6-methoxy-N'-trityl-6,7-dihydro-5H-pyrazolo[5,1-b][1,3]oxazine-3-sulfonimidamide (244 mg, 0.3 mmol) was separated by chiral prep-HPLC to give two isomers of unknown absolute stereochemistry as yellow solids (peak 1, 140 mg; peak 2, 120 mg).

Step 4—Synthesis of (R,6S)—N'-((2,4-diisopropyl-6-methoxypyridin-3-yl)carbamoyl)-6-methoxy-6,7-dihydro-5H-pyrazolo[5,1-b][1,3]oxazine-3-sulfonimidamide and (S,6S)—N'-((2,4-diisopropyl-6-methoxypyridin-3-yl)carbamoyl)-6-methoxy-6,7-dihydro-5H-pyrazolo[5,1-b][1,3]oxazine-3-sulfonimidamide (Example 52 and Example 53)

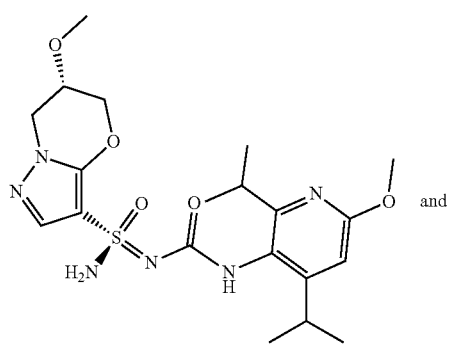

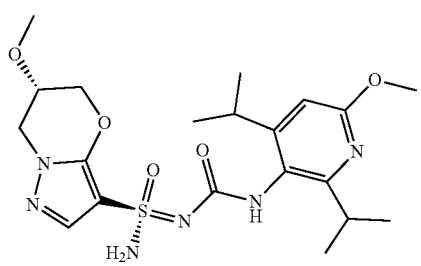

Methanesulfonic acid (6 drops) was added to a solution of the material from Peak 1 (140 mg, 0.2 mmol) in THF (2 mL) at 0° C. After 30 minutes, the reaction was adjusted to pH=8 with the addition of saturated aqueous NaHCO₃. The reaction mixture was concentrated and the crude residue was purified by reverse phase column (0~95% MeCN in H₂O) to deliver (R,6S)—N'-((2,4-diisopropyl-6-methoxypyridin-3-yl)carbamoyl)-6-methoxy-6,7-dihydro-5H-pyrazolo[5,1-b][1,3]oxazine-3-sulfonimidamide (63 mg, yield: 68%) as a white solid. Stereochemistry was arbitrarily assigned to each stereoisomer. $^1$H NMR (400 MHz, DMSO-$d_6$): δ=8.06 (s, 1H), 7.56 (s, 1H), 7.35 (s, 2H), 6.48 (s, 1H), 4.64-4.60 (m, 1H), 4.33-4.22 (m, 3H), 4.07 (s, 1H), 3.84 (s, 3H), 3.39 (s, 3H), 3.24-3.19 (m, 1H), 3.06-3.01 (m, 1H), 1.22-1.09 (m, 12H). MS: m/z 467.1 (M+H⁺).

The material from peak 2 was deprotected and isolated in the same manner to deliver (S,6S)—N'-((2,4-diisopropyl-6-methoxypyridin-3-yl)carbamoyl)-6-methoxy-6,7-dihydro-5H-pyrazolo[5,1-b][1,3]oxazine-3-sulfonimidamide. Stereochemistry was arbitrarily assigned to each stereoisomer. $^1$H NMR (400 MHz, DMSO-$d_6$): δ=8.06 (s, 1H), 7.53 (s, 1H), 7.32 (s, 2H), 6.48 (s, 1H), 4.66-4.62 (m, 1H), 4.30-4.21 (m, 3H), 4.08-4.05 (m, 1H), 3.84 (s, 3H), 3.40 (s, 3H), 3.27-3.18 (m, 1H), 3.09-3.02 (m, 1H), 1.17-1.09 (m, 12H). MS: m/z 467.1 (M+H⁺).

Example 54 and Example 55 (R,6S)—N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide

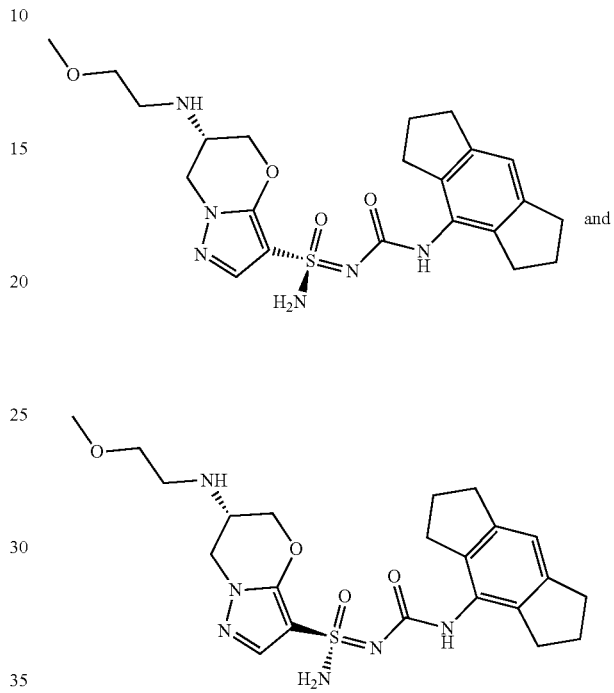

(R,6S)—N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-((2-methoxyethyl)amino)-6,7-dihydro-5H-pyrazolo[5,1-b][1,3]oxazine-3-sulfonimidamide were prepared using the general procedure described for the preparation of (R,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 35 and Example 36) by replacing 1-bromo-2-fluoroethane with 1-bromo-2-methoxyethane in Step 1. After prep-HPLC two isomers of unknown absolute stereochemistry were isolated.

Peak 1: $^1$H NMR (400 MHz, DMSO-$d_6$): δ=8.17 (brs, 1H), 7.51 (s, 1H), 7.24 (s, 2H), 6.86 (s, 1H), 4.39 (dd, J=11.6, 2.8 Hz, 1H), 4.24 (dd, J=12.0, 5.2 Hz, 2H), 3.95 (dd, J=12.4, 5.2 Hz, 1H), 3.37 (t, J=5.6 Hz, 2H), 3.31 (overlap, 1H), 3.23 (s, 3H), 2.77 (t, J=7.2 Hz, 6H), 2.70 (t, J=7.2 Hz, 4H), 2.09-2.01 (m, 1H), 2.00-1.89 (m, 4H). MS: m/z 475.1 (M+H⁺).

Peak 2: $^1$H NMR (400 MHz, DMSO-$d_6$): δ=8.16 (brs, 1H), 7.52 (s, 1H), 7.24 (s, 2H), 6.86 (s, 1H), 4.39 (dd, J=9.6, 2.0 Hz, 1H), 4.25-4.19 (m, 2H), 3.94 (dd, J=12.0, 4.8 Hz, 1H), 3.37 (t, J=5.6 Hz, 2H), 3.31 (overlap, 1H), 3.23 (s, 3H), 2.77 (t, J=5.6 Hz, 6H), 2.70 (t, J=7.2 Hz, 4H), 2.10-2.00 (m, 1H), 1.97-1.89 (m, 4H). MS: m/z 475.1 (M+H⁺).

Example 56 and Example 57

(R,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide

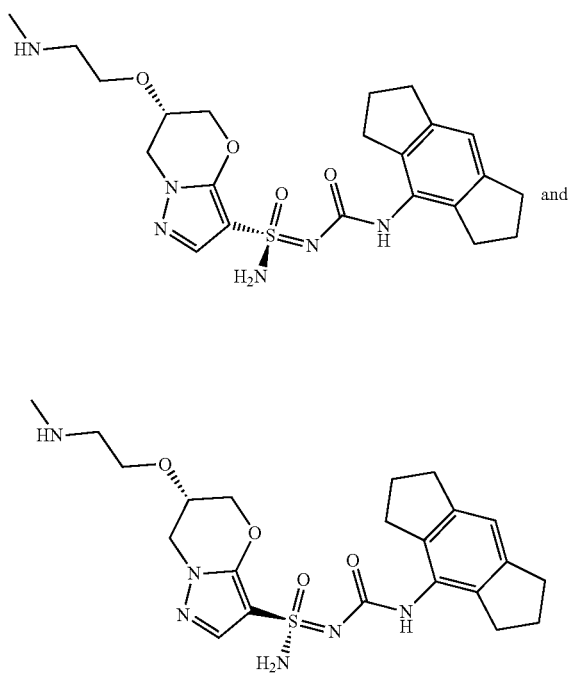 [SMILES: CNCCO[C@@H]1COc2c([S@](N)(=O)=NC(=O)Nc3c4c(cc5c3CCC5)CCC4)cnn2C1 ; CNCCO[C@@H]1COc2c([S@@](N)(=O)=NC(=O)Nc3c4c(cc5c3CCC5)CCC4)cnn2C1]

Step 1—Synthesis of tert-butyl (S)-(2-((6,7-dihydro-5H-pyrazolo[5,1-b][1,3]oxazin-6-yl)oxy)ethyl)(methyl)carbamate

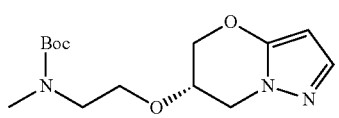 [SMILES: CN(CCO[C@@H]1COc2ccnn2C1)C(=O)OC(C)(C)C]

To a solution of (S)-2-((6,7-dihydro-5H-pyrazolo[5,1-b][1,3]oxazin-6-yl)oxy)-N-methylethanamine (900 mg, 4.6 mmol) in dioxane (8 mL) was added a solution of NaOH (910 mg, 22.8 mmol) in H$_2$O (8 mL) and Boc$_2$O (1.1 g, 5.0 mmol) at 0° C. After 5 minutes, the reaction was warmed room temperature and stirred for an additional 3 hours. The reaction was diluted with H$_2$O (30 mL) and extracted with EtOAc (30 mL). The organic layer was dried over Na$_2$SO$_4$, concentrated and the crude residue was purified by silica gel column (PE/EtOAc=1/2 to 100% EtOAc) to deliver tert-butyl (S)-(2-((6,7-dihydro-5H-pyrazolo[5,1-b][1,3]oxazin-6-yl)oxy)ethyl)(methyl)carbamate (1.0 g, yield: 79%) as a colorless oil. MS: m/z 298.4 (M+H$^+$).

Step 2~6—(R,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide (Example 56 and Example 57)

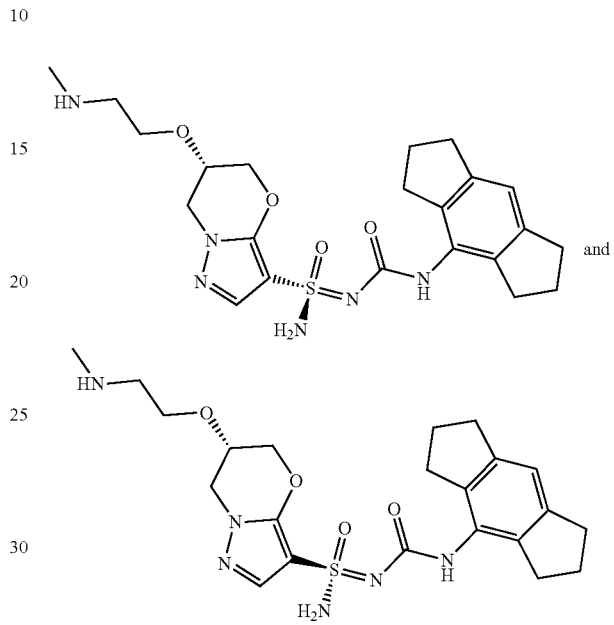

(R,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide and (S,6S)—N'-((1,2,3,5,6,7-hexahydro-s-indacen-4-yl)carbamoyl)-6-(2-(methylamino)ethoxy)-6,7-dihydro-5H-pyrazolo[5,1-b][1,3]oxazine-3-sulfonimidamide were prepared using the general procedure described for the preparation of (R,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-(dimethylamino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 33 and Example 34) by replacing (S)—N,N-dimethyl-6,7-dihydro-5H-pyrazolo[5,1-b][1,3]oxazin-6-amine with tert-butyl (S)-(2-((6,7-dihydro-5H-pyrazolo[5,1-b][1,3]oxazin-6-yl)oxy)ethyl)(methyl)carbamate in Step 2. After prep-HPLC, two isomers of unknown absolute stereochemistry were isolated.

Peak 1: $^1$H NMR (400 MHz, DMSO-d$_6$): δ=8.17 (brs, 1H), 7.54 (s, 1H), 6.86 (s, 1H), 4.58-4.54 (m, 1H), 4.32-4.24 (m, 2H), 4.19-4.15 (m, 2H), 3.65-3.59 (m, 2H), 2.78 (t, J=7.2 Hz, 4H), 2.69 (t, J=7.2 Hz, 4H), 2.60-2.58 (m, 2H), 2.25 (s, 3H), 1.97-1.90 (m, 4H). MS: m/z 475.1 (M+H$^+$).

Peak 2: $^1$H NMR (400 MHz, DMSO-d$_6$): δ=8.15 (brs, 1H), 7.52 (s, 1H), 6.85 (s, 1H), 4.58-4.54 (m, 1H), 4.29-4.25 (m, 2H), 4.19-4.15 (m, 2H), 3.62-3.59 (m, 2H), 2.78 (t, J=7.2 Hz, 4H), 2.70 (t, J=7.2 Hz, 4H), 2.58 (t, J=5.6 Hz, 2H), 2.24 (s, 3H), 1.97-1.90 (m, 4H). MS: m/z 475.1 (M+H$^+$).

Example 58 and Example 59

(R,6S)-6-amino-N'-((1,2,3,5,6,7-hexahydro-s-indacen-4-yl)carbamoyl)-6,7-dihydro-5H-pyrazolo[5,1-b][1,3]

oxazine-3-sulfonimidamide and (S,6S)-6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide

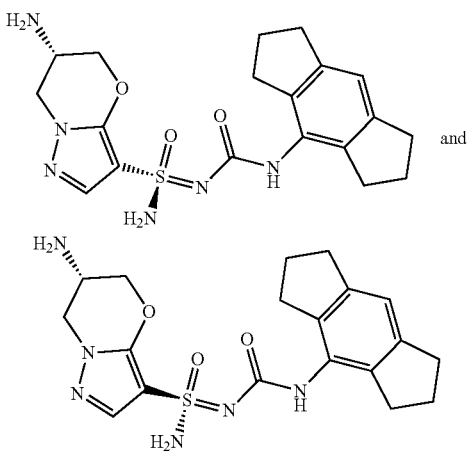
and (R,6S)-6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-amino-N'-((1,2,3,5,6,7-hexahydro-s-indacen-4-yl)carbamoyl)-6,7-dihydro-5H-pyrazolo[5,1-b][1,3]oxazine-3-sulfonimidamide were prepared using the general procedure described for the preparation of (R,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide and (S,6S)-6-((2-fluoroethyl)amino)-N'-((1,2,3,5,6,7-hexahydro-s-indacen-4-yl)carbamoyl)-6,7-dihydro-5H-pyrazolo[5,1-b][1,3]oxazine-3-sulfonimidamide (Example 35 and Example 36) by replacing 1-bromo-2-fluoroethane with bromo(methoxy)methane in Step 1. After prep-HPLC two isomers of unknown absolute stereochemistry were isolated.

Peak 1: $^1$H NMR (400 MHz, DMSO-$d_6$): δ=8.19 (brs, 1H), 7.52 (s, 1H), 7.25 (brs, 2H), 6.86 (s, 1H), 4.32 (dd, J=10.8, 2.4 Hz, 1H), 4.21 (dd, J=12.8, 4.8 Hz, 1H), 4.04-4.00 (m, 1H), 3.79-3.74 (m, 1H), 3.45-3.40 (m, 1H), 2.79 (t, J=7.2 Hz, 4H), 2.70 (t, J=7.2 Hz, 4H), 2.32-1.89 (m, 4H). MS: m/z 417.1 (M+H$^+$).

Peak 2: $^1$H NMR (400 MHz, DMSO-$d_6$): δ=8.16 (brs, 1H), 7.52 (s, 1H), 7.24 (brs, 2H), 6.86 (s, 1H), 4.30 (d, J=5.6 Hz, 1H), 4.21 (dd, J=12.0, 4.4 Hz, 1H), 4.04-4.00 (m, 1H), 3.77 (dd, J=12.0, 6.0 Hz, 1H), 3.47-3.40 (m, 1H), 2.77 (t, J=6.8 Hz, 4H), 2.70 (t, J=7.2 Hz, 4H), 2.07-1.91 (m, 4H). MS: m/z 417.1 (M+H$^+$).

Example 60

N'-((1,2,3,5,6,7-hexahydro-s-indacen-4-yl)carbamoyl)-4,5,6,7-tetrahydropyrazolo[1,5-a]pyridine-3-sulfonimidamide

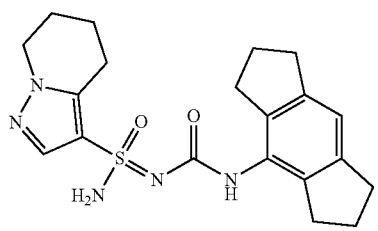 [SMILES: NS(=O)(=NC(=O)Nc1c2c(cc3c1CCC3)CCC2)c1cnn2c1CCCC2]

Step 1—Synthesis of N-trityl-4,5,6,7-tetrahydropyrazolo[1,5-a]pyridine-3-sulfinamide

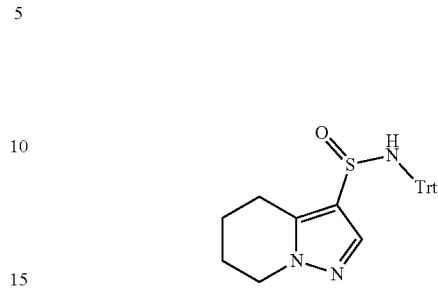

n-BuLi (2.5 Min hexane, 0.72 mL, 1.79 mmol) was added dropwise to a solution of 3-bromo-4,5,6,7-tetrahydropyrazolo[1,5-a]pyridine (300 mg, 1.49 mmol) in anhydrous THF (2 mL) at −78° C. After 1 hour, a solution of TrtNSO (547 mg, 1.79 mmol) in THF (2 mL) was added dropwise. The reaction was allowed to stir for 25 minutes and then was placed in a 0° C. ice bath. After 20 minutes, water (20 mL) was added. The mixture was extracted with EtOAc (3×20 mL). The combined organic layers were washed with water, brine, dried over Na$_2$SO$_4$, concentrated and the crude residue was purified by silica chromatography (EtOAc/Hex 0 to 100%) to afford N-trityl-4,5,6,7-tetrahydropyrazolo[1,5-a]pyridine-3-sulfinamide (130 mg, 20.4%) as a white solid. LCMS: m/z 428 (M+H$^+$).

Step 2—Synthesis of N'-trityl-4,5,6,7-tetrahydropyrazolo[1,5-a]pyridine-3-sulfonimidamide

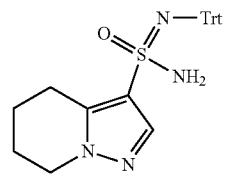

tert-Butyl hydroperoxide (38 μL, 0.395 mmol) was added to a solution of N-trityl-4,5,6,7-tetrahydropyrazolo[1,5-a]pyridine-3-sulfinamide (130 mg, 0.304 mmol) in THF (1 mL) at 0° C. After 1 hour, ammonia (1M in THF, 1.3 mL) was added. The reaction was warmed to room temperature and was allowed to stir for an additional 3 hours. Water (20 mL) was added and the aqueous layer was extracted with EtOAc (3×15 mL). The combined organic layers were washed with brine, dried over Na$_2$SO$_4$, and concentrated under reduced pressure to afford N'-trityl-4,5,6,7-tetrahydropyrazolo[1,5-a]pyridine-3-sulfonimidamide (135 mg, 100%) as a white solid, which was used in the next step without further purification.

309

Step 3-4—Synthesis of N'-((1,2,3,5,6,7-hexahydro-s-indacen-4-yl)carbamoyl)-4,5,6,7-tetrahydropyrazolo[1,5-a]pyridine-3-sulfonimidamide (Example 60)

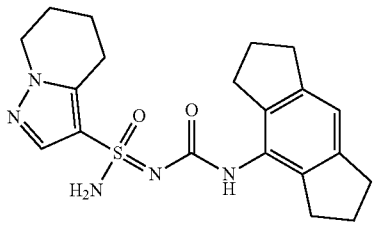 [SMILES: NS(=O)(=NC(=O)Nc1c2c(cc3c1CCC3)CCC2)c1cnn2c1CCCC2]

NaH (60% in mineral oil, 18 mg, 0.458 mmol) was added to a solution of N'-trityl-4,5,6,7-tetrahydropyrazolo[1,5-a]pyridine-3-sulfonimidamide (135 mg, 0.305 mmol) and 4-isocyanato-1,2,3,5,6,7-hexahydro-s-indacene (60.8 mg, 0.305 mmol) in THF (2 mL) at 0° C. After 5 minutes, the reaction was warmed to room temperature and stirred for an additional 1 hour. MeOH (5 mL) was added and the solvent was removed under reduced pressure to afford N-((1,2,3,5,6,7-hexahydro-s-indacen-4-yl)carbamoyl)-N'-trityl-4,5,6,7-tetrahydropyrazolo[1,5-a]pyridine-3-sulfonimidamide which was used in the next step without further purification.

The crude material was dissolved in anhydrous DCM (2 mL) and methanesulfonic acid (58.6 mg, 39.6 µL, 0.610 mmol) was added dropwise at 0° C. After 30 minutes, toluene (10 mL) was added and the solvent was removed under reduced pressure. The crude residue was dissolved in MeOH and purified by prep-HPLC to afford N'-((1,2,3,5,6,7-hexahydro-s-indacen-4-yl)carbamoyl)-4,5,6,7-tetrahydropyrazolo[1,5-a]pyridine-3-sulfonimidamide (16 mg, yield: 13%—as a mixture of enantiomers) as white solids. LCMS: m/z 400 (M+H$^+$).

Example 61 and Example 62

(S)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide and (R)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide

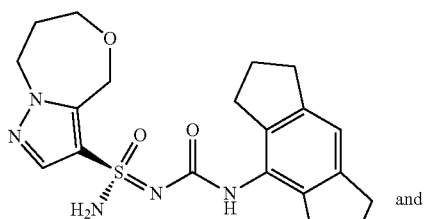

and

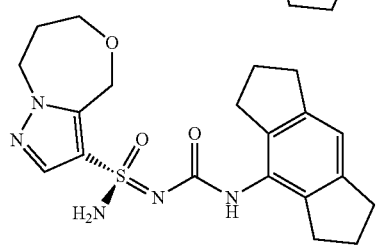

310

Step 1—Synthesis of ethyl 1-(3-hydroxypropyl)-1H-pyrazole-5-carboxylate

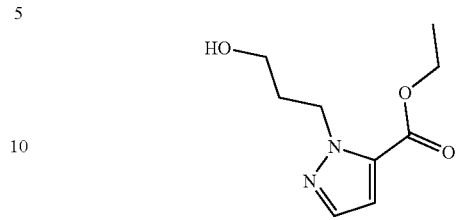

To a solution of ethyl 1H-pyrazole-5-carboxylate (5.0 g, 35.7 mmol) in DMF (35 mL) was added 3-bromo-1-propanol (9.9 g, 71.3 mmol) and K$_2$CO3 (14.8 g, 107 mmol). The mixture was stirred at 60° C. for 16 hours. After cooling to room temperature, the reaction mixture was filtered and concentrated. The residue was purified by silica gel chromatography (0-35% EtOAc in petroleum ether) to give ethyl 1-(3-hydroxypropyl)-1H-pyrazole-5-carboxylate (4 g, yield: 56%) as a colorless oil. The regio-isomer was discarded during the purification. $^1$H NMR (400 MHz, CDCl$_3$) δ=7.49 (d, J=1.6 Hz, 1H), 6.83 (d, J=1.6 Hz, 1H), 4.71 (t, J=6.4 Hz, 2H), 4.34 (q, J=7.2 Hz, 2H), 3.55-3.49 (m, 2H), 2.11-2.04 (m, 2H), 1.42-1.31 (m, 1H), 1.37 (t, J=6.8 Hz, 3H). MS: m/z 198.9 (M+H$^+$).

Step 2—Synthesis of 3-(5-(hydroxymethyl)-1H-pyrazol-1-yl)propan-1-ol

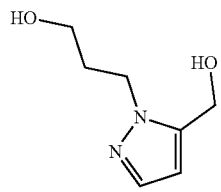

To a solution of LiAlH$_4$ (1.2 g, 30.3 mmol) in THF (80 mL) was added ethyl 1-(3-hydroxypropyl)-1H-pyrazole-5-carboxylate (4.0 g, 20.2 mmol) at 0° C. under nitrogen atmosphere. After 1 hour, the reaction was quenched with Na$_2$SO$_4$.10H$_2$O. The reaction was warmed to room temperature and was allowed to stir for 10 minutes before the solids were removed by filtration. The filtrate was concentrated to give 3-(5-(hydroxymethyl)-1H-pyrazol-1-yl)propan-1-ol (3 g, yield: 95%) as a colorless oil, which was used in the next step without further purification. MS: m/z 156.8 (M+H$^+$).

Step 3—Synthesis of 4,6,7,8-tetrahydropyrazolo[5,1-c][1,4]oxazepine

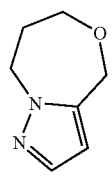

A solution of 3-(5-(hydroxymethyl)-1H-pyrazol-1-yl)propan-1-ol (1.7 g, 10.9 mmol) in phosphoric acid (30 mL, 54.4 mmol) was stirred at 130° C. for 20 hours. After cooling to room temperature, the reaction was quenched with water (40 mL). The resulting mixture was adjusted to pH=8 with saturated aqueous NaHCO$_3$, and then extracted with DCM (30 mL×2). The combined organic layers were washed with brine (30 mL×2), dried over Na$_2$SO$_4$, filtered and concentrated to give 4,6,7,8-tetrahydropyrazolo[5,1-c][1,4]oxazepine (400 mg crude) as a colorless oil, which was used in the next step without further purification. MS: m/z 139.0 (M+H$^+$).

Step 4—Synthesis of 3-bromo-4,6,7,8-tetrahydropyrazolo[5,1-c][1,4]oxazepine

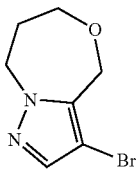 [SMILES: Brc1cnn2c1COCCC2]

To a solution of 4,6,7,8-tetrahydropyrazolo[5,1-c][1,4]oxazepine (650 mg, 4.7 mmol) in MeCN (10 mL) was added NBS (921 mg, 5.2 mmol) at 0° C. After stirring at room temperature for 16 hours, the reaction was quenched with water (20 mL) and extracted with DCM (2×20 mL). The combined organic layers were washed with brine (20 mL×2), dried over anhydrous Na$_2$SO$_4$, filtered and concentrated. The crude residue was purified by silica gel column (0-50% EtOAc in petroleum ether) to give 3-bromo-4,6,7,8-tetrahydropyrazolo[5,1-c][1,4]oxazepine (900 mg, yield: 88%) as a white solid. $^1$H NMR (400 MHz, CDCl$_3$) δ=7.33 (s, 1H), 4.66 (s, 2H), 4.46 (t, J=5.2 Hz, 2H), 4.05 (t, J=5.2 Hz, 2H), 2.05-1.96 (m, 2H). MS: m/z 216.9 (M+H$^+$).

Step 5—Synthesis of N'-trityl-4,6,7,8-tetrahydropyrazolo[5,1-c][1,4]oxazepine-3-sulfonimidamide

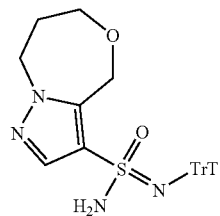

To a solution of 3-bromo-4,6,7,8-tetrahydropyrazolo[5,1-c][1,4]oxazepine (200 mg, 0.9 mmol) in THF (5 mL) was added n-BuLi (2.5 M in hexane, 0.4 mL, 1.0 mmol) dropwise at −78° C. under nitrogen atmosphere. After stirring at −78° C. for 0.5 hours, a solution of TrtNSO (310 mg, 1.0 mmol) in THF (2 mL) was added dropwise. The mixture was stirred at −78° C. for 30 minutes before being placed in an ice bath. The reaction was quenched with water (5 mL). The aqueous layer was extracted with DCM (2×10 mL). The combined organic layers were washed with brine (20 mL), dried over Na$_2$SO$_4$, filtered and concentrated. The crude residue was purified by Prep-TLC (silica, 5% methanol in DCM) to give N-trityl-4,6,7,8-tetrahydropyrazolo[5,1-c][1,4]oxazepine-3-sulfinamide (180 mg, yield: 44%) as a white solid. MS: m/z 466.1 (M+Na$^+$).

To a solution of N-trityl-4,6,7,8-tetrahydropyrazolo[5,1-c][1,4]oxazepine-3-sulfinamide (180 mg, 0.4 mmol) in THF (4 mL) was added tert-butyl hypochlorite (49 mg, 0.4 mmol) dropwise at 0° C. under nitrogen atmosphere. After stirring at 0° C. for 30 minutes, NH$_3$ gas was bubbled through the mixture for 10 minutes and the resulting mixture was stirred at room temperature for 16 hours. The mixture was concentrated and the residue was purified by silica gel column (0-50% EtOAc in petroleum ether) to give N'-trityl-4,6,7,8-tetrahydropyrazolo[5,1-c][1,4]oxazepine-3-sulfonimidamide (160 mg, yield: 86%) as a white solid. MS: m/z 481.1 (M+Na$^+$).

Step 6—Synthesis of N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide

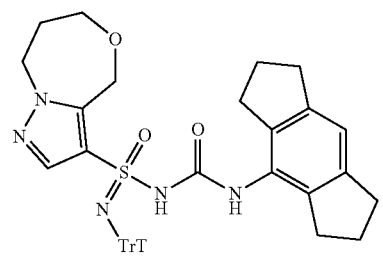

To a solution of N'-trityl-4,6,7,8-tetrahydropyrazolo[5,1-c][1,4]oxazepine-3-sulfonimidamide (160 mg, 0.3 mmol) in THF (5 mL) was added MeONa (23 mg, 0.4 mmol) at 0° C. After stirring for 15 minutes, 4-isocyanato-1,2,3,5,6,7-hexahydro-s-indacene (84 mg, 0.4 mmol) was added. The reaction mixture was stirred at room temperature for 16 hours. The reaction was quenched with MeOH (1 mL) and the mixture was concentrated. The crude residue was purified by silica gel column (0-5% methanol in DCM) to give N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide (160 mg, yield: 70%) as a white solid. $^1$H NMR (400 MHz, CDCl$_3$) δ=10.72 (s, 1H), 7.48-7.39 (m, 6H), 7.24-7.16 (m, 10H), 7.02 (s, 1H), 6.51 (s, 1H), 4.79 (d, J=15.2 Hz, 1H), 4.42-4.18 (m, 3H), 4.06-3.81 (m, 2H), 2.91 (d, J=5.6 Hz, 8H), 2.14-2.07 (m, 4H), 2.00-1.90 (m, 2H).

Step 7—(S)—N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide and (R)—N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide

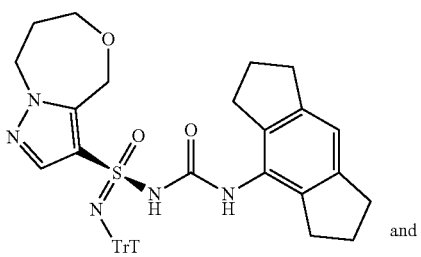

and

313

-continued

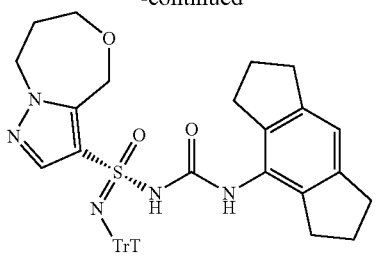

N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide (160 mg, 0.2 mmol) was purified by using chiral SFC (Chiralpak OD (250 mm*30 mm, 10 um), Supercritical CO$_2$/MeOH+0.1% NH$_4$OH=55/45; 50 mL/min) to give (R)—N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide (peak 1, 80 mg, yield: 50%) and (S)—N-((1,2,3,5,6,7-hexahydro-s-indacen-4-yl)carbamoyl)-N'-trityl-4,6,7,8-tetrahydropyrazolo[5,1-c][1,4]oxazepine-3-sulfonimidamide (peak 2, 65 mg, yield: 40%) both as light yellow solids. Stereochemistry was arbitrarily assigned to each stereoisomer. MS: m/z 680.1 (M+Na$^+$).

Step 8—Synthesis of (S)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide and (R)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide (Example 61 and Example 62)

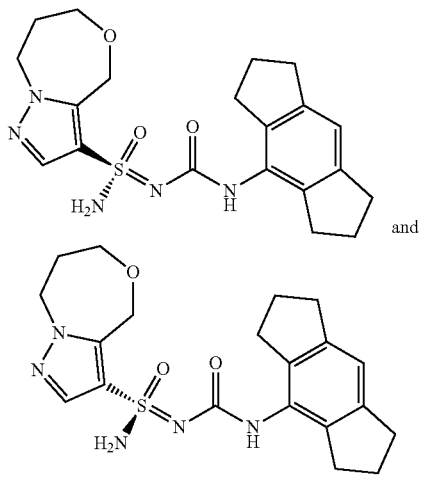

and

To a solution of the material from peak 1 (80 mg, 0.1 mmol) in DCM (5 mL) was added MeSO$_3$H (59 mg, 0.6 mmol) at room temperature. After 20 minutes, the reaction mixture was adjusted to pH=8 with saturated aqueous NaHCO$_3$ and concentrated. The crude residue was purified by reverse phase chromatography (MeCN 35-65%/(0.04% NH$_4$OH+0.1% NH$_4$HCO$_3$) in water) to give (S)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide (Method A, 1.55 min, 5.1 mg, 10% yield) as a white solid. Stereochemistry was arbitrarily assigned to each stereoisomer. $^1$H NMR (400 MHz, DMSO-d$_6$): δ=8.21 (s, 1H), 7.62 (s, 1H), 7.30 (s, 2H), 6.85 (s, 1H), 4.99 (d, J=15.2 Hz, 1H), 4.81 (d, J=15.2 Hz, 1H), 4.46 (t, J=5.2 Hz, 2H), 4.04-3.89 (m, 2H), 2.76 (t, J=7.2 Hz, 4H), 2.69-2.61 (m, 4H), 1.95-1.85 (m, 6H). MS: m/z 416.0 (M+H$^+$).

The material from Peak 2 above was deprotected and isolated in the same manner to give (R)—N'-((1,2,3,5,6,7-hexahydro-s-indacen-4-yl)carbamoyl)-7,8-dihydro-4H,6H-pyrazolo[5,1-c][1,4]oxazepine-3-sulfonimidamide (Method A, 1.69 min, 14.4 mg, yield: 35%) as a white solid. Stereochemistry was arbitrarily assigned to each stereoisomer. $^1$H NMR (400 MHz, DMSO-d$_6$): δ=8.21 (s, 1H), 7.62 (s, 1H), 7.30 (s, 2H), 6.85 (s, 1H), 4.99 (d, J=15.2 Hz, 1H), 4.81 (d, J=15.2 Hz, 1H), 4.46 (t, J=5.2 Hz, 2H), 4.04-3.89 (m, 2H), 2.76 (t, J=7.2 Hz, 4H), 2.69-2.61 (m, 4H), 1.95-1.85 (m, 6H). MS: m/z 416.1 (M+H$^+$).

Example 63

(R,6S)—N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide, ammonia

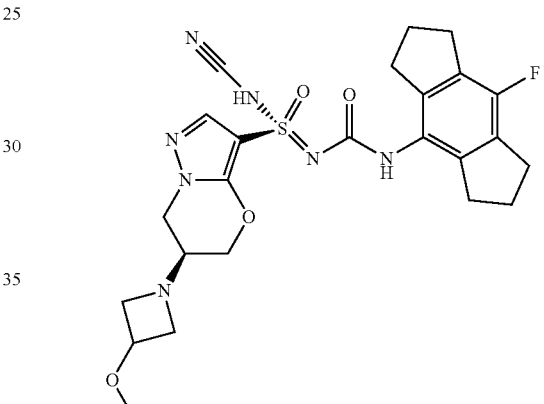

Step 1—Synthesis of (R,6S)—N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide, ammonia (Example 63)

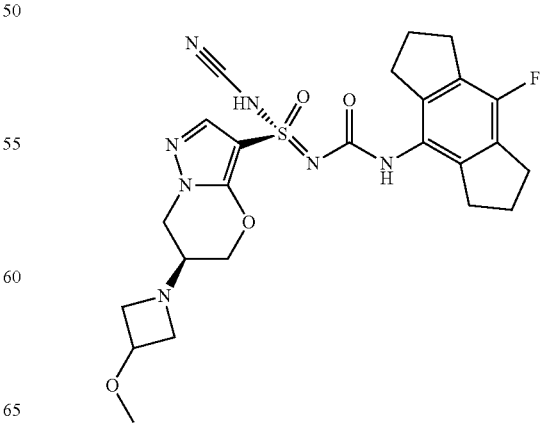

(S,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (10 mg, 0.02 mmol) was dissolved of DMF (0.5 mL) and charged with triethylamine (1M in DMF, 60 μL) and cyanogen bromide (1M in CH$_2$Cl$_2$, 30 μL) at room temperature. After 30 minutes, 50 mL of saturated aqueous NaHCO$_3$ was added. The mixture was directly purified by reverse-phase HPLC (5%-50% ACN in 0.1% aqueous NH$_4$OH) to afford the desired compound (4.5 mg, 45% yield). $^1$H NMR (400 MHz, DMSO-d$_6$) δ 7.78 (s, 1H), 7.38 (s, 1H), 7.07 (t, J=72 Hz, 3H), 4.40-4.20 (m, 4H), 4.10-3.90 (m, 2H), 3.16 (s, 3H), 2.78 (t, J=7.2 Hz, 4H), 2.72 (t, J=7.2 Hz, 4H), 2.05-1.95 (m, 4H). MS: m/z 530.2 (M+H$^+$).

Example 64, Example 65, Example 66 and Example 67

(S,7S)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide, (R,7R)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide and (S,7R)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide

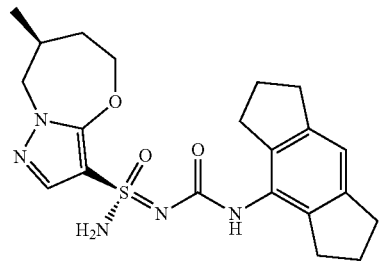

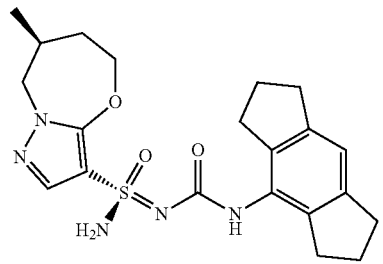

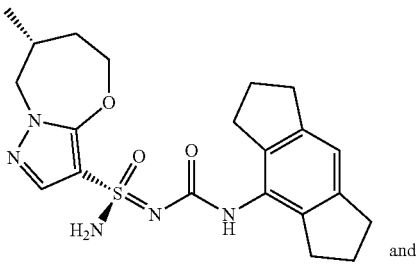

and

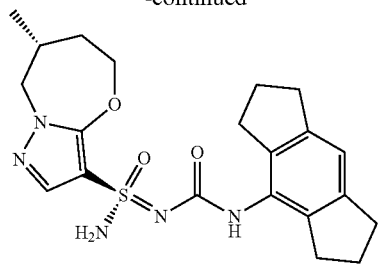

-continued

Step 1—Synthesis of 2-methylbutane-1,4-diol

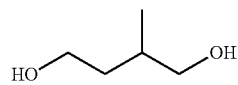

A solution of 2-methylsuccinic acid (10 g, 75.7 mmol) in THF (200 mL) was added dropwise into a suspension of LiAlH$_4$ (8.9 g, 234.6 mmol) in THF (200 mL) and the reaction mixture was stirred at 70° C. for 24 hours. After cooling to room temperature, a saturated aqueous solution of Na$_2$SO$_4$ was added slowly to quench the reaction. The mixture was filtered and the organic phase was concentrated to give a crude product, which was purified by silica gel chromatography (0-100% EtOAc in petroleum ether) to give 2-methylbutane-1,4-diol (6.5 g, yield: 82%) as a colorless oil. $^1$H NMR (400 MHz, DMSO-d$_6$) δ=4.43 (t, J=5.2 Hz, 1H), 4.36 (t, J=5.2 Hz, 1H), 3.50-3.38 (m, 2H), 3.29-3.22 (m, 1H), 3.21-3.13 (m, 1H), 1.63-1.47 (m, 2H), 1.22-1.10 (m, 1H), 0.82 (d, J=6.8 Hz, 3H).

Step 2—Synthesis of 2-methylbutane-1,4-diyl dimethanesulfonate

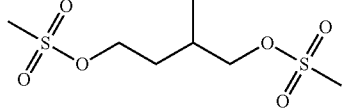

To a solution of 2-methylbutane-1,4-diol (6 g, 57.6 mmol) and triethylamine (40 mL, 288 mmol) in DCM (120 mL) was added MsCl (11.5 mL, 148 mmol) dropwise at 0° C. The reaction was warmed to room temperature. After 16 hours, the reaction was diluted with DCM (150 mL). The organic layer was washed with with water (50 mL×2), brine (100 mL), dried over Na$_2$SO$_4$, filtered and concentrated to give 2-methylbutane-1,4-diyl dimethanesulfonate (14.6 g, yield: 97%) as a colorless oil. $^1$H NMR (400 MHz, DMSO-d$_6$): δ=4.33-4.20 (m, 2H), 4.14-4.02 (m, 2H), 3.19 (s, 6H), 2.03-1.93 (m, 1H), 1.88-1.75 (m, 1H), 1.62-1.47 (m, 1H), 0.96 (d, J=6.8 Hz, 3H).

Step 3—Synthesis of 7-methyl-5,6,7,8-tetrahydropyrazolo[5,1-b][1,3]oxazepine and 6-methyl-5,6,7,8-tetrahydropyrazolo[5,1-b][1,3]oxazepine

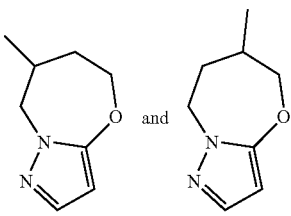

To a stirred solution of 1H-pyrazol-5-ol (1.3 g, 15.6 mmol) in DMF (52 mL) was added K₂CO₃ (7.5 g, 54.1 mmol). The mixture was stirred at 100° C. for 1 hour under nitrogen atmosphere. Then 2-methylbutane-1,4-diyl dimethanesulfonate (4.8 g, 18.5 mmol) was added and the mixture continued to stir at 100° C. for an additional 12 hours. The mixture was concentrated and the residue was purified by silica gel chromatography (30% EtOAc in petroleum ether) to give 7-methyl-5,6,7,8-tetrahydropyrazolo[5,1-b][1,3]oxazepine (300 mg, yield: 13%) and 6-methyl-5,6,7,8-tetrahydropyrazolo[5,1-b][1,3]oxazepine (190 mg, yield: 8%) both as colorless oil. ¹H NMR (400 MHz, CDCl₃): δ=7.24 (d, J=2.0 Hz, 1H), 5.68 (d, J=2.0 Hz, 1H), 4.31-4.22 (m, 2H), 3.91-3.81 (m, 2H), 2.04-1.96 (m, 2H), 1.90-1.79 (m, 1H), 1.04 (d, J=6.4 Hz, 3H). ¹H NMR (400 MHz, CDCl₃): δ=7.24 (d, J=2.0 Hz, 1H), 5.68 (d, J=2.0 Hz, 1H), 4.37-4.20 (m, 1H), 4.22-4.16 (m, 1H), 4.14-4.03 (m, 1H), 3.49-3.44 (m, 1H), 2.26-2.12 (m, 1H), 2.01-1.93 (m, 1H), 1.57-1.43 (m, 1H), 0.99 (d, J=6.8 Hz, 3H).

Step 4—Synthesis of 3-bromo-7-methyl-5,6,7,8-tetrahydropyrazolo[5,1-b][1,3]oxazepine

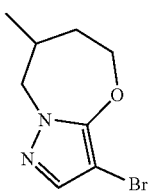

To a solution of 7-methyl-5,6,7,8-tetrahydropyrazolo[5,1-b][1,3]oxazepine (1.2 g, 7.9 mmol) in MeCN (26 mL) was added NBS (1.4 g, 7.9 mmol). The mixture was stirred at room temperature for 16 hours. The solvent was removed and the mixture was purified by flash chromatography (silica, 0-30% EtOAc in petroleum ether) to afford 3-bromo-7-methyl-5,6,7,8-tetrahydropyrazolo[5,1-b][1,3]oxazepine (1.6 g, yield: 88%) as a white solid. MS: m/z 230.9 (M+H⁺).

Step 5—Synthesis of 7-methyl-N'-trityl-5,6,7,8-tetrahydropyrazolo[5,1-b][1,3]oxazepine-3-sulfonimidamide

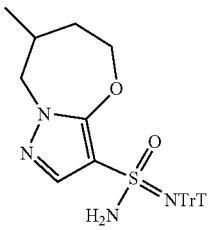

To a solution of 3-bromo-7-methyl-5,6,7,8-tetrahydropyrazolo[5,1-b][1,3]oxazepine (200 mg, 0.87 mmol) in THF (3 mL) was added n-BuLi (2.5M in hexane, 0.4 mL, 0.95 mmol) dropwise at −78° C. The mixture was stirred at this temperature for 30 minutes. A solution of TrtNSO (291 mg, 0.95 mmol) in THF (1 mL) was added drop wise and the mixture was stirred at −78° C. for 30 minutes before being placed in a 0° C. ice bath. Then, tert-butyl hypochlorite (0.11 mL, 0.95 mmol) was added and the mixture was stirred at 0° C. for 0.5 hours. NH₃ gas was bubbled through the mixture for 10 minutes at 0° C. and the resulting solution was stirred for 16 hours at room temperature. The mixture was concentrated and the crude residue was purified by silica gel column chromatography (solvent gradient: 0-80% EtOAc in petroleum ether) to give 7-methyl-N'-trityl-5,6,7,8-tetrahydropyrazolo[5,1-b][1,3]oxazepine-3-sulfonimidamide (250 mg, yield: 61%) as a white solid. ¹H NMR (400 MHz, DMSO-d₆): δ=7.48-7.41 (m, 6H), 7.21-7.17 (m, 6H), 7.14-7.08 (m, 3H), 7.04 (d, J=12.0 Hz, 1H), 6.20 (d, J=12.8 Hz, 2H), 4.32-4.18 (m, 1H), 4.11-4.04 (m, 1H), 3.94-3.75 (m, 2H), 2.06-1.99 (m, 1H), 1.91-1.86 (m, 1H), 1.84-1.69 (m, 1H), 0.94 (d, J=6.4 Hz, 3H).

Step 6—Synthesis of N-((1,2,3,5,6,7-hexahydro-s-indacen-4-yl)carbamoyl)-7-methyl-N'-trityl-5,6,7,8-tetrahydropyrazolo[5,1-b][1,3]oxazepine-3-sulfonimidamide

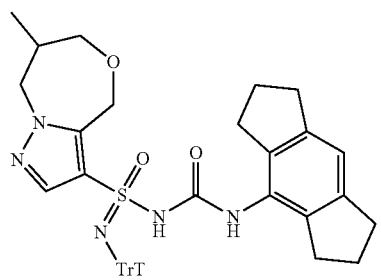

To a stirred solution of 7-methyl-N'-trityl-5,6,7,8-tetrahydropyrazolo[5,1-b][1,3]oxazepine-3-sulfonimidamide (150 mg, 0.32 mmol) in THF (5 mL) was added MeONa (34 mg, 0.63 mmol) at 0° C. After 15 minutes, 4-isocyanato-1,2,3,5,6,7-hexahydro-s-indacene (76 mg, 0.38 mmol) was added. The reaction mixture was warmed to room temperature and continued to stir for 16 hours. The reaction was quenched with MeOH (1 mL). The mixture was concentrated and the crude residue was purified by silica gel column chromatography (0-5% MeOH in DCM) to give N-((1,2,3,5,6,7-hexahydro-s-indacen-4-yl)carbamoyl)-7-methyl-N'-trityl-5,6,7,8-tetrahydropyrazolo[5,1-b][1,3]oxazepine-3-sulfonimidamide (200 mg, yield: 94%) as a white solid.

Step 7—Synthesis of N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide

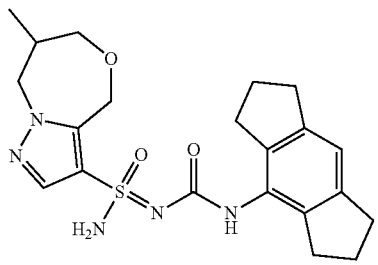 [SMILES: CC1COCc2c(S(N)(=O)=NC(=O)Nc3c4c(cc5c3CCC5)CCC4)cnn2C1]

To a solution of N-((1,2,3,5,6,7-hexahydro-s-indacen-4-yl)carbamoyl)-7-methyl-N'-trityl-5,6,7,8-tetrahydropyrazolo[5,1-b][1,3]oxazepine-3-sulfonimidamide (200 mg, 0.30 mmol) in DCM (15 mL) was added MeSO$_3$H (10 drops) at room temperature. After 0.5 h, the reaction mixture was adjusted to pH=8 with saturated aqueous NaHCO$_3$. The reaction was concentrated to dryness and the crude residue was purified by flash chromatography (silica, 0-1% MeOH in DCM) to give N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide (100 mg, yield: 78%) as a white solid. MS: m/z 430.1 (M+H$^+$).

Step 7—(S,7S)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide, (R,7R)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide and (S,7R)—N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide (Example 64, Example 65, Example 66 and example 67)

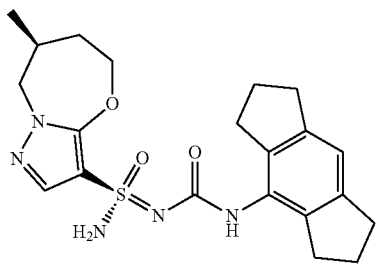

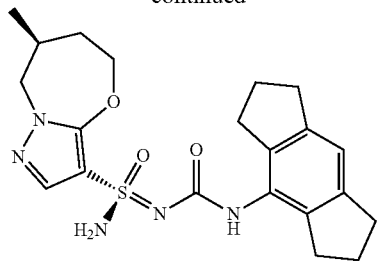

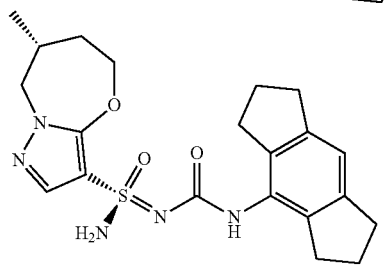

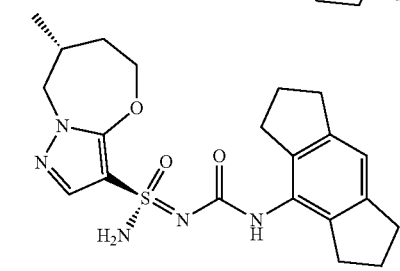

and

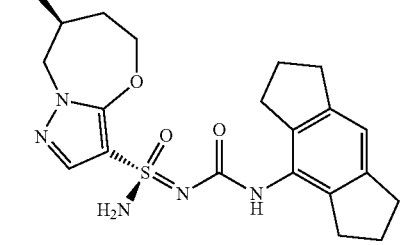

N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide (160 mg, 0.37 mmol) was separated by SFC (Chiralpak ad (250 mm*50 mm, 10 um)); supercritical CO$_2$/EtOH (0.1% NH$_4$OH)=40/40, 80 mL/min)) to afford peak 1 (Method B, 3.04 min, 17 mg, yield: 11%), peak 2 (Method B, 3.45 min, 16.1 mg, yield: 10%) and a 50 mg mixture of peak 3 and peak 4 which was separated by SFC (Cellulose-2 (250 mm*30 mm, 10 um); supercritical CO$_2$/EtOH (0.1% NH$_4$OH)=40/40, 70 mL/min) to give peak 3 (Method B, 4.63 min, 22.3 mg, yield: 14%) and peak 4 (Method B, 4.66 min, 23.8 mg, yield: 15%). Stereochemistry was arbitrarily assigned to each stereoisomer.

Peak 1: $^1$H NMR (400 MHz, DMSO-d$_6$): δ=8.23 (s, 1H), 7.50 (s, 1H), 7.30 (s, 2H), 6.85 (s, 1H), 4.34-4.30 (m, 1H), 4.21-4.17 (m, 1H), 4.01-3.87 (m, 2H), 2.77 (t, J=7.2 Hz, 4H), 2.68-2.64 (m, 4H), 2.08-1.99 (m, 1H), 1.97-1.87 (m, 5H), 1.85-1.75 (m, 1H), 0.94 (d, J=6.8 Hz, 3H). MS: m/z 430.1 (M+H$^+$). Compound 64

Peak 2: $^1$H NMR (400 MHz, DMSO-d$_6$): δ=8.20 (s, 1H), 7.50 (s, 1H), 7.31 (s, 2H), 6.85 (s, 1H), 4.32-4.27 (s, 1H), 4.20-4.17 (m, 1H), 4.05-3.87 (m, 2H), 2.77 (t, J=7.2 Hz, 4H), 2.75-2.66 (m, 4H), 2.05-2.01 (m, 1H), 1.98-1.86 (m, 5H), 1.86-1.73 (m, 1H), 0.94 (d, J=6.8 Hz, 3H). Compound 66

Peak 3: $^1$H NMR (400 MHz, DMSO-d$_6$): δ=8.20 (s, 1H), 7.49 (s, 1H), 7.25 (s, 2H), 6.85 (s, 1H), 4.32-4.27 (s, 1H), 4.20-4.17 (m, 1H), 3.97-3.87 (m, 2H), 2.77 (t, J=7.2 Hz, 4H), 2.70-2.60 (m, 4H), 2.05-2.01 (m, 1H), 1.98-1.86 (m, 5H), 1.86-1.73 (m, 1H), 0.94 (d, J=7.2 Hz, 3H). MS: m/z 430.1 (M+H$^+$). Compound 65

Peak 4: $^1$H NMR (400 MHz, DMSO-d$_6$): δ=8.16 (s, 1H), 7.48 (s, 1H), 7.19 (s, 2H), 6.84 (s, 1H), 4.31-4.27 (m, 1H), 4.19-4.16 (m, 1H), 4.02-3.88 (m, 2H), 2.76 (t, J=7.2 Hz, 4H), 2.70-2.60 (m, 4H), 2.04-1.99 (m, 1H), 1.98-1.86 (m, 5H), 1.85-1.72 (m, 1H), 0.94 (d, J=6.8 Hz, 3H). MS: m/z 430.1 (M+H⁺). Compound 67

Example 68

(R)—N-cyano-N'-((1,2,3,5,6,7-hexahydro-s-indacen-4-yl)carbamoyl)-6,7-dihydro-5H-pyrazolo[5,1-b][1,3]oxazine-3-sulfonimidamide, ammonia

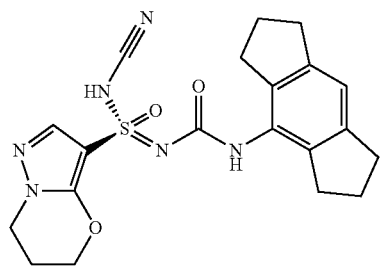 [SMILES: N#CN[S@](=O)(=NC(=O)Nc1c2c(cc3c1CCC3)CCC2)c1cnn2c1OCCC2]

(R)—N-cyano-N'-((1,2,3,5,6,7-hexahydro-s-indacen-4-yl)carbamoyl)-6,7-dihydro-5H-pyrazolo[5,1-b][1,3]oxazine-3-sulfonimidamide, ammonia was prepared using the general procedure described for the preparation of (R,6S)—N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (Example 63), by replacing (S,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide with (S)—N'-((1,2,3,5,6,7-hexahydro-s-indacen-4-yl)carbamoyl)-6,7-dihydro-5H-pyrazolo[5,1-b][1,3]oxazine-3-sulfonimidamide in Step 1. ¹H NMR (400 MHz, DMSO-d₆) δ 7.78 (s, 1H), 7.41 (s, 1H), 7.07 (t, J=72 Hz, 3H), 6.82 (s, 1H), 4.43-4.25 (m, 2H), 4.08 (t, J=6.1 Hz, 2H), 2.76 (t, J=7.4 Hz, 4H), 2.72-2.60 (m, 4H), 2.17 (h, J=6.1 Hz, 2H), 1.92 (p, J=7.4 Hz, 4H). MS: m/z 427.2 (M+H⁺).

Example 69

(S)—N-cyano-N'-((1,2,3,5,6,7-hexahydro-s-indacen-4-yl)carbamoyl)-6,7-dihydro-5H-pyrazolo[5,1-b][1,3]oxazine-3-sulfonimidamide, ammonia

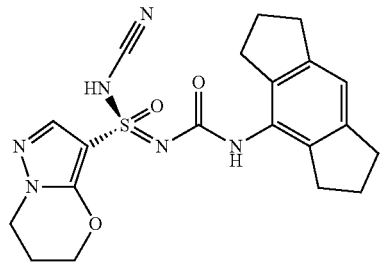 [SMILES: N#CN[S@@](=O)(=NC(=O)Nc1c2c(cc3c1CCC3)CCC2)c1cnn2c1OCCC2]

(S)—N-cyano-N'-((1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of (R,6S)—N-cyano-N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide (Example 63), by replacing (S,6S)—N'-((8-fluoro-1,2,3,5,6,7-hexahydro-s-indacen-4-yl)carbamoyl)-6-(3-methoxyazetidin-1-yl)-6,7-dihydro-5H-pyrazolo[5,1-b][1,3]oxazine-3-sulfonimidamide with (R)—N'-((1,2,3,5,6,7-hexahydro-s-indacen-4-yl)carbamoyl)-6,7-dihydro-5H-pyrazolo[5,1-b][1,3]oxazine-3-sulfonimidamide in Step 1. ¹H NMR (400 MHz, DMSO-d₆) δ 7.72 (s, 1H), 7.36 (s, 1H), 6.79 (s, 1H), 6.51 (s, 1H), 4.42-4.21 (m, 2H), 4.07 (t, J=6.1 Hz, 2H), 2.76 (t, J=7.4 Hz, 4H), 2.70-2.60 (m, 4H), 2.20-2.10 (m, 2H), 2.00-1.79 (m, 4H). MS: m/z 427.2 (M+H⁺).

Example 70 and Example 71

(S)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide and (R)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide

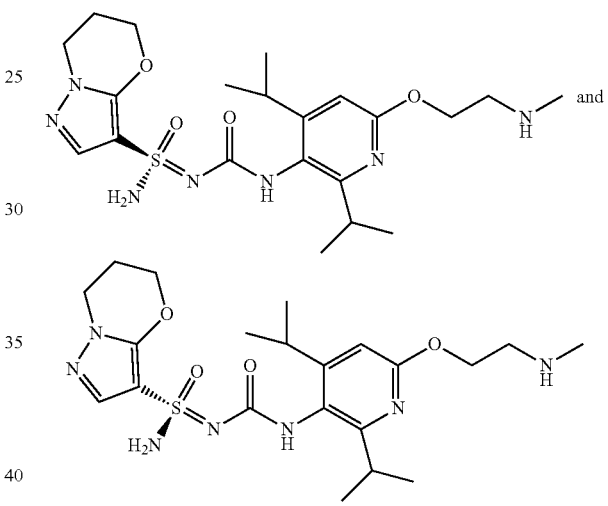

Step 1—Synthesis of 2-((4,diisopropyl-5-nitropyridin-2 yl)oxy)-N-methylethanamine

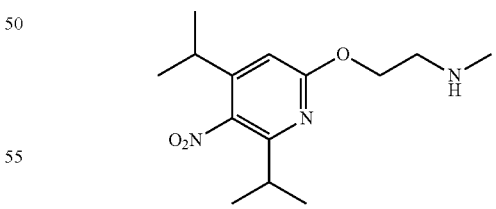

To a mixture of NaH (60% in mineral oil, 660 mg, 16.48 mmol) in THF (20 mL) was added tert-butyl (2-hydroxyethyl)(methyl)carbamate (1.59 g, 9.06 mmol) in THF (10 mL) dropwise at room temperature under nitrogen atmosphere. The mixture was stirred at 70° C. for 0.5 hour. After cooling to room temperature, 6-chloro-2,4-diisopropyl-3-nitropyridine (2 g, 8.24 mmol) in THF (10 mL) was added dropwise. The resulting mixture was stirred at 70° C. for 16 hours. After cooling to room temperature, the reaction was quenched with water (50 mL) and extracted with EtOAc (50 mL×2). The combined organic layers were washed with brine (30 mL), dried over anhydrous Na$_2$SO$_4$, filtered and concentrated. The crude residue was purified by silica gel column (0-10% MeOH in DCM) to give 2-((4,6-diisopropyl-5-nitropyridin-2-yl)oxy)-N-methylethanamine (380 mg, yield: 17%) as a colorless oil. MS: m/z 282.1 (M+H$^+$).

Step 2—Synthesis of tert-butyl (2-((4,6-diisopropyl-5-nitropyridin-2-yl)oxy)ethyl)(methyl)carbamate

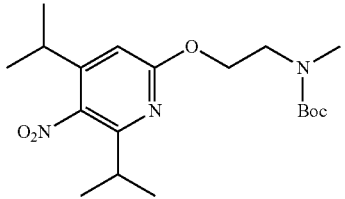 [SMILES: CC(C)c1cc(OCCN(C)C(=O)OC(C)(C)C)nc(C(C)C)c1[N+](=O)[O-]]

To a solution of 2-((4,6-diisopropyl-5-nitropyridin-2-yl)oxy)-N-methylethanamine (380 mg, 1.35 mmol) and triethylamine (273 mg, 2.7 mmol) in DCM (5.4 mL) was added di-tert-butyl carbonate (354 mg, 1.62 mmol) at room temperature. After 16 hours, the reaction was concentrated. The crude residue was purified by TLC (silica, 20% EtOAc in petroleum ether) to give tert-butyl (2-((4,6-diisopropyl-5-nitropyridin-2-yl)oxy)ethyl)(methyl)carbamate (385 mg, yield: 75%) as colorless oil. $^1$H NMR (400 MHz, CDCl$_3$) δ=6.59 (s, 1H), 4.52 (t, J=5.2 Hz, 2H), 3.05 (t, J=5.2 Hz, 2H), 2.98-2.92 (m, 1H), 2.87-2.80 (m, 1H), 2.56 (s, 3H), 1.30-1.10 (m, 21H)

Step 3—Synthesis of tert-butyl (2-((5-amino-4,6-diisopropylpyridin-2-yl)oxy)ethyl)(methyl)carbamate

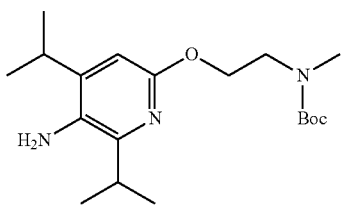

To a solution of tert-butyl (2-((4,6-diisopropyl-5-nitropyridin-2-yl)oxy)ethyl)(methyl)carbamate (385 mg, 1.01 mmol) in EtOH (16 mL) was added 10% Pd (118 mg, 1.11 mmol) on carbon. The mixture was stirred at room temperature for 16 hours under hydrogen atmosphere (15 psi). The mixture was filtered and the filtrate was concentrated to give tert-butyl (2-((5-amino-4,6-diisopropylpyridin-2-yl)oxy)ethyl)(methyl)carbamate (335 mg, yield: 94%) as colorless liquid. $^1$H NMR (400 MHz, CDCl$_3$) δ=6.40 (s, 1H), 4.44-4.34 (m, 2H), 3.62-3.56 (m, 2H), 3.32 (s, 2H), 3.06-3.01 (m, 1H), 2.96 (s, 3H), 2.94-2.86 (m, 1H), 1.40 (s, 9H), 1.27-1.22 (m, 12H)

Step 4—Synthesis of tert-butyl (2-((5-isocyanato-4,6-diisopropylpyridin-2-yl)oxy)ethyl)(methyl)carbamate

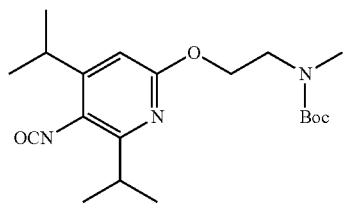

To a solution of tert-butyl (2-((5-amino-4,6-diisopropylpyridin-2-yl)oxy)ethyl)(methyl)carbamate (260 mg, 0.74 mmol) and triethylamine (0.15 mL, 1.11 mmol) in anhydrous THF (3.7 mL) was added triphosgene (110 mg, 0.37 mmol) at room temperature. The mixture was stirred at 70° C. for 1 hour. After cooling to room temperature, the mixture was filtered and the filtrate concentrated to give tert-butyl (2-((5-isocyanato-4,6-diisopropylpyridin-2-yl)oxy)ethyl)(methyl)carbamate (279 mg, yield: 99%) as a white solid.

Step 5—Synthesis of tert-butyl (2-((4,6-diisopropyl-5-(3-(N-trityl-6,7-dihydro-5H-pyrazolo[5,1-b][1,3]oxazine-3-sulfonimidoyl)ureido)pyridin-2-yl)oxy)ethyl)(methyl)carbamate

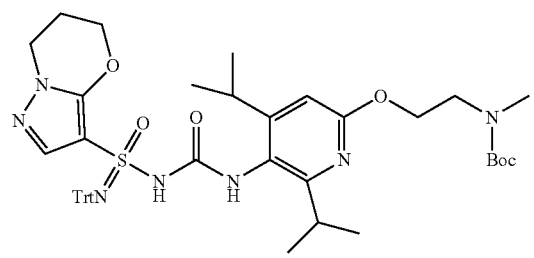

To a solution of N'-trityl-6,7-dihydro-5H-pyrazolo[5,1-b][1,3]oxazine-3-sulfonimidamide (219 mg, 0.49 mmol) in THF (13 mL) was added MeONa (40 mg, 0.74 mmol) at 0° C. under nitrogen atmosphere. After stirring for 20 minutes, a solution of tert-butyl (2-((5-isocyanato-4,6-diisopropylpyridin-2-yl)oxy)ethyl)(methyl)carbamate (279 mg, 0.74 mmol) in THF (8 mL) was added dropwise at 0° C. The reaction mixture was stirred at room temperature for 16 hours. The mixture was concentrated and the residue was purified by prep-TLC (silica, 5% methanol in DCM) to give tert-butyl (2-((4,6-diisopropyl-5-(3-(N-trityl-6,7-dihydro-5H-pyrazolo[5,1-b][1,3]oxazine-3-sulfonimidoyl)ureido)pyridin-2-yl)oxy)ethyl)(methyl)carbamate (226 mg, yield: 56%) as a white solid. MS: m/z 844.3 (M+Na$^+$)

Step 6—Synthesis of N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide

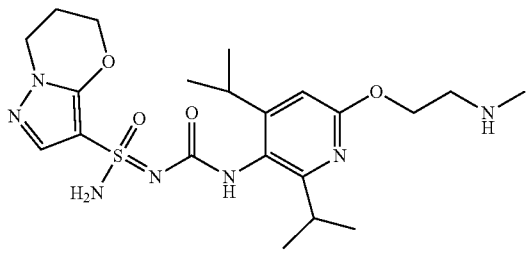 [SMILES: CNCCOc1cc(C(C)C)c(NC(=O)N=S(N)(=O)c2cnn3c2OCCC3)c(C(C)C)n1]

To a solution of tert-butyl (2-((4,6-diisopropyl-5-(3-(N-trityl-6,7-dihydro-5H-pyrazolo[5,1-b][1,3]oxazine-3-sulfonimidoyl)ureido)pyridin-2-yl)oxy)ethyl)(methyl)carbamate (226 mg, 0.27 mmol) in DCM (13 mL) was added MeSO₃H (10 drops) at room temperature. After 1 hour, the reaction solution was adjusted to pH=8 with saturated aqueous NaHCO₃. The reaction was filtered and concentrated. The crude residue was purified by TLC (silica, 10% MeOH in DCM) to give N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide (104 mg, yield: 79%) as a white solid. MS: m/z 480.1 (M+H⁺).

Step 7—(S)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide and (R)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide (Example 70 and Example 71)

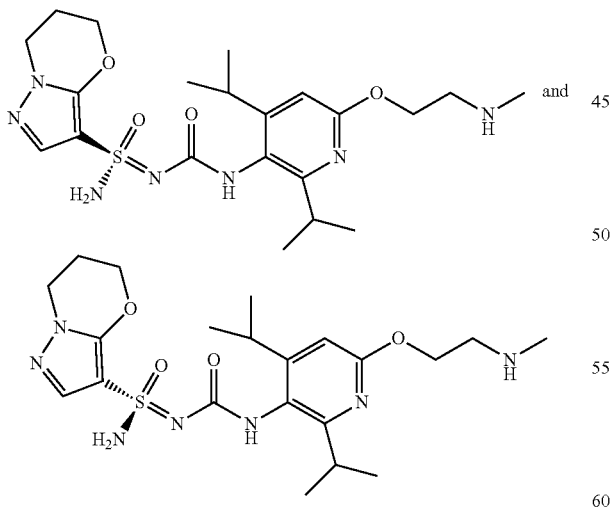

N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide (104 mg, 0.22 mmol) was separated using chiral SFC (Chiralpak AD, (250 mm*30 mm, 10 um), Supercritical CO₂/EtOH+0.1% NH₄OH=65/35; 80 mL/min) to give (S)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide (Method S, 5.92 min, peak 1, 28.8 mg, yield: 27%) and (R)—N'-((2,4-diisopropyl-6-(2-(methylamino)ethoxy)pyridin-3-yl)carbamoyl)-6,7-dihydro-5H-pyrazolo[5,1-b][1,3]oxazine-3-sulfonimidamide (Method S, 6.51 min, peak 2, 27.4 mg, yield: 26%) both as white solids. Stereochemistry was arbitrarily assigned to each stereoisomer.

Peak 1: ¹H NMR (400 MHz, DMSO-d₆): δ=7.97 (s, 1H), 7.47 (s, 1H), 6.43 (s, 1H), 4.41-4.32 (m, 2H), 4.26 (t, J=5.6 Hz, 2H), 4.08 (m, J=6.0 Hz, 2H), 3.24-3.11 (m, 1H), 3.07-2.93 (m, 1H), 2.78 (t, J=5.6 Hz, 2H), 2.30 (s, 3H), 2.20-2.12 (m, 2H), 1.12-1.00 (m, 12H). MS: m/z 480.2 (M+H⁺).

Peak 2: ¹H NMR (400 MHz, DMSO-d₆): δ=7.98 (s, 1H), 7.48 (s, 1H), 6.43 (s, 1H), 4.42-4.33 (m, 2H), 4.26 (t, J=6.0 Hz, 2H), 4.10 (t, J=6.0 Hz, 2H), 3.25-3.10 (m, 1H), 3.06-2.91 (m, 1H), 2.79 (t, J=5.6 Hz, 2H), 2.31 (s, 3H), 2.21-2.14 (m, 2H), 1.12-1.00 (m, 12H). MS: m/z 480.2 (M+H⁺).

Example 72 and Example 73

(S)—N'-((1,2,3,5,6,7-hexahydro-s-indacen-4-yl)carbamoyl)-4,5,6,7-tetrahydropyrazolo[1,5-a]pyrimidine-3-sulfonimidamide and (R)—N'-((1,2,3,5,6,7-hexahydro-s-indacen-4-yl)carbamoyl)-4,5,6,7-tetrahydropyrazolo[1,5-a]pyrimidine-3-sulfonimidamide

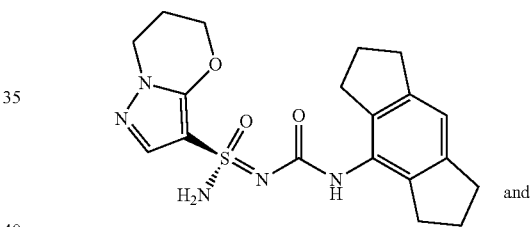

and

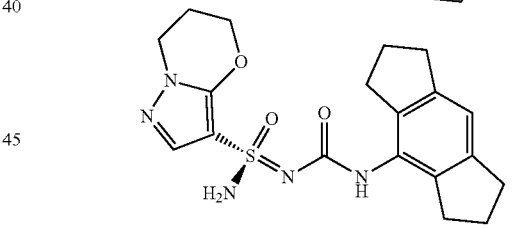

Step 1—Synthesis of tert-butyl 3-(N'-tritylsulfamimidoyl)-6,7-dihydropyrazolo[1,5-a]pyrimidine-4(5H)-carboxylate

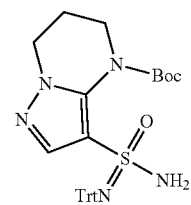

To a solution of tert-butyl 3-bromo-6,7-dihydro-5H-pyrazolo[1,5-a]pyrimidine-4-carboxylate (2.0 g, 6.62 mmol) in THF (32 mL) was added n-BuLi (2.5 M in hexane, 2.91 mL, 7.28 mmol) dropwise at −78° C. under nitrogen atmosphere. After stirring at −78° C. for 0.5 hour, a solution of TrtNSO (2.22 g, 7.28 mmol) in THF (14 mL) was added dropwise. The mixture was stirred at −78° C. for 20 minutes and then stirred at 0° C. for 10 minutes. Then, tert-butyl hypochlorite (0.8 mL, 7.07 mmol) was added dropwise at 0° C. and the mixture was stirred at 0° C. for 0.5 hour. $NH_3$ gas was bubbled through the mixture for 10 minutes at 0° C. and the resulting mixture was stirred for 16 hours at room temperature. The mixture was concentrated and DCM/MeOH (20/1, 15 mL) was added. The resulting mixture was filtered and the solid was dissolved in water (20 mL), extracted with DCM/MeOH (9/1, 100 mL×3). The combined organic layers were dried over anhydrous $Na_2SO_4$, filtered and concentrated to give tert-butyl 3-(N-tritylsulfamimidoyl)-6,7-dihydropyrazolo[1,5-a]pyrimidine-4(5H)-carboxylate (1.9 g, yield: 54%) as white solid. MS: m/z 566.1 (M+Na+).

Step 2—Synthesis of tert-butyl 3-(N-((1,2,3,5,6,7-hexahydro-s-indacen-4-yl)carbamoyl)-N'-tritylsulfamimidoyl)-6,7-dihydropyrazolo[1,5-a]pyrimidine-4(5H)-carboxylate

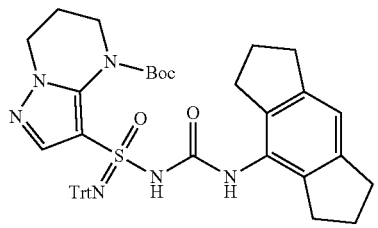

To a solution of tert-butyl 3-(N'-tritylsulfamimidoyl)-6,7-dihydropyrazolo[1,5-a]pyrimidine-4(5H)-carboxylate (120 mg, 0.22 mmol) in THF (5 mL) was added $CH_3ONa$ (18 mg, 0.33 mmol) at 0° C. under nitrogen atmosphere. After stirring at 0° C. for 20 minutes, a solution of 4-isocyanato-1,2,3,5,6,7-hexahydro-s-indacene (88 mg, 0.44 mmol) in THF (2 mL) was added. The reaction mixture was stirred at room temperature for 16 hours. MeOH (5 mL) was added and the mixture was filtered. The filtrate was concentrated and the residue was purified by silica gel column chromatography (0-1.5% methanol in DCM) to give tert-butyl 3-(N-((1,2,3,5,6,7-hexahydro-s-indacen-4-yl)carbamoyl)-N'-tritylsulfamimidoyl)-6,7-dihydropyrazolo[1,5-a]pyrimidine-4(5H)-carboxylate (120 mg, yield: 73%) as a white solid. MS: m/z 743.4 (M+H+).

Step 3—Synthesis of N'-((1,2,3,5,6,7-hexahydro-s-indacen-4-yl)carbamoyl)-4,5,6,7-tetrahydropyrazolo[1,5-a]pyrimidine-3-sulfonimidamide

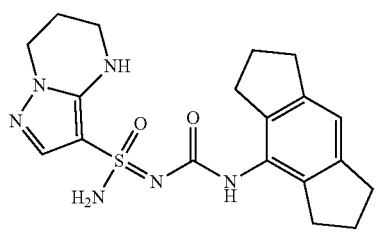 [SMILES: NS(=O)(=NC(=O)Nc1c2c(cc3c1CCC3)CCC2)c1cnn2c1NCCC2]

To a solution of tert-butyl 3-(N-((1,2,3,5,6,7-hexahydro-s-indacen-4-yl)carbamoyl)-N'-tritylsulfamimidoyl)-6,7-dihydropyrazolo[1,5-a]pyrimidine-4(5H)-carboxylate (120 mg, 0.16 mmol) in DCM (9 mL) was added $MeSO_3H$ (78 mg, 0.81 mmol). The mixture was stirred at room temperature for 1 hour. The reaction solution was adjusted to pH=8 with saturated aqueous $NaHCO_3$, dried over $Na_2SO_4$, filtered and concentrated. The residue was purified by prep-TLC (silica, 10% methanol in DCM) to give N'-((1,2,3,5,6,7-hexahydro-s-indacen-4-yl)carbamoyl)-4,5,6,7-tetrahydropyrazolo[1,5-a]pyrimidine-3-sulfonimidamide (65 mg, yield: 91%) as white solid. MS: m/z 401.2 (M+H+).

Step 4—(S)—N'-((1,2,3,5,6,7-hexahydro-s-indacen-4-yl)carbamoyl)-4,5,6,7-tetrahydropyrazolo[1,5-a]pyrimidine-3-sulfonimidamide and (R)—N'-((1,2,3,5,6,7-hexahydro-s-indacen-4-yl)carbamoyl)-4,5,6,7-tetrahydropyrazolo[1,5-a]pyrimidine-3-sulfonimidamide (Example 72 and example 73)

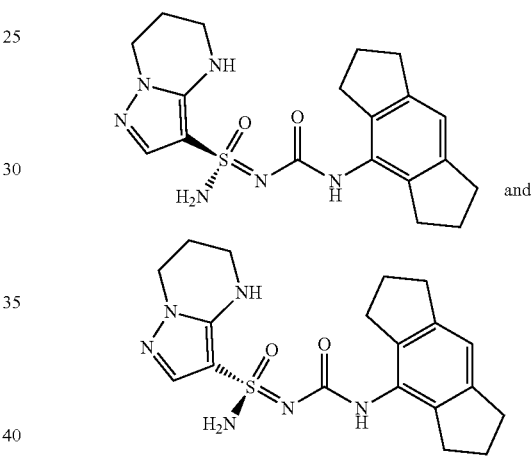

N'-((1,2,3,5,6,7-hexahydro-s-indacen-4-yl)carbamoyl)-4,5,6,7-tetrahydropyrazolo[1,5-a]pyrimidine-3-sulfonimidamide (65 mg, 0.16 mmol) was separated by using chiral SFC (Chiralpak AS (250 mm*30 mm, 10 um), Supercritical $CO_2$/EtOH+0.1% $NH_4OH$=75/25; 60 mL/min) to give (S)—N'-((1,2,3,5,6,7-hexahydro-s-indacen-4-yl)carbamoyl)-4,5,6,7-tetrahydropyrazolo[1,5-a]pyrimidine-3-sulfonimidamide (Method C, 3.65 min, peak 1, 29.1 mg, yield: 44%) and (R)—N'-((1,2,3,5,6,7-hexahydro-s-indacen-4-yl)carbamoyl)-4,5,6,7-tetrahydropyrazolo[1,5-a]pyrimidine-3-sulfonimidamide (Method C, 4.47 min, peak 2, 31.4 mg, yield: 47%) both as white solids. Stereochemistry was arbitrarily assigned to each stereoisomer.

Peak 1: $^1$H NMR (400 MHz, DMSO-$d_6$): δ=8.24 (s, 1H), 7.38 (s, 1H), 7.09 (s, 2H), 6.88 (s, 1H), 6.43 (s, 1H), 3.96 (t, J=6.0 Hz, 2H), 3.29-3.10 (m, 2H), 2.79 (t, J=7.2 Hz, 4H), 2.71 (t, J=7.2 Hz, 4H), 2.04-1.86 (m, 6H). MS: m/z 401.2 (M+H+).

Peak 2: $^1$H NMR (400 MHz, DMSO-$d_6$): δ=8.23 (s, 1H), 7.37 (s, 1H), 7.09 (s, 2H), 6.88 (s, 1H), 6.37 (s, 1H), 3.96 (t, J=6.0 Hz, 2H), 3.25-3.15 (m, 2H), 2.79 (t, J=7.2 Hz, 4H), 2.71 (t, J=7.2 Hz, 4H), 2.03-1.89 (m, 6H). MS: m/z 401.2 (M+H+).

Example 74, Example 75, Example 78 and Example 79

(S,6R)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide, (R,6S)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide and (S,6S)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide

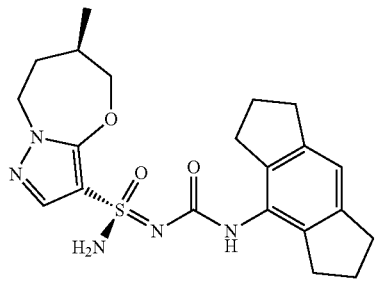

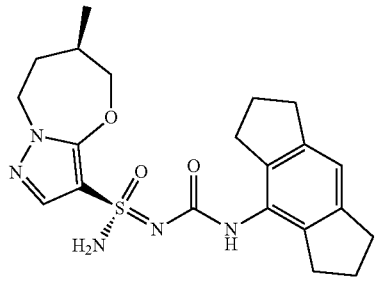

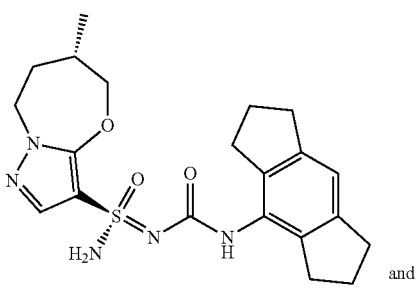

and

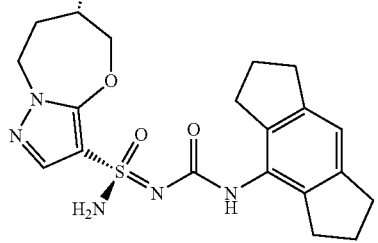

Step 1~4—Synthesis of N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide

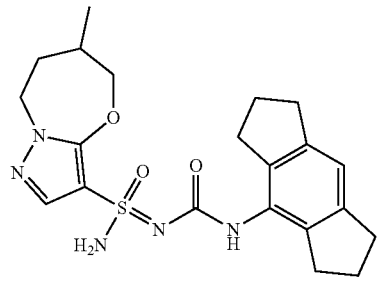 [SMILES: CC1CCn2ncc(S(N)(=O)=NC(=O)Nc3c4c(cc5c3CCC5)CCC4)c2OC1]

N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide was prepared using the general procedure described for the preparation of N'-((1,2,3,5,6,7-hexahydro-s-indacen-4-yl)carbamoyl)-7-methyl-5,6,7,8-tetrahydropyrazolo[5,1-b][1,3]oxazepine-3-sulfonimidamide (Example 64, Example 65, Example 66 and Example 67) by replacing 7-methyl-5,6,7,8-tetrahydropyrazolo[5,1-b][1,3]oxazepine with 6-methyl-5,6,7,8-tetrahydropyrazolo[5,1-b][1,3]oxazepine in Step 4.

Step 5—(S,6R)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide, (R,6S)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide and (S,6S)—N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide. (Example 74, Example 75, Example 78 and example 79)

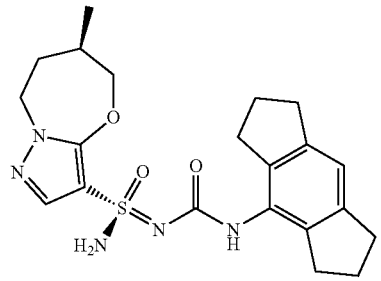

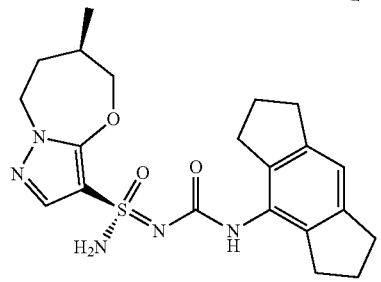

331

-continued

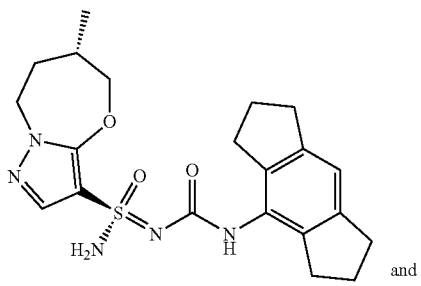

and

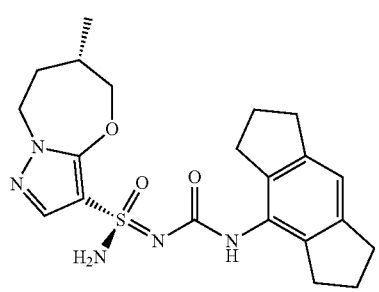

N'-((1,2,3,5,6,7-hexahydro-s-indacen-4-yl)carbamoyl)-6-methyl-5,6,7,8-tetrahydropyrazolo[5,1-b][1,3]oxazepine-3-sulfonimidamide (150 mg, 0.35 mmol) was separated by SFC (daicel chiralpak AD (250 mm*30 mm, 10 um); supercritical $CO_2$/MeOH (0.1% $NH_3H_2O$)=50/50 at 70 mL/min) to give peak 3 (Method B, 5.32 min, 21.1 mg, yield: 14%), peak 4 (Method B, 7.55 min, 22.5 mg, yield: 15%) and 50 mg mixture of peak 1 and peak 2 which was separated by SFC (regis (s,s) whelk-ol (250 mm*30 mm, 5 um); supercritical $CO_2$/IPA (0.1% $NH_3H_2O$)=40/40 at 70 mL/min) to give peak 1 (Method B, 3.32 min, 20.2 mg, yield: 13%) and peak 2 (Method B, 3.49 min, 18.7 mg, yield: 12%).

Peak 1: $^1$H NMR (400 MHz, DMSO-$d_6$): δ=8.22 (s, 1H), 7.49 (s, 1H), 7.28 (s, 2H), 6.86 (s, 1H), 4.36-4.19 (m, 2H), 4.14-4.00 (m, 1H), 3.60-3.55 (m, 1H), 2.77 (t, J=7.6 Hz, 4H), 2.70-2.66 (m, 4H), 2.23-2.13 (m, 1H), 1.97-1.90 (m, 5H), 1.43-1.35 (m, 1H), 0.92 (d, J=6.8 Hz, 3H). m/z 430.1 (M+H$^+$). Compound 75

Peak 2: $^1$H NMR (400 MHz, DMSO-$d_6$): δ=8.21 (s, 1H), 7.51 (s, 1H), 7.31 (s, 2H), 6.85 (s, 1H), 4.34-4.17 (m, 2H), 4.13-4.02 (m, 1H), 3.66-3.61 (m, 1H), 2.77 (t, J=7.2 Hz, 4H), 2.68-2.66 (m, 4H), 2.20-2.13 (m, 1H), 1.96-1.89 (m, 5H), 1.44-1.35 (m, 1H), 0.93 (d, J=6.8 Hz, 3H). m/z 430.1 (M+H$^+$). Compound 74

Peak 3: $^1$H NMR (400 MHz, DMSO-$d_6$): δ=8.21 (s, 1H), 7.51 (s, 1H), 7.31 (s, 2H), 6.85 (s, 1H), 4.33-4.20 (m, 2H), 4.11-4.00 (m, 1H), 3.66-3.61 (m, 1H), 2.77 (t, J=7.2 Hz, 4H), 2.70-2.66 (m, 4H), 2.21-2.13 (m, 1H), 1.98-1.89 (m, 5H), 1.44-1.35 (m, 1H), 0.93 (d, J=6.8 Hz, 3H). MS: m/z 430.1 (M+H$^+$). Compound 78

Peak 4: $^1$H NMR (400 MHz, DMSO-$d_6$): δ=8.19 (s, 1H), 7.48 (s, 1H), 7.22 (s, 2H), 6.85 (s, 1H), 4.34-4.20 (m, 2H), 4.13-4.02 (m, 1H), 3.60-3.55 (m, 1H), 2.77 (t, J=7.2 Hz, 4H), 2.70-2.64 (m, 4H), 2.23-2.14 (m, 1H), 1.96-1.89 (m, 5H), 1.45-1.34 (m, 1H), 0.93 (d, J=6.8 Hz, 3H). m/z 430.1 (M+H$^+$). Compound 79

332

Example 76 and Example 77

(R)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide and (S)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide

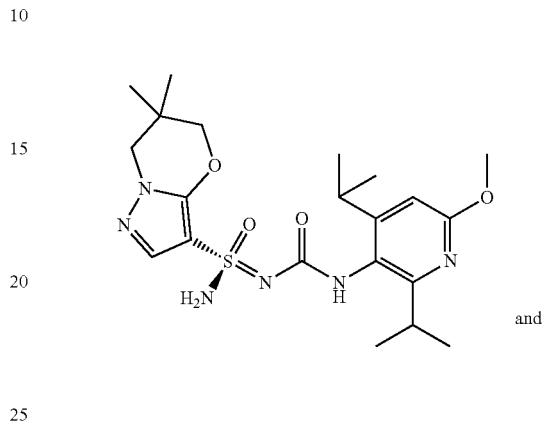

and

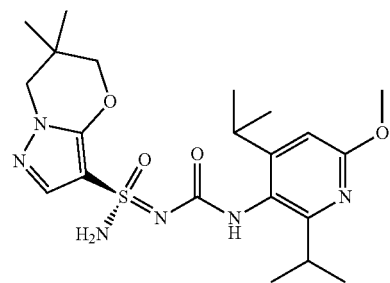

Step 1—Synthesis of 3-bromo-6,6-dimethyl-5,7-dihydropyrazolo[5,1-b][1,3]oxazine

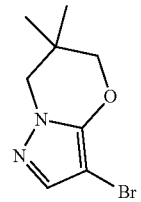

To a solution of 6,6-dimethyl-5,7-dihydropyrazolo[5,1-b][1,3]oxazine (1.27 g, 8.34 mmol) in MeCN (25 mL) was added NBS (1.49 g, 8.34 mmol) portion-wise at 0° C. The mixture was stirred at room temperature for 3 hours and then concentrated. The residue was purified by silica gel column chromatography (0-50% EtOAc in petroleum ether) to give 3-bromo-6,6-dimethyl-5,7-dihydropyrazolo[5,1-b][1,3]oxazine (1.63 g, yield: 85%) as a light yellow solid. $^1$H NMR (400 MHz, CDCl$_3$): δ=7.33 (s, 1H), 3.96 (s, 2H), 3.84 (s, 2H), 1.15 (s, 6H).

Step 2—Synthesis of 6,6-dimethyl-N'-trityl-6,7-dihydro-5H-pyrazolo[5,1-b][1,3]oxazine-3-sulfonimidamide

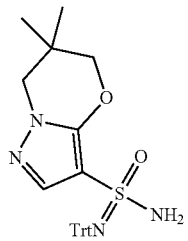

To a solution of 3-bromo-6,6-dimethyl-5,7-dihydropyrazolo[5,1-b][1,3]oxazine (1.0 g, 4.33 mmol) in THF (15 mL) was added n-BuLi (2.5 M in hexane, 1.9 mL, 4.76 mmol) dropwise at −78° C. under a nitrogen atmosphere. After 1 hour, a solution of TrtNSO (1.45 g, 4.76 mmol) in THF (15 mL) was added dropwise. The mixture was stirred at −78° C. for 30 minutes before being placed in a 0° C. ice bath. tert-Butyl hypochlorite (0.54 mL, 4.76 mmol) was added. After 30 minutes, NH$_3$ gas was bubbled through the mixture for 10 minutes at 0° C. The resulting mixture warmed to room temperature and stirred for 16 hours. The mixture was concentrated and the crude residue was purified by silica gel column chromatography (0-100% EtOAc in petroleum ether) to give 6,6-dimethyl-N'-trityl-6,7-dihydro-5H-pyrazolo[5,1-b][1,3]oxazine-3-sulfonimidamide (960 mg, yield: 47%) as a white solid. $^1$H NMR (400 MHz, DMSO-d$_6$): δ=7.43 (d, J=7.6 Hz, 6H), 7.20-7.14 (m, 6H), 7.12-7.06 (m, 3H), 6.98 (s, 1H), 6.25 (s, 2H), 3.98-3.87 (m, 2H), 3.74-3.63 (m, 2H), 1.01 (s, 3H), 0.99 (s, 3H).

Step 3—Synthesis of N-((2,4-diisopropyl-6-methoxypyridin-3-yl)carbamoyl)-6,6-dimethyl-N'-trityl-6,7-dihydro-5H-pyrazolo[5,1-b][1,3]oxazine-3-sulfonimidamide

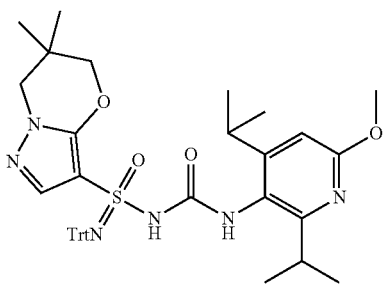

To a stirred mixture of 2,4-diisopropyl-6-methoxy-pyridin-3-amine (400 mg, 1.92 mmol) and triethylamine (0.4 mL, 2.88 mmol) in THF (8 mL) was added triphosgene (170 mg, 0.57 mmol). The reaction mixture was stirred at 70° C. for 1 hour. After cooling to room temperature, the reaction mixture was filtered and the filtrate was concentrated to give 3-isocyanato-2,4-diisopropyl-6-methoxy-pyridine (400 mg, yield: 89%) as a yellow oil.

To a solution of 6,6-dimethyl-N'-trityl-6,7-dihydro-5H-pyrazolo[5,1-b][1,3]oxazine-3-sulfonimidamide (400 mg, 0.85 mmol) in THF (16 mL) was added MeONa (69 mg, 1.27 mmol) at 0° C. under nitrogen atmosphere. After 15 minutes, 3-isocyanato-2,4-diisopropyl-6-methoxy-pyridine (397 mg, 1.69 mmol) was added. The reaction mixture was stirred at room temperature for 16 hours. The mixture was concentrated and the residue was purified by Prep-TLC (silica, 50% ethyl acetate in petroleum ether) to give N-((2,4-diisopropyl-6-methoxypyridin-3-yl)carbamoyl)-6,6-dimethyl-N'-trityl-6,7-dihydro-5H-pyrazolo[5,1-b][1,3]oxazine-3-sulfonimidamide (430 mg, yield: 72%) as a white solid. $^1$H NMR (400 MHz, MeOD): δ=7.46-7.37 (m, 6H), 7.25-7.19 (m, 9H), 6.86 (s, 1H), 6.52 (s, 1H), 4.00 (s, 2H), 3.91-3.85 (m, 3H), 3.73-3.62 (m, 2H), 3.42-3.34 (m, 1H), 3.20 (m, 1H), 1.30-1.18 (m, 1H), 1.30-1.18 (m, 10H), 1.12-1.03 (m, 7H).

Step 4—Synthesis of N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide

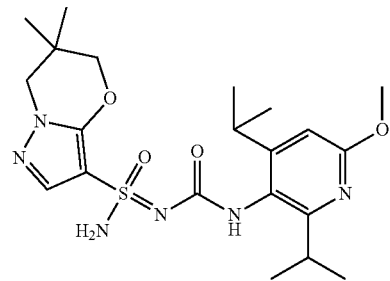 [SMILES: COc1cc(C(C)C)c(NC(=O)N=S(N)(=O)c2cnn3c2OCC(C)(C)C3)c(C(C)C)n1]

To a solution of N-((2,4-diisopropyl-6-methoxypyridin-3-yl)carbamoyl)-6,6-dimethyl-N'-trityl-6,7-dihydro-5H-pyrazolo[5,1-b][1,3]oxazine-3-sulfonimidamide (380 mg, 0.54 mmol) in THF (30 mL) was added MeSO$_3$H (0.17 mL, 2.69 mmol) at 0° C. The mixture was stirred at room temperature for 1 hour. The reaction solution was adjusted to pH=8 with saturated aqueous NaHCO$_3$ and concentrated. The residue was purified by Prep-TLC to give N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (300 mg crude, purity: 80%) as a white solid. MS: m/z 465.1 (M+H$^+$).

Step 5—(R)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide and (S)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (Example 76 and Example 77)

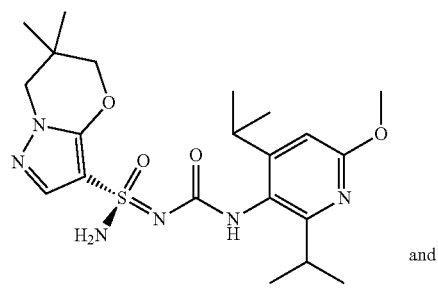

and

-continued

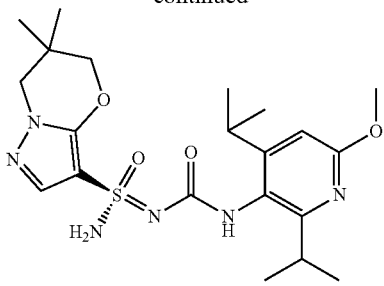

N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (240 mg, 0.52 mmol) was separated by using chiral SFC (Chiralpak IC (250 mm*30 mm, 5 um), Supercritical $CO_2$/EtOH+0.1% $NH_4OH$=30/70; 65 mL/min) to give (R)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (Method D, 4.07 min, peak 1, 36.4 mg, yield: 15%) and (S)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (Method D, 4.46 min, peak 2, 39.2 mg, yield: 16%) both as white solids. Stereochemistry was arbitrarily assigned to each stereoisomer.

Peak 1: $^1$H NMR (400 MHz, DMSO-$d_6$): δ=7.98 (s, 1H), 7.52 (s, 1H), 7.26 (s, 2H), 6.44 (s, 1H), 4.11-3.98 (m, 2H), 3.85 (s, 2H), 3.80 (s, 3H), 3.21-3.12 (m, 1H), 3.05-2.94 (m, 1H), 1.15-0.96 (m, 18H). MS: m/z 465.1 (M+H$^+$). Compound 76

Peak 2: $^1$H NMR (400 MHz, DMSO-$d_6$): δ=7.98 (s, 1H), 7.52 (s, 1H), 7.26 (s, 2H), 6.44 (s, 1H), 4.09-3.98 (m, 2H), 3.84 (s, 2H), 3.79 (s, 3H), 3.20-3.13 (m, 1H), 3.03-2.93 (m, 1H), 1.15-0.94 (m, 18H). MS: m/z 465.1 (M+H$^+$). Compound 77 Example 80 and Example 81 (S)—N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)—N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

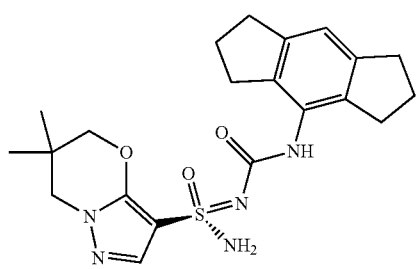

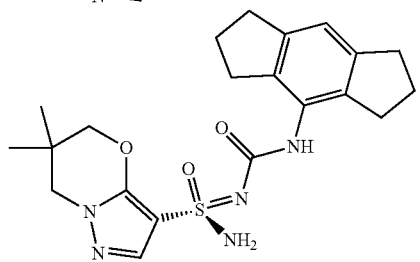

(S)—N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)—N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide were prepared by separating a racemic mixture of N'-(tert-butyldimethylsilyl)-N-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide by chiral prep-HPLC (deprotection of TBS protecting group occurs during the purification process) to deliver the two desired isomers Peak 1 (Method U, 0.60 min) and Peak 2 (Method U, 1.17 min), as white solids. Stereochemistry was arbitrarily assigned to each stereoisomer.

Peak 1: $^1$H NMR (400 MHz, DMSO-$d_6$) δ 8.13 (bs, 1H), 7.54 (s, 1H), 7.24 (bs, 2H), 6.85 (s, 1H), 4.11-4.02 (m, 2H), 3.86 (s, 2H), 2.77 (t, J=7.4 Hz, 4H), 2.68 (t, J=7.4 Hz, 4H), 1.99-1.86 (m, 4H), 1.04 (s, 3H), 1.03 (s, 3H). MS: m/z 430.2 (M+H$^+$).

Peak 2: $^1$H NMR (400 MHz, DMSO-$d_6$) δ 8.08 (bs, 1H), 7.51 (s, 1H), 7.11 (bs, 2H), 6.84 (s, 1H), 4.08-4.02 (m, 2H), 3.85 (s, 2H), 2.77 (t, J=7.4 Hz, 4H), 2.68 (t, J=7.4 Hz, 4H), 1.98-1.86 (m, 4H), 1.04 (s, 3H), 1.03 (s, 3H). MS: m/z 430.2 (M+H$^+$).

Example 82 and Example 83

(S,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

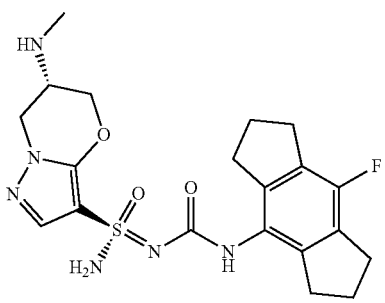

and

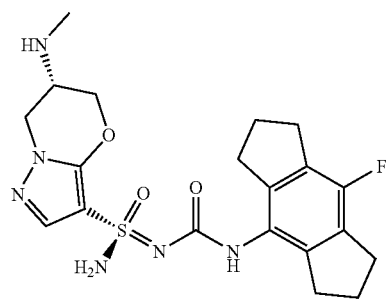

Step 1—Synthesis of tert-butyl ((6S)-3-(N-((8-fluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate

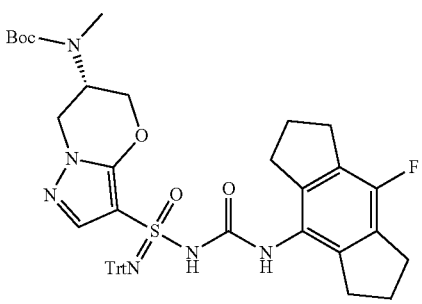

To a stirred solution of tert-butyl methyl((6S)-3-(N'-tritylsulfamimidoyl)-6,7-dihydro-5H-pyrazolo[5,1-b][1,3]oxazin-6-yl)carbamate (1.2 g, 2.09 mmol) in THF (30 mL) was added MeONa (226 mg, 4.18 mmol) in a 0° C. ice bath. After 15 minutes, a solution of 4-fluoro-8-isocyanato-1,2,3,5,6,7-hexahydro-s-indacene (1.02 g, 4.70 mmol) was added. The reaction mixture was stirred at room temperature for 16 hours. The reaction was quenched with MeOH (5 mL) and concentrated. The crude residue was purified by silica gel column chromatography (0-9% methanol in dichloromethane) to give tert-butyl ((6S)-3-(N-((8-fluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate (610 mg, yield: 53%) as a white solid. $^1$H NMR (400 MHz, DMSO-d$_6$) δ=8.29-8.13 (m, 1H), 7.58-7.57 (m, 1H), 7.29-7.28 (m, 2H), 4.55-4.25 (m, 5H), 2.82-2.79 (m, 4H), 2.76-2.65 (m, 7H), 2.13-1.88 (m, 4H), 1.42 (s, 9H). MS: m/z 571.1 (M+H$^+$).

Step 2—Synthesis of (6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide

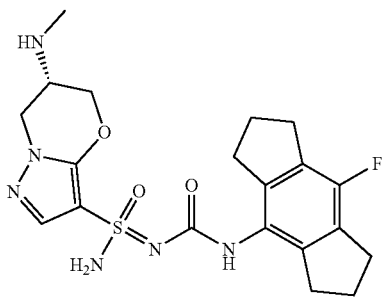 [SMILES: CN[C@@H]1COc2c(S(N)(=O)=NC(=O)Nc3c4c(c(F)c5c3CCC5)CCC4)cnn2C1]

To a stirred solution of tert-butyl ((6S)-3-(N-((8-fluoro-1,2,3,5,6,7-hexahydro-s-indacen-4-yl)carbamoyl)-N'-tritylsulfamimidoyl)-6,7-dihydro-5H-pyrazolo[5,1-b][1,3]oxazin-6-yl)(methyl)carbamate (150 mg, 0.27 mmol) in DCM (6.4 mL) was added MeSO$_3$H (0.06 mL, 0.94 mmol) at 0° C. After 30 minutes, NaHCO$_3$ (solid) and H$_2$O (0.1 ml) were added until the reaction solution was basic. The mixture was concentrated and the crude residue was purified by prep-TLC (silica, 10% MeOH in DCM, 1% NH$_3$·H$_2$O) to give (6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (44 mg, yield: 36%) as a white solid.
MS: m/z 449.0 (M+H$^+$).

Step 3—(S,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide and (R,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Example 82 and example 83)

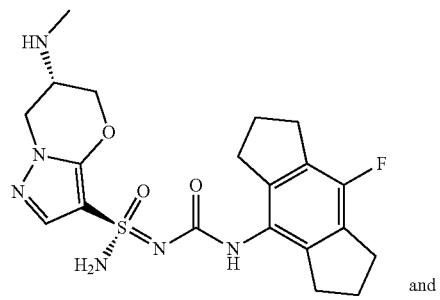

and

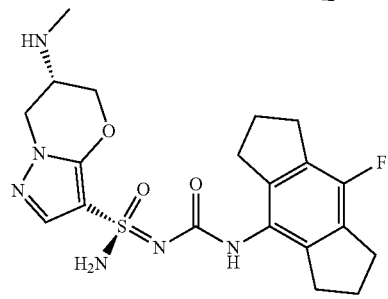

(6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (110 mg, 0.25 mmol) was separated by chiral SFC (Chiralpak AD (250 mm*30 mm, 10 um), Supercritical CO$_2$/EtOH+0.1% NH$_4$OH=40/60; 60 mL/min) to give (S,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Method E, 2.16 min, peak 1, 37.8 mg, yield: 32%) and (R,6S)—N'-((8-fluoro-1,2,3,5,6,7-hexahydro-s-indacen-4-yl)carbamoyl)-6-(methylamino)-6,7-dihydro-5H-pyrazolo[5,1-b][1,3]oxazine-3-sulfonimidamide (Method E, 2.32 min, peak 2, 30.9 mg, yield: 26%) both as white solid. Stereochemistry was arbitrarily assigned to each stereoisomer.
Peak 1: $^1$H NMR (400 MHz, DMSO-d$_6$) δ=8.16 (s, 1H), 7.47 (s, 1H), 7.21 (s, 2H), 4.33-4.30 (m, 1H), 4.24-4.16 (m, 2H), 3.91-3.87 (m, 1H), 3.20-3.13 (m, 1H), 2.77 (t, J=7.2 Hz, 4H), 2.69 (t, J=7.2 Hz, 4H), 2.30 (s, 3H), 2.01-1.92 (m, 4H). MS: m/z 449.1 (M+H$^+$).
Peak 2: $^1$H NMR (400 MHz, DMSO-d$_6$) δ=8.20 (s, 1H), 7.50 (s, 1H), 7.24 (s, 2H), 4.36-4.20 (m, 3H), 3.96-3.92 (m, 1H), 3.20-3.13 (m, 2H), 2.81 (t, J=7.2 Hz, 4H), 2.74 (t, J=6.8 Hz, 4H), 2.34 (s, 3H), 2.04-1.97 (m, 4H), MS: m/z 449.1 (M+H$^+$).

Example 84 and Example 85

(S)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide and (R)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide

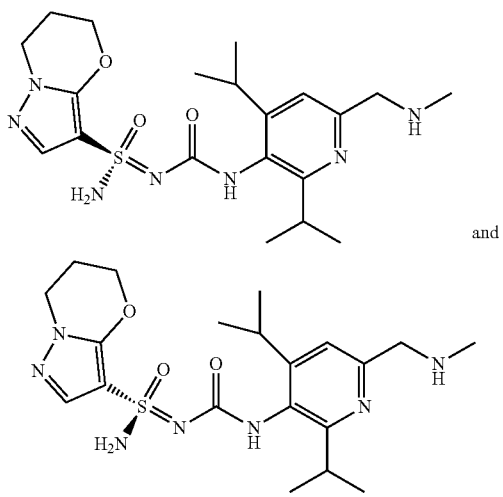

and

Step 1—Synthesis of tert-butyl ((4,6-diisopropyl-5-nitropyridin-2-yl)methyl)(methyl)carbamate

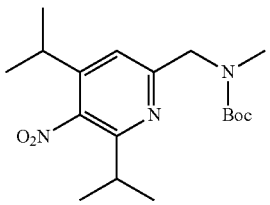 [SMILES: CC(C)c1cc(CN(C)C(=O)OC(C)(C)C)nc(C(C)C)c1[N+](=O)[O-]]

To a solution of 6-chloro-2,4-diisopropyl-3-nitro-pyridine (500 mg, 2.06 mmol), tert-butyl methyl((4,4,5,5-tetramethyl-1,3,2-dioxaborolan-2-yl)methyl)carbamate (726 mg, 2.68 mmol), K₃PO⁴ (1.3 g, 6.18 mmol) in 1,4-dioxane (5 mL) and water (0.5 mL) was added CataCXium A Pd G2 (138 mg, 0.21 mmol) under nitrogen atmosphere. The mixture was stirred at 80° C. for 16 hours. After cooling to room temperature, the reaction mixture was diluted with water (50 mL) and extracted with EtOAc (50 mL×2). The combined organic layers were washed with brine (50 mL×2), dried over anhydrous Na₂SO₄, filtered and concentrated. The residue was purified by silica gel column chromatography (0-10% EtOAc in petroleum ether) to give tert-butyl ((4,6-diisopropyl-5-nitropyridin-2-yl)methyl)(methyl)carbamate (440 mg, yield: 61%) as a yellow solid. $^1$H NMR (400 MHz, CDCl₃) δ=7.08-7.00 (m, 1H), 4.55-4.45 (m, 2H), 3.07-2.94 (m, 4H), 2.91-2.81 (m, 1H), 1.46-1.41 (m, 9H), 1.29-1.23 (m, 12H).

Step 2—Synthesis of tert-butyl ((5-amino-4,6-diisopropylpyridin-2-yl)methyl)(methyl)carbamate

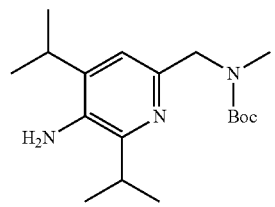 [SMILES: CC(C)c1cc(CN(C)C(=O)OC(C)(C)C)nc(C(C)C)c1N]

To a solution of tert-butyl ((4,6-diisopropyl-5-nitropyridin-2-yl)methyl)(methyl)carbamate (440 mg, 1.25 mmol) in EtOH (10 mL) was added 10% palladium (133 mg, 0.13 mmol) on carbon. The mixture was stirred at room temperature under hydrogen atmosphere (15 psi). After 2 hours, the mixture was filtered and the filtrate was concentrated to give tert-butyl ((5-amino-4,6-diisopropylpyridin-2-yl)methyl)(methyl)carbamate (300 mg, yield: 75%) as yellow oil. $^1$H NMR (400 MHz, CDCl₃) δ=6.88-6.80 (m, 1H), 4.45-4.34 (m, 2H), 3.60 (s, 2H), 3.07-3.02 (m, 1H), 2.96-2.83 (m, 4H), 1.57-1.46 (m, 9H), 1.29-1.20 (m, 12H).

Step 3—Synthesis of tert-butyl ((5-isocyanato-4,6-diisopropylpyridin-2-yl)methyl)(methyl)carbamate

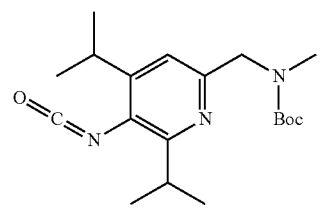 [SMILES: CC(C)c1cc(CN(C)C(=O)OC(C)(C)C)nc(C(C)C)c1N=C=O]

To a solution of tert-butyl ((5-amino-4,6-diisopropylpyridin-2-yl)methyl)(methyl)carbamate (300 mg, 0.93 mmol) and triethylamine (0.26 mL, 1.87 mmol) in THF (6 mL) was added triphosgene (70 mg, 0.24 mmol) at 0° C. The reaction mixture was stirred at 50° C. for 1 hour. After cooling to room temperature, the mixture was filtered and the filtrate concentrated to give tert-butyl ((5-isocyanato-4,6-diisopropylpyridin-2-yl)methyl)(methyl)carbamate (300 mg, yield: 93%) as a yellow oil.

Step 4—Synthesis of tert-butyl ((4,6-diisopropyl-5-(3-(N-trityl-6,7-dihydro-5H-pyrazolo[5,1-b][1,3]oxazine-3-sulfonimidoyl)ureido)pyridin-2-yl)methyl)(methyl)carbamate

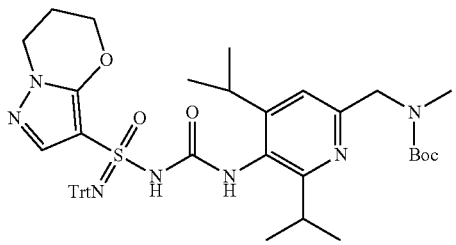

To a stirred solution of N'-trityl-6,7-dihydro-5H-pyrazolo[5,1-b][1,3]oxazine-3-sulfonimidamide (300 mg, 0.67 mmol) in THF (12 mL) was added MeONa (73 mg, 1.35 mmol) at 0° C. under nitrogen atmosphere. After 15 minutes, tert-butyl ((5-isocyanato-4,6-diisopropylpyridin-2-yl)methyl)(methyl)carbamate (281 mg, 0.81 mmol). The reaction mixture was stirred at room temperature for 16 hours. The reaction was quenched with MeOH (1 mL) and the resulting mixture was concentrated. The residue was purified by silica gel column chromatography (0-5% methanol in DCM) to give tert-butyl ((4,6-diisopropyl-5-(3-(N-trityl-6,7-dihydro-5H-pyrazolo[5,1-b][1,3]oxazine-3-sulfonimidoyl)ureido)pyridin-2-yl)methyl)(methyl)carbamate (260 mg, yield: 49%) as a light yellow solid. MS: m/z 792.3 (M+H$^+$).

Step 5—Synthesis of N'-((2,4-diisopropyl-6-((methylamino)methyl)pyridin-3-yl)carbamoyl)-6,7-dihydro-5H-pyrazolo[5,1-b][1,3]oxazine-3-sulfonimidamide

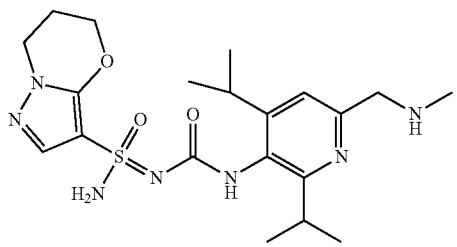 [SMILES: CNCc1cc(C(C)C)c(NC(=O)N=S(N)(=O)c2cnn3c2OCCC3)c(C(C)C)n1]

To a solution of tert-butyl ((4,6-diisopropyl-5-(3-(N-trityl-6,7-dihydro-5H-pyrazolo[5,1-b][1,3]oxazine-3-sulfonimidoyl)ureido)pyridin-2-yl)methyl)(methyl)carbamate (200 mg, 0.25 mmol) in DCM (12 mL) was added MeSO$_3$H (121 mg, 1.26 mmol) at room temperature. After 2 hours, the reaction was adjusted to pH=8 with saturated aqueous NaHCO$_3$, and concentrated. The crude residue was purified by prep-TLC (silica, 10% methanol in DCM) to give N'-((2,4-diisopropyl-6-((methylamino)methyl)pyridin-3-yl)carbamoyl)-6,7-dihydro-5H-pyrazolo[5,1-b][1,3]oxazine-3-sulfonimidamide (90 mg, yield: 79%) as alight yellow solid. MS: m/z 450.2 (M+H$^+$).

Step 6—(S)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide and (R)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide (Example 84 and example 85)

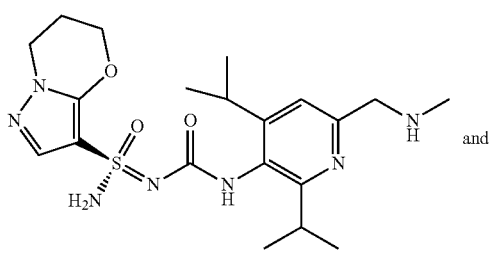 and

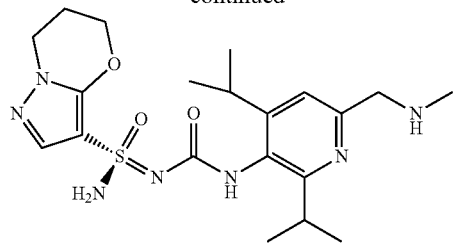

N'-((2,4-diisopropyl-6-((methylamino)methyl)pyridin-3-yl)carbamoyl)-6,7-dihydro-5H-pyrazolo[5,1-b][1,3]oxazine-3-sulfonimidamide (105 mg, 0.23 mmol) was purified by using chiral SFC (Chiralpak IC (250 mm*30 mm, 10 um), Supercritical CO$_2$/EtOH+0.1% NH$_4$OH=50/50; 70 mL/min) give (S)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide (Method F, 5.43 min, peak 1, 19 mg, yield: 17%) and (R)—N'-((2,4-diisopropyl-6-((methylamino)methyl)pyridin-3-yl)carbamoyl)-6,7-dihydro-5H-pyrazolo[5,1-b][1,3]oxazine-3-sulfonimidamide (Method F, 7.26 min, peak 2, 17.3 mg, yield: 15%) both as light yellow solids. Stereochemistry was arbitrarily assigned to each stereoisomer.

Peak 1: $^1$H NMR (400 MHz, DMSO-d$_6$): δ=8.10 (s, 1H), 7.46 (s, 1H), 7.06 (s, 1H), 4.37-4.25 (m, 2H), 4.10-4.01 (m, 2H), 3.63 (s, 2H), 3.22-3.15 (m, 1H), 3.08-2.99 (m, 1H), 2.29 (s, 3H), 2.20-2.10 (m, 2H), 1.10-1.00 (m, 12H). MS: m/z 450.3 (M+H$^+$).

Peak 2: $^1$H NMR (400 MHz, DMSO-d$_6$): δ=8.11 (s, 1H), 7.49 (s, 1H), 7.09 (s, 1H), 4.46-4.30 (m, 2H), 4.10 (t, J=6.0 Hz, 2H), 3.63 (s, 2H), 3.25-3.15 (m, 1H), 3.13-3.01 (m, 1H), 2.30 (s, 3H), 2.20-2.10 (m, 2H), 1.12-1.00 (m, 12H). MS: m/z 450.3 (M+H$^+$).

Example 88, Example 89, Example 90 and Example 91

(S,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, (S,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide and (R,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide

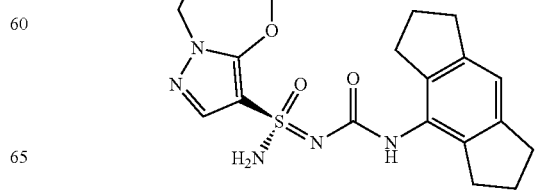

-continued

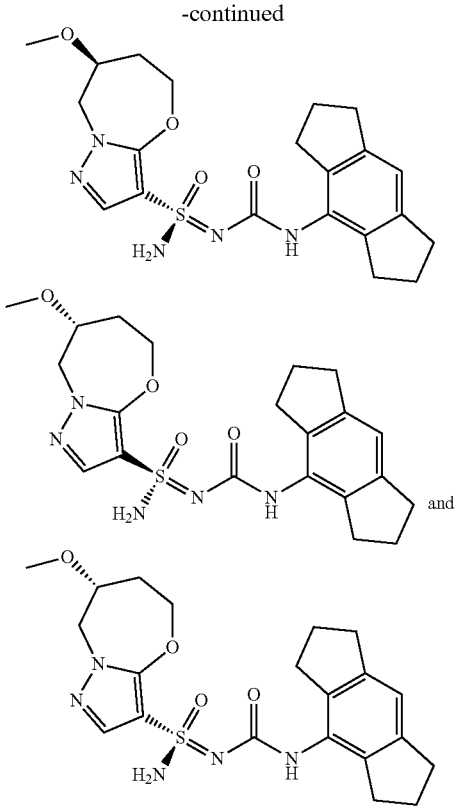

and

Step 1—Synthesis of diethyl 2-(benzyloxy)succinate

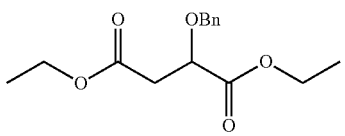 [SMILES: CCOC(=O)CC(OCc1ccccc1)C(=O)OCC]

To a mixture of diethyl malate (35 g, 184 mmol) and Ag$_2$O (85.3 g, 368.1 mmol) in EtOAc (460 mL) was added BnBr (31.5 g, 184.0 mmol) dropwise at 0° C. The reaction was stirred at room temperature for 12 hours in a dark environment. The reaction mixture was filtered over a short pad of celite. The filtrate was concentrated to give diethyl 2-(benzyloxy)succinate (50 g, yield: 97%) as a colorless oil. $^1$H NMR (400 MHz, CDCl$_3$)=7.39-7.28 (m, 5H), 4.83-4.49 (m, 2H), 4.41-4.38 (m, 1H), 4.29-4.09 (m, 4H), 2.88-2.71 (m, 2H), 1.33-1.22 (m, 6H).

Step 2—Synthesis of 2-benzyloxybutane-1,4-diol

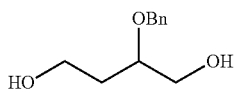

To a mixture of LiAlH$_4$ (10.2 g, 267.6 mmol) in THF (381 mL) was added a solution of diethyl 2-(benzyloxy)succinate (30 g, 107.0 mmol) in THF (96 mL) at 0° C. under nitrogen atmosphere. The reaction mixture was warmed to room temperature and stirred for 12 hours. The mixture was cooled to 0° C. and successively quenched with water (12 mL), 15% aqueous NaOH (12 mL) and finally additional water (36 mL). The mixture was filtered and concentrated to give 2-benzyloxybutane-1,4-diol (15 g, yield: 71%) as a colorless oil. $^1$H NMR (400 MHz, CDCl$_3$) δ=7.40-7.28 (m, 5H), 4.61 (d, J=2.0 Hz, 2H), 3.81-3.68 (m, 4H), 3.65-3.58 (m, 1H), 2.63 (s, 2H), 1.94-1.77 (m, 2H)

Step 3—Synthesis of 2-(benzyloxy)butane-1,4-diyl dimethanesulfonate

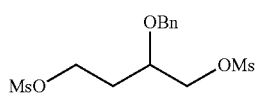 [SMILES: CS(=O)(=O)OCCC(COS(C)(=O)=O)OCc1ccccc1]

To a solution of 2-benzyloxybutane-1,4-diol (10 g, 50.9 mmol) and triethylamine (24 .mL, 173.1 mmol) in DCM (108 mL) was added MsCl (9.6 mL, 124.0 mmol) drop-wise at 0° C. The reaction mixture was stirred at room temperature for 1 hour. The reaction was quenched with water (80 mL). The aqueous layer was extracted with DCM (50 mL×2). The combined organic layers were dried over anhydrous Na$_2$SO$_4$, filtered and concentrated to give 2-(benzyloxy)butane-1,4-diyl dimethanesulfonate (17.5 g, yield: 97%) as a brown oil. $^1$H NMR (400 MHz, CDCl$_3$) δ=7.41-7.29 (m, 5H), 4.75-4.54 (m, 2H), 4.44-4.31 (m, 3H), 4.24-4.20 (m, 1H), 3.92-3.85 (m, 1H), 3.02 (s, 3H), 2.96 (s, 3H), 2.10-1.97 (m, 2H).

Step 4—Synthesis of 7-benzyloxy-5,6,7,8-tetrahydropyrazolo[5,1-b][1,3]oxazepine and 6-benzyloxy-5,6,7,8-tetrahydropyrazolo[5,1-b][1,3]oxazepine

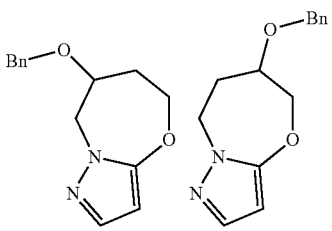

To a stirred solution of 1H-pyrazol-5-ol (55 g, 65.4 mmol) in DMF (200 mL) was added K$_2$CO$_3$ (31.6 g, 229 mmol) and the mixture was stirred at 130° C. for 30 minutes. Then, a solution of 2-(benzyloxy)butane-1,4-diyl dimethanesulfonate (27.7 g, 78.5 mmol) in DMF (50 mL) was added and the mixture was allowed to stir at 130° C. for an additional 16 hours. After cooling to room temperature, the mixture was filtered and concentrated. The crude residue was purified by silica gel column chromatography (10% EtOAc in petroleum ether) to give 7-benzyloxy-5,6,7,8-tetrahydropyrazolo[5,1-b][1,3]oxazepine (5.7 g, yield: 36%) and 6-benzyloxy-5,6,7,8-tetrahydropyrazolo[5,1-b][1,3] oxazepine (720 mg, yield: 5%) both as colorless oil.

7-Benzyloxy-5,6,7,8-tetrahydropyrazolo[5,1-b][1,3] oxazepine: $^1$H NMR (400 MHz, CDCl$_3$) δ=7.37-7.29 (m, 6H), 5.71 (d, J=2.0 Hz, 1H), 4.72 (d, J=12 Hz, 1H), 4.55-4.52 (m, 2H), 4.29-4.19 (m, 2H), 4.13-4.05 (m, 1H), 3.82-3.78 (m, 1H), 2.23-2.18 (m, 2H).

6-Benzyloxy-5,6,7,8-tetrahydropyrazolo[5,1-b][1,3]oxazepine: ¹H NMR (400 MHz, CDCl₃) δ=7.41-7.29 (m, 5H), 7.24 (d, J=2.0 Hz, 1H), 5.71 (d, J=2.0 Hz, 1H), 4.68 (s, 2H), 4.53-4.44 (m, 1H), 4.16-4.07 (m, 2H), 4.07-4.02 (m, 1H), 3.86-3.80 (m, 1H), 2.11-2.04 (m, 2H).

Step 5—Synthesis of 5,6,7,8-tetrahydropyrazolo[5,1-b][1,3]oxazepin-7-ol

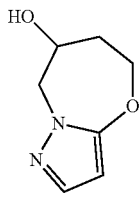

To a stirred solution of 7-benzyloxy-5,6,7,8-tetrahydropyrazolo[5,1-b][1,3]oxazepine (3 g, 12.3 mmol) in EtOH (30 mL) was added 10% wet palladium (1.5 g, 1.4 mmol) on carbon and the mixture was stirred at 50° C. under a H₂ atmosphere (45 psi). After 12 hours, the reaction was cooled to room temperature, and filtered over a short pad of Celite. The filtrate was concentrated and the crude residue was purified by silica gel column chromatography (50% EtOAc in petroleum ether) to give 5,6,7,8-tetrahydropyrazolo[5,1-b][1,3]oxazepin-7-ol (1.4 g, yield: 75%) as a white solid. MS: m/z 154.8 (M+H⁺).

Step 6—Synthesis of 7-methoxy-5,6,7,8-tetrahydropyrazolo[5,1-b][1,3]oxazepine

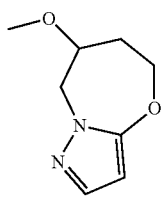

To a solution of 5,6,7,8-tetrahydropyrazolo[5,1-b][1,3]oxazepin-7-ol (1.5 g, 9.7 mmol) in MeCN (30 mL) was added MeI (1.8 mL, 28.9 mmol) and Ag₂O (4.5 g, 19.5 mmol) at room temperature. After 16 hours, the reaction mixture was filtered over a short pad of Celite. The celite pad was washed with EtOH (2 mL×3). The filtrate was concentrated and the crude residue was purified by silica gel column chromatography (40% EtOAc in petroleum ether) to give 7-methoxy-5,6,7,8-tetrahydropyrazolo[5,1-b][1,3]oxazepine (1.25 g, yield: 76%) as a yellow oil. ¹H NMR (400 MHz, CDCl₃) δ=7.30-7.26 (m, 1H), 5.69 (d, J=2.0 Hz, 1H), 4.50-4.45 (m, 1H), 4.25-4.07 (m, 3H), 3.64-3.58 (m, 1H), 3.41 (s, 3H), 2.22-2.16 (m, 2H).

Step 7—Synthesis of 3-bromo-7-methoxy-5,6,7,8-tetrahydropyrazolo[5,1-b][1,3]oxazepine

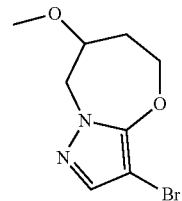

To a solution of 7-methoxy-5,6,7,8-tetrahydropyrazolo[5,1-b][1,3]oxazepine (1.13 g, 6.7 mmol) in MeCN (24 mL) was added NBS (1.2 g, 6.7 mmol). The resulting solution was stirred at room temperature for 12 hours. The reaction mixture was concentrated and the crude residue was purified by flash column chromatography (silica, 30% EtOAc in petroleum ether) to give 3-bromo-7-methoxy-5,6,7,8-tetrahydropyrazolo[5,1-b][1,3]oxazepine (1.38 g, yield: 83%) as a yellow solid. ¹H NMR (400 MHz, CDCl₃) δ=7.28 (s, 1H), 4.53-4.48 (m, 1H), 4.24-4.17 (m, 3H), 3.65-3.61 (m, 1H), 3.39 (s, 3H), 2.24-2.20 (m, 2H).

Step 8—Synthesis of 7-methoxy-N'-trityl-5,6,7,8-tetrahydropyrazolo[5,1-b][1,3]oxazepine-3-sulfonimidamide

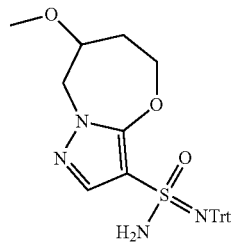

To a solution of 3-bromo-7-methoxy-5,6,7,8-tetrahydropyrazolo[5,1-b][1,3]oxazepine (600 mg, 2.4 mmol) in THF (20 mL) was added n-BuLi (2.5 M in hexane, 1.2 mL, 3.0 mmol) drop-wise at −78° C. After 1 hour, a solution of TrtNSO (890 mg, 2.9 mmol) in THF (2 mL) was added-drop wise. The reaction was allowed to stir at −78° C. for 20 minutes at which point it was placed in a 0° C. ice bath where it stirred for an additional 10 minutes. t-BuOCl (0.3 mL, 2.9 mmol) was added drop-wise at 0° C. After 20 minutes, NH₃ gas was bubbled through the mixture for 10 minutes. The reaction was warmed to room temperature and stirred for an additional 16 hours. The reaction mixture was concentrated and the crude residue was purified by silica gel column chromatography (50% EtOAc in petroleum ether) to give 7-methoxy-N'-trityl-5,6,7,8-tetrahydropyrazolo[5,1-b][1,3]oxazepine-3-sulfonimidamide (200 mg, yield 33%) as a white solid. MS: m/z 511.1 (M+H⁺).

Step 9—Synthesis of N'-((1,2,3,5,6,7-hexahydro-s-indacen-4-yl)carbamoyl)-7-methoxy-N'-trityl-5,6,7,8-tetrahydropyrazolo[5,1-b][1,3]oxazepine-3-sulfonimidamide

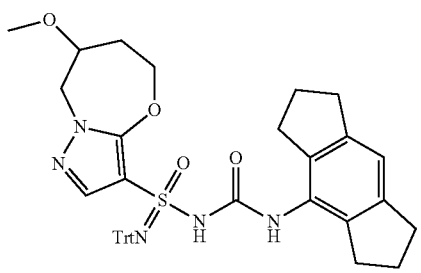

To a stirred solution of 7-methoxy-N'-trityl-5,6,7,8-tetrahydropyrazolo[5,1-b][1,3]oxazepine-3-sulfonimidamide (657 mg, 1.3 mmol) in THF (10 mL) was added MeONa (109 mg, 2.0 mmol) in at 0° C. under a nitrogen atmosphere. After 20 minutes, a solution of 4-isocyanato-1,2,3,5,6,7-hexahydro-s-indacene (536 mg, 2.7 mmol) in THF (2 mL) was added. The reaction mixture was allowed to stir at room temperature for 16 hours. The reaction mixture was filtered and the filtrate was concentrated. The crude residue was purified by column chromatography (silica, 50% EtOAc in petroleum ether) to give N-((1,2,3,5,6,7-hexahydro-s-indacen-4-yl)carbamoyl)-7-methoxy-N'-trityl-5,6,7,8-tetrahydropyrazolo[5,1-b][1,3]oxazepine-3-sulfonimidamide (605 mg, yield: 65%) as white solid. MS: m/z 710.1 (M+H⁺).

Step 10—Synthesis of N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide

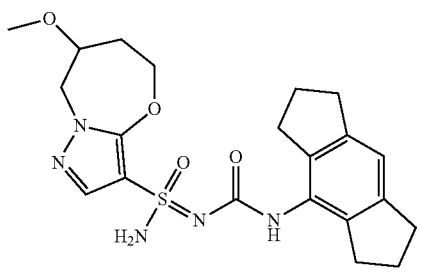 [SMILES: COC1CCOc2c(S(N)(=O)=NC(=O)Nc3c4c(cc5c3CCC5)CCC4)cnn2C1]

To a stirred solution of N-((1,2,3,5,6,7-hexahydro-s-indacen-4-yl)carbamoyl)-7-methoxy-N'-trityl-5,6,7,8-tetrahydropyrazolo[5,1-b][1,3]oxazepine-3-sulfonimidamide (605 mg, 0.9 mmol) in DCM (46 mL) was added MeSO₃H (0.06 mL, 0.9 mmol) at room temperature. After 1 hour, water (1 mL) was added and the reaction was basified with NaHCO₃ (solid) to pH=8. The mixture was filtered and washed with MeOH (20 mL). The filtrate was concentrated and the crude residue was purified by prep-TLC (silica, 5% MeOH in DCM) to give N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (191 mg, yield: 49%) as a white solid. MS: m/z 446.0 (M+H⁺).

Step 11—(S,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, (S,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide and (R,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (Example 88, Example 89, Example 90 and Example 91)

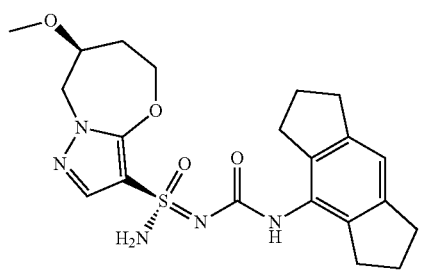

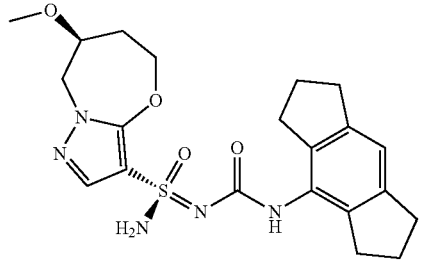

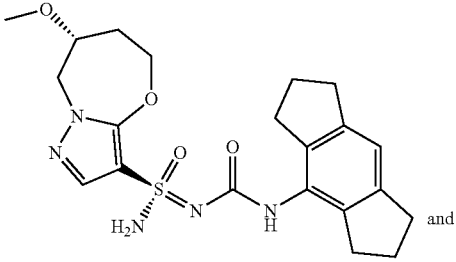

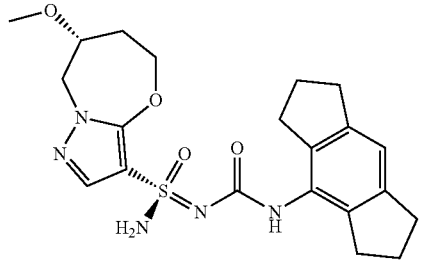

and

N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (212 mg, 0.48 mmol) was separated by using chiral SFC (Chiralpak AD (250 mm*30 mm, 10 um, Supercritical CO₂/MeOH+0.1% NH₄OH=60/40; 80 mL/min) to give peak 3 (Method G, 4.71 min, 331.5 mg, yield: 15%), peak 4 ((Method G, 7.64 min, 34.8 mg, yield: 16%) and 84 mg mixture of peak 1 and peak 2, which was separated by using chiral SFC (Cellulose-2 (250 mm*30 mm, 10 um, Supercritical CO$_2$/MeOH+0.1% NH$_4$OH=45/55; 80 mL/min) to give peak 1 (Method H, 3.68 min, 35 mg, yield: 17%) and peak 2 (Method H, 4.78 min, 30.4 mg, yield: 14%) all as white solids. Stereochemistry was arbitrarily assigned to each stereoisomer.

Peak 1: $^1$H NMR (400 MHz, DMSO-d$_6$) δ=8.19 (s, 1H), 7.52 (s, 1H), 7.33 (s, 2H), 6.86 (s, 1H), 4.52-4.48 (m, 1H), 4.28-4.20 (m, 2H), 4.12-4.05 (m, 1H), 3.70-3.67 (m, 1H), 3.26 (s, 3H), 2.77 (t, J=7.2 Hz, 4H), 2.67 (t, J=7.2 Hz, 4H), 2.20-2.12 (m, 2H), 1.96-1.89 (m, 4H). MS: m/z 446.1 (M+H$^+$). Compound 90

Peak 2: $^1$H NMR (400 MHz, DMSO-d$_6$) δ=8.23 (s, 1H), 7.50 (s, 1H), 7.31 (s, 2H), 6.86 (s, 1H), 4.52-4.48 (m, 1H), 4.28-4.21 (m, 2H), 4.07-4.02 (m, 1H), 3.69-3.66 (m, 1H), 3.26 (s, 3H), 2.78 (t, J=7.2 Hz, 4H), 2.69-2.62 (m, 4H), 2.19-2.13 (m, 2H), 1.97-1.89 (m, 4H). MS: m/z 446.1 (M+H$^+$). Compound 91

Peak 3: $^1$H NMR (400 MHz, DMSO-d$_6$) δ=8.22 (s, 1H), 7.50 (s, 1H), 7.30 (s, 2H), 6.86 (s, 1H), 4.52-4.47 (m, 1H), 4.28-4.20 (m, 2H), 4.07-4.02 (m, 1H), 3.70-3.66 (m, 1H), 3.26 (s, 3H), 2.77 (t, J=7.2 Hz, 4H), 2.70-2.60 (m, 4H), 2.20-2.11 (m, 2H), 1.96-1.89 (m, 4H), MS: m/z 446.1 (M+H$^+$). Compound 88

Peak 4: $^1$H NMR (400 MHz, DMSO-d$_6$) δ=8.18 (s, 1H), 7.52 (s, 1H), 7.32 (s, 2H), 6.86 (s, 1H), 4.53-4.48 (m, 1H), 4.27-4.20 (m, 2H), 4.11-4.06 (m, 1H), 3.70-3.66 (m, 1H), 3.26 (s, 3H), 2.77 (t, J=7.2 Hz, 4H), 2.67-2.61 (m, 4H), 2.20-2.12 (m, 2H), 1.96-1.91 (m, 4H), MS: m/z 446.1 (M+H$^+$). Compound 89

Example 86, Example 87, Example 92 and Example 93

(S,6R)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide, (S,6S)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide and (R,6S)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide

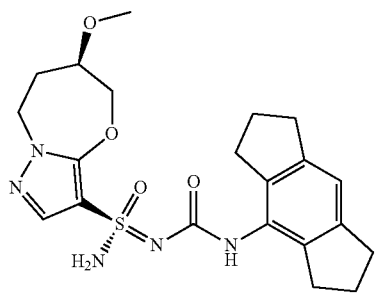

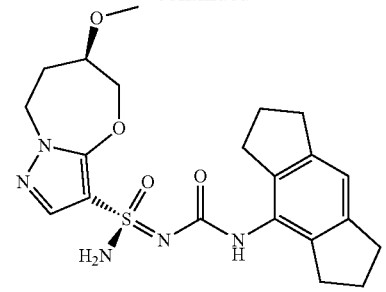

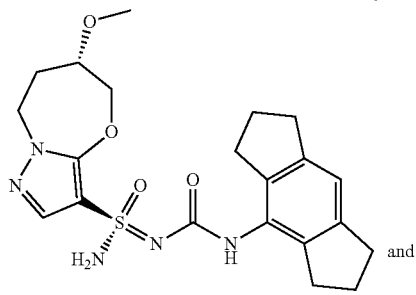

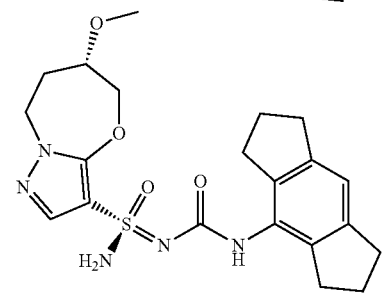

Step 1~6—Synthesis of N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide

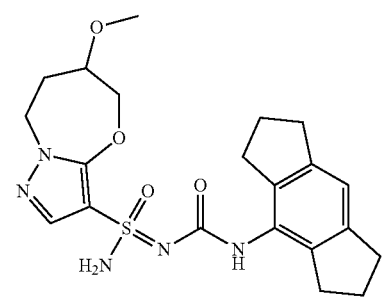 [SMILES: COC1CCn2ncc(S(N)(=O)=NC(=O)Nc3c4c(cc5c3CCC5)CCC4)c2OC1]

N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide was prepared using the general procedure described for the preparation of N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide (Example 86, Example 87, Example 92 and Example 93) by replacing 7-(benzyloxy)-5,6,7,8-tetrahydropyrazolo[5,1-b][1,3]oxazepine with 6-(benzyloxy)-5,6,7,8-tetrahydropyrazolo[5,1-b][1,3]oxazepine in Step 5.

Step 7—(S,6R)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide, (S,6S)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide and (R,6S)—N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide (Example 86, Example 87, Example 92 and Example 93)

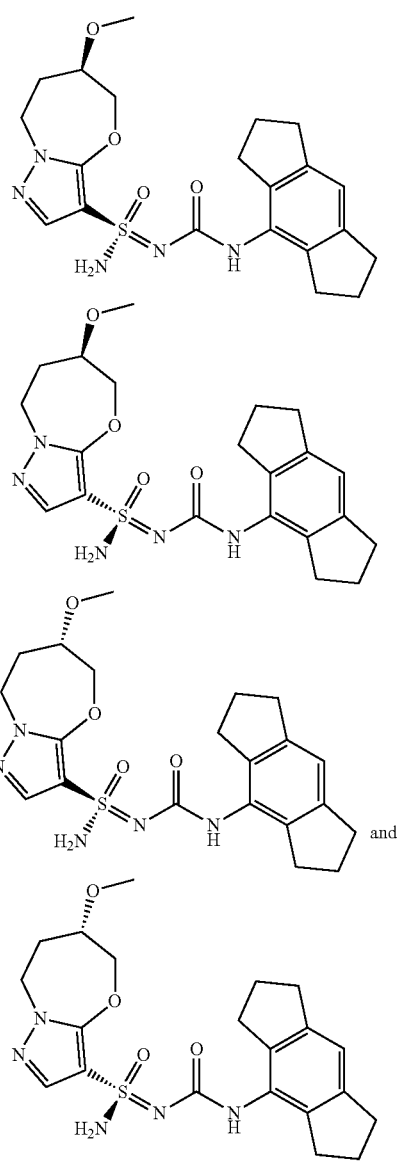

N'-((1,2,3,5,6,7-hexahydro-s-indacen-4-yl)carbamoyl)-6-methoxy-5,6,7,8-tetrahydropyrazolo[5,1-b][1,3]oxazepine-3-sulfonimidamide (103 mg, 0.23 mmol) was separated by using chiral SFC (Chiralpak AD (250 mm*30 mm, 10 um), Supercritical CO$_2$/EtOH+0.1% NH$_4$OH=50/50; 70 mL/min) to give peak 1 (Method I, 2.95 min, 14.9 mg, yield: 14%), peak 2 (Method I, 3.69 min, 14 mg, yield: 13%), peak 3 (Method I, 4.59 min, 15.9 mg, yield: 14%) and peak 4 (Method I, 8.46 min, 18 mg, yield: 17%) all as white solid. Stereochemistry was arbitrarily assigned to each stereoisomer.

Peak 1: $^1$H NMR (400 MHz, DMSO-d$_6$) δ=8.22 (s, 1H), 7.50 (s, 1H), 7.29 (s, 2H), 6.85 (s, 1H), 4.27-4.22 (m, 2H), 4.12-4.04 (m, 2H), 3.73-3.67 (m, 1H), 3.32 (s, 3H), 2.76 (t, J=6.8 Hz, 4H), 2.71-2.66 (m, 4H), 1.96-1.90 (m, 6H). MS: m/z 446.1 (M+H$^+$). Compound 86

Peak 2: $^1$H NMR (400 MHz, DMSO-d$_6$) δ=8.14 (s, 1H), 7.47 (s, 1H), 7.27 (s, 2H), 6.82 (s, 1H), 4.23-4.18 (m, 2H), 4.07-4.04 (m, 2H), 3.67-3.66 (m, 1H), 3.32 (s, 3H), 2.73 (t, J=7.2 Hz, 4H), 2.62-2.52 (m, 4H), 1.92-1.84 (m, 6H). MS: m/z 446.1 (M+H$^+$). Compound 87

Peak 3: $^1$H NMR (400 MHz, DMSO-d$_6$) δ=8.13 (s, 1H), 7.46 (s, 1H), 7.22 (s, 2H), 6.81 (s, 1H), 4.24-4.18 (m, 2H), 4.15-4.05 (m, 2H), 3.69-3.66 (m, 1H), 3.32 (s, 3H), 2.73 (t, J=7.2 Hz, 4H), 2.60 (t, J=7.2 Hz, 4H), 1.92-1.80 (m, 6H). MS: m/z 446.1 (M+H$^+$). Compound 92

Peak 4: $^1$H NMR (400 MHz, DMSO-d$_6$) δ=8.19 (s, 1H), 7.50 (s, 1H), 7.25 (s, 1H), 6.85 (s, 1H), 4.27-4.21 (m, 2H), 4.13-4.02 (m, 4H), 3.72-3.68 (m, 1H), 3.35 (s, 3H), 2.76 (t, J=7.2 Hz, 4H), 2.69-2.60 (m, 4H), 1.96-1.88 (m, 6H). MS: m/z 446.1 (M+H$^+$). Compound 93

Example 94

N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

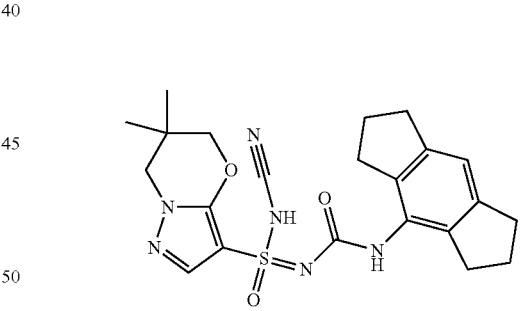

(N-cyano-N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (N'-((1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide in Step 1 (mixture of enantiomers). $^1$H NMR (400 MHz, DMSO-d₆) δ 7.71 (s, 1H), 7.38 (s, 1H), 6.79 (s, 1H), 4.05-3.94 (m, 2H), 3.82 (s, 2H), 2.79-2.61 (m, 8H), 1.90 (p, J=7.3 Hz, 4H), 1.03 (s, 3H), 1.02 (s, 3H). MS: m/z 455.2 (M+H⁺).

Example 95

(S)—N—(N-((8-fluoro-1,2,3,5,6,7-hexahydro-s-indacen-4-yl)carbamoyl)-6,7-dihydro-5H-pyrazolo[5,1-b][1/3]oxazine-3-sulfonimidoyl)acetamide

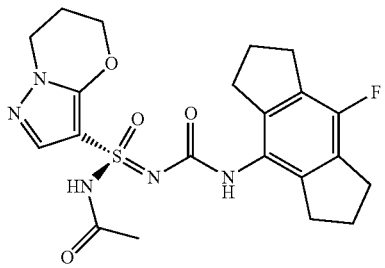 [SMILES: CC(=O)N[S@@](=O)(=NC(=O)Nc1c2c(c(F)c3c1CCC3)CCC2)c1cnn2c1OCCC2]

Step 1—Synthesis of (S)—N—(N-((8-fluoro-1,2,3,5,6,7-hexahydro-s-indacen-4-yl)carbamoyl)-6,7-dihydro-5H-pyrazolo[5,1-b][1,3]oxazine-3-sulfonimidoyl)acetamide (Example 95)

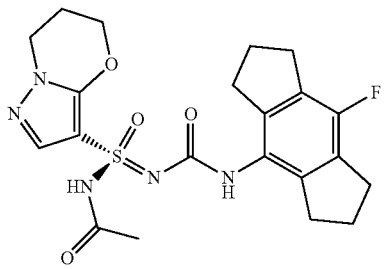 [SMILES: CC(=O)N[S@@](=O)(=NC(=O)Nc1c2c(c(F)c3c1CCC3)CCC2)c1cnn2c1OCCC2]

Acetyl chloride (2.1 mg, 1.9 μL, 26 μmol) was added dropwise to a solution of (R)—N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (10 mg, 24 μmol) in pyridine (1.0 mL) at 0° C. After 1 hour, toluene (10 mL) was added and the mixture was concentrated under reduced pressure. The crude residue was dissolved in MeOH (1 mL) and purified by prep-HPLC to afford (S)—N—(N-((8-fluoro-1,2,3,5,6,7-hexahydro-s-indacen-4-yl)carbamoyl)-6,7-dihydro-5H-pyrazolo[5,1-b][1,3]oxazine-3-sulfonimidoyl)acetamide (2.0 mg, yield: 18%—as an unknown stereoisomer) as a white solid. MS: m/z 462 (M+H⁺).

Example 96 and Example 97

(R)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide and (S)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide

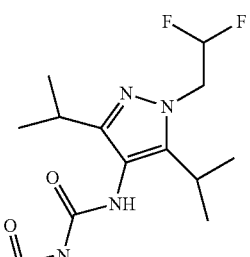

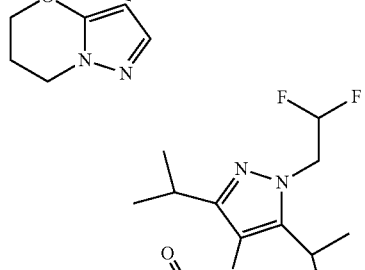

(R)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide and (S)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide were prepared using the general procedure described for the preparation of (S)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide and (R)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide (Example 98 and Example 99), by replacing iodoethane with 1,1-difluoro-2-iodoethane in Step 3. After prep-HPLC and chiral prep-SFC (Step 6), two isomers of unknown absolute stereochemistry were isolated Peak 1 (Method T, 0.49 min) and Peak 2 (Method T, 0.78 min).

Peak 1: ¹H NMR (400 MHz, DMSO-d₆) δ 7.61 (s, 1H), 7.48 (s, 1H), 7.21 (s, 2H), 6.52-5.98 (m, 1H), 4.56-4.21 (m, 4H), 4.09 (t, J=6.1 Hz, 2H), 2.96 (q, J=7.0 Hz, 1H), 2.79-2.65 (m, 1H), 2.17 (q, J=4.8 Hz, 2H), 1.27-0.96 (m, 12H). MS: m/z 460.2 (M+H⁺).

Peak 2: ¹H NMR (400 MHz, DMSO-d₆) δ 7.61 (s, 1H), 7.48 (s, 1H), 7.24 (d, J=19.3 Hz, 2H), 6.46-6.03 (m, 1H), 4.56-4.21 (m, 4H), 4.09 (t, J=6.1 Hz, 2H), 2.97 (p, J=7.0 Hz, 1H), 2.73 (p, J=6.9 Hz, 1H), 2.25-2.07 (m, 2H), 1.32-0.88 (m, 12H). MS: m/z 460.2 (M+H$^+$).

Example 98 and Example 99

(S)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide and (R)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide

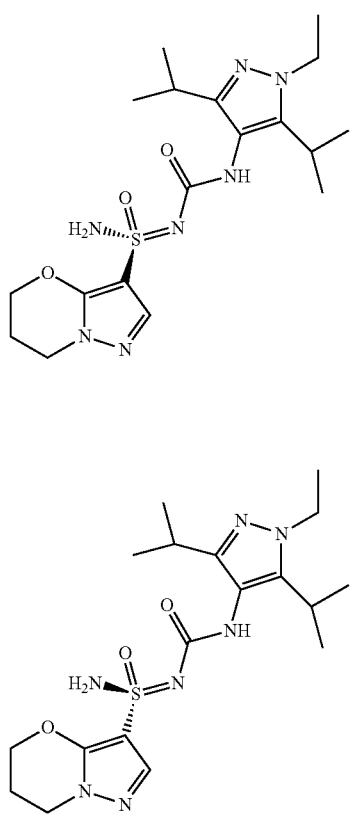

Step 1: Synthesis of 3,5-diisopropyl-1H-pyrazole

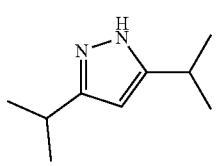

Hydrazine (330 mg, 10 mmol) was added to a solution of 2,6-dimethylheptane-3,5-dione (1.6 g, 10 mmol) in ethanol (40 mL) at room temperature. After 2 hours, the reaction was concentrated in vacuo to afford 3,5-diisopropyl-1H-pyrazole (1.5 g, 10 mmol, yield: 100%) which was used in the next step without further purification. MS: m/z 153.1 (M+H$^+$).

Step 2: Synthesis of 3,5-diisopropyl-4-nitro-1H-pyrazole

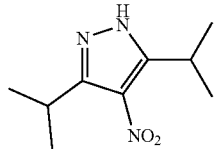

3,5-Diisopropyl-1H-pyrazole (1.5 g, 10.0 mmol) was dissolved in concentrated nitric acid (3.2 mL) and concentrated sulfuric acid (2.4 mL) and the solution was heated at 100° C. After 10 hours, the reaction was diluted with ethyl acetate. The organic layer was washed water (2×), brine, dried over magnesium sulfate, filtered and concentrated in vacuo to afford 3,5-diisopropyl-4-nitro-1H-pyrazole (1.6 g, 8.4 mmol, yield: 84%) which was used in the next step without further purification. MS: m/z 198.1 (M+H$^+$).

Step 3: Synthesis of 1-ethyl-3,5-diisopropyl-4-nitro-1H-pyrazole

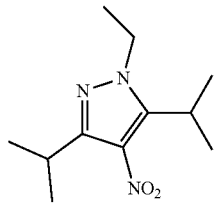 [SMILES: CCn1nc(C(C)C)c([N+](=O)[O-])c1C(C)C]

Iodoethane (1.1 g, 6.8 mmol) was added to a mixture of 3,5-diisopropyl-4-nitro-1H-pyrazole (1.2 g, 6.2 mmol) and K$_2$CO$_3$ (940 mg, 6.8 mmol) in DMF (30 mL) and the reaction was heated at 50° C. After 4 hours, the reaction was diluted with ethyl acetate. The organic was washed with water (3×), dried over magnesium sulfate, filtered and concentrated in vacuo afford 1-ethyl-3,5-diisopropyl-4-nitro-1H-pyrazole (1.5 g, 6.0 mmol, yield: 96%) which was used in the next step without further purification. MS: m/z 226.1 (M+H$^+$).

Step 4: Synthesis of 1-ethyl-3,5-diisopropyl-1H-pyrazol-4-amine

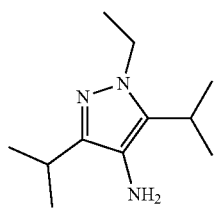

Concentrated HCl (1.5 mL) was added to a mixture of 1-ethyl-3,5-diisopropyl-4-nitro-1H-pyrazole (1.5 g, 6.0 mmol) and zinc (1.2 g, 18.0 mmol) in acetic acid (80 mL) at room temperature. After 15 minutes, the reaction was diluted with ethyl acetate. The organic was washed with saturated aqueous sodium bicarbonate and concentrated in vacuo. The crude residue was purified by flash column chromatography (silica, 1-10% MeOH in DCM) to afford 1-ethyl-3,5-diisopropyl-1H-pyrazol-4-amine (1.1 g, 5.0 mmol, yield: 83%). MS: m/z 1961.2 (M+H⁺).

Step 5: Synthesis of 1-ethyl-4-isocyanato-3,5-diisopropyl-1H-pyrazole

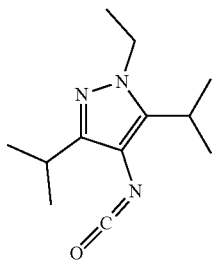 [SMILES: CCn1nc(C(C)C)c(N=C=O)c1C(C)C]

Triphosgene (177 mg, 0.6 mmol) was added to a solution of 1-ethyl-3,5-diisopropyl-1H-pyrazol-4-amine (361 mg, 1.7 mmol) and triethylamine (201 mg, 2.0 mmol) in THF (8 mL) and the mixture was heated at 80° C. After 1 hour, the reaction was filtered and concentrated in vacuo to afford 1-ethyl-4-isocyanato-3,5-diisopropyl-1H-pyrazole (375 mg, 1.7 mmol, 100% yield) which was used immediately in the next step without further purification. MS: m/z 222.1 (M+H⁺).

Step 6: Synthesis of (S)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide and (R)—N'-((1-ethyl-3,5-diisopropyl-1H-pyrazol-4-yl)carbamoyl)-6,7-dihydro-5H-pyrazolo[5,1-b][1,3]oxazine-3-sulfonimidamide (Example 98 and Example 99)

NaH (60% in mineral oil, 46 mg, 1.8 mmol) was added to a solution of N'-(tert-butyldimethylsilyl)-6,7-dihydro-5H-pyrazolo[5,1-b][1,3]oxazine-3-sulfonimidamide (397 mg, 0.9 mmol) and 1-ethyl-4-isocyanato-3,5-diisopropyl-1H-pyrazole (200 mg, 0.9 mmol) in THF (3 mL) at room temperature. After 10 minutes, the reaction was cooled to 0° C. Water (0.5 mL) was added and the reaction was concentrated in vacuo. HCl (4M in dioxane, 2 mL) was added to the crude residue and the reaction was allowed to stir at room temperature for 30 minutes. The mixture was concentrated in vacuo. The crude residue was co-evaporated with dioxane (2×), then purified by reverse-phase HPLC (0.1% NH₄OH: ACN) and chiral SFC (Chiralcel OX (150×21 mm, 5 um), methanol w/0.1% NH₄OH) to give peak 1 ((Method V, 0.45 min, 20 mg, yield: 5.2%) and peak 2 (Method V, 0.67 min, 20 mg, yield: 5.2%). Stereochemistry was arbitrarily assigned to each stereoisomer.

Peak 1: ¹H NMR (400 MHz, DMSO-d₆) δ 7.53 (s, 1H), 7.48 (s, 1H), 7.21 (s, 2H), 4.44-4.29 (m, 2H), 4.09 (t, J=6.1 Hz, 2H), 3.93 (q, J=7.1 Hz, 2H), 2.93 (p, J=7.0 Hz, 2H), 2.73 (h, J=7.1 Hz, 2H), 2.17 (q, J=4.6 Hz, 2H), 1.24 (t, J=7.1 Hz, 3H), 1.17 (d, J=7.0 Hz, 6H), 1.09 (dd, J=6.9, 2.1 Hz, 6H). MS: m/z 424.2 (M+H⁺).

Peak 2: ¹H NMR (400 MHz, DMSO-d₆) δ 7.53 (s, 1H), 7.47 (s, 1H), 7.21 (s, 2H), 4.44-4.29 (m, 2H), 4.09 (t, J=6.1 Hz, 2H), 3.93 (q, J=7.1 Hz, 2H), 2.92 (h, J=7.1 Hz, 1H), 2.73 (h, J=7.1 Hz, 1H), 2.17 (q, J=4.6 Hz, 2H), 1.24 (t, J=7.1 Hz, 3H), 1.17 (d, J=7.1 Hz, 5H), 1.08 (dd, J=7.0, 2.1 Hz, 6H). MS: m/z 424.2 (M+H⁺).

Example 100 and Example 101

(S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide

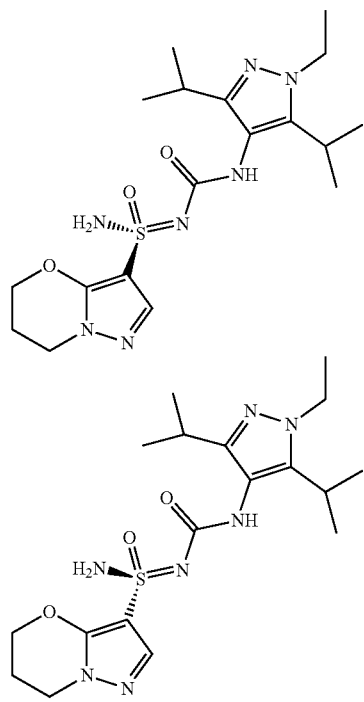

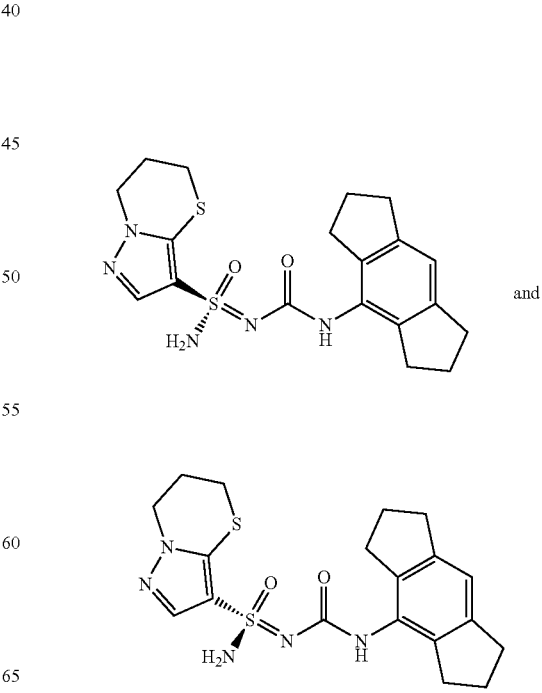

and

Step 1—Synthesis of 3-bromo-6,7-dihydro-5H-pyrazolo[5,1-b][1,3]thiazine

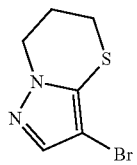

To a solution of 6,7-dihydro-5H-pyrazolo[5,1-b][1,3]thiazine (190 mg, 1.36 mmol) in MeCN (6 mL) was added NBS (241 mg, 1.36 mmol) at 0° C. The reaction was stirred at room temperature for 16 hours. The mixture was concentrated to dryness and the crude residue was purified by silica gel column chromatography (0-9% EtOAc in PE) to give 3-bromo-6,7-dihydro-5H-pyrazolo[5,1-b][1,3]thiazine (260 mg, yield: 87%) as a white solid. $^1$H NMR (400 MHz, CDCl$_3$): δ=7.45 (s, 1H), 4.23 (t, J=6.0 Hz, 2H), 3.12 (t, J=5.6 Hz, 2H), 2.45-2.35 (m, 2H). MS: m/z 219.0 (M+H$^+$).

Step 2—Synthesis of N'-trityl-6,7-dihydro-5H-pyrazolo[5,1-b][1,3]thiazine-3-sulfonimidamide

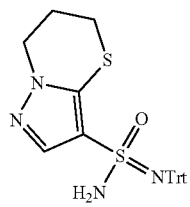

To a solution of 3-bromo-6,7-dihydro-5H-pyrazolo[5,1-b][1,3]thiazine (260 mg, 1.19 mmol) in THF (5 mL) was added n-BuLi (2.5 M in hexane, 0.5 mL, 1.31 mmol) drop-wise at −78° C. under a N$_2$ atmosphere. After 30 minutes, a solution of TrtNSO (400 mg, 1.31 mmol) in THF (1 mL) was added drop-wise. The reaction was allowed to stir at −78° C. for 30 minutes at which point it was placed in a 0° C. ice bath where it stirred for an additional 10 minutes. tert-Butyl hypochlorite (0.15 mL, 1.31 mmol) was added drop-wise at 0° C. After 30 minutes, NH$_3$ gas was bubbled through the mixture for 10 minutes. The reaction was warmed to room temperature and stirred for an additional 16 hours. The reaction was concentrated to dryness and the crude residue was purified by silica gel column chromatography (0-80% EtOAc in PE) to give N'-trityl-6,7-dihydro-5H-pyrazolo[5,1-b][1,3]thiazine-3-sulfonimidamide (300 mg, yield: 54%) as a white solid. $^1$H NMR (400 MHz, DMSO-d$_6$) δ 7.47-7.40 (m, 7H), 7.20-7.11 (m, 6H), 7.10-7.05 (m, 3H), 6.32 (s, 2H), 4.11-3.95 (m, 2H), 2.99 (t, J=5.6 Hz, 2H), 2.24-2.11 (m, 2H).

Step 3—Synthesis of N'-((1,2,3,5,6,7-hexahydro-s-indacen-4-yl)carbamoyl)-N'-trityl-6,7-dihydro-5H-pyrazolo[5,1-b][1,3]thiazine-3-sulfonimidamide

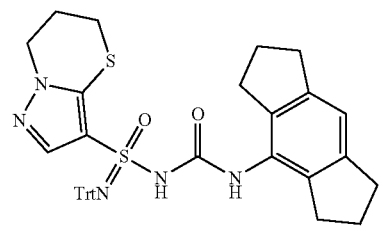

To a stirred solution of N'-trityl-6,7-dihydro-5H-pyrazolo[5,1-b][1,3]thiazine-3-sulfonimidamide (200 mg, 0.43 mmol) in THF (6 mL) was added MeONa (26 mg, 0.48 mmol) at 0° C. After 15 minutes, 4-isocyanato-1,2,3,5,6,7-hexahydro-s-indacene (104 mg, 0.52 mmol) was added. The reaction mixture was stirred at room temperature for 16 hours. The reaction was quenched with MeOH (1 mL), concentrated to dryness and the crude residue was purified by silica gel column chromatography (0-5% MeOH in DCM) to afford N-((1,2,3,5,6,7-hexahydro-s-indacen-4-yl)carbamoyl)-N'-trityl-6,7-dihydro-5H-pyrazolo[5,1-b][1,3]thiazine-3-sulfonimidamide (220 mg, yield: 77%) as a white solid.

Step 4—Synthesis of N'-((1,2,3,5,6,7-hexahydro-s-indacen-4-yl)carbamoyl)-6,7-dihydro-5H-pyrazolo[5,1-b][1,3]thiazine-3-sulfonimidamide

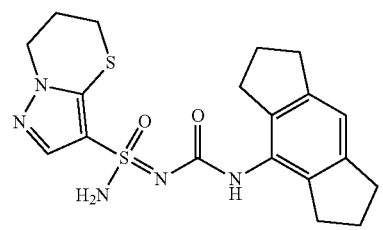 [SMILES: NS(=O)(=NC(=O)Nc1c2c(cc3c1CCC3)CCC2)c1cnn2c1SCCC2]

To a solution of N-((1,2,3,5,6,7-hexahydro-s-indacen-4-yl)carbamoyl)-N'-trityl-6,7-dihydro-5H-pyrazolo[5,1-b][1,3]thiazine-3-sulfonimidamide (220 mg, 0.33 mmol) in DCM (12 mL) was added MeSO$_3$H (6 drops) at 0° C. The reaction was warmed to room temperature. After 1 hour, the reaction was basified with saturated aqueous NaHCO$_3$, concentrated to dryness and the crude residue was purified by silica gel column chromatography (0-1% MeOH in DCM) to give N'-((1,2,3,5,6,7-hexahydro-s-indacen-4-yl)carbamoyl)-6,7-dihydro-5H-pyrazolo[5,1-b][1,3]thiazine-3-sulfonimidamide (80 mg, yield: 40%) as a white solid. MS: m/z 418.2 (M+H$^+$).

Step 5—Synthesis of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Example 100 and Example 101)

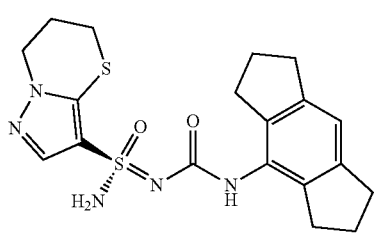

and

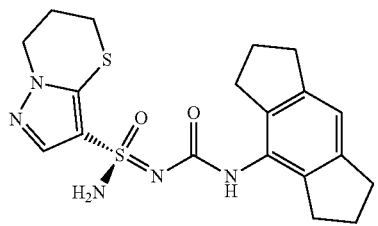

N'-((1,2,3,5,6,7-hexahydro-s-indacen-4-yl)carbamoyl)-6,7-dihydro-5H-pyrazolo[5,1-b][1,3]thiazine-3-sulfonimidamide (80 mg, 0.19 mmol) was separated by chiral SFC (Chiralpak AS (250 mm*30 mm, 10 um); Supercritical CO$_2$/EtOH+0.1% NH$_4$OH=65/35; 70 mL/min) to give (S)—N'-((1,2,3,5,6,7-hexahydro-s-indacen-4-yl)carbamoyl)-6,7-dihydro-5H-pyrazolo[5,1-b][1,3]thiazine-3-sulfonimidamide (peak 1, 25 mg, 70% purity) as a white solid and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Method C, 4.21 min, peak 2, 17.2 mg, yield: 22%). Peak 1 was further purified by chiral SFC (Chiralpak AD (250 mm*30 mm, 10 um); Supercritical CO$_2$/EtOH+ 0.1% NH$_4$OH=40/40; 80 mL/min) to give (S)—N'-((1,2,3,5,6,7-hexahydro-s-indacen-4-yl)carbamoyl)-6,7-dihydro-5H-pyrazolo[5,1-b][1,3]thiazine-3-sulfonimidamide (Method C, 3.97 min, peak 1, 14.4 mg, yield: 18%) as a white solid. Stereochemistry was arbitrarily assigned to each stereoisomer.

Peak 1: $^1$H NMR (400 MHz, DMSO-d$_6$): δ=8.17 (s, 1H), 7.70 (s, 1H), 7.33 (s, 2H), 6.85 (s, 1H), 4.19 (t, J=6.0 Hz, 2H), 3.12 (t, J=5.2 Hz, 2H), 2.77 (t, J=7.2 Hz, 4H), 2.70-2.65 (m, 4H), 2.28-2.21 (m, 2H), 1.96-1.85 (m, 4H). MS: m/z 418.0 (M+H$^+$).

Peak 2: $^1$H NMR (400 MHz, DMSO-d$_6$): δ=8.18 (s, 1H), 7.71 (s, 1H), 7.36 (s, 2H), 6.86 (s, 1H), 4.20 (t, J=5.6 Hz, 2H), 3.12 (t, J=5.6 Hz, 2H), 2.77 (t, J=7.6 Hz, 4H), 2.73-2.65 (m, 4H), 2.28-2.21 (m, 2H), 1.96-1.85 (m, 4H). MS: m/z 418.0 (M+H$^+$).

Example 102 and Example 103

(S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide

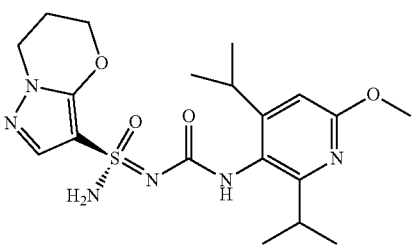

and

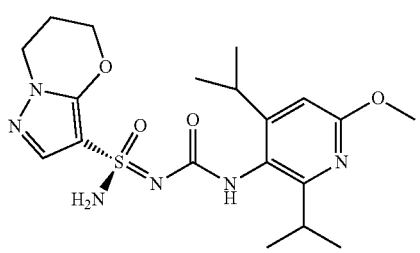

Step 1—Synthesis of N-((2,4-diisopropyl-6-methoxypyridin-3-yl)carbamoyl)-N'-trityl-6,7-dihydro-5H-pyrazolo[5,1-b][1,3]oxazine-3-sulfonimidamide

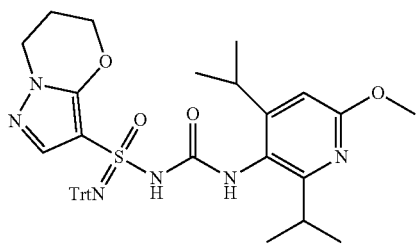

To a solution of N'-trityl-6,7-dihydro-5H-pyrazolo[5,1-b][1,3]oxazine-3-sulfonimidamide (200 mg, 0.45 mmol) in THF (12 mL) was added MeONa (37 mg, 0.67 mmol) at 0° C. under an nitrogen atmosphere. After 20 minutes, a solution of 3-isocyanato-2,4-diisopropyl-6-methoxypyridine (159 mg, 0.68 mmol) in THF (8 mL) was added. The reaction mixture was stirred at room temperature for 16 hours. The reaction was quenched with MeOH (5 mL), filtered and concentrated to dryness. The crude residue was purified by Prep-TLC (EtOAc) to give N-((2,4-diisopropyl-6-methoxypyridin-3-yl)carbamoyl)-N'-trityl-6,7-dihydro-5H-pyrazolo[5,1-b][1,3]oxazine-3-sulfonimidamide (99 mg, yield: 32%) as a white solid. MS: m/z 679.3 (M+H$^+$).

Step 2—Synthesis of N'-((2,4-diisopropyl-6-methoxypyridin-3-yl)carbamoyl)-6,7-dihydro-5H-pyrazolo[5,1-b][1,3]oxazine-3-sulfonimidamide

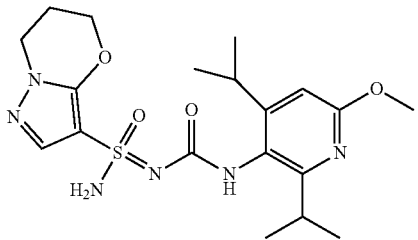 [SMILES: COc1cc(C(C)C)c(NC(=O)N=S(N)(=O)c2cnn3c2OCCC3)c(C(C)C)n1]

To a stirred solution of N'-((2,4-diisopropyl-6-methoxypyridin-3-yl)carbamoyl)-N-trityl-6,7-dihydro-5H-pyrazolo[5,1-b][1,3]oxazine-3-sulfonimidamide (99 mg, 0.15 mmol) in DCM (8 mL) was added MeSO₃H (0.01 mL, 0.15 mmol) at 0° C. After 1 hour, the reaction mixture was basified with saturated aqueous NaHCO₃ and diluted DCM (10 mL). The organic layer was dried over Na₂SO₄, filtered and concentrated. The crude residue was purified by prep-TLC (5% MeOH in dichloromethane) to give N'-((2,4-diisopropyl-6-methoxypyridin-3-yl)carbamoyl)-6,7-dihydro-5H-pyrazolo[5,1-b][1,3]oxazine-3-sulfonimidamide (60 mg, yield: 94%) as a white solid. MS: m/z 437.1 (M+H⁺).

Step 3—Synthesis of (S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide (Example 102 and Example 103)

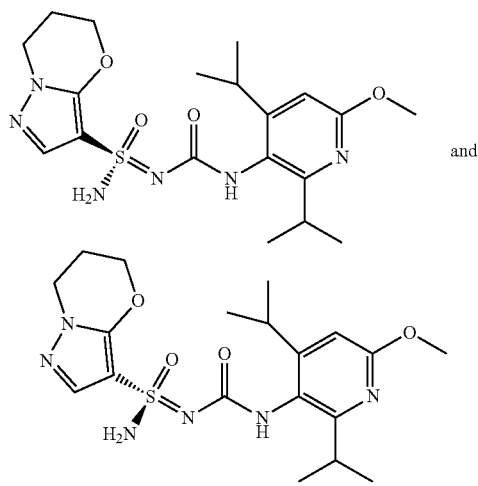

N'-((2,4-diisopropyl-6-methoxypyridin-3-yl)carbamoyl)-6,7-dihydro-5H-pyrazolo[5,1-b][1,3]oxazine-3-sulfonimidamide (60 mg, 0.14 mmol) was separated by chiral SFC (Chiralpak OJ (250 mm*30 mm, 5 um), Supercritical CO₂/EtOH+0.1% NH₄OH=40/60; 60 mL/min) to give (S)—N'-((2,4-diisopropyl-6-methoxypyridin-3-yl)carbamoyl)-6,7-dihydro-5H-pyrazolo[5,1-b][1,3]oxazine-3-sulfonimidamide (Method J, 2.57 min, peak 1, 9 mg, yield: 15%) and (R)—N'-((2,4-diisopropyl-6-methoxypyridin-3-yl)carbamoyl)-6,7-dihydro-5H-pyrazolo[5,1-b][1,3]oxazine-3-sulfonimidamide (Method J, 2.74 min, peak 2, 15.7 mg, yield: 26%) both as white solids. Stereochemistry was arbitrarily assigned to each stereoisomer.

Peak 1: ¹H NMR (400 MHz, DMSO-d₆) δ=8.00 (s, 1H), 7.49 (s, 1H), 7.24 (s, 2H), 6.45 (s, 1H), 4.42-4.34 (m, 2H), 4.09 (t, J=5.6 Hz, 2H), 3.80 (s, 3H), 3.21-3.15 (m, 1H), 3.04-2.97 (m, 1H), 2.19-2.11 (m, 2H), 1.10-1.00 (m, 12H). MS: m/z 437.1 (M+H⁺).

Peak 2: ¹H NMR (400 MHz, DMSO-d₆) δ=8.00 (s, 1H), 7.49 (s, 1H), 7.24 (s, 2H), 6.45 (s, 1H), 4.42-4.33 (m, 2H), 4.10 (t, J=5.6 Hz, 2H), 3.80 (s, 3H), 3.21-3.15 (m, 1H), 3.00-2.95 (m, 1H), 2.19-2.11 (m, 2H), 1.10-1.00 (m, 12H). MS: m/z 437.1 (M+H⁺).

Example 104

(R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide, ammonia

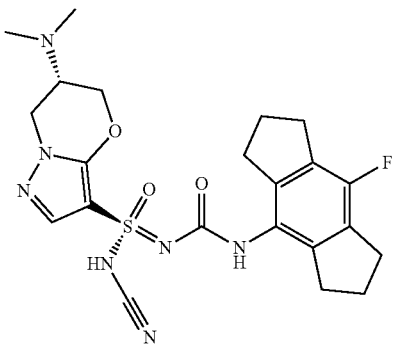 [SMILES: CN(C)[C@@H]1COc2c([S@@](=O)(=NC(=O)Nc3c4c(c(F)c5c3CCC5)CCC4)NC#N)cnn2C1]

Step 1—Synthesis of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide, ammonia (Example 104)

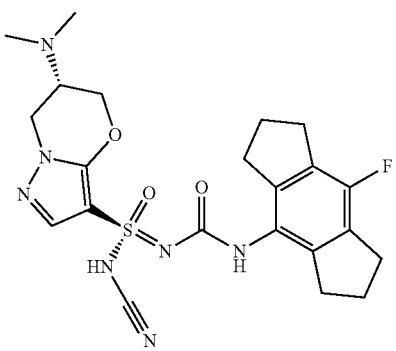 [SMILES: CN(C)[C@@H]1COc2c([S@@](=O)(=NC(=O)Nc3c4c(c(F)c5c3CCC5)CCC4)NC#N)cnn2C1]

Cyanogen bromide (1 M in dichloromethane, 30 μL, 30 μmol) was added to a solution of (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3- sulfonimidamide (10 mg, 0.02 mmol) in DMF (0.5 mL) at room temperature. After 30 minutes, saturated aqueous sodium bicarbonate (50 mL) was added and the resulting solution was directly purified by reverse-phase HPLC (5-50% ACN in 0.1% NH$_4$OH (aq)) to give (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide, ammonia (4.5 mg, yield: 45%). $^1$H NMR (400 MHz, DMSO-d$_6$) δ=7.87 (s, 1H), 7.43 (s, 1H), 7.20 (s, 1H), 7.07 (s, 1H), 6.98 (s, 1H), 6.51 (s, 1H), 4.72-4.08 (m, 4H), 2.74 (ddd, J=30.2, 15.2, 7.9 Hz, 8H), 2.10-1.84 (m, 4H). MS: m/z 488.2 (M+H$^+$).

Example 105, Example 106, Example 109 and Example 110

(S,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (S,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide and (R,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide

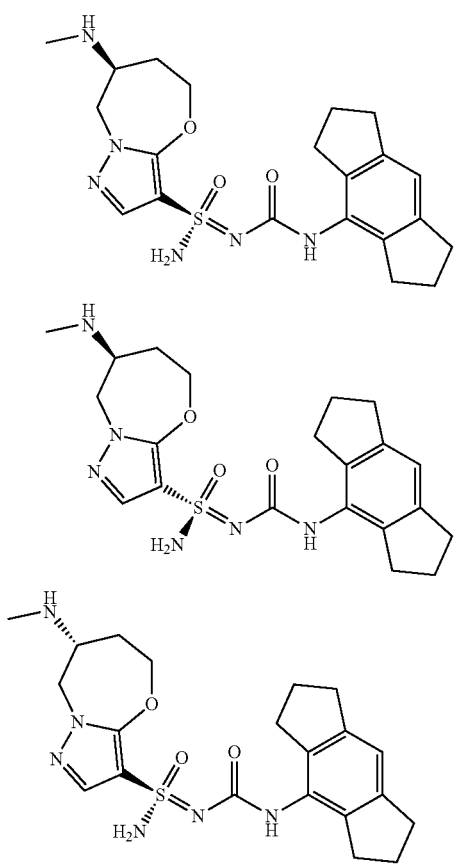

and

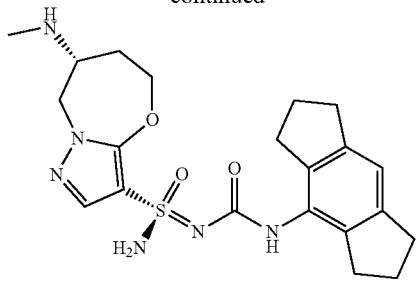

Step 1—Synthesis of 5,6,7,8-tetrahydropyrazolo[5,1-b][1,3]oxazepin-7-ol

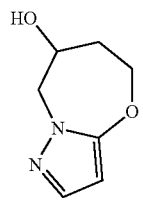 [SMILES: OC1CCOc2ccnn2C1]

To a solution of 7-(benzyloxy)-5,6,7,8-tetrahydropyrazolo[5,1-b][1,3]oxazepine (7.2 g, 29.47 mmol) in EtOH (72 mL) was added a 10% Pd (3.6 g, 3.38 mmol) on carbon. The mixture was stirred at 50° C. under a hydrogen atmosphere (45 psi) for 96 hours. After cooling to room temperature, the reaction mixture was filtered and the filtrate was concentrated to give 5,6,7,8-tetrahydropyrazolo[5,1-b][1,3]oxazepin-7-ol (4.11 g, yield: 91%) as a white solid, which was used in the next step without further purification. $^1$H NMR (400 MHz, CDCl$_3$)=7.27 (d, J=2.0 Hz, 1H), 5.73 (d, J=2.0 Hz, 1H), 4.72 (s, 1H), 4.43-4.30 (m, 1H), 4.28-4.12 (m, 4H), 2.25-2.07 (m, 2H). MS: m/z 154.8 (M+H$^+$).

Step 2—Synthesis of 5,6,7,8-tetrahydropyrazolo[5,1-b][1,3]oxazepin-7-yl methanesulfonate

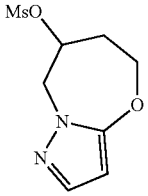

To a solution of 5,6,7,8-tetrahydropyrazolo[5,1-b][1,3]oxazepin-7-ol (3.81 g, 24.71 mmol) in pyridine (38 mL) was added MsCl (3.94 g, 34.4 mmol) at room temperature under nitrogen atmosphere. After 4 hours, the reaction was concentrated and water (50 mL) was added. The aqueous layer was extracted with EtOAc (100 mL×2). The combined organic layers were washed with brine (30 mL×2), died over Na$_2$SO$_4$ and concentrated to give 5,6,7,8-tetrahydropyrazolo[5,1-b][1,3]oxazepin-7-yl methanesulfonate (5.7 g, yield: 99%) as a white solid, which was used in the next step without further purification. MS: m/z 232.9 (M+H$^+$).

Step 3—Synthesis of tert-butyl (5,6,7,8-tetrahydropyrazolo[5,1-b][1,3]oxazepin-7-yl)carbamate

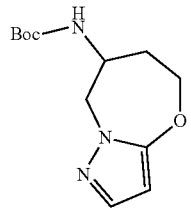

A mixture of 5,6,7,8-tetrahydropyrazolo[5,1-b][1,3]oxazepin-7-yl methanesulfonate (2.36 g, 10.16 mmol) and NaN$_3$ (1.88 g, 28.89 mmol) in DMF (25 mL) were stirred at 120° C. under nitrogen atmosphere for 2 hours. After cooling to room temperature, the reaction mixture was used in next step directly. MS: m/z 179.9 (M+H$^+$).

To the reaction mixture was added was added 10% Pd (1.39 g, 13.04 mmol) on carbon, Boc$_2$O (3.33 g, 15.24 mmol) and MeOH (25 mL) at room temperature. The reaction mixture was allowed to stir under hydrogen atmosphere (50 psi) for 16 hours. The reaction was filtered and the filtrate was concentrated. Water (10 mL) was added to the crude residue. The aqueous layer was extracted with EtOAc (100 mL×2). The combined organic layers were washed with brine (30 mL×2), dried over Na$_2$SO$_4$, concentrated and the crude residue was purified by silica gel column (0-50% EtOAc in petroleum ether) to give tert-butyl (5,6,7,8-tetrahydropyrazolo[5,1-b][1,3]oxazepin-7-yl)carbamate (2.45 g, yield: 95%) as a white solid. MS: m/z 197.9 (M−56+H$^+$).

Step 4—Synthesis of tert-butyl (3-bromo-5,6,7,8-tetrahydropyrazolo[5,1-b][1,3]oxazepin-7-yl)carbamate

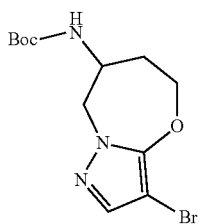 [SMILES: CC(C)(C)OC(=O)NC1CCOc2c(Br)cnn2C1]

To a solution of tert-butyl (5,6,7,8-tetrahydropyrazolo[5,1-b][1,3]oxazepin-7-yl)carbamate (2.45 g, 9.67 mmol) in MeCN (50 mL) was added NBS (2.07 g, 11.61 mmol) at 0° C. The reaction mixture was stirred at room temperature for 16 hours. The mixture was concentrated to dryness and the residue was purified by silica gel column (0-50% EtOAc in petroleum ether) to give tert-butyl (3-bromo-5,6,7,8-tetrahydropyrazolo[5,1-b][1,3]oxazepin-7-yl)carbamate (2.78 g, yield: 86%) as a yellow solid. MS: m/z 276.8 (M−56+H$^+$).

Step 5—Synthesis of tert-butyl (3-bromo-5,6,7,8-tetrahydropyrazolo[5,1-b][1,3]oxazepin-7-yl)(methyl)carbamate

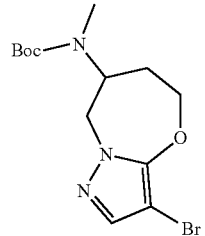

To a solution of tert-butyl (3-bromo-5,6,7,8-tetrahydropyrazolo[5,1-b][1,3]oxazepin-7-yl)carbamate (2.78 g, 8.35 mmol) in DMF (25 mL) was added NaH (60% in mineral oil, 0.67 g, 16.71 mmol) at 0° C. under nitrogen atmosphere. After 1 hour, MeI (2.6 mL, 41.77 mmol) was added dropwise. The resulting mixture was warmed to room temperature and was allowed to stir for an additional 16 hours. The reaction was poured to water (100 mL). The aqueous layer was extracted with ethyl acetate (50 mL×3). The combined organic layers were washed with brine (50 mL×3), dried over Na$_2$SO$_4$ and concentrated to dryness. The crude residue was purified by silica gel column (0-33% EtOAc in petroleum ether) to give tert-butyl (3-bromo-5,6,7,8-tetrahydropyrazolo[5,1-b][1,3]oxazepin-7-yl)(methyl)carbamate (2.25 g, yield: 78%) as a white solid. MS: m/z 289.8 (M+H$^+$).

Step 6—Synthesis of tert-butyl methyl(3-(N'-tritylsulfamimidoyl)-5,6,7,8-tetrahydropyrazolo[5,1-b][1,3]oxazepin-7-yl)carbamate

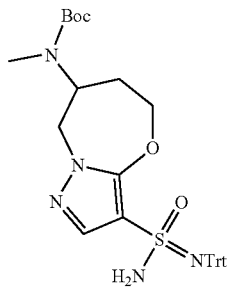

To a solution of tert-butyl (3-bromo-5,6,7,8-tetrahydropyrazolo[5,1-b][1,3]oxazepin-7-yl)(methyl)carbamate (740 mg, 2.14 mmol) in THF (10 mL) was added n-BuLi (2.5 M in hexane, 1.06 mL, 2.64 mmol) dropwise at −78° C. under a nitrogen atmosphere. After 1 h, a solution of TrtNSO (783 mg, 2.56 mmol) in THF (1.84 mL) was added drop-wise. The reaction was allowed to stir at −78° C. for 20 minutes at which point it was placed in a 0° C. ice bath where it stirred for an additional 10 minutes. tert-Butyl hypochlorite (0.29 mL, 2.57 mmol) was added drop-wise at 0° C. After 20 minutes, NH$_3$ gas was bubbled through the mixture for 10 minutes. The reaction was warmed to room temperature and stirred for an additional 16 hours. The reaction mixture was concentrated to dryness and the residue was purified by silica gel column (0-70% EtOAc in petroleum ether) to give tert-butyl methyl(3-(N'-tritylsulfamimidoyl)-5,6,7,8-tetrahydropyrazolo[5,1-b][1,3]oxazepin-7-yl)carbamate (430 mg, yield: 35%) as a yellow solid. MS: m/z 610.1 (M+Na⁺).

Step 7—Synthesis of tert-butyl (3-(N-((1,2,3,5,6,7-hexahydro-s-indacen-4-yl)carbamoyl)-N'-tritylsulfamimidoyl)-5,6,7,8-tetrahydropyrazolo[5,1-b][1,3]oxazepin-7-yl)(methyl)carbamate

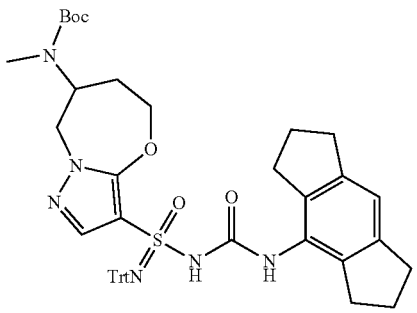

To a solution of tert-butyl methyl(3-(N'-tritylsulfamimidoyl)-5,6,7,8-tetrahydropyrazolo[5,1-b][1,3]oxazepin-7-yl) carbamate (330 mg, 0.56 mmol) in DMF (3 mL) and THF (15 mL) was added MeONa (46 mg, 0.84 mmol) at 0° C. under a nitrogen atmosphere. After 20 minutes, a solution of 4-isocyanato-1,2,3,5,6,7-hexahydro-s-indacene (224 mg, 1.12 mmol) in THF (9 mL) was added drop-wise. The reaction mixture was warmed to room temperature. After 16 hours, the reaction was concentrated to dryness and the crude residue was purified by prep-TLC (50% EtOAc in petroleum ether) to give tert-butyl (3-(N-((1,2,3,5,6,7-hexahydro-s-indacen-4-yl)carbamoyl)-N'-tritylsulfamimidoyl)-5,6,7,8-tetrahydropyrazolo[5,1-b][1,3]oxazepin-7-yl) (methyl)carbamate (316 mg, yield: 72%) as a white solid. MS: m/z 809.3 (M+Na⁺).

Step 8—Synthesis of N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide

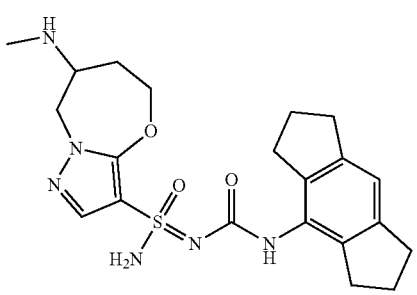 [SMILES: CNC1CCOc2c(S(N)(=O)=NC(=O)Nc3c4c(cc5c3CCC5)CCC4)cnn2C1]

To a solution of tert-butyl (3-(N-((1,2,3,5,6,7-hexahydro-s-indacen-4-yl)carbamoyl)-N'-tritylsulfamimidoyl)-5,6,7,8-tetrahydropyrazolo[5,1-b][1,3]oxazepin-7-yl)(methyl)carbamate (320 mg, 0.41 mmol) in DCM (20 mL) was added MeSO₃H (16 drops) at 0° C. The reaction was warmed to room temperature. After 1 hour, the reaction mixture was adjusted to pH=8 with the addition of saturated aqueous NaHCO₃. The reaction was concentrated to dryness and the crude residue was purified by prep-TLC (10% MeOH in DCM) to give N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (117 mg, yield: 65%) as a yellow solid. MS: m/z 445.1 (M+H⁺).

Step 9—Synthesis of (S,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (S,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide and (R,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Example 105, Example 106, Example 109, and Example 110)

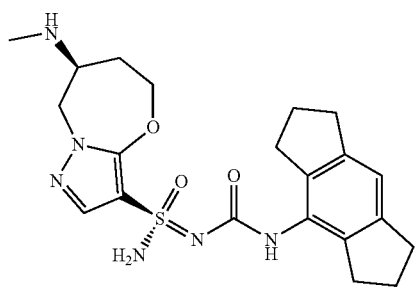

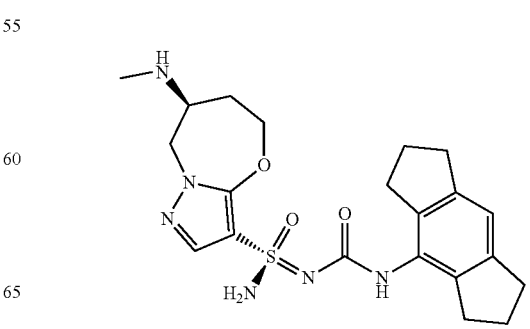

-continued

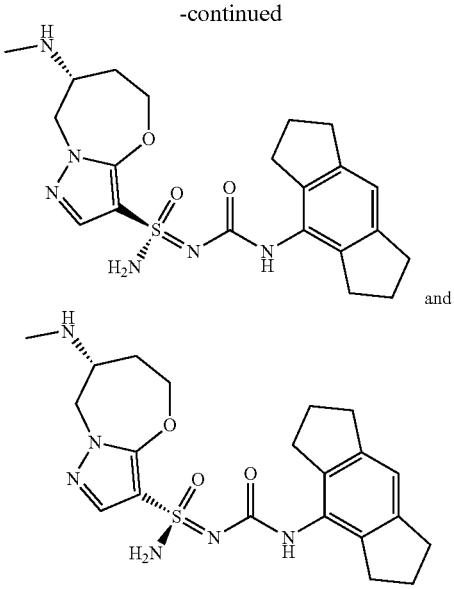

N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (154 mg, 0.35 mmol) was separated by chiral SFC (Chiralpak AD (250 mm*30 mm, 10 um); Supercritical $CO_2$/0.1% EtOH+$NH_4OH$=55/45; 80 mL/min) to give (S,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Method I, 2.96 min, peak 1, 22.4 mg, yield: 14%) as a white solid, (R,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Method I, 4.76 min, peak 4, 15.9 mg, yield: 10%) as a white solid and (7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (a mixture of peaks 2 and 3, 76 mg, yield: 50%) as a white solid. (7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (mixture of peaks 2 and 3, 76 mg, 0.17 mmol) was separated by chiral SFC (Chiralpak OD (250 mm*30 mm, 5 um); Supercritical $CO_2$/0.1% MeOH+$NH_4OH$=70/30; 50 mL/min) to give (S,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Method K, 4.75 min, peak 2, 15.6 mg, yield: 21%) and (R,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Method K, 4.91 min, peak 3, 11 mg, yield: 14%) both as white solid. Stereochemistry was arbitrarily assigned to each stereoisomer.

Peak 1: $^1$H NMR (400 MHz, DMSO-$d_6$): δ=8.19 (s, 1H), 7.48 (s, 1H), 7.27 (s, 2H), 6.85 (s, 1H), 4.38-4.02 (m, 4H), 2.77 (t, J=7.2 Hz, 4H), 2.67 (t, J=7.2 Hz, 4H), 2.26 (s, 3H), 2.20-2.09 (m, 1H), 2.02-1.75 (m, 6H). MS: m/z 445.1 (M+H$^+$). Compound 105

Peak 2: $^1$H NMR (400 MHz, DMSO-$d_6$): δ=8.20 (s, 1H), 7.47 (s, 1H), 7.23 (s, 1H), 6.85 (s, 1H), 4.43-4.05 (m, 4H), 2.77 (t, J=7.2 Hz, 4H), 2.67 (t, J=7.2 Hz, 4H), 2.26 (s, 3H), 2.20-2.10 (m, 1H), 1.99-1.89 (m, 6H). MS: m/z 445.1 (M+H$^+$). Compound 109

Peak 3: 1H NMR (400 MHz, DMSO-$d_6$): δ=8.22 (s, 1H), 7.52 (s, 1H), 7.33 (s, 2H), 6.86 (s, 1H), 4.40-4.30 (m, 2H), 4.26-4.04 (m, 2H), 2.77 (t, J=7.2 Hz, 4H), 2.67 (t, J=7.2 Hz, 4H), 2.39 (s, 3H), 2.22-2.14 (m, 1H), 2.13-1.87 (m, 6H). MS: m/z 445.1 (M+H$^+$). Compound 110

Peak 4: $^1$H NMR (400 MHz, DMSO-$d_6$): δ=8.18 (s, 1H), 7.47 (s, 1H), 7.21 (s, 2H), 6.85 (s, 1H), 4.30-4.03 (m, 4H), 2.77 (t, J=7.2 Hz, 4H), 2.67 (t, J=7.2 Hz, 4H), 2.26 (s, 3H), 2.19-2.08 (m, 1H), 1.99-1.72 (m, 6H). MS: m/z 445.1 (M+H$^+$). Compound 106

Example 107 and Example 108

(S)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide and (R)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide

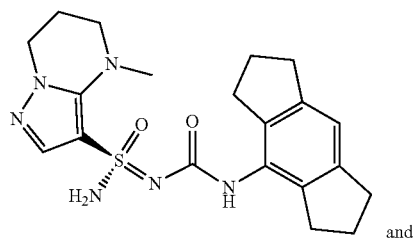

and

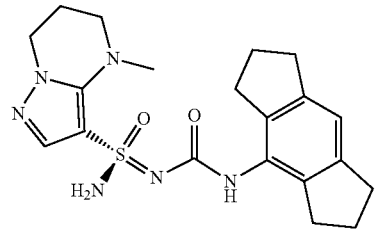

Step 1—Synthesis of 3-bromo-4,5,6,7-tetrahydropyrazolo[1,5-a]pyrimidine

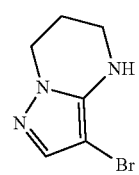

To a stirred solution of tert-butyl 3-bromo-6,7-dihydropyrazolo[1,5-a]pyrimidine-4(5H)-carboxylate (3.0 g, 9.93 mmol) in DCM (33 mL) was added TFA (6.6 mL, 88.56 mmol) at room temperature. After 1 hour, the reaction mixture was concentrated to dryness. Saturated aqueous $NaHCO_3$ (20 mL) was added to the crude residue. The aqueous layer was extracted with EtOAc (20 mL). The combined organic layers were washed with water (50 mL), brine (30 mL), dried over $Na_2SO_4$, filtered and concentrated to give 3-bromo-4,5,6,7-tetrahydropyrazolo[1,5-a]pyrimidine (1.67 g, yield: 83%) as a yellow oil, which was used in the next step without further purification. ¹H NMR (400 MHz, CDCl₃): δ=7.24 (s, 1H), 4.11 (t, J=6.0 Hz, 2H), 4.03 (s, 1H), 3.38 (t, J=6.0 Hz, 2H), 2.20-2.13 (m, 2H).

Step 2—Synthesis of 3-bromo-4-methyl-4,5,6,7-tetrahydropyrazolo[1,5-a]pyrimidine

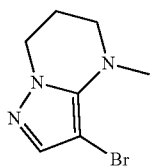

To a solution of NaH (60% in mineral oil, 554 mg, 13.86 mmol) in DMF (21 mL) was added 3-bromo-4,5,6,7-tetrahydropyrazolo[1,5-a]pyrimidine (1.4 g, 6.93 mmol) at 0° C. under nitrogen atmosphere. After 30 minutes, MeI (0.86 mL, 13.86 mmol) was added dropwise. The reaction was warmed to room temperature. After 16 hours, saturated aqueous NH₄Cl (50 ml) and EtOAc (100 ml) were added. The aqueous layer was extracted with EtOAc. The combined organic layers were washed with water (100 mL), brine (50 mL), dried over Na₂SO₄ filtered and concentrated to give 3-bromo-4-methyl-4,5,6,7-tetrahydropyrazolo[1,5-a]pyrimidine (1.3 g, yield: 87%) as a yellow solid. ¹H NMR (400 MHz, CDCl₃): δ=7.22 (s, 1H), 4.07 (t, J=6.0 Hz, 2H), 3.15-3.10 (m, 5H), 2.19-2.09 (m, 2H).

Step 3—Synthesis of 4-methyl-N'-trityl-4,5,6,7-tetrahydropyrazolo[1,5-a]pyrimidine-3-sulfonimidamide

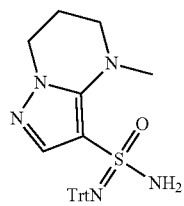

To a solution of 3-bromo-4-methyl-4,5,6,7-tetrahydropyrazolo[1,5-a]pyrimidine (1.1 g, 5.09 mmol) in THF (24 mL) was added a n-BuLi (2.5 M in hexane, 2.5 mL, 6.29 mmol) drop-wise at −78° C. under a nitrogen atmosphere. After 1 hour, a solution of TrtNSO (1.86 g, 6.11 mmol) in THF (4 mL) was added drop-wise. The reaction was allowed to stir at −78° C. for 20 minutes at which point it was placed in a 0° C. ice bath where it stirred for an additional 10 minutes. tert-Butyl hypochlorite (0.7 mL, 6.19) was added drop-wise at 0° C. After 20 minutes, NH₃ gas was bubbled through the mixture for 10 minutes. The reaction was warmed to room temperature and stirred for an additional 16 hours. The reaction mixture was concentrated and the crude residue was purified by silica gel column chromatography (50% EtOAc in petroleum ether) to give 4-methyl-N'-trityl-4,5,6,7-tetrahydropyrazolo[1,5-a]pyrimidine-3-sulfonimidamide (480 mg, yield: 21%) as a white solid. ¹H NMR (400 MHz, DMSO-d₆) δ=7.46-7.41 (m, 6H), 7.16-7.10 (m, 6H), 7.07-7.02 (m, 3H), 6.73 (s, 1H), 6.41 (s, 2H), 3.80-3.70 (m, 2H), 3.27 (s, 3H), 3.02-2.99 (m, 2H), 1.94-1.85 (m, 2H).

Step 4~5—Synthesis of N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide

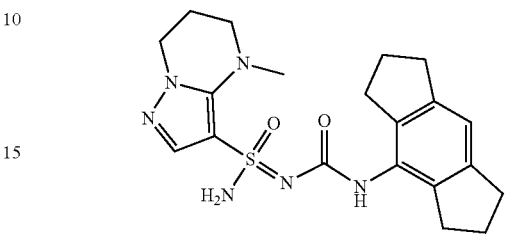

N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide was prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide (Example 100 and Example 101) by replacing N'-trityl-6,7-dihydro-5H-pyrazolo[5,1-b][1,3]thiazine-3-sulfonimidamide with 4-methyl-N'-trityl-4,5,6,7-tetrahydropyrazolo[1,5-a]pyrimidine-3-sulfonimidamide in step 3.

Step 6—Synthesis of (S)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide and (R)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide (Example 107 and Example 108)

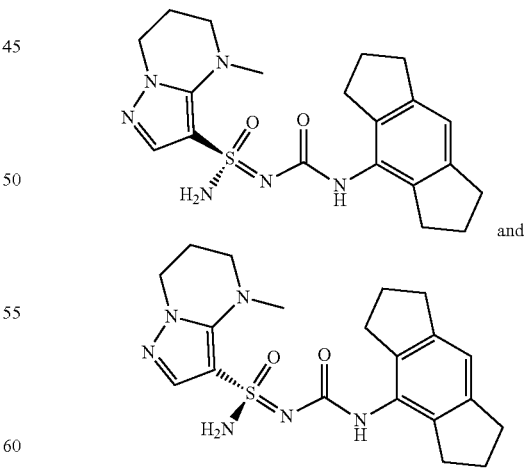

N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide (100 mg, 0.24 mmol) was separated by chiral SFC (Chiralpak AS (250 mm*50 mm, 10 um), Supercritical CO₂/MeOH+0.1% NH₄OH=70/30; 70 mL/min) to give (S)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide (Method C, 3.20 min, peak 1, 27.2 mg, yield: 27%) and (R)—N'-((1,2,3,5,6,7-hexahydro-s-indacen-4-yl)carbamoyl)-4-methyl-4,5,6,7-tetrahydropyrazolo[1,5-a]pyrimidine-3-sulfonimidamide (Method C, 3.37 min, peak 2, 30.4 mg, yield: 30%) both as white solids. Stereochemistry was arbitrarily assigned to each stereoisomer.

Peak 1: $^1$H NMR (400 MHz, DMSO-$d_6$): δ=8.23 (s, 1H), 7.43 (s, 1H), 7.27 (s, 2H), 6.86 (s, 1H), 3.96 (t, J=6.0 Hz, 2H), 3.27-3.21 (m, 5H), 2.78 (t, J=7.2 Hz, 4H), 2.68 (t, J=7.6 Hz, 4H), 2.04-1.99 (m, 2H), 1.97-1.88 (m, 4H). MS: m/z 415.1 (M+H$^+$).

Peak 2: $^1$H NMR (400 MHz, DMSO-$d_6$): δ=8.23 (s, 1H), 7.43 (s, 1H), 7.27 (s, 2H), 6.85 (s, 1H), 3.95 (t, J=6.0 Hz, 2H), 3.27-3.20 (m, 5H), 2.77 (t, J=7.2 Hz, 4H), 2.67 (t, J=7.6 Hz, 4H), 2.04-1.98 (m, 2H), 1.96-1.87 (m, 4H). MS: m/z 415.1 (M+H$^+$).

Example 111

(S,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide, ammonia

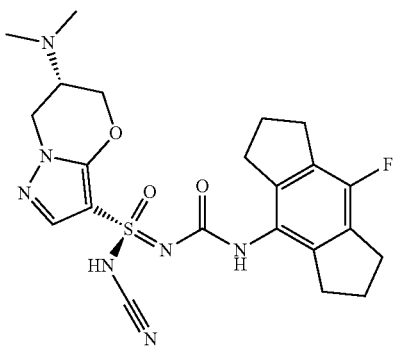 [SMILES: CN(C)[C@@H]1COc2c([S@](=O)(=NC(=O)Nc3c4c(c(F)c5c3CCC5)CCC4)NC#N)cnn2C1]

(S,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide, ammonia was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (R,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide in Step 1 (single unknown stereoisomer). $^1$H NMR (400 MHz, DMSO-$d_6$) δ 7.76 (s, 1H), 7.43 (s, 1H), 7.20 (s, 1H), 7.07 (s, 1H), 6.94 (s, 1H), 6.51 (s, 1H), 4.72-4.08 (m, 4H), 2.74 (ddd, J=30.2, 15.2, 7.9 Hz, 8H), 2.10-1.84 (m, 4H). MS: m/z 488.2 (M+H$^+$).

Example 112

(R,7S)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia

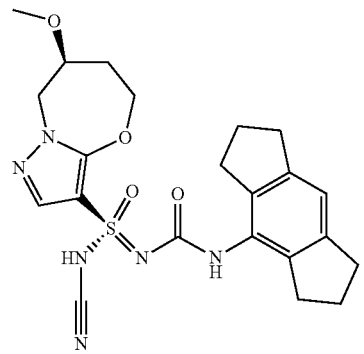 [SMILES: CO[C@H]1CCOc2c([S@@](=O)(=NC(=O)Nc3c4c(cc5c3CCC5)CCC4)NC#N)cnn2C1]

(R,7S)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (S,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide in Step 1. Single unknown stereoisomer. $^1$H NMR (400 MHz, DMSO-$d_6$) δ 7.85 (s, 1H), 7.37 (s, 1H), 7.20 (s, 1H), 7.07 (s, 1H), 6.95 (s, 1H), 6.81 (s, 1H), 4.43 (ddd, J=14.5, 5.5, 1.4 Hz, 1H), 4.31-4.11 (m, 2H), 4.01 (ddd, J=12.4, 10.2, 2.4 Hz, 1H), 3.64 (m, 1H), 2.86-2.59 (m, 8H), 2.16 (m, 2H), 1.91 (p, J=7.5 Hz, 4H). MS: m/z 471.2 (M+H$^+$).

Example 113 and Example 114

(S)—N'-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonimidamide and (R)—N'-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonimidamide

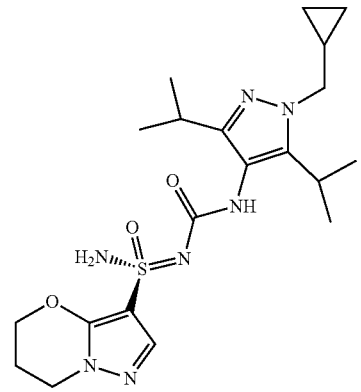

377

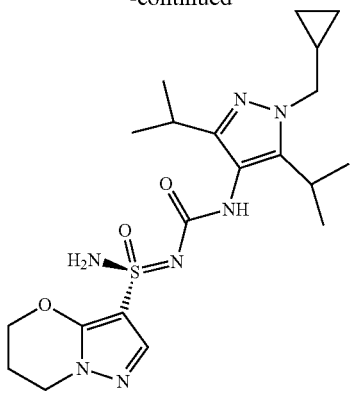

(S)—N'-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonimidamide and (R)—N'-((1-(cyclopropylmethyl)-3,5-diisopropyl-1H-pyrazol-4-yl)carbamoyl)-6,7-dihydro-5H-pyrazolo[5,1-b][1,3]oxazine-3-sulfonimidamide were prepared using the general procedure described for the preparation of (R)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide and (S)—N'-((1-(2,2-difluoroethyl)-3,5-diisopropyl-1H-pyrazol-4-yl)carbamoyl)-6,7-dihydro-5H-pyrazolo[5,1-b][1,3]oxazine-3-sulfonimidamide (Example 96 and Example 97), by replacing iodoethane with (bromomethyl)cyclopropane in Step 3. After prep-HPLC and prep-SFC (Step 6), two isomers of unknown absolute stereochemistry were isolated Peak 1 (Method T, 1.02 min) and Peak 2 (Method T, 1.74 min).

Peak 1: ¹H NMR (400 MHz, DMSO-d₆) δ 7.52 (s, 1H), 7.48 (s, 1H), 7.22 (s, 2H), 4.50-4.21 (m, 2H), 4.09 (t, J=6.1 Hz, 2H), 3.79 (d, J=6.7 Hz, 2H), 2.82-2.64 (m, 2H), 2.28-2.08 (m, 2H), 1.17 (d, J=7.1 Hz, 6H), 1.09 (dt, J=6.9, 3.1 Hz, 7H), 0.56-0.38 (m, 2H), 0.38-0.22 (m, 2H). MS: m/z 450.3 (M+H⁺).

Peak 2: ¹H NMR (400 MHz, DMSO-d₆) δ 7.52 (s, 1H), 7.48 (s, 1H), 7.21 (s, 2H), 4.45-4.29 (m, 2H), 4.09 (t, J=6.1 Hz, 2H), 3.79 (d, J=6.7 Hz, 2H), 2.80-2.63 (m, 2H), 2.17 (m, 2H), 1.18 (m, 6H), 1.16-0.99 (m, 7H), 0.54-0.38 (m, 2H), 0.30 (dt, J=4.9, 2.9 Hz, 2H). MS: m/z 450.2 (M+H⁺).

Example 115 and Example 116

N—((S,6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide and N—((R,6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide

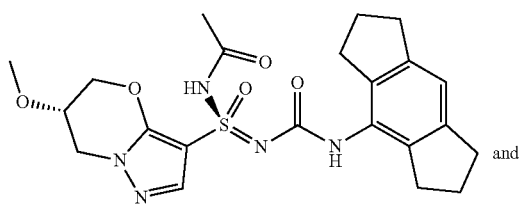

378

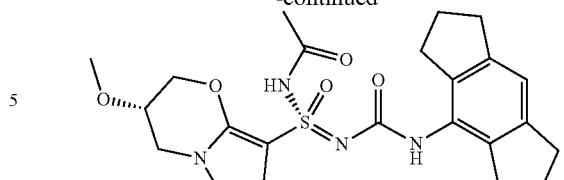

Step 1—Synthesis of N—((S,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide and N—((R,6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide (Example 115 and Example 116)

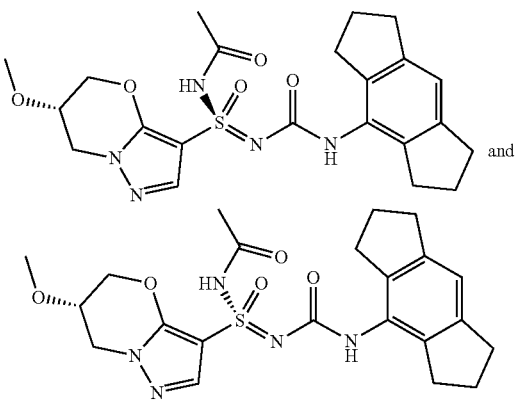

To a solution of (6S)—N'-((1,2,3,5,6,7-hexahydro-s-indacen-4-yl)carbamoyl)-6-methoxy-6,7-dihydro-5H-pyrazolo[5,1-b][1,3]oxazine-3-sulfonimidamide (180 mg, 0.4171 mmol) in dichloromethane (8 mL) was added triethylamine (1.16 mL, 8.343 mmol) and acetic anhydride (0.39 mL, 4.171 mmol) at 0° C. After addition, the reaction was allowed to slowly warm to room temperature. After 1.5 hours, additional trimethylamine (1.16 mL, 8.343 mmol) and acetic anhydride (0.39 mL, 4.171 mmol) were added. After stirring for an additional 1.5 hours, the reaction mixture was directly subjected to flash column chromatography (silica, 100% dichloromethane then, a gradient of DCM/MeOH/H₂O/NH₄OH (90/10/0.6/0.6)) to deliver the desired product. The material was further purified by chiral SFC (2.1×25.0 cm (S,S) Whelk0-1 from Regis Technologies (Morton Grove, Ill.) column and an isocratic method consisting of CO₂ and 45% ethanol with 0.25% ammonium hydroxide at 100 bar and 25° C.) to give N—((R,6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide (peak 1, Method W, 1.3 min, 32 mg, yield: 16%) and N—((S,6S)—N-((1,2,3,5,6,7-hexahydro-s-indacen-4-yl)carbamoyl)-6-methoxy-6,7-dihydro-5H-pyrazolo[5,1-b][1,3]oxazine-3-sulfonimidoyl)acetamide (peak 2, Method W, 2.2 min, 13 mg, yield: 7%). Stereochemistry was arbitrarily assigned to each stereoisomer.

Peak 1: ¹H NMR (400 MHz, DMSO-d₆) δ 8.12 (s, 1H), 7.57-7.51 (m, 1H), 7.46 (dd, J=6.7, 4.0 Hz, 1H), 6.84 (s, 1H), 4.54 (d, J=11.5 Hz, 1H), 4.29 (d, J=11.5 Hz, 1H), 4.23 (dd, J=13.2, 3.7 Hz, 1H), 4.14 (d, J=13.2 Hz, 1H), 4.01 (s, 1H), 3.35 (d, J=1.4 Hz, 4H), 2.77 (t, J=7.4 Hz, 4H), 2.69 (t, J=7.2 Hz, 4H), 1.99-1.89 (m, 4H), 1.86 (d, J=2.9 Hz, 3H). MS: m/z 474.2 (M+H$^+$). Compound 116

Peak 2: $^1$H NMR (400 MHz, DMSO-d$_6$) δ 11.70 (s, 1H), 8.33 (s, 1H), 7.79-7.51 (m, 1H), 6.88 (s, 1H), 4.61 (d, J=11.8 Hz, 1H), 4.33 (d, J=11.7 Hz, 1H), 4.26 (dd, J=13.3, 3.5 Hz, 1H), 4.18 (d, J=13.4 Hz, 1H), 4.05 (s, 1H), 3.36 (s, 3H), 2.79 (t, J=7.4 Hz, 4H), 2.69 (d, J=7.9 Hz, 4H), 2.03-1.88 (m, 7H). MS: m/z 474.2 (M+H$^+$). Compound 115

Example 117 and Example 118

(S)—N'-((1,2,3,5,6,7-hexahydro-s-indacen-4-yl)carbamoyl)-4,5,7,8-tetrahydropyrazolo[1,5-d][1,4]oxazepine-3-sulfonimidamide and (R)—N'-((1,2,3,5,6,7-hexahydro-s-indacen-4-yl)carbamoyl)-4,5,7,8-tetrahydropyrazolo[1,5-d][1,4]oxazepine-3-sulfonimidamide

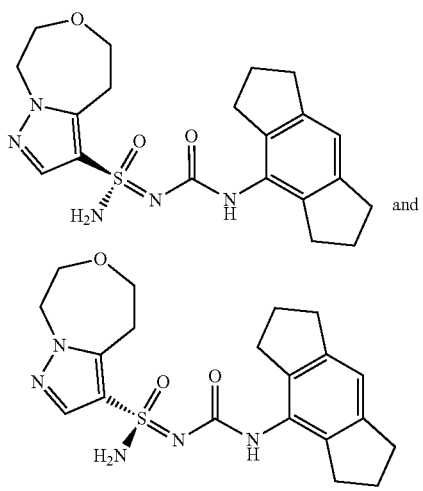

Step 1—Synthesis of ethyl 2-(1-(tetrahydro-2H-pyran-2-yl)-1H-pyrazol-5-yl)acetate and ethyl 2-(1-(tetrahydro-2H-pyran-2-yl)-1H-pyrazol-3-yl)acetate

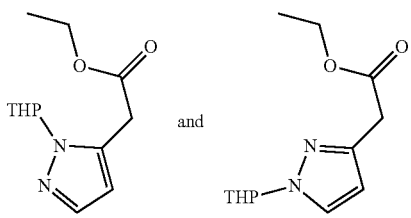

To a solution of ethyl 2-(1H-pyrazol-5-yl)acetate (10.0 g, 64.86 mmol) in DCM (300 mL) was added 3,4-dihydro-2H-pyran (11 g, 129.73 mmol) and TsOH (3.21 g, 16.86 mmol) at room temperature. After 16 hours, the reaction mixture was concentrated and the crude residue was purified by silica gel column chromatography (0-50% EtOAc in petroleum ether) to give a mixture of ethyl 2-(1-(tetrahydro-2H-pyran-2-yl)-1H-pyrazol-5-yl)acetate and ethyl 2-(1-(tetrahydro-2H-pyran-2-yl)-1H-pyrazol-3-yl)acetate (12 g, yield: 77.6%) as a colorless oil. MS: m/z 239.2 (M+H$^+$).

Step 2—Synthesis of 2-(1-(tetrahydro-2H-pyran-2-yl)-1H-pyrazol-5-yl)ethanol and 2-(1-(tetrahydro-2H-pyran-2-yl)-1H-pyrazol-3-yl)ethanol

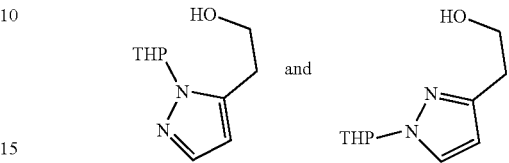

To a suspension of LiAlH$_4$ (5.2 g, 151.08 mmol) in THF (100 mL) was added a solution of ethyl 2-(1-(tetrahydro-2H-pyran-2-yl)-1H-pyrazol-5-yl)acetate and ethyl 2-(1-(tetrahydro-2H-pyran-2-yl)-1H-pyrazol-3-yl)acetate (12 g, 50.36 mmol) in THF (100 mL) drop-wise at 0° C. After addition, the reaction mixture was warmed to room temperature. After 3 hours, the reaction was cooled to 0° C. and saturated aqueous Na$_2$SO$_4$ was added slowly to quench the reaction. The mixture was dried over Na$_2$SO$_4$. The solids were removed by filtration and the filtrate was concentrated to dryness to give a mixture of 2-(1-(tetrahydro-2H-pyran-2-yl)-1H-pyrazol-5-yl)ethanol and 2-(1-(tetrahydro-2H-pyran-2-yl)-1H-pyrazol-3-yl)ethanol (7 g crude) which was used in the next step without further purification. MS: m/z 197.0 (M+H$^+$).

Step 3—Synthesis of 1-(tetrahydro-2H-pyran-2-yl)-5-(2-(2-((tetrahydro-2H-pyran-2-yl)oxy)ethoxy)ethyl)-1H-pyrazole and 1-(tetrahydro-2H-pyran-2-yl)-3-(2-(2-((tetrahydro-2H-pyran-2-yl)oxy)ethoxy)ethyl)-1H-pyrazole

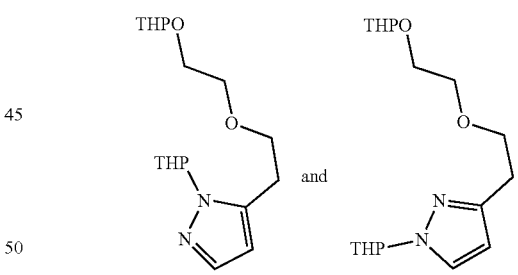

To a solution of 2-(1-(tetrahydro-2H-pyran-2-yl)-1H-pyrazol-5-yl)ethanol and 2-(1-(tetrahydro-2H-pyran-2-yl)-1H-pyrazol-3-yl)ethanol (7 g, 35.67 mmol) in DMF (150 mL) was added NaH (60% in mineral oil, 2.1 g, 53.5 mmol) at 0° C. After 30 minutes, 2-(2-bromoethoxy)tetrahydropyran (22.3 g, 107.01 mmol) was added. The reaction was warmed to room temperature. After 32 hours, the reaction was quenched with saturated aqueous NH$_4$Cl (50 mL). The aqueous layer was extracted with DCM (3×300 mL). The combined organic layers were dried over Na$_2$SO$_4$, filtered and concentrated to dryness. The crude residue was purified by silica gel column chromatography (0-30% EtOAc in petroleum ether) to give a mixture of 1-(tetrahydro-2H-pyran-2-yl)-5-(2-(2-((tetrahydro-2H-pyran-2-yl)oxy)ethoxy)ethyl)-1H-pyrazole and 1-(tetrahydro-2H-pyran-2- yl)-3-(2-(2-((tetrahydro-2H-pyran-2-yl)oxy)ethoxy)ethyl)-1H-pyrazole (4.8 g, yield: 41%) as a colorless oil. MS: m/z 325.1 (M+H⁺).

Step 4—Synthesis of 2-(2-(1H-pyrazol-5-yl)ethoxy)ethanol

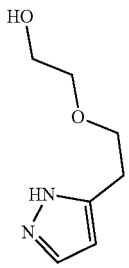

To a solution of 1-(tetrahydro-2H-pyran-2-yl)-5-(2-(2-((tetrahydro-2H-pyran-2-yl)oxy)ethoxy)ethyl)-1H-pyrazole and 1-(tetrahydro-2H-pyran-2-yl)-3-(2-(2-((tetrahydro-2H-pyran-2-yl)oxy)ethoxy)ethyl)-1H-pyrazole (4.8 g, 7.4 mmol) in EtOH (80 mL) was added concentrated HCl (7.0 mL, 84 mmol) at 0° C. After addition, the reaction was warmed to 30° C. After 16 hours, the reaction was concentrated to dryness. Saturated aqueous NaHCO₃ was added to the crude residue to adjust the solution to pH=8. The resulting mixture was extracted with DCM (50 mL×3). The combined organic layers were dried over Na₂SO₄, filtered and concentrated to dryness. The crude residue was purified by silica gel column chromatography (MeOH/DCM=1:10) to give 2-(2-(1H-pyrazol-5-yl)ethoxy)ethanol (2 g, yield: 86%) as a colorless oil. ¹H NMR (400 MHz, DMSO-d₆): δ=12.45 (s, 1H), 7.50-7.20 (m, 1H), 6.07 (s, 1H), 4.62 (s, 1H), 3.61 (t, J=7.2 Hz, 2H), 3.52-3.46 (m, 2H), 3.44-3.40 (m, 2H), 2.83-2.74 (m, 2H).

Step 5—Synthesis of 2-(2-(1H-pyrazol-5-yl)ethoxy)ethyl methanesulfonate

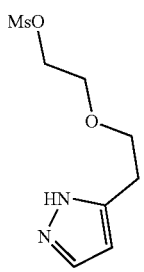 [SMILES: CS(=O)(=O)OCCOCCc1ccn[nH]1]

To a stirred solution of 2-(2-(1-pyrazol-5-yl)ethoxy)ethanol (2.0 g, 12.81 mmol) and triethylamine (5.3 mL, 38.42 mmol) in DCM (60 mL) was added MsCl (1.0 mL, 12.81 mmol) at 0° C. After 1 hour, water (2 mL) was added. The aqueous layer was extracted with DCM (50 mL×3). The combined organic layers were dried over Na₂SO₄, filtered and concentrated to dryness. The crude residue was purified by silica gel column chromatography (0-5% MeOH in DCM) to give 2-(2-(1H-pyrazol-5-yl)ethoxy)ethyl methanesulfonate (1.1 g, yield: 26%) as a colorless oil. MS: m/z 234.9 (M+H⁺).

Step 6—Synthesis of 4,5,7,8-tetrahydropyrazolo[1,5-d][1,4]oxazepine

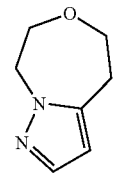

To a solution of 2-(2-(1H-pyrazol-5-yl)ethoxy)ethyl methanesulfonate (1.1 g, 4.7 mmol) in DMF (18 mL) was added NaH (60% in mineral oil, 226 mg, 5.63 mmol) at 0° C. The reaction mixture was warmed room temperature. After 12 hours, the reaction was cooled to 0° C. and saturated aqueous NH₄Cl (3 mL) was added. The reaction mixture was concentrated to dryness and the crude residue was purified by silica gel column chromatography (0-20% EtOAc in petroleum ether) to give 4,5,7,8-tetrahydropyrazolo[1,5-d][1,4]oxazepine (480 mg, yield: 70%) as a colorless oil. ¹H NMR (400 MHz, CDCl₃): δ=7.33 (d, J=1.6 Hz, 1H), 6.05 (d, J=1.6 Hz, 1H), 4.45-4.42 (m, 2H), 3.90-3.87 (m, 2H), 3.86-3.83 (m, 2H), 3.01-2.98 (m, 2H).

Step 7—Synthesis of 3-bromo-4,5,7,8-tetrahydropyrazolo[1,5-d][1,4]oxazepine

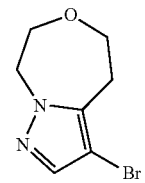 [SMILES: Brc1cnn2c1CCOCC2]

To a solution of 4,5,7,8-tetrahydropyrazolo[1,5-d][1,4]oxazepine (480 mg, 3.47 mmol) in MeCN (15 mL) was added NBS (618 mg, 3.47 mmol) at 0° C. The reaction was warmed to room temperature. After 1 hour, the reaction mixture was concentrated and the crude residue was purified by silica gel column chromatography (0-30% EtOAc in petroleum ether) to give 3-bromo-4,5,7,8-tetrahydropyrazolo[1,5-d][1,4]oxazepine (420 mg, yield: 56%) as a white solid. ¹H NMR (400 MHz, CDCl₃): δ=7.35 (s, 1H), 4.43 (t, J=4.0 Hz, 2H), 3.90-3.84 (m, 4H), 2.99 (t, J=4.8 Hz, 2H).

Step 8—Synthesis of N'-trityl-4,5,7,8-tetrahydropyrazolo[1,5-d][1,4]oxazepine-3-sulfonimidamide

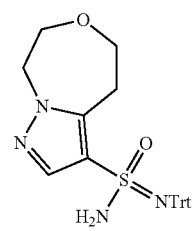

To a solution of 3-bromo-4,5,7,8-tetrahydropyrazolo[1,5-d][1,4]oxazepine (200 mg, 0.92 mmol) in THF (4 mL) was added n-BuLi (2.5 M in hexane, 0.41 mL, 1.01 mmol) drop-wise at −78° C. under a nitrogen atmosphere. After 1 hour, a solution of TrtNSO (310 mg, 1.01 mmol) in THF (1 mL) was added drop-wise. The reaction was allowed to stir at −78° C. for 30 minutes at which point it was placed in a 0° C. ice bath where it stirred for an additional 10 minutes. tert-Butyl hypochlorite (0.11 mL, 0.99 mmol) was added drop-wise at 0° C. After 30 minutes, $NH_3$ gas was bubbled through the mixture for 10 minutes. The reaction was warmed to room temperature and stirred for an additional 16 hours. The reaction mixture was concentrated and the crude residue was purified by silica gel column chromatography (0-80% EtOAc in petroleum ether) to give N'-trityl-4,5,7,8-tetrahydropyrazolo[1,5-d][1,4]oxazepine-3-sulfonimidamide (200 mg, yield: 34%) as a white solid. $^1$H NMR (400 MHz, DMSO-$d_6$) δ=7.42-7.30 (m, 6H), 7.18-7.12 (m, 6H), 7.10-7.07 (m, 4H), 6.5 (s, 2H), 4.25-4.19 (m, 2H), 3.71-3.59 (m, 4H), 3.08-3.03 (m, 2H).

Step 9—Synthesis of N-((1,2,3,5,6,7-hexahydro-s-indacen-4-yl)carbamoyl)-N'-trityl-4,5,7,8-tetrahydropyrazolo[1,5-d][1,4]oxazepine-3-sulfonimidamide

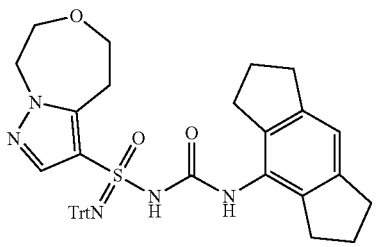

To a stirred solution of N-trityl-4,5,7,8-tetrahydropyrazolo[1,5-d][1,4]oxazepine-3-sulfonimidamide (100 mg, 0.22 mmol) in THF (5 mL) was added MeONa (24 mg, 0.44 mmol) at 0° C. After 15 minutes, 4-isocyanato-1,2,3,5,6,7-hexahydro-s-indacene (52 mg, 0.26 mmol) was added and the reaction mixture was warmed to room temperature. After 16 hours, MeOH (1 mL) was added and the reaction was concentrated. The crude residue was purified by silica gel column chromatography (0-5% MeOH in DCM) to give N'-((1,2,3,5,6,7-hexahydro-s-indacen-4-yl)carbamoyl)-N'-trityl-4,5,7,8-tetrahydropyrazolo[1,5-d][1,4]oxazepine-3-sulfonimidamide (100 mg, yield: 70%) as a white solid.

Step 10—Synthesis of N'-((1,2,3,5,6,7-hexahydro-s-indacen-4-yl)carbamoyl)-4,5,7,8-tetrahydropyrazolo[1,5-d][1,4]oxazepine-3-sulfonimidamide

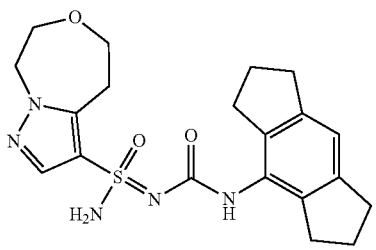 [SMILES: NS(=O)(=NC(=O)Nc1c2c(cc3c1CCC3)CCC2)c1cnn2c1CCOCC2]

To a solution of N-((1,2,3,5,6,7-hexahydro-s-indacen-4-yl)carbamoyl)-N'-trityl-4,5,7,8-tetrahydropyrazolo[1,5-d][1,4]oxazepine-3-sulfonimidamide (200 mg, 0.3 mmol) in DCM (10 mL) was added $MeSO_3H$ (6 drops) at 0° C. After addition, the reaction was warmed to room temperature. After 1 hour, the reaction was adjusted to pH=8 with the addition of saturated aqueous $NaHCO_3$. The reaction was concentrated to dryness and the crude residue was purified by silica gel column chromatography (0-2% MeOH in DCM) to give N'-((1,2,3,5,6,7-hexahydro-s-indacen-4-yl)carbamoyl)-4,5,7,8-tetrahydropyrazolo[1,5-d][1,4]oxazepine-3-sulfonimidamide (100 mg, yield: 79%) as a white solid. MS: m/z 416.1 (M+H$^+$).

Step 11—Synthesis of (S)—N'-((1,2,3,5,6,7-hexahydro-s-indacen-4-yl)carbamoyl)-4,5,7,8-tetrahydropyrazolo[1,5-d][1,4]oxazepine-3-sulfonimidamide and (R)—N'-((1,2,3,5,6,7-hexahydro-s-indacen-4-yl)carbamoyl)-4,5,7,8-tetrahydropyrazolo[1,5-d][1,4]oxazepine-3-sulfonimidamide (Example 117 and Example 118)

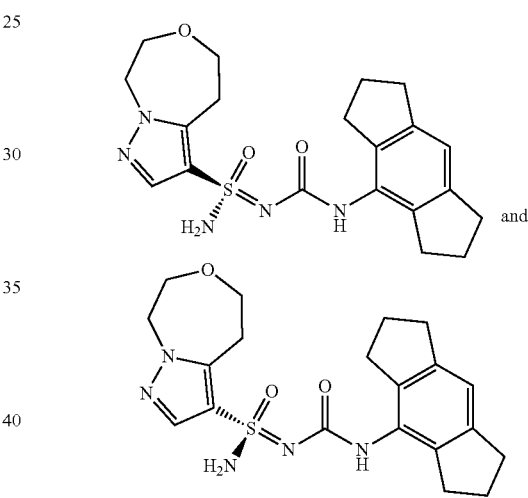

N'-((1,2,3,5,6,7-hexahydro-s-indacen-4-yl)carbamoyl)-4,5,7,8-tetrahydropyrazolo[1,5-d][1,4]oxazepine-3-sulfonimidamide (100 mg, 0.24 mmol) was separated by chiral SFC (Chiralpak AD (250 mm*50 mm, 10 um); Supercritical $CO_2$/EtOH+0.1% $NH_4OH$=45/55; 80 mL/min) to give (S)—N'-((1,2,3,5,6,7-hexahydro-s-indacen-4-yl)carbamoyl)-4,5,7,8-tetrahydropyrazolo[1,5-d][1,4]oxazepine-3-sulfonimidamide (Method E, 2.30 min, peak 1, 12.9 mg, yield: 12%) as a white and (R)—N'-((1,2,3,5,6,7-hexahydro-s-indacen-4-yl)carbamoyl)-4,5,7,8-tetrahydropyrazolo[1,5-d][1,4]oxazepine-3-sulfonimidamide (Method E, 2.92 min, peak 2, 11.8 mg, yield: 11%) both as white solids. Stereochemistry was arbitrarily assigned to each stereoisomer.

Peak 1: $^1$H NMR (400 MHz, DMSO-$d_6$): δ=8.17 (s, 1H), 7.62 (s, 1H), 7.32 (s, 2H), 6.85 (s, 1H), 4.47-4.38 (m, 2H), 3.78-3.66 (m, 4H), 3.21-3.16 (m, 2H), 2.76 (t, J=7.2 Hz, 4H), 2.64 (t, J=7.2 Hz, 4H), 1.96-1.88 (m, 4H). MS: m/z 416.1 (M+H$^+$).

Peak 2: $^1$H NMR (400 MHz, DMSO-$d_6$): δ=8.20 (s, 1H), 7.63 (s, 1H), 7.38 (s, 2H), 6.85 (s, 1H), 4.43 (t, J=4.0 Hz, 2H), 3.80-3.64 (m, 4H), 3.29-3.28 (m, 1H), 3.23-3.14 (m, 1H), 2.76 (t, J=7.2 Hz, 4H), 2.64 (t, J=6.8 Hz, 4H), 1.99-1.86 (m, 4H). MS: m/z 416.1 (M+H$^+$).

Example 119 and Example 120

(S)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide and (R)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide

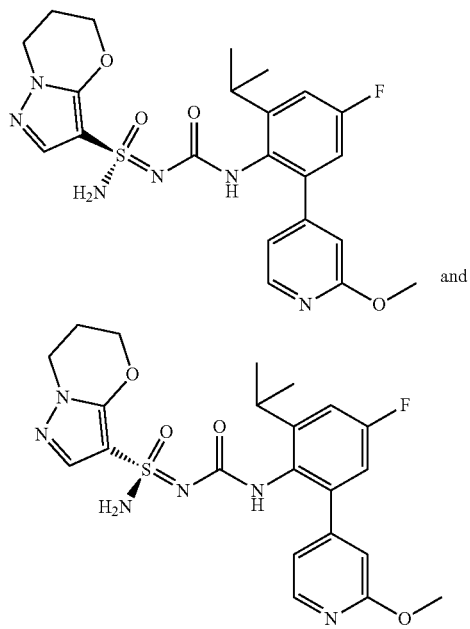

Step 1—Synthesis of 4-(5-fluoro-2-isocyanato-3-isopropylphenyl)-2-methoxypyridine

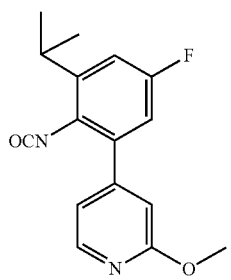

To a solution of 4-fluoro-2-isopropyl-6-(2-methoxypyridin-4-yl) aniline (synthesized as reported in WO2019008025, 240 mg, 0.92 mmol) and triethylamine (0.35 mL, 2.49 mmol) in THF (12 mL) was added triphosgene (109 mg, 0.37 mmol) at room temperature under a nitrogen atmosphere. The mixture was heated 70° C. After 1 hour, the reaction was cooled to room temperature and filtered through a pad of silica gel. The silica gel pad was washed with THF (5 mL×3). The filtrate, containing 4-(5-fluoro-2-isocyanato-3-isopropylphenyl)-2-methoxypyridine, was used directly as a THF solution in the next step.

Step 2—Synthesis of N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide

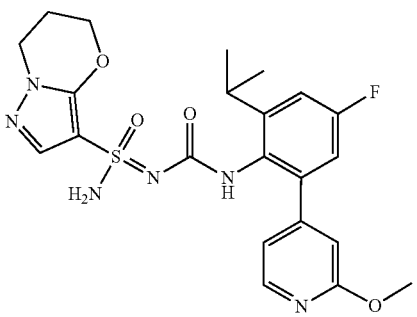 [SMILES: COc1cc(-c2cc(F)cc(C(C)C)c2NC(=O)N=S(N)(=O)c2cnn3c2OCCC3)ccn1]

N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide was were prepared using the general procedure described for the preparation of (S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide (Example 102 and Example 103), by replacing 3-isocyanato-2,4-diisopropyl-6-methoxypyridine with 4-(5-fluoro-2-isocyanato-3-isopropylphenyl)-2-methoxypyridine in Step 1.

Step 3—Synthesis of (S)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide and (R)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (Example 119 and Example 120)

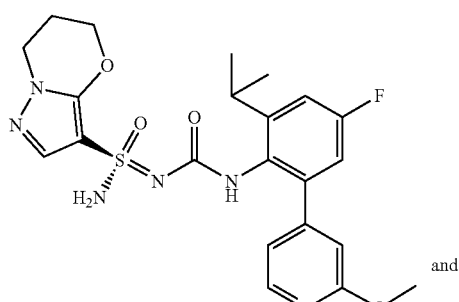

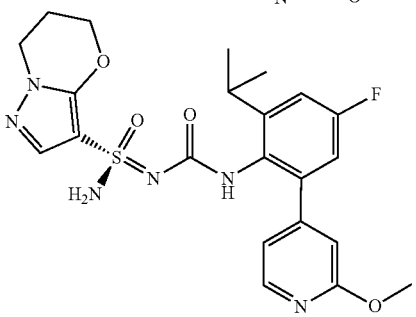

N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (107 mg, 0.22 mmol) was separated by chiral SFC (Chiralpak IC (250 mm*30 mm, 10 um), CO₂/EtOH+0.1% NH₄OH=40/60; 80 mL/min) to give (S)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (Method L, 3.63 min, peak 1, 32 mg, yield: 29%) and (R)—N'-((4-fluoro-2-isopropyl-6-(2-methoxypyridin-4-yl)phenyl)carbamoyl)-6,7-dihydro-5H-pyrazolo[5,1-b][1,3]oxazine-3-sulfonimidamide (Method L, 6.88 min, peak 2, 38 mg, yield: 34%) both as white solids. Stereochemistry was arbitrarily assigned to each stereoisomer.

Peak 1: $^1$H NMR (400 MHz, DMSO-d₆): δ=8.18-8.10 (m, 2H), 7.27 (s, 1H), 7.18-7.12 (m, 3H), 7.00-6.90 (m, 2H), 6.79 (s, 1H), 4.36-4.30 (m, 2H), 4.09 (t, J=6.4 Hz, 2H), 3.87 (s, 3H), 3.15-3.08 (m, 1H), 2.20-2.12 (m, 2H), 1.11-1.05 (m, 6H). MS: m/z 489.1 (M+H⁺).

Peak 2: $^1$H NMR (400 MHz, DMSO-d₆): δ=8.16-8.08 (m, 2H), 7.27 (s, 1H), 7.20-7.10 (m, 3H), 7.00-6.90 (m, 2H), 6.79 (s, 1H), 4.38-4.31 (m, 2H), 4.10 (t, J=6.4 Hz, 2H), 3.87 (s, 3H), 3.15-3.06 (m, 1H), 2.20-2.12 (m, 2H), 1.13-1.06 (m, 6H). MS: m/z 489.1 (M+H⁺).

Example 121

(S,7R)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia

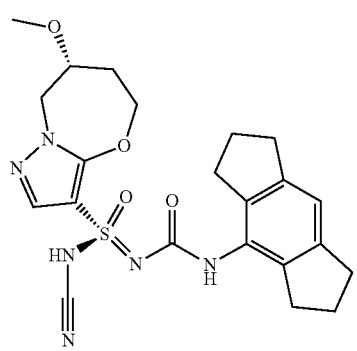 [SMILES: CO[C@@H]1CCOc2c([S@](=O)(=NC(=O)Nc3c4c(cc5c3CCC5)CCC4)NC#N)cnn2C1]

(S,7R)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (R,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide in Step 1 (single unknown stereoisomer). $^1$H NMR (400 MHz, DMSO-d₆) δ 7.86 (s, 1H), 7.39 (s, 1H), 7.21 (s, 1H), 7.08 (s, 1H), 6.96 (s, 1H), 6.82 (s, 1H), 4.44 (ddd, J=14.5, 5.5, 1.4 Hz, 1H), 4.27-4.13 (m, 2H), 4.02 (ddd, J=12.4, 10.2, 2.4 Hz, 1H), 3.65 (q, J=4.3, 3.1 Hz, 1H), 3.27 (s, 3H), 2.87-2.61 (m, 8H), 2.15 (ddd, J=16.7, 7.9, 3.7 Hz, 2H), 2.03-1.81 (m, 4H). MS: m/z 471.2 (M+H⁺).

Example 122

(R,7R)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia

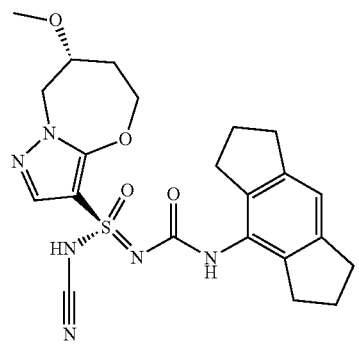 [SMILES: CO[C@@H]1CCOc2c([S@@](=O)(=NC(=O)Nc3c4c(cc5c3CCC5)CCC4)NC#N)cnn2C1]

(R,7R)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (S,7R)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide in Step 1 (single unknown stereoisomer). $^1$H NMR (400 MHz, DMSO-d₆) δ 7.83 (s, 1H), 7.41 (s, 1H), 7.20 (s, 1H), 7.07 (s, 1H), 6.94 (s, 1H), 6.82 (s, 1H), 4.51-4.37 (m, 1H), 4.28-4.15 (m, 2H), 4.10 (ddd, J=12.3, 8.4, 4.0 Hz, 1H), 3.65 (q, J=4.5 Hz, 1H), 3.27 (s, 3H), 2.76 (m, 4H), 2.72-2.57 (m, 4H), 2.14 (dt, J=8.3, 3.8 Hz, 2H), 2.01-1.84 (m, 4H). MS: m/z 471.2 (M+H⁺).

Example 123

(S,7S)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia

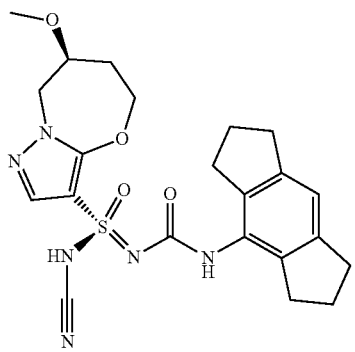 [SMILES: CO[C@H]1CCOc2c([S@](=O)(=NC(=O)Nc3c4c(cc5c3CCC5)CCC4)NC#N)cnn2C1]

(S,7S)—N-cyano-N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide, ammonia was prepared using the general procedure described for the preparation of (R,6S)—N-cyano-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide (Example 104), by replacing (S,6S)-6-(dimethylamino)-N'-((8-fluoro-1,2,3,5,6,7-hexahydro-s-indacen-4-yl)carbamoyl)-6,7-dihydro-5H-pyrazolo[5,1-b][1,3]oxazine-3-sulfonimidamide with (R,7S)—N'-((1,2,3,5,6,7-hexahydro-s-indacen-4-yl)carbamoyl)-7-methoxy-5,6,7,8-tetrahydropyrazolo[5,1-b][1,3]oxazepine-3-sulfonimidamide in Step 1 (single unknown stereoisomer). $^1$H NMR (400 MHz, DMSO-$d_6$) δ 7.80 (s, 1H), 7.39 (s, 1H), 7.20 (s, 1H), 7.07 (s, 1H), 6.94 (s, 1H), 6.81 (s, 1H), 4.44-4.37 (m, 1H), 4.26-4.15 (m, 2H), 4.09 (ddd, J=12.3, 8.6, 3.9 Hz, 1H), 3.27 (s, 3H), 2.76 (m, 4H), 2.68 (m, 4H), 2.14 (dt, J=8.9, 4.1 Hz, 2H), 2.02-1.80 (m, 4H). MS: m/z 471.2 (M+H⁺).

Example 124 and Example 125

(R)—N'-((1,2,3,5,6,7-hexahydro-s-indacen-4-yl)carbamoyl)-2,3-dihydropyrazolo[5,1-b]oxazole-7-sulfonimidamide and (S)—N'-((1,2,3,5,6,7-hexahydro-s-indacen-4-yl)carbamoyl)-2,3-dihydropyrazolo[5,1-b]oxazole-7-sulfonimidamide

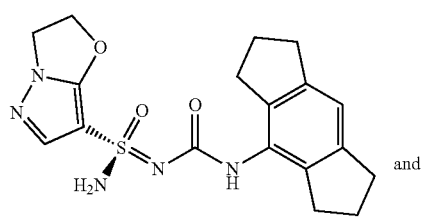

and

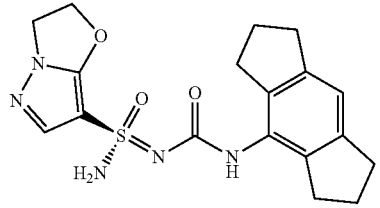

Step 1—Synthesis of N'-trityl-2,3-dihydropyrazolo[5,1-b]oxazole-7-sulfonimidamide

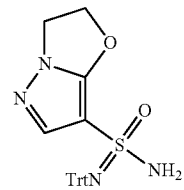

To a stirred solution of 7-bromo-2,3-dihydropyrazolo[5,1-b]oxazole (200 mg, 1.06 mmol) in THF (6 mL) was added n-BuLi (2.5 M in hexane, 0.51 mL, 1.27 mmol) drop-wise at −78° C. under a N₂ atmosphere. After 1 hour, a solution of TrtNSO (388 mg, 1.27 mmol) in THF (1 mL) was added drop-wise. The reaction was allowed to stir at −78° C. for 20 minutes at which point it was placed in a 0° C. ice bath where it stirred for an additional 10 minutes. tert-Butyl hypochlorite (0.15 mL, 1.33 mmol) was added drop-wise at 0° C. After 20 minutes, NH₃ gas was bubbled through the mixture for 10 minutes. The reaction was warmed to room temperature and stirred for an additional 16 hours. The reaction mixture was concentrated and the crude residue was purified by silica gel column chromatography (0-2% MeOH in DCM) to give N'-trityl-2,3-dihydropyrazolo[5,1-b]oxazole-7-sulfonimidamide (140 mg, yield: 31%) as a yellow solid. $^1$H NMR (400 MHz, DMSO-$d_6$) δ=7.43 (d, J=7.6 Hz, 6H), 7.22-7.13 (m, 6H), 7.13-7.06 (m, 3H), 7.04 (s, 1H), 6.38 (s, 2H), 5.03 (t, J=8.0 Hz, 2H), 4.18-4.07 (m, 2H).

Step 2~3—Synthesis of N'-((1,2,3,5,6,7-hexahydro-s-indacen-4-yl)carbamoyl)-2,3-dihydropyrazolo[5,1-b]oxazole-7-sulfonimidamide

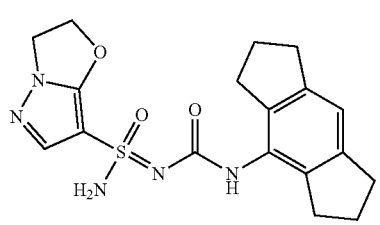

N'-((1,2,3,5,6,7-hexahydro-s-indacen-4-yl)carbamoyl)-2,3-dihydropyrazolo[5,1-b]oxazole-7-sulfonimidamide was prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Example 100 and Example 101), by replacing N'-trityl-6,7-dihydro-5H-pyrazolo[5,1-b][1,3]thiazine-3-sulfonimidamide with N'-trityl-2,3-dihydropyrazolo[5,1-b]oxazole-7-sulfonimidamide in Step 3.

Step 4—Synthesis of (R)—N'-((1,2,3,5,6,7-hexahydro-s-indacen-4-yl)carbamoyl)-2,3-dihydropyrazolo[5,1-b]oxazole-7-sulfonimidamide and (S)—N'-((1,2,3,5,6,7-hexahydro-s-indacen-4-yl)carbamoyl)-2,3-dihydropyrazolo[5,1-b]oxazole-7-sulfonimidamide (Example 124 and Example 125)

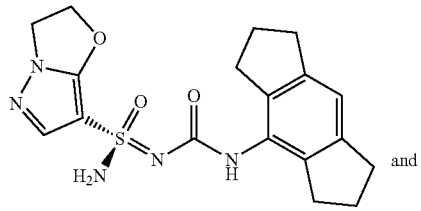

and

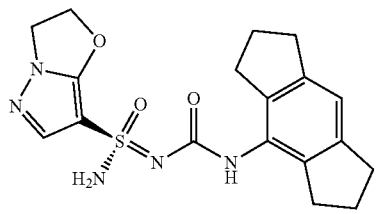

N'-((1,2,3,5,6,7-hexahydro-s-indacen-4-yl)carbamoyl)-2,3-dihydropyrazolo[5,1-b]oxazole-7-sulfonimidamide (53 mg, 0.14 mmol) was separated by chiral SFC (Chiralcel OD (250 mm*30 mm, 5 um); Supercritical $CO_2$/MeOH+0.1% $NH_4OH$=40/60; 50 mL/min) to give (R)—N'-((1,2,3,5,6,7-hexahydro-s-indacen-4-yl)carbamoyl)-2,3-dihydropyrazolo[5,1-b]oxazole-7-sulfonimidamide (Method M, 5.71 min, peak 1, 4.8 mg, yield: 9%) and (S)—N'-((1,2,3,5,6,7-hexahydro-s-indacen-4-yl)carbamoyl)-2,3-dihydropyrazolo[5,1-b]oxazole-7-sulfonimidamide (Method M, 6.07 min, peak 2, 6.3 mg, yield: 11%) both as white solids. Stereochemistry was arbitrarily assigned to each stereoisomer.

Peak 1: $^1$H NMR (400 MHz, DMSO-$d_6$): δ=8.21 (s, 1H), 7.54 (s, 1H), 7.33 (s, 2H), 6.86 (s, 1H), 5.23-5.16 (m, 2H), 4.34 (t, J=8.4 Hz, 2H), 2.78 (t, J=7.2 Hz, 4H), 2.72-2.66 (m, 4H), 1.99-1.89 (m, 4H). MS: m/z 388.1 (M+H$^+$).

Peak 2: $^1$H NMR (400 MHz, DMSO-$d_6$): δ=8.20 (s, 1H), 7.54 (s, 1H), 7.33 (s, 2H), 6.86 (s, 1H), 5.23-5.16 (m, 2H), 4.33 (t, J=8.4 Hz, 2H), 2.77 (t, J=7.2 Hz, 4H), 2.70-2.64 (m, 4H), 1.99-1.89 (m, 4H). MS: m/z 388.0 (M+H$^+$).

Example 126, Example 127, Example 128 and Example 129

(S)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

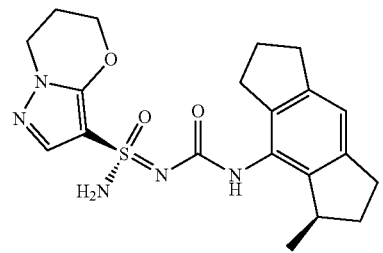

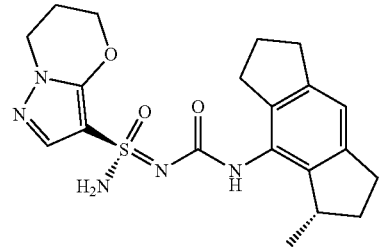

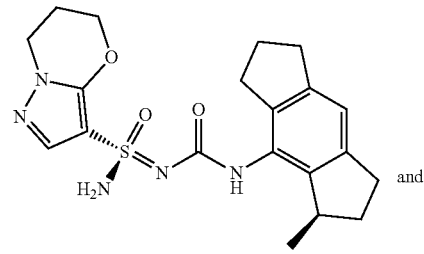

and

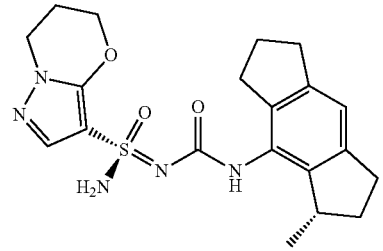

Step 1—Synthesis of methylene-8-nitro-1,2,3,5,6,7-hexahydro-s-indacene

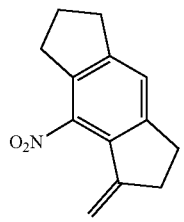 [SMILES: C=C1CCc2cc3c(c([N+](=O)[O-])c21)CCC3]

To a solution of methyltriphenylphosphonium bromide (18.5 g, 51.8 mmol) in THF (180 mL) was added a solution of t-BuOK (1.0 M in THF, 41.4 mL, 41.48 mmol) drop-wise at 0° C. under a nitrogen atmosphere. After 2 hours, a solution of 8-nitro-3,5,6,7-tetrahydro-2H-s-indacen-1-one (4.5 g, 20.7 mmol) in THF (27 mL) was added drop-wise. After addition, the reaction was warmed to room temperature. After 16 hours, the reaction was quenched with water (80 mL). The aqueous layer was extracted with EtOAc (100 mL×2). The combined organic layers were washed with brine (80 mL×2), dried over $Na_2SO_4$, filtered and concentrated. The crude residue was purified by silica gel column chromatography (2% EtOAc in petroleum ether) to give methylene-8-nitro-1,2,3,5,6,7-hexahydro-s-indacene (2.1 g, 47% yield) as a yellow solid. $^1$H NMR (400 MHz, $CDCl_3$): δ=7.23 (s, 1H), 5.24 (s, 1H), 5.20 (s, 1H), 2.97-2.91 (m, 6H), 2.89-2.83 (m, 2H), 2.21-2.10 (m, 2H).

Step 2—Synthesis of 3-methyl-1,2,3,5,6,7-hexahydro-s-indacen-4-amine

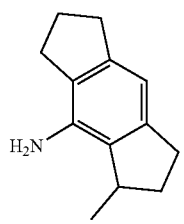

A mixture of methylene-8-nitro-1,2,3,5,6,7-hexahydro-s-indacene (2.1 g, 9.76 mmol) and 10% Pd/C on carbon (1.04 g, 0.98 mmol) in EtOH (147 mL) was stirred at room temperature under a hydrogen atmosphere (15 psi). After 16 hours, the reaction mixture was filtered through a pad of Celite. The filtrate was concentrated and the crude residue was purified by silica gel column chromatography (0-10% EtOAc in petroleum ether) to give 3-methyl-1,2,3,5,6,7-hexahydro-s-indacen-4-amine (800 mg, 44% yield) as a yellow solid. $^1$H NMR (400 MHz, $CDCl_3$): δ=6.61 (s, 1H), 3.53 (s, 2H), 3.24-3.14 (m, 1H), 3.06-2.93 (m, 1H), 2.91-2.83 (m, 2H), 2.80-2.62 (m, 3H), 2.35-2.23 (m, 1H), 2.17-2.06 (m, 2H), 1.83-1.73 (m, 1H), 1.21 (d, J=6.8 Hz, 3H).

Step 3—Synthesis of 8-isocyanato-1-methyl-1,2,3,5,6,7-hexahydro-s-indacene

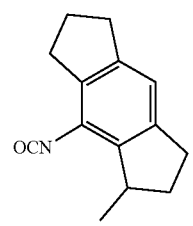

To a solution of 3-methyl-1,2,3,5,6,7-hexahydro-s-indacen-4-amine (306 mg, 1.63 mmol) and triethylamine (0.61 mL, 4.41 mmol) in THF (20 mL) was added triphosgene (194 mg, 0.65 mmol) at room temperature under a nitrogen atmosphere. The reaction was heated at 70° C. for 1 hour. After cooling to room temperature, the reaction mixture was filtered through a pad of silica gel. The silica gel pad was washed with THF (5 mL×3). The filtrate, containing 8-isocyanato-1-methyl-1,2,3,5,6,7-hexahydro-s-indacene, was used directly as a THF solution in the next step.

Step 4~5—Synthesis of N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide

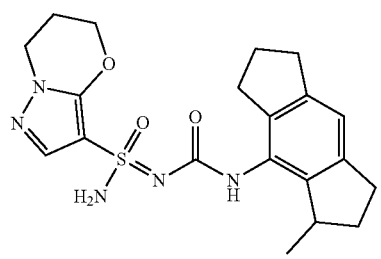 [SMILES: CC1CCc2cc3c(c(NC(=O)N=S(N)(=O)c4cnn5c4OCCC5)c21)CCC3]

N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of (S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide (Example 102 and Example 103), by replacing 3-isocyanato-2,4-diisopropyl-6-methoxypyridine with 8-isocyanato-1-methyl-1,2,3,5,6,7-hexahydro-s-indacene in Step 1.

Step 6—Synthesis of (S)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 126, Example 127, Example 128 and Example 129)

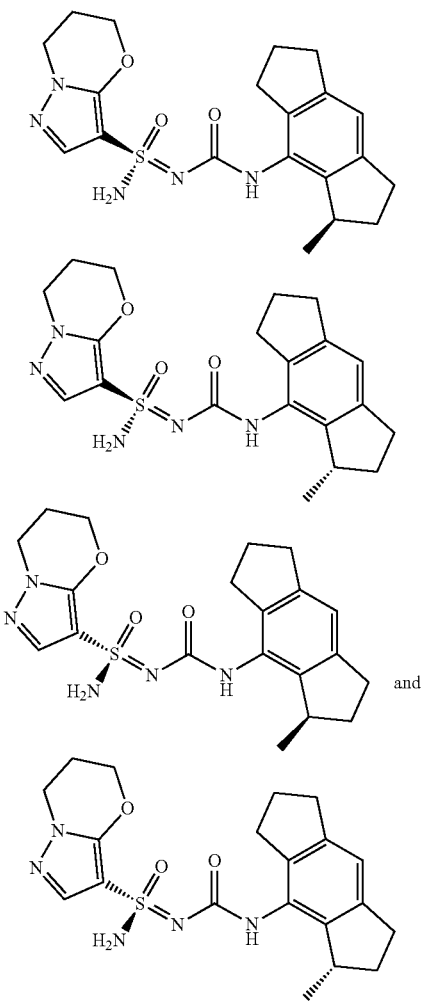

N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (116 mg, 0.28 mmol) was separated by chiral SFC (Chiralpak AD (250 mm*50 mm, 10 um), Supercritical CO$_2$/EtOH+0.1% NH$_4$OH=65/35; 70 mL/min) to give (S)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 2.58 min, peak 1, 7 mg, yield: 6%), (S)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 3.30 min, peak 2, 7 mg, yield: 6%), (R)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 3.86 min, peak 3, 9 mg, yield: 7%) and (R)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 4.32 min, peak 4, 8 mg, yield: 6%) all as white solids. Stereochemistry was arbitrarily assigned to each stereoisomer.

Peak 1: $^1$H NMR (400 MHz, DMSO-d$_6$): δ=8.08 (s, 1H), 7.49 (s, 1H), 7.19 (s, 2H), 6.83 (s, 1H), 4.40-4.33 (m, 2H), 4.09 (t, J=6.0 Hz, 2H), 2.88-2.60 (m, 7H), 2.18-2.05 (m, 3H), 1.97-1.85 (m, 2H), 1.60-1.52 (m, 1H), 1.03 (d, J=6.8 Hz, 3H). MS: m/z 416.1 (M+H$^+$).

Peak 2: $^1$H NMR (400 MHz, DMSO-d$_6$): δ=8.10 (s, 1H), 7.49 (s, 1H), 7.18 (s, 2H), 6.84 (s, 1H), 4.40-4.35 (m, 2H), 4.10 (t, J=6.0 Hz, 2H), 2.85-2.60 (m, 7H), 2.19-2.06 (m, 3H), 1.95-1.85 (m, 2H), 1.58-1.52 (m, 1H), 1.04 (d, J=6.8 Hz, 3H). MS: m/z 416.2 (M+H$^+$).

Peak 3: $^1$H NMR (400 MHz, DMSO-d$_6$): δ=8.09 (s, 1H), 7.49 (s, 1H), 7.18 (s, 2H), 6.84 (s, 1H), 4.40-4.33 (m, 2H), 4.10 (t, J=6.0 Hz, 2H), 2.85-2.60 (m, 7H), 2.19-2.09 (m, 3H), 1.95-1.85 (m, 2H), 1.60-1.52 (m, 1H), 1.04 (d, J=6.8 Hz, 3H). MS: m/z 416.1 (M+H$^+$).

Peak 4: $^1$H NMR (400 MHz, DMSO-d$_6$): δ=8.09 (s, 1H), 7.49 (s, 1H), 7.22 (s, 2H), 6.84 (s, 1H), 4.40-4.34 (m, 2H), 4.09 (t, J=6.0 Hz, 2H), 2.86-2.60 (m, 7H), 2.16-2.07 (m, 3H), 1.97-1.89 (m, 2H), 1.58-1.52 (m, 1H), 1. 1.03 (d, J=6.8 Hz, 3H). MS: m/z 416.1 (M+H$^+$).

Example 130, Example 131, and Example 132

(S,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide and (6S)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide

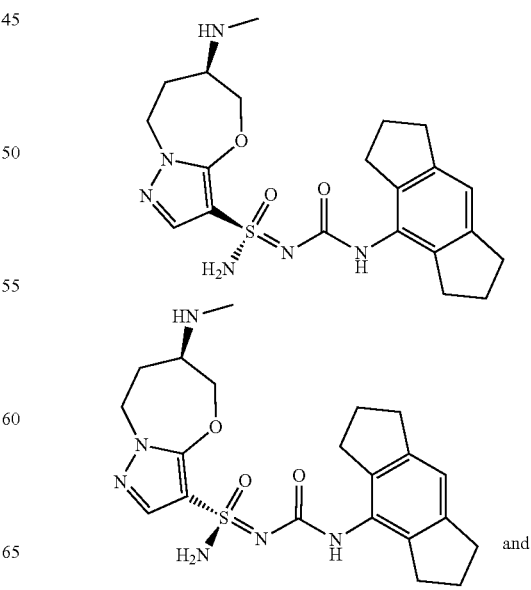

-continued

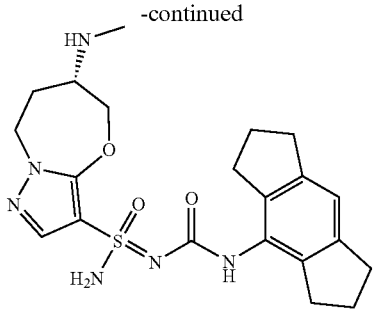

Step 1~8—Synthesis of N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide

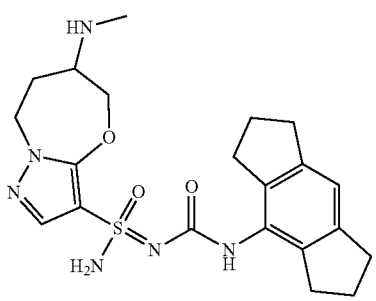 [SMILES: CNC1CCn2ncc(S(N)(=O)=NC(=O)Nc3c4c(cc5c3CCC5)CCC4)c2OC1]

N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide was prepared using the general procedure described for the preparation of (S,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (R,7S)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide, (S,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide and (R,7R)—N'-((1,2,3,5,6,7-hexahydro-s-indacen-4-yl)carbamoyl)-7-(methylamino)-5,6,7,8-tetrahydropyrazolo[5,1-b][1,3]oxazepine-3-sulfonimidamide (Example 105, Example 106, Example 109 and Example 110) by replacing 7-(benzyloxy)-5,6,7,8-tetrahydropyrazolo[5,1-b][1,3]oxazepine with 6-(benzyloxy)-5,6,7,8-tetrahydropyrazolo[5,1-b][1,3]oxazepine in Step 1.

Step 9—Synthesis of (S,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide, (R,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide and (6S)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide (Example 130, Example 131 and Example 132)

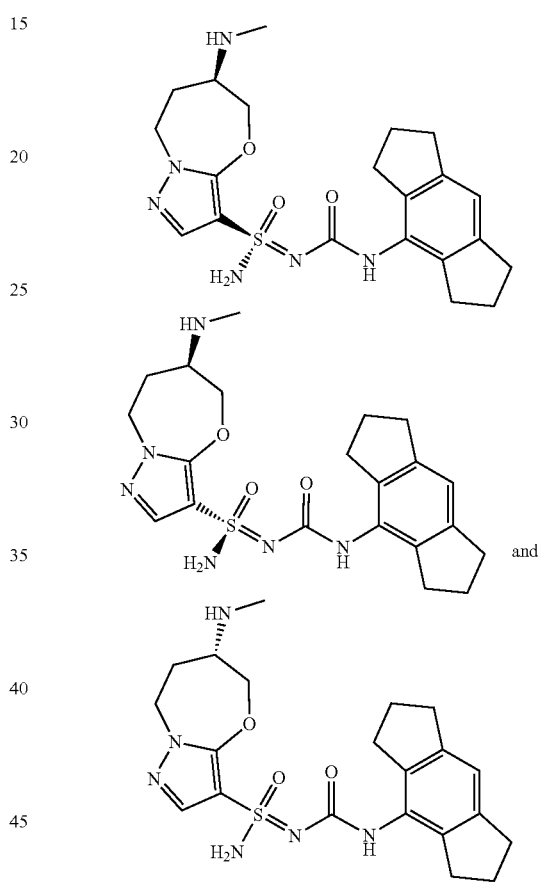

N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide (72 mg, 0.16 mmol) was separated by chiral SFC (Chiralpak AD (250 mm*30 mm, 5 um), Supercritical $CO_2$/EtOH+0.1% $NH_4OH$=40/60; 60 mL/min) to give (S,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide (Method N, 6.56 min, peak 1, 11.2 mg, yield: 16%), (R,6R)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide (Method N, 7.11 min, peak 2, 2.9 mg, yield 4%) and (6S)—N'-((1,2,3,5,6,7-hexahydro-s-indacen-4-yl)carbamoyl)-6-(methylamino)-5,6,7,8-tetrahydropyrazolo[5,1-b][1,3]oxazepine-3-sulfonimidamide (Method N, 7.37 min, peak 3, 4.3 mg, yield: 6%) all as white solids. Stereochemistry was arbitrarily assigned to each stereoisomer.

Peak 1: ¹H NMR (400 MHz, DMSO-d₆): δ=8.23 (s, 1H), 7.50 (s, 1H), 7.31 (s, 2H), 6.85 (s, 1H), 4.39-4.29 (m, 1H), 4.20-4.14 (m, 1H), 4.11-4.01 (m, 1H), 3.94-3.82 (m, 1H), 2.92-1.86 (s, 1H), 2.77 (t, J=7.2 Hz, 4H), 2.68-2.65 (m, 4H), 2.33 (s, 3H), 1.97-1.85 (m, 5H), 1.74-1.60 (m, 1H). MS: m/z 445.1 (M+H⁺).

Peak 2: ¹H NMR (400 MHz, DMSO-d₆): δ=8.24 (s, 1H), 7.51 (s, 1H), 7.32 (s, 2H), 6.86 (s, 1H), 4.41-4.32 (m, 1H), 4.26-4.19 (m, 1H), 4.14-4.03 (m, 1H), 3.97-3.85 (m, 1H), 2.95-2.90 (m, 1H), 2.78 (t, J=7.2 Hz, 4H), 2.69-2.66 (m, 4H), 2.37 (s, 3H), 1.98-1.88 (m, 5H), 1.77-1.64 (m, 1H). MS: m/z 445.3 (M+H⁺).

Peak 3: ¹H NMR (400 MHz, DMSO-d₆): δ=8.25 (s, 1H), 7.50 (s, 1H), 7.31 (s, 2H), 6.85 (s, 1H), 4.41-4.30 (m, 1H), 4.23-4.13 (m, 1H), 4.10-4.00 (m, 1H), 3.91-3.77 (m, 1H), 2.92-1.86 (s, 1H), 2.78 (t, J=7.2 Hz, 4H), 2.68-2.64 (m, 4H), 2.33 (s, 3H), 1.99-1.87 (m, 5H), 1.76-1.62 (m, 1H). MS: m/z 445.2 (M+H⁺).

Example 133 and Example 134

(S)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide and (R)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide

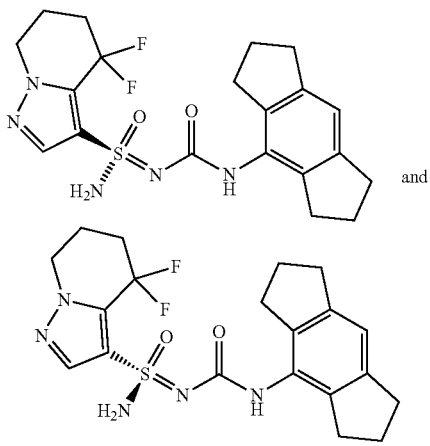

Step 1—Synthesis of 6',7'-dihydro-5'H-spiro[[1,3]dithiolane-2,4'-pyrazolo[1,5-a]pyridine]

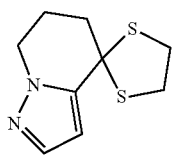

To a solution of 6,7-dihydro-5H-pyrazolo[1,5-a]pyridin-4-one (4.0 g, 29.4 mmol) in DCM (168 mL) was added 1,2-ethanedithiol (3.7 mL, 44.0 mmol) and boron trifluoride-acetic acid complex (6.1 mL, 43.8 mmol) at room temperature. After 48 hours, the reaction was quenched with water (200 mL). The aqueous layer was extracted with DCM (200 mL×3). The combined organic layers were washed with water (200 mL), brine (200 mL), dried over Na₂SO₄, filtered and concentrated. The crude residue was purified by silica gel column chromatography (0-20% EtOAc in petroleum ether) to give 6',7'-dihydro-5'H-spiro[[1,3]dithiolane-2,4'-pyrazolo[1,5-a]pyridine] (4.2 g, yield: 67%) as a light yellow oil. ¹H NMR (400 MHz, CDCl₃) δ=7.43 (d, J=2.0 Hz, 1H), 6.40 (d, J=2.0 Hz, 1H), 4.18 (t, J=6.0 Hz, 2H), 3.58-3.53 (m, 2H), 3.48-3.34 (m, 2H), 2.42 (t, J=6.0 Hz, 2H), 2.28-2.22 (m, 2H). MS: m/z 212.9 (M+H⁺).

Step 2—Synthesis of 3-bromo-4,4-difluoro-4,5,6,7-tetrahydropyrazolo[1,5-a]pyridine

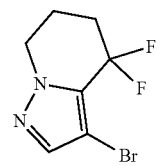 [SMILES: FC1(F)CCCn2ncc(Br)c21]

To a solution of 1,3-dibromo-5,5-dimethyl-2,4-imidazolidinedione (23.0 g, 80.4 mmol) in DCM (46 mL) was added HF·pyridine (38 mL, 421.8 mmol) drop-wise at −78° C., followed by 6',7'-dihydro-5'H-spiro[[1,3]dithiolane-2,4'-pyrazolo[1,5-a]pyridine] (4.2 g, 19.8 mmol). After 4 hours, the reaction was warmed to 0° C. and was allowed to stir for an additional 1 hour. The reaction was quenched with water (100 mL). The aqueous layer was extracted with DCM (2×100 mL). The combined organic layers were washed with water (100 mL), brine (100 mL), dried over Na₂SO₄, filtered and concentrated. The crude residue was purified by silica gel column chromatography (0-20% EtOAc in petroleum ether) to give 3-bromo-4,4-difluoro-4,5,6,7-tetrahydropyrazolo[1,5-a]pyridine (3.13 g, yield: 67%) as a yellow oil. ¹H NMR (400 MHz, CDCl₃) δ=7.48 (s, 1H), 4.20 (t, J=6.0 Hz, 2H), 2.43-2.34 (m, 2H), 2.27-2.21 (m, 2H). MS: m/z 236.9 (M+H⁺).

Step 3—Synthesis of 4,4-difluoro-N'-trityl-4,5,6,7-tetrahydropyrazolo[1,5-a]pyridine-3-sulfonimidamide

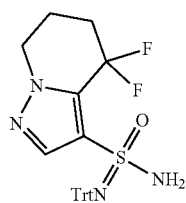

To a solution of 3-bromo-4,4-difluoro-4,5,6,7-tetrahydropyrazolo[1,5-a]pyridinein (400 mg, 1.69 mmol) in THF (8 mL) was added n-BuLi (2.5 M in hexane, 0.84 mL, 2.1 mmol) drop-wise at −78° C. under under a nitrogen atmosphere. After 1 hour, a solution of TrtNSO (618 mg, 2.02 mmol) in THF (8 mL) was added drop-wise. The reaction was allowed to stir at −78° C. for 20 minutes at which point it was placed in a 0° C. ice bath where it stirred for an additional 10 minutes. tert-Butyl hypochlorite (0.24 mL, 2.12 mmol) was added at 0° C. After 20 minutes, NH₃ gas was bubbled through the mixture for 10 minutes. The resulting solution was allowed to warm to room temperature and stirred for an additional 16 hours. The reaction was concentrated and the crude residue was purified by silica gel column chromatography (0-70% EtOAc in petroleum ether) to give 4,4-difluoro-N'-trityl-4,5,6,7-tetrahydropyrazolo[1,5-a]pyridine-3-sulfonimidamide (315 mg, yield: 39%) as a yellow solid. $^1$H NMR (400 MHz, DMSO-d$_6$): δ=7.43-7.39 (m, 6H), 7.18-7.15 (m, 6H), 7.14-7.08 (m, 3H), 6.33 (s, 2H), 4.16-4.09 (m, 2H), 2.40-2.32 (m, 2H), 2.10-2.04 (m, 2H). MS: m/z 501.1 (M+Na$^+$).

Step 4~5—Synthesis of 4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide

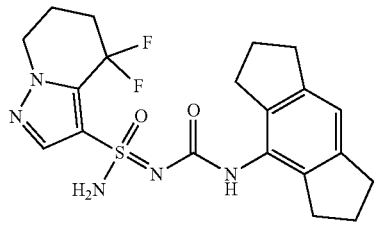 [SMILES: NS(=O)(=NC(=O)Nc1c2c(cc3c1CCC3)CCC2)c1cnn2c1C(F)(F)CCC2]

4,4-Difluoro-N'-((1,2,3,5,6,7-hexahydro-s-indacen-4-yl)carbamoyl)-4,5,6,7-tetrahydropyrazolo[1,5-a]pyridine-3-sulfonimidamide was prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Example 100 and Example 101), by replacing N'-trityl-6,7-dihydro-5H-pyrazolo[5,1-b][1,3]thiazine-3-sulfonimidamide with 4,4-difluoro-N'-trityl-4,5,6,7-tetrahydropyrazolo[1,5-a]pyridine-3-sulfonimidamide in Step 3.

Step 6—Synthesis of (S)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide and (R)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide (Example 133 and Example 134)

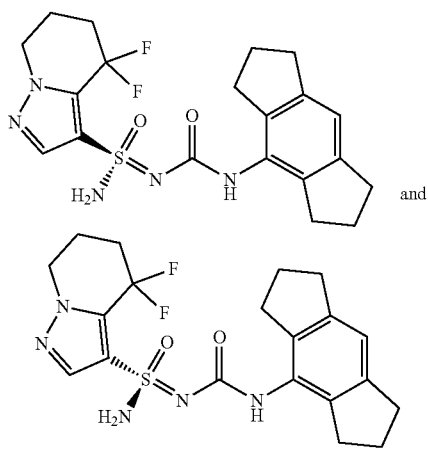

4,4-Difluoro-N'-((1,2,3,5,6,7-hexahydro-s-indacen-4-yl)carbamoyl)-4,5,6,7-tetrahydropyrazolo[1,5-a]pyridine-3-sulfonimidamide (78 mg, 0.18 mmol) was separated by chiral SFC (Chiralpak AS (250 mm*30 mm, 10 um), Supercritical CO$_2$/EtOH+0.1% NH$_4$OH=65/35; 70 mL/min) to give (S)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide (Method C, 3.31 min, peak 1, 11.1 mg, yield: 14%) and (R)-4,4-difluoro-N'-((1,2,3,5,6,7-hexahydro-s-indacen-4-yl)carbamoyl)-4,5,6,7-tetrahydropyrazolo[1,5-a]pyridine-3-sulfonimidamide (Method C, 3.55 min, peak 2, 14.5 mg, yield: 18%) both as white solids. Stereochemistry was arbitrarily assigned to each stereoisomer.

Peak 1: $^1$H NMR (400 MHz, DMSO-d$_6$): δ=8.21 (s, 1H), 7.85 (s, 1H), 7.41 (s, 2H), 6.85 (s, 1H), 4.26 (t, J=6.0 Hz, 2H), 2.76 (t, J=7.2 Hz, 4H), 2.67 (t, J=7.2 Hz, 4H), 2.48-2.40 (m, 2H), 2.17-2.10 (m, 2H), 1.95-1.88 (m, 4H). MS: m/z 436.1 (M+H$^+$).

Peak 2: $^1$H NMR (400 MHz, DMSO-d$_6$): δ=8.21 (s, 1H), 7.85 (s, 1H), 7.41 (s, 2H), 6.85 (s, 1H), 4.26 (t, J=6.0 Hz, 2H), 2.76 (t, J=7.2 Hz, 4H), 2.67 (t, J=6.8 Hz, 4H), 2.48-2.40 (m, 2H), 2.17-2.10 (m, 2H), 1.96-1.86 (m, 4H). MS: m/z 436.1 (M+H$^+$).

Example 135, Example 136, Example 137 and Example 138

(S)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

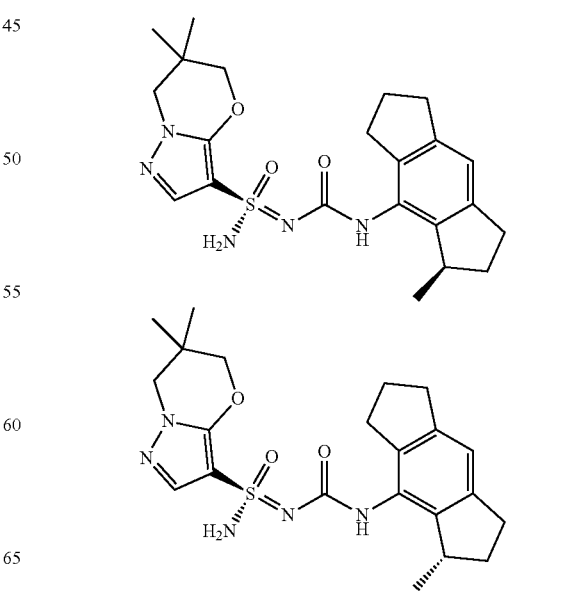

-continued

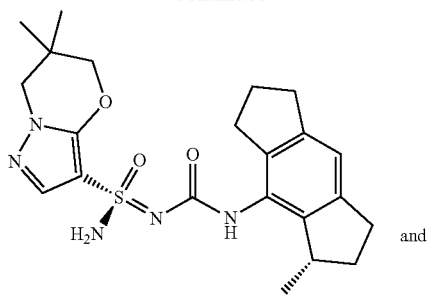

and

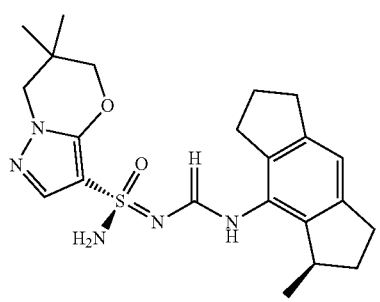

Step 1~2—Synthesis of 6,6-dimethyl-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide

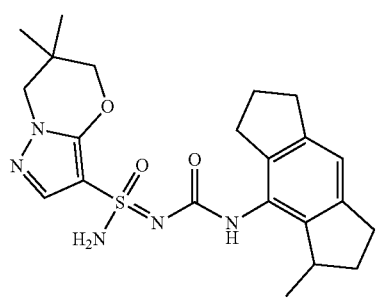 [SMILES: CC1CCc2cc3c(c(NC(=O)N=S(N)(=O)c4cnn5c4OCC(C)(C)C5)c21)CCC3]

6,6-Dimethyl-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of (R)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide and (S)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (Example 76 and Example 77), by replacing 3-isocyanato-2,4-diisopropyl-6-methoxy-pyridine with 8-isocyanato-1-methyl-1,2,3,5,6,7-hexahydro-s-indacene in Step 3.

Step 3—Synthesis of (S)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 135, Example 136, Example 137 and Example 138)

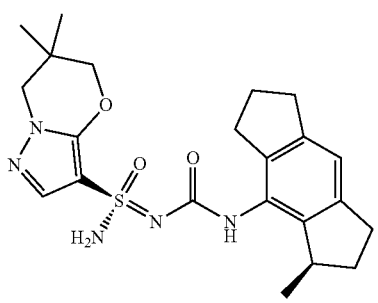

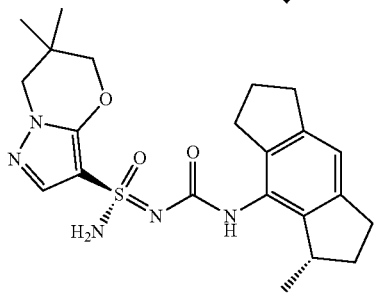

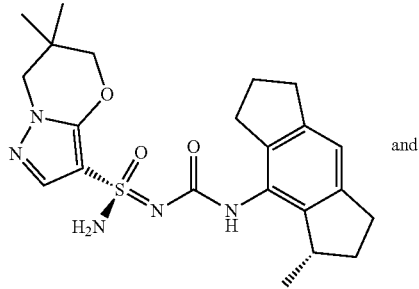

and

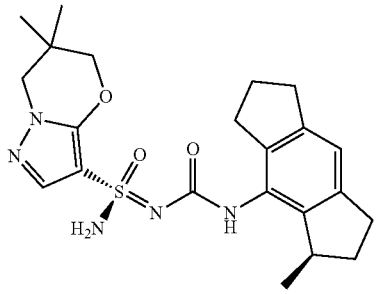

6,6-Dimethyl-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (95 mg, 0.21 mmol) was separated by chiral SFC (Chiralpak AD (250 mm*30 mm, 10 um), Supercritical CO₂/MeOH+0.1% NH₄OH=40/60; 70 mL/min) to give (S)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method O, 5.58 min, Peak 1, 17.8 mg, yield: 19%), (S)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method O, 6.28 min, Peak 2, 12.9 mg, yield: 13%), (R)-6,6-dimethyl-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method O, 7.67 min, Peak 3, 18.4 mg, yield: 19%) and (R)-6,6-dimethyl-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method O, 8.39 min, Peak 4, 12.7 mg, yield: 13%) all as white solids. Stereochemistry was arbitrarily assigned to each stereoisomer.

Peak 1: ¹H NMR (400 MHz, DMSO-d₆): δ=8.04 (s, 1H), 7.52 (s, 1H), 7.24 (s, 2H), 6.83 (s, 1H), 4.05 (s, 2H), 3.85 (s, 2H), 2.89-2.73 (m, 4H), 2.70-2.55 (m, 3H), 2.17-2.05 (m, 1H), 1.98-1.85 (m, 2H), 1.60-1.49 (m, 1H), 1.05-1.01 (m, 9H). MS: m/z 444.1 (M+H⁺).

Peak 2: ¹H NMR (400 MHz, DMSO-d₆): δ=8.06 (s, 1H), 7.52 (s, 1H), 7.26 (s, 2H), 6.84 (s, 1H), 4.06 (s, 2H), 3.86 (s, 2H), 2.89-2.73 (m, 4H), 2.70-2.55 (m, 3H), 2.17-2.05 (m, 1H), 1.98-1.85 (m, 2H), 1.60-1.49 (m, 1H), 1.06-1.01 (m, 9H). MS: m/z 444.1 (M+H⁺).

Peak 3: ¹H NMR (400 MHz, DMSO-d₆): δ=8.06 (s, 1H), 7.52 (s, 1H), 7.25 (s, 2H), 6.83 (s, 1H), 4.08 (s, 2H), 3.83 (s, 2H), 2.89-2.73 (m, 4H), 2.70-2.55 (m, 3H), 2.17-2.07 (m, 1H), 1.99-1.84 (m, 2H), 1.60-1.50 (m, 1H), 1.06-1.00 (m, 9H). MS: m/z 444.1 (M+H⁺).

Peak 4: ¹H NMR (400 MHz, DMSO-d₆): δ=8.07 (s, 1H), 7.52 (s, 1H), 7.25 (s, 2H), 6.84 (s, 1H), 4.05 (s, 2H), 3.86 (s, 2H), 3.28-3.25 (m, 1H), 2.87-2.72 (m, 4H), 2.70-2.51 (m, 2H), 2.15-2.07 (m, 1H), 1.99-1.85 (m, 2H), 1.61-1.53 (m, 1H), 1.06-1.01 (m, 9H). MS: m/z 444.1 (M+H⁺).

Example 139 and Example 140

(S)—N'-((1,2,3,5,6,7-hexahydro-s-indacen-4-yl)carbamoyl)-2,2-dimethyl-2,3-dihydropyrazolo[5,1-b]oxazole-7-sulfonimidamide and (R)—N'-((1,2,3,5,6,7-hexahydro-s-indacen-4-yl)carbamoyl)-2,2-dimethyl-2,3-dihydropyrazolo[5,1-b]oxazole-7-sulfonimidamide

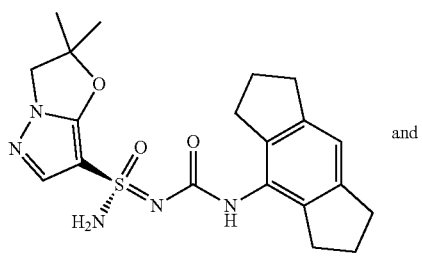

and

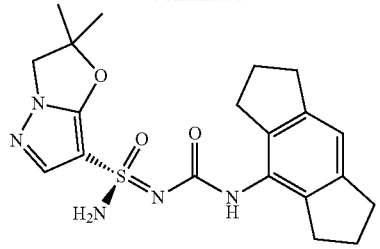

Step 1—Synthesis of tert-butyl 3-hydroxy-1H-pyrazole-1-carboxylate

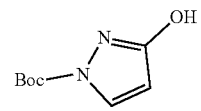

To a solution of 1H-pyrazol-3(2H)-one (20.0 g, 238 mmol) in DCM (300 mL) was added triethylamine (37 mL, 267 mmol) at 0° C. After 10 minutes, Boc₂O (57.11 g, 262 mmol) in DCM (100 mL) was added drop-wise. After addition, the reaction was warmed to room temperature and was allowed to stir for 16 hours. The reaction was concentrated under reduced pressure and the crude residue was dissolved in water (100 mL). The aqueous layer was extracted with EtOAc (200 mL×2). The combined organic layers were dried over Na₂SO₄, filtered and concentrated. The crude residue was purified by silica gel column chromatography (0-5% MeOH in DCM) to give tert-butyl 3-hydroxy-1H-pyrazole-1-carboxylate (2.8 g, yield: 6%) as a yellow solid. ¹H NMR (400 MHz, DMSO-d₆): δ=10.92 (s, 1H), 7.97 (d, J=3.2 Hz, 1H), 5.89 (d, J=2.8 Hz, 1H), 1.53 (s, 9H).

Step 2—Synthesis of tert-butyl 3-((1-ethoxy-2-methyl-1-oxopropan-2-yl)oxy)-1H-pyrazole-1-carboxylate

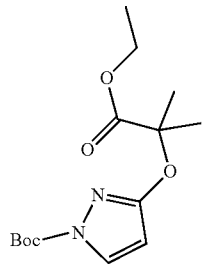 [SMILES: CCOC(=O)C(C)(C)Oc1ccn(C(=O)OC(C)(C)C)n1]

To a solution of tert-butyl 3-hydroxy-1H-pyrazole-1-carboxylate (2.8 g, 15.2 mmol) in MeCN (56 mL) was added K₂CO₃ (4.2 g, 30.4 mmol) at room temperature under a nitrogen atmosphere. The reaction was heated at 80° C. After 1 hour, ethyl 2-bromo-2-methylpropanoate (3.0 g, 15.2 mmol) was added and the mixture was allowed to stir at 80° C. for an additional 16 hours. After cooling to room temperature, the reaction mixture was filtered and concentrated. The crude residue was purified by silica gel column chromatography (20% EtOAc in petroleum ether) to give tert-butyl 3-((1-ethoxy-2-methyl-1-oxopropan-2-yl)oxy)-1H-pyrazole-1-carboxylate (3.1 g, yield: 68%) as a yellow oil. $^1$H NMR (400 MHz, CDCl$_3$): δ=7.84 (d, J=2.8 Hz, 1H), 5.87 (d, J=3.2 Hz, 1H), 4.22 (q, J=6.8 Hz, 2H), 1.70 (s, 6H), 1.59 (s, 9H), 1.23 (t, J=7.2 Hz, 3H).

Step 3—Synthesis of 2-((1H-pyrazol-5-yl)oxy)-2-methylpropan-1-ol

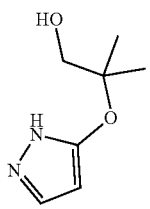

To a suspension of LiAlH$_4$ (1.2 g, 31.17 mmol) in THF (90 mL) was added a solution of tert-butyl 3-((1-ethoxy-2-methyl-1-oxopropan-2-yl)oxy)-1H-pyrazole-1-carboxylate (3.1 g, 10.39 mmol) in THF (20 mL) drop-wise at 0° C. under a nitrogen atmosphere. After addition, the reaction mixture was warmed to room temperature and stirred for an additional 30 minutes. The reaction was quenched by adding saturated aqueous Na$_2$SO$_4$. The resulting mixture was dried over Na$_2$SO$_4$. The solids were removed by filtration and the filtrate was concentrated to give 2-((1H-pyrazol-5-yl)oxy)-2-methylpropan-1-ol (1.5 g, yield: 92%), which was used in the next step without further purification. $^1$H NMR (400 MHz, CDCl$_3$): δ=9.45 (s, 1H), 7.39 (d, J=2.4 Hz, 1H), 5.80 (d, J=2.4 Hz, 1H), 4.85 (s, 1H), 3.63 (s, 2H), 1.37 (s, 6H).

Step 4—Synthesis of 2-((1H-pyrazol-5-yl)oxy)-2-methylpropyl methanesulfonate

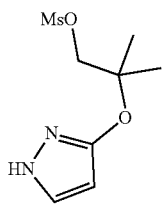

To a stirred solution of 2-((1H-pyrazol-5-yl)oxy)-2-methylpropan-1-ol (1.1 g, 7.04 mmol) and triethylamine (2.93 mL, 21.13 mmol) in DCM (33 mL) was added MsCl (0.5 mL, 7.04 mmol) at 0° C. under a nitrogen atmosphere. After 1 hour, water (10 mL) was added. The aqueous layer was extracted with DCM (50 mL×3). The combined organic layers were dried over Na$_2$SO$_4$, filtered and concentrated. The crude residue was purified by silica gel column chromatography (0-5% MeOH in DCM) to give 2-((1H-pyrazol-5-yl)oxy)-2-methylpropyl methanesulfonate (600 mg, yield: 14%) as a yellow oil. MS: m/z 234.9 (M+H$^+$).

Step 5—Synthesis of 2,2-dimethyl-2,3-dihydropyrazolo[5,1-b]oxazole

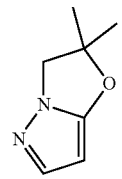

To a solution of 2-((1H-pyrazol-5-yl)oxy)-2-methylpropyl methanesulfonate (500 mg, 0.79 mmol) in DMF (10 mL) was added NaH (60% in mineral oil, 38 mg, 0.95 mmol) at 0° C. under a nitrogen atmosphere. After addition, the reaction was warmed to room temperature and stirred for an additional 12 hours. The reaction was cooled to 0° C. and saturated aqueous NH$_4$Cl (3 mL) was added. The reaction mixture was concentrated the crude residue was purified by silica gel column chromatography (0-20% EtOAc in petroleum ether) to give 2,2-dimethyl-2,3-dihydropyrazolo[5,1-b]oxazole (180 mg, yield: 50%) as a colorless oil. $^1$H NMR (400 MHz, CDCl$_3$): δ=7.36 (d, J=2.0 Hz, 1H), 5.30 (d, J=1.6 Hz, 1H), 4.03 (s, 2H), 1.63 (s, 6H).

Step 6—Synthesis of 7-bromo-2,2-dimethyl-2,3-dihydropyrazolo[5,1-b]oxazole

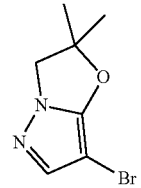

To a solution of 2,2-dimethyl-2,3-dihydropyrazolo[5,1-b]oxazole (150 mg, 1.09 mmol) in MeCN (5 mL) was added NBS (193 mg, 1.09 mmol) at 0° C. After addition, the reaction was warmed to room temperature. After 1 hour, the reaction mixture was concentrated and the crude residue was purified by silica gel column chromatography (0-30% EtOAc in petroleum ether) to give 7-bromo-2,2-dimethyl-2,3-dihydropyrazolo[5,1-b]oxazole (120 mg, yield: 51%) as a white solid. $^1$H NMR (400 MHz, CDCl$_3$): δ=7.32 (s, 1H), 4.07 (s, 2H), 1.67 (s, 6H).

Step 7—Synthesis of 2,2-dimethyl-N'-trityl-2,3-dihydropyrazolo[5,1-b]oxazole-7-sulfonimidamide

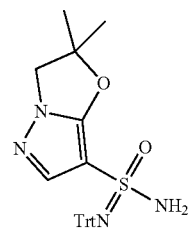

To a solution of 7-bromo-2,2-dimethyl-2,3-dihydropyrazolo[5,1-b]oxazole (120 mg, 0.55 mmol) in THF (5 mL) was added n-BuLi (2.5 M in hexane, 0.3 mL, 0.61 mmol) drop-wise at −78° C. under a nitrogen atmosphere. After 30 minutes, a solution of TrtNSO (186 mg, 0.61 mmol) in THF (1 mL) was added drop-wise. The reaction was allowed to stir at −78° C. for 30 minutes at which point it was placed in a 0° C. ice bath where it stirred for an additional 10 minutes. tert-Butyl hypochlorite (0.1 mL, 0.6 mmol) was added at 0° C. After 30 minutes, NH$_3$ gas was bubbled through the mixture for 10 minutes. The resulting solution was allowed to warm to room temperature and stirred for an additional 16 hours. The mixture was concentrated and the crude residue was purified by silica gel column chromatography (0-80% EtOAc in petroleum ether) to give 2,2-dimethyl-N'-trityl-2,3-dihydropyrazolo[5,1-b]oxazole-7-sulfonimidamide (120 mg, yield: 50%) as a white solid. MS: m/z 481.1 (M+Na$^+$).

Step 8~9—Synthesis of N'-((1,2,3,5,6,7-hexahydro-s-indacen-4-yl)carbamoyl)-2,2-dimethyl-2,3-dihydropyrazolo[5,1-b]oxazole-7-sulfonimidamide

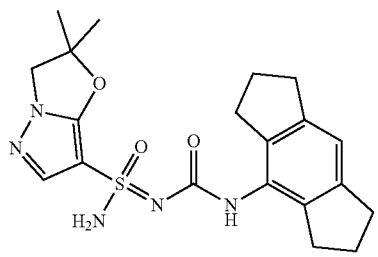 [SMILES: CC1(C)Cn2ncc(S(N)(=O)=NC(=O)Nc3c4c(cc5c3CCC5)CCC4)c2O1]

N'-((1,2,3,5,6,7-hexahydro-s-indacen-4-yl)carbamoyl)-2,2-dimethyl-2,3-dihydropyrazolo[5,1-b]oxazole-7-sulfonimidamide was prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Example 100 and Example 101), by replacing N'-trityl-6,7-dihydro-5H-pyrazolo[5,1-b][1,3]thiazine-3-sulfonimidamide with 2,2-dimethyl-N'-trityl-2,3-dihydropyrazolo[5,1-b]oxazole-7-sulfonimidamide in Step 3.

Step 10—Synthesis of (S)—N'-((1,2,3,5,6,7-hexahydro-s-indacen-4-yl)carbamoyl)-2,2-dimethyl-2,3-dihydropyrazolo[5,1-b]oxazole-7-sulfonimidamide and (R)—N'-((1,2,3,5,6,7-hexahydro-s-indacen-4-yl)carbamoyl)-2,2-dimethyl-2,3-dihydropyrazolo[5,1-b]oxazole-7-sulfonimidamide (Example 139 and example 140)

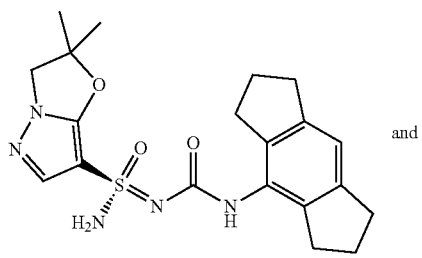

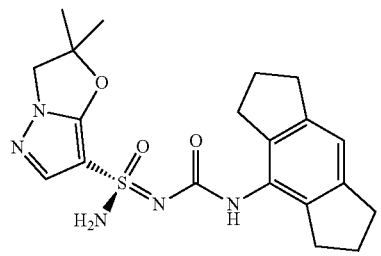

N'-((1,2,3,5,6,7-hexahydro-s-indacen-4-yl)carbamoyl)-2,2-dimethyl-2,3-dihydropyrazolo[5,1-b]oxazole-7-sulfonimidamide (60 mg, 0.14 mmol) was separated by chiral SFC (Phenomenex Cellulose 2 (250 mm*30 mm, 10 um), Supercritical CO$_2$/EtOH+0.1% NH$_4$OH=60/40; 70 mL/min) to give (S)—N'-((1,2,3,5,6,7-hexahydro-s-indacen-4-yl)carbamoyl)-2,2-dimethyl-2,3-dihydropyrazolo[5,1-b]oxazole-7-sulfonimidamide (Method P, 4.31 min, peak 1, 21.5 mg, yield: 36%) and (R)—N'-((1,2,3,5,6,7-hexahydro-s-indacen-4-yl)carbamoyl)-2,2-dimethyl-2,3-dihydropyrazolo[5,1-b]oxazole-7-sulfonimidamide (Method P, 4.91 min, peak 2, 17.5 mg, yield: 29%) both as white solids. Stereochemistry was arbitrarily assigned to each stereoisomer.

Peak 1: $^1$H NMR (400 MHz, DMSO-d$_6$): δ=8.17 (s, 1H), 7.54 (s, 1H), 7.31 (s, 2H), 6.85 (s, 1H), 4.15 (s, 2H), 2.77 (t, J=6.8 Hz, 4H), 2.68 (t, J=6.8 Hz, 4H), 1.96-1.86 (m, 4H), 1.60 (d, J=5.6 Hz, 6H). MS: m/z 416.1 (M+H$^+$).

Peak 2: $^1$H NMR (400 MHz, DMSO-d$_6$): δ=8.17 (s, 1H), 7.54 (s, 1H), 7.29 (s, 2H), 6.85 (s, 1H), 4.15 (s, 2H), 2.77 (t, J=7.2 Hz, 4H), 2.68 (t, J=6.8 Hz, 4H), 1.96-1.88 (m, 4H), 1.60 (d, J=5.6 Hz, 6H). MS: m/z 416.1 (M+H$^+$).

Example 141 and Example 142

(R)—N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide and (S)—N'-((2,4,5,6-tetrahydro-1H-cyclobuta[f]inden-3-yl)carbamoyl)-6,7-dihydro-5H-pyrazolo[5,1-b][13]oxazine-3-sulfonimidamide

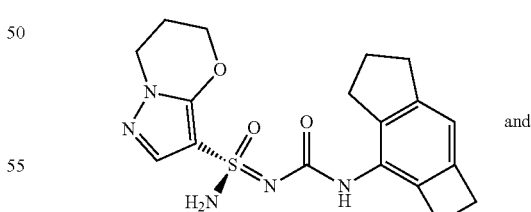

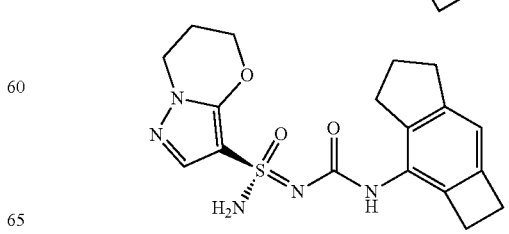

411

Step 1—Synthesis of 3-isocyanato-2,4,5,6-tetrahydro-1H-cyclobuta[f]indene

To a solution of 2,4,5,6-tetrahydro-1H-cyclobuta[f]inden-3-amine (synthesis reported in WO2019023147, 20 mg, 0.13 mmol) and triethylamine (0.03 mL, 0.19 mmol) in THF (0.5 mL) was added triphosgene (19 mg, 0.06 mmol) at room temperature. After 1 hour, the reaction mixture was filtered over a short pad of Celite. The Celite pad was washed with THF (2 mL). The filtrate was concentrated to give 3-isocyanato-2,4,5,6-tetrahydro-1H-cyclobuta[/]indene (20 mg, yield: 86%) as a light yellow oil.

Step 2~3—Synthesis of N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide

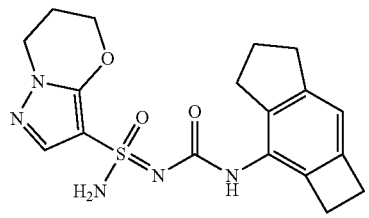 [SMILES: NS(=O)(=NC(=O)Nc1c2c(cc3c1CC3)CCC2)c1cnn2c1OCCC2]

N'-((2,4,5,6-tetrahydro-1H-cyclobuta[/]inden-3-yl)carbamoyl)-6,7-dihydro-5H-pyrazolo[5,1-b][1,3]oxazine-3-sulfonimidamide was prepared using the general procedure described for the preparation of (S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide (Example 102 and Example 103), by replacing 3-isocyanato-2,4-diisopropyl-6-methoxypyridine with 3-isocyanato-2,4,5,6-tetrahydro-1H-cyclobuta[/]indene in Step 1. MS: m/z 388.0 (M+H$^+$).

Step 4—Synthesis of (R)—N'-((2,4,5,6-tetrahydro-1H-cyclobuta[ ]inden-3-yl)carbamoyl)-6,7-dihydro-5H-pyrazolo[5,1-b][1,3]oxazine-3-sulfonimidamide and (S)—N'-((2,4,5,6-tetrahydro-1H-cyclobuta[f]inden-3-yl)carbamoyl)-6,7-dihydro-5H-pyrazolo[5,1-b][1,3]oxazine-3-sulfonimidamide (Example 141 and Example 142)

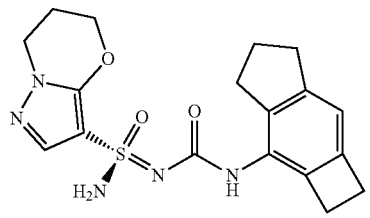

and

412

-continued

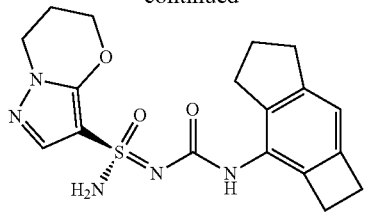

N'-((2,4,5,6-tetrahydro-1H-cyclobuta[/]inden-3-yl)carbamoyl)-6,7-dihydro-5H-pyrazolo[5,1-b][1,3]oxazine-3-sulfonimidamide was purified by chiral SFC (Chiralpak AS (250 mm*30 mm, 10 um); Supercritical CO$_2$/EtOH+0.1% NH$_4$OH=65/35; 70 mL/min) to give (R)—N'-((2,4,5,6-tetrahydro-1H-cyclobuta[/]inden-3-yl)carbamoyl)-6,7-dihydro-5H-pyrazolo[5,1-b][1,3]oxazine-3-sulfonimidamide (Method C, 3.65 min, peak 1, 1 mg, yield: 9%) and (S)—N'-((2,4,5,6-tetrahydro-1H-cyclobuta[/]inden-3-yl)carbamoyl)-6,7-dihydro-5H-pyrazolo[5,1-b][1,3]oxazine-3-sulfonimidamide (Method C, 3.87 min, peak 2, 1.1 mg, yield: 10%) both as white solids. Stereochemistry was arbitrarily assigned to each stereoisomer.

Peak 1: $^1$H NMR (400 MHz, CDCl$_3$): δ=7.68 (s, 1H), 6.72 (s, 2H), 4.48-4.44 (m, 2H), 4.18-4.14 (m, 2H), 3.25-3.20 (m, 2H), 2.98-2.95 (m, 2H), 2.91-2.87 (m, 2H), 2.75-2.70 (m, 2H), 2.33-2.28 (m, 2H), 2.06-2.00 (m, 2H). MS: m/z 388.0 (M+H$^+$).

Peak 2: $^1$H NMR (400 MHz, CDCl$_3$): δ=7.68 (s, 1H), 6.72 (s, 1H), 6.69 (s, 1H), 4.48-4.44 (m, 2H), 4.20-4.15 (m, 2H), 3.25-3.20 (m, 2H), 3.00-2.95 (m, 2H), 2.90 (t, J=7.2 Hz, 2H), 2.75 (t, J=7.2 Hz, 2H), 2.35-2.29 (m, 2H), 2.08-2.02 (m, 2H). MS: m/z 388.0 (M+H$^+$).

Example 143, Example 144, Example 145, and Example 146

(S)—N'—(((R)-3-methyl-1,2,3,5,6,7-hexahydro-s-indacen-4-yl)carbamoyl)-2,3-dihydropyrazolo[5,1-b]oxazole-7-sulfonimidamide, (S)—N'—(((S)-3-methyl-1,2,3,5,6,7-hexahydro-s-indacen-4-yl)carbamoyl)-2,3-dihydropyrazolo[5,1-b]oxazole-7-sulfonimidamide, (R)—N'—(((R)-3-methyl-1,2,3,5,6,7-hexahydro-s-indacen-4-yl)carbamoyl)-2,3-dihydropyrazolo[5,1-b]oxazole-7-sulfonimidamide and (R)—N'—(((S)-3-methyl-1,2,3,5,6,7-hexahydro-s-indacen-4-yl)carbamoyl)-2,3-dihydropyrazolo[5,1-b]oxazole-7-sulfonimidamide

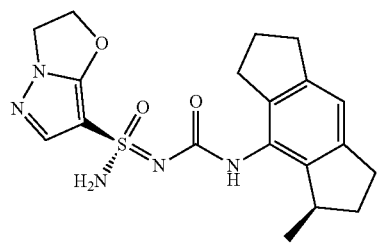

-continued

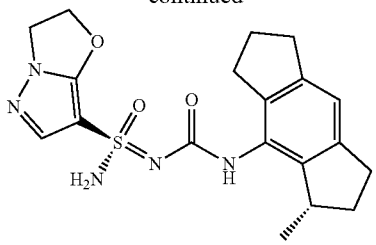

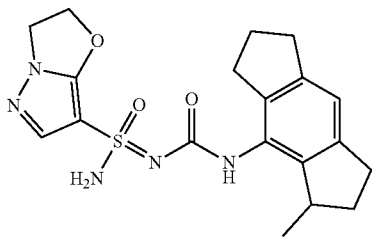 [SMILES: CC1CCc2cc3c(c(NC(=O)N=S(N)(=O)c4cnn5c4OCC5)c21)CCC3]

Step 1~2—Synthesis of N'-((3-methyl-1,2,3,5,6,7-hexahydro-s-indacen-4-yl)carbamoyl)-2,3-dihydropyrazolo[5,1-b]oxazole-7-sulfonimidamide N'-((3-methyl-1,2,3,5,6,7-hexahydro-s-indacen-4-yl)carbamoyl)-2,3-dihydropyrazolo[5,1-b]oxazole-7-sulfonimidamide was prepared using the general procedure described for the preparation of (R)—N'-((1,2,3,5,6,7-hexahydro-s-indacen-4-yl)carbamoyl)-2,3-dihydropyrazolo[5,1-b]oxazole-7-sulfonimidamide and (S)—N'-((1,2,3,5,6,7-hexahydro-s-indacen-4-yl)carbamoyl)-2,3-dihydropyrazolo[5,1-b]oxazole-7-sulfonimidamide (Example 124 and Example 125), by replacing 4-isocyanato-1,2,3,5,6,7-hexahydro-s-indacene with 8-isocyanato-1-methyl-1,2,3,5,6,7-hexahydro-s-indacene in Step 2.

Step 3—Synthesis of (S)—N'—(((R)-3-methyl-1,2,3,5,6,7-hexahydro-s-indacen-4-yl)carbamoyl)-2,3-dihydropyrazolo[5,1-b]oxazole-7-sulfonimidamide, (S)—N'—(((S)-3-methyl-1,2,3,5,6,7-hexahydro-s-indacen-4-yl)carbamoyl)-2,3-dihydropyrazolo[5,1-b]oxazole-7-sulfonimidamide, (R)—N'—(((R)-3-methyl-1,2,3,5,6,7-hexahydro-s-indacen-4-yl)carbamoyl)-2,3-dihydropyrazolo[5,1-b]oxazole-7-sulfonimidamide and (R)—N'—(((S)-3-methyl-1,2,3,5,6,7-hexahydro-s-indacen-4-yl)carbamoyl)-2,3-dihydropyrazolo[5,1-b]oxazole-7-sulfonimidamide (Example 143, Example 144, Example 145 and Example 146)

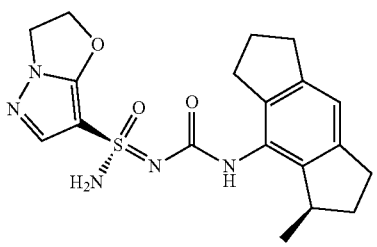

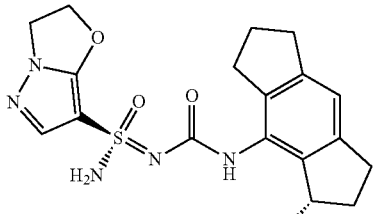

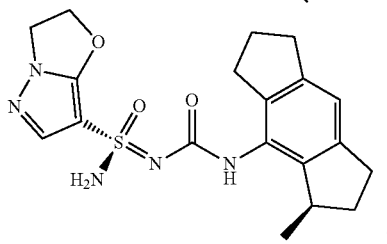

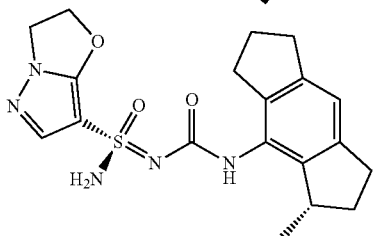

N'-((3-methyl-1,2,3,5,6,7-hexahydro-s-indacen-4-yl)carbamoyl)-2,3-dihydropyrazolo[5,1-b]oxazole-7-sulfonimidamide (200 mg, 0.50 mmol) was separated by chiral SFC (Chiralcel AD (250 mm*30 mm, 5 um), Supercritical $CO_2$/MeOH+0.1% $NH_4OH$=65/35; 50 mL/min) to give (S)—N'—(((R)-3-methyl-1,2,3,5,6,7-hexahydro-s-indacen-4-yl)carbamoyl)-2,3-dihydropyrazolo[5,1-b]oxazole-7-sulfonimidamide (Method Q, 5.25 min, peak 1, 4 mg, yield: 2%), (S)—N'—(((S)-3-methyl-1,2,3,5,6,7-hexahydro-s-indacen-4-yl)carbamoyl)-2,3-dihydropyrazolo[5,1-b]oxazole-7-sulfonimidamide (Method Q, 5.38 min, peak 2, 5 mg, yield: 2.5%), ((R)—N'—(((R)-3-methyl-1,2,3,5,6,7-hexahydro-s-indacen-4-yl)carbamoyl)-2,3-dihydropyrazolo[5,1- b]oxazole-7-sulfonimidamide (Method Q, 5.53 min, peak 3, 3 mg, yield: 1.5%), (R)—N'—(((S)-3-methyl-1,2,3,5,6,7-hexahydro-s-indacen-4-yl)carbamoyl)-2,3-dihydropyrazolo[5,1-b]oxazole-7-sulfonimidamide (Method Q, 5.67 min, peak 4, 5 mg, yield: 2.5%) all as white solids. Stereochemistry was arbitrarily assigned to each stereoisomer.

Peak 1: $^1$H NMR (400 MHz, DMSO-d$_6$): δ=8.12 (s, 1H), 7.52 (s, 1H), 7.32 (s, 2H), 6.84 (s, 1H), 5.22-5.12 (m, 2H), 4.33 (t, J=8.0 Hz, 2H), 2.89-2.72 (m, 5H), 2.70-2.55 (m, 2H), 2.16-2.06 (m, 1H), 1.98-1.88 (m, 2H), 1.62-1.54 (m, 1H), 1.04 (d, J=6.8 Hz, 3H). MS: m/z 402.2 (M+H$^+$).

Peak 2: $^1$H NMR (400 MHz, DMSO-d$_6$): δ=8.10 (s, 1H), 7.52 (s, 1H), 7.32 (s, 2H), 6.84 (s, 1H), 5.21-5.15 (m, 2H), 4.32 (t, J=8.0 Hz, 2H), 2.86-2.72 (m, 5H), 2.70-2.55 (m, 2H), 2.14-2.05 (m, 1H), 1.98-1.89 (m, 2H), 1.62-1.55 (m, 1H), 1.03 (d, J=6.8 Hz, 3H) MS: m/z 402.2 (M+H$^+$).

Peak 3: $^1$H NMR (400 MHz, DMSO-d$_6$): δ=8.11 (s, 1H), 7.52 (s, 1H), 7.32 (s, 2H), 6.84 (s, 1H), 5.21-5.15 (m, 2H), 4.32 (t, J=8.4 Hz, 2H), 2.87-2.74 (m, 5H), 2.70-2.60 (m, 2H), 2.14-2.05 (m, 1H), 1.98-1.86 (m, 2H), 1.62-1.53 (m, 1H), 1.03 (d, J=6.4 Hz, 3H). MS: m/z 402.1 (M+H$^+$).

Peak 4: $^1$H NMR (400 MHz, DMSO-d$_6$): δ=8.12 (s, 1H), 7.52 (s, 1H), 7.32 (s, 2H), 6.84 (s, 1H), 5.23-5.16 (m, 2H), 4.33 (t, J=8.4 Hz, 2H), 2.89-2.73 (m, 5H), 2.70-2.55 (m, 2H), 2.14-2.06 (m, 1H), 1.98-1.88 (m, 2H), 1.62-1.54 (m, 1H), 1.04 (d, J=6.8 Hz, 3H). MS: m/z 402.2 (M+H$^+$).

Example 147, Example 148, Example 149, and Example 150

(S,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide

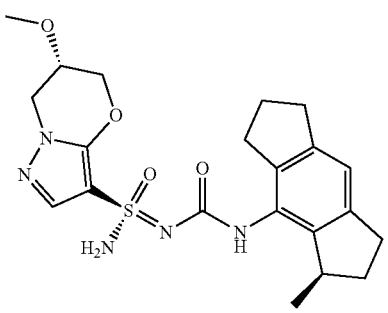 [SMILES: CO[C@@H]1COc2c(S(N)(=O)=NC(=O)Nc3c4c(cc5c3C(C)CC5)CCC4)cnn2C1]

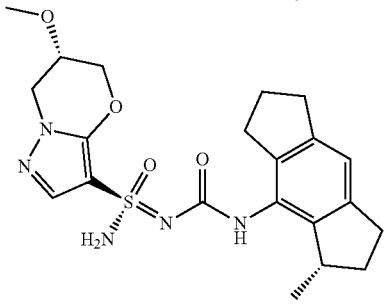

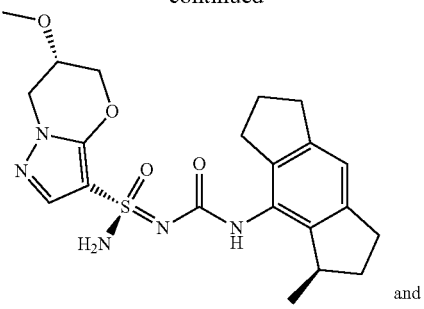

and

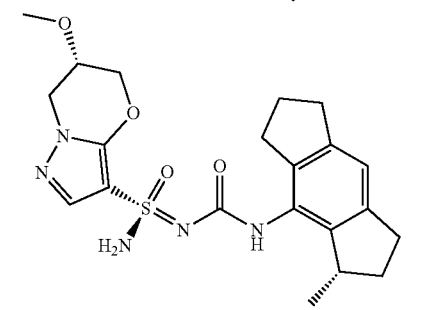

Step 1~2—Synthesis of (6S)-6-methoxy-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide

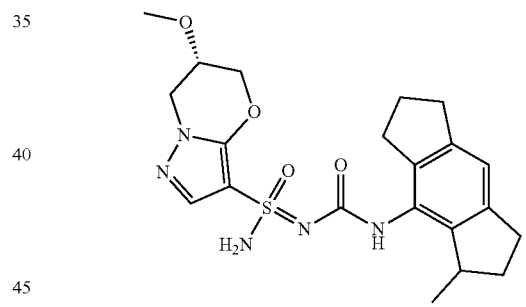

(6S)-6-methoxy-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide was prepared using the general procedure described for the preparation of (S)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R)—N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R)—N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 126, Example 127, Example 128 and Example 129), by replacing N'-trityl-6,7-dihydro-5H-pyrazolo[5,1-b][1,3]oxazine-3-sulfonimidamide with (6S)-6-methoxy-N'-trityl-6,7-dihydro-5H-pyrazolo[5,1-b][1,3]oxazine-3-sulfonimidamide in Step 4.

Step 3—Synthesis of (S,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (S,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide, (R,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide and (R,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Example 147, Example 148, Example 149 and Example 150)

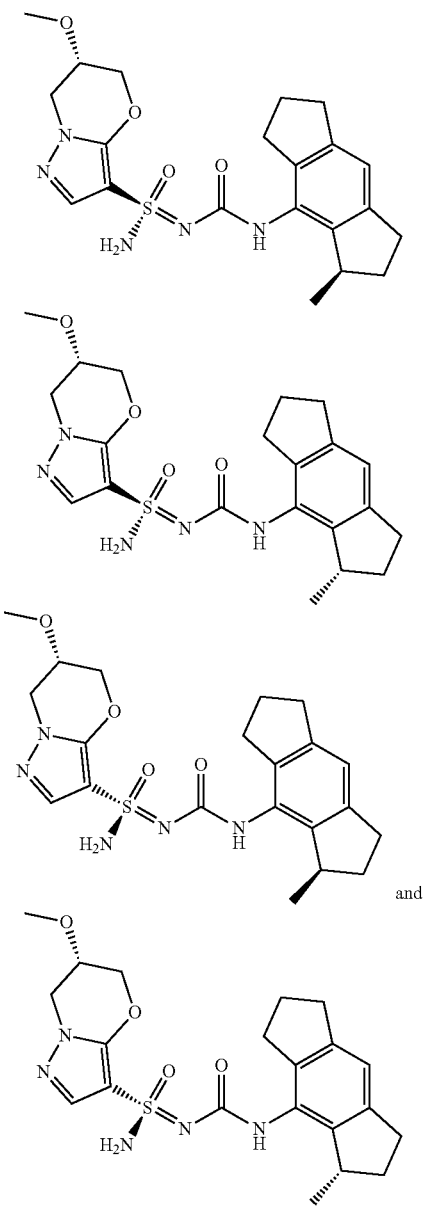

(6S)-6-methoxy-N'-((3-methyl-1,2,3,5,6,7-hexahydro-s-indacen-4-yl)carbamoyl)-6,7-dihydro-5H-pyrazolo[5,1-b][1,3]oxazine-3-sulfonimidamide (80 mg, 0.18 mmol) was separated by chiral SFC (Chiralpak AD (250 mm*30 mm, 10 um), Supercritical $CO_2$/EtOH+0.1% $NH_4OH$=55/45; 70 mL/min) to give (S,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 3.06 min, peak 1, 13.7 mg, yield: 17%), (S,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 4.19 min, peak 2, 6.5 mg, yield: 8%), (R,6S)-6-methoxy-N'—(((R)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 4.90 min, peak 3, 5.5 mg, yield: 7%) and (R,6S)-6-methoxy-N'—(((S)-3-methyl-1,2,3,5,6,7-hexahydro-s-indacen-4-yl)carbamoyl)-6,7-dihydro-5H-pyrazolo[5,1-b][1,3]oxazine-3-sulfonimidamide (Method I, 6.08 min, peak 4, 14 mg, yield: 18%) all as a white solids. Stereochemistry was arbitrarily assigned to each stereoisomer.

Peak 1: $^1$H NMR (400 MHz, DMSO-$d_6$): δ=8.11 (s, 1H), 7.52 (s, 1H), 7.29 (s, 2H), 6.84 (s, 1H), 4.60-4.56 (m, 1H), 4.30-4.15 (m, 3H), 4.04-4.01 (m, 1H), 3.28-3.24 (s, 3H), 2.86-2.75 (m, 4H), 2.71-2.66 (m, 1H), 2.64-2.55 (m, 2H), 2.18-2.06 (m, 1H), 1.96-1.87 (m, 2H), 1.59-1.54 (m, 1H), 1.03 (d, J=6.8 Hz, 3H). MS: m/z 446.1 (M+H$^+$).

Peak 2: $^1$H NMR (400 MHz, DMSO-$d_6$): δ=8.12 (s, 1H), 7.51 (s, 1H), 7.29 (s, 2H), 6.84 (s, 1H), 4.60-4.56 (m, 1H), 4.31-4.16 (m, 3H), 4.04-4.01 (m, 1H), 3.28-3.24 (m, 3H), 2.90-2.74 (m, 4H), 2.71-2.65 (m, 1H), 2.64-2.53 (m, 2H), 2.15-2.06 (m, 1H), 1.99-1.85 (m, 2H), 1.59-1.54 (m, 1H), 1.04 (d, J=6.8 Hz, 3H). MS: m/z 446.2 (M+H$^+$).

Peak 3: $^1$H NMR (400 MHz, DMSO-$d_6$): δ=8.12 (s, 1H), 7.50 (s, 1H), 7.27 (s, 2H), 6.84 (s, 1H), 4.60-4.56 (m, 1H), 4.31-4.15 (m, 3H), 4.04-4.01 (m, 1H), 3.28-3.24 (m, 3H), 2.89-2.74 (m, 4H), 2.71-2.64 (m, 1H), 2.61-2.52 (m, 2H), 2.16-2.07 (m, 1H), 2.00-1.84 (m, 2H), 1.61-1.53 (m, 1H), 1.05 (d, J=6.8 Hz, 3H). MS: m/z 446.2 (M+H$^+$).

Peak 4: $^1$H NMR (400 MHz, DMSO-$d_6$): δ=8.11 (s, 1H), 7.50 (s, 1H), 7.24 (s, 2H), 6.84 (s, 1H), 4.60-4.56 (m, 1H), 4.26-4.16 (m, 3H), 4.04-4.01 (m, 1H), 3.32-3.31 (m, 3H), 2.86-2.75 (m, 4H), 2.73-2.67 (m, 1H), 2.63-2.55 (m, 2H), 2.18-2.06 (m, 1H), 1.98-1.87 (m, 2H), 1.60-1.54 (m, 1H), 1.05 (d, J=6.8 Hz, 3H). MS: m/z 446.2 (M+H$^+$).

Example 151 and Example 152

(S,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

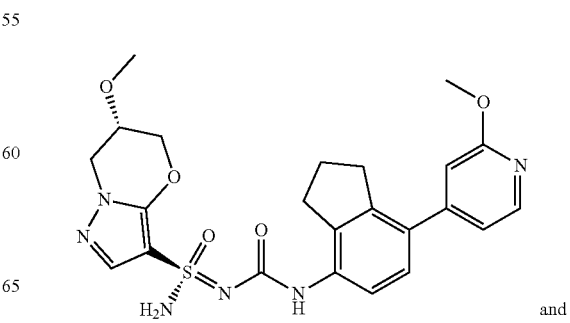

and

-continued

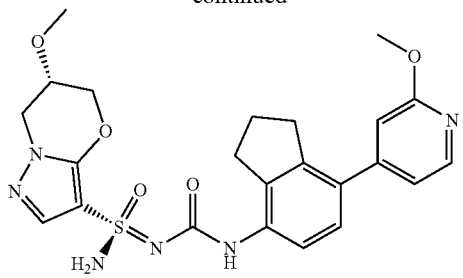

Step 1—Synthesis of N-(2,3-dihydro-1H-inden-4-yl)pivalamide

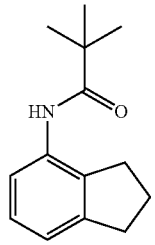 [SMILES: CC(C)(C)C(=O)Nc1cccc2c1CCC2]

To a solution of 2,3-dihydro-1H-inden-4-amine (3 g 22.5 mmol) and triethylamine (4.7 mL, 33.8 mmol) in DCM (30 mL) was added pivaloyl chloride (3.1 mL, 24.8 mmol) drop-wise at room temperature. After 1 hour, water (50 mL) was added. The aqueous layer was extracted with DCM (50 mL×3). The combined organic layers was dried over $Na_2SO_4$, filtered and concentrated to give N-(2,3-dihydro-1H-inden-4-yl)pivalamide (4.8 g, yield: 98%) as a white solid, which was used in the next step without further purification. $^1$H NMR (400 MHz, CDCl$_3$): δ 7.82 (d, J=8.0 Hz, 1H), 7.23 (s, 1H), 7.16 (t, J=8.0 Hz, 1H), 7.02 (d, J=7.6 Hz, 1H), 2.96 (t, J=7.2 Hz, 2H), 2.81 (t, J=7.6 Hz, 2H), 2.26-2.05 (m, 2H), 1.33 (s, 9H). MS: m/z 218.2 (M+H$^+$).

Step 2—Synthesis of N-(7-bromo-2,3-dihydro-1H-inden-4-yl)pivalamide

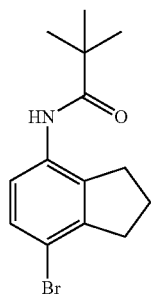 [SMILES: CC(C)(C)C(=O)Nc1ccc(Br)c2c1CCC2]

To a solution of N-(2,3-dihydro-1H-inden-4-yl)pivalamide (4.8 g, 22.1 mmol) in MeCN (40 mL) was added NBS (4.7 g, 26.5 mmol) at room temperature. After 15 hours, the reaction was concentrated under reduced pressure and the crude residue was dissolved in DCM (50 mL). The organic layer was washed with saturated aqueous $Na_2CO_3$ (50 mL×3), dried over $Na_2SO_4$, filtered and concentrated to give N-(7-bromo-2,3-dihydro-1H-inden-4-yl)pivalamide (6.5 g, yield: 99%) as a white solid, which was used in the next step without further purification. MS: m/z 296.1 (M+H$^+$).

Step 3—Synthesis of 7-bromo-2,3-dihydro-1H-inden-4-amine

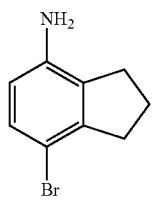 [SMILES: Nc1ccc(Br)c2c1CCC2]

N-(7-bromo-2,3-dihydro-1H-inden-4-yl)pivalamide (6.5 g, 21.9 mmol) was dissolved in concentrated HCl (100 mL) and was heated at 100° C. for 36 hours. After cooling to room temperature, water (50 mL) was added and the mixture was filtered. The solids were washed with EtOAc (20 mL×3) to give 7-bromo-2,3-dihydro-1H-inden-4-amine (3.44 g, yield: 74%) as a brown solid, which was used in the next step without further purification. $^1$H NMR (400 MHz, DMSO-d$_6$): δ 7.41 (d, J=8.4 Hz, 1H), 7.11 (d, J=8.0 Hz, 1H), 3.06 (t, J=7.6 Hz, 2H), 2.90 (t, J=7.2 Hz, 2H), 2.13-1.99 (m, 2H). MS: m/z 212.0 (M+H$^+$).

Step 4—Synthesis of 7-(2-methoxypyridin-4-yl)-2,3-dihydro-1H-inden-4-amine

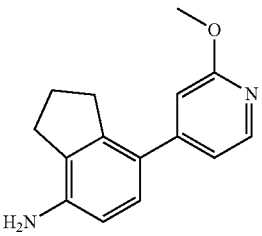 [SMILES: COc1cc(-c2ccc(N)c3c2CCC3)ccn1]

To a solution of 7-bromo-2,3-dihydro-1H-inden-4-amine (2.7 g, 12.7 mmol) in H$_2$O (5 mL) and 1,4-dioxane (40 mL) was added (2-methoxypyridin-4-yl)boronic acid (2.3 g, 15.3 mmol), K$_2$CO$_3$ (5.3 g, 38.2 mmol) and Pd(dppf)Cl$_2$ (0.9 g, 1.3 mmol) under a nitrogen atmosphere. The mixture was stirred at 80° C. for 2 hours. After cooling to room temperature, the reaction was diluted with H$_2$O (50 mL). The aqueous layer was extracted with EtOAc (50 mL×3). The combined organic layers were washed with brine (50 mL×2), dried over Na$_2$SO$_4$, filtered and concentrated. The crude residue was purified by silica gel column (0-30% EtOAc in petroleum ether) to give 7-(2-methoxypyridin-4-yl)-2,3-dihydro-1H-inden-4-amine as a yellow solid. $^1$H NMR (400 MHz, CDCl$_3$): 8.15 (d, J=5.2 Hz, 1H), 7.11 (d, J=8.4 Hz, 1H), 6.95 (d, J=2.0, 5.2 Hz, 1H), 6.78 (s, 1H), 6.62 (d, J=8.0 Hz, 1H), 3.97 (s, 3H), 3.74 (s, 2H), 3.03 (t, J=7.6 Hz, 2H), 2.78 (t, J=7.2 Hz, 2H), 2.17-2.04 (m, 2H). MS: m/z 241.0 (M+H$^+$).

Step 5—Synthesis of 4-(7-isocyanato-2,3-dihydro-1H-inden-4-yl)-2-methoxypyridine

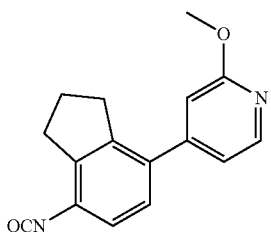

To a solution of 7-(2-methoxypyridin-4-yl)-2,3-dihydro-1H-inden-4-amine (150 mg, 0.6 mmol) and triethylamine (0.1 mL, 0.7 mmol) in THF (5 mL) was added triphosgene (67 mg, 0.2 mmol) at room temperature. After 1 hour, the mixture was filtered through a plug of silica gel to remove the triethylamine hydrochloride. The filtrate was concentrated to give 4-(7-isocyanato-2,3-dihydro-1H-inden-4-yl)-2-methoxypyridine (135 mg, 81%) as a yellow solid, which was used in the next step without further purification.

Step 6~7—Synthesis of (6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide

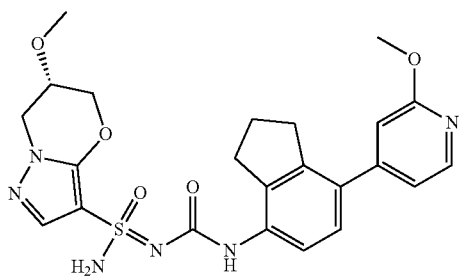 [SMILES: COc1cc(-c2ccc(NC(=O)N=S(N)(=O)c3cnn4c3OC[C@@H](OC)C4)c3c2CCC3)ccn1]

(6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide was prepared using the general procedure described for the preparation of (S)—N'-((1,2,3,5,6,7-hexahydro-s-indacen-4-yl)carbamoyl)-6,7-dihydro-5H-pyrazolo[5,1-b][1,3]thiazine-3-sulfonimidamide and (R)—N'-((1,2,3,5,6,7-hexahydro-s-indacen-4-yl)carbamoyl)-6,7-dihydro-5H-pyrazolo[5,1-b][1,3]thiazine-3-sulfonimidamide (Example 100 and Example 101), by replacing N'-trityl-6,7-dihydro-5H-pyrazolo[5,1-b][1,3]thiazine-3-sulfonimidamide and 4-isocyanato-1,2,3,5,6,7-hexahydro-s-indacene with (6S)-6-methoxy-N'-trityl-6,7-dihydro-5H-pyrazolo[5,1-b][1,3]oxazine-3-sulfonimidamide and 4-(7-isocyanato-2,3-dihydro-1H-inden-4-yl)-2-methoxypyridine in Step 3.

Step 8—Synthesis of (S,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide and (R,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Example 151 and Example 152)

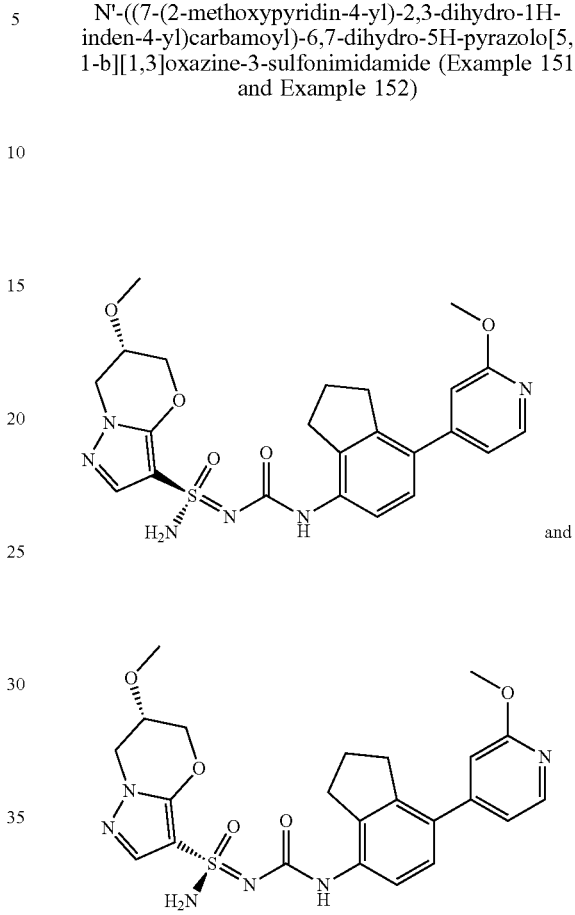

(6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (60 mg, 0.12 mmol) was separated by chiral SFC (Chiralcel OJ (250 mm*30 mm, 5 um), Supercritical $CO_2$/IPA+0.1% $NH_4OH$=60/40; 60 mL/min), to give (S,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Method R, 1.84 min, peak 1, 4 mg, yield: 5%) and (R,6S)-6-methoxy-N'-((7-(2-methoxypyridin-4-yl)-2,3-dihydro-1H-inden-4-yl)carbamoyl)-6,7-dihydro-5H-pyrazolo[5,1-b][1,3]oxazine-3-sulfonimidamide (Method R, 2.25 min, peak 2, 5 mg, yield: 5%) both as white solids. Stereochemistry was arbitrarily assigned to each stereoisomer.

Peak 1: $^1$H NMR (400 MHz, DMSO-$d_6$): δ=8.24 (s, 1H), 8.17 (d, J=5.6 Hz, 1H), 7.64-7.60 (m, 2H), 7.36 (s, 2H), 7.16 (d, J=8.4 Hz, 1H), 7.05 (d, J=4.8 Hz, 1H), 6.81 (s, 1H), 4.62-4.58 (m, 1H), 4.32-4.18 (m, 3H), 4.05-4.01 (m, 1H), 3.87 (s, 3H), 3.41-3.37 (m, 3H), 2.94 (t, J=7.6 Hz, 2H), 2.85-2.80 (m, 2H), 1.99-1.91 (m, 2H). MS: m/z 499.1 (M+H$^+$).

Peak 2: $^1$H NMR (400 MHz, DMSO-$d_6$): δ=8.25 (s, 1H), 8.16 (d, J=5.2 Hz, 1H), 7.65-7.60 (m, 2H), 7.40 (s, 2H), 7.16 (d, J=8.4 Hz, 1H), 7.05 (d, J=5.6 Hz, 1H), 6.81 (s, 1H), 4.62-4.58 (m, 1H), 4.34-4.18 (m, 3H), 4.05-4.01 (m, 1H), 3.87 (s, 3H), 3.37-3.36 (m, 3H), 2.94 (t, J=7.6 Hz, 2H), 2.85-2.80 (m, 2H), 1.99-1.90 (m, 2H). MS: m/z 499.1 (M+H$^+$).

Example 153, Example 154, Example 155, and Example 156

(S)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

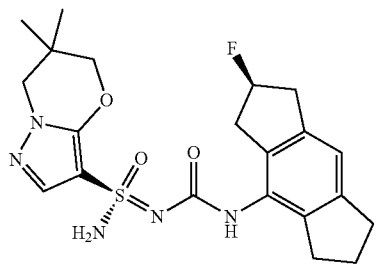

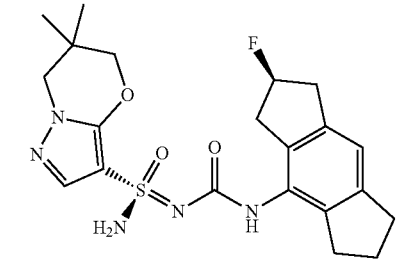

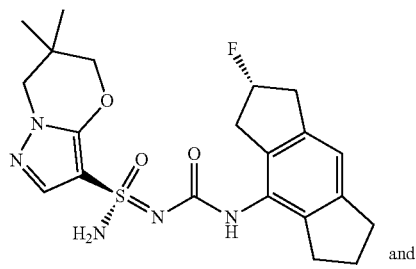

and

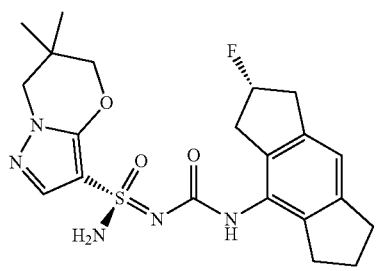

Step 1—Synthesis of 8-nitro-1,2,3,5,6,7-hexahydro-s-indacen-1-ol

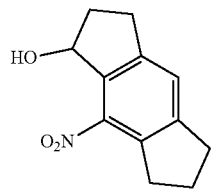 [SMILES: O=[N+]([O-])c1c2c(cc3c1C(O)CC3)CCC2]

To a solution of 8-nitro-3,5,6,7-tetrahydro-2H-s-indacen-1-one (7.9 g, 36.37 mmol) in MeOH (100 mL) was added NaBH$_4$ (6.9 g, 181.84 mmol) at 0° C. under a nitrogen atmosphere. After addition, the reaction was warmed to room temperature. After 1 hour, the solvent was removed in vacuo and H$_2$O (10 mL) was added to the crude residue. The aqueous layer was extracted with EtOAc (20 mL×2). The combined organic layers were washed with brine (40 mL), dried over Na$_2$SO$_4$, filtered and concentrated. The crude residue was purified by silica gel column chromatography (15% EtOAc in petroleum ether) to give 8-nitro-1,2,3,5,6,7-hexahydro-s-indacen-1-ol (7.5 g, yield: 94%) as a light yellow oil.

Step 2—Synthesis of 8-nitro-1,2,3,5-tetrahydro-s-indacene

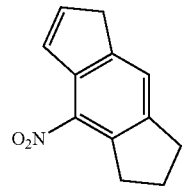 [SMILES: O=[N+]([O-])c1c2c(cc3c1CCC3)CC=C2]

TsOH (3.3 g, 17 mmol) was added to a flask, equipped with a Dean-Stark trap, containing a solution of 8-nitro-1,2,3,5,6,7-hexahydro-s-indacen-1-ol (7.5 g, 34.21 mmol) in toluene (100 mL). The reaction was heated at 110° C. for 2 hours. After cooling to room temperature, the mixture was diluted in EtOAc (50 mL). The organic layer was washed with saturated aqueous NaHCO$_3$ (100 mL×2), brine (100 mL), dried over anhydrous Na$_2$SO$_4$, filtered and concentrated. The crude residue was triturated with hexane to give 8-nitro-1,2,3,5-tetrahydro-s-indacene (5.9 g, yield: 86%) as a light yellow solid. $^1$H NMR (400 MHz, CDCl$_3$) δ=7.53 (s, 1H), 7.49 (d, J=6.0 Hz, 1H), 6.79-6.77 (m, 1H), 3.45 (s, 2H), 3.35 (t, J=7.6 Hz, 2H), 3.02 (t, J=7.6 Hz, 2H), 2.21-2.16 (m, 2H).

Step 3—Synthesis of 2-nitro-1a,3,4,5,7,7a-hexahydro-s-indaceno[1,2-b]oxirene

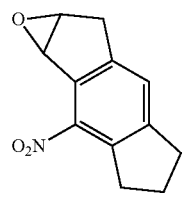 [SMILES: O=[N+]([O-])c1c2c(cc3c1C1OC1C3)CCC2]

To a solution of 8-nitro-1,2,3,5-tetrahydro-s-indacene (5.9 g, 29.32 mmol) in DCM (80 mL) was added 85% m-CPBA (9.7 g, 38.12 mmol) at 0° C. under a nitrogen atmosphere. After addition, the reaction was allowed to warm to room temperature. After 12 hours, the reaction mixture was washed with saturated aqueous NaHCO₃ (80 mL) and Na₂S₂O₃ solution (80 mL).

The organic layer was dried over anhydrous Na₂SO₄, filtered, and concentrated. The crude residue was purified by silica gel column (10% EtOAc in petroleum ether) to give 2-nitro-1a,3,4,5,7,7a-hexahydro-s-indaceno[1,2-b]oxirene (4.2 g, yield: 66%) as a white solid.

Step 4—Synthesis of 4-nitro-1,2,3,5,6,7-hexahydro-s-indacen-2-ol

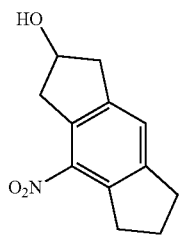 [SMILES: O=[N+]([O-])c1c2c(cc3c1CC(O)C3)CCC2]

To a solution of 2-nitro-1a,3,4,5,7,7a-hexahydro-s-indaceno[1,2-b]oxirene (4.0 g, 18.41 mmol) in DCE (60 mL) was added ZnI₂ (8.8 g, 27.62 mmol) and NaBH₃CN (9.3 g, 147.32 mmol) at room temperature. The reaction was heated to 80° C. for 4 hours. After cooling to room temperature, the mixture was poured into aqueous 6 N HCl (10 mL). The aqueous layer was extracted with DCM (50 mL×3). The combined organic layers were dried over Na₂SO₄, filtered, and concentrated. The residue was purified by silica gel column (20% EtOAc in petroleum ether) to give 4-nitro-1,2,3,5,6,7-hexahydro-s-indacen-2-ol (3.4 g, 84% yield) as a white solid. ¹H NMR (400 MHz, DMSO-d₆) δ=7.43 (s, 1H), 4.94 (s, 1H), 4.51 (s, 1H), 3.29-3.25 (m, 1H), 3.18-3.05 (m, 4H), 2.89 (t, J=7.6 Hz, 2H), 2.83-2.75 (m, 1H), 2.10-2.04 (m, 2H).

Step 5—Synthesis of 2-fluoro-4-nitro-1,2,3,5,6,7-hexahydro-s-indacene

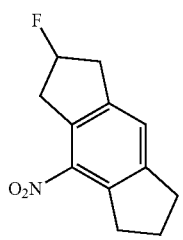

To a solution of 4-nitro-1,2,3,5,6,7-hexahydro-s-indacen-2-ol (800 mg, 3.65 mmol) in DCM (20 mL) was added DAST (1.50 mL, 10.95 mmol) dropwise at 0° C. under a nitrogen atmosphere. After 1 hour, saturated aqueous Na₂CO₃ (5 mL) was added carefully. The organic layer was washed with brine (50 mL), dried over Na₂SO₄, filtered and concentrated. The residue was purified by silica gel column (15% EtOAc in petroleum ether) to give 2-fluoro-4-nitro-1,2,3,5,6,7-hexahydro-s-indacene (370 mg, yield: 46%) as yellow oil. ¹H NMR (400 MHz, CDCl₃) δ=7.39 (s, 1H), 5.63-5.45 (m, 1H), 3.70-3.63 (m, 2H), 3.58-3.25 (m, 4H), 3.21-2.98 (m, 2H), 2.18-2.13 (m, 2H).

Step 6—Synthesis of 2-fluoro-1,2,3,5,6,7-hexahydro-s-indacen-4-amine

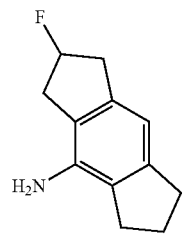 [SMILES: O=[N+]([O-])c1c2c(cc3c1CC(F)C3)CCC2]

A mixture of 2-fluoro-4-nitro-1,2,3,5,6,7-hexahydro-s-indacene (370 mg, 1.67 mmol) and 10% Pd on carbon (178 mg, 1.67 mmol) in EtOH (8 mL) was stirred at room temperature under hydrogen atmosphere (15 PSI). After 2 hours, the reaction mixture was filtered through a pad of Celite. The filtrate was concentrated under reduced pressure to give 2-fluoro-1,2,3,5,6,7-hexahydro-s-indacen-4-amine (350 mg crude) as a yellow oil, which was used in the next step without further purification. ¹H NMR (400 MHz, CDCl₃) δ=6.65 (s, 1H), 5.60-5.44 (m, 1H), 3.52 (s, 2H), 3.23-3.13 (m, 2H), 3.07-2.95 (m, 2H), 2.88 (t, J=7.6 Hz, 2H), 2.71 (t, J=7.6 Hz, 2H), 2.15-2.05 (m, 2H). MS: m/z 192.1 (M+H⁺).

Step 7—Synthesis of 2-fluoro-4-isocyanato-1,2,3,5,6,7-hexahydro-s-indacene

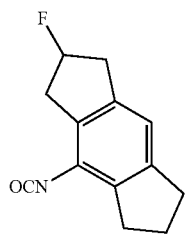

To a solution of 2-fluoro-1,2,3,5,6,7-hexahydro-s-indacen-4-amine (150 mg, 0.78 mmol) and triethylamine (0.11 mL, 0.78 mmol) in anhydrous THF (9 mL) was added triphosgene (93 mg, 0.31 mmol) at room temperature. The reaction was heated at 70° C. for 2 hours. After cooling to room temperature, the mixture was filtered through a plug of silica gel to remove the triethylamine hydrochloride. The filtrate was used in the next step directly.

427

Step 8~9—Synthesis of N'-((2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide

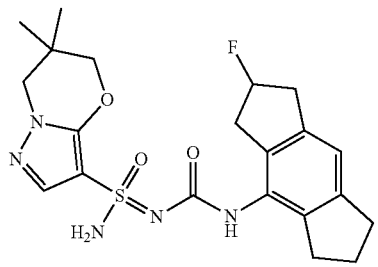 [SMILES: CC1(C)COc2c(S(N)(=O)=NC(=O)Nc3c4c(cc5c3CC(F)C5)CCC4)cnn2C1]

N'-((2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide was prepared using the general procedure described for the preparation of (R)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide and (S)—N'-((2,4-diisopropyl-6-methoxypyridin-3-yl)carbamoyl)-6,6-dimethyl-6,7-dihydro-5H-pyrazolo[5,1-b][1,3]oxazine-3-sulfonimidamide (Example 76 and Example 77), by replacing 3-isocyanato-2,4-diisopropyl-6-methoxy-pyridine with 2-fluoro-4-isocyanato-1,2,3,5,6,7-hexahydro-s-indacene in Step 3.

Step 10—Synthesis of (S)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (R)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide, (S)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide and (R)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Example 153, Example 154, Example 155, and Example 156)

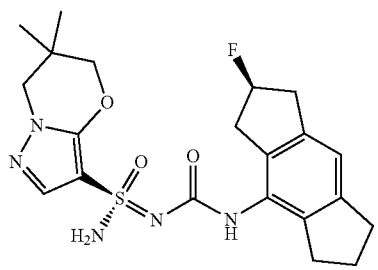

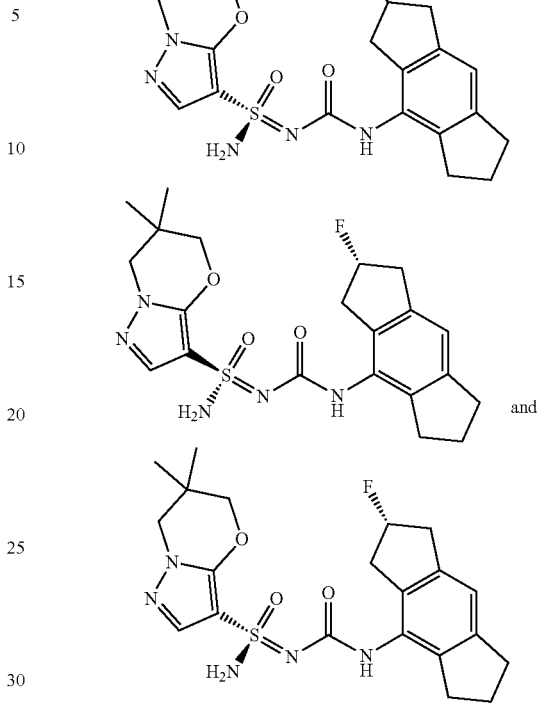

and

N'-((2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (180 mg, 0.40 mmol) was purified by chiral SFC (Chiralpak AD (250 mm*30 mm, 10 um); Supercritical $CO_2$/EtOH+0.1% $NH_4OH$=55/45; 60 mL/min) to give (S)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Method G, 4.97 min, peak 3, peak 3, 21.3 mg, yield: 12%), (R)—N'—(((S)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Method G, 5.27 min, peak 4, 10.8 mg, yield: 6%) and N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (a mixture of peak 1 and peak 2, 44 mg, yield: 24%) all as white solids. N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (mixture of peak 1 and peak 2, 44 mg) was purified by chiral SFC (Chiralcel OJ (250 mm*30 mm, 5 um); Supercritical $CO_2$/IPA+0.1% $NH_4OH$=75/25, 60 mL/min) to give (S)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Method G, 4.14 min, peak 1, 11.2 mg, yield: 25%), and (R)—N'—(((R)-2-fluoro-1,2,3,5,6,7-hexahydro-s-indacen-4-yl)carbamoyl)-6,6-dimethyl-6,7-dihydro-5H-pyrazolo[5,1-b][1,3]oxazine-3-sulfonimidamide (Method G, 4.73 min, peak 2.14 mg, 32% yield) both as white solids. Stereochemistry was arbitrarily assigned to each stereoisomer.

Peak 1: $^1$H NMR (400 MHz, DMSO-$d_6$): δ=8.30 (s, 1H), 7.55 (s, 1H), 7.26 (s, 2H), 6.91 (s, 1H), 5.53-5.33 (m, 1H), 4.07 (s, 2H), 3.87 (s, 2H), 3.23-2.84 (m, 4H), 2.84-2.63 (m, 4H), 1.99-1.88 (m, 2H), 1.04 (s, 6H). MS: m/z 448.1 (M+H$^+$). Compound 155

Peak 2: ¹H NMR (400 MHz, DMSO-d₆): δ=8.28 (s, 1H), 7.55 (s, 1H), 7.27 (s, 2H), 6.91 (s, 1H), 5.55-5.33 (m, 1H), 4.07 (s, 2H), 3.86 (s, 2H), 3.25-2.85 (m, 4H), 2.84-2.60 (m, 4H), 2.01-1.87 (m, 2H), 1.03 (d, J=6.8 Hz, 6H). MS: m/z 448.1 (M+H⁺). Compound 156

Peak 3: ¹H NMR (400 MHz, DMSO-d₆): δ=8.27 (s, 1H), 7.55 (s, 1H), 7.27 (s, 2H), 6.91 (s, 1H), 5.55-5.30 (m, 1H), 4.10 (s, 2H), 3.86 (s, 2H), 3.24-2.83 (m, 4H), 2.81-2.65 (m, 4H), 2.00-1.87 (m, 2H), 1.03 (d, J=6.8 Hz, 6H). MS: m/z 448.1 (M+H⁺). Compound 153

Peak 4: ¹H NMR (400 MHz, DMSO-d₆): δ=8.29 (s, 1H), 7.55 (s, 1H), 7.26 (s, 2H), 6.91 (s, 1H), 5.55-5.30 (m, 1H), 4.07 (s, 2H), 3.87 (s, 2H), 3.23-2.85 (m, 4H), 2.84-2.60 (m, 4H), 1.99-1.90 (m, 2H), 1.04 (s, 6H). MS: m/z 448.1 (M+H⁺). Compound 154

Example 157 and Example 158

(S)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide and
(R)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide

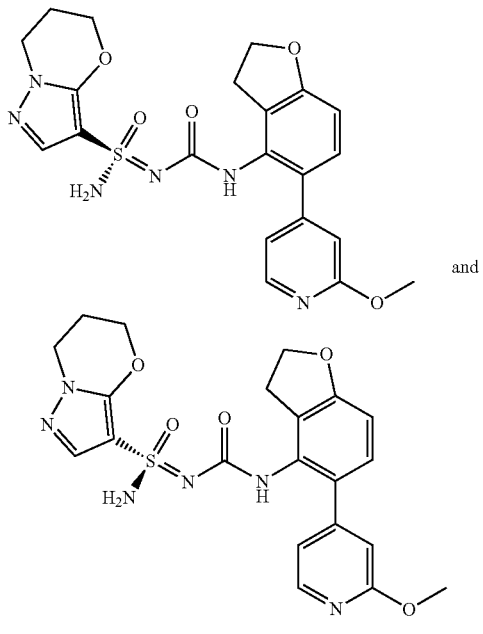

and

Step 1—Synthesis of N-(2,3-dihydrobenzofuran-4-yl)acetamide

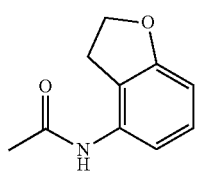

A mixture of 2,3-dihydrobenzofuran-4-amine (4.0 g, 29.6 mmol) in acetic anhydride (40 mL, 59.2 mmol) was stirred at room temperature. After 16 hours, the reaction mixture was concentrated to give N-(2,3-dihydrobenzofuran-4-yl)acetamide (3.4 g, yield: 65%) as a white solid, which was used in the next step without further purification. MS: m/z 178.0 (M+H⁺).

Step 2—Synthesis of N-(5-bromo-2,3-dihydrobenzofuran-4-yl)acetamide

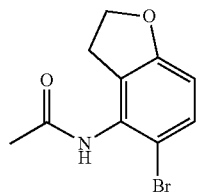

To a solution of N-(2,3-dihydrobenzofuran-4-yl)acetamide (3.4 g, 19.2 mmol) in DCM (70 mL) was added NBS (3.76 g, 21.1 mmol) portion-wise at 0° C. under a nitrogen atmosphere.

After addition, the reaction was warmed to room temperature. After 16 hours, the reaction mixture was concentrated and the crude residue was purified by silica gel column (1% MeOH in DCM) to give N-(5-bromo-2,3-dihydrobenzofuran-4-yl)acetamide (3.3 g, yield: 67%) as a white solid. ¹H NMR (400 MHz, CDCl₃) δ 7.30 (d, J=8.4 Hz, 1H), 7.15 (s, 1H), 6.58 (d, J=8.4 Hz, 1H), 4.61 (t, J=8.8 Hz, 2H), 3.22 (t, J=8.8 Hz, 2H), 2.23 (s, 3H).

Step 3—Synthesis of 5-bromo-2,3-dihydrobenzofuran-4-amine

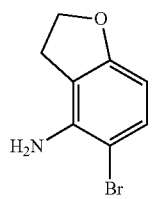

A mixture of N-(5-bromo-2,3-dihydrobenzofuran-4-yl)acetamide (3.3 g, 12.9 mmol) and NaOH (5.15 g, 128.9 mmol) in water (500 mL) and EtOH (100 mL) was heated at 90° C. under a nitrogen atmosphere. After 80 hours, the reaction mixture was concentrated to remove EtOH. The residue was filtered and the white solid was dissolved in ethyl acetate (60 mL) and water (10 mL). The pH was adjusted to 2.0 with the addition of concentrated HCl. The resulting solid was filtered to give 5-bromo-2,3-dihydrobenzofuran-4-amine (1.7 g, yield: 62%) as a white solid, which was used in the next step without further purification. ¹H NMR (400 MHz, DMSO-d₆) δ 7.06 (d, J=8.4 Hz, 1H), 6.00 (d, J=8.4 Hz, 1H), 4.50 (t, J=8.8 Hz, 2H), 3.01 (t, J=8.8 Hz, 2H).

Step 4—Synthesis of 5-(2-methoxypyridin-4-yl)-2,3-dihydrobenzofuran-4-amine

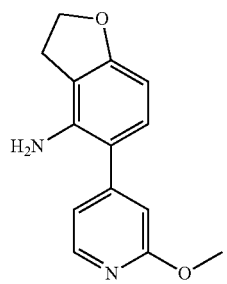 [SMILES: COc1cc(-c2ccc3c(c2N)CCO3)ccn1]

To a solution of 5-bromo-2,3-dihydrobenzofuran-4-amine (1.7 g, 7.94 mmol) in 1,4-dioxane (95 mL) and water (15 mL) was added 2-methoxypyridine-4-boronic acid (1.46 g, 9.53 mmol), Pd(dppf)Cl$_2$ (581 mg, 0.79 mmol) and Na$_2$CO$_3$ (2.52 g, 23.8 mmol) under a nitrogen atmosphere. The resulting mixture was heated at 80° C. for 3 hours. After cooling to room temperature, the mixture was filtered and the filtrate was concentrated. The crude residue was purified by silica gel column (10-20% EtOAc in petroleum ether) to give 5-(2-methoxypyridin-4-yl)-2,3-dihydrobenzofuran-4-amine (1.8 g, yield: 94%) as a white solid. $^1$H NMR (400 MHz, DMSO-d$_6$) δ 8.15 (d, J=5.2 Hz, 1H), 7.00-6.98 (m, 1H), 6.83 (d, J=8.0 Hz, 1H), 6.77 (s, 1H), 6.13 (d, J=8.0 Hz, 1H), 4.92 (s, 2H), 4.53 (t, J=8.8 Hz, 2H), 3.86 (s, 3H), 3.00 (t, J=8.8 Hz, 2H).

Step 5—Synthesis of 4-(4-isocyanato-2,3-dihydrobenzofuran-5-yl)-2-methoxypyridine

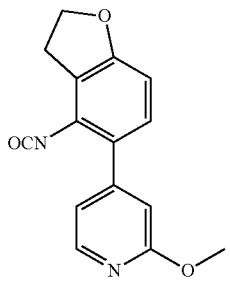

To a solution of 5-(2-methoxypyridin-4-yl)-2,3-dihydrobenzofuran-4-amine (150 mg, 0.62 mmol) and triethylamine (0.26 mL, 1.86 mmol) in THF (30 mL) was added triphosgene (74 mg, 0.25 mmol) in one portion at 0° C. under a nitrogen atmosphere. After 1 hour, the reaction mixture was filtered through a plug of silica gel to remove the triethylamine hydrochloride. The filtrate, containing 4-(4-isocyanato-2,3-dihydrobenzofuran-5-yl)-2-methoxypyridine, was used in next step directly.

Step 6-7—Synthesis of N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide

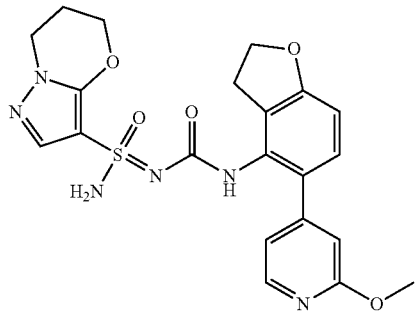 [SMILES: COc1cc(-c2ccc3c(c2NC(=O)N=S(N)(=O)c2cnn4c2OCCC4)CCO3)ccn1]

N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide was prepared using the general procedure described for the preparation of (S)—N'-((2,4-diisopropyl-6-methoxypyridin-3-yl)carbamoyl)-6,7-dihydro-5H-pyrazolo[5,1-b][1,3]oxazine-3-sulfonimidamide and (R)—N'-((2,4-diisopropyl-6-methoxypyridin-3-yl)carbamoyl)-6,7-dihydro-5H-pyrazolo[5,1-b][1,3]oxazine-3-sulfonimidamide (Example 102 and Example 103), by replacing 3-isocyanato-2,4-diisopropyl-6-methoxypyridine with 4-(4-isocyanato-2,3-dihydrobenzofuran-5-yl)-2-methoxypyridine in Step 1. MS: m/z 471.2 (M+H$^+$).

Step 8—Synthesis of (S)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide and (R)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide (Example 157 and Example 158)

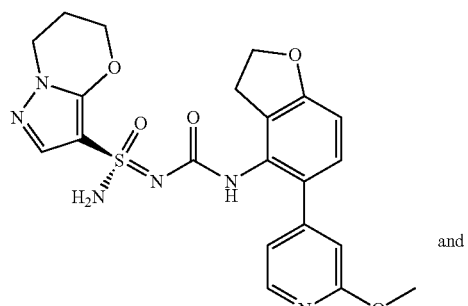

and

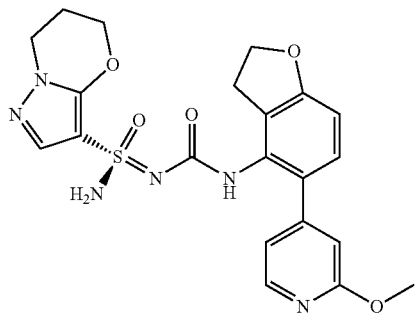

N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide (95 mg, 0.20 mmol) was separated by chiral SFC (Phenomenex Cellulose-2 (250 mm*30 mm, 10 um); Supercritical $CO_2$/MeOH+0.1% $NH_4OH$=45/55; 70 mL/min) to give (S)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide (Method G, 8.12 min, peak 1, 25.4 mg, yield: 26%) and (R)—N'-((5-(2-methoxypyridin-4-yl)-2,3-dihydrobenzofuran-4-yl)carbamoyl)-6,7-dihydro-5H-pyrazolo[5,1-b][1,3]oxazine-3-sulfonimidamide (Method G, 10.22 min, peak 2, 30.8 mg, yield: 31%) both as white solids. Stereochemistry was arbitrarily assigned to each stereoisomer.

Peak 1: $^1$H NMR (400 MHz, DMSO-$d_6$) δ=8.19 (s, 1H), 8.09 (d, J=5.2 Hz, 1H), 7.41 (s, 1H), 7.23 (s, 2H), 7.07 (d, J=8.4 Hz, 1H), 6.92 (d, J=5.2 Hz, 1H), 6.74 (s, 1H), 6.70 (d, J=8.0 Hz, 1H), 4.56 (t, J=8.8 Hz, 2H), 4.37 (t, J=4.8 Hz, 2H), 4.11 (t, J=6.0 Hz, 2H), 3.86 (s, 3H), 3.11-3.06 (m, 2H), 2.22-2.13 (m, 2H). MS: m/z 471.1 (M+H$^+$).

Peak 2: $^1$H NMR (400 MHz, DMSO-$d_6$) δ=8.18 (s, 1H), 8.09 (d, J=5.2 Hz, 1H), 7.41 (s, 1H), 7.22 (s, 2H), 7.07 (d, J=8.0 Hz, 1H), 6.92 (d, J=5.2 Hz, 1H), 6.74 (s, 1H), 6.70 (d, J=8.0 Hz, 1H), 4.56 (t, J=8.8 Hz, 2H), 4.37 (t, J=4.4 Hz, 2H), 4.11 (t, J=6.0 Hz, 2H), 3.86 (s, 3H), 3.11-3.06 (m, 2H), 2.24-2.11 (m, 2H). MS: m/z 471.1 (M+H$^+$).

Biological Testing Methods

Abbreviations

PBMCs: peripheral blood mononuclear cells
KCs: Kupffer cells
FBS: fetal bovine serum
LPS: lipopolysaccharides
NLRP3 Activation and Inhibitory Assays Some of the following assays were used to determine the inhibitory activity of the compounds on the NLRP3 inflammasome using a common inflammasome activation stimuli—nigericin.

Example B1: Cell Culture

Human peripheral blood mononuclear cells (PBMCs), consisting of lymphocytes (T, B and NK cells), monocytes and dendritic cells, were freshly isolated from human peripheral blood from healthy donors. Cells were obtained through an IRB approved donor program by iXCells Biotechnologies where all the donors were tested for bacterial and viral infections. Cells were purified from peripheral blood using ficoll gradient centrifugation.

Human Kupffer cells (KCs), specialized liver macrophages residing in the space of Disse, were obtained by gradient isolation from liver specimens harvested post-mortem by Samsara Sciences. Cells were obtained through an IRB approved donor program by Samsara Sciences and all donors tested negative for bacterial and viral infections.

Biological Example B2: NLRP3 Inflammasome Activation Assays

Fresh or cryopreserved PMBCs were seeded in V-bottom 96-well plate at 0.5-1×10$^5$ cells per well and incubated overnight at 37° C. with 5% $CO_2$ in RPMI 1640 medium with GlutaMAX supplement, 4.5 g/L D-glucose, 10% Fetal Bovine Serum (FBS), 100 mM Sodium Pyruvate, 1% Penicillin/Streptomycin, 10 mM HEPES and 0.05 mM of β-mercaptoethanol. Freshly isolated or cryopreserved KCs cells were seeded in flat-bottom 96-well plates at 0.6-1.5×10$^5$ cells/well and incubated overnight at 37° C. 5% $CO_2$ in RPMI 1640 Medium with GlutaMAX supplement, FBS, 1% Penicillin/Streptomycin and 10 mM HEPES. The following day, the cells were primed with 100 ng/mL of lipopolysaccharides (LPS; Sigma Aldrich) in FBS-free RPMI 1640 for 3 h. After the priming step, the media was removed and PBMCs were pre-incubated with serial concentrations of test compounds (0.00017-10 uM) or vehicle (DMSO) for 30 min in FBS-free media prior to addition of the NLRP3 activator. Cells were then stimulated with 10 uM Nigericin (Sigma Aldrich; InvivoGen) for 1.5 h. Plates were centrifuged at 1,500 rpm for 3 minutes to pellet cells and supernatant was transferred into new plates for subsequent experiments.

Measurement of Cytokines/Assessment of NLRP3 Inflammasome Activity

For ELISA assays cells were seeded into 96-well plates. Post study, supernatants were removed and the levels of mature IL-1β, IL18 and TNFα (Quantikine ELISA, R&D systems) were measured in cell conditioned media by ELISA according to manufacturer's instructions.

Example B3: CTG (CellTitre-Glo) Assay

Viability of compound treated cells was measured using CellTiter-Glo® assay (Promega, Madison, Wis.) that measures the ATP content of cells which is proportional to the number of live cells within a well. This is a counter-screen to establish that the reduction of IL-1β levels in LPS and nigericin stimulated and compound treated cells is not due to cytotoxicity, but rather through the inhibition of the inflammasome pathway. Compounds inhibiting NRLP3 inflammasome activation ultimately increase the viability of LPS and nigericin stimulated cells by blocking NLRP3 mediated pyroptosis that would otherwise lead to cell lysis.

Example B4: TNF-α

TNFα levels of LPS and nigericin stimulated cells were measured by HTRF assay (Cisbio, Bedford, MA). Inflammasome pathway selective compounds do not inhibit TNFα production that is solely dependent on LPS stimulation and proceeds through the TLR4/NFkB pathway. Measuring TNFalpha production also serves as a technical counter-screen to eliminate compounds that interfere with the HTRF reagents. Thus compounds that inhibit both IL-1β and TNFα levels are triaged for either being non-selective for inflammasome or interfering with the HTRF readout.

Assay Results

Results of certain compounds are shown below. For the table below, A: <100 nM; B: 100 nM-1 µM; C: 1-10 µM; D: >10 µM.

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| | N | A | B | | B | B | |
| | N | A | A | | | | |
| | N | B | B | | | | |
| | N | A | A | | | | |
| | N | B | B | | | | |
| | N | A | A | | | | |

-continued

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| | Y | B | A | | | | |
| | Y | B | A | | | | |
| | N | D | D | | | | |
| | N | B | B | | | | |
| | N | D | | | | | |

-continued

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| | N | C | A | D | | | |
| | Y | A | A | D | | | |
| | Y | C | A | D | | | |
| | N | B | A | D | | | |
| | N | B | B | D | | | |

-continued

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| (structure) | N | A | A | D | | | |
| (structure) | N | A | A | D | | | |
| (structure) | Y | B | B | D | | | |
| (structure) | Y | A | A | D | A | A | D |
| (structure) | Y | A | A | D | | | |

-continued

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| | Y | C | B | D | | | |
| | Y | C | A | D | | | |
| | Y | B | B | D | | | |
| | Y | B | | | | | |
| | Y | A | A | D | A | A | D |

-continued

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| (structure) | Y | B | D | D | | | |
| (structure) | Y | D | | D | | | |
| (structure) | N | A | C | D | | | |
| (structure) | N | A | D | D | | | |
| (structure) | Y | B | A | D | | | |

| Compound | single stereo-isomer | PBMC IL-1 β IC50 | PBMC CTG IC50 | PBMC TNF α IC50 | Kupffer IL-β B IC50 | Kupffer CTG IC50 | Kupffer TNF α IC50 |
|---|---|---|---|---|---|---|---|
| | Y | A | A | D | | | |
| | Y | B | A | D | | | |
| | Y | A | A | D | | | |
| | Y | A | B | D | | | |
| | N | D | D | D | | | |

Example B5: PMBC IL-1β HTRF Assay

Cell Culture and NLRP3 Inflammasome Activation Assay:

Human frozen PBMCs were purchased from StemCells Technologies. Cells were rapidly thawed in 37° C. water bath and resuspended in fresh assay media consisting of RPMI 1640 Medium containing 1% sodium pyruvate, 10 mM HEPES, 2.5 g/L glucose and 55 µM 2-Mercaptoethanol. Cell density was adjusted to $8.1 \times 10^5$ cells/mL. Cells were primed by adding lipopolysaccharide (Invivogen Ultrapure lipopolysaccharide from *E. coli*, tlrl-3pelps) at a final concentration of 100 ng/mL in cell suspension. 37 µL of cell suspension with LPS was seeded per well of a 384 well plate and incubated for 3 hours at 37° C. and 5% $CO_2$. After priming, PBMCs were preincubated with serially diluted test compounds with starting concentration of 40 µM followed by 2-fold dilution for a 20-point curve or vehicle (DMSO) for 30 min in assay media at 37° C. and 5% $CO_2$. Cells were then stimulated with 10 µM nigericin (Invivogen, tlrl-nig-5) for 90 min at 37° C. and 5% $CO_2$ to activate NLRP3 dependent inflammasome pathway and IL-1β release in cell culture supernatant. Cells were centrifuged at 1200 RPM for 1 min and 40 µL of supernatant was transferred into fresh plates and stored at −80° C. until IL-1β analysis.

IL-1β HTRF Assay:

16 µL of supernatant was added to white 384 well HTRF plates, followed by addition of 4 µL of HTRF cocktail in each well. Plates were quickly centrifuged, sealed and incubated overnight at room temperature. Next day, HTRF signal was read on a Pherastar and ratio of 665/620 was calculated based on manufacturer's protocol to obtain concentration of IL-1β in cell culture supernatant.

Example B6: THP-1 ASC-GFP Speck Assay

Cell Culture:

THP-1 ASC-GFP cell line was purchased from Invivogen, San Diego, for inflammasome activation assay. THP-1 ASC-GFP cells stably express a 37.6 kDa ASC::GFP fusion protein that enables monitoring of spec formation by microscopy after activation of NLRP3 dependent inflammasome pathway. Cells were maintained at a density of 600,000 cells/mL in growth media consisting of RPMI 1640, 2 mM L-glutamine, 25 mM HEPES and 10% heat inactivated fetal bovine serum at 37° C. and 5% $CO_2$. Cells were passaged every 3-4 days and used for assays for up to 20 passages.

NLRP3 Inflammasome Activation Assay:

THP-1 ASC-GFP cells were collected by centrifuging cells at 800 RPM for 5 minutes. Cell culture supernatant was removed and cells were re-suspended in fresh media at density of $1 \times 10^6$ cells/mL in assay media consisting of RPMI 1640, 2 mM L-glutamine, 25 mM HEPES and 10% heat inactivated fetal bovine serum. Phorbol 12-myristate 13-acetate (PMA) (Invivogen, tlrl-pma) was added to the cell suspension at a final concentration of 500 ng/ml and mixed thoroughly. 40,000 cells were added per well of a 384 well plate and differentiated into macrophages overnight at 37° C. and 5% $CO_2$. Cells were primed with 1 µg/mL of lipopolysaccharide (Invivogen Ultrapure lipopolysaccharide from *E. coli*, tlrl-3pelps) in assay media for 3 hours at 37° C. and 5% $CO_2$. After priming, media was removed and THP-1 ASC-GFP cells were preincubated with serially diluted test compounds with starting concentration of 40 µM followed by 2-fold dilution for a 20-point curve or vehicle (DMSO) for 30 min in assay media at 37° C. and 5% $CO_2$. Cells were then stimulated with 10 µM nigericin (Invivogen, tlrl-nig-5) for 90 min at 37° C. and 5% $CO_2$ to activate NLRP3 dependent inflammasome pathway and spec formation. After stimulation, cells were fixed with 4.8% paraformaldehyde (Electron Microscopy Sciences #15710-S) and incubated at room temperature for 15 min. Cells were then washed 3-times with 100 µL of phosphate buffered saline and permeabilized in the presence of premeablization/block buffer for 20 min at room temperature. Cells were then washed 3-times with 100 µL phosphate buffered saline and incubated for 1 hr at room temperature in the presence of hoechst. After staining with Hoechst, cells were washed 3-times with 100 µL phosphate buffered saline and imaged for ASC spec formation.

Imaging ASC-GFP Specks:

THP-1 ASC-GFP cells were imaged in 488 and Hoechst channels. Hoechst channel was used for cell count and 488 channel was used to identify number of GFP ASC specks in imaged fields. Percentage of cells with a spec was calculated by dividing the number of GFP positive spots by total number of cells.

Additional assay results are provided in Table B1-a, Table B1-b, and Table B1-c.

TABLE B1-a

| Ex. No. | PBMC IL-1β $IC_{50}$ (µM) | PBMC CTG $IC_{50}$ (µM) | PBMC TNFα $IC_{50}$ (µM) |
|---|---|---|---|
| 1 | 0.082 | 0.30 | |
| 2 | 0.024 | 0.100 | |
| 3 | 0.41 | 0.176 | |
| 4 | 0.050 | 0.035 | |
| 5 | 1.02 | 0.648 | |
| 6 | 0.014 | 0.003 | |
| 7 | 0.29 | 0.003 | |
| 8 | 1.00 | 0.002 | |
| 9 | >10 | >10 | |
| 10 | 0.35 | 0.36 | |
| 11 | >10 | | |
| 12 | 1.39 | 0.006 | >10 |
| 13 | 0.035 | 0.008 | >10 |
| 14 | 1.91 | 0.001 | >10 |
| 15 | 0.30 | 0.095 | >10 |
| 16 | 0.27 | 0.131 | >10 |
| 17 | 0.019 | 0.008 | >10 |
| 18 | 0.016 | 0.0001 | >10 |
| 19 | 1.12 | 0.86 | >10 |
| 20 | 0.004 | 0.019 | >10 |
| 21 | 4.72 | 1.05 | >10 |
| 22 | 0.095 | 0.066 | |
| 23 | 8.82 | 0.039 | >10 |
| 24 | 0.24 | 0.127 | >10 |
| 25 | 0.30 | 0.008 | |
| 26 | 0.0076 | 0.002 | >10 |
| 27 | 0.12 | >10 | >10 |
| 28 | >10 | | >10 |
| 29 | 0.094 | 3.75 | >10 |
| 30 | 0.067 | >10 | >10 |
| 31 | 0.15 | 0.020 | >10 |
| 32 | 0.013 | 0.005 | >10 |
| 33 | 0.89 | 0.002 | >10 |
| 34 | 0.006 | 0.004 | >10 |
| 35 | 0.18 | 0.25 | |
| 36 | 0.050 | 0.17 | |
| 37 | >10 | >10 | |
| 38 | 2.03 | 1.16 | |
| 39 | 0.019 | 0.15 | |
| 40 | 0.0049 | 0.003 | |
| 41 | 6.8 | 1.31 | |
| 42 | 0.005 | | |
| 43 | 0.43 | | |
| 44 | 0.086 | | |
| 45 | 0.0007 | | |
| 46 | 0.007 | | |
| 47 | 0.33 | | |

TABLE B1-a-continued

| Ex. No. | PBMC IL-1β IC$_{50}$ (μM) | PBMC CTG IC$_{50}$ (μM) | PBMC TNFα IC$_{50}$ (μM) |
|---|---|---|---|
| 48 | >10 | | |
| 49 | 0.49 | | |
| 50 | 0.20 | | |
| 51 | >10 | | |
| 52 | 15.1 | | |
| 53 | 0.47 | | |
| 54 | 0.33 | | |
| 55 | >10 | | |
| 56 | >10 | | |
| 57 | 1.67 | | |
| 58 | >10 | | |
| 59 | 0.095 | | |
| 60 | 3.64 | | |
| 64 | >20 | | |
| 66 | >20 | | |
| 67 | 0.22 | | |
| 68 | 0.38 | | |
| 95 | 2.23 | | |

TABLE B1-b

| Ex. No. | Kupffer IL-1β IC$_{50}$ (μM) | Kupffer CTG IC$_{50}$ (μM) | Kupffer TNFα IC$_{50}$ (μM) |
|---|---|---|---|
| 1 | 0.123 | 0.103 | |
| 20 | <0.1 | <0.1 | >10 |
| 26 | 0.020 | 0.021 | >10 |

TABLE B1-c

| Ex. No. | THP1 ASC Speck IC$_{50}$ (μM) |
|---|---|
| 8 | 9.4 |
| 13 | 0.075 |
| 14 | 1.2 |
| 19 | 0.64 |
| 22 | 0.15 |
| 26 | 0.0097 |
| 27 | 0.20 |
| 28 | 4.40 |
| 29 | 0.14 |
| 30 | 0.36 |
| 31 | 0.62 |
| 32 | 0.045 |
| 33 | 1.60 |
| 36 | 0.066 |
| 37 | >20 |
| 38 | 1.5 |
| 40 | 0.0088 |
| 41 | 0.43 |
| 42 | 0.018 |
| 43 | 1.90 |
| 44 | 0.45 |
| 45 | 0.011 |
| 46 | 0.081 |
| 47 | 1.7 |
| 49 | 0.4 |
| 50 | 0.43 |
| 51 | 17 |
| 52 | >20 |
| 53 | 1.2 |
| 54 | 0.36 |
| 55 | 7.2 |
| 56 | >20 |
| 58 | 5.5 |

TABLE B1-c-continued

| Ex. No. | THP1 ASC Speck IC$_{50}$ (μM) |
|---|---|
| 59 | 0.26 |
| 61 | >20 |
| 62 | 0.92 |
| 63 | 0.14 |
| 64 | >20 |
| 65 | 0.34 |
| 66 | >20 |
| 67 | 1.4 |
| 68 | 0.33 |
| 69 | 0.03 |
| 70 | >20 |
| 71 | >20 |
| 72 | 2.5 |
| 73 | >20 |
| 74 | >20 |
| 75 | 15 |
| 76 | 2.6 |
| 77 | >20 |
| 78 | 0.093 |
| 79 | 1.0 |
| 80 | 4.5 |
| 81 | 0.02 |
| 82 | 0.27 |
| 83 | 0.008 |
| 84 | >20 |
| 85 | >20 |
| 86 | >20 |
| 87 | 2.9 |
| 88 | 7.7 |
| 89 | >20 |
| 90 | 0.32 |
| 91 | 0.49 |
| 92 | 8.2 |
| 93 | 0.36 |
| 94 | 0.36 |
| 96 | >20 |
| 97 | 1.3 |
| 98 | >20 |
| 99 | 1.7 |
| 100 | 2.7 |
| 101 | >20 |
| 102 | 5.1 |
| 103 | >20 |
| 104 | 0.32 |
| 105 | 9.9 |
| 106 | 0.15 |
| 107 | 9.0 |
| 108 | >20 |
| 109 | 5.7 |
| 110 | 0.12 |
| 111 | 0.1 |
| 112 | 0.61 |
| 113 | >20 |
| 114 | 4.4 |
| 115 | 2.5 |
| 116 | 2.1 |
| 117 | 4.3 |
| 118 | >20 |
| 119 | 0.058 |
| 120 | 1.2 |
| 121 | 2.7 |
| 122 | 0.8 |
| 123 | 0.12 |
| 124 | 0.054 |
| 125 | 1.7 |
| 126 | >20 |
| 127 | 3.3 |
| 128 | 1.7 |
| 129 | 0.019 |
| 130 | 14 |
| 131 | 0.92 |
| 132 | 1.2 |
| 133 | 2.8 |
| 134 | >20 |
| 135 | >20 |

453

TABLE B1-c-continued

| Ex. No. | THP1 ASC Speck IC$_{50}$ (µM) |
|---|---|
| 136 | 3.8 |
| 137 | 0.028 |
| 138 | 0.79 |
| 139 | 0.0043 |
| 140 | 0.56 |
| 141 | 1.6 |
| 142 | 0.084 |
| 143 | 1.2 |
| 144 | 0.056 |
| 145 | 3.8 |
| 146 | 2.6 |
| 147 | >20 |
| 148 | 0.71 |
| 149 | 0.65 |
| 150 | 0.024 |
| 151 | >20 |
| 152 | 4.1 |
| 153 | 1.4 |
| 154 | 1.8 |
| 155 | 0.008 |
| 156 | 0.013 |
| 157 | 0.71 |
| 158 | 0.025 |

EQUIVALENTS

While the present disclosure has been described in conjunction with the specific embodiments set forth herein, many alternatives, modifications and other variations thereof will be apparent to those of ordinary skill in the art. All such alternatives, modifications and variations are intended to fall within the spirit and scope of the present disclosure.

The invention claimed is:

1. A compound of Formula (I-5),

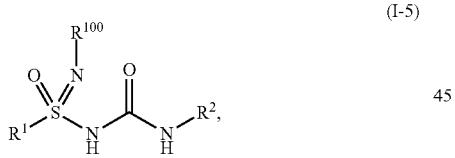

(I-5)

or a pharmaceutically acceptable salt thereof, wherein:

$R^{100}$ is selected from the group consisting of H, Cl, D, —CN, —NO$_2$, —OR$^{3a}$, —C(O)R$^{3b}$, —S(O)$_2$R$^{3b}$, —S(O)R$^{3b}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{3a}$, —C(O)R$^{3b}$, —P(O)R$^{3b}$R$^{4b}$, —S(O)$_2$R$^{3b}$, —S(O)R$^{3b}$, —NR$^{3a}$R$^{4a}$, —NR$^{3a}$C(O)R$^{4a}$, —NR$^{3a}$C(O)OR$^{4a}$, —NR$^{3a}$C(O)NR$^{4a}$, —NR$^{3a}$S(O)$_2$R$^{4a}$, C$_3$-C$_{10}$cycloalkyl, C$_6$aryl, 3-7-membered heterocyclyl, and 5-6 membered heteroaryl;

$R^1$ is selected from the group consisting of

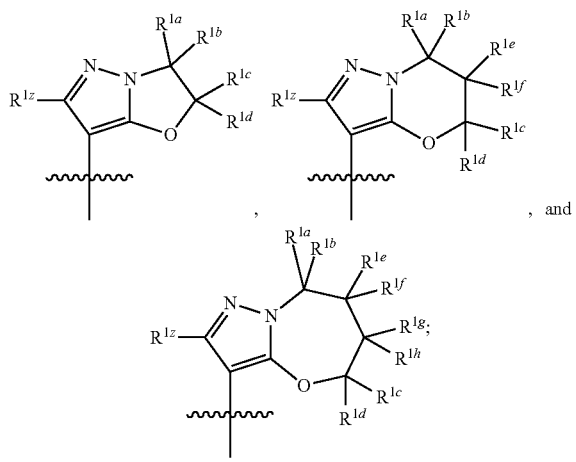

, and wherein $R^{1z}$ is H, D, halogen, —CN, —NO$_2$, —SR$^{7a}$, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, or 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6 membered heteroaryl are independently unsubstituted or substituted with one or more substituents selected from the group consisting of D, —CN, halogen, C$_1$-C$_6$alkyl, —OR$^{7a}$, —C(O)R$^{7b}$, —P(O)R$^{7b}$R$^{8b}$, —S(O)$_2$R$^{7b}$, —S(O)R$^{7b}$, —NR$^{7a}$R$^{8a}$, —NR$^{7a}$C(O)R$^{8a}$, —NR$^{7a}$C(O)OR$^{8a}$, —NR$^{7a}$C(O)NR$^{8a}$, —NR$^{7a}$S(O)$_2$R$^{8a}$, C$_3$-C$_{10}$cycloalkyl, C$_6$aryl, 3-7-membered heterocyclyl, and 5-6 membered heteroaryl;

each $R^{1a}$, $R^{1b}$, $R^{1c}$, $R^{1d}$, $R^{1e}$, $R^{1f}$, $R^{1g}$, and $R^{1h}$ is independently selected from the group consisting of H, D, halogen, —CN, —NO$_2$, —SR$^{11a}$, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl; wherein the C$_1$-C$_6$alkyl, C$_2$-C$_6$alkenyl, C$_4$-C$_8$cycloalkenyl, C$_2$-C$_6$alkynyl, C$_3$-C$_{10}$cycloalkyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OR$^{11a}$, —C(O)R$^{11b}$, —P(O)R$^{11b}$R$^{12b}$, —S(O)$_2$R$^{11b}$, —S(O)R$^{11b}$, —NR$^{11a}$R$^{12a}$, —NR$^{11a}$C(O)R$^{12a}$, —NR$^{11a}$C(O)OR$^{12a}$, —NR$^{11a}$C(O)NR$^{12a}$, —NR$^{11a}$S(O)$_2$R$^{12a}$, C$_3$-C$_{10}$cycloalkyl, C$_6$aryl, 3-7-membered heterocyclyl, and 5-6 membered heteroaryl; or two of the following groups, $R^{1a}$, $R^{1b}$, $R^{1c}$, $R^{1d}$, $R^{1e}$, $R^{1f}$, $R^{1g}$, and $R^{1h}$, when present, together with the atoms to which they are attached can form a C$_3$-C$_{10}$cycloalkyl or a 3-7-membered heterocyclyl; wherein the C$_3$-C$_{10}$cycloalkyl and 3-7-membered heterocyclyl are independently unsubstituted or substituted with one or more substituents selected from the group consisting of D, —CN, halogen, $C_1$-$C_6$alkyl, —$OR^{13a}$, —$C(O)R^{13b}$, —$P(O)R^{13b}R^{14b}$, —$S(O)_2R^{13b}$, —$S(O)R^{13b}$, —$NR^{13a}R^{14a}$, —$NR^{13a}C(O)R^{14a}$, —$NR^{13a}C(O)OR^{14a}$, —$NR^{13a}C(O)NR^{14a}$, and —$NR^{13a}S(O)_2R^{14a}$, or two geminal groups $R^{1a}$ and $R^{1b}$, $R^{1c}$ and $R^{1d}$, $R^{1e}$ and $R^{1f}$, or $R^{1g}$ and $R^{1h}$, when present, can form an oxo group;

$R^2$ is

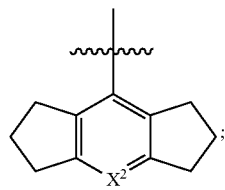

$X^2$ is N or $CR^{2a}$;
$X^3$ is N or $CR^{2c}$;
$X^4$ is N or $CR^{2d}$;
$X^5$ is N or $CR^{2e}$;
$X^6$ and $X^7$ are independently N or $CR^{2n}$, wherein at least one of $X^6$ and $X^7$ is N;

$R^{2a}$ is H, D, halogen, —CN, —$OR^{15a}$, $C_1$-$C_6$alkyl, $C_3$-$C_{10}$cycloalkyl, —C(O) $NR^{15a}R^{16a}$, —C(O)$OR^{15a}$, —$NR^{15a}R^{16a}$, —$NR^{15a}C(O)R^{16a}$, —$NR^{15a}C(O)OR^{16a}$, —$NR^{15a}C(O)NR^{16a}$, or —$NR^{15a}S(O)_2R^{16a}$, wherein the $C_1$-$C_6$alkyl and $C_3$-$C_{10}$cycloalkyl are independently unsubstituted or substituted with one or more substituents selected from the group consisting of D, halogen, —CN, —$OR^{15a}$, —$C(O)R^{15b}$, —$NR^{15a}R^{16a}$, $C_3$-$C_{10}$cycloalkyl, $C_6$aryl, 3-7-membered heterocyclyl, and 5-6 membered heteroaryl;

each $R^{2b}$, $R^{2c}$, $R^{2d}$, $R^{2e}$, and $R^{2f}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2b}$, $R^{2c}$, $R^{2d}$, $R^{2e}$, and $R^{2f}$ together with the atoms to which they are attached can form $C_3$-$C_{10}$cycloalkyl, $C_6$aryl, 3-7-membered heterocyclyl, or 5-6-membered heteroaryl; wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

each $R^{2j}$, $R^{2k}$, $R^{2m}$, and $R^{2n}$ is independently H, D, halogen, —CN, —$NO_2$, —$SR^{17a}$, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, or 5-6 membered heteroaryl; wherein the $C_1$-$C_6$alkyl, $C_2$-$C_6$alkenyl, $C_4$-$C_8$cycloalkenyl, $C_2$-$C_6$alkynyl, $C_3$-$C_{10}$cycloalkyl, $C_6$aryl, 3-7-membered heterocyclyl, and 5-6 membered heteroaryl are independently unsubstituted or substituted with one or more substituents selected from the group consisting of D, —CN, halogen, —$OR^{17a}$, —$C(O)R^{17b}$, —$P(O)R^{17b}R^{18b}$, —$S(O)_2R^{17b}$, —$S(O)R^{17b}$, —$NR^{17a}R^{18a}$, —$NR^{17a}C(O)R^{18a}$, —$NR^{17a}C(O)OR^{18a}$, —$NR^{17a}C(O)NR^{18a}$, —$NR^{17a}S(O)_2R^{18a}$, $C_3$-$C_{10}$cycloalkyl, $C_6$aryl, 3-7-membered heterocyclyl, and 5-6 membered heteroaryl; or two adjacent $R^{2j}$, $R^{2k}$, $R^{2m}$, and $R^{2n}$ together with the atoms to which they are attached can form $C_3$-$C_{10}$cycloalkyl, $C_6$aryl, 3-7-membered heterocyclyl, or 5-6-membered heteroaryl; wherein the $C_3$-$C_{10}$cycloalkyl, $C_6$aryl, 3-7-membered heterocyclyl, and 5-6-membered heteroaryl are independently unsubstituted or substituted with one or more substituents selected from the group consisting of halogen, D, —CN, $C_1$-$C_6$alkyl, —$OR^{19a}$, and $NR^{19a}R^{20a}$;

each $R^{2g}$ and $R^{2h}$ is independently H, $C_1$-$C_6$alkyl, $C_3$-$C_{10}$cycloalkyl, 3-7-membered heterocyclyl, $C_6$aryl, or 5-membered heteroaryl, wherein the 3-7-membered heterocyclyl and 5-membered heteroaryl are attached to the nitrogen at a carbon on the 3-7-membered heterocyclyl or 5-membered heteroaryl, and wherein the $C_1$-$C_6$alkyl, $C_3$-$C_{10}$cycloalkyl, 3-7-membered heterocyclyl, $C_6$aryl, or 5-membered heteroaryl are independently unsubstituted or substituted with one or more substituents selected from the group consisting of D, —CN, halogen, $C_1$-$C_6$alkyl, —$OR^{21a}$, —$C(O)R^{21b}$, —$P(O)R^{21b}R^{22b}$, —$S(O)_2R^{21b}$, —$S(O)R^{21b}$, —$NR^{21a}R^{22a}$, —$NR^{21a}C(O)R^{22a}$, —$NR^{21a}C(O)OR^{22a}$, —$NR^{21a}C(O)NR^{22a}$, —$NR^{21a}S(O)_2R^{22a}$, $C_3$-$C_{10}$cycloalkyl, $C_6$aryl, 3-7-membered heterocyclyl, and 5-membered heteroaryl;

$R^{3a}$, $R^{4a}$, $R^{7a}$, $R^{8a}$, $R^{11a}$, $R^{12a}$, $R^{13a}$, $R^{14a}$, $R^{15a}$, $R^{16a}$, $R^{17a}$, $R^{18a}$, $R^{19a}$, $R^{20a}$ $R^{21a}$, $R^{22a}$, $R^{23a}$, and $R^{24a}$ are independently, at each occurrence, H, D, $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, or 5-6-membered heteroaryl; wherein the $C_1$-$C_8$alkyl, $C_2$-$C_8$alkenyl, $C_2$-$C_8$alkynyl, $C_3$-$C_{10}$cycloalkyl, $C_4$-$C_8$cycloalkenyl, $C_6$aryl, 3-7-membered heterocyclyl, and 5-6-membered heteroaryl are independently unsubstituted or substituted with one or more substituents selected from the group consisting of D, —CN, halogen, $C_1$-$C_6$alkyl, —OH, —O—$C_1$-$C_6$alkyl, —$NH_2$, —NH($C_1$-$C_6$alkyl), —N($C_1$-$C_6$alkyl)$_2$, $C_3$-$C_{10}$cycloalkyl, $C_6$aryl, 3-7-membered heterocyclyl, and 5-6 membered heteroaryl;

$R^{3b}$, $R^{4b}$, $R^{7b}$, $R^{8b}$, $R^{11b}$, $R^{12b}$, $R^{13b}$, $R^{14b}$, $R^{15b}$, $R^{17b}$, $R^{18b}$, $R^{21b}$, $R^{22b}$, $R^{23b}$, and $R^{24b}$ are independently, at each occurrence, H, D, —OH, —O($C_1$-$C_6$alkyl), —$NH_2$, —NH($C_1$-$C_6$alkyl), —N($C_1$-$C_6$alkyl)$_2$, —NHS(O)$_2$CH$_3$, C$_1$-C$_6$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, or 5-6-membered heteroaryl; wherein the C$_1$-C$_8$alkyl, C$_2$-C$_8$alkenyl, C$_2$-C$_8$alkynyl, C$_3$-C$_{10}$cycloalkyl, C$_4$-C$_8$cycloalkenyl, C$_6$aryl, 3-7-membered heterocyclyl, and 5-6-membered heteroaryl are independently unsubstituted or substituted with one or more substituents selected from the group consisting of D, —CN, halogen, C$_1$-C$_6$alkyl, —OH, —O—C$_1$-C$_6$alkyl, —NH$_2$, —NH(C$_1$-C$_6$alkyl), —N(C$_1$-C$_6$alkyl)$_2$, C$_3$-C$_{10}$cycloalkyl, C$_6$aryl, 3-7-membered heterocyclyl, and 5-6 membered heteroaryl.

2. The compound of claim 1, or a pharmaceutically acceptable salt thereof, wherein R$^{100}$ is H, —CN, —C(O)R$^{3b}$, or C$_1$-C$_6$alkyl; wherein the C$_1$-C$_6$alkyl is unsubstituted or substituted with C$_6$aryl.

3. The compound of claim 1, or a pharmaceutically acceptable salt thereof, wherein R$^{100}$ is H.

4. The compound of claim 1, or a pharmaceutically acceptable salt thereof, wherein X$^2$ is CR$^{2a}$ and R$^{2a}$ is H, halogen, —CN, —OR$^{15a}$, —C(O)OR$^{15a}$, or C$_1$-C$_6$alkyl; wherein the C$_1$-C$_6$alkyl is unsubstituted or substituted with one or more substituents selected from the group consisting of D, halogen, —CN, —OR$^{15a}$, —C(O)R$^{15b}$, —P(O)R$^{15b}$R$^{16b}$, —NR$^{15a}$R$^{16a}$, C$_3$-C$_{10}$cycloalkyl, C$_6$aryl, 3-7-membered heterocyclyl, and 5-6-membered heteroaryl.

5. The compound of claim 1, or a pharmaceutically acceptable salt thereof, wherein R$^2$ is selected from the group consisting of:

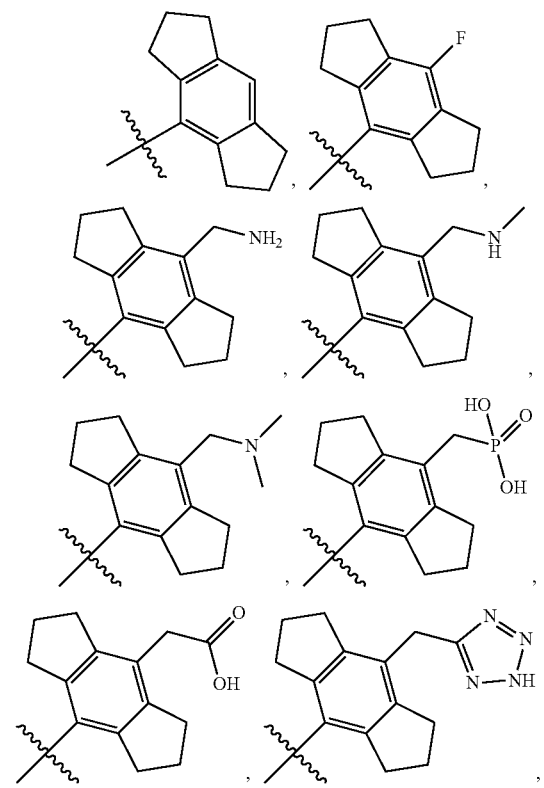
, and

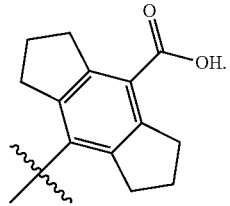

6. The compound of claim 1, or a pharmaceutically acceptable salt thereof, wherein R$^1$ is

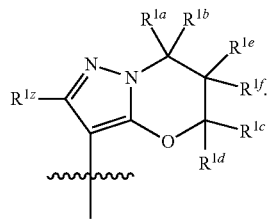

7. The compound of claim 1, or a pharmaceutically acceptable salt thereof, wherein R$^1$ is

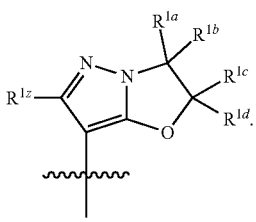

8. The compound of claim 1, or a pharmaceutically acceptable salt thereof, wherein R$^1$ is

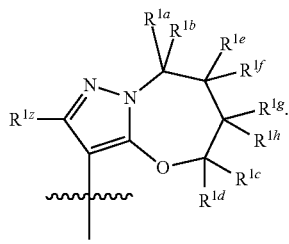

9. The compound of claim 1, or a pharmaceutically acceptable salt thereof, wherein R$^1$ is selected from the group consisting of

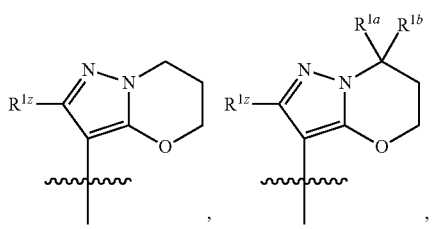
,

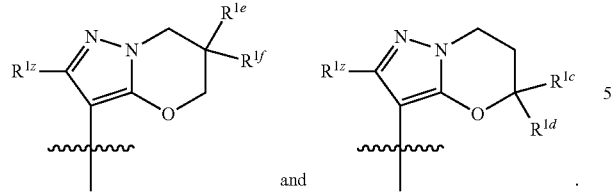
and
10. The compound of claim 1, or a pharmaceutically acceptable salt thereof, wherein $R^1$ is selected from the group consisting of
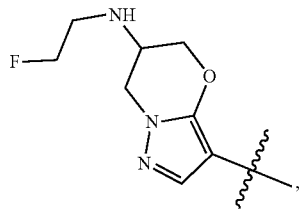
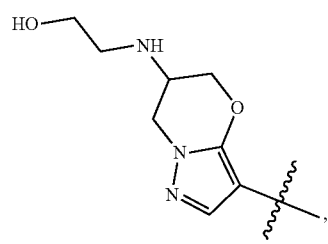
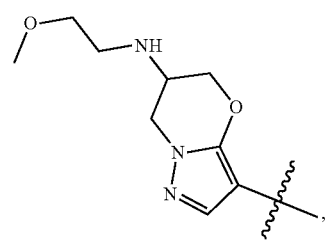
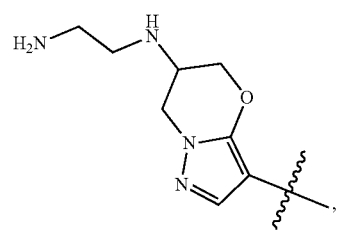
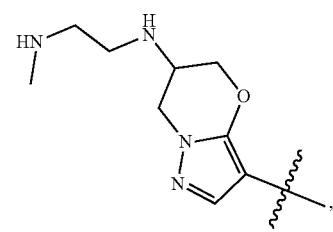
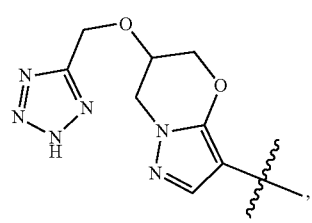 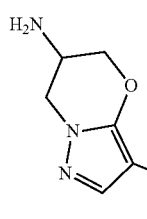
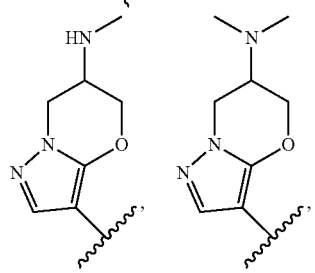

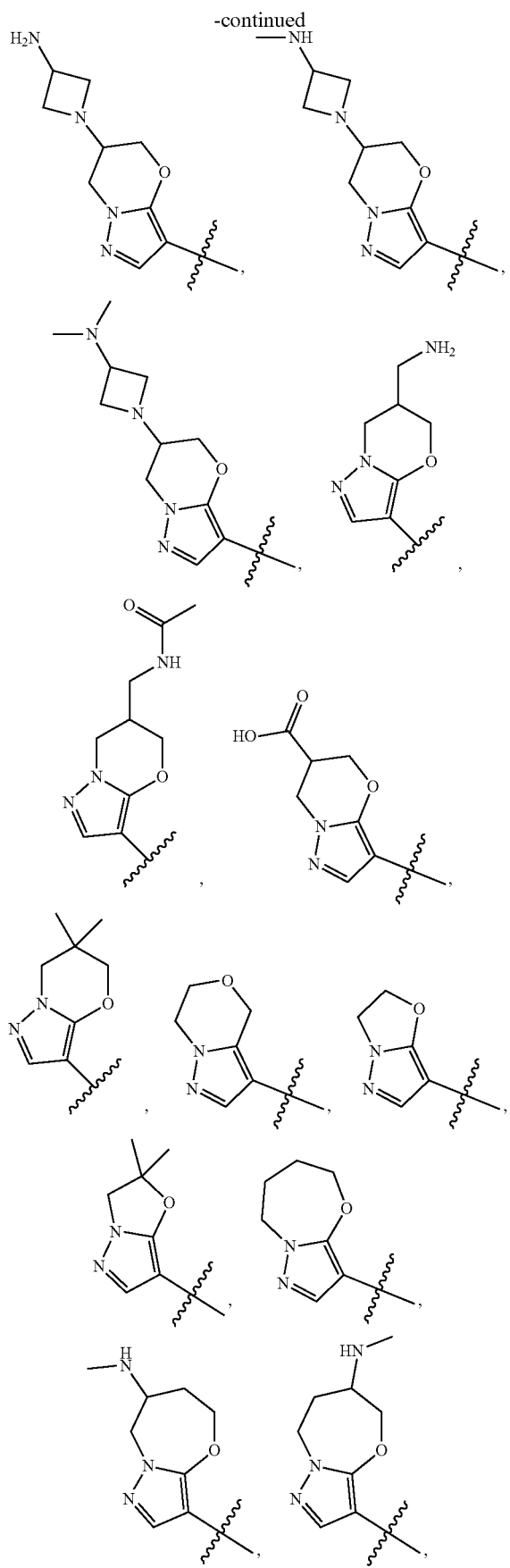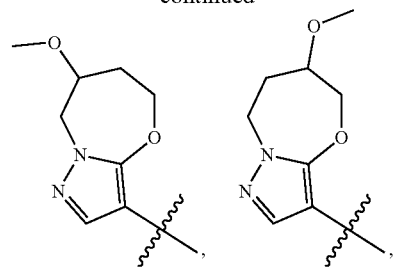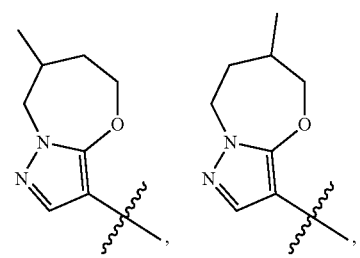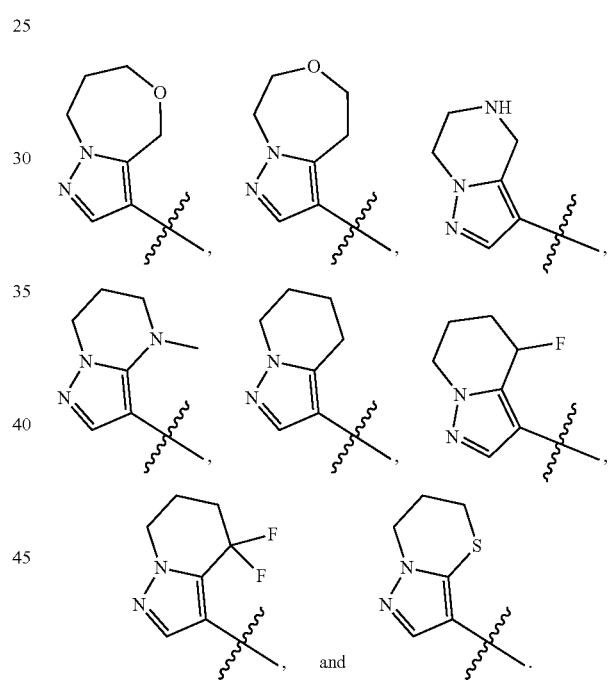
and
11. The compound of claim 1, or a pharmaceutically acceptable salt thereof, wherein R¹ is selected from the group consisting of
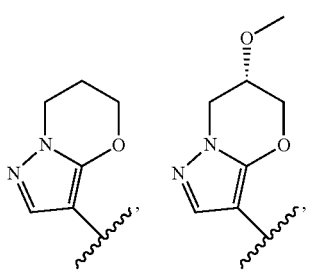

463
-continued
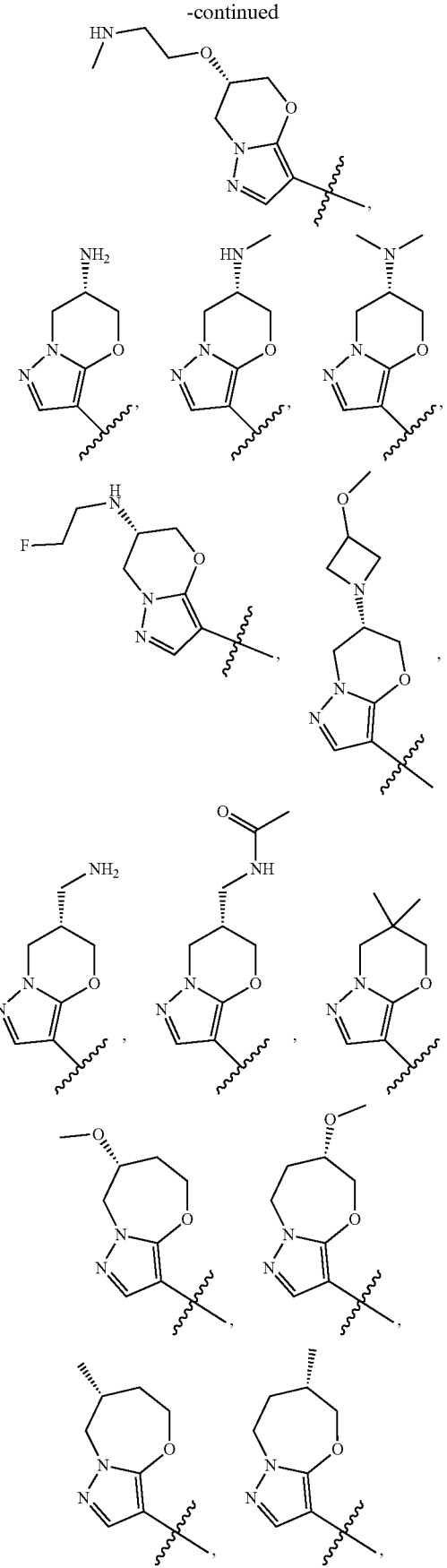
464
-continued
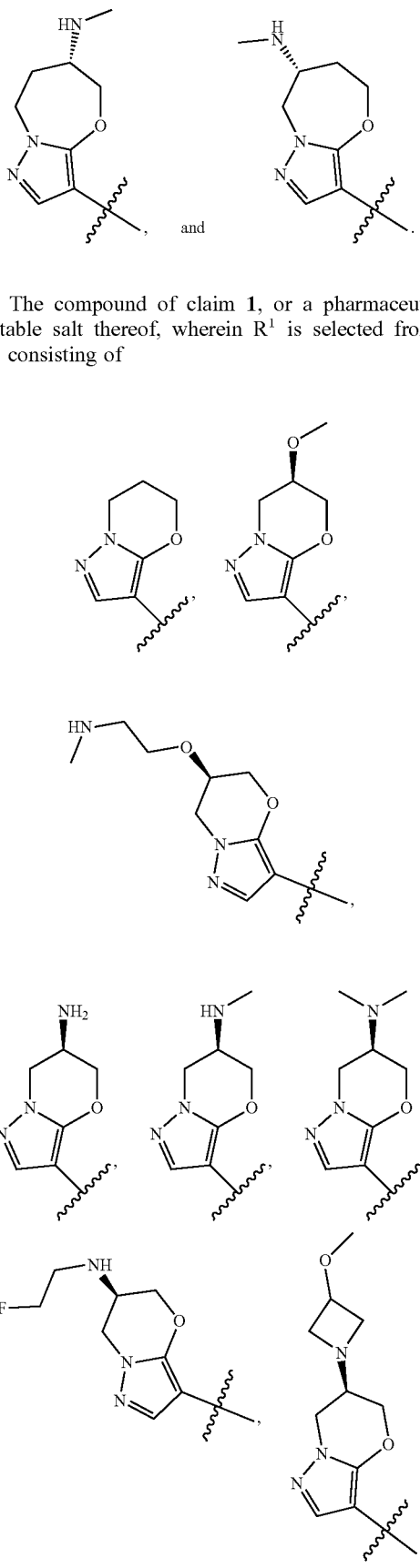
12. The compound of claim 1, or a pharmaceutically acceptable salt thereof, wherein R¹ is selected from the group consisting of

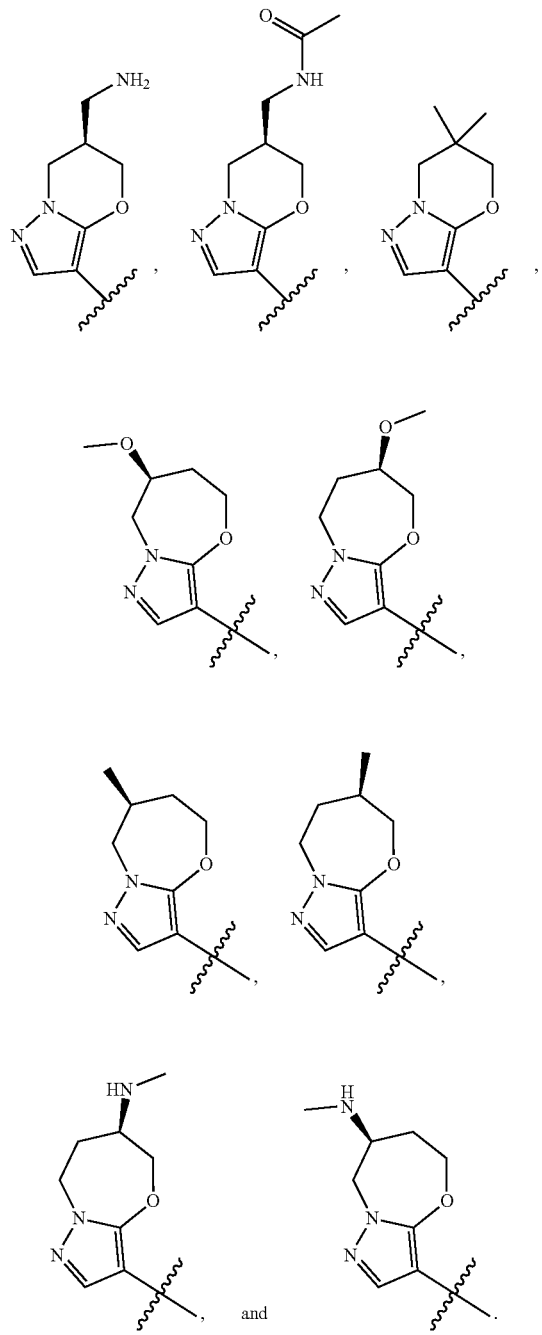

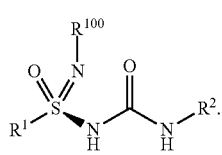

and

13. The compound of claim 1, or a pharmaceutically acceptable salt thereof, wherein the compound is of formula:

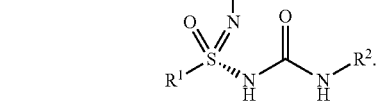
(Ia)

14. The compound of claim 1, or a pharmaceutically acceptable salt thereof, wherein the compound is of formula:

(Ib)

15. A pharmaceutical composition comprising a compound of claim 1, or a pharmaceutically acceptable salt thereof, and a pharmaceutically acceptable carrier.

16. The compound of claim 1, wherein the compound is:

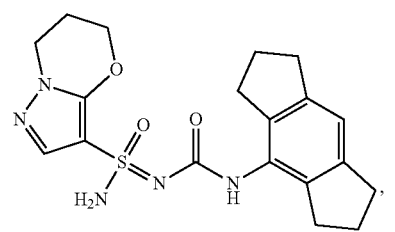

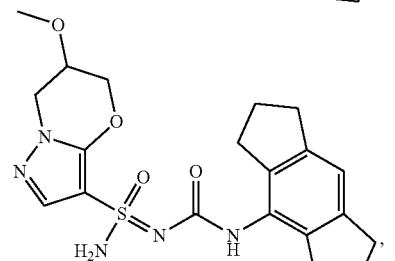

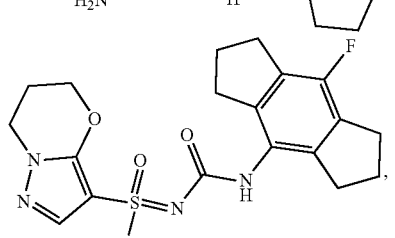

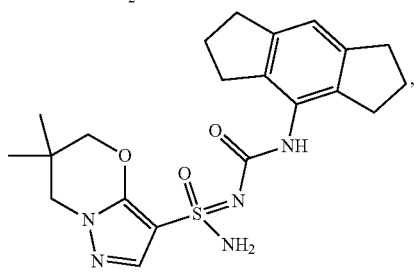

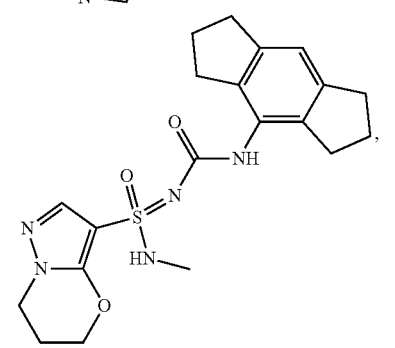

-continued
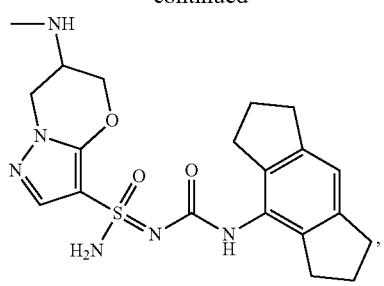
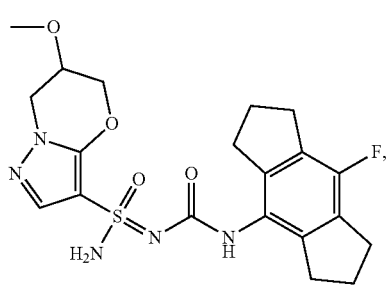
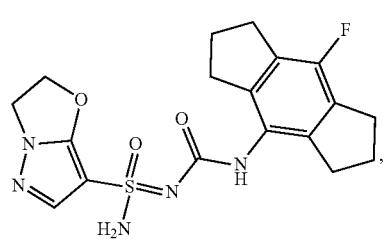
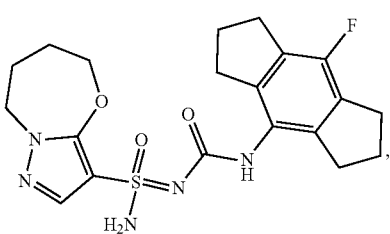
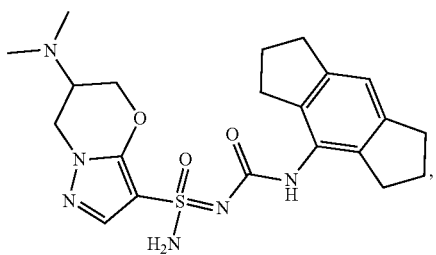
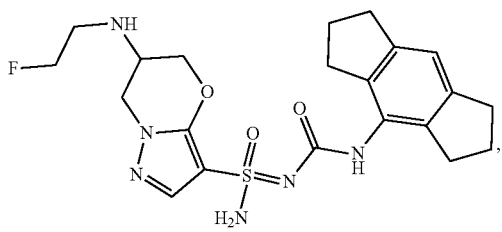
-continued
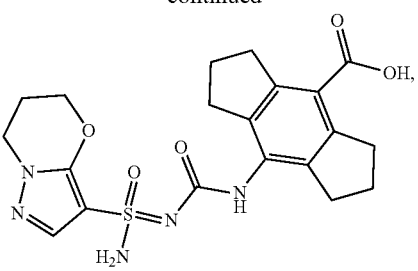
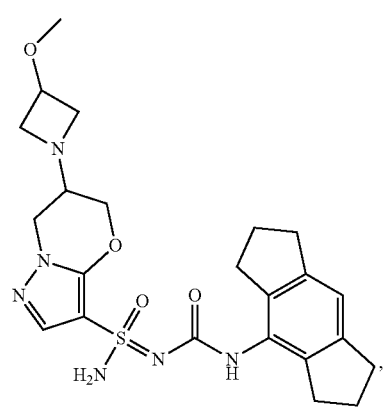
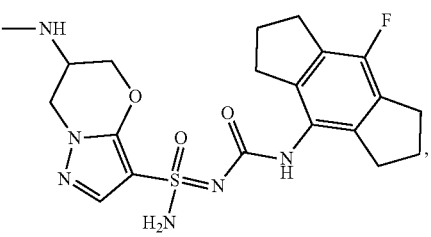
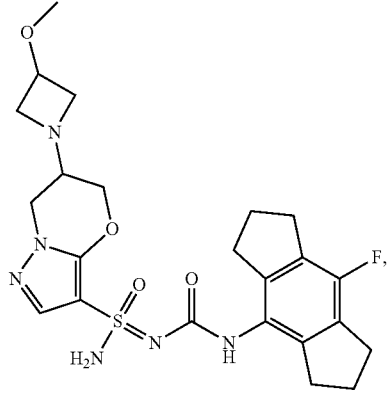
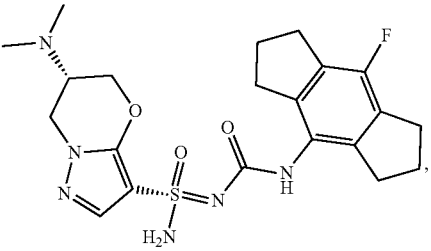

469
-continued
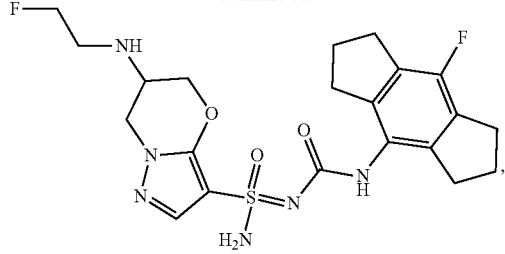
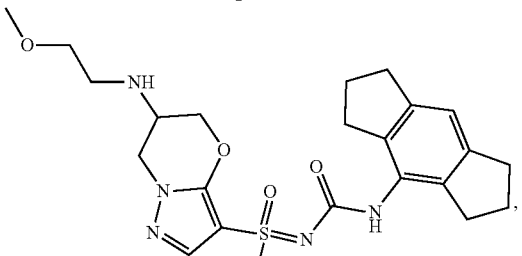
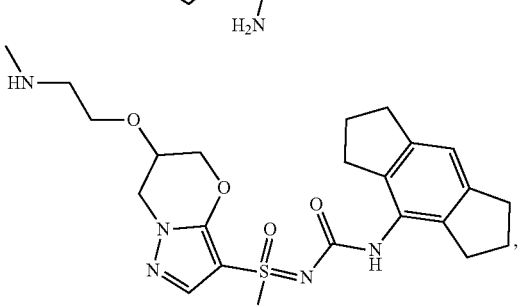
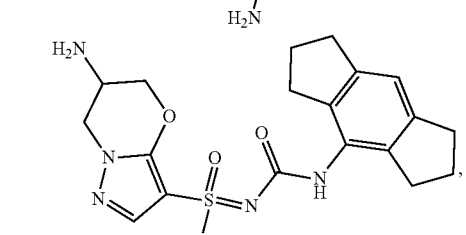
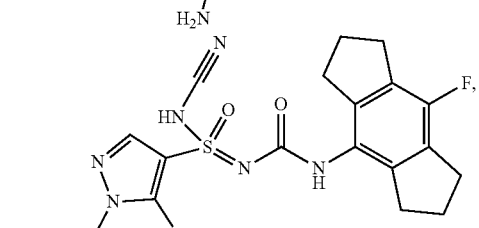
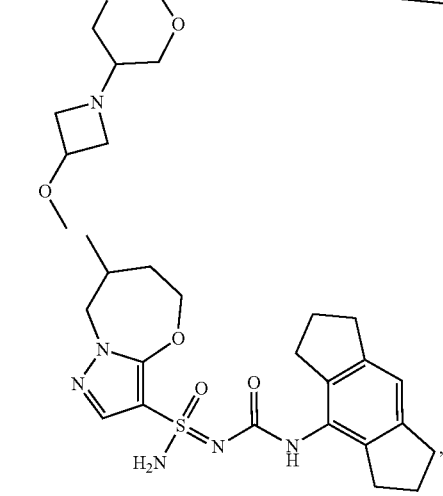
470
-continued
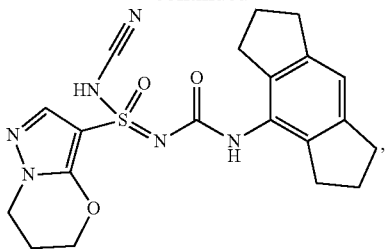
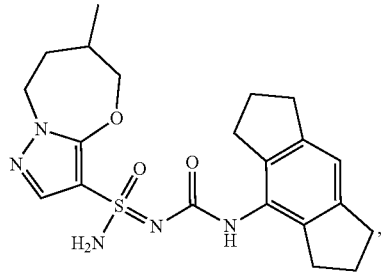
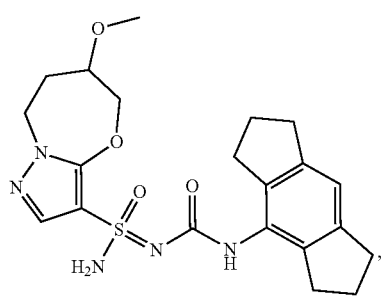
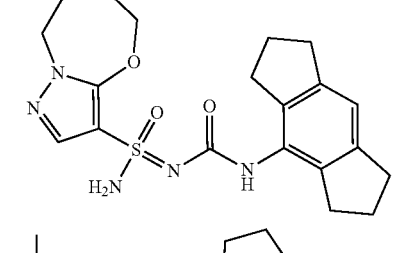
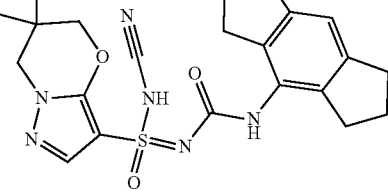
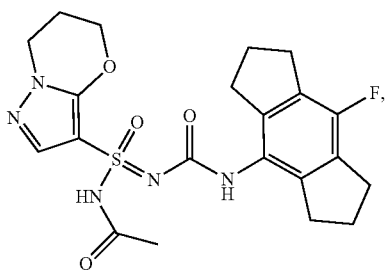

471
-continued
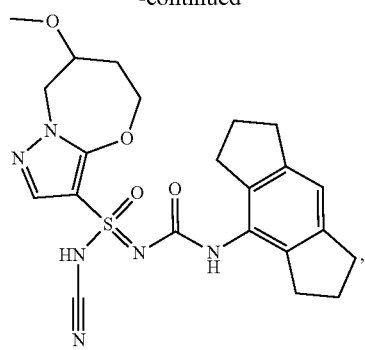
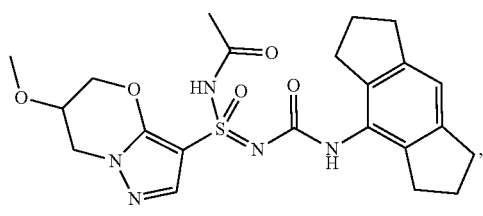
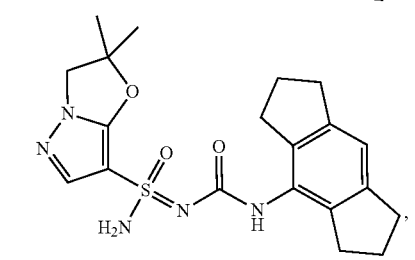
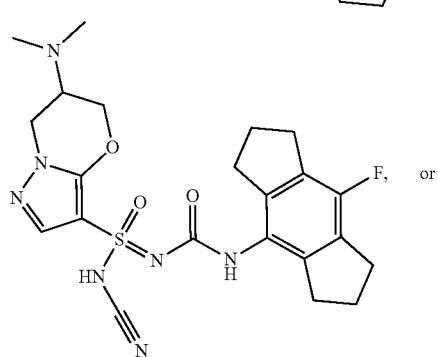
472
-continued
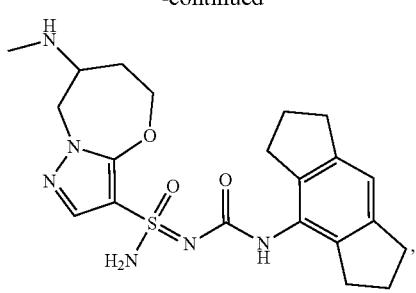
or a pharmaceutically acceptable salt thereof.
17. The compound of claim 1, wherein the compound is:
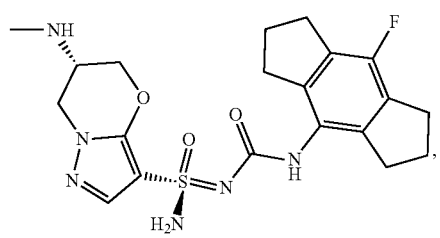
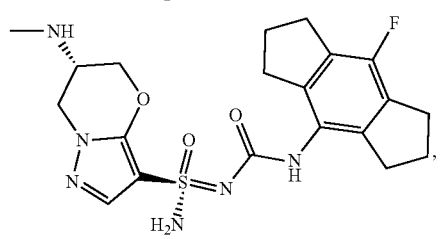
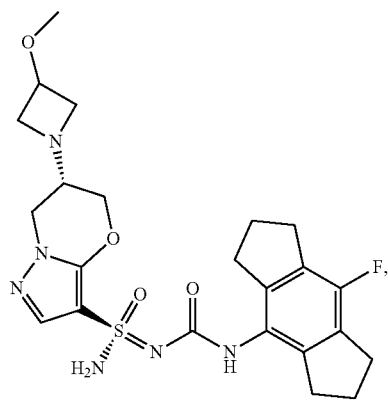

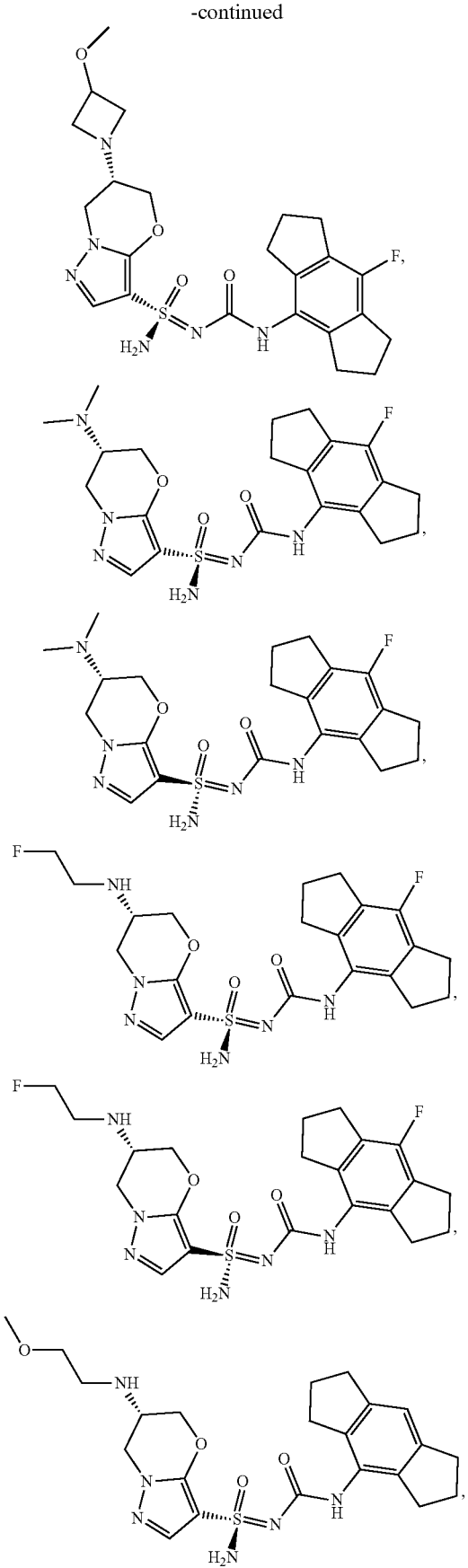
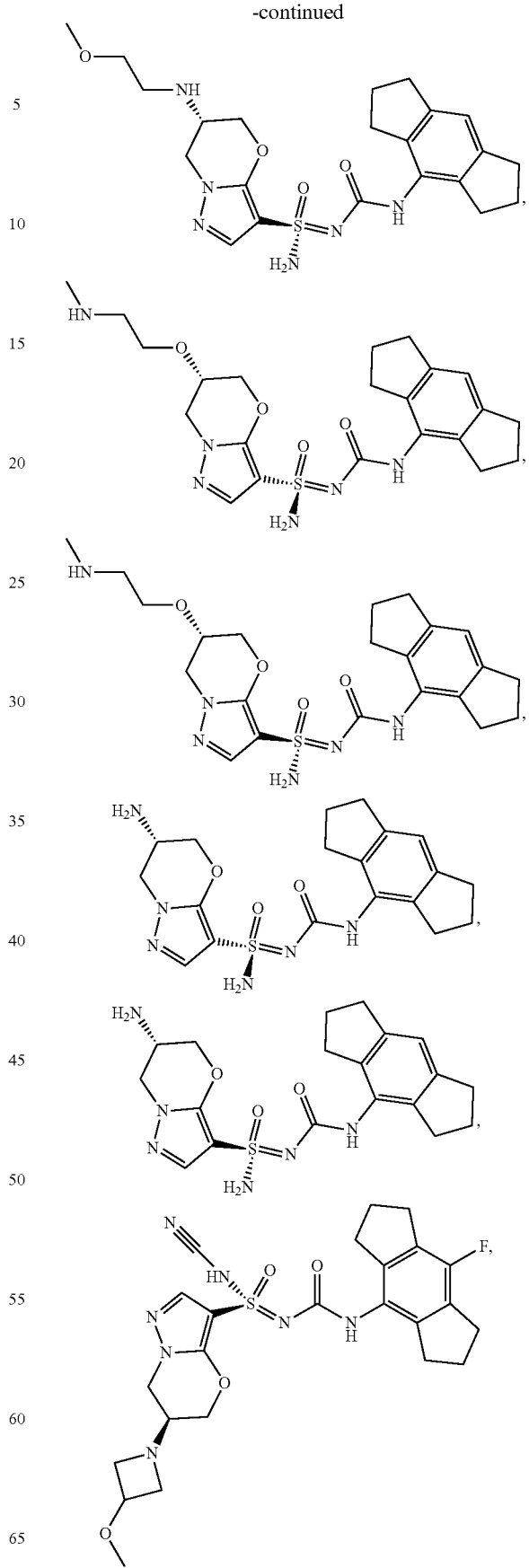

475
-continued
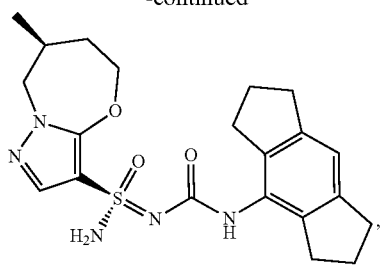
476
-continued
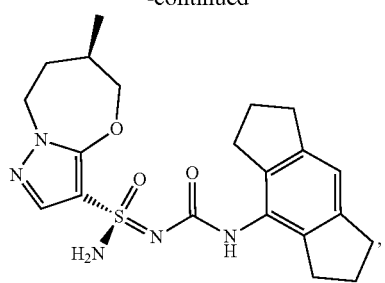
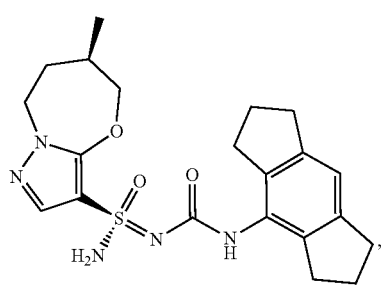
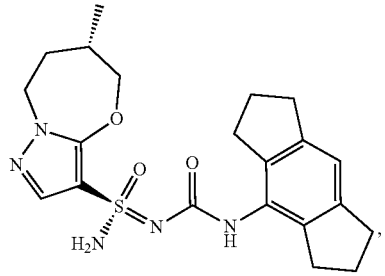
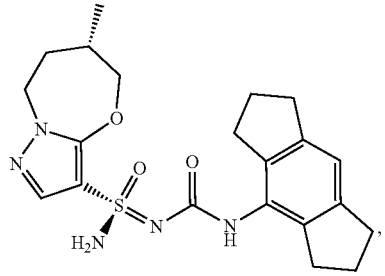
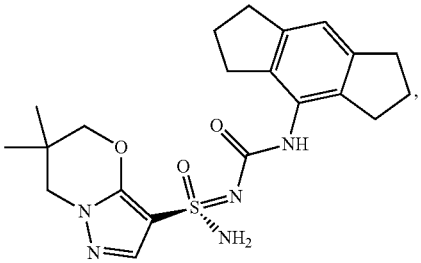
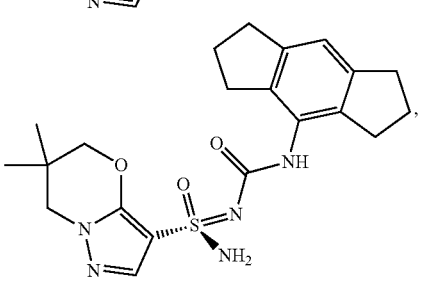

477
-continued
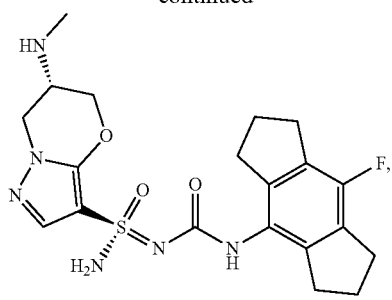
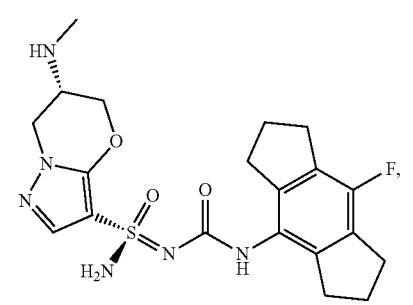
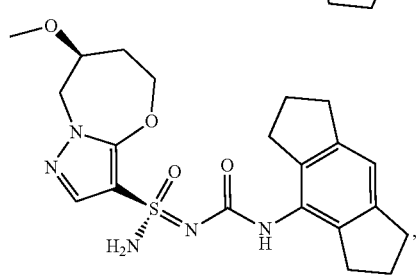
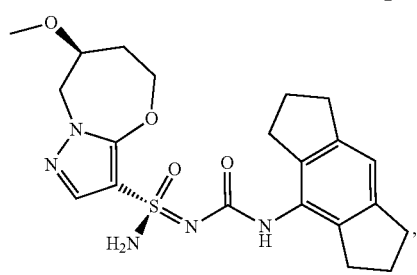
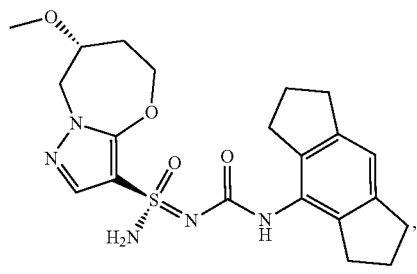
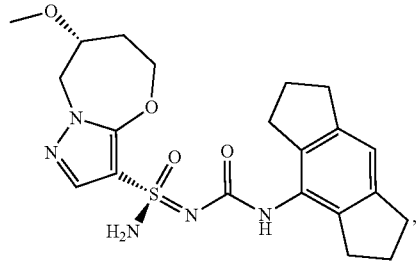
478
-continued
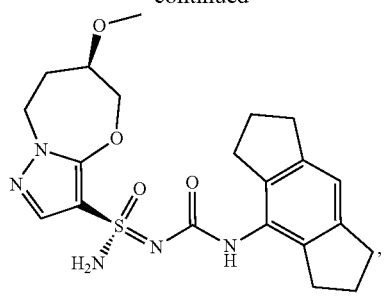
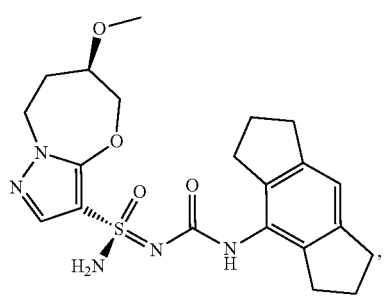
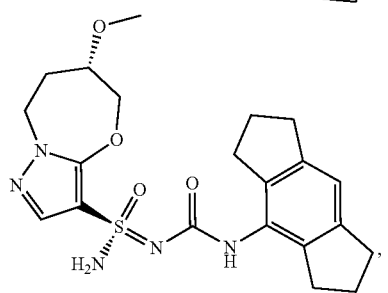
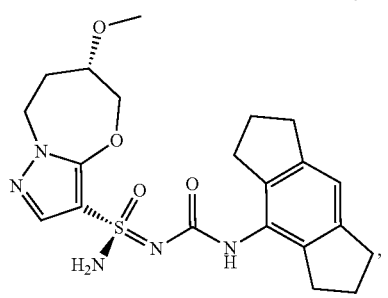
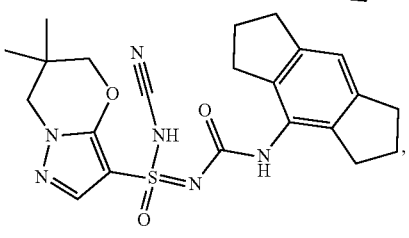
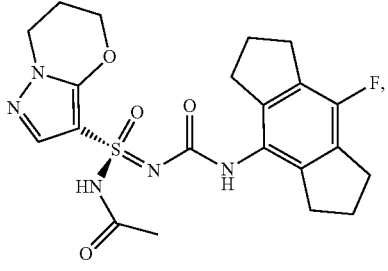

479
-continued
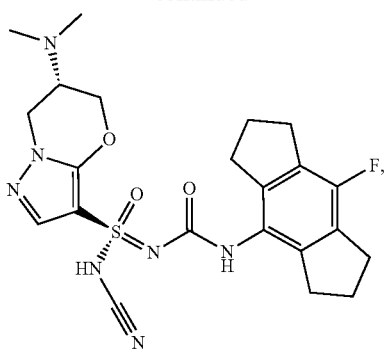
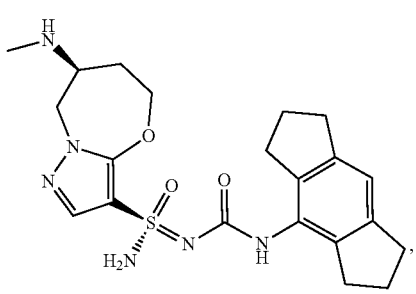
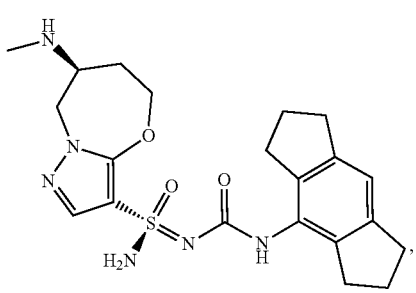
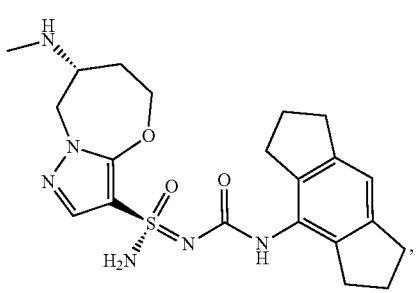
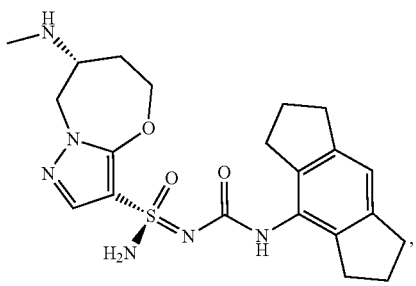
480
-continued
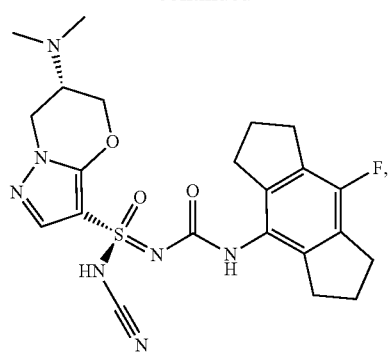
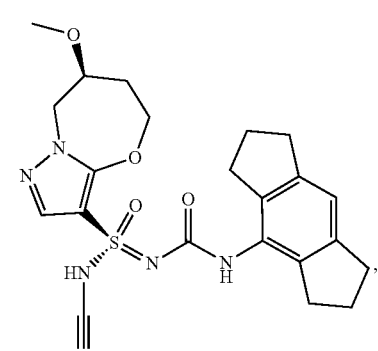
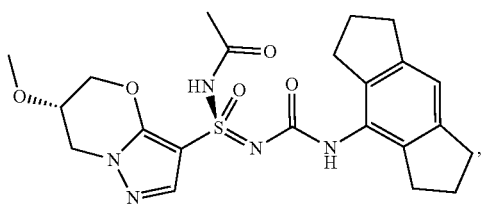
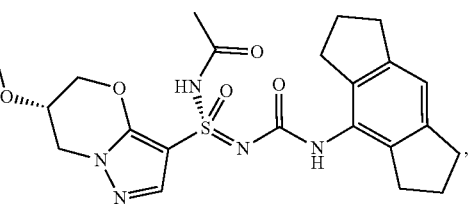
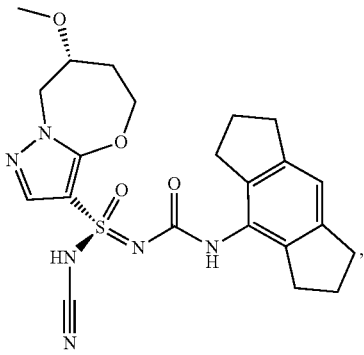

481
-continued
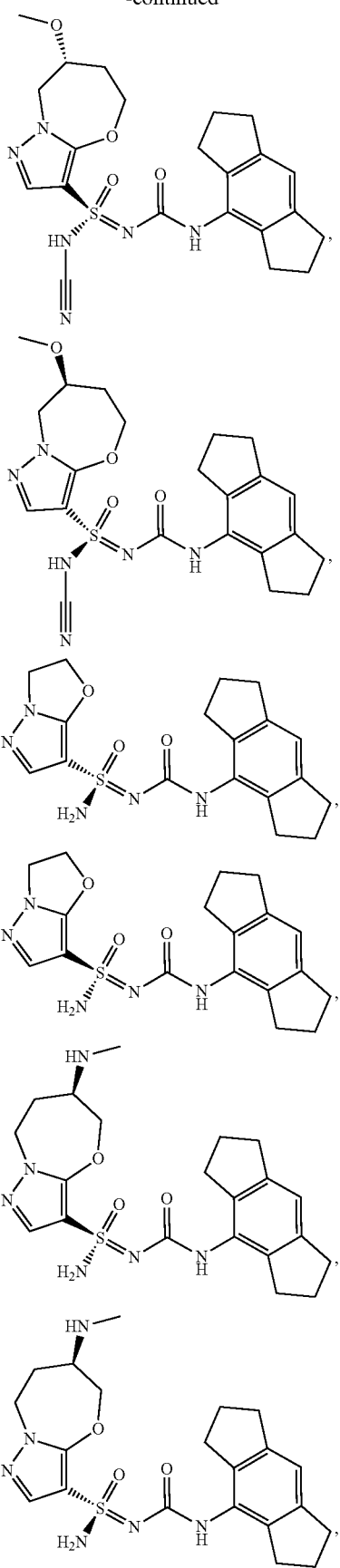
482
-continued
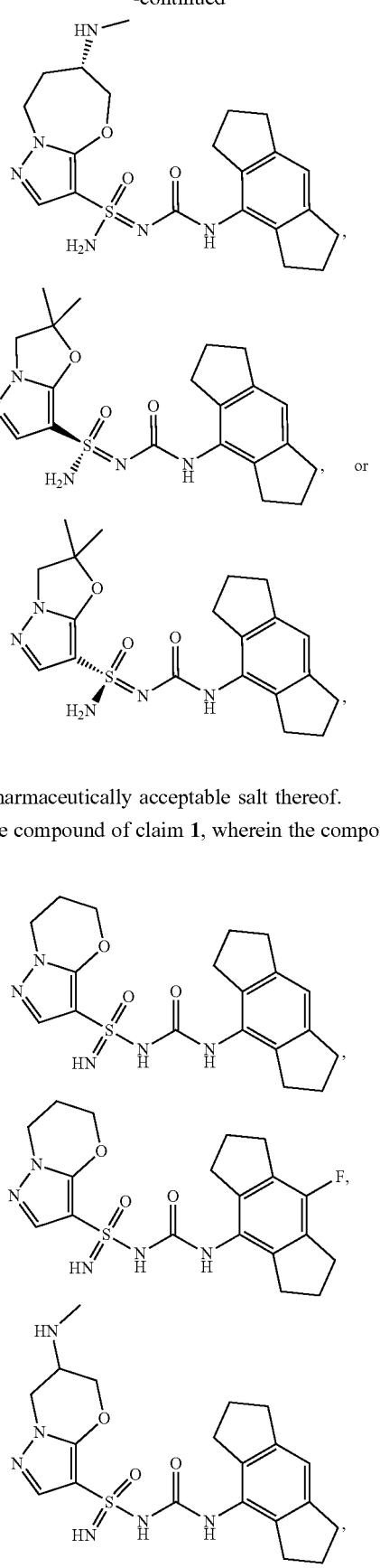
or a pharmaceutically acceptable salt thereof.
18. The compound of claim 1, wherein the compound is:

483
-continued
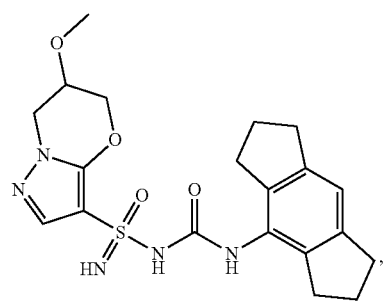
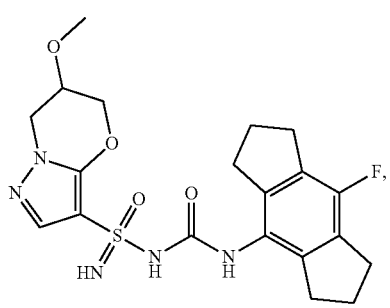
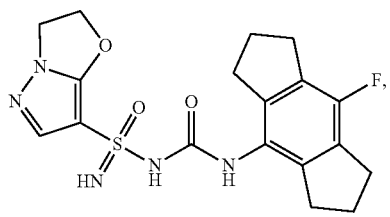
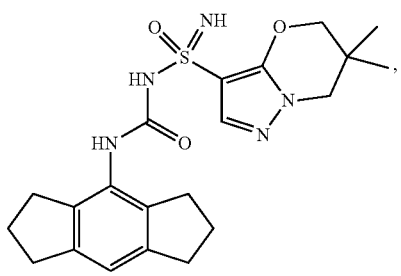
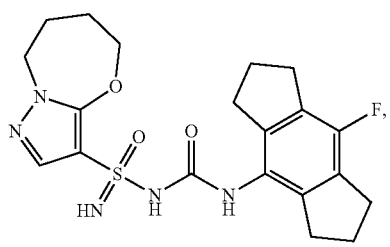
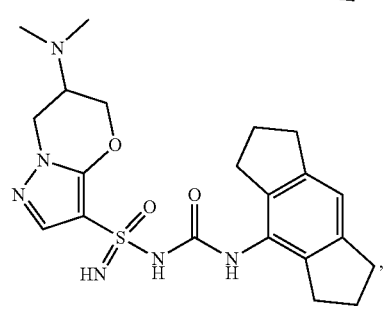
484
-continued
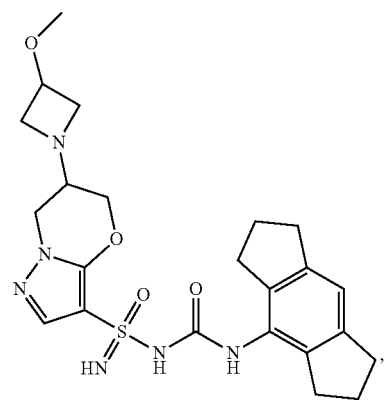
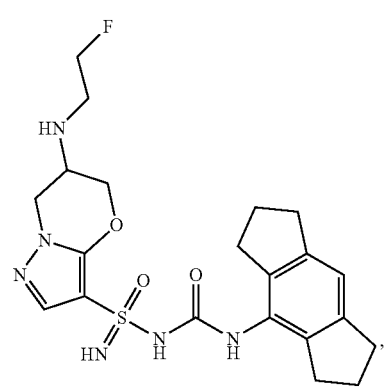
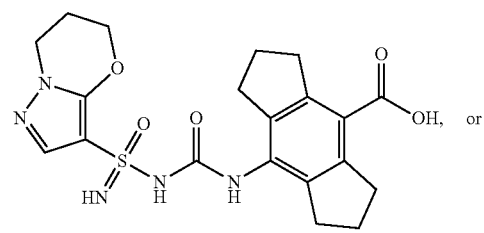, or
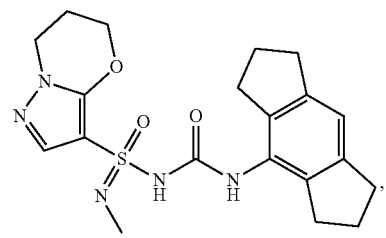
or a pharmaceutically acceptable salt thereof.
19. The compound of claim 1, wherein the compound is:
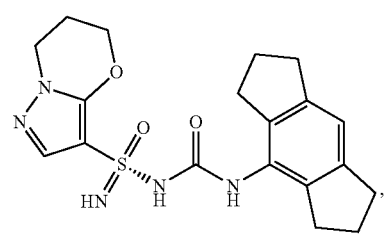

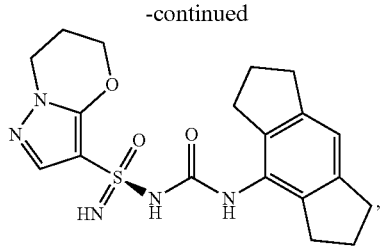
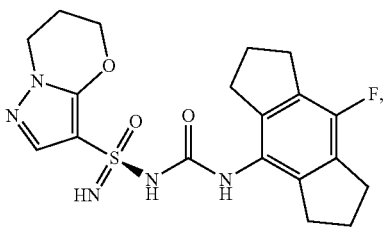
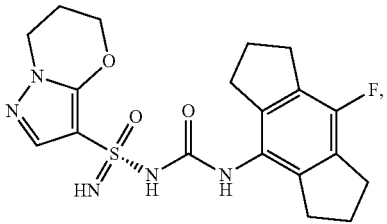
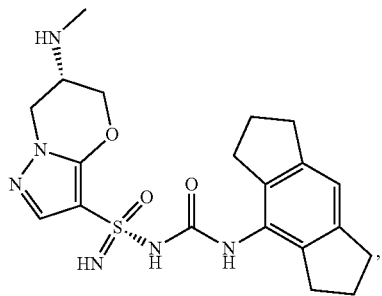
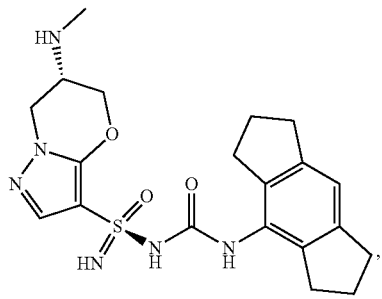
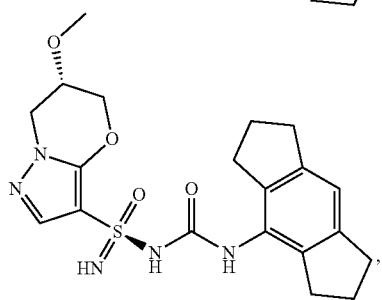
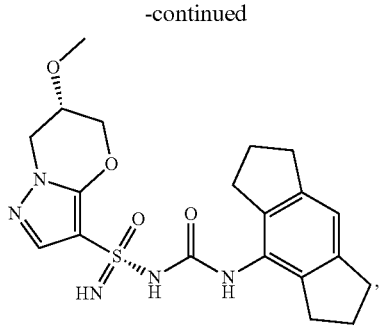
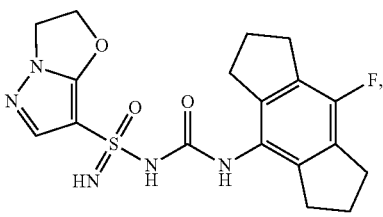
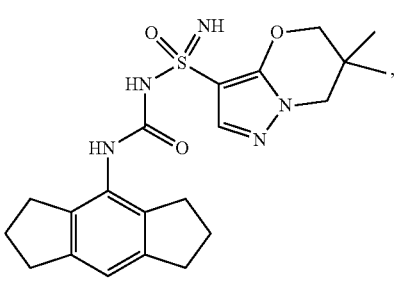
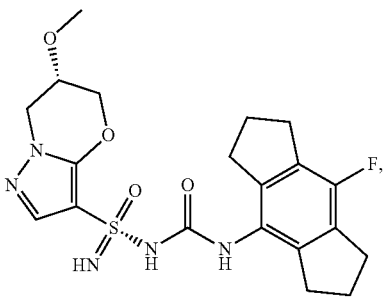
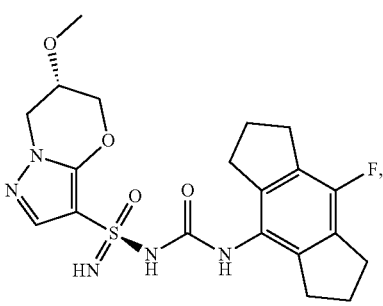
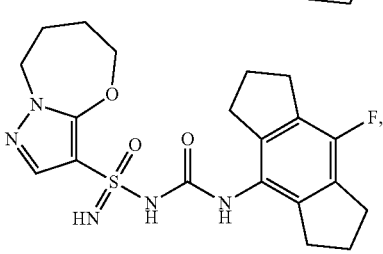

487
-continued
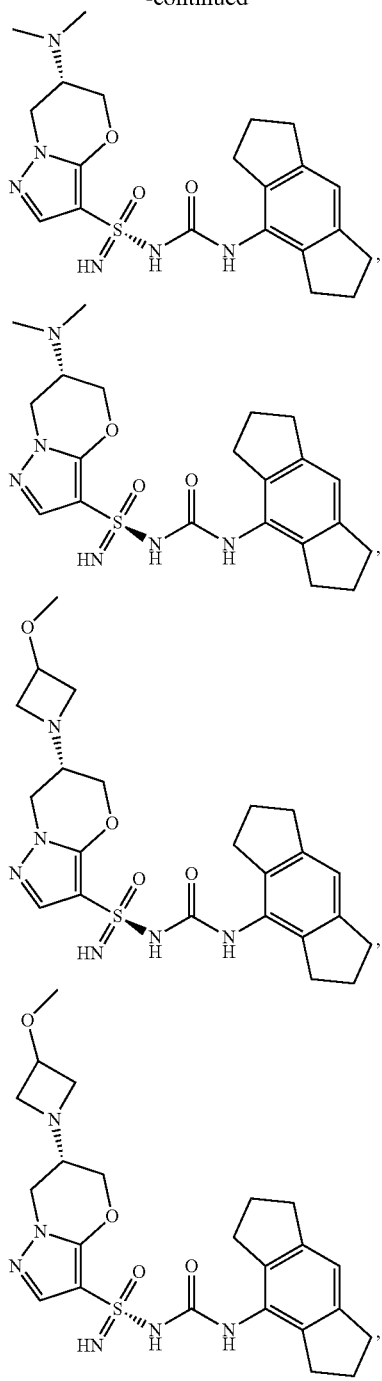
488
-continued
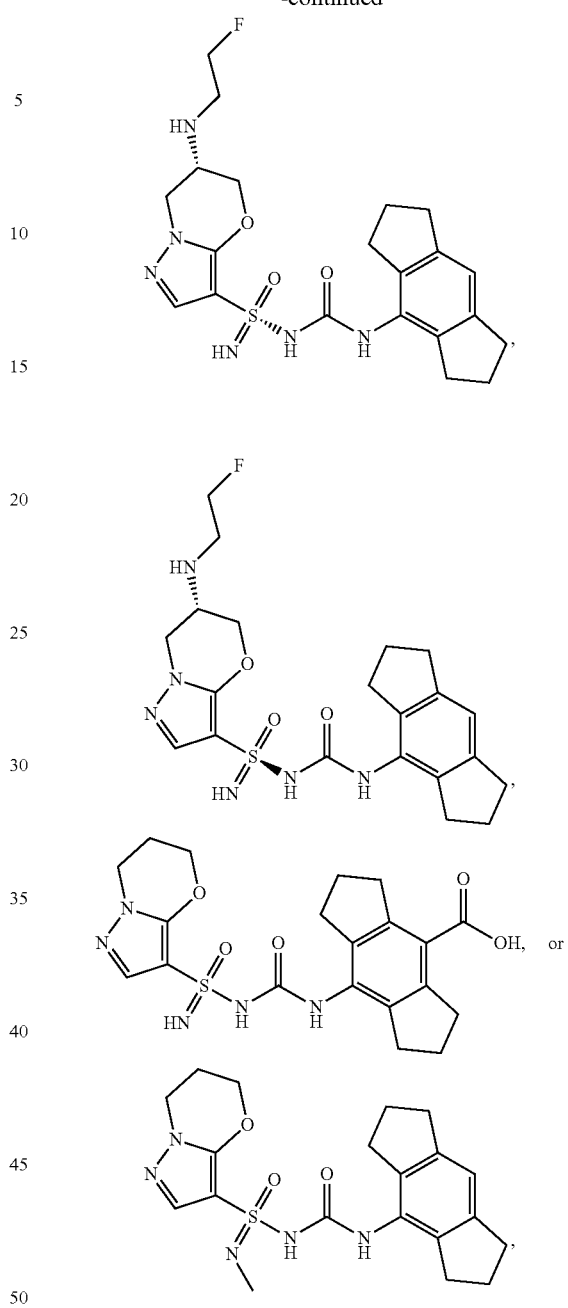
or a pharmaceutically acceptable salt thereof.
* * * * *